US008173811B2

(12) United States Patent
Bruncko et al.

(10) Patent No.: US 8,173,811 B2
(45) Date of Patent: *May 8, 2012

(54) APOPTOSIS PROMOTERS

(75) Inventors: Milan Bruncko, Green Oaks, IL (US);
Hong Ding, Gurnee, IL (US); Steven Elmore, Gurnee, IL (US); Aaron Kunzer, Schaumburg, IL (US); Christopher L. Lynch, Trevor, WI (US); William McClellan, Waukegan, IL (US); Cheol-Min Park, Gurnee, IL (US); Andrew Petros, Mundelein, IL (US); Xiaohong Song, Grayslake, IL (US); Xilu Wang, Grayslake, IL (US); Noah Tu, Singapore (SG); Michael Wendt, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 28 days.

This patent is subject to a terminal disclaimer.

(21) Appl. No.: 12/800,702

(22) Filed: May 19, 2010

(65) Prior Publication Data

US 2010/0240715 A1    Sep. 23, 2010

Related U.S. Application Data

(63) Continuation of application No. 11/127,940, filed on May 12, 2005, now Pat. No. 7,767,684, which is a continuation-in-part of application No. 10/988,338, filed on Nov. 12, 2004, now abandoned.

(60) Provisional application No. 60/519,695, filed on Nov. 13, 2003.

(51) Int. Cl.
*C07D 235/02* (2006.01)
(52) U.S. Cl. .................. 546/117; 548/303.1; 548/303.4
(58) Field of Classification Search ............... 548/303.1, 548/303.4
See application file for complete search history.

(56) References Cited

U.S. PATENT DOCUMENTS

| | | | |
|---|---|---|---|
| 5,138,069 A | 8/1992 | Carini et al. | |
| 6,410,584 B1 | 6/2002 | Pamukcu et al. | |
| 6,720,338 B2 | 4/2004 | Augeri et al. | |
| 7,030,115 B2 | 4/2006 | Elmore et al. | |
| 7,358,251 B2 | 4/2008 | Elmore et al. | |
| 7,390,799 B2 | 6/2008 | Bruncko et al. | |
| 7,449,485 B2 | 11/2008 | Elmore et al. | |
| 7,504,512 B2 | 3/2009 | Augeri et al. | |
| 7,585,858 B2 | 9/2009 | Elmore et al. | |
| 7,642,260 B2 | 1/2010 | Bruncko et al. | |
| 7,767,684 B2 * | 8/2010 | Bruncko et al. | 514/255.03 |
| 7,973,161 B2 * | 7/2011 | Bruncko et al. | 544/393 |
| 2002/0086887 A1 | 7/2002 | Augeri et al. | |
| 2003/0119894 A1 | 6/2003 | Murthy et al. | |
| 2006/0258657 A1 | 11/2006 | Bruncko et al. | |
| 2007/0015787 A1 | 1/2007 | Bruncko et al. | |
| 2007/0072860 A1 | 3/2007 | Bruncko et al. | |
| 2008/0076779 A1 | 3/2008 | Elmore et al. | |
| 2008/0287419 A1 | 11/2008 | Bruncko et al. | |
| 2010/0152183 A1 * | 6/2010 | Bruncko et al. | 514/234.5 |
| 2010/0298321 A1 * | 11/2010 | Bruncko et al. | 514/234.5 |

FOREIGN PATENT DOCUMENTS

| | | |
|---|---|---|
| NZ | 230136 | 12/1991 |
| WO | WO 02/24636 | 3/2002 |
| WO | WO 02/098848 | 12/2002 |
| WO | WO 03/040107 | 5/2003 |
| WO | WO 03/080586 | 10/2003 |
| WO | WO 2004/043950 | 5/2004 |
| WO | WO 2004/048329 | 6/2004 |
| WO | WO 2005/049593 | 6/2005 |
| WO | WO 2005/049594 | 6/2005 |

OTHER PUBLICATIONS

Grunager, et al., Addition Reaction of Sulfonyl Azides on Ethoxyacetylene, Tetrahedron Letters, 26, 1839-40 (1963).*
Banker, Gilbert S. et al., Modern Pharmaceuticals, 1996, Marcel Dekker, New York, pp. 596 and 451.
Corbett et al., "Discovery and preclinical antitumor efficacy evaluations of LY32262 and LY33169," Investigational New Drugs, 2003, vol. 21, pp. 33-45.
Degterev, et al., "Identification of small-molecule inhibitors of interaction between the BH3 domain and Bcl-$x_L$," Nature Cell Biology, 2001, vol. 3, pp. 173-182.
Enyedy, et al., "Discovery of Small-Molecule Inhibitors of Bcl-2 through Structure-Based Computer Screening," J. Med. Chem., 2001, 44, pp. 4313-4324.
ISA, PCT International Preliminary Report on Patentability dated May 15, 2006, in International Application No. PCT/US2004/036770, filed Nov. 3, 2004.
ISA, PCT International Preliminary Report on Patentability dated May 15, 2006, in International Application No. PCT/US2004/037911, filed Nov. 12, 2004.
ISA, PCT International Search Report dated May 13, 2005, in International Application No. PCT/US2004/036770, filed Nov. 3, 2004.
ISA, PCT International Search Report dated May 13, 2005, in International Application No. PCT/US2004/037911, filed Nov. 12, 2004.
Kutzki, et al., "Development of Potent Bcl-xl Antagonist Based on α-Helix Mimicry," J. Am. Chem. Soc., 2002, 124, pp. 11838-11839.
Oltersdorf, et al., "An inhibitor of Bcl-2 Family proteins induces regression of solid tumours", Nature, 2005, 4 35, pp. 677-681.
TSE et al., "ABT-263: A Potent and Orally Bioavailable Bcl-2 Family Inhibitor," Cancer Research May 1, 2008, 68(9), pp. 3421-3428.
U.S.P.T.O., Non-final Office Action dated Nov. 28, 2008 in U.S. Appl. No. 12/120,914.
Wang, et al., "Structure-based discovery of an organic compound that binds Bcl-2 protein and induces apoptosis of tumor cells," PNAS, Jun. 20, 2000, vol. 97, No. 13, pp. 7124-7129.

(Continued)

*Primary Examiner* — Andrew D Kosar
*Assistant Examiner* — Erich A Leeser
(74) *Attorney, Agent, or Firm* — Jones Day

(57) ABSTRACT

Disclosed are compounds which inhibit the activity of anti-apoptotic protein family members, compositions containing the compounds and uses of the compounds for preparing medicaments for treating diseases during which occurs expression one or more than one of an anti-apoptotic protein family member.

4 Claims, No Drawings

OTHER PUBLICATIONS

Wang, et al., "A novel small molecule inhibitor of Bcl-$X_L$ inhibits tumor growth in a human head and neck squamous cell carcinoma xenograft model," Proceedings of the American Association for Cancer Research, Jul. 2003, vol. 44, 2nd Ed., p. 942, #4740 Abstract.

Wang, et al., "An Efficient Synthesis of ABT-263, a Novel Inhibition of Anti-apoptotic Bcl-2 Proteins," Synthesis, 2008, 15, 2398-2404.

Wolff, Manfred E., Burger's Medicinal Chemistry and Drug Discovery, Fifth Ed. vol. 1: Principles and Practice, John Wiley & Sons, 1995, pp. 975-977.

Amendment and Response filed on Oct. 8, 2009 in U.S. Appl. No. 11/600,445.

Final Office Action dated Aug. 12, 2009 for U.S. Appl. No. 12/120,914.

Hattori et al., CAS Accession No. 2006: 298664.

* cited by examiner

US 8,173,811 B2

APOPTOSIS PROMOTERS

This application is a continuation of U.S. patent application Ser. No. 11/127,940, filed May 12, 2005, now U.S. Pat. No. 7,767,684, which is a continuation-in-part of U.S.patent application Ser. No. 10/988,338, filed Nov. 12, 2004, now abandoned, which claims priority to U.S. Provisional Application 60/519,695, filed Nov. 13, 2003, the specifications of which are hereby incorporated by reference into this application.

FIELD OF THE INVENTION

This invention pertains to compounds which inhibit the activity of anti-apoptotic protein family members, compositions containing the compounds, and methods of treating diseases during which are expressed of one or more than one of an anti-apoptotic protein family member.

BACKGROUND OF THE INVENTION

Anti-apoptotic protein family members are associated with a number of diseases. There is therefore an existing need in the therapeutic arts for compounds which inhibit the activity of one of more than one of an anti-apoptotic protein family member.

SUMMARY OF THE INVENTION

One embodiment of this invention, therefore, pertains to compounds or therapeutically acceptable salts, prodrugs or salts of prodrugs thereof, which are useful as inhibitors one or more than one anti-apoptotic protein family member, the compounds having formula (I)

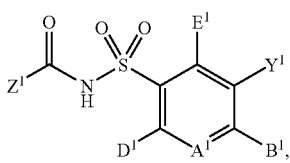

wherein $A^1$ is N or $C(A^2)$;
one or two or three or each of $A^2$, $B^1$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, CN, $CF_3$, C(O)OH, $C(O)NH_2$ or $C(O)OR^{14}$; and
$Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$;
or
$B^1$ and $Y^1$, together with the atoms to which they are attached, are imidazole or triazole; and
one or two or each of $A^2$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NHC(O)NHR^1$, $N(CH_3)C(O)N(CH_3)R^1$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, $CF_3$, C(O)OH, $C(O)NH_2$ or $C(O)OR^{14}$;
$R^1$ is $R^2$, $R^3$, $R^4$ or $R^5$;
$R^{14}$ is $C_1$-$C_6$-alkyl, $C_3$-$C_6$-alkenyl or $C_3$-$C_6$-alkynyl;
$R^2$ is phenyl which is unfused or fused with arene, heteroarene or $R^{2A}$; $R^{2A}$ is cycloalkane or heterocycloalkane;
$R^3$ is heteroaryl which is unfused or fused with benzene, heteroarene or $R^{3A}$; $R^{3A}$ is cycloalkane or heterocycloalkane;
$R^4$ is cycloalkyl, cycloalkenyl, heterocycloalkyl or heterocycloalkenyl, each of which is unfused or fused with arene, heteroarene or $R^{4A}$; $R^{4A}$ is cycloalkane, cycloalkene, heterocycloalkane or heterocycloalkene;
$R^5$ is alkyl, alkenyl or alkynyl, each of which is unsubstituted or substituted with one or two or three) independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;
$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;
$R^{6A}$ and $R^{6B}$ are independently selected alkyl or, together with the N to which they are attached, $R^{6C}$;
$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;
$R^7$ is $R^8$, $R^9$, $R^{10}$ or $R^{11}$;
$R^8$ is phenyl which is unfused or fused with arene, heteroarene or $R^{8A}$;
$R^{8A}$ is cycloalkane, cycloalkene, heterocycloalkane or heterocycloalkene;
$R^9$ is heteroaryl which is unfused or fused with arene, heteroarene or $R^{9A}$; $R^{9A}$ is cycloalkane, cycloalkene, heterocycloalkane or heterocycloalkene;
$R^{10}$ is $C_3$-$C_{10}$-cycloalkyl or $C_4$-$C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{10A}$; $R^{10A}$ is cycloalkane, cycloalkene, heterocycloalkane or heterocycloalkene;
$R^{11}$ is alkyl, alkenyl or alkynyl, each of which is unsubstituted or substituted with one or two or three independently selected $R^{12}$, $OR^{12}$, $NHR^{12}$, $N(R^{12})_2$, $C(O)NH_2$, $C(O)NHR^{12}$, $C(O)N(R^{12})_2$, OH, (O), C(O)OH, $N_3$, CN, $NH_2$, $CF_3$, $CF_2CF_3$, F, Cl, Br or I substituents;
$R^{12}$ is $R^{13}$, $R^{14}$, $R^{15}$ or $R^{16}$;
$R^{13}$ is phenyl which is unfused or fused with arene, heteroarene or $R^{13A}$; $R^{13A}$ is cycloalkane, cycloalkene, heterocycloalkane or heterocycloalkene;
$R^{14}$ is heteroaryl, each of which is unfused or fused with arene, heteroarene or $R^{14A}$; $R^{14A}$ is cycloalkane, cycloalkene, heterocycloalkane or heterocycloalkene;
$R^{15}$ is cycloalkane, cycloalkene, heterocycloalkane or heterocycloalkene, each of which is unfused or fused with arene, heteroarene or $R^{15A}$; $R^{15A}$ is cycloalkane, cycloalkene, heterocycloalkane or heterocycloalkene;
$R^{16}$ is alkyl, alkenyl or alkynyl;
$R^{17}$ is $R^{18}$, $R^{19}$, $R^{20}$ or $R^{21}$;
$R^{18}$ is phenyl which is unfused or fused with arene, heteroarene or $R^{18A}$; $R^{18A}$ is cycloalkane, cycloalkene, heterocycloalkane or heterocycloalkene;

$R^{19}$ is heteroaryl which is unfused or fused with arene, heteroarene or $R^{19A}$; $R^{19A}$ is cycloalkane, cycloalkene, heterocycloalkane or heterocycloalkene;

$R^{20}$ is $C_3$-$C_{10}$-cycloalkyl or $C_4$-$C_{10}$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{20A}$; $R^{20A}$ is cycloalkane, cycloalkene, heterocycloalkane or heterocycloalkene;

$R^{21}$ is alkyl, alkenyl or alkynyl, each of which is unsubstituted or substituted with one or two or three independently selected $R^{22}$, OR$^{22}$, NHR$^{22}$, N(R$^{22}$)$_2$, C(O)NH$_2$, C(O)NHR$^{22}$, C(O)N(R$^{22}$)$_2$, OH, (O), C(O)OH, N$_3$, CN, NH$_2$, CF$_3$, CF$_2$CF$_3$, F, Cl, Br or I substituents;

$R^{22}$ is $R^{23}$, $R^{24}$ or $R^{25}$;

$R^{23}$ is phenyl which is unfused or fused with arene, heteroarene or $R^{23A}$; $R^{23A}$ is cycloalkane, cycloalkene, heterocycloalkane or heterocycloalkene;

$R^{24}$ is heteroarene which is unfused or fused with arene, heteroarene or $R^{24A}$; $R^{24A}$ is cycloalkane, cycloalkene, heterocycloalkane or heterocycloalkene;

$R^{25}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{25A}$; $R^{25A}$ is cycloalkane, cycloalkene, heterocycloalkane or heterocycloalkene;

$Z^1$ is $R^{26}$ or $R^{27}$, each of which is substituted with $R^{28}$, $R^{29}$ or $R^{30}$, each of which is substituted with F, Cl, Br, I, CH$_2$R$^{37}$, CH(R$^{31}$)(R$^{37}$), C(R$^{31}$)(R$^{31A}$)(R$^{37}$), C(O)R$^{37}$, OR$^{37}$, SR$^{37}$, S(O)R$^{37}$, SO$_2$R$^{37}$, NHR$^{37}$ or N(R$^{32}$)R$^{37}$;

$R^{26}$ is phenyl which is unfused or fused with arene or heteroarene;

$R^{27}$ is heteroarene which is unfused or fused with arene or heteroarene;

$R^{28}$ is phenyl which is unfused or fused with arene, heteroarene or $R^{28A}$; $R^{28A}$ is cycloalkane, cycloalkene, heterocycloalkane or heterocycloalkene $R^{29}$ is heteroaryl or $R^{29A}$; $R^{29A}$ is cycloalkane, cycloalkene, heterocycloalkane or heterocycloalkene;

$R^{30}$ is cycloalkyl or cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{30A}$; $R^{30A}$ is cycloalkane, cycloalkene, heterocycloalkane or heterocycloalkene;

$R^{31}$ and $R^{31A}$ are independently F, Cl, Br or alkyl or are taken together and are $C_2$-$C_5$-spiroalkyl;

$R^{32}$ is $R^{33}$, C(O)R$^{33}$ or C(O)OR$^{33}$;

$R^{33}$ is $R^{34}$ or $R^{35}$;

$R^{34}$ is phenyl which is unfused or fused with aryl, heteroaryl or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with arene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with F, Cl, Br, I, $R^{41}$, OR$^{41}$, NHR$^{41}$, N(R$^{41}$)$_2$, NHC(O)OR$^{41}$, SR$^{41}$, S(O)R$^{41}$ or SO$_2$R$^{41}$;

$R^{38}$ is phenyl which is unfused or fused with arene, heteroarene or $R^{38A}$; $R^{38A}$ is cycloalkane, cycloalkene, heterocycloalkane or heterocycloalkene;

$R^{39}$ is heteroaryl which is unfused or fused with arene, heteroarene or $R^{39A}$; $R^{39A}$ is cycloalkane, cycloalkene, heterocycloalkane or heterocycloalkene;

$R^{40}$ is $C_3$-$C_8$-cycloalkyl or $C_4$-$C_8$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with arene, heteroarene or $R^{42A}$; $R^{42A}$ is cycloalkane, cycloalkene, heterocycloalkane or heterocycloalkene;

$R^{43}$ is heteroaryl which is unfused or fused with arene, heteroarene or $R^{43A}$; $R^{43A}$ is cycloalkane, cycloalkene, heterocycloalkane or heterocycloalkene;

$R^{44}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, OR$^{46}$, NHR$^{46}$, N(R$^{46}$)$_2$, C(O)NH$_2$, C(O)NHR$^{46}$, C(O)N(R$^{46}$)$_2$, OH, (O), C(O)OH, N$_3$, CN, NH$_2$, CF$_3$, CF$_2$CF$_3$, F, Cl, Br or I substituents;

$R^{46}$ is $R^{47}$, $R^{48}$ or $R^{49}$;

$R^{47}$ is phenyl which is unfused or fused with arene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkane, cycloalkene, heterocycloalkane or heterocycloalkene;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{49A}$; $R^{49A}$ is cycloalkane, cycloalkene, heterocycloalkane or heterocycloalkene;

wherein each foregoing cyclic moiety is independently unsubstituted, further unsubstituted, substituted or further substituted with one or two or three or four or five independently selected $R^{50}$, OR$^{50}$, SR$^{50}$, S(O)R$^{50}$, SO$_2$R$^{50}$, C(O)R$^{50}$, CO(O)R$^{50}$, OC(O)R$^{50}$, OC(O)OR$^{50}$, NH$_2$, NHR$^{50}$, N(R$^{50}$)$_2$, C(O)NH$_2$, C(O)NHR$^{50}$, C(O)N(R$^{50}$)$_2$, C(O)NHOH, C(O)NHOR$^{50}$, C(O)NHSO$_2$R$^{50}$, C(O)NR$^{55}$SO$_2$R$^{50}$, SO$_2$NH$_2$, SO$_2$NHR$^{50}$, SO$_2$N(R$^{50}$)$_2$, CF$_3$, CF$_2$CF$_3$, C(O)H, C(O)OH, C(N)NH$_2$, C(N)NHR$^{50}$, C(N)N(R$^{50}$)$_2$, OH, (O), N$_3$, NO$_2$, CF$_3$, CF$_2$CF$_3$, OCF$_3$, OCF$_2$CF$_3$, F, Cl, Br or I substituents;

$R^{50}$ is $R^{51}$, $R^{52}$, $R^{53}$ or $R^{54}$;

$R^{51}$ is phenyl which is unfused or fused with arene, heteroarene or $R^{51A}$; $R^{51A}$ is cycloalkane, cycloalkene, heterocycloalkane or heterocycloalkene;

$R^{52}$ is heteroaryl or $R^{52A}$; $R^{52A}$ is cycloalkane, cycloalkene, heterocycloalkane or heterocycloalkene;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $NHR^{55}$, $N(R^{55})_2$, $C(O)R^{55}$, $C(O)NH_2$, $C(O)NHR^{55}$, $NHC(O)R^{55}$, $NHSO_2R^{55}$, $NHC(O)OR^{55}$, $SO_2NH_2$, $SO_2NHR^{55}$, $SO_2N(R^{55})_2$, $NHC(O)NH_2$, $NHC(O)NHR^{55}$, OH, (O), C(O)OH, (O), $N_3$, CN, $NH_2$, $CF_3$, $OCF_3$, $CF_2CF_3$, $OCF_2CF_3$, F, Cl, Br or I substituents;

$R^{55}$ is alkyl, alkenyl, alkynyl, phenyl, heteroaryl or $R^{56}$;

$R^{56}$ is $C_3$-$C_6$-cycloalkyl or $C_4$-$C_6$-cycloalkyl, each having one or two $CH_2$ moieties unreplaced or replaced with independently selected O, C(O), CNOH, $CNOCH_3$, S, S(O), $SO_2$ or NH and one or two CH moieties unreplaced or replaced with N.

Still another embodiment pertains to compounds having formula (I)-a

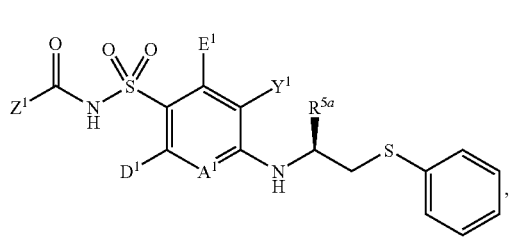

(I)-a or therapeutically acceptable salts, prodrugs or salts of prodrugs thereof, wherein $R^{5a}$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents.

Still another embodiment pertains to compounds having formula (I), or therapeutically acceptable salts, prodrugs or salts of prodrugs thereof, wherein $A^1$ is N or $C(A^2)$;

$A^2$ is H, F, CN, C(O)OH, $C(O)NH_2$ or $C(O)OR^{14}$;

$B^1$ is $R^1$, $OR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$, $NHSO_2NHR^1$ or $N(CH_3)SO_2N(CH_3)R^1$;

$D^1$ is H, F, Cl or $CF_3$;

$E^1$ is H, F or Cl;

$Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$;
or $B^1$ and $Y^1$, together with the atoms to which they are attached, are imidazole or triazole;

$R^1$ is $R^2$, $R^3$, $R^4$ or $R^5$;

$R^{1A}$ is $C_1$-alkyl, $C_2$-alkyl, $C_3$-alkyl, $C_4$-alkyl, $C_5$-alkyl, $C_6$-alkyl;

$R^2$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^3$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^4$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^5$ is $C_1$-alkyl, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl, $C_6$-alkenyl, $C_3$-alkynyl, $C_4$-alkynyl, $C_5$-alkynyl or $C_6$-alkynyl, each of which is unsubstituted or substituted with one or two or three independently selected $R^6$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, OH, (O), C(O)OH, (O), $N_3$, CN, $NH_2$, $CF_3$, $CF_2CF_3$, F, Cl, Br or I substituents;

$R^6$ is $C_2$-spiroalkyl, $C_3$-spiroalkyl, $C_4$-spiroalkyl or $C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^7$ is $R^8$, $R^9$, $R^{10}$ or $R^{11}$;

$R^8$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{8A}$;

$R^{8A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^9$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{10}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^{11}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_2$-alkynyl, $C_3$-alkynyl, $C_4$-alkynyl, $C_5$-alkynyl or $C_6$-alkynyl, each of which is unsubstituted or substituted with one or two or three independently selected $R^{12}$, $OR^{12}$, $NHR^{12}$, $N(R^{12})_2$, $C(O)NH_2$, $C(O)NHR^{12}$, $C(O)N(R^{12})_2$, OH, (O), C(O)OH, $N_3$, CN, $NH_2$, $CF_3$, $CF_2CF_3$, F, Cl, Br or I substituents;

$R^{12}$ is $R^{13}$, $R^{14}$, $R^{15}$ or $R^{16}$;

$R^{13}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{13A}$;

$R^{13A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^{14}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl, 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole; pyridazine, pyridine, pyrimidine, pyrrole, thiazole, thiophene, triazine or 1,2,3-triazole;

$R^{15}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^{16}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_3$-alkynyl, $C_4$-alkynyl, $C_5$-alkynyl or $C_6$-alkynyl;

$R^{17}$ is $R^{18}$, $R^{19}$, $R^{20}$ or $R^{21}$;

$R^{18}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{19}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{20}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^{21}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_2$-alkynyl, $C_3$-alkynyl, $C_4$-alkynyl, $C_5$-alkynyl or $C_6$-alkynyl, each of which is unsubstituted or substituted with one or two or three independently selected $R^{22}$, $OR^{22}$, $NHR^{22}$, $N(R^{22})_2$, $C(O)NH_2$, $C(O)NHR^{22}$, $C(O)N(R^{22})_2$, OH, (O), C(O)OH, $N_3$, CN, $NH_2$, $CF_3$, $CF_2CF_3$, F, Cl, Br or I substituents;

$R^{22}$ is $R^{23}$, $R^{24}$ or $R^{25}$;

$R^{23}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{24}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl, 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{25}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$Z^1$ is $R^{26}$ or $R^{27}$, each of which is substituted with $R^{28}$, $R^{29}$ or $R^{30}$, each of which is substituted with F, Cl, Br, I, $CH_2R^{37}$, $CH(R^{31})(R^{37})$, $C(R^{31})(R^{31A})(R^{37})$, $C(O)R^{37}$, $OR^{37}$, $SR^{37}$, $S(O)R^{37}$, $SO_2R$ $NHR^{37}$, $NHR^{37}$ or $N(R^{32})R^{37}$;

$R^{26}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{27}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{28}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{29}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{30}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl, $C_{13}$-cycloalkyl, $C_{14}$-cycloalkyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl or $C_{10}$-cycloalkenyl, each having one or two $CH_2$ moieties unreplaced or replaced with independently selected O, C(O), S, S(O), $SO_2$ or NH and one or two CH moieties unreplaced or replaced with N;

$R^{31}$ and $R^{31A}$ are independently F, Cl, Br, $C_1$-alkyl, $C_2$-alkyl, $C_3$-alkyl, $C_4$-alkyl, $C_5$-alkyl or $C_6$-alkyl or are taken together and are $C_2$-spiroalkyl, $C_3$-spiroalkyl, $C_4$-spiroalkyl or $C_5$-spiroalkyl;

$R^{32}$ is $R^{33}$, $C(O)R^{33}$ or $C(O)OR^{33}$;

$R^{33}$ is $R^{34}$ or $R^{35}$;

$R^{34}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{35}$ is $C_1$-alkyl, $C_2$-alkyl, $C_3$-alkyl, $C_4$-alkyl, $C_5$-alkyl or $C_6$-alkyl, each of which is unsubstituted or substituted with $R^{36}$;

$R^{36}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{37}$ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{39}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{40}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_4$-cycloalkenyl, $C_5$-cycloalkenyl, $C_6$-cycloalkenyl, $C_7$-cycloalkenyl or $C_8$-cycloalkenyl, each having one or two $CH_2$ moieties unreplaced or replaced with independently selected O, C(O), S, S(O), $SO_2$ or NH and one or two CH moieties unreplaced or replaced with N;

$R^{41}$ is $R^{42}$, $R^{43}$, $R^{44}$ or $R^{45}$;

$R^{42}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{42A}$;

$R^{42A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), S, S(O), $SO_2$ or NH and one or two CH moieties unreplaced or replaced with N;

$R^{43}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{44}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{45}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_2$-alkynyl, $C_3$-alkynyl, $C_4$-alkynyl, $C_5$-alkynyl or $C_6$-alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, OH, (O), C(O)OH, $N_3$, CN, $NH_2$, $CF_3$, $CF_2CF_3$, F, Cl, Br or I substituents;

$R^{46}$ is $R^{47}$, $R^{48}$ or $R^{49}$;

$R^{47}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{48}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{49}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), S, S(O), $SO_2$ or NH and one or two CH moieties unreplaced or replaced with N;

wherein the moieties represented by $B^1$ and $Y^1$ together are substituted with $C_1$-alkyl, $C_2$-alkyl, $C_3$-alkyl, $C_4$-alkyl, $C_5$-alkyl or $C_6$-alkyl, each of which is substituted with one or two independently selected $SR^{55}$ or $N(R^{55})_2$ substituents, wherein $R^{55}$ is independently selected phenyl, $C_1$-alkyl, $C_2$-alkyl, $C_3$-alkyl, $C_4$-alkyl, $C_5$-alkyl or $C_6$-alkyl;

the moieties represented by $R^2$, $R^3$ and $R^4$ are unsubstituted or substituted with one or two independently selected $R^{50}$, $OR^{50}$, $SR^{50}$, $SO_2R^{50}$, $CO(O)R^{50}$ or $OCF_3$ substituents, wherein $R^{50}$ is phenyl, $C_1$-alkyl, $C_2$-alkyl, $C_3$-alkyl, $C_4$-alkyl, $C_5$-alkyl or $C_6$-alkyl;

the moieties represented by $R^8$, $R^9$ and $R^{10}$ are unsubstituted or substituted with one or two independently selected $R^{50}$, $OR^{50}$, $C(O)NHSO_2R^{50}$, $CO(O)R^{50}$, $C(O)R^{50}$, C(O)OH, C(O)NHOH, OH, $NH_2$, F, Cl, Br or I substituents, wherein $R^{50}$ is phenyl, tetrazolyl or $R^{54}$, wherein $R^{54}$ is $C_1$-alkyl, $C_2$-alkyl, $C_3$-alkyl, $C_4$-alkyl; $C_5$-alkyl or $C_6$-alkyl, each of which is unsubstituted or substituted with phenyl;

the moieties represented by $R^{26}$ and $R^{27}$ are further unsubstituted or substituted with one or two independently selected F, Br, Cl or I substituents;

the moieties represented by $R^{28}$, $R^{29}$ and $R^{30}$ are further unsubstituted or substituted with $OR^{54}$, wherein $R^{54}$ is $C_1$-alkyl, $C_2$-alkyl, $C_3$-alkyl, $C_4$-alkyl, $C_5$-alkyl or $C_6$-alkyl, each of which is unsubstituted or substituted with $R^{56}$, wherein $R^{56}$ is $C_3$-cycloalkyl, $C_4$-cycloalkyl $C_5$-cycloalkyl or $C_6$-cycloalkyl, each having one or two $CH_2$ moieties replaced with independently selected O or NH and one CH moiety unreplaced or replaced with N;

the moieties represented by $R^{38}$, $R^{39}$ and $R^{40}$ are unsubstituted or substituted with one or two independently selected $R^{54}$ F, Br, Cl or I substituent, wherein $R^{54}$ is $C_1$-alkyl, $C_2$-alkyl, $C_3$-alkyl, $C_4$-alkyl, $C_5$-alkyl or $C_6$-alkyl; and the moieties represented by $R^{42}$, $R^{43}$, $R^{44}$ and $R^{45}$ are unsubstituted or substituted with one or two independently selected $R^{50}$, $OR^{50}$, $SR^{50}$, $N(R^{50})_2$, $SO_2R^{50}$, CN, $CF_3$, F, Cl, Br or I substituents, wherein $R^{50}$ is phenyl or $R^{54}$, wherein $R^{54}$ is $C_1$-alkyl, $C_2$-alkyl, $C_3$-alkyl, $C_4$-alkyl, $C_5$-alkyl or $C_6$-alkyl, each of which is unsubstituted or substituted with $N(R^{55})_2$ or $R^{56}$, wherein $R^{55}$ is $C_1$-alkyl, $C_2$-alkyl, $C_3$-alkyl, $C_4$-alkyl, $C_5$-alkyl or $C_6$-alkyl and $R^{56}$ is $C_3$-cycloalkyl, $C_4$-cycloalkyl, $C_5$-cycloalkyl or $C_6$-cycloalkyl, each having one $CH_2$ moiety unreplaced or replaced with independently selected O, C(O), S, S(O), $SO_2$ or NH and one or two CH moieties unreplaced or replaced with N.

Still another embodiment pertains to compounds having formula (I), or therapeutically acceptable salts, prodrugs or salts of prodrugs thereof, wherein $A^1$ is $C(A^2)$;

$A^2$ is H, F, CN, C(O)OH, $C(O)NH_2$ or $C(O)OR^{1A}$;

$B^1$ is $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC (O)R$^1$, NHC(O)OR$^1$, NR$^1$C(O)NHR$^1$, NR$^1$C(O)N(R$^1$)$_2$, SO$_2$NHR$^1$, SO$_2$N(R$^1$)$_2$, NHSO$_2$R$^1$, NHSO$_2$NHR$^1$ or N(CH$_3$)SO$_2$N(CH$_3$)R$^1$;

D$^1$ is H, F, Cl or CF$_3$;

E$^1$ is H, F or Cl;

Y$^1$ is H, CN, NO$_2$, C(O)OH, F, Cl, Br, CF$_3$, OCF$_3$, NH$_2$, C(O)NH$_2$ or

B$^1$ and Y$^1$, together with the atoms to which they are attached, are imidazole or triazole;

R$^1$ is R$^2$, R$^3$, R$^4$ or R$^5$;

R is C$_1$-alkyl, C$_2$-alkyl, C$_3$-alkyl, C$_4$-alkyl, C$_5$-alkyl, C$_6$-alkyl;

R$^2$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

R$^3$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

R$^4$ is C$_3$-cycloalkyl, C$_4$-cycloalkyl, C$_5$-cycloalkyl, C$_6$-cycloalkyl, C$_4$-cycloalkenyl, C$_5$-cycloalkenyl or C$_6$-cycloalkenyl, each having one or two CH$_2$ moieties unreplaced or replaced with independently selected O, C(O), S, S(O), SO$_2$ or NH and one or two CH moieties unreplaced or replaced with N;

R$^5$ is C$_1$-alkyl, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl, C$_3$-alkynyl, C$_4$-alkynyl, C$_5$-alkynyl or C$_6$-alkynyl, each of which is unsubstituted or substituted with one or two or three independently selected R$^6$, R$^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, NHC(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, OH, (O), C(O)OH, (O), N$_3$, CN, NH$_2$, CF$_3$, CF$_2$CF$_3$, F, Cl, Br or I substituents;

R$^6$ is C$_2$-spiroalkyl, C$_3$-spiroalkyl, C$_4$-spiroalkyl or C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^7$ is R$^8$, R$^9$, R$^{10}$ or R$^{11}$;

R$^8$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or R$^{8.4}$;

R$^{8.4}$ is C$_4$-cycloalkane, C$_5$-cycloalkane, C$_6$-cycloalkane, C$_4$-cycloalkene, C$_5$-cycloalkene or C$_6$-cycloalkene, each having one or two CH$_2$ moieties unreplaced or replaced with independently selected O, C(O), S, S(O), SO$_2$ or NH and one or two CH moieties unreplaced or replaced with N;

R$^9$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

R$^{10}$ is C$_3$-cycloalkyl, C$_4$-cycloalkyl, C$_5$-cycloalkyl, C$_6$-cycloalkyl, C$_7$-cycloalkyl, C$_8$-cycloalkyl, C$_9$-cycloalkyl, C$_{10}$-cycloalkyl, C$_4$-cycloalkenyl, C$_5$-cycloalkenyl, C$_6$-cycloalkenyl, C$_7$-cycloalkenyl, C$_8$-cycloalkenyl, C$_9$-cycloalkenyl, C$_{10}$-cycloalkenyl, each having one or two CH$_2$ moieties unreplaced or replaced with independently selected O, C(O), CNOCH$_3$, S, S(O), SO$_2$ or NH and one or two CH moieties unreplaced or replaced with N;

R$^{11}$ is C$_1$-alkyl, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl, C$_2$-alkynyl, C$_3$-alkynyl, C$_4$-alkynyl, C$_5$-alkynyl or C$_6$-alkynyl, each of which is unsubstituted or substituted with one or two or three independently selected R$^{12}$, OR$^{12}$, NHR$^{12}$, N(R$^{12}$)$_2$, C(O)NH$_2$, C(O)NHR$^{12}$, C(O)N(R$^{12}$)$_2$, OH, (O), C(O)OH, N$_3$, CN, NH$_2$, CF$_3$, CF$_2$CF$_3$, F, Cl, Br or I substituents;

R$^{12}$ is R$^{13}$, R$^{14}$, R$^{15}$ or R$^{16}$;

R$^{13}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or R$^{13.4}$;

R$^{13.4}$ is C$_4$-cycloalkane, C$_5$-cycloalkane, C$_6$-cycloalkane, C$_4$-cycloalkene, C$_5$-cycloalkene or C$_6$-cycloalkene, each having one or two CH$_2$ moieties unreplaced or replaced with independently selected O, C(O), S, S(O), SO$_2$ or NH and one or two CH moieties unreplaced or replaced with N;

R$^{14}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl, 1,2,3-triazolyl, each of which is unfused or fused with benzene;

R$^{15}$ is C$_3$-cycloalkyl, C$_4$-cycloalkyl, C$_5$-cycloalkyl, C$_6$-cycloalkyl, C$_4$-cycloalkenyl, C$_5$-cycloalkenyl or C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N;

R$^{16}$ is C$_1$-alkyl, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl, C$_3$-alkynyl, C$_4$-alkynyl, C$_5$-alkynyl or C$_6$-alkynyl;

Z$^1$ is R$^{26}$ or R$^{27}$, each of which is substituted with R$^{28}$, R$^{29}$ or R$^{30}$, each of which is substituted with Cl, Br, CH$_2$R$^{37}$, C(R$^{31}$)(R$^{31.4}$)(R$^{37}$), C(O)R$^{37}$, OR$^{37}$, SR$^{37}$, S(O)R$^{37}$, SO$_2$R$^{37}$ or NHR$^{37}$;

R$^{26}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

R$^{27}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

R$^{28}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

R$^{29}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

R$^{30}$ is C$_3$-cycloalkyl, C$_4$-cycloalkyl, C$_5$-cycloalkyl, C$_6$-cycloalkyl, C$_7$-cycloalkyl, C$_8$-cycloalkyl, C$_9$-cycloalkyl, C$_{10}$-cycloalkyl, C$_{11}$-cycloalkyl, C$_{12}$-cycloalkyl, C$_{13}$-cycloalkyl, C$_{14}$-cycloalkyl, C$_4$-cycloalkenyl, C$_5$-cycloalkenyl, C$_6$-cycloalkenyl, C$_7$-cycloalkenyl, C$_8$-cycloalkenyl, C$_9$-cycloalkenyl or C$_{10}$-cycloalkenyl, each having one or two CH$_2$ moieties unreplaced or replaced with independently selected O, C(O), S, S(O), SO$_2$ or NH and one or two CH moieties unreplaced or replaced with N;

$R^{31}$ and $R^{31A}$ are independently F, Cl, Br, $C_1$-alkyl, $C_2$-alkyl, $C_3$-alkyl, $C_4$-alkyl, $C_5$-alkyl or $C_6$-alkyl or are taken together and are $C_2$-spiroalkyl, $C_3$-spiroalkyl, $C_4$-spiroalkyl or $C_5$-spiroalkyl;

$R^{37}$ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{39}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

$R^{40}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_4$-cycloalkenyl, $C_5$-cycloalkenyl, $C_6$-cycloalkenyl, $C_7$-cycloalkenyl or $C_8$-cycloalkenyl, each having one or two $CH_2$ moieties unreplaced or replaced with independently selected O, C(O), S, S(O), $SO_2$ or NH and one or two CH moieties unreplaced or replaced with N;

$R^{41}$ is $R^{42}$, $R^{43}$, $R^{44}$ or $R^{45}$;

$R^{42}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{42A}$;

$R^{42A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), S, S(O), $SO_2$ or NH and one or two CH moieties unreplaced or replaced with N;

$R^{43}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

$R^{44}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{45}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_2$-alkynyl, $C_3$-alkynyl, $C_4$-alkynyl, $C_5$-alkynyl or $C_6$-alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, OH, (O), C(O)OH, $N_3$, CN, $NH_2$, $CF_3$, $CF_2CF_3$, F, Cl, Br or I substituents;

$R^{46}$ is $R^{47}$, $R^{48}$ or $R^{49}$;

$R^{47}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{48}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

$R^{49}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), S, S(O), $SO_2$ or NH and one or two CH moieties unreplaced or replaced with N;

wherein the moieties represented by $B^1$ and $Y^1$ together are substituted with $C_2$-alkyl, $C_3$-alkyl or $C_4$-alkyl, each of which is substituted with one or two independently selected $SR^{55}$ or $N(R^{55})_2$ substituents, wherein $R^{55}$ is independently selected phenyl or $C_1$-alkyl;

the moieties represented by $R^2$, $R^3$ and $R^4$ are unsubstituted or substituted with one or two independently selected $R^{50}$, $OR^{50}$, $SR^{50}$, $SO_2R^{50}$, $CO(O)R^{50}$ or $OCF_3$ substituents, wherein $R^{50}$ is phenyl, $C_1$-alkyl, $C_2$-alkyl, $C_3$-alkyl or $C_4$-alkyl;

the moieties represented by $R^8$, $R^9$ and $R^{10}$ are unsubstituted or substituted with one or two independently selected $R^{50}$, $OR^{50}$, $C(O)NHSO_2R^{50}$, $CO(O)R^{50}$, $C(O)R^{50}$, C(O)OH, C(O)NHOH, OH, $NH_2$, F, Cl, Br or I substituents, wherein $R^{50}$ is phenyl, tetrazolyl or $R^{54}$, wherein $R^{54}$ is $C_1$-alkyl, $C_2$-alkyl or $C_3$-alkyl, each of which is unsubstituted or substituted with phenyl;

the moieties represented by $R^{26}$ and $R^{27}$ are further unsubstituted or substituted with one or two independently selected F, Br, Cl or I substituents;

the moieties represented by $R^{28}$, $R^{29}$ and $R^{30}$ are further unsubstituted or substituted with $OR^{54}$, wherein $R^{54}$ is $C_1$-alkyl or $C_2$-alkyl, each of which is unsubstituted or substituted with $N(R^{55})_2$ or $R^{56}$, wherein $R^{55}$ is $C_1$-alkyl, $C_2$-alkyl, $C_3$-alkyl, $C_4$-alkyl, $C_5$-alkyl or $C_6$-alkyl, and $R^{56}$ is $C_5$-cycloalkyl or $C_6$-cycloalkyl, each having one or two $CH_2$ moieties replaced with independently selected O or NH and one CH moiety unreplaced or replaced with N;

the moieties represented by $R^{38}$, $R^{39}$ and $R^{40}$ are unsubstituted or substituted with one or two independently selected $C_1$-alkyl, F, Br, Cl or I substituents; and the moieties represented by $R^{42}$, $R^{43}$, $R^{44}$ and $R^{45}$ are unsubstituted or substituted with one or two independently selected $R^{50}$, $OR^{50}$, $SR^{50}$, $N(R^{50})_2$, $SO_2R^{50}$, CN, $CF_3$, F, Cl, Br or I substituents, wherein $R^{50}$ is phenyl or $R^{54}$, wherein $R^{54}$ is $C_1$-alkyl, $C_2$-alkyl or $C_3$-alkyl, each of which is unsubstituted or substituted with $N(C_1$-alkyl$)_2$ or $C_6$-cycloalkyl having one $CH_2$ moiety replaced with O and one CH moiety replaced with N.

Still another embodiment pertains to compounds having formula (I), or therapeutically acceptable salts, prodrugs or salts of prodrugs thereof, wherein $A^1$ is $C(A^2)$;

$A^2$ is H, F, CN, C(O)OH, $C(O)NH_2$ or $C(O)OCH_3$;

$B^1$ is $R^1$, $OR^1$, $NHR^1$, $N(R^1)_2$ or $NR^1C(O)N(R^1)_2$;

$D^1$ is H, F, Cl or $CF_3$;

$E^1$ is H, F or Cl;

$Y^1$ is H, CN, $NO_2$, F, Cl, $CF_3$, $OCF_3$, $NH_2$, $C(O)NH_2$, or $B^1$ and $Y^1$, together with the atoms to which they are attached, are imidazole or triazole;

$R^1$ is phenyl, pyrrolyl, cyclopentyl, cyclohexyl, piperidinyl, tetrahydrofuranyl, tetrahydropyranyl, tetrahydrothiopyranyl or $R^5$;

$R^5$ is $C_1$-alkyl, $C_2$-alkyl, $C_3$-alkyl, $C_4$-alkyl, $C_5$-alkyl or $C_6$-alkyl, each of which is unsubstituted or substituted with one or two or three independently selected $C_4$-spiroalkyl, $C_5$-spiroalkyl, $R^7$, $OR^7$, $SR^7$, $SO_2R^7$, $NHR^7$, $N(R^7)_2$, C(O)$R^7$, $C(O)NH_2$, $C(O)NHR^7$, $NHC(O)R^7$, $NHSO_2R^7$, NHC(O)$OR^7$, $NHC(O)NH_2$, $NHC(O)CH(CH_3)NHC(O)CH(CH_3)NH_2$, OH, C(O)OH or $NH_2$ substituents;

R⁷ is phenyl, furanyl, imidazolyl, pyridinyl, tetrazolyl, thiazolyl, thienyl, 1,3-benzoxazolyl, 1,3-benzodioxolyl, 1,3-benzothiazole, cyclopropyl, cyclobutyl, cyclohexyl, azetidinyl, morpholinyl, piperazinyl, piperidinyl, thiomorpholinyl, thiomorpholinyl sulfone 7-azabicyclo[2.2.1]heptanyl, 8-azabicyclo[3.2.1]octanyl, 4,5-dihydro-1H-imidazolyl 2-oxa-5-azabicyclo[2.2.1]heptanyl, 1,4,5,6-tetrahydropyrimidinyl or $R^{11}$;

$R^{11}$ is $C_1$-alkyl, $C_2$-alkyl, $C_3$-alkyl or $C_4$-alkyl, each of which is unsubstituted or substituted with one or two or three independently selected $R^{12}$, $OR^{12}$, $N(R^{12})_2$, $C(O)N(R^{12})_2$, OH, C(O)OH, $NH_2$, $CF_3$, F, Cl, Br or I substituents;

$R^{12}$ is 1,3-benzodioxolyl, pyridinyl, morpholinyl or $C_1$-alkyl;

$Z^1$ is phenyl or pyridinyl, each of which is substituted with cyclohexenyl, piperazinyl, piperidinyl, 1,2,3,6-tetrahydropyridinyl or octahydropyrrolo[3,4-c]pyrrolyl, each of which is substituted with $CH_2R^{37}$, $C(C_2$-spiroalkyl)($R^{37}$) or $C(O)R^{37}$;

$R^{37}$ is phenyl, naphthyl, imidazolyl, pyrazolyl, pyridinyl, cyclopentenyl, cyclohexenyl, cycloheptenyl, cyclooctenyl or 3,6-dihydro-2H-pyranyl, each of which is substituted with F, Cl, Br, I, $R^{41}$, $NHR^{41}$, $N(R^{41})_2$, $NHC(O)OR^{41}$ or $SR^{41}$;

$R^{45}$ is phenyl, naphthyl, cyclohexyl, morpholinyl, piperidinyl, thienyl, pyridinyl, quinolinyl, benzofuranyl, 1,3-benzodioxolyl, isoindolinyl, 1,3-oxazolidin-2-onyl or $R^{45}$;

$R^{45}$ is $C_1$-alkyl, $C_2$-alkyl, $C_3$-alkyl or $C_4$-alkyl, each of which is unsubstituted or substituted with phenyl;

wherein the moieties represented by $B^1$ and $Y^1$ together are substituted with $C_2$-alkyl, $C_3$-alkyl or $C_4$-alkyl, each of which is substituted with one or two independently selected $SR^{55}$ or $N(R^{55})_2$ substituents, wherein $R^{55}$ is independently selected phenyl or $C_1$-alkyl;

the moieties represented by $R^1$ are unsubstituted or substituted with one or two independently selected $R^{50}$, $OR^{50}$, $SR^{50}$, $SO_2R^{50}$, $CO(O)R^{50}$ or $OCF_3$ substituents, wherein $R^{50}$ is phenyl, $C_1$-alkyl, $C_2$-alkyl, $C_3$-alkyl or $C_4$-alkyl;

the moieties represented by $R^7$ are unsubstituted or substituted with one or two independently selected $R^{50}$, $OR^{50}$, $C(O)NHSO_2R^{50}$, $CO(O)R^{50}$, $C(O)R^{50}$, C(O)OH, C(O)NHOH, OH, $NH_2$, F, Cl, Br or I substituents, wherein $R^{50}$ is phenyl, tetrazolyl or $R^{54}$, wherein $R^{54}$ is $C_1$-alkyl, $C_2$-alkyl or $C_3$-alkyl, each of which is unsubstituted or substituted with phenyl;

the phenyl and pyridinyl moieties of $Z^1$ are further unsubstituted or substituted with one or two independently selected F, Br, Cl or I substituents;

the cyclohexenyl, piperazinyl, piperidinyl, 1,2,3,6-tetrahydropyridinyl and octahydropyrrolo[3,4-c]pyrrolyl moieties of $Z^1$ are further unsubstituted or substituted with $OR^{54}$, wherein $R^{54}$ is $C_1$-alkyl or $C_2$-alkyl, each of which is unsubstituted or substituted with $N(C_1$-alkyl$)_2$, morpholinyl, piperidinyl or piperidinyl;

the moieties represented by $R^{37}$ are unsubstituted or substituted with one or two independently selected $C_1$-alkyl, F, Br, Cl or I substituents;
and the moieties represented by $R^{41}$ are unsubstituted or substituted with one or two independently selected $R^{50}$, $OR^{50}$, $SR^{50}$, $N(R^{50})_2$, $SO_2R^{50}$, CN, $CF_3$, F, Cl, Br or I substituents, wherein $R^{50}$ is phenyl or $R^{54}$, wherein $R^{54}$ is $C_1$-alkyl, $C_2$-alkyl or $C_3$-alkyl, each of which is unsubstituted or substituted with $N(C_1$-alkyl$)_2$ or morpholinyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, $C(O)OCH_3$ or $C(O)NH_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoro-ethyl)amino)-1-((phenylsulfanyl)methyl)propylamino, (1R)-3-(5,6-dihydro-1(4H)-pyrimidin-1-yl)-1-((phenylsulfanyl)methyl)propylamino, (1R)-3-(diisopropylamino)-1-((phenylsulfanyl)methyl)propylamino, (1R)-2-62-(dimethylamino)ethyl)(methyl)amino)-1 -((phenylsulfanyl)methyl)ethylamino, (1R)-2-(2-(dimethylamino)ethoxy)-1-((phenylsulfanyl)methyl)ethylamino, (3R)-5-(N-((dimethylamino)methylcarbonyl)amino)-1-((phenylsulfanyl)methyl)pentylamino, (1R)-3-(dimethylamino)-1-((phenylsulfanyl)methyl)propoxy, (1R)-3-(dimethylamino)-1-((phenylsulfanyl)methyl)propylamino, (1S)-3-(dimethylamino)-1-((phenylsulfanyl)methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl)propylamino, (1R)-3-(dimethylamino)-1-((thien-2-ylsulfanyl)methyl)propylamino, (1R)-3-(dimethylamino)-1-(((4-(trifluoromethoxy)phenyl)sulfanyl)methyl)propylamino, (1R)-3-(2,4-dimethyl-4,5-dihydro-1H-imidazol-1-yl)-1 -((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl)propylamino, (1R)-3-((2R,6S)-2,6-dimethylpiperidin-1-yl)-1-((phenylsulfanyl)methyl)-propylamino, 1,1-dimethyl-2-(pyrimidin-2-ylsulfanyl)ethylamino, (1R)-4-((2R,5S)-2,5-dimethylpyrrolidin-1-yl)-1-((phenylsulfanyl)methyl)butylamino, (1R)-3-((2R,5R)-2,5-dimethylpyrrolidin-1-yl)-1-((phenylsulfanyl)methyl)propylamino, (1R)-3-(2,5-dimethylpyrrolidin-1-yl)-1-((phenylsulfanyl)methyl)propylamino, (1R)-3-((2R,5S)-2,5-dimethylpyrrolidin-1-yl)-1-((phenylsulfanyl)methyl)propylamino, (1R)-3-((2S,5S)-2,5-dimethylpyrrolidin-1-yl)-1-((phenylsulfanyl)methyl)propylamino, 1,1-dimethyl-2-(thien-2-ylsulfanyl)ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)-3-((2-fluoroethyl)amino)-1-((phenylsulfanyl)methyl)propylamino, (1R)-1-(((4-fluorophenyl)sulfanyl)methyl)-3-(morpholin-4-yl)propylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or C(O)$NH_2$; and $Z^1$ is 4-(4-(2-(1,3-benzodioxol-5-yl)phenylmethyl)piperazin-1 -yl)phenylcarbonyl, 4-(4-(2-(benzofuran-2-ylphenyl)phenylmethyl)piperazin-1-yl)phenylcarbonyl, 4-(2-bromocyclohex-1-en-1-ylmethyl)piperazin-1-yl)phenylcarbonyl, 4-(2-bromocyclopent-1-en-1-ylmethyl)piperazin-1-yl)phenylcarbonyl, 4-(2-(4-bromophenyl)phenylmethyl)piperazin-1-yl)phenylcarbonyl, 4-(4-(2-(4-chlorophenyl)cyclohept-1-en-1-ylmethyl)piperazin-1-yl)phenylcarbonyl, 4-(1-(2-(4-chlorophenyl)cyclohex-1-en-1-ylmethyl)-1,2, 3, 6-tetrahydropyridin-4-yl)phenylcarbonyl, 4-(4-(2-(4-chlorophenyl)cyclohex-1-en-1-ylmethyl)piperazin-1-yl)phenylcarbonyl, 4-(4-(2-(4-chlorophenyl)cyclopent-1-en-1-ylmethyl)piperazin-1-yl)phenylcarbonyl, 4-(4-(2-(4 -chlorophenyl)cyclooct-1-en-1-ylmethyl)piperazin-1-yl)phenylcarbonyl, 4-(4-((4-chlorophenyl)-5,6-dihydro-2H-pyran-3-yl)methyl)piperazin-1-yl)phenylcarbonyl, 4-(4-((4-(4-chlorophenyl)-5,6-dihydro-2H-pyran-3-yl)methyl)- piperazin-1-yl)phenylcarbonyl, 4-(1-((2-(4-chlorophenyl)-5,5-dimethyl-1-cyclohex-1-en-1-yl)methyl)-1,2,3,6-tetrahydropyridin-4-yl)phenylmethyl, 4-(4-(2-(4-chlorophenyl)naphth-3-ylmethyl)piperazin-1-yl) phenylcarbonyl, 4-(4-(2-(4-chlorophenyl)pyridin-3-ylmethyl)piperazin-1-yl)phenylcarbonyl, 4-(4-(3-(4-chlorophenyl)pyridin-4-ylmethyl)piperazin-1-yl) phenylcarbonyl, 4-(4-((4-(4-chlorophenyl)pyridin-5-yl)methyl)-piperazin-1-yl)phenylcarbonyl, 4-(4-(2-(4-chlorophenyl)phenylcarbonyl) piperazin-1-yl) phenylcarbonyl, 4-(1-(2-(4-chlorophenyl)phenylcycloprop-1-yl)piperazin-1 -yl)phenylcarbonyl or 4-(4-(2-(4-chlorophenyl)phenylmethyl)cyclohex-1-en-1-yl) phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoroethyl)amino)-1-((phenylsulfanyl)methyl) propylamino, (1R)-3-(5,6-dihydro-1(4H)-pyrimidin-1-yl)-1-((phenylsulfanyl)methyl)propylamino, (1R)-3-(diisopropylamino)-1-((phenylsulfanyl)methyl) propylamino, (1R)-2-((2-(dimethylamino)ethyl)(methyl)amino)-1 -((phenylsulfanyl)methyl)ethylamino, (1R)-2-(2-(dimethylamino)ethoxy)-1-((phenylsulfanyl)methyl) ethylamino, (3R)-5-(N-((dimethylamino)methylcarbonyl)amino)-1-((phenylsulfanyl)methyl)pentylamino, (1R)-3-(dimethylamino)-1-((phenylsulfanyl)methyl)propoxy, (1R)-3-(dimethylamino)-1-((phenylsulfanyl)methyl) propylamino, (1S)-3-(dimethylamino)-1-((phenylsulfanyl)methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl) propylamino, (1R)-3-(dimethylamino)-1-((thien-2-ylsulfanyl)methyl)propylamino, (1R)-3-(dimethylamino)-1-(((4 -(trifluoromethoxy)phenyl)sulfanyl)methyl) propylamino, (1R)-3-(2,4-dimethyl-4,5-dihydro-1H-imidazol-1-yl)-1 -((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)-pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl) propylamino, (1R)-3-((2R,6S)-2,6-dimethylpiperidin-1-yl)-1-((phenylsulfanyl)methyl)propylamino, 1,1-dimethyl-2-(pyrimidin-2-ylsulfanyl)ethylamino, (1R)-4-((2R,5S)-2,5-dimethyl-pyrrolidin-1-yl)-1-((phenylsulfanyl)methyl) butylamino, (1R)-3-((2R,5R)-2,5-dimethylpyrrolidin-1-yl)-1-((phenylsulfanyl)methyl)propylamino, (1R)-3-(2,5-dimethyl-pyrrolidin-1-yl)-1-((phenylsulfanyl)methyl) propylamino, (1R)-3-((2R,5S)-2,5-dimethylpyrrolidin-1-yl)-1 -((phenylsulfanyl)methyl)propylamino, (1R)-3-((2S,5S)-2,5-dimethylpyrrolidin-1-yl)-1-((phenylsulfanyl)methyl)propylamino, 1,1-dimethyl-2-(thien-2-ylsulfanyl) ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)-3-((2-fluoroethyl) amino)-1-((phenylsulfanyl)methyl)propylamino, (1R)-1-(((4-fluorophenyl)sulfanyl)methyl)-3-(morpholin-4 -yl) propylamino; $D^1$ is H, F, Cl or CF$_3$; $E^1$ is H, F or Cl; $Y^1$ is H, CN, NO$_2$, F, Cl, CF$_3$, OCF$_3$, NH$_2$ or C(O)NH$_2$; and $Z^1$ is 4-(5-(2-(4-chlorophenyl)phenylmethyl)hexahydropyrrolo[3,4-c]pyrrol-2(1H)-yl)phenylcarbonyl, 4-(4-(2-(4 -chlorophenyl)phenylmethyl)piperazin-1-yl)phenylcarbonyl, 4-(4-(2-(4-chlorophenyl)phenylmethyl)-4-methoxypiperidin-1 -yl) phenylcarbonyl, 4-(4-(2-(4-chlorophenyl)phenylmethyl)-piperazin-1-yl)-3,5-difluorophenylcarbonyl, 4-(4-(2-(4 -chlorophenyl)phenylmethyl)piperazin-1-yl)-2-fluorophenylcarbonyl, 4-(4-(2-(4-chlorophenyl)phenylmethyl)piperazin-1-yl)-3-fluorophenylcarbonyl, 2-(4-(2-(4-chlorophenyl)phenylmethyl)piperazin-1-yl)pyridin-5-ylcarbonyl, 4-(1-(2-(4-chlorophenyl)phenylmethyl)piperidin-4-yl)phenylcarbonyl, 5-(4-(2-(4-chlorophenyl)phenylmethyl)-piperazin-1-yl)pyridin-2-ylcarbonyl, 4-(1-(2-(4 -chlorophenyl) phenylmethyl)-1,2,3,6-tetrahydropyridin-4-yl) phenylcarbonyl, 4-(4-(2-(cyclohex-1-ylamino) phenylmethyl)piperazin-1-yl)phenylcarbonyl4-(4-(2-cyclohex-1-ylphenylmethyl)piperazin-1-yl)phenylcarbonyl, 4-(4-(2-(3-cyanophenyl)phenylmethyl)piperazin-1-yl)phenylcarbonyl, 4-(4-(2-(2,4-dichlorophenyl)phenylmethyl) piperazin-1-yl)phenylcarbonyl, 4-(4-(2-(3,4-dichlorophenyl)phenylmethyl)piperazin-1 -yl)phenylcarbonyl, 4-(4-(2-(2,4-difluorophenyl)phenylmethyl)piperazin-1-yl) phenylcarbonyl, 4-(2-(1,3-dihydro-2H-isoindol-2-yl) phenylmethyl)piperazin-1-yl)phenylcarbonyl, 4-(4-(3-(1,1-dimethylethoxycarbonylamino)phenyl)piperazin-1-yl) phenylcarbonyl, 4-(2-(4-(2-(dimethylamino)ethoxy)phenyl) phenylmethyl)piperazin-1-yl)phenylcarbonyl or 4-(4-(3-(dimethylamino)phenyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoroethyl)amino)-1-((phenylsulfanyl)methyl) propylamino, (1R)-3-(5,6-dihydro-1(4H)-pyrimidin-1-yl)-1-((phenylsulfanyl)methyl)propylamino, (1R)-3-(diisopropylamino)-1-((phenylsulfanyl)methyl) propylamino, (1R)-2-((2-(dimethylamino)ethyl)(methyl)amino)-1 -((phenylsulfanyl)methyl)ethylamino, (1R)-2-(2-(dimethylamino)ethoxy)-1-((phenylsulfanyl)methyl) ethylamino, (3R)-5-(N-((dimethylamino)methylcarbonyl) amino)-1-((phenylsulfanyl)methyl)pentylamino, (1R)-3-(dimethylamino)-1-((phenylsulfanyl)methyl)propoxy, (1R)-3-(dimethylamino)-1-((phenylsulfanyl)methyl) propylamino, (1S)-3-(dimethylamino)-1-((phenylsulfanyl) methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl) propylamino, (1R)-3-(dimethylamino)-1-((thien-2-ylsulfanyl)methyl)propylamino, (1R)-3-(dimethylamino)-1-(((4 -(trifluoromethoxy)phenyl)sulfanyl)methyl) propylamino, (1R)-3-(2,4-dimethyl-4,5-dihydro-1H-imidazol-1-yl)-1 -((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)-pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl) propylamino, (1R)-3-((2R,6S)-2,6-dimethylpiperidin-1-yl)-1-((phenylsulfanyl)methyl)propylamino, 1,1-dimethyl-2-

(pyrimidin-2-ylsulfanyl)ethylamino, (1R)-4-((2R,5S)-2,5-dimethyl-pyrrolidin-1-yl)-1-((phenylsulfanyl)methyl) butylamino, (1R)-3-((2R,5R)-2,5-dimethylpyrrolidin-1-yl)-1-((phenylsulfanyl)methyl)propylamino, (1R)-3-(2,5-dimethylpyrrolidin-1-yl)-1-((phenylsulfanyl)methyl) propylamino, (1R)-3-((2R,5S)-2,5-dimethylpyrrolidin-1-yl)-1-((phenylsulfanyl)methyl)propylamino, (1R)-3-((2S,5S)-2,5-dimethylpyrrolidin-1-yl)-1-((phenylsulfanyl) methyl)propylamino, 1,1-dimethyl-2-(thien-2-ylsulfanyl) ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)-3-((2-fluoroethyl) amino)-1-((phenylsulfanyl)methyl)propylamino, (1R)-1-(((4-fluorophenyl)sulfanyl)methyl)-3-(morpholin-4 -yl) propylamino; $D^1$ is H, F, Cl or $CF_3$; $E^1$ is H, F or Cl; Y is H, CN, $NO_2$, F, Cl, $CF_3$, $OCF_3$, $NH_2$ or $C(O)NH_2$; and $Z^1$ is 4-(2-(4-(dimethylamino)phenyl)phenylcarbonyl)piperazin-1 - yl)phenylcarbonyl, 4-(4-(2-(4-(dimethylamino)phenyl) phenylmethyl)piperazin-1-yl)phenylcarbonyl, 4-(4-((2-(4-(dimethylamino)phenyl)pyridin-3-yl)methyl)piperazin-1-yl)phenylcarbonyl, 4-(4-(2-(5,5-dimethyl-2-oxo-1,3-oxazolidin-3-yl)phenylmethyl)piperazin-1-yl) phenylcarbonyl, 4-(4-(2-(4-fluorophenyl)cyclopent-1-en-1-ylmethyl) piperazin-1-yl)phenylcarbonyl, 4-(4-(2-(4-fluorophenyl)-3-fluorophenylmethyl)piperazin-1-yl) phenylcarbonyl, 4-(4-(2-(4-fluorophenyl)phenylmethyl) piperazin-1-yl)phenylcarbonyl, 4-(4-((2-(4-fluorophenyl) pyridin-3-yl)methyl)piperazin-1 -yl)phenylcarbonyl, 4-(2-(isopropylamino)phenylmethyl)piperazin-1-yl) phenylcarbonyl, 4-(4-(2-(4-(isopropylsulfanyl)phenyl) phenylmethyl)piperazin-1-yl)phenylcarbonyl, 4-(4-(2-(4-methoxyphenyl)cyclopent-1-en-1-ylmethyl)piperazin-1-yl) phenylcarbonyl, 4-(4-(2-(3 -methoxyphenyl)phenylmethyl) piperazin-1-yl)phenylcarbonyl, 4-(4-(2-(4-methoxyphenyl) phenylmethyl)piperazin-1 -yl)phenylcarbonyl, 4-(4-((2-(4-methoxyphenyl)pyridin-3-yl)methyl)piperazin-1-yl) phenylcarbonyl, 4-(4-methoxy-4-(2-(pyridin-3-yl) phenylmethyl)piperidin-1-yl)phenylcarbonyl, 4-(4-(2-(2-methyl-4-dichlorophenyl)phenylmethyl)piperazin-1-yl) phenylcarbonyl, 4-(4-(2-(2-methylphenyl)phenylmethyl) piperazin-1-yl)phenylcarbonyl, 4-(4-(2-(4-(methylsulfonyl) phenyl)methyl)piperazin-1-yl)phenylcarbonyl, 4-(4-(2-(4-methylsulfonylphenyl)phenylmethyl)piperazin-1-yl) phenylcarbonyl or 4-(4-((2-(4-methylsulfonylphenyl) pyridin-3-yl)methyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, $C(O)OCH_3$ or $C(O)NH_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoroethyl)amino)-1-((phenylsulfanyl)methyl) propylamino, (1R)-3-(5,6-dihydro-1(4H)-pyrimidin-1-yl)-1-((phenylsulfanyl)methyl)propylamino, (1R)-3-(diisopropylamino)-1-((phenylsulfanyl)methyl) propylamino, (1R)-2-((2-(dimethylamino)ethyl)(methyl) amino)-1 -((phenylsulfanyl)methyl)ethylamino, (1R)-2-(2-(dimethylamino)ethoxy)-1-((phenylsulfanyl)methyl) ethylamino, (3R)-5-(N-((dimethylamino)methylcarbonyl) amino)-1-((phenylsulfanyl)methyl)pentylamino, (1R)-3-(dimethylamino)-1-((phenylsulfanyl)methyl)propoxy, (1R)-3-(dimethylamino)-1-((phenylsulfanyl)methyl) propylamino, (1S)-3-(dimethylamino)-1-((phenylsulfanyl) methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl) propylamino, (1R)-3-(dimethylamino)-1-((thien-2-ylsulfanyl)methyl)propylamino, (1R)-3-(dimethylamino)-1-(((4-(trifluoromethoxy)phenyl)sulfanyl)methyl) propylamino, (1R)-3-(2,4-dimethyl-4,5-dihydro-1H-imidazol-1-yl)-1 -((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)-pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl) propylamino, (1R)-3-((2R,6S)-2,6-dimethylpiperidin-1-yl)-1-((phenylsulfanyl)methyl)propylamino, 1,1-dimethyl-2-(pyrimidin-2-ylsulfanyl)ethylamino, (1R)-4-((2R,5S)-2,5-dimethyl-pyrrolidin-1-yl)-1-((phenylsulfanyl)methyl) butylamino, (1R)-3-((2R,5R)-2,5-dimethylpyrrolidin-1-yl)-1-((phenylsulfanyl)methyl)propylamino, (1R)-3-(2,5-dimethylpyrrolidin-1-yl)-1-((phenylsulfanyl)methyl) propylamino, (1R)-3-((2R,5S)-2,5-dimethylpyrrolidin-1-yl)-1-((phenylsulfanyl)methyl)propylamino, (1R)-3-((2S, 5S)-2,5-dimethylpyrrolidin-1-yl)-1-((phenylsulfanyl) methyl)propylamino, 1,1-dimethyl-2-(thien-2-ylsulfanyl) ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)-3-((2-fluoroethyl) amino)-1-((phenylsulfanyl)methyl)propylamino, (1R)-1-(((4-fluorophenyl)sulfanyl)methyl)-3-(morpholin-4 -yl) propylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or $C(O)NH_2$; and $Z^1$ is 4-(4-(2-(5-methylthien-2-yl)phenylmethyl)piperazin-1 -yl) phenylcarbonyl, 4-(4-(2-(4-methylsulfanylphenyl)cyclohex-1-en-1-ylmethyl)piperazin-1-yl)phenylcarbonyl, 4-(4-(2-(4-methylsulfanylphenyl)phenylcarbonyl)piperazin-1-yl) phenylcarbonyl, 4-(4-((2-(4-methylsulfanylphenyl)pyridin-3-yl)methyl)piperazin-1-yl)phenylcarbonyl, 4-(2-(4-methylsulfanylphenyl)phenylmethyl)piperazin-1-yl)-phenylcarbonyl, 4-(4-(2-(4-(2-(morpholin-1-yl)ethoxy)-phenyl)phenylmethyl)piperazin-1-yl)phenylcarbonyl, 4-(4-(2-(morpholin-1-yl)phenylmethyl)piperazin-1-yl) phenylcarbonyl, 4-(4-(2-(naphth-1-yl)phenylmethyl) piperazin-1-yl)phenylcarbonyl, 4-(4-(2-(naphth-2-yl) phenylmethyl)-piperazin-1-yl)phenylcarbonyl or 4-(4-(2-(4-phenoxyphenyl)phenylmethyl)piperazin-1-yl) phenylcarbonyl, 4-(4-((1-phenyl-1H-imidazol-2-yl)methyl) piperazin-1 -yl)phenylcarbonyl, 4-(4-((1-phenyl-1H-imidazol-5-yl)methyl)piperazin-1-yl)phenylcarbonyl, 4-(2-((phenylmethyl)amino)phenylmethyl)piperazin-1-yl) phenylcarbonyl, 4-(4-(2-(phenyl)phenylmethyl)-4-(2 -(dimethylamino)ethoxy))piperidin-1-yl)phenylcarbonyl, 4-((2-(phenyl)phenylmethyl)-4-methoxypiperidin-1-yl)phenylcarbonyl, 4-(4-(2-(phenyl)phenylmethyl)-4-(2-(morpholin-1-yl)ethoxy))piperidin-1-yl)phenylcarbonyl, 4-(4-(2-(phenyl)phenylmethyl)piperazin-1-yl)phenylcarbonyl, 4-(4-(3-(phenyl)phenylmethyl)piperazin-1-yl)phenylcarbonyl, 4-(4-(2-(4-(phenyl)phenyl)phenylmethyl)piperazin-1 -yl) phenylcarbonyl or 4-(4-(2-(phenyl)phenylmethyl)-4-(2-(piperidin-1-yl)ethoxy))piperidin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoroethyl)amino)-1-((phenylsulfanyl)methyl)propylamino, (1R)-3-(5,6-dihydro-1(4H)-pyrimidin-1-yl)-1-((phenylsulfanyl)methyl)propylamino, (1R)-3-(diisopropylamino)-1-((phenylsulfanyl)methyl)propylamino, (1R)-2-((2-(dimethylamino)ethyl)(methyl)amino)-1-((phenylsulfanyl)methyl)ethylamino, (1R)-2-(2-(dimethylamino)ethoxy)-1-((phenylsulfanyl)methyl)ethylamino, (3R)-5-(N-((dimethylamino)methylcarbonyl)amino)-1-((phenylsulfanyl)methyl)pentylamino, (1R)-3-(dimethylamino)-1-((phenylsulfanyl)methyl)propoxy, (1R)-3-(dimethylamino)-1-((phenylsulfanyl)methyl)propylamino, (1S)-3-(dimethylamino)-1-((phenylsulfanyl)methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl)propylamino, (1R)-3-(dimethylamino)-1-((thien-2-ylsulfanyl)methyl)propylamino, (1R)-3-(dimethylamino)-1-(((4-(trifluoromethoxy)phenyl)sulfanyl)methyl)propylamino, (1R)-3-(2,4-dimethyl-4,5-dihydro-1H-imidazol-1-yl)-1-((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl)propylamino, (1R)-3-((2R,6S)-2,6-dimethylpiperidin-1-yl)-1-((phenylsulfanyl)methyl)propylamino, 1,1-dimethyl-2-(pyrimidin-2-ylsulfanyl)ethylamino, (1R)-4-((2R,5S)-2,5-dimethylpyrrolidin-1-yl)-1-((phenylsulfanyl)methyl)butylamino, (1R)-3-((2R,5R)-2,5-dimethylpyrrolidin-1-yl)-1-((phenylsulfanyl)methyl)propylamino, (1R)-3-(2,5-dimethylpyrrolidin-1-yl)-1-((phenylsulfanyl)methyl)propylamino, (1R)-3-((2R,5S)-2,5-dimethylpyrrolidin-1-yl)-1-((phenylsulfanyl)methyl)propylamino, (1R)-3-((2S,5S)-2,5-dimethylpyrrolidin-1-yl)-1-((phenylsulfanyl)methyl)propylamino, 1,1-dimethyl-2-(thien-2-ylsulfanyl)ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)-3-((2-fluoroethyl)amino)-1-((phenylsulfanyl)methyl)propylamino, (1R)-1-(((4-fluorophenyl)sulfanyl)methyl)-3-(morpholin-4-yl)propylamino; $D^1$ is H, F, Cl or CF$_3$; $E^1$ is H, F or Cl; $Y^1$ is H, CN, NO$_2$, F, Cl, CF$_3$, OCF$_3$, NH$_2$ or C(O)NH$_2$; and $Z^1$ is 4-(4-(2-(phenyl)phenylmethyl)-4-(2-(pyrrolidin-1-yl)ethoxy))piperidin-1-yl)phenylcarbonyl, 4-(4-((2-(phenyl)pyridin-3-yl)methyl)piperazin-1-yl)phenylcarbonyl, 4-(4-((1-phenyl-1H-pyrazol-5-yl)methyl)piperazin-1-yl)phenylcarbonyl, 4-(4-(2-(piperidin-1-yl)phenylmethyl)piperazin-1-yl)phenylcarbonyl, 4-(4-(2-(pyrid-3-yl)phenyl)phenylmethyl)piperazin-1-yl)phenylcarbonyl, 4-(4-2-(quinolin-3-ylphenyl)phenylmethyl)piperazin-1-yl)phenylcarbonyl, 4-(4-(2-(quinolin-8-yl)phenyl)phenylmethyl)piperazin-1-yl)phenylcarbonyl, 4-(4-(2-(thien-2-yl)-4-methoxypiperazin-1-yl)phenylcarbonyl, 4-(4-(2-(thien-2-yl)phenylmethyl)-piperazin-1-yl)phenylcarbonyl, 4-(4-(2-(4-trifluoromethoxyphenyl)phenylmethyl)piperazin-1-yl)phenylcarbonyl or 4-(4-(2-(4-trifluoromethylphenyl)phenylmethyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoroethyl)amino)-1-((phenylsulfanyl)methyl)propylamino, (1R)-3-(5,6-dihydro-1(4H)-pyrimidin-1-yl)-1-((phenylsulfanyl)methyl)propylamino, (1R)-3-(diisopropylamino)1-((phenylsulfanyl)methyl)propylamino, (1R)-2-((2-(dimethylamino)ethyl)(methyl)amino)-1-((phenylsulfanyl)methyl)ethylamino, (1R)-2-(2-(dimethylamino)ethoxy)-1-((phenylsulfanyl)methyl)ethylamino, (3R)-5-(N-((dimethylamino)methylcarbonyl)amino)-1-((phenylsulfanyl)methyl)pentylamino, (1R)-3-(dimethylamino)-1-((phenylsulfanyl)methyl)propoxy, (1R)-3-(dimethylamino)-1-((phenylsulfanyl)methyl)propylamino, (1S)-3-(dimethylamino)-1-((phenylsulfanyl)methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl)propylamino, (1R)-3-(dimethylamino)-1-((thien-2-ylsulfanyl)methyl)propylamino, (1R)-3-(dimethylamino)-1-(((4-(trifluoromethoxy)phenyl)sulfanyl)methyl)propylamino, (1R)-3-(2,4-dimethyl-4,5-dihydro-1H-imidazol-1-yl)-1-((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl)propylamino, (1R)-3-((2R,6S)-2,6-dimethylpiperidin-1-yl)-1-((phenylsulfanyl)methyl)propylamino, 1,1-dimethyl-2-(pyrimidin-2-ylsulfanyl)ethylamino, (1R)-4-((2R,5S)-2,5-dimethylpyrrolidin-1-yl)-1-((phenylsulfanyl)methyl)butylamino, (1R)-3-((2R,5R)-2,5-dimethylpyrrolidin-1-yl)-1-((phenylsulfanyl)methyl)propylamino, (1R)-3-(2,5-dimethylpyrrolidin-1-yl)-1-((phenylsulfanyl)methyl)propylamino, (1R)-3-((2R,5S)-2,5-dimethylpyrrolidin-1-yl)-1-((phenylsulfanyl)methyl)propylamino, (1R)-3-((2S,5S)-2,5-dimethylpyrrolidin-1-yl)-1-((phenylsulfanyl)methyl)propylamino, 1,1-dimethyl-2-(thien-2-ylsulfanyl)ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)-3-((2-fluoroethyl)amino)-1-((phenylsulfanyl)methyl)propylamino, (1R)-1-(((4-fluorophenyl)sulfanyl)methyl)-3-(morpholin-4-yl)propylamino; $D^1$ is H, F, Cl or CF$_3$; $E^1$ is H, F or Cl; $Y^1$ is H, CN, NO$_2$, F, Cl, CF$_3$, OCF$_3$, NH$_2$ or C(O)NH$_2$; and $Z^1$ is 4-(4-(2-(1,3-benzodioxol-5-yl)phenylmethyl)piperazin-1-yl)phenylcarbonyl, 4-(4-(2-(benzofuran-2-yl)phenyl)phenylmethyl)piperazin-1-yl)phenylcarbonyl, 4-(2-bromocyclohex-1-en-1-ylmethyl)piperazin-1-yl)phenylcarbonyl, 4-(2-bromocyclopent-1-en-1-ylmethyl)piperazin-1-yl)phenylcarbonyl, 4-(2-(4-bromophenyl)phenylmethyl)piperazin-1-yl)phenylcarbonyl, 4-(4-(2-(4-chlorophenyl)cyclohept-1-en-1-ylmethyl)piperazin-1-yl)

phenylcarbonyl, 4-(1-(2-(4-chlorophenyl)cyclohex-1-en-1-ylmethyl)-1,2,3,6-tetrahydropyridin-4-yl)phenylcarbonyl, 4-(4-(2-(4-chlorophenyl)cyclohex-1-en-1-ylmethyl)piperazin-1-yl)phenylcarbonyl, 4-(4-(2-(4-chlorophenyl)cyclopent-1-en-1-ylmethyl)piperazin-1-yl)phenylcarbonyl, 4-(4-(2-(4-chlorophenyl)cyclooct-1-en-1-ylmethyl)piperazin-1-yl)phenylcarbonyl, 4-(4-((4-(4-chlorophenyl)-5,6-dihydro-2H-pyran-3-yl)methyl)piperazin-1-yl)phenylcarbonyl, 4-(4-((4-(4-chlorophenyl)-5,6-dihydro-2H-pyran-3-yl)methyl)piperazin-1-yl)phenylcarbonyl, 4-(1-((2-(4-chlorophenyl)-5,5-dimethyl-1-cyclohex-1-en-1-yl)methyl)-1,2,3,6-tetrahydropyridin-4-yl)phenylmethyl, 4-(4-(2-(4-chlorophenyl)naphth-3-ylmethyl)piperazin-1-yl)phenylcarbonyl, 4-(4-(2-(4-chlorophenyl)pyridin-3-ylmethyl)piperazin-1-yl)phenylcarbonyl, 4-(4-(3-(4-chlorophenyl)pyridin-4-ylmethyl)piperazin-1-yl)phenylcarbonyl, 4-(4-((4-(4-chlorophenyl)pyridin-5-yl)methyl)piperazin-1-yl)phenylcarbonyl, 4-(4-(2-(4-chlorophenyl)phenylcarbonyl)piperazin-1-yl)phenylcarbonyl, 4-(1-(2-(4-chlorophenyl)phenylcycloprop-1-yl)piperazin-1-yl)phenylcarbonyl or 4-(4-(2-(4-chlorophenyl)phenylmethyl)cyclohex-1-en-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoroethyl)amino)-1-((phenylsulfanyl)methyl)propylamino, (1R)-3-(5,6-dihydro-1(4H)-pyrimidin-1-yl)-1-((phenylsulfanyl)methyl)propylamino, (1R)-3-(diisopropylamino)-1-((phenylsulfanyl)methyl)propylamino, (1R)-2-((2-(dimethylamino)ethyl)(methyl)amino)-1-((phenylsulfanyl)methyl)ethylamino, (1R)-2-(2-(dimethylamino)ethoxy)-1-((phenylsulfanyl)methyl)ethylamino, (3R)-5-(N-((dimethylamino)methylcarbonyl)amino)-1-((phenylsulfanyl)methyl)pentylamino, (1R)-3-(dimethylamino)-1-((phenylsulfanyl)methyl)propoxy, (1R)-3-(dimethylamino)-1-((phenylsulfanyl)methyl)propylamino, (1S)-3-(dimethylamino)-1-((phenylsulfanyl)methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl)propylamino, (1R)-3-(dimethylamino)-1-((thien-2-ylsulfanyl)methyl)propylamino, (1R)-3-(dimethylamino)-1-(((4-(trifluoromethoxy)phenyl)sulfanyl)methyl)propylamino, (1R)-3-(2,4-dimethyl-4,5-dihydro-1H-imidazol-1-yl)-1-((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)-pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl)propylamino, (1R)-3-((2R,6S)-2,6-dimethylpiperidin-1-yl)-1-((phenylsulfanyl)methyl)propylamino, 1,1-dimethyl-2-(pyrimidin-2-ylsulfanyl)ethylamino, (1R)-4-((2R,5S)-2,5-dimethylpyrrolidin-1-yl)-1-((phenylsulfanyl)methyl)butylamino, (1R)-3-((2R,5R)-2,5-dimethylpyrrolidin-1-yl)-1-((phenylsulfanyl)methyl)propylamino, (1R)-3-(2,5-dimethyl-pyrrolidin-1-yl)-1-((phenylsulfanyl)methyl)propylamino, (1R)-3-((2R,5S)-2,5-dimethylpyrrolidin-1-yl)-1-((phenylsulfanyl)methyl)propylamino, (1R)-3-((2S,5S)-2,5-dimethylpyrrolidin-1-yl)-1-((phenylsulfanyl) methyl)propylamino, 1,1-dimethyl-2-(thien-2-ylsulfanyl)ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)-3-((2-fluoroethyl)amino)-1-((phenylsulfanyl)methyl)propylamino, (1R)-1-(((4-fluorophenyl)sulfanyl)methyl)-3-(morpholin-4-yl)propylamino; $D^1$ is H, F, Cl or CF$_3$; $E^1$ is H, F or Cl; $Y^1$ is H, CN, NO$_2$, F, Cl, CF$_3$, OCF$_3$, NH$_2$ or C(O)NH$_2$; and $Z^1$ is 4-(5-(2-(4-chlorophenyl)phenylmethyl)hexahydropyrrolo[3,4-c]pyrrol-2(1H)-yl)phenylcarbonyl, 4-(4-(2-(4-chlorophenyl)phenylmethyl)piperazin-1-yl)phenylcarbonyl, 4-(4-(2-(4-chlorophenyl)phenylmethyl)-4-methoxypiperidin-1-yl)phenylcarbonyl, 4-(4-(2-(4-chlorophenyl)phenylmethyl)-piperazin-1-yl)-3,5-difluorophenylcarbonyl, 4-(4-(2-(4-chlorophenyl)phenylmethyl)piperazin-1-yl)-2-fluorophenylcarbonyl, 4-(4-(2-(4-chlorophenyl)phenylmethyl)piperazin-1-yl)-3-fluorophenylcarbonyl, 2-(4-(2-(4-chlorophenyl)phenylmethyl)piperazin-1-yl)pyridin-5-ylcarbonyl, 4-(1-(2-(4-chlorophenyl)phenylmethyl)piperidin-4-yl)phenylcarbonyl, 5-(4-(2-(4-chlorophenyl)phenylmethyl)-piperazin-1-yl)pyridin-2-ylcarbonyl, 4-(1-(2-(4-chlorophenyl)phenylmethyl)-1,2,3,6-tetrahydropyridin-4-yl)phenylcarbonyl, 4-(4-(2-(cyclohex-1-ylamino)phenylmethyl)piperazin-1-yl)phenylcarbonyl4-(4-(2-cyclohex-1-ylphenylmethyl)piperazin-1-yl) phenylcarbonyl, 4-(4-(2-(3-cyanophenyl)phenylmethyl)piperazin-1-yl)phenylcarbonyl, 4-(4-(2-(2,4-dichlorophenyl)phenylmethyl)piperazin-1-yl) phenylcarbonyl, 4-(4-(2-(3,4-dichlorophenyl)phenylmethyl)piperazin-1-yl)phenylcarbonyl, 4-(4-(2-(2,4-difluorophenyl)phenylmethyl)piperazin-1-yl)phenylcarbonyl, 4-(2-(1,3-dihydro-2H-isoindol-2-yl)phenylmethyl)piperazin-1-yl)phenylcarbonyl, 4-(4-(3-(1,1-dimethylethoxycarbonylamino)phenyl)piperazin-1-yl)phenylcarbonyl, 4-(2-(4-(2-(dimethylamino)ethoxy)phenyl)phenylmethyl)piperazin-1-yl)phenylcarbonyl or 4-(4-(3-(dimethylamino)phenyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoroethyl)amino)-1-((phenylsulfanyl)methyl)propylamino, (1R)-3-(5,6-dihydro-1(4H)-pyrimidin-1-yl)-1-((phenylsulfanyl)methyl)propylamino, (1R)-3-(diisopropylamino)-1-((phenylsulfanyl)methyl)propylamino, (1R)-2-((2-(dimethylamino)ethyl)(methyl)amino)-1-((phenylsulfanyl)methyl)ethylamino, (1R)-2-(2-(dimethylamino)ethoxy)-1-((phenylsulfanyl)methyl)ethylamino, (3R)-5-(N-((dimethylamino)methylcarbonyl)amino)-1-((phenylsulfanyl)methyl)pentylamino, (1R)-3-(dimethylamino)-1-((phenylsulfanyl)methyl)propoxy, (1R)-3-(dimethylamino)-1-((phenylsulfanyl)methyl)propylamino, (1S)-3-(dimethylamino)-1-((phenylsulfanyl)methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl)propylamino, (1R)-3-(dimethylamino)-1-((thien-2-ylsulfanyl)methyl)propylamino, (1R)-3-(dimethylamino)-1-(((4-(trifluoromethoxy)phenyl)sulfanyl)methyl)propylamino, (1R)-3-(2,4-dimethyl-4,5-dihydro-1H-imidazol-1-yl)-1-((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl)propylamino, (1R)-3-((2R,6S)-2,6-dimethylpiperidin-1-yl)-1-((phenylsulfanyl)methyl)propylamino, 1,1-dimethyl-2-(pyrimidin-2-ylsulfanyl)ethylamino, (1R)-4-((2R,5S)-2,5-dimethylpyrrolidin-1-yl)-1-((phenylsulfanyl)methyl)butylamino, (1R)-3-((2R,5R)-2,5-dimethylpyrrolidin-1-yl)-1-((phenylsulfanyl)methyl)propylamino, (1R)-3-(2,5-dimethylpyrrolidin-1-yl)-1-((phenylsulfanyl)methyl)propylamino, (1R)-3-((2R,5S)-2,5-dimethylpyrrolidin-1-yl)-1-((phenylsulfanyl)methyl)propylamino, (1R)-3-((2S,5S)-2,5-dimethylpyrrolidin-1-yl)-1-((phenylsulfanyl)methyl)propylamino, 1,1-dimethyl-2-(thien-2-ylsulfanyl)ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)-3-((2-fluoroethyl)amino)-1-((phenylsulfanyl)methyl)propylamino, (1R)-1-(((4-fluorophenyl)sulfanyl)methyl)-3-(morpholin-4-yl)propylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or C(O)$NH_2$; and $Z^1$ is 4-(2-(4-(dimethylamino)phenyl)phenylcarbonyl)piperazin-1-yl)phenylcarbonyl, 4-(4-(2-(4-(dimethylamino)phenyl)phenylmethyl)piperazin-1-yl)phenylcarbonyl, 4-(4-((2-(4-(dimethylamino)phenyl)pyridin-3-yl)methyl)piperazin-1-yl)phenylcarbonyl, 4-(4-(2-(5,5-dimethyl-2-oxo-1,3-oxazolidin-3-yl)phenylmethyl)piperazin-1-yl)phenylcarbonyl, 4-(4-(2-(4-fluorophenyl)cyclopent-1-en-1-ylmethyl)piperazin-1-yl)phenylcarbonyl, 4-(4-(2-(4-fluorophenyl)-3-fluorophenylmethyl)piperazin-1-yl)phenylcarbonyl, 4-(4-(2-(4-fluorophenyl)phenylmethyl)piperazin-1-yl)phenylcarbonyl, 4-(4-((2-(4-fluorophenyl)pyridin-3-yl)methyl)piperazin-1-yl)phenylcarbonyl, 4-(2-(isopropylamino)phenylmethyl)-piperazin-1-yl)phenylcarbonyl, 4-(4-(2-(4-(isopropylsulfanyl)phenyl)phenylmethyl)piperazin-1-yl)phenylcarbonyl, 4-(4-(2-(4-methoxyphenyl)cyclopent-1-en-1-ylmethyl)piperazin-1-yl) phenylcarbonyl, 4-(4-(2-(3-methoxyphenyl)phenylmethyl)piperazin-1-yl)phenylcarbonyl, 4-(4-(2-(4-methoxyphenyl)phenylmethyl)piperazin-1-yl)phenylcarbonyl, 4-(4-((2-(4-methoxyphenyl)pyridin-3-yl)methyl)piperazin-1-yl)phenylcarbonyl, 4-(4-methoxy-4-(2-(pyridin-3-yl)phenylmethyl)piperidin-1-yl)phenylcarbonyl, 4-(4-(2-(2-methyl-4-dichlorophenyl)phenylmethyl)piperazin-1-yl)phenylcarbonyl, 4-(4-(2-(2-methylphenyl)phenylmethyl)piperazin-1-yl)phenylcarbonyl, 4-(4-(2-(4-(methylsulfonyl)phenyl)methyl)piperazin-1-yl)phenylcarbonyl, 4-(4-(2-(4-methylsulfonylphenyl)phenylmethyl)piperazin-1-yl)phenylcarbonyl or 4-(4-((2-(4-methylsulfonylphenyl)pyridin-3-yl)methyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, $C(O)OCH_3$ or $C(O)NH_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoroethyl)amino)-1-((phenylsulfanyl)methyl)propylamino, (1R)-3-(5,6-dihydro-1(4H)-pyrimidin-1-yl)-1-((phenylsulfanyl)methyl)propylamino, (1R)-3-(diisopropylamino)-1-((phenylsulfanyl)methyl)propylamino, (1R)-2-((2-(dimethylamino)ethyl)(methyl)amino)-1-((phenylsulfanyl)methyl)ethylamino, (1R)-2-(2-(dimethylamino)ethoxy)-1-((phenylsulfanyl)methyl)ethylamino, (3R)-5-(N-((dimethylamino)methylcarbonyl)amino)-1-((phenylsulfanyl)methyl)pentylamino, (1R)-3-(dimethylamino)-1-((phenylsulfanyl)methyl)propoxy, (1R)-3-(dimethylamino)-1-((phenylsulfanyl)methyl)propylamino, (1S)-3-(dimethylamino)-1-((phenylsulfanyl)methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl)propylamino, (1R)-3-(dimethylamino)-1-((thien-2-ylsulfanyl)methyl)propylamino, (1R)-3-(dimethylamino)-1-(((4-(trifluoromethoxy)phenyl)sulfanyl)methyl)propylamino, (1R)-3-(2,4-dimethyl-4,5-dihydro-1H-imidazol-1-yl)-1-((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl)propylamino, (1R)-3-((2R,6S)-2,6-dimethylpiperidin-1-yl)-1-((phenylsulfanyl)methyl)propylamino, 1,1-dimethyl-2-(pyrimidin-2-ylsulfanyl)ethylamino, (1R)-4-((2R,5S)-2,5-dimethylpyrrolidin-1-yl)-1-((phenylsulfanyl)methyl)butylamino, (1R)-3-((2R,5R)-2,5-dimethylpyrrolidin-1-yl)-1-((phenylsulfanyl)methyl)propylamino, (1R)-3-(2,5-dimethylpyrrolidin-1-yl)-1-((phenylsulfanyl)methyl)propylamino, (1R)-3-((2R,5S)-2,5-dimethylpyrrolidin-1-yl)-1-((phenylsulfanyl)methyl)propylamino, (1R)-3-((2S,5S)-2,5-dimethylpyrrolidin-1-yl)-1-((phenylsulfanyl)methyl)propylamino, 1,1-dimethyl-2-(thien-2-ylsulfanyl)ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)-3-((2-fluoroethyl)amino)-1-((phenylsulfanyl)methyl)propylamino, (1R)-1-(((4-fluorophenyl)sulfanyl)methyl)-3-(morpholin-4-yl)propylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or C(O)$NH_2$; and $Z^1$ is 4-(4-(2-(5-methylthien-2-yl)phenylmethyl)piperazin-1-yl)phenylcarbonyl, 4-(4-(2-(4-methylsulfanylphenyl)cyclohex-1-en-1-ylmethyl)piperazin-1-yl)phenylcarbonyl, 4-(4-(2-(4-methylsulfanylphenyl)phenylcarbonyl)piperazin-1-yl)phenylcarbonyl, 4-(4-((2-(4-methylsulfanylphenyl)pyridin-3-yl)methyl)piperazin-1-yl)phenylcarbonyl, 4-(4-(2-(4-methylsulfanylphenyl)phenylmethyl)piperazin-1-yl)-phenylcarbonyl, 4-(4-(2-(4-(2-(morpholin-1-yl)ethoxy)phenyl)phenylmethyl)piperazin-1-yl)phenylcarbonyl, 4-(4-(2-(morpholin-1-yl)phenylmethyl)piperazin-1-yl)phenylcarbonyl, 4-(4-(2-(naphth-1-yl)phenylmethyl)piperazin-1-yl)phenylcarbonyl, 4-(4-(2-(naphth-2-yl)phenylmethyl)piperazin-1-yl)phenylcarbonyl or 4-(4-(2-(4-phenoxyphenyl)phenylmethyl)piperazin-1-yl)phenylcarbonyl, 4-(4-((1-phenyl-1H-imidazol-2-yl)methyl)piperazin-1-yl)phenylcarbonyl, 4-(4-((1-phenyl-1H-imidazol-5-yl)methyl)piperazin-1-yl)phenylcarbonyl, 4-(2-((phenylmethyl)amino)phenylmethyl)piperazin-1-yl)phenylcarbonyl, 4-(4-(2-(phenyl)phenylmethyl)-4-(2-(dimethylamino)ethoxy))piperidin-1-yl)phenylcarbonyl, 4-((2-(phenyl)phenylmethyl)-4-methoxypiperidin-1-yl)

phenylcarbonyl, 4-(4-(2-(phenyl)phenylmethyl)-4-(2-(morpholin-1-yl)ethoxy))piperidin-1-yl)phenylcarbonyl, 4-(4-(2-(phenyl)phenylmethyl)piperazin-1-yl)phenylcarbonyl, 4-(4-(3-(phenyl)phenylmethyl)piperazin-1-yl)phenylcarbonyl, 4-(4-(2-(4-(phenyl)phenyl)phenylmethyl)piperazin-1-yl)phenylcarbonyl or 4-(4-(2-(phenyl)phenylmethyl)-4-(2-(piperidin-1-yl)ethoxy))piperidin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-2-(diethylamino)-1-((phenylsulfanyl)methyl)ethylamino, (1R)-3-(diethylamino)-1-((phenylsulfanyl)methyl)propylamino, (1R)-3-((2,2-difluoroethyl)amino)-1-((phenylsulfanyl)methyl)propylamino, (1R)-3-(5,6-dihydro-1(4H)-pyrimidin-1-yl)-1-((phenylsulfanyl)methyl)propylamino, (1R)-3-(diisopropylamino)-1-((phenylsulfanyl)methyl)propylamino, (1R)-2-((2-(dimethylamino)ethyl)(methyl)amino)-1-((phenylsulfanyl)methyl)ethylamino, (1R)-2-(2-(dimethylamino)ethoxy)-1-((phenylsulfanyl)methyl)ethylamino, (3R)-5-(N-((dimethylamino)methylcarbonyl)amino)-1-((phenylsulfanyl)methyl)pentylamino,(1R)-3-(dimethylamino)-1-((phenylsulfanyl)methyl)propoxy, (1R)-3-(dimethylamino)-1-((phenylsulfanyl)methyl)propylamino, (1S)-3-(dimethylamino)-1-((phenylsulfanyl)methyl)propylamino, (1R)-3-(dimethylamino)-3-oxo-1-((pyrimidin-2-ylsulfanyl)methyl)propylamino, (1R)-3-(dimethylamino)-3-oxo-1-((1,3-thiazol-2-yl)methyl)propylamino, (1R)-3-(dimethylamino)-1-((thien-2-ylsulfanyl)methyl)propylamino, (1R)-3-(dimethylamino)-1-(((4-(trifluoromethoxy)phenyl)sulfanyl)methyl)propylamino, (1R)-3-(2,4-dimethyl-4,5-dihydro-1H-imidazol-1-yl)-1-((phenylsulfanyl)methyl)propylamino, (1R)-3-(4,4-dimethyl-4,5-dihydro-1H-imidazol-1-yl)-1-((phenylsulfanyl)methyl)propylamino, (1R)-5-((1,1-dimethylethoxy)carbonylamino)-1-((phenylsulfanyl)methyl)pentylamino, 1-(1,1-dimethylethoxycarbonyl)piperidin-4-yloxy, 1,1-dimethyl-2-(phenylsulfonyl)ethylamino, (1,1-dimethyl-2-(phenylsulfanyl)ethyl)amino, 1,1-dimethyl-2-(phenylsulfanyl)ethyl, 4,4-dimethylpiperidin-1-yl, (1R)-3-(2,6-dimethylpiperidin-1-yl)-1-((phenylsulfanyl)methyl)propylamino, (1R)-3-((2R,6S)-2,6-dimethylpiperidin-1-yl)-1-((phenylsulfanyl)methyl)propylamino, 1,1-dimethyl-2-(pyrimidin-2-ylsulfanyl)ethylamino, (1R)-4-((2R,5S)-2,5-dimethylpyrrolidin-1-yl)-1-((phenylsulfanyl)methyl)butylamino, (1R)-3-((2R,5R)-2,5-dimethylpyrrolidin-1-yl)-1-((phenylsulfanyl)methyl)propylamino, (1R)-3-(2,5-dimethylpyrrolidin-1-yl)-1-((phenylsulfanyl)methyl)propylamino, (1R)-3-((2R,5S)-2,5-dimethylpyrrolidin-1-yl)-1-((phenylsulfanyl)methyl)propylamino, (1R)-3-((2S,5S)-2,5-dimethylpyrrolidin-1-yl)-1-((phenylsulfanyl)methyl)-propylamino, 1,1-dimethyl-2-(thien-2-ylsulfanyl)ethylamino, (1R)-3-(1,1-dioxothiomorpholin-4-yl)-1-((phenylsulfanyl)methyl)propylamino, (1R)-3-(dipropylamino)-1-((phenylsulfanyl)methyl)propylamino, (1R)-3-(dipropylamino)-1-((phenylsulfanyl)methyl)propylamino, (1R)-3-(ethyl(2,2,2-trifluoroethyl)amino)-1-((phenylsulfanyl)methyl)propylamino, 1-(ethoxycarbonyl)piperidin-4-yloxy, (1R)73-((2-fluoroethyl)amino)-1-((phenylsulfanyl)methyl)propylamino, (1R)-1-(((4-fluorophenyl)sulfanyl)methyl)-3-(morpholin-4-yl)propylamino; $D^1$ is H, F, Cl or CF$_3$; $E^1$ is H, F or Cl; $Y^1$ is H, CN, NO$_2$, F, Cl, CF$_3$, OCF$_3$, NH$_2$ or C(O)NH$_2$; and $Z^1$ is 4-(4-(2-(phenyl)phenylmethyl)-4-(2-(pyrrolidin-1-yl)ethoxy))piperidin-1-yl)phenylcarbonyl, 4-(4-((2-(phenyl)pyridin-3-yl)phenylmethyl)piperazin-1-yl) phenylcarbonyl, 4-(4-((1-phenyl-1H-pyrazol-5-yl)methyl)piperazin-1-yl)phenylcarbonyl, 4-(4-(2-(piperidin-1-yl)phenylmethyl)piperazin-1-yl)phenylcarbonyl, 4-(4-(2-(pyrid-3-yl)phenyl)phenylmethyl)piperazin-1-yl) phenylcarbonyl, 4-(4-(2-(quinolin-3-ylphenyl) phenylmethyl)piperazin-1-yl)phenylcarbonyl, 4-(4-(2-(quinolin-8-ylphenyl)phenylmethyl)piperazin-1-yl) phenylcarbonyl, 4-(4-(2-(thien-2-yl)phenylmethyl)-4-methoxypiperazin-1-yl)phenylcarbonyl, 4-(4-(2-(thien-2-yl) phenylmethyl)piperazin-1-yl)phenylcarbonyl, 4-(4-(2-(4-trifluoromethoxyphenyl)phenylmethyl)piperazin-1-yl) phenylcarbonyl or 4-(4-(2-(4-trifluoromethylphenyl) phenylmethyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-3-(4-(hydroxyaminocarbonyl)piperidin-1-yl)-1-((phenylsulfanyl)methyl)propylamino, (1R)-3-(2-hydroxy-2-methylpropyl)amino)-1-((phenylsulfanyl)methyl)propylamino, (1R)-3-(4-hydroxypiperidin-1-yl)-1-((phenylsulfanyl)methyl)propylamino, (3R)-3-(3-hydroxypyrrolidin-1-yl)-1-((phenylsulfanyl)methyl)propylamino, isopropylamino, (1R)-3-(isopropylamino)-1-((phenylsulfanyl)methyl)propylamino, (1R)-3-(1H-imidazol-1-yl)-1-((phenylsulfanyl)methyl)propylamino, (1R)-3-(isopropyl(methyl)amino)-1-((phenylsulfanyl)methyl)-propylamino, (4-methoxycyclohex-1-yl)methyl)amino, (1R)-3-(4-(methoxyimino)piperidin-1-yl)-1-((phenylsulfanyl)methyl)-propylamino, (1R)-3-(N-methyl-N-carboxymethyl)amino)-1-((phenylsulfanyl)methyl)propylamino, (methyl)(cyclohexyl)amino, (methyl)(cyclohexylmethyl)amino, (1R)-3-(2-methyl-4,5-dihydro-1H-imidazol-1-yl)-1-((phenylsulfanyl)methyl)propylamino, (3R)-3-(N-methyl-N-(dimethylcarbonylmethyl))-1-((phenylsulfanyl)methyl)propylamino, (1R)-3-(N-methyl-N-(1,1-dimethylethyl)amino)-1-((phenylsulfanyl)methyl)propylamino, (N-methyl-N-(1,2-diphenyl)amino)carbonyl)-N-methylamino, (N-methyl-N-((diphenylmethyl)amino)carbonyl)-N-methylamino, (2-methylfuran-3-yl)sulfanyl)(1,1-spirobutyl)ethylamino, (1R)-3-(N-methyl-N-(2-hydroxyethyl))amino)-1-((phenylsulfanyl)methyl)propylamino, (1R)-3-(N-methyl-N-isopropylamino)-1-((phenylsulfanyl)methyl) propylamino, (N-methyl-N-(4-methoxyphenyl)amino) carbonyl)-N-methylamino, 1-methyl-4-(phenylsulfanyl) pyrrolidin-3-ylamino, (N-methyl-N-(4-methylphenyl) amino)carbonyl)-N-methylamino, (N-methyl-N-(2-methylphenyl)amino)carbonyl)-N-methylamino, (1R)-3-(4-methylpiperazin-1-yl)-1-((phenylsulfanyl)methyl) propylamino, 1-methylpiperidin-4-yloxy, (N-methyl-N-((S)-1-phenylethyl)amino)carbonyl)-N-methylamino, (N-methyl-N-(1-phenyl-2-(4-methylpiperazin-4-yl))amino) carbonyl)-N-methylamino, (N-methyl-N-(1-phenyl-2-(morpholin-1-yl))amino)carbonyl)-N-methylamino, (N-methyl-N-(1-phenyl-2-(N,N-dimethylamino)amino)carbonyl)-N-methylamino, (1R)-1-methyl-2-((phenylsulfanyl)methyl) ethylamino, (1S)-1-methyl-2-((phenylsulfanyl)methyl) ethylamino, (1R)-4-(4-methylpiperazin-1-yl)-1-((phenylsulfanyl)methyl)butylamino, (1R)-3-(methyl (pyridin-4-yl)amino)-1-((phenylsulfanyl)methyl) propylamino, (1R)-5-((methylsulfonylamino)-1-((phenylsulfanyl)methyl)pentylamino, (1R)-3-(4-(methylsulfonylaminocarbonyl)piperidin-1-yl)-1-((phenylsulfanyl)methyl)-propylamino, 2-((4-methyl-1,3-thiazol-2-yl)sulfanyl)ethylamino, (N-methyl-N-(4-trifluoromethoxyphenyl)amino)carbonyl)-N-methylamino, (1R)-3-(morpholin-4-ylamino)-1-((phenylsulfanyl)methyl) propylamino, (1R)-3-((2-(morpholin-4-yl)ethyl)amino)-1-((phenylsulfanyl)methyl)propylamino, (1R)-3-(morpholin- 4-yl)-3-oxo-1-((2-thienylsulfanyl)methyl)-propylamino, (1R)-3-(morpholin-4-yl)-1-((1,3-thiazol-2-ylsulfanyl)methyl)propylamino, (1R)-3-(morpholin-4-yl)-1-((thien-2-ylsulfanyl)methyl)propylamino, (1R)-3-(morpholin-4-yl)-1-((phenylsulfanyl)methyl)propylamino, (1R)-3-(morpholin-4-yl)-1-(((4-(methoxy)phenyl)sulfanyl)methyl) propylamino, (1R)-3-(morpholin-4-yl)-1-(((4-(methyl)phenyl)sulfanyl)methyl)propylamino, (1R)-3-(morpholin-4-yl)-1-((phenylsulfonyl)methyl)propylamino, (1R)-3-(morpholin-4-yl)-1-(((4-(trifluoromethoxy)phenyl)sulfanyl) methyl)propylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or $C(O)NH_2$; and $Z^1$ is 4-(4-(2-(1,3-benzodioxol-5-yl)phenylmethyl)piperazin-1-yl)phenylcarbonyl, 4-(4-(2-(benzofuran-2-ylphenyl) phenylmethyl)piperazin-1-yl)phenylcarbonyl, 4-(2-bromocyclohex-1-en-1-ylmethyl)piperazin-1-yl) phenylcarbonyl, 4-(2-bromocyclopent-1-en-1-ylmethyl) piperazin-1-yl)phenylcarbonyl, 4-(2-(4-bromophenyl) phenylmethyl)piperazin-1-yl)phenylcarbonyl, 4-(4-(2-(4-chlorophenyl)cyclohept-1-en-1-ylmethyl)piperazin-1-yl) phenylcarbonyl, 4-(1-(2-(4-chlorophenyl)cyclohex-1-en-1-ylmethyl)-1,2,3,6-tetrahydropyridin-4-yl)phenylcarbonyl, 4-(4-(2-(4-chlorophenyl)cyclohex-1-en-1-ylmethyl)piperazin-1-yl)phenylcarbonyl, 4-(4-(2-(4-chlorophenyl)cyclopent-1-en-1-ylmethyl)piperazin-1-yl)phenylcarbonyl, 4-(4-(2-(4-chlorophenyl)cyclooct-1-en-1-ylmethyl)piperazin-1-yl)phenylcarbonyl, 4-(4-((4-(4-chlorophenyl)-5,6-dihydro-2H-pyran-3-yl)methyl)piperazin-1-yl)phenylcarbonyl, 4-(4-((4-(4-chlorophenyl)-5,6-dihydro-2H-pyran-3-yl)methyl) piperazin-1-yl)phenylcarbonyl, 4-(1-((2-(4-chlorophenyl)-5, 5-dimethyl-1-cyclohex-1-en-1-yl)methyl)-1,2,3,6-tetrahydropyridin-4-yl)phenylmethyl, 4-(4-(2-(4-chlorophenyl) naphth-3-ylmethyl)piperazin-1-yl)-phenylcarbonyl, 4-(4-(2-(4-chlorophenyl)pyridin-3-ylmethyl)piperazin-1-yl)phenylcarbonyl, 4-(4-(3-(4-chlorophenyl)pyridin-4-ylmethyl)piperazin-1-yl) phenylcarbonyl, 4-(4-((4-(4-chlorophenyl)pyridin-5-yl) methyl)piperazin-1-yl)phenylcarbonyl, 4-(4-(2-(4-chlorophenyl)phenylcarbonyl)piperazin-1-yl) phenylcarbonyl, 4-(1-(2-(4-chlorophenyl)phenylcycloprop-1-yl)piperazin-1-yl)phenylcarbonyl or 4-(4-(2-(4-chlorophenyl)phenylmethyl)cyclohex-1-en-1-yl) phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, $C(O)OCH_3$ or $C(O)NH_2$; $B^1$ is (1R)-3-(4-(hydroxyaminocarbonyl)piperidin-1-yl)-1-((phenylsulfanyl) methyl)propylamino, (1R)-3-(2-hydroxy-2-methylpropyl) amino)-1-((phenylsulfanyl)methyl)propylamino, (1R)-3-(4-hydroxypiperidin-1-yl)-1-((phenylsulfanyl)methyl) propylamino, (3R)-3-(3-hydroxypyrrolidin-1-yl)-1-((phenylsulfanyl)methyl)propylamino, isopropylamino, (1R)-3-(isopropylamino)-1-((phenylsulfanyl)methyl)propylamino, (1R)-3-(1H-imidazol-1-yl)-1-((phenylsulfanyl)methyl)propylamino, (1R)-3-(isopropyl(methyl)amino)-1-((phenylsulfanyl)methyl)-propylamino, (4-methoxycyclohex-1-yl)methyl)amino, (1R)-3-(4-(methoxyimino)piperidin-1-yl)-1-((phenylsulfanyl)methyl)-propylamino, (1R)-3-(N-methyl-N-carboxymethyl)amino)-1-((phenylsulfanyl)methyl)propylamino, (methyl)(cyclohexyl) amino,(methyl)(cyclohexylmethyl)amino, (1R)-3-(2-methyl-4,5-dihydro-1H-imidazol-1-yl)-1-((phenylsulfanyl) methyl)propylamino, (3R)-3-(N-methyl-N-(dimethylcarbonylmethyl))-1-((phenylsulfanyl)methyl) propylamino, (1R)-3-(N-methyl-N-(1,1-dimethylethyl) amino)-1-((phenylsulfanyl)methyl)propylamino, (N-methyl-N-(1,2-diphenyl)amino)carbonyl)-N-methylamino, (N-methyl-N-((diphenylmethyl)amino)carbonyl)-N-methylamino, (2-methylfuran-3-yl)sulfanyl)-(1,1-spirobutyl)ethylamino, (1R)-3-(N-methyl-N-(2-hydroxyethyl))amino)-1-((phenylsulfanyl)methyl)propylamino, (1R)-3-(N-methyl-N-isopropylamino)-1-((phenylsulfanyl)methyl)propylamino, (N-methyl-N-(4-methoxyphenyl)amino)carbonyl)-N-methylamino, 1-methyl-4-(phenylsulfanyl)pyrrolidin-3-ylamino, (N-methyl-N-(4-methylphenyl)amino)carbonyl)-N-methylamino, (N-methyl-N-(2-methylphenyl)amino) carbonyl)-N-methylamino, (1R)-3-(4-methylpiperazin-1-yl)-1-((phenylsulfanyl)methyl)propylamino, 1-methylpiperidin-4-yloxy, (N-methyl-N-((S)-1-phenylethyl)amino)carbonyl)-N-methylamino, (N-methyl-N-(1-phenyl-2-(4-methylpiperazin-4-yl))amino)carbonyl)-N-methylamino, (N-methyl-N-(1-phenyl-2-(morpholin-1-yl)) amino)carbonyl)-N-methylamino, (N-methyl-N-(1-phenyl-2-(N,N-dimethylamino))amino)carbonyl)-N-methylamino, (1R)-1-methyl-2-((phenylsulfanyl)methyl)ethylamino, (1S)-1-methyl-2-((phenylsulfanyl)methyl)ethylamino, (1R)-4-(4-methylpiperazin-1-yl)-1-((phenylsulfanyl)methyl)butylamino, (1R)-3-(methyl(pyridin-4-yl)amino)-1-((phenylsulfanyl)methyl)propylamino, (1R)-5-((methylsulfonylamino)-1-((phenylsulfanyl)methyl) pentylamino, (1R)-3-(4-(methylsulfonylaminocarbonyl) piperidin-1-yl)-1-((phenylsulfanyl)methyl)-propylamino, 2-((4-methyl-1,3-thiazol-2-yl)sulfanyl)ethylamino, (N-methyl-N-(4-trifluoromethoxyphenyl)amino)carbonyl)-N-methylamino, (1R)-3-(morpholin-4-ylamino)-1-((phenylsulfanyl)methyl)propylamino, (1R)-3-((2-(morpholin-4-yl)ethyl) amino)-1-((phenylsulfanyl)methyl)propylamino, (1R)-3-(morpholin-4-yl)-3-oxo-1-((2-thienylsulfanyl)methyl)-propylamino, (1R)-3-(morpholin-4-yl)-1-((1,3-thiazol-2-ylsulfanyl)methyl)propylamino, (1R)-3-(morpholin-4-yl)-1-((thien-2-ylsulfanyl)methyl)propylamino, (1R)-3-(morpholin-4-yl)-1-((phenylsulfanyl)methyl)propylamino, (1R)-3-(morpholin-4-yl)-1-(((4-(methoxy)phenyl)sulfanyl) methyl)propylamino, (1R)-3-(morpholin-4-yl)-1-(((4-(methyl)phenyl)sulfanyl)methyl)propylamino, (1R)-3-(morpholin-4-yl)-1-((phenylsulfonyl)-methyl)propylamino, (1R)-3-(morpholin-4-yl)-1-(((4-(trifluoromethoxy)phenyl)sulfanyl) methyl)propylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or $C(O)NH_2$; and $Z^1$ is 4-(5-(2-(4-chlorophenyl)phenylmethyl)hexahydropyrrolo[3,4-c]pyrrol-2(1H)-yl)phenylcarbonyl, 4-(4-(2-(4-chlorophenyl)phenylmethyl)-piperazin-1-yl)phenylcarbonyl, 4-(4-(2-(4-chlorophenyl)phenylmethyl)-4-methoxypiperidin-1-yl)phenylcarbonyl, 4-(4-(2-(4-chlorophenyl)phenylmethyl)piperazin-1-yl)-3,5-difluorophenylcarbonyl, 4-(4-(2-(4-chlorophenyl)phenylmethyl)piperazin-1-yl)-2-fluorophenylcarbonyl, 4-(4-(2-(4-chlorophenyl) phenylmethyl)piperazin-1-yl)-3-fluorophenylcarbonyl, 2-(4-(2-(4-chlorophenyl)phenylmethyl)piperazin-1-yl)pyridin-5-ylcarbonyl, 4-(1-(2-(4-chlorophenyl)phenylmethyl) piperidin-4-yl)phenylcarbonyl, 5-(4-(2-(4-chlorophenyl) phenylmethyl)piperazin-1-yl)pyridin-2-ylcarbonyl, 4-(1-(2-(4-chlorophenyl)phenylmethyl)-1,2,3,6-tetrahydropyridin-4-yl)phenylcarbonyl, 4-(4-(2-(cyclohex-1-ylamino) phenylmethyl)piperazin-1-yl)phenylcarbonyl4-(4-(2-cyclohex-1-ylphenylmethyl)piperazin-1-yl)phenylcarbonyl, 4-(4-(2-(3-cyanophenyl)phenylmethyl)piperazin-1-yl)phenylcarbonyl, 4-(4-(2-(2,4-dichlorophenyl)phenylmethyl) piperazin-1-yl)phenylcarbonyl, 4-(4-(2-(3,4-dichlorophenyl)phenylmethyl)piperazin-1-yl)phenylcarbonyl, 4-(4-(2-(2,4-difluorophenyl)phenylmethyl)piperazin-1-yl) phenylcarbonyl, 4-(2-(1,3-dihydro-2H-isoindol-2-yl) phenylmethyl)piperazin-1-yl)phenylcarbonyl, 4-(4-(3-(1,1- dimethylethoxycarbonylamino)phenyl)piperazin-1-yl) phenylcarbonyl, 4-(2-(4-(2-(dimethylamino)ethoxy)phenyl) phenylmethyl)piperazin-1-yl)phenylcarbonyl or 4-(4-(3-(dimethylamino)phenyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-3-(4-(hydroxyaminocarbonyl)piperidin-1-yl)-1-((phenylsulfanyl) methyl)propylamino, (1R)-3-(2-hydroxy-2-methylpropyl) amino)-1-((phenylsulfanyl)methyl)propylamino, (1R)-3-(4-hydroxypiperidin-1-yl)-1-((phenylsulfanyl)methyl) propylamino, (3R)-3-(3-hydroxypyrrolidin-1-yl)-1-((phenylsulfanyl)methyl)propylamino, isopropylamino, (1R)-3-(isopropylamino)-1-((phenylsulfanyl)methyl)propylamino, (1R)-3-(1H-imidazol-1-yl)-1-((phenylsulfanyl)methyl)propylamino, (1R)-3-(isopropyl(methyl)amino)-1-((phenylsulfanyl)methyl)propylamino, (4-methoxycyclohex-1-yl)methyl)amino, (1R)-3-(4-(methoxyimino)piperidin-1-yl)-1-((phenylsulfanyl)methyl)propylamino, (1R)-3-(N-methyl-N-carboxymethyl)amino)-1-((phenylsulfanyl)methyl)propylamino, (methyl)(cyclohexyl) amino, (methyl)(cyclohexylmethyl)amino, (1R)-3-(2-methyl-4,5-dihydro-1H-imidazol-1-yl)-1-((phenylsulfanyl) methyl)propylamino, (3R)-3-(N-methyl-N-(dimethylcarbonylmethyl))-1-((phenylsulfanyl)methyl) propylamino, (1R)-3-(N-methyl-N-(1,1-dimethylethyl) amino)-1-((phenylsulfanyl)methyl)propylamino, (N-methyl-N-(1,2-diphenyl)amino)carbonyl)-N-methylamino, (N-methyl-N-((diphenylmethyl)amino)carbonyl)-N-methylamino, (2-methylfuran-3-yl)sulfanyl)-(1,1-spirobutyl)ethylamino, (1R)-3-(N-methyl-N-(2-hydroxyethyl))amino)-1-((phenylsulfanyl)methyl)propylamino, (1R)-3-(N-methyl-N-isopropylamino)-1-((phenylsulfanyl)methyl) propylamino, (N-methyl-N-(4-methoxyphenyl)amino) carbonyl)-N-methylamino, 1-methyl-4-(phenylsulfanyl) pyrrolidin-3-ylamino, (N-methyl-N-(4-methylphenyl) amino)carbonyl)-N-methylamino, (N-methyl-N-(2-methylphenyl)amino)carbonyl)-N-methylamino, (1R)-3-(4-methylpiperazin-1-yl)-1-((phenylsulfanyl)methyl) propylamino, 1-methylpiperidin-4-yloxy, (N-methyl-N-((S)-1-phenylethyl)amino)carbonyl)-N-methylamino, (N-methyl-N-(1-phenyl-2-(4-methylpiperazin-4-yl))amino) carbonyl)-N-methylamino, (N-methyl-N-(1-phenyl-2-(morpholin-1-yl))amino)carbonyl)-N-methylamino, (N-methyl-N-(1-phenyl-2-(N,N-dimethylamino))amino)carbonyl)-N-methylamino, (1R)-1-methyl-2-((phenylsulfanyl)methyl) ethylamino, (1S)-1-methyl-2-((phenylsulfanyl)methyl) ethylamino, (1R)-4-(4-methylpiperazin-1-yl)-1-((phenylsulfanyl)methyl)butylamino, (1R)-3-(methyl (pyridin-4-yl)amino)-1-((phenylsulfanyl)methyl) propylamino, (1R)-5-((methylsulfonylamino)-1-((phenylsulfanyl)methyl)pentylamino, (1R)-3-(4-(methylsulfonylaminocarbonyl)piperidin-1-yl)-1-((phenylsulfanyl)methyl)propylamino, 2-((4-methyl-1,3-thiazol-2-yl)sulfanyl)ethylamino, (N-methyl-N-(4-trifluoromethoxyphenyl)amino)carbonyl)-N-methylamino, (1R)-3-(morpholin-4-ylamino)-1-((phenylsulfanyl)methyl) propylamino, (1R)-3-((2-(morpholin-4-yl)ethyl)amino)-1-((phenylsulfanyl)methyl)propylamino, (1R)-3-(morpholin-4-yl)-3-oxo-1-((2-thienylsulfanyl)methyl)propylamino, (1R)-3-(morpholin-4-yl)-1-((1,3-thiazol-2-ylsulfanyl)methyl)propylamino, (1R)-3-(morpholin-4-yl)-1-((thien-2-yl-sulfanyl)methyl)propylamino, (1R)-3-(morpholin-4-yl)-1-((phenylsulfanyl)methyl)propylamino, (1R)-3-(morpholin-4-yl)-1-(((4-(methoxy)phenyl)sulfanyl)methyl) propylamino, (1R)-3-(morpholin-4-yl)-1-(((4-(methyl) phenyl)sulfanyl)methyl)propylamino, (1R)-3-(morpholin-4-yl)-1-((phenylsulfonyl)methyl)propylamino, (1R)-3-(morpholin-4-yl)-1-(((4-(trifluoromethoxy)phenyl)sulfanyl) methyl)propylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or $C(O)NH_2$; and $Z^1$ is 4-(2-(4-(dimethylamino)phenyl)phenylcarbonyl)piperazin-1-yl)phenylcarbonyl, 4-(4-(2-(4-(dimethylamino)phenyl)phenylmethyl)piperazin-1-yl)phenylcarbonyl, 4-(4-((2-(4-(dimethylamino)phenyl)pyridin-3-yl)methyl)piperazin-1-yl)phenylcarbonyl, 4-(4-(2-(5,5-dimethyl-2-oxo-1,3-oxazolidin-3-yl)phenylmethyl)-piperazin-1-yl) phenylcarbonyl, 4-(4-(2-(4-fluorophenyl)cyclopent-1-en-1-ylmethyl)piperazin-1-yl)phenylcarbonyl, 4-(4-(2-(4-fluorophenyl)-3-fluorophenylmethyl)piperazin-1-yl) phenylcarbonyl, 4-(4-(2-(4-fluorophenyl)phenylmethyl) piperazin-1-yl)phenylcarbonyl, 4-(4-((2-(4-fluorophenyl) pyridin-3-yl)methyl)piperazin-1-yl)phenylcarbonyl, 4-(2-(isopropylamino)phenylmethyl)-piperazin-1-yl) phenylcarbonyl, 4-(4-(2-(4-(isopropylsulfanyl)phenyl) phenylmethyl)piperazin-1-yl)phenylcarbonyl, 4-(4-(2-(4-methoxyphenyl)cyclopent-1-en-1-ylmethyl)piperazin-1-yl) phenylcarbonyl, 4-(4-(2-(3-methoxyphenyl)phenylmethyl) piperazin-1-yl)phenylcarbonyl, 4-(4-(2-(4-methoxyphenyl) phenylmethyl)piperazin-1-yl)phenylcarbonyl, 4-(4-((2-(4-methoxyphenyl)pyridin-3-yl)methyl)piperazin-1-yl) phenylcarbonyl, 4-(4-methoxy-4-(2-(pyridin-3-yl) phenylmethyl)piperidin-1-yl)phenylcarbonyl, 4-(4-(2-(2-methyl-4-dichlorophenyl)phenylmethyl)piperazin-1-yl) phenylcarbonyl, 4-(4-(2-(2-methylphenyl)phenylmethyl)-piperazin-1-yl)phenylcarbonyl, 4-(4-(2-(4-(methylsulfonyl)-phenyl)methyl)piperazin-1-yl)phenylcarbonyl, 4-(4-(2-(4-methylsulfonylphenyl)phenylmethyl)piperazin-1-yl) phenylcarbonyl or 4-(4-((2-(4-methylsulfonylphenyl) pyridin-3-yl)methyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-3-(4-(hydroxyaminocarbonyl)piperidin-1-yl)-1-((phenylsulfanyl) methyl)propylamino, (1R)-3-(2-hydroxy-2-methylpropyl) amino)-1-((phenylsulfanyl)methyl)propylamino, (1R)-3-(4-hydroxypiperidin-1-yl)-1-((phenylsulfanyl)methyl) propylamino, (3R)-3-(3-hydroxypyrrolidin-1-yl)-1-((phenylsulfanyl)methyl)propylamino, isopropylamino, (1R)-3-(isopropylamino)-1-((phenylsulfanyl)methyl)propylamino, (1R)-3-(1H-imidazol-1-yl)-1-((phenylsulfanyl)methyl)propylamino, (1R)-3-(isopropyl(methyl)amino)-1-((phenylsulfanyl)methyl)propylamino, (4-methoxycyclohex-1-yl)methyl)amino, (1R)-3-(4-(methoxyimino)piperidin-1-yl)-1-((phenylsulfanyl)methyl)propylamino, (1R)-3-(N-methyl-N-carboxymethyl)amino)-1-((phenylsulfanyl)methyl)propylamino, (methyl)(cyclohexyl) amino, (methyl)(cyclohexylmethyl)amino, (1R)-3-(2-methyl-4,5-dihydro-1H-imidazol-1-yl)-1-((phenylsulfanyl) methyl)propylamino, (3R)-3-(N-methyl-N-(dimethylcarbonylmethyl))-1-((phenylsulfanyl)methyl) propylamino, (1R)-3-(N-methyl-N-(1,1-dimethylethyl) amino)-1-((phenylsulfanyl)methyl)propylamino, (N-methyl-N-(1,2-diphenyl)amino)carbonyl)-N-methylamino, (N-methyl-N-((diphenylmethyl)amino)carbonyl)-N-methylamino, (2-methylfuran-3-yl)sulfanyl)-(1,1-spirobutyl)ethylamino, (1R)-3-(N-methyl-N-(2-hydroxyethyl))amino)-1-((phenylsulfanyl)methyl)propylamino, (1R)-3-(N-methyl-N-isopropylamino)-1-((phenylsulfanyl)methyl) propylamino, (N-methyl-N-(4-methoxyphenyl)amino) carbonyl)-N-methylamino, 1-methyl-4-(phenylsulfanyl) pyrrolidin-3-ylamino, (N-methyl-N-(4-methylphenyl)

amino)carbonyl)-N-methylamino, (N-methyl-N-(2-methylphenyl)amino)carbonyl)-N-methylamino, (1R)-3-(4-methylpiperazin-1-yl)-1-((phenylsulfanyl)methyl)propylamino, 1-methylpiperidin-4-yloxy, (N-methyl-N-((S)-1-phenylethyl)amino)carbonyl)-N-methylamino, (N-methyl-N-(1-phenyl-2-(4-methylpiperazin-4-yl))amino)carbonyl)-N-methylamino, (N-methyl-N-(1-phenyl-2-(morpholin-1-yl))amino)carbonyl)-N-methylamino, (N-methyl-N-(1-phenyl-2-(N,N-dimethylamino))amino)carbonyl)-N-methylamino, (1R)-1-methyl-2-((phenylsulfanyl)methyl) ethylamino, (1S)-1-methyl-2-((phenylsulfanyl)methyl)ethylamino, (1R)-4-(4-methylpiperazin-1-yl)-1-((phenylsulfanyl)methyl)butylamino, (1R)-3-(methyl(pyridin-4-yl)amino)-1-((phenylsulfanyl)methyl)propylamino, (1R)-5-((methylsulfonylamino)-1-((phenylsulfanyl)methyl)pentylamino, (1R)-3-(4-(methylsulfonylaminocarbonyl)piperidin-1-yl)-1-((phenylsulfanyl)methyl)propylamino, 2-((4-methyl-1,3-thiazol-2-yl)sulfanyl)ethylamino, (N-methyl-N-(4-trifluoromethoxyphenyl)amino)carbonyl)-N-methylamino, (1R)-3-(morpholin-4-ylamino)-1-((phenylsulfanyl)methyl)propylamino, (1R)-3-((2-(morpholin-4-yl)ethyl)amino)-1-((phenylsulfanyl)methyl)propylamino, (1R)-3-(morpholin-4-yl)-3-oxo-1-((2-thienylsulfanyl)methyl)propylamino, (1R)-3-(morpholin-4-yl)-1-((1,3-thiazol-2-ylsulfanyl)methyl)propylamino, (1R)-3-(morpholin-4-yl)-1-((thien-2-ylsulfanyl)methyl)propylamino, (1R)-3-(morpholin-4-yl)-1-((phenylsulfanyl)methyl)propylamino, (1R)-3-(morpholin-4-yl)-1-(((4-(methoxy)phenyl)sulfanyl)methyl)propylamino, (1R)-3-(morpholin-4-yl)-1-(((4-(methyl)phenyl)sulfanyl)methylpropylamino, (1R)-3-(morpholin-4-yl)-1-((phenylsulfonyl)methyl)propylamino, (1R)-3-(morpholin-4-yl)-1-(((4-(trifluoromethoxy)phenyl)sulfanyl)methyl)propylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or $C(O)NH_2$; and $Z^1$ is 4-(4-(2-(5-methylthien-2-yl)phenylmethyl)piperazin-1-yl)phenylcarbonyl, 4-(4-(2-(4-methylsulfanylphenyl)cyclohex-1-en-1-ylmethyl)piperazin-1-yl)phenylcarbonyl, 4-(4-(2-(4-methylsulfanylphenyl)phenylcarbonyl)piperazin-1-yl)phenylcarbonyl, 4-(4-((2-(4-methylsulfanylphenyl)pyridin-3-yl)methyl)piperazin-1-yl)phenylcarbonyl, 4-(4-(2-(4-methylsulfanylphenyl)phenylmethyl)piperazin-1-yl)phenylcarbonyl, 4-(4-(2-(4-(2-(morpholin-1-yl)ethoxy)phenyl)phenylmethyl)piperazin-1-yl)phenylcarbonyl, 4-(4-(2-(morpholin-1-yl)phenylmethyl)piperazin-1-yl)phenylcarbonyl, 4-(4-(2-(naphth-1-yl)phenylmethyl)piperazin-1-yl)phenylcarbonyl, 4-(4-(2-(naphth-2-yl)phenylmethyl)piperazin-1-yl)phenylcarbonyl or 4-(4-(2-(4-phenoxyphenyl)phenylmethyl)piperazin-1-yl)phenylcarbonyl, 4-(4-((1-phenyl-1H-imidazol-2-yl)methyl)piperazin-1-yl)phenylcarbonyl, 4-(4-((1-phenyl-1H-imidazol-5-yl)methyl)piperazin-1-yl)phenylcarbonyl, 4-(2-((phenylmethyl)amino)phenylmethyl)piperazin-1-yl)phenylcarbonyl, 4-(4-(2-(phenyl)phenylmethyl)-4-(2-(dimethylamino)ethoxy))piperidin-1-yl)phenylcarbonyl, 4-((2-(phenyl)phenylmethyl)-4-methoxypiperidin-1-yl)phenylcarbonyl, 4-(4-(2-(phenyl)phenylmethyl)-4-(2-(morpholin-1-yl)ethoxy))piperidin-1-yl)phenylcarbonyl, 4-(4-(2-(phenyl)phenylmethyl)piperazin-1-yl)phenylcarbonyl, 4-(4-(3-(phenyl)phenylmethyl)piperazin-1-yl)phenylcarbonyl, 4-(4-(2-(4-(phenyl)phenyl)phenylmethyl)piperazin-1-yl)phenylcarbonyl or 4-(4-(2-(phenyl)phenylmethyl)-4-(2-(piperidin-1-yl)ethoxy))piperidin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, $C(O)OCH_3$ or $C(O)NH_2$; $B^1$ is (1R)-3-(4-(hydroxyaminocarbonyl)piperidin-1-yl)-1-((phenylsulfanyl)methyl)propylamino, (1R)-3-(2-hydroxy-2-methylpropyl)amino)-1-((phenylsulfanyl)methyl)propylamino, (1R)-3-(4-hydroxypiperidin-1-yl)-1-((phenylsulfanyl)methyl)propylamino, (3R)-3-(3-hydroxypyrrolidin-1-yl)-1-((phenylsulfanyl)methyl)propylamino, isopropylamino, (1R)-3-(isopropylamino)-1-((phenylsulfanyl)methyl)propylamino, (1R)-3-(1H-imidazol-1-yl)-1-((phenylsulfanyl)methyl)propylamino, (1R)-3-(isopropyl(methyl)amino)-1-((phenylsulfanyl)methyl)-propylamino, (4-methoxycyclohex-1-yl)methyl)amino, (1R)-3-(4-(methoxyimino)piperidin-1-yl)-1-((phenylsulfanyl)methyl)propylamino, (1R)-3-(N-methyl-N-carboxymethyl)amino)-1-((phenylsulfanyl)methyl)propylamino, (methyl)(cyclohexyl)amino, (methyl)(cyclohexylmethyl)amino, (1R)-3-(2-methyl-4,5-dihydro-1H-imidazol-1-yl)-1-((phenylsulfanyl)methyl)propylamino, (3R)-3-(N-methyl-N-(dimethylcarbonylmethyl))-1-((phenylsulfanyl)methyl)propylamino, (1R)-3-(N-methyl-N-(1,1-dimethylethyl)amino)-1-((phenylsulfanyl)methyl)propylamino, (N-methyl-N-(1,2-diphenyl)amino)carbonyl)-N-methylamino, (N-methyl-N-((diphenylmethyl)amino)carbonyl)-N-methylamino, (2-methylfuran-3-yl)sulfanyl)-(1,1-spirobutyl)ethylamino, (1R)-3-(N-methyl-N-(2-hydroxyethyl))amino)-1-((phenylsulfanyl)methyl)propylamino, (1R)-3-(N-methyl-N-isopropylamino)-1-((phenylsulfanyl)methyl)propylamino, (N-methyl-N-(4-methoxyphenyl)amino)carbonyl)-N-methylamino, 1-methyl-4-(phenylsulfanyl)pyrrolidin-3-ylamino, (N-methyl-N-(4-methylphenyl)amino)carbonyl)-N-methylamino, (N-methyl-N-(2-methylphenyl)amino)carbonyl)-N-methylamino, (1R)-3-(4-methylpiperazin-1-yl)-1-((phenylsulfanyl)methyl)propylamino, 1-methylpiperidin-4-yloxy, (N-methyl-N-((S)-1-phenylethyl)amino)carbonyl)-N-methylamino, (N-methyl-N-(1-phenyl-2-(4-methylpiperazin-4-yl))amino)carbonyl)-N-methylamino, (N-methyl-N-(1-phenyl-2-(morpholin-1-yl))amino)carbonyl)-N-methylamino, (N-methyl-N-(1-phenyl-2-(N,N-dimethylamino))amino)carbonyl)-N-methylamino, (1R)-1-methyl-2-((phenylsulfanyl)methyl)ethylamino, (1S)-1-methyl-2-((phenylsulfanyl)methyl)ethylamino, (1R)-4-(4-methylpiperazin-1-yl)-1-((phenylsulfanyl)methyl)butylamino, (1R)-3-(methyl(pyridin-4-yl)amino)-1-((phenylsulfanyl)methyl)propylamino, (1R)-5-((methylsulfonylamino)-1-((phenylsulfanyl)methyl)pentylamino, (1R)-3-(4-(methylsulfonylaminocarbonyl)piperidin-1-yl)-1-((phenylsulfanyl)methyl)propylamino, 2-((4-methyl-1,3-thiazol-2-yl)sulfanyl)ethylamino, (N-methyl-N-(4-trifluoromethoxyphenyl)amino)carbonyl)-N-methylamino, (1R)-3-(morpholin-4-ylamino)-1-((phenylsulfanyl)methyl)propylamino, (1R)-3-((2-(morpholin-4-yl)ethyl)amino)-1-((phenylsulfanyl)methyl)propylamino, (1R)-3-(morpholin-4-yl)-3-oxo-1-((2-thienylsulfanyl)methyl)propylamino, (1R)-3-(morpholin-4-yl)-1-((1,3-thiazol-2-ylsulfanyl)methyl)propylamino, (1R)-3-(morpholin-4-yl)-1-((thien-2-ylsulfanyl)methyl)propylamino, (1R)-3-(morpholin-4-yl)-1-((phenylsulfanyl)methyl)propylamino, (1R)-3-(morpholin-4-yl)-1-(((4-(methoxy)phenyl)sulfanyl)methyl)propylamino, (1R)-3-(morpholin-4-yl)-1-(((4-(methyl)phenyl)sulfanyl)methyl)propylamino, (1R)-3-(morpholin-4-yl)-1-((phenylsulfonyl)methyl)propylamino, (1R)-3-(morpholin-4-yl)-1-(((4-(trifluoromethoxy)phenyl)sulfanyl)methyl)propylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or $C(O)NH_2$; and $Z^1$ is 4-(4-(2-(phenyl)phenylmethyl)-4-(2-(pyrrolidin-1-yl)ethoxy))piperidin-1-yl)phenylcarbonyl, 4-(4-((2-(phenyl)pyridin-3-yl)methyl)piperazin-1-yl)phenylcarbonyl, 4-(4-

((1-phenyl-1H-pyrazol-5-yl)methyl)piperazin-1-yl) phenylcarbonyl, 4-(4-(2-(piperidin-1-yl)phenylmethyl) piperazin-1-yl)phenylcarbonyl, 4-(4-(2-(pyrid-3-yl)phenyl) phenylmethyl)piperazin-1-yl)phenylcarbonyl, 4-(4-(2-(quinolin-3-ylphenyl)phenylmethyl)piperazin-1-yl) phenylcarbonyl, 4-(4-(2-(quinolin-8-ylphenyl) phenylmethyl)piperazin-1-yl)phenylcarbonyl, 4-(4-(2-(thien-2-yl)phenylmethyl)-4-methoxypiperazin-1-yl) phenylcarbonyl, 4-(4-(2-(thien-2-yl)phenylmethyl) piperazin-1-yl)phenylcarbonyl, 4-(4-(2-(4-trifluoromethoxyphenyl)phenylmethyl)piperazin-1-yl) phenylcarbonyl or 4-(4-(2-(4-trifluoromethyl-phenyl) phenylmethyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-3-((1S,4S)-2-oxa-5-azabicyclo[2.2.1]hept-5-yl)-1-((phenylsulfanyl)methyl)propylamino, (1R)-3-((1R,4R)-2-oxa-5-azabicyclo[2.2.1]hept-5-yl)-1-((phenylsulfanyl)methyl)propylamino, (1R)-3-oxo-3-(azetidin-1-yl)-1-((phenylsulfanyl)methyl) propylamino, (1R)-3-oxo-3-(cyclobutylamino)-1-((phenylsulfanyl)methyl)propylamino, (1R)-3-oxo-3-(cyclopropylamino)-1-((phenylsulfanyl)methyl)propylamino, (1R)-3-oxo-3-(dimethylamino)-1-((phenylsulfanyl)methyl) propylamino, (1R)-3-oxo-3-(dimethylamino)-1-((phenylsulfonylmethyl)methyl)propylamino, (1R)-3-oxo-3-(dimethylamino)-1-((pyrimidin-1-ylsulfanyl)methyl) propylamino, (1R)-3-oxo-3-((1,1-dimethylethyl)amino)-1-((phenylsulfanyl)methyl)propylamino, (1R)-3-oxo-3-(diisopropylamino)-1-((phenylsulfanyl)methyl)-propylamino, (1R)-3-oxo-3-(1,1-dioxothiomorpholin-4-yl)-1-((phenylsulfanyl)methyl)propylamino, (1R)-3-oxo-3-(N-methyl-N-(1,1-dimethylethyl)amino)-1-((phenylsulfanyl) methyl)propylamino, (1R)-3-oxo-3-(piperidin-1-yl)-1-((phenylsulfanyl)methyl)propylamino, (1R)-3-oxo-3-amino-1-((phenylsulfanyl)methyl)propylamino, (1R)-3-oxo-3-(methylamino)-1-((phenylsulfanyl)methyl) propylamino, (1R)-3-oxo-3-(4-methylpiperazin-1-yl)-1-((phenylsulfanyl)methyl)propylamino, (1R)-3-oxo-3-(morpholin-1-yl)-1-((phenylsulfanyl)methyl)propylamino, (1R)-3-oxo-3-(2-(morpholin-1-yl)ethyl)-1-((phenylsulfanyl) methyl)propylamino, (2-phenoxyethyl)amino, 4-(1-(phenylmethyl)piperidin-4-yl)amino, 4-(1-(phenylmethyl)piperidin-4-yl)methylamino, (4-phenyl-1,3-thiazol-2-ylsulfanyl) ethylamino, (1R,2S)-2-(phenylsulfanyl)cyclohex-1-ylamino, (1S,2R)-2-(phenylsulfanyl)cyclohex-1-ylamino, 2-(phenylsulfanyl)cyclopentylamino, 2-(phenylsulfanyl) ethoxy, 2-(phenylsulfanyl)ethylamino, 2-(phenylsulfonyl) ethylamino, (1R)-1-((phenylsulfanyl)methyl)-3-(morpholin-4-yl)propylamino, (1R)-1-((phenylsulfanyl)methyl)-3-((2,2,2-trifluoroethyl)amino)propylamino, 4-(phenylsulfonyl) tetrahydrofuran-3-ylamino, 4-(phenylsulfanyl) tetrahydrofuran-3-ylamino, (1R)-1-((phenylsulfanyl) methyl)-3-((2,2,2-trifluoroethyl)amino)propylamino, (1S)-1-((phenylsulfanyl)methyl)propylamino, (1R)-1-((phenylsulfanyl)methyl)-3-(pyridin-4-ylsulfanyl) propylamino, (1R)-1-((phenylsulfanyl)methyl)-3-(thiomorpholin-4-yl)propylamino, (1R)-1-((phenylsulfanyl) methyl)-3-(piperazin-1-yl)propylamino, (1R)-1-((phenylsulfanyl)methyl)-3-((2-(pyridin-2-yl)ethyl)amino) propylamino, (1R)-1-((phenylsulfanyl)methyl)-3-((pyridin-4-ylmethyl)amino)propylamino, (1R)-1-((phenylsulfanyl) methyl)-3-(pyridin-3-ylamino)propylamino, (1R)-1-((phenylsulfanyl)methyl)-3-(pyrrolidin-1-ylamino) propylamino), (1R)-1-((phenylsulfanyl)methyl)-3-(2H-tetrazol-5-yl)propylamino, (1R)-1-((phenylsulfanyl) methyl)-3-(pyrrolidin-1-yl)propylamino, (1R)-1-((phenylsulfanyl)methyl)3-((pyridin-2-ylmethyl)amino) propylamino, (1S)-2-(phenylsulfanyl)-1-(pyridin-3-ylmethyl)ethylamino, (3S,4R)-(phenylsulfanyl)pyrrolidin-4-ylamino, 2-(phenylsulfanyl)-1,1-spirobutylethylamino, 2-(phenylsulfanyl)-1,1-spiroethylethylamino, 2-(phenylsulfanyl)-1,1-spiropentylethylamino, piperidin-4-yloxy, (1-propylpiperidin-4-yl)methylamino, pyran-4-ylamino, 2-(pyridin-4-ylsulfanyl)ethylamino, 2-(pyrimidin-2-ylsulfanyl) ethylamino, 1,1-spirobutyl-2-(phenylsulfanyl)ethyl, 2-(thien-2-ylsulfanyl)ethylamino, sulfanylpyran-4-ylamino, (1R)-3-(2-(2H-tetrazol-3-yl)pyrrolidin-1-yl)-1-((phenylsulfanyl)methyl)propylamino, (1R)-3-(3-(2H-tetrazol-3-yl)azetidin-1-yl)-1-((phenylsulfanyl)methyl)propylamino or 2-(1,3-thiazol-2-ylsulfanyl)ethylamino; $D^1$ is H, F, Cl or CF$_3$; $E^1$ is H, F or Cl; $Y^1$ is H, CN, NO$_2$, F, Cl, CF$_3$, OCF$_3$, NH$_2$ or C(O)NH$_2$; and $Z^1$ Z is 4-(4-(2-(1,3-benzodioxol-5-yl)phenylmethyl)piperazin-1-yl)phenylcarbonyl, 4-(4-(2-(benzofuran-2-ylphenyl)phenylmethyl)piperazin-1-yl)phenylcarbonyl, 4-(2-bromocyclohex-1-en-1-ylmethyl)piperazin-1-yl) phenylcarbonyl, 4-(2-bromocyclopent-1-en-1-ylmethyl) piperazin-1-yl)phenylcarbonyl, 4-(2-(4-bromophenyl) phenylmethyl)piperazin-1-yl)phenylcarbonyl, 4-(4-(2-(4-chlorophenyl)cyclohept-1-en-1-ylmethyl)piperazin-1-yl) phenylcarbonyl, 4-(1-(2-(4-chlorophenyl)cyclohex-1-en-1-ylmethyl)-1,2,3,6-tetrahydropyridin-4-yl)phenylcarbonyl, 4-(4-(2-(4-chlorophenyl)cyclohex-1-en-1-ylmethyl)piperazin-1-yl)phenylcarbonyl, 4-(4-(2-(4-chlorophenyl)cyclopent-1-en-1-ylmethyl)piperazin-1-yl)phenylcarbonyl, 4-(4-(2-(4-chlorophenyl)cyclooct-1-en-1-ylmethyl)piperazin-1-yl)phenylcarbonyl, 4-(4-((4-(4-chlorophenyl)-5,6-dihydro-2H-pyran-3-yl)methyl)piperazin-1-yl)phenylcarbonyl, 4-(4-((4-(4-chlorophenyl)-5,6-dihydro-2H-pyran-3-yl)methyl) piperazin-1-yl)phenylcarbonyl, 4-(1-((2-(4-chlorophenyl)-5,5-dimethyl-1-cyclohex-1-en-1-yl)methyl)-1,2,3,6-tetrahydropyridin-4-yl)phenylmethyl, 4-(4-(2-(4-chlorophenyl)naphth-3-ylmethyl)piperazin-1-yl) phenylcarbonyl, 4-(4-(2-(4-chlorophenyl)pyridin-3-ylmethyl)piperazin-1-yl)phenylcarbonyl, 4-(4-(3-(4-chlorophenyl)pyridin-4-ylmethyl)piperazin-1-yl) phenylcarbonyl, 4-(4-((4-(4-chlorophenyl)pyridin-5-yl) methyl)piperazin-1-yl)phenylcarbonyl, 4-(4-(2-(4-chlorophenyl)phenylcarbonyl)piperazin-1-yl) phenylcarbonyl, 4-(1-(2-(4-chlorophenyl)phenylcycloprop-1-yl)piperazin-1-yl)phenylcarbonyl or 4-(4-(2-(4-chlorophenyl)phenylmethyl)cyclohex-1-en-1-yl) phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-3-((1S,4S)-2-oxa-5-azabicyclo[2.2.1]hept-5-yl)-1-((phenylsulfanyl)methyl)propylamino, (1R)-3-((1R,4R)-2-oxa-5-azabicyclo[2.2.1]hept-5-yl)-1-((phenylsulfanyl)methyl)propylamino, (1R)-3-oxo-3-(azetidin-1-yl)-1-((phenylsulfanyl)methyl) propylamino, (1R)-3-oxo-3-(cyclobutylamino)-1-((phenylsulfanyl)methyl)propylamino, (1R)-3-oxo-3-(cyclopropylamino)-1-((phenylsulfanyl)methyl)propylamino, (1R)-3-oxo-3-(dimethylamino)-1-((phenylsulfanyl)methyl) propylamino, (1R)-3-oxo-3-(dimethylamino)-1-((phenylsulfonylmethyl)methyl)propylamino, (1R)-3-oxo-3-(dimethylamino)-1-((pyrimidin-1-ylsulfanyl)methyl) propylamino, (1R)-3-oxo-3-((1,1-dimethylethyl)amino)-1-((phenylsulfanyl)methyl)propylamino, (1R)-3-oxo-3-(diisopropylamino)-1-((phenylsulfanyl)methyl)-propylamino, (1R)-3-oxo-3-(1,1-dioxothiomorpholin-4-yl)-1-((phenylsulfanyl)methyl)propylamino, (1R)-3-oxo-3-(N- methyl-N-(1,1-dimethylethyl)amino)-1-((phenylsulfanyl) methyl)propylamino, (1R)-3-oxo-3-(piperidin-1-yl)-1-((phenylsulfanyl)methyl)propylamino, (1R)-3-oxo-3-amino-1-((phenylsulfanyl)methyl)propylamino, (1R)-3-oxo-3-(methylamino)-1-((phenylsulfanyl)methyl) propylamino, (1R)-3-oxo-3-(4-methylpiperazin-1-yl)-1-((phenylsulfanyl)methyl)-propylamino, (1R)-3-oxo-3-(morpholin-1-yl)-1-((phenylsulfanyl)methyl)propylamino, (1R)-3-oxo-3-(2-(morpholin-1-yl)ethyl)-1-((phenylsulfanyl) methyl)propylamino, (2-phenoxyethyl)amino, 4-(1-(phenylmethyl)piperidin-4-yl)amino, 4-(1-(phenylmethyl)piperidin-4-yl)methylamino, (4-phenyl-1,3-thiazol-2-ylsulfanyl) ethylamino, (1R,2S)-2-(phenylsulfanyl)cyclohex-1-ylamino, (1S,2R)-2-(phenylsulfanyl)cyclohex-1-ylamino, 2-(phenylsulfanyl)cyclopentylamino, 2-(phenylsulfanyl) ethoxy, 2-(phenylsulfanyl)ethylamino, 2-(phenylsulfonyl) ethylamino, (1R)-1-((phenylsulfanyl)methyl)-3-(morpholin-4-yl)propylamino, (1R)-1-((phenylsulfanyl)methyl)-3-((2,2,2-trifluoroethyl)amino)propylamino, 4-(phenylsulfonyl) tetrahydrofuran-3-ylamino, 4-(phenylsulfanyl) tetrahydrofuran-3-ylamino, (1R)-1-((phenylsulfanyl) methyl)-3-((2,2,2-trifluoroethyl)-amino)propylamino, (1S)-1-((phenylsulfanyl)methyl)propylamino, (1R)-1-((phenylsulfanyl)methyl)-3-(pyridin-4-ylsulfanyl) propylamino, (1R)-1-((phenylsulfanyl)methyl)-3-(thiomorpholin-4-yl)propylamino, (1R)-1-((phenylsulfanyl) methyl)-3-(piperazin-1-yl)propylamino, (1R)-1-((phenylsulfanyl)methyl)-3-((2-(pyridin-2-yl)ethyl)amino) propylamino, (1R)-1-((phenylsulfanyl)methyl)-3-((pyridin-4-ylmethyl)amino)propylamino, (1R)-1-((phenylsulfanyl) methyl)-3-(pyridin-3-ylamino)propylamino, (1R)-1-((phenylsulfanyl)methyl)-3-(pyrrolidin-1-ylamino) propylamino), (1R)-1-((phenylsulfanyl)methyl)-3-(2H-tetrazol-5-yl)propylamino, (1R)-1-((phenylsulfanyl) methyl)-3-(pyrrolidin-1-yl)propylamino, (1R)-1-((phenylsulfanyl)methyl)3-((pyridin-2-ylmethyl)amino) propylamino, (1S)-2-(phenylsulfanyl)-1-(pyridin-3-ylmethyl)ethylamino, (3S,4R)-(phenylsulfanyl)pyrrolidin-4-ylamino, 2-(phenylsulfanyl)-1,1-spirobutylethylamino, 2-(phenylsulfanyl)-1,1-spiroethylethylamino, 2-(phenylsulfanyl)-1,1-spiropentylethylamino, piperidin-4-yloxy, (1-propylpiperidin-4-yl)methylamino, pyran-4-ylamino, 2-(pyridin-4-ylsulfanyl)ethylamino, 2-(pyrimidin-2-ylsulfanyl) ethylamino, 1,1-spirobutyl-2-(phenylsulfanyl)ethyl, 2-(thien-2-ylsulfanyl)ethylamino, sulfanylpyran-4-ylamino, (1R)-3-(2-(2H-tetrazol-3-yl)pyrrolidin-1-yl)-1-((phenylsulfanyl)methyl)propylamino, (1R)-3-(3-(2H-tetrazol-3-yl)azetidin-1-yl)-1-((phenylsulfanyl)methyl)propylamino or 2-(1,3-thiazol-2-ylsulfanyl)ethylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or $C(O)NH_2$; and $Z^1$ is 4-(5-(2-(4-chlorophenyl)phenylmethyl) hexahydropyrrolo[3,4-c]pyrrol-2(1H)-yl)phenylcarbonyl, 4-(4-(2-(4-chlorophenyl)phenylmethyl)piperazin-1-yl)phenylcarbonyl, 4-(4-(2-(4-chlorophenyl)phenylmethyl)-4-methoxypiperidin-1-yl)phenylcarbonyl, 4-(4-(2-(4-chlorophenyl)phenylmethyl)-piperazin-1-yl)-3,5-difluorophenylcarbonyl, 4-(4-(2-(4-chlorophenyl) phenylmethyl)piperazin-1-yl)-2-fluorophenylcarbonyl, 4-(4-(2-(4-chlorophenyl)phenylmethyl)piperazin-1-yl)-3-fluorophenylcarbonyl, 2-(4-(2-(4-chlorophenyl) phenylmethyl)piperazin-1-yl)pyridin-5-ylcarbonyl, 4-(1-(2-(4-chlorophenyl)phenylmethyl)piperidin-4-yl) phenylcarbonyl, 5-(4-(2-(4-chlorophenyl)phenylmethyl) piperazin-1-yl)pyridin-2-ylcarbonyl, 4-(1-(2-(4-chlorophenyl)phenylmethyl)-1,2,3,6-tetrahydropyridin-4-yl)phenylcarbonyl, 4-(4-(2-(cyclohex-1-ylamino) phenylmethyl)piperazin-1-yl)phenylcarbonyl4-(4-(2-cyclohex-1-ylphenylmethyl)piperazin-1-yl)phenylcarbonyl, 4-(4-(2-(3-cyanophenyl)phenylmethyl)piperazin-1-yl)phenylcarbonyl, 4-(4-(2-(2,4-dichlorophenyl)phenylmethyl) piperazin-1-yl)phenylcarbonyl, 4-(4-(2-(3,4-dichlorophenyl)phenylmethyl)piperazin-1-yl)phenylcarbonyl, 4-(4-(2-(2,4-difluorophenyl)phenylmethyl)piperazin-1-yl) phenylcarbonyl, 4-(2-(1,3-dihydro-2H-isoindol-2-yl) phenylmethyl)piperazin-1-yl)phenylcarbonyl, 4-(4-(3-(1,1-dimethylethoxycarbonylamino)phenyl)piperazin-1-yl) phenylcarbonyl, 4-(2-(4-(2-(dimethylamino)ethoxy)phenyl) phenylmethyl)piperazin-1-yl)phenylcarbonyl or 4-(4-(3-(dimethylamino)phenyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, $C(O)OH$, $C(O)OCH_3$ or $C(O)NH_2$; $B^1$ is (1R)-3-((1S,4S)-2-oxa-5-azabicyclo[2.2.1]hept-5-yl)-1-((phenylsulfanyl)methyl)propylamino, (1R)-3-((1R,4R)-2-oxa-5-azabicyclo [2.2.1]hept-5-yl)-1-((phenylsulfanyl)methyl)-propylamino, (1R)-3-oxo-3-(azetidin-1-yl)-1-((phenylsulfanyl)methyl) propylamino, (1R)-3-oxo-3-(cyclobutylamino)-1-((phenylsulfanyl)methyl)propylamino, (1R)-3-oxo-3-(cyclopropylamino)-1-((phenylsulfanyl)methyl)propylamino, (1R)-3-oxo-3-(dimethylamino)-1-((phenylsulfanyl)methyl) propylamino, (1R)-3-oxo-3-(dimethylamino)-1-((phenylsulfonylmethyl)methyl)propylamino, (1R)-3-oxo-3-(dimethylamino)-1-((pyrimidin-1-ylsulfanyl)methyl) propylamino, (1R)-3-oxo-3-((1,1-dimethylethyl)amino)-1-((phenylsulfanyl)methyl)propylamino, (1R)-3-oxo-3-(diisopropylamino)-1-((phenylsulfanyl)methyl)-propylamino, (1R)-3-oxo-3-(1,1-dioxothiomorpholin-4-yl)-1-((phenylsulfanyl)methyl)propylamino, (1R)-3-oxo-3-(N-methyl-N-(1,1-dimethylethyl)amino)-1-((phenylsulfanyl) methyl)propylamino, (1R)-3-oxo-3-(piperidin-1-yl)-1-((phenylsulfanyl)methyl)propylamino, (1R)-3-oxo-3-amino-1-((phenylsulfanyl)methyl)propylamino, (1R)-3-oxo-3-(methylamino)-1-((phenylsulfanyl)methyl) propylamino, (1R)-3-oxo-3-(4-methylpiperazin-1-yl)-1-((phenylsulfanyl)methyl)propylamino, (1R)-3-oxo-3-(morpholin-1-yl)-1-((phenylsulfanyl)methyl)propylamino, (1R)-3-oxo-3-(2-(morpholin-1-yl)ethyl)-1-((phenylsulfanyl) methyl)propylamino, (2-phenoxyethyl)amino, 4-(1-(phenylmethyl)piperidin-4-yl)amino, 4-(1-(phenylmethyl)piperidin-4-yl)methylamino, (4-phenyl-1,3-thiazol-2-ylsulfanyl) ethylamino, (1R,2S)-2-(phenylsulfanyl)cyclohex-1-ylamino, (1S,2R)-2-(phenylsulfanyl)cyclohex-1-ylamino, 2-(phenylsulfanyl)cyclopentylamino, 2-(phenylsulfanyl) ethoxy, 2-(phenylsulfanyl)ethylamino, 2-(phenylsulfonyl) ethylamino, (1R)-1-((phenylsulfanyl)methyl)-3-(morpholin-4-yl)propylamino, (1R)-1-((phenylsulfanyl)methyl)-3-((2,2,2-trifluoroethyl)amino)propylamino, 4-(phenylsulfonyl) tetrahydrofuran-3-ylamino, 4-(phenylsulfanyl) tetrahydrofuran-3-ylamino, (1R)-1-((phenylsulfanyl) methyl)-3-((2,2,2-trifluoroethyl)amino)propylamino, (1S)-1-((phenylsulfanyl)methyl)propylamino, (1R)-1-((phenylsulfanyl)methyl)-3-(pyridin-4-ylsulfanyl) propylamino, (1R)-1-((phenylsulfanyl)methyl)-3-(thiomorpholin-4-yl)propylamino, (1R)-1-((phenylsulfanyl) methyl)-3-(piperazin-1-yl)propylamino, (1R)-1-((phenylsulfanyl)methyl)-3-((2-(pyridin-2-yl)ethyl)amino) propylamino, (1R)-1-((phenylsulfanyl)methyl)-3-((pyridin-4-ylmethyl)amino)propylamino, (1R)-1-((phenylsulfanyl) methyl)-3-(pyridin-3-ylamino)propylamino, (1R)-1-((phenylsulfanyl)methyl)-3-(pyrrolidin-1-ylamino) propylamino), (1R)-1-((phenylsulfanyl)methyl)-3-(2H-tetrazol-5-yl)propylamino, (1R)-1-((phenylsulfanyl) methyl)-3-(pyrrolidin-1-yl)propylamino, (1R)-1-

((phenylsulfanyl)methyl)-3-((pyridin-2-ylmethyl)amino) propylamino, (1S)-2-(phenylsulfanyl)-1-(pyridin-3-ylmethyl)ethylamino, (3S,4R)-(phenylsulfanyl)pyrrolidin-4-ylamino, 2-(phenylsulfanyl)-1,1-spirobutylethylamino, 2-(phenylsulfanyl)-1,1-spiroethylethylamino, 2-(phenylsulfanyl)-1,1-spiropentylethylamino, piperidin-4-yloxy, (1-propylpiperidin-4-yl)methylamino, pyran-4-ylamino, 2-(pyridin-4-ylsulfanyl)ethylamino, 2-(pyrimidin-2-ylsulfanyl) ethylamino, 1,1-spirobutyl-2-(phenylsulfanyl)ethyl, 2-(thien-2-ylsulfanyl)ethylamino, sulfanylpyran-4-ylamino, (1R)-3-(2-(2H-tetrazol-3-yl)pyrrolidin-1-yl)-1-((phenylsulfanyl)methyl)propylamino, (1R)-3-(3-(2H-tetrazol-3-yl)azetidin-1-yl)-1-((phenylsulfanyl)methyl)propylamino or 2-(1,3-thiazol-2-ylsulfanyl)ethylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or $C(O)NH_2$; and $Z^1$ is 4-(2-(4-(dimethylamino)phenyl)phenylcarbonyl)piperazin-1-yl)phenylcarbonyl, 4-(4-(2-(4-(dimethylamino)phenyl)phenylmethyl)piperazin-1-yl)phenylcarbonyl, 4-(4-((2-(4-(dimethylamino)phenyl)pyridin-3-yl) methyl)piperazin-1-yl)phenylcarbonyl, 4-(4-(2-(5,5-dimethyl-2-oxo-1,3-oxazolidin-3-yl)phenylmethyl) piperazin-1-yl)phenylcarbonyl, 4-(4-(2-(4-fluorophenyl)cyclopent-1-en-1-ylmethyl)piperazin-1-yl)phenylcarbonyl, 4-(4-(2-(4-fluorophenyl)-3-fluorophenylmethyl)piperazin-1-yl)phenylcarbonyl, 4-(4-(2-(4-fluorophenyl)phenylmethyl)piperazin-1-yl)phenylcarbonyl, 4-(4-((2-(4-fluorophenyl)pyridin-3-yl)methyl)piperazin-1-yl)phenylcarbonyl, 4-(2-(isopropylamino)phenylmethyl)piperazin-1-yl)phenylcarbonyl, 4-(4-(2-(4-(isopropylsulfanyl)phenyl)phenylmethyl)piperazin-1-yl)phenylcarbonyl, 4-(4-(2-(4-methoxyphenyl)cyclopent-1-en-1-ylmethyl)piperazin-1-yl) phenylcarbonyl, 4-(4-(2-(3-methoxyphenyl)phenylmethyl) piperazin-1-yl)phenylcarbonyl, 4-(4-(2-(4-methoxyphenyl) phenylmethyl)piperazin-1-yl)phenylcarbonyl, 4-(4-((2-(4-methoxyphenyl)pyridin-3-yl)methyl)piperazin-1-yl) phenylcarbonyl, 4-(4-methoxy-4-(2-(pyridin-3-yl) phenylmethyl)piperidin-1-yl)phenylcarbonyl, 4-(4-(2-(2-methyl-4-dichlorophenyl)phenylmethyl)piperazin-1-yl) phenylcarbonyl, 4-(4-(2-(2-methylphenyl)phenylmethyl) piperazin-1-yl)phenylcarbonyl, 4-(4-(2-(4-(methylsulfonyl) phenyl)methyl)piperazin-1-yl)phenylcarbonyl, 4-(4-(2-(4-methylsulfonylphenyl)phenylmethyl)piperazin-1-yl) phenylcarbonyl or 4-(4-((2-(4-methylsulfonylphenyl) pyridin-3-yl)methyl)piperazin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, $C(O)OCH_3$ or $C(O)NH_2$; $B^1$ is (1R)-3-((1S,4S)-2-oxa-5-azabicyclo[2.2.1]hept-5-yl)-1-((phenylsulfanyl)methyl)propylamino, (1R)-3-((1R,4R)-2-oxa-5-azabicyclo[2.2.1]hept-5-yl)-1-((phenylsulfanyl)methyl)propylamino, (1R)-3-oxo-3-(azetidin-1-yl)-1-((phenylsulfanyl)methyl) propylamino, (1R)-3-oxo-3-(cyclobutylamino)-1-((phenylsulfanyl)methyl)propylamino, (1R)-3-oxo-3-(cyclopropylamino)-1-((phenylsulfanyl)methyl)propylamino, (1R)-3-oxo-3-(dimethylamino)-1-((phenylsulfanyl)methyl) propylamino, (1R)-3-oxo-3-(dimethylamino)-1-((phenylsulfonylmethyl)methyl)propylamino, (1R)-3-oxo-3-(dimethylamino)-1-((pyrimidin-1-ylsulfanyl)methyl) propylamino, (1R)-3-oxo-3-((1,1-dimethylethyl)amino)-1-((phenylsulfanyl)methyl)propylamino, (1R)-3-oxo-3-(diisopropylamino)-1-((phenylsulfanyl)methyl) propylamino, (1R)-3-oxo-3-(1,1-dioxothiomorpholin-4-yl)-1-((phenylsulfanyl)methyl)propylamino, (1R)-3-oxo-3-(N-methyl-N-(1,1-dimethylethyl)amino)-1-((phenylsulfanyl) methyl)propylamino, (1R)-3-oxo-3-(piperidin-1-yl)-1-((phenylsulfanyl)methyl)propylamino, (1R)-3-oxo-3-amino-1-((phenylsulfanyl)methyl)propylamino, (1R)-3-oxo-3-(methylamino)-1-((phenylsulfanyl)methyl)propylamino, (1R)-3-oxo-3-(4-methylpiperazin-1-yl)-1-((phenylsulfanyl)methyl)propylamino, (1R)-3-oxo-3-(morpholin-1-yl)-1-((phenylsulfanyl)methyl)propylamino, (1R)-3-oxo-3-(2-(morpholin-1-yl)ethyl)-1-((phenylsulfanyl)methyl) propylamino, (2-phenoxyethyl)amino, 4-(1-(phenylmethyl) piperidin-4-yl)amino, 4-(1-(phenylmethyl)piperidin-4-yl) methylamino, (4-phenyl-1,3-thiazol-2-ylsulfanyl) ethylamino, (1R,2S)-2-(phenylsulfanyl)cyclohex-1-ylamino, (1S,2R)-2-(phenylsulfanyl)cyclohex-1-ylamino, 2-(phenylsulfanyl)cyclopentylamino, 2-(phenylsulfanyl) ethoxy, 2-(phenylsulfanyl)ethylamino, 2-(phenylsulfonyl) ethylamino, (1R)-1-((phenylsulfanyl)methyl)-3-(morpholin-4-yl)propylamino, (1R)-1-((phenylsulfanyl)methyl)-3-((2,2,2-trifluoroethyl)amino)propylamino, 4-(phenylsulfonyl) tetrahydrofuran-3-ylamino, 4-(phenylsulfanyl) tetrahydrofuran-3-ylamino, (1R)-1-((phenylsulfanyl) methyl)-3-((2,2,2-trifluoroethyl)-amino)propylamino, (1S)-1-((phenylsulfanyl)methyl)propylamino, (1R)-1-((phenylsulfanyl)methyl)-3-(pyridin-4-ylsulfanyl) propylamino, (1R)-1-((phenylsulfanyl)methyl)-3-(thiomorpholin-4-yl)propylamino, (1R)-1-((phenylsulfanyl) methyl)-3-(piperazin-1-yl)propylamino, (1R)-1-((phenylsulfanyl)methyl)-3-((2-(pyridin-2-yl)ethyl)amino) propylamino, (1R)-1-((phenylsulfanyl)methyl)-3-((pyridin-4-ylmethyl)amino)propylamino, (1R)-1-((phenylsulfanyl) methyl)-3-(pyridin-3-ylamino)propylamino, (1R)-1-((phenylsulfanyl)methyl)-3-(pyrrolidin-1-ylamino) propylamino), (1R)-1-((phenylsulfanyl)methyl)-3-(2H-tetrazol-5-yl)propylamino, (1R)-1-((phenylsulfanyl) methyl)-3-(pyrrolidin-1-yl)propylamino, (1R)-1-((phenylsulfanyl)methyl)-3-((pyridin-2-ylmethyl)amino) propylamino, (1S)-2-(phenylsulfanyl)-1-(pyridin-3-ylmethyl)ethylamino, (3S,4R)-(phenylsulfanyl)pyrrolidin-4-ylamino, 2-(phenylsulfanyl)-1,1-spirobutylethylamino, 2-(phenylsulfanyl)-1,1-spiroethylethylamino, 2-(phenylsulfanyl)-1,1-spiropentylethylamino, piperidin-4-yloxy, (1-propyl-piperidin-4-yl)methylamino, pyran-4-ylamino, 2-(pyridin-4-ylsulfanyl)ethylamino, 2-(pyrimidin-2-ylsulfanyl) ethylamino, 1,1-spirobutyl-2-(phenylsulfanyl)ethyl, 2-(thien-2-ylsulfanyl)ethylamino, sulfanylpyran-4-ylamino, (1R)-3-(2-(2H-tetrazol-3-yl)pyrrolidin-1-yl)-1-((phenylsulfanyl)methyl)propylamino, (1R)-3-(3-(2H-tetrazol-3-yl)azetidin-1-yl)-1-((phenylsulfanyl)methyl)propylamino or 2-(1,3-thiazol-2-ylsulfanyl)ethylamino; $D^1$ is H, F, Cl or $CF_3$; $E^1$ is H, F or Cl; $Y^1$ is H, CN, $NO_2$, F, Cl, $CF_3$, $OCF_3$, $NH_2$ or $C(O)NH_2$; and $Z^1$ is 4-(4-(2-(5-methylthien-2-yl)phenylmethyl)piperazin-1-yl)phenylcarbonyl, 4-(4-(2-(4-methylsulfanylphenyl)cyclohex-1-en-l-ylmethyl)piperazin-1-yl)phenylcarbonyl, 4-(4-(2-(4-methylsulfanylphenyl) phenylcarbonyl)piperazin-1-yl)phenylcarbonyl, 4-(4-((2-(4-methylsulfanylphenyl)pyridin-3-yl)methyl)piperazin-1-yl) phenylcarbonyl, 4-(4-(2-(4-methylsulfanylphenyl) phenylmethyl)piperazin-1-yl)phenylcarbonyl, 4-(4-(2-(4-(2-(morpholin-1-yl)ethoxy)phenyl)phenylmethyl)piperazin-1-yl)phenylcarbonyl, 4-(4-(2-(morpholin-1-yl)phenylmethyl) piperazin-1-yl)phenylcarbonyl, 4-(4-(2-(naphth-1-yl) phenylmethyl)piperazin-1-yl)phenylcarbonyl, 4-(4-(2-(naphth-2-yl)phenylmethyl)piperazin-1-yl)phenylcarbonyl 4-(4-(2-(4-phenoxyphenyl)phenylmethyl)piperazin-1-yl) phenylcarbonyl, 4-(4-((1-phenyl-1H-imidazol-2-yl)methyl) piperazin-1-yl)phenylcarbonyl, 4-(4-((1-phenyl-1H-imidazol-5-yl)methyl)piperazin-1-yl)phenylcarbonyl, 4-(2-((phenylmethyl)amino)phenylmethyl)piperazin-1-yl) phenylcarbonyl, 4-(4-(2-(phenyl)phenylmethyl)-4-(2-(dimethylamino)ethoxy))piperidin-1-yl)phenylcarbonyl, 4-((2-(phenyl)phenylmethyl)-4-methoxypiperidin-1-yl)phenylcarbonyl, 4-(4-(2-(phenyl)phenylmethyl)-4-(2-(morpholin-1-yl)ethoxy))piperidin-1-yl)phenylcarbonyl, 4-(4-(2-(phenyl)phenylmethyl)piperazin-1-yl)phenylcarbonyl, 4-(4-(3-(phenyl)phenylmethyl)piperazin-1-yl)phenylcarbonyl, 4-(4-(2-(4-(phenyl)phenyl)phenylmethyl)piperazin-1-yl)phenylcarbonyl or 4-(4-(2-(phenyl)phenylmethyl)-4-(2-(piperidin-1-yl)ethoxy))piperidin-1-yl)phenylcarbonyl.

Still another embodiment pertains to compounds having formula (I), or therapeutically acceptable salts, prodrugs or salts of prodrugs thereof, wherein $A^1$ is $C(A^2)$; $A^2$ is H, F, CN, C(O)OH, C(O)OCH$_3$ or C(O)NH$_2$; $B^1$ is (1R)-3-((1S,4S)-2-oxa-5-azabicyclo[2.2.1]hept-5-yl)-1-((phenylsulfanyl)methyl)propylamino, (1R)-3-((1R,4R)-2-oxa-5-azabicyclo[2.2.1]hept-5-yl)-1-((phenylsulfanyl)methyl)propylamino, (1R)-3-oxo-3-(azetidin-1-yl)-1-((phenylsulfanyl)methyl)propylamino, (1R)-3-oxo-3-(cyclobutylamino)-1-((phenylsulfanyl)methyl)propylamino, (1R)-3-oxo-3-(cyclopropylamino)-1-((phenylsulfanyl)methyl)propylamino, (1R)-3-oxo-3-(dimethylamino)-1-((phenylsulfanyl)methyl)propylamino, (1R)-3-oxo-3-(dimethylamino)-1-((phenylsulfonylmethyl)methyl)propylamino, (1R)-3-oxo-3-(dimethylamino)-1-((pyrimidin-1-ylsulfanyl)methyl)propylamino, (1R)-3-oxo-3-((1,1-dimethylethyl)amino)-1-((phenylsulfanyl)methyl)propylamino, (1R)-3-oxo-3-(diisopropylamino)-1-((phenylsulfanyl)methyl)propylamino, (1R)-3-oxo-3-(1,1-dioxothiomorpholin-4-yl)-1-((phenylsulfanyl)methyl)propylamino, (1R)-3-oxo-3-(N-methyl-N-(1,1-dimethylethyl)amino)-1-((phenylsulfanyl)methyl)propylamino, (1R)-3-oxo-3-(piperidin-1-yl)-1-((phenylsulfanyl)methyl)propylamino, (1R)-3-oxo-3-amino-1-((phenylsulfanyl)methyl)propylamino, (1R)-3-oxo-3-(methylamino)-1-((phenylsulfanyl)methyl)propylamino, (1R)-3-oxo-3-(4-methylpiperazin-1-yl)-1-((phenylsulfanyl)methyl)propylamino, (1R)-3-oxo-3-(morpholin-1-yl)-1-((phenylsulfanyl)methyl)propylamino, (1R)-3-oxo-3-(2-(morpholin-1-yl)ethyl)-1-((phenylsulfanyl)methyl)propylamino, (2-phenoxyethyl)amino, 4-(1-(phenylmethyl)piperidin-4-yl)amino, 4-(1-(phenylmethyl)piperidin-4-yl)methylamino, (4-phenyl-1,3-thiazol-2-ylsulfanyl)ethylamino, (1R,2S)-2-(phenylsulfanyl)cyclohex-1-ylamino, (1S,2R)-2-(phenylsulfanyl)cyclohex-1-ylamino, 2-(phenylsulfanyl)cyclopentylamino, 2-(phenylsulfanyl)ethoxy, 2-(phenylsulfanyl)ethylamino, 2-(phenylsulfonyl)ethylamino, (1R)-1-((phenylsulfanyl)methyl)-3-(morpholin-4-yl)propylamino, (1R)-1-((phenylsulfanyl)methyl)-3-((2,2,2-trifluoroethyl)amino)propylamino, 4-(phenylsulfonyl)tetrahydrofuran-3-ylamino, 4-(phenylsulfanyl)tetrahydrofuran-3-ylamino, (1R)-1-((phenylsulfanyl)methyl)-3-((2,2,2-trifluoroethyl)amino)propylamino, (1S)-1-((phenylsulfanyl)methyl)propylamino, (1R)-1-((phenylsulfanyl)methyl)-3-(pyridin-4-ylsulfanyl)propylamino, (1R)-1-((phenylsulfanyl)methyl)-3-(thiomorpholin-4-yl)propylamino, (1R)-1-((phenylsulfanyl)methyl)-3-(piperazin-1-yl)propylamino, (1R)-1-((phenylsulfanyl)methyl)-3-((2-(pyridin-2-yl)ethyl)amino)propylamino, (1R)-1-((phenylsulfanyl)methyl)-3-((pyridin-4-ylmethyl)amino)propylamino, (1R)-1-((phenylsulfanyl)methyl)-3-(pyridin-3-ylamino)propylamino, (1R)-1-((phenylsulfanyl)methyl)-3-(pyrrolidin-1-ylamino)propylamino), (1R)-1-((phenylsulfanyl)methyl)-3-(2H-tetrazol-5-yl)propylamino, (1R)-1-((phenylsulfanyl)methyl)-3-(pyrrolidin-1-yl)propylamino, (1R)-1-((phenylsulfanyl)methyl)-3-((pyridin-2-ylmethyl)amino)propylamino, (1S)-2-(phenylsulfanyl)-1-(pyridin-3-ylmethyl)ethylamino, (3S,4R)-(phenylsulfanyl)pyrrolidin-4-ylamino, 2-(phenylsulfanyl)-1,1-spirobutylethylamino, 2-(phenylsulfanyl)-1,1-spiroethylethylamino, 2-(phenylsulfanyl)-1,1-spiropentylethylamino, piperidin-4-yloxy, (1-propylpiperidin-4-yl)methylamino, pyran-4-ylamino, 2-(pyridin-4-ylsulfanyl)ethylamino, 2-(pyrimidin-2-ylsulfanyl)ethylamino, 1,1-spirobutyl-2-(phenylsulfanyl)ethyl, 2-(thien-2-ylsulfanyl)ethylamino, sulfanylpyran-4-ylamino, (1R)-3-(2-(2H-tetrazol-3-yl)pyrrolidin-1-yl)-1-((phenylsulfanyl)methyl)propylamino, (1R)-3-(3-(2H-tetrazol-3-yl)azetidin-1-yl)-1-((phenylsulfanyl)methyl)propylamino or 2-(1,3-thiazol-2-ylsulfanyl)ethylamino; $D^1$ is H, F, Cl or CF$_3$; $E^1$ is H, F or Cl; $Y^1$ is H, CN, NO$_2$, F, Cl, CF$_3$, OCF$_3$, NH$_2$ or C(O)NH$_2$ and $Z^1$ is 4-(4-(2-(phenyl)phenylmethyl)-4-(2-(pyrrolidin-1-yl)ethoxy))piperidin-1-yl)phenylcarbonyl, 4-(4-((2-(phenyl)pyridin-3-yl)methyl)piperazin-1-yl)phenylcarbonyl, 4-(4-((1-phenyl-1H-pyrazol-5-yl)methyl)piperazin-1-yl)phenylcarbonyl, 4-(4-(2-(piperidin-1-yl)phenylmethyl)piperazin-1-yl)phenylcarbonyl, 4-(4-(2-(pyrid-3-yl)phenyl)phenylmethyl)piperazin-1-yl)phenylcarbonyl, 4-(4-(2-(quinolin-3-ylphenyl)phenylmethyl)piperazin-1-yl)phenylcarbonyl, 4-(4-(2-(quinolin-8-ylphenyl)phenylmethyl)piperazin-1-yl)phenylcarbonyl, 4-(4-(2-(thien-2-yl)phenylmethyl)-4-methoxypiperazin-1-yl)phenylcarbonyl, 4-(4-(2-(thien-2-yl)phenylmethyl)piperazin-1-yl)phenylcarbonyl, 4-(4-(2-(4-trifluoromethoxyphenyl)phenylmethyl)piperazin-1-yl)phenylcarbonyl or 4-(4-(2-(4-trifluoromethyl-phenyl)phenylmethyl)piperazin-1-yl)phenylcarbonyl.

Still another embodiment pertains to compounds having formula (I) which are

N-(4-(4-((1,1'-biphenyl)-2-ylmethyl)piperazin-1-yl)benzoyl)-4-(MR)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(MR)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((4'-methoxy(1,1'-biphenyl)-2-yl)methyl)piperazin-1-yl)benzoyl)-3-nitrobenzenesulfonamide, 4-(((1R)-3-(dimethylamino)-1-((phenylsulfanyl)methyl)propyl)amino)-N-(4-(4-((4'-fluoro(1,1'-biphenyl)-2-yl)methyl)piperazin-1-yl)benzoyl)-3-nitrobenzenesulfonamide, 4-(((1R)-3-(dimethylamino)-1-((phenylsulfanyl)methyl)propyl)amino)-N-(4-(4-((4'-(methylsulfanyl)(1,1'-biphenyl)-2-yl)methyl)piperazin-1-yl)benzoyl)-3-nitrobenzenesulfonamide, N-((4-(((1R)-3-(dimethylamino)-1-((phenylsulfanyl)methyl)propyl)amino)-3-nitrophenyl)sulfonyl)-4-(4-(4'-phenyl-1,1'-biphenyl-2-ylmethyl)piperazin-1-yl)benzamide, 4-(((1R)-3-(dimethylamino)-1-((phenylsulfanyl)methyl)propyl)amino)-3-nitro-N-(4-(4-((4'-phenoxy(1,1'-biphenyl)-2-yl)methyl)piperazin-1-yl)benzoyl)benzenesulfonamide, N-(4-(4-((1,1'-biphenyl)-2-ylmethyl)piperazin-1-yl)benzoyl)-4-((1,1-dimethyl-2-(phenylsulfanyl)ethyl)amino)-3-nitrobenzenesulfonamide, N-(4-(4-((1,1'-biphenyl)-2-ylmethyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((1,1'-biphenyl)-2-ylmethyl)piperazin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-((1,1-dimethyl-2-(phenylsulfanyl)ethylamino)-3-nitrobenzenesulfonamide, N-(4-(4-((4'-chloro(1,1'-biphenyl)-2-yl)methyl)piperazin-1-yl)benzoyl)-4-(((1R)-4-(dimethylamino)-1-((phenylsulfanyl)methyl)butyl)amino)-3-nitrobenzenesulfonamide, N-(4-(4-((4'-chloro(1,1'-biphenyl)-2-yl)methyl)piperazin-1-yl)benzoyl)-4-(((1R)-5-(dimethylamino)-1-((phenylsulfanyl)methyl)pentyl)amino)-3-nitrobenzenesulfonamide, N-(4-(4-((4'-fluoro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro-4-fluoro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyrrolidin-1-yl)propyl)amino)benzenesulfonamide, N-(4-(4-((4'-chloro(1,1'-biphenyl)-2-yl)methyl)piperazin-1-yl)benzoyl)-4-((1,1-dimethyl-2-(1,3-thiazol-2-ylsulfanyl)ethylamino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((1,3-thiazol-2-ylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((thien-2-ylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-2-(2-(dimethylamino)ethoxy)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1S)-3-(dimethylamino)-1-methyl-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(methylamino)-1-((phenylsulfanyl)methyl)propyl)amino)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanoic acid, (3R)-3-(4-(((4-(4-((4'-chloro(1,1'-biphenyl)-2-yl)methyl)piperazin-1-yl)benzoyl)amino)sulfonyl)-2-nitroanilino)-N-isopropyl-4-(phenylsulfanyl)butanamide, N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-nitrobenzenesulfonamide, 4-(((1R)-3-(azetidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-((4-(phenylsulfanyl)tetrahydro-3-furanyl)amino)benzenesulfonamide, N-(4-(4-((4'-chloro(1,1'-biphenyl)-2-yl)methyl)-4-methoxypiperidin-1-yl)benzoyl)-4-(((1R)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl-4-methoxypiperidin-1-yl)benzoyl)-4-(((1R)-3-(morpholin-4-yl)-1-((phenylsulfanyl)methyl)propyl)amino)-3-nitrobenzenesulfonamide N-(4-(4-((4'-chloro(1,1'-biphenyl)-2-yl)methyl)piperazin-1-yl)benzoyl)-4-(((1R)-3-hydroxy-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(isopropylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-(2-(2-naphthyl)benzyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(1-naphthyl)benzyl)piperazin-1-yl)benzoyl)-3-nitrobenzenesulfonamide, N-(4-(4-((3'-cyano(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((3'-methoxy(1,1'-biphenyl)-2-yl)methyl)piperazin-1-yl)benzoyl)-3-nitrobenzenesulfonamide, N-(4-(4-((3'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide N-(4-(4-((2'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-(2-(1,3-benzodioxol-5-yl)benzyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-3-nitro-N-(4-(4-(2-(3-thienyl)benzyl)piperazin-1-yl)benzoyl)benzenesulfonamide, 4-(((1R)-3-(dimethylamino)-1-((phenylsulfanyl)methyl)propyl)amino)-3-nitro-N-(4-(4-(2-(pyridin-3-yl)benzyl)piperazin-1-yl)benzoyl)benzenesulfonamide, 4-(((1R)-3-(dimethylamino)-1-((phenylsulfanyl)methyl)propyl)amino)-3-nitro-N-(4-(4-(2-(quinolin-8-yl)benzyl)piperazin-1-yl)benzoyl)benzenesulfonamide, N-(4-(4-(2-(1-benzofuran-2-yl)benzyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((2'-methyl(1,1'-biphenyl)-2-yl)methyl)piperazin-1-yl)benzoyl)-3-nitrobenzenesulfonamide, 4-(((1R)-3-(dimethylamino)-1-((phenylsulfanyl)methyl)propyl)amino)-3-nitro-N-(4-(4-(2-(quinolin-3-yl)benzyl)piperazin-1-yl)benzoyl)benzenesulfonamide, N-(4-(4-((1-(4-chlorophenyl)-2-naphthyl)methyl)piperazin-1-yl)benzoyl)-3-nitro-4-((2-(phenylsulfanyl)ethyl)amino)benzenesulfonamide, N-(4-(4-((1-(4-chlorophenyl)-2-naphthyl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((1-(4-chlorophenyl)-2-naphthyl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-((2-(phenylsulfanyl)cyclopentyl)amino)benzenesulfonamide, N-(4-(4-((1,1'-biphenyl)-2-ylmethyl)-4-methoxypiperidin-1-yl)benzoyl)-3-nitro-4-((2-(phenylsulfanyl)cyclopentyl)amino)benzenesulfonamide, N-(4-(4-((4'-fluoro(1,1'-biphenyl)-2-yl)methyl)piperazin-1-yl)benzoyl)-3-nitro-4-((2-(phenylsulfanyl)ethylamino) benzenesulfonamide, N-(4-(4-((3',4'-dichloro(1,1'-biphenyl)-2-yl)methyl)piperazin-1-yl)benzoyl)-3-nitro-4-((2-(phenylsulfanyl)ethyl) amino)benzenesulfonamide, N-(4-(4-((3',4'-dichloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((3',4'-dichloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, 3-nitro-4-((2-(phenylsulfanyl)ethyl)amino)-N-(4-(4-((4'-(trifluoromethyl)(1,1'-biphenyl)-2-yl)methyl)piperazin-1-yl)benzoyl)benzenesulfonamide, 4-(((1R)-3-(dimethylamino)-1-((phenylsulfanyl)methyl) propyl)amino)-3-nitro-N-(4-(4-((4'-(trifluoromethyl)(1,1'-biphenyl)-2-yl)methyl)piperazin-1-yl)benzoyl)benzenesulfonamide, 4-(((1R)-3-(morpholin-4-yl)-1-((phenylsulfanyl)methyl) propyl)amino)-3-nitro-N-(4-(4-((4'-(trifluoromethyl)(1,1'-biphenyl)-2-yl)methyl)piperazin-1-yl)benzoyl)benzenesulfonamide, 3-nitro-4-((2-(phenylsulfanyl)ethyl)amino)-N-(4-(4-((4'-(trifluoromethoxy)(1,1'-biphenyl)-2-yl)methyl)piperazin-1-yl)benzoyl)benzenesulfonamide, 3-nitro-4-((2-(phenylsulfanyl)ethyl)amino)-N-(4-(4-((4'-(trifluoromethoxy)(1,1'-biphenyl)-2-yl)methyl)piperazin-1-yl)benzoyl)benzenesulfonamide, 4-(((1R)-3-(morpholin-4-yl)-1-((phenylsulfanyl)methyl) propyl)amino)-3-nitro-N-(4-(4-((4'-(trifluoromethoxy)(1,1'-biphenyl)-2-yl)methyl)piperazin-1-yl)benzoyl)benzenesulfonamide, 3-nitro-N-(4-(4-((4'-phenoxy(1,1'-biphenyl)-2-yl)methyl) piperazin-1-yl)benzoyl)-4-((2-(phenylsulfanyl)ethyl)amino) benzenesulfonamide, 4-(((1R)-3-(morpholin-4-yl)-1-((phenylsulfanyl)methyl) propyl)amino)-3-nitro-N-(4-(4-((4'-phenoxy(1,1'-biphenyl)-2-yl)methyl)piperazin-1-yl)benzoyl)benzenesulfonamide, N-(4-(4-((4'-chloro(1,1'-biphenyl)-2-yl)methyl)piperazin-1-yl)benzoyl)-4-(((1S)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-((1,1-dimethyl-2-(phenylsulfonyl)ethyl) amino)-3-nitrobenzenesulfonamide, N-(4-(4-((2',4'-dichloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl) propyl)amino)-3-nitro-N-(4-(4-(2-(2-thienyl)benzyl)piperazin-1-yl)benzoyl)benzenesulfonamide, N-(4-(4-((4'-chloro-2'-methyl(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2',4'-difluoro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((1,1'-biphenyl)-2-ylmethyl)piperazin-1-yl)benzoyl)-3-nitro-4-((2-(phenylsulfonyl)ethyl)amino)benzenesulfonamide, N-(4-(4-((4'-chloro(1,1'-biphenyl)-2-yl)methyl)piperazin-1-yl)benzoyl)-3-nitro-4-((2-(phenylsulfonyl)ethyl)amino) benzenesulfonamide, N-(4-(4-((1,1'-biphenyl)-2-ylmethyl)piperazin-1-yl)benzoyl)-3-nitro-4-((4-(phenylsulfanyl)tetrahydro-3-furanyl) amino)benzenesulfonamide, 4-(((1R)-3-(dimethylamino)-1-((phenylsulfanyl)methyl) propyl)amino)-N-(4-(4-(2-(5-methyl-2-thienyl)benzyl)piperazin-1-yl)benzoyl)-3-nitrobenzenesulfonamide, N-(4-(4-((4'-chloro(1,1-biphenyl)-2-yl)methyl)piperazin-1-yl)benzoyl)-3-nitro-4-((4-(phenylsulfonyl)tetrahydro-3-furanyl)amino)benzenesulfonamide, N-(4-(4-((1,1'-biphenyl)-2-ylmethyl)piperazin-1-yl)benzoyl)-3-nitro-4-((4-(phenylsulfonyl)tetrahydro-3-furanyl) amino)benzenesulfonamide, N-(4-(4-((4'-chloro(1,1'-biphenyl)-2-yl)methyl)piperazin-1-yl)benzoyl)-4-((1-methyl-4-(phenylsulfanyl)pyrrolidin-3-yl)amino)-3-nitrobenzenesulfonamide, N-(4-(4-((2-(4-chlorophenyl)-1-cyclohexen-1-yl)methyl) piperazin-1-yl)benzoyl)-4-(((1R)-3-(morpholin-4-yl)-1-((phenylsulfanyl)methyl)propyl)amino)-3-nitrobenzenesulfonamide, N-(4-(4-((2-(4-chlorophenyl)-1-cyclohexen-1-yl)methyl) piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-bromo(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-(1-(4'-chloro(1,1'-biphenyl)-2-yl)cyclopropyl) piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-1-cyclohexen-1-yl)methyl) piperazin-1-yl)benzoyl)-4-(((1R)-2-(dimethylamino)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-2-(dimethylamino)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-2-(diethylamino)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-2-(morpholin-4-yl)-1-((phenylsulfanyl)methyl)ethyl)amino)-3-nitrobenzenesulfonamide, N-(4-(4-((2-(4-chlorophenyl)-1-cyclohexen-1-yl)methyl) piperazin-1-yl)benzoyl)-4-(((1R)-2-(diethylamino)-1-((phenylsulfanyl)methyl)ethyl)amino)-3-nitrobenzenesulfonamide, N-(4-(4-((2-(4-chlorophenyl)-1-cyclohexen-1-yl)methyl) piperazin-1-yl)benzoyl)-4-(((1R)-2-(morpholin-4-yl)-1-((phenylsulfanyl)methyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-3-(cyclopropyl(methyl)amino)-1-((phenylsulfanyl)methyl)propyl)amino)-3-nitrobenzenesulfonamide, N-(4-(4-((1,1'-biphenyl)-2-ylmethyl)-4-methoxypiperidin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl) propyl)amino)-N-(4-(4-methoxy-4-(2-(pyridin-3-yl)benzyl) piperidin-1-yl)benzoyl)-3-nitrobenzenesulfonamide, 4-(((1R)-3-(dimethylamino)-1-((phenylsulfanyl)methyl) propyl)amino)-N-(4-(4-methoxy-4-(2-(pyridin-4-yl)benzyl) piperidin-1-yl)benzoyl)-3-nitrobenzenesulfonamide, 4-(((1R)-3-(dimethylamino)-1-((phenylsulfanyl)methyl) propyl)amino)-N-(4-(4-methoxy-4-(2-(2-thienyl)benzyl)piperidin-1-yl)benzoyl)-3-nitrobenzenesulfonamide, 4-(((1R)-3-(dimethylamino)-1-((phenylsulfanyl)methyl) propyl)amino)-N-(4-(4-methoxy-4-(2-(3-thienyl)benzyl)piperidin-1-yl)benzoyl)-3-nitrobenzenesulfonamide, 4-(((1R)-3-(azetidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-((2,2,2-trifluoroethyl)amino)propyl)amino)benzenesulfonamide, N-(4-(4-((4'-chloro(1,1'-biphenyl)-2-yl)methyl)piperazin-1-yl)benzoyl)-4-(((1R)-3-(methyl(2,2,2-trifluoroethyl)amino)-1-((phenylsulfanyl)methyl)propyl)amino)-3-nitrobenzenesulfonamide, N-(4-(4-((4'-chloro(1,1'-biphenyl)-2-yl)methyl)-4-methoxypiperidin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)-4-methoxypiperidin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-4-(((1R)-3-(ethyl(2,2,2-trifluoroethyl)amino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-((2-fluoroethyl)amino)-1-((phenylsulfanyl)methyl)propyl)amino)-3-nitrobenzenesulfonamide, N-(4-(4-((4'-chloro(1,1-biphenyl)-2-yl)methyl)piperazin-1-yl)benzoyl)-4-(((1R)-3-((2,2-difluoroethyl)amino)-1-amino)-3-nitrobenzenesulfonamide, N-(4-(4-((4'-chloro(1,1'-biphenyl)-2-yl)methyl)piperazin-1-yl)benzoyl)-1-((1R)-3-(dimethylamino)-1-((phenylsulfanyl)methyl)propyl)-1H-benzimidazole-5-sulfonamide, N-(4-(4-((4'-chloro(1,1'-biphenyl)-2-yl)methyl)piperazin-1-yl)benzoyl)-1-((1R)-3-(dimethylamino)-1-((phenylsulfanyl)methyl)propyl)-1H-1,2,3-benzotriazole-5-sulfonamide, 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)benzamide, N-(4-(4-((4'-(dimethylamino)(1,1'-biphenyl)-2-yl)carbonyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-((4'-(methylsulfanyl)(1,1'-biphenyl)-2-yl)carbonyl)piperazin-1-yl)benzoyl)-3-nitrobenzenesulfonamide, 4-(((1R)-3-(dimethylamino)-1-((phenylsulfanyl)methyl)propyl)amino)-N-(4-(4-((4'-(methylsulfanyl)(1,1'-biphenyl)-2-yl)carbonyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-cyano-4-(((1R)-3-(dimethylamino)-1-((phenylsulfanyl)methyl)propyl)amino)benzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)oxy)-3-nitrobenzenesulfonamide, N-(4-(4-((4'-chloro(1,1'-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(5,6-dihydro-1(4H)-pyrimidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(5,6-dihydro-1(4H)-pyrimidin-1-yl)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(2,4-dimethyl-4,5-dihydro-1H-imidazol-1-yl)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-(trifluoromethyl)benzenesulfonamide, N-(4-(4-((4'-chloro(1,1-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-(trifluoromethyl)benzenesulfonamide, N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)oxy)-3-(trifluoromethyl)benzenesulfonamide, N-(4-(4-((2-(4-chlorophenyl)cyclohept-1-en-1-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, 4-(((1R)-3-(bis(2-methoxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, 4-(((1R)-3-(bis(2-methoxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-(trifluoromethyl)benzenesulfonamide, 4-(((1R)-5-amino-1-((phenylsulfanyl)methyl)pentyl)amino)-N-(4-(4-((4'-chloro(1,1'-biphenyl)-4-yl)methyl)-1-piperazinyl)benzoyl)-3-nitrobenzenesulfonamide, N-(4-(4-(((1,1'-biphenyl)-2-ylmethyl)piperazin-1-yl)benzoyl)-4-(((1R)-4-methyl-1-((phenylsulfanyl)methyl)pentyl)amino)-3-nitrobenzenesulfonamide, tert-butyl(5R)-5-(4-(((4-(4-((4'-chloro(1,1'-biphenyl)-2-yl)methyl)piperazin-1-yl)benzoyl)amino)sulfonyl)-2-nitroanilino)-6-(phenylsulfanyl)hexylcarbamate, 4-(((1R)-5-amino-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1-biphenyl)-2-yl)methyl)piperazin-1-yl)benzoyl)-4-(((1R)-5-((methylsulfonyl)amino)-1-((phenylsulfanyl)methyl)pentyl)amino)-3-nitrobenzenesulfonamide, 4-(((1R)-5-((aminocarbonyl)amino)-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(methylsulfanyl)benzyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(methylsulfonyl)benzyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(5,5-dimethyl-2-oxo-1,3-oxazolidin-3-yl)benzyl)piperazin-1-yl)benzoyl)-3-nitrobenzenesulfonamide, N-(4-(4-(2-cyclohexylbenzyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-(2-(morpholin-4-yl)benzyl)piperazin-1-yl)benzoyl)-3-nitrobenzenesulfonamide, 4-(((1R)-3-(dimethylamino)-1-((phenylsulfanyl)methyl)propyl)amino)-N-(4-(4-(2-(isopropylsulfanyl)benzyl)piperazin-1-yl)benzoyl)-3-nitrobenzenesulfonamide, N-(4-(4-((2-(4-chlorophenyl)-1-cyclohexen-1-yl)methyl)piperazin-1-yl)benzoyl)-4-(((1R)-3-(isopropyl(methyl)amino)-1-((phenylsulfanyl)methyl)propyl)amino)-3-nitrobenzenesulfonamide, N-(4-(4-((2-(4-chlorophenyl)-1-cyclohexen-1-yl)methyl)piperazin-1-yl)benzoyl)-4-(((1R)-3-(dipropylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dipropylamino)-1-((phenylsulfanyl)methyl)propyl)amino)-3-nitrobenzenesulfonamide, N-(4-(4-((2-(4-chlorophenyl)-1-cyclohexen-1-yl)methyl)piperazin-1-yl)benzoyl)-4-(((1R)-3-(diethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-nitrobenzenesulfonamide, N-(4-(4-((1,1'-biphenyl)-3-ylmethyl)piperazin-1-yl)benzoyl)-3-nitro-4-((2-(phenylsulfanyl)ethyl)amino)benzenesulfonamide, N-(4-(4-((1,1'-biphenyl)-3-ylmethyl)piperazin-1-yl)benzoyl)-4-(((1R)-3-(dimethylamino)-1-((phenylsulfanyl)methyl)propyl)amino)-3-nitrobenzenesulfonamide, N-(4-(4-((1,1'-biphenyl)-3-ylmethyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((1,1'-biphenyl)-2-ylmethyl)piperazin-1-yl)-3-fluorobenzoyl)-4-(((1R)-3-(dimethylamino)-1-((phenylsulfanyl)methyl)propyl)amino)-3-nitrobenzenesulfonamide, N-(4-(4-((1,1'-biphenyl)-2-ylmethyl)piperazin-1-yl)-3-fluorobenzoyl)-3-nitro-4-((2-(phenylsulfanyl)ethyl)amino)benzenesulfonamide, N-(4-(4-((1,1'-biphenyl)-2-ylmethyl)piperazin-1-yl)-3-fluorobenzoyl)-4-(((1R)-3-(morpholin-4-yl)-1-((phenylsulfanyl)methyl)propyl)amino)-3-nitrobenzenesulfonamide, N-(4-(4-((1,1'-biphenyl)-2-ylmethyl)piperazin-1-yl)-3,5-difluorobenzoyl)-4-(((1R)-3-(dimethylamino)-1-((phenylsulfanyl)methyl)propyl)amino)-3-nitrobenzenesulfonamide N-(4-(4-((1,1'-biphenyl)-2-ylmethyl)piperazin-1-yl)-3,5-difluorobenzoyl)-3-nitro-4-((2-(phenylsulfanyl)ethyl)amino)benzenesulfonamide, N-(4-(4-((1,1'-biphenyl)-2-ylmethyl)piperazin-1-yl)-3,5-difluorobenzoyl)-4-(((1R)-3-(morpholin-4-yl)-1-((phenylsulfanyl)methyl)propyl)amino)-3-nitrobenzenesulfonamide, 3-nitro-N-(4-(4-((1-phenyl-1H-imidazol-2-yl)methyl)piperazin-1-yl)benzoyl)-4-((2-(phenylsulfanyl)ethyl)amino)benzenesulfonamide, 4-(((1R)-3-(morpholin-4-yl)-1-((phenylsulfanyl)methyl)propyl)amino)-3-nitro-N-(4-(4-((1-phenyl-1H-imidazol-2-yl)methyl)piperazin-1-yl)benzoyl)benzenesulfonamide, 3-nitro-N-(4-(4-((1-phenyl-1H-pyrazol-5-yl)methyl)piperazin-1-yl)benzoyl)-4-((2-(phenylsulfanyl)ethylamino)benzenesulfonamide, 4-(((1R)-3-(morpholin-4-yl)-1-((phenylsulfanyl)methyl)propyl)amino)-3-nitro-N-(4-(4-((1-phenyl-1H-pyrazol-5'-yl)methyl)piperazin-1-yl)benzoyl)benzenesulfonamide, 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide 4-(((1R)-3-(morpholin-4-yl)-1-((phenylsulfanyl)methyl)propyl)amino)-3-nitro-N-(4-(4-((1-phenyl-1H-imidazol-5-yl)methyl)piperazin-1-yl)benzoyl)benzenesulfonamide, 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-3-azetidinecarboxylic acid, N-(4-(4-((4'-chloro(1,1-biphenyl)-2-yl)methyl)piperazin-1-yl)benzoyl)-4-(((1R)-3-((2-hydroxy-2-methylpropyl)amino)-1-((phenylsulfanyl)methyl)propyl)amino)-3-nitrobenzenesulfonamide, (((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)(methyl)amino)acetic acid, (2R)-1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-2-pyrrolidinecarboxylic acid 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-4-piperidinecarboxylic acid N-(4-(4-((4'-chloro(1,1'-biphenyl)-2-yl)methyl)piperazin-1-yl)benzoyl)-4-(((1R)-3-((2-hydroxyethyl)(methyl)amino)-1-((phenylsulfanyl)methyl)propyl)amino)-3-nitrobenzenesulfonamide, (2S)-1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-2-pyrrolidinecarboxylic acid, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(3-(2H-tetrazol-5-yl)azetidin-1-yl)propyl)amino)benzenesulfonamide, (2S)-2-amino-N-((1S)-2-(((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)amino)-1-methyl-2-oxoethyl)propanamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(2-(2H-tetrazol-5-yl)pyrrolidin-1-yl)propyl)amino)benzenesulfonamide, N-(4-(4-((4'-chloro(1,1'-biphenyl)-2-yl)methyl)piperazin-1-yl)benzoyl)-4-(((1R)-3-(4-(((methylsulfonyl)amino)carbonyl)piperidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide, 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-N-hydroxy-4-piperidinecarboxamide, 2-chloro-N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide, 2,6-dichloro-N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide, 4-(((1R)-3-((1R,5S)-8-azabicyclo[3.2.1]oct-8-yl)-1-((phenylsulfanyl)methyl)propyl)amino)-N-(4-(4-((4'-chloro(1,1-biphenyl)-2-yl)methyl)piperazin-1-yl)benzoyl)-3-nitrobenzenesulfonamide, 4-(((1R)-3-(7-azabicyclo[2.2.1]hept-7-yl)-1-((phenylsulfanyl)methyl)propyl)amino)-N-(4-(4-((4'-chloro(1,1-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(2-(phenylsulfanyl)ethoxy)benzenesulfonamide, N-(4-(4-((4'-chloro(1,1'-biphenyl)-2-yl)methyl)piperazin-1-yl)benzoyl)-4-(2-(phenylsulfanyl)ethoxy)-3-(trifluoromethyl)benzenesulfonamide, N-(4-(4-((4'-chloro(1,1'-biphenyl)-2-yl)methyl)piperazin-1-yl)benzoyl)-3-nitro-4-(((1R)-3-((1S,4S)-2-oxa-5-azabicyclo[2.2.1]hept-5-yl)-1-((phenylsulfanyl)methyl)propyl)amino)benzenesulfonamide, N-(4-(4-((4'-chloro(1,1'-biphenyl)-2-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide, N-(4-(4-((2-(4-chlorophenyl)-1-cyclohexen-1-yl)methyl)piperazin-1-yl)benzoyl)-3-nitro-4-(((1R)-3-((1S,4S)-2-oxa-5-azabicyclo[2.2.1]hept-5-yl)-1-((phenylsulfanyl)methyl)propyl)amino)benzenesulfonamide, N-(4-(4-((2-(4-chlorophenyl)-1-cyclohexen-1-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide, 4-(((1R)-3-(7-azabicyclo[2.2.1]hept-7-yl)-1-((phenylsulfanyl)methyl)propyl)amino)-N-(4-(4-((2-(4-chlorophenyl)-1-cyclohexen-1-yl)methyl)piperazin-1-yl)benzoyl)-3-nitrobenzenesulfonamide, N-(4-(4-((2-(4-chlorophenyl)-1-cyclohexen-1-yl)methyl)piperazin-1-yl)benzoyl)-4-(((1R)-3-((2R,5S)-2,5-dimethylpyrrolidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide, N-(4-(4-((1,1'-biphenyl)-2-ylmethyl)piperazin-1-yl)benzoyl)-4-(cyclohexyloxy)-3-nitrobenzenesulfonamide, N-(4-(4-((1,1'-biphenyl)-2-ylmethyl)piperazin-1-yl)benzoyl)-4-(cyclohexylmethoxy)-3-nitrobenzenesulfonamide, N-(4-(4-((1,1'-biphenyl)-2-ylmethyl)piperazin-1-yl)benzoyl)-4-(2-cyclohexylethoxy)-3-nitrobenzenesulfonamide, N-(4-(4-((1,1'-biphenyl)-2-ylmethyl)piperazin-1-yl)benzoyl)-3-nitro-4-(tetrahydro-2H-pyran-4-ylamino)benzenesulfonamide, N-(4-(4-((1,1'-biphenyl)-2-ylmethyl)piperazin-1-yl)benzoyl)-4-((2-cyclohexylethyl)amino)-3-nitrobenzenesulfonamide, N-(4-(4-((1,1'-biphenyl)-2-ylmethyl)piperazin-1-yl)benzoyl)-4-(cyclohexyl(methyl)amino)-3-nitrobenzenesulfonamide, N-(4-(4-((1,1'-biphenyl)-2-ylmethyl)piperazin-1-yl)benzoyl)-4-(4,4-dimethylpiperidin-1-yl)-3-nitrobenzenesulfonamide, tert-butyl 4-(4-(((4-(4-((1,1'-biphenyl)-2-ylmethyl)piperazin-1-yl)benzoyl)amino)sulfonyl)-2-nitrophenoxy)-1-piperidinecarboxylate, N-(4-(4-((1,1'-biphenyl)-2-ylmethyl)piperazin-1-yl)benzoyl)-3-nitro-4-(piperidin-4-yloxy)benzenesulfonamide, N-(4-(4-((1,1'-biphenyl)-2-ylmethyl)piperazin-1-yl)benzoyl)-4-((1-methylpiperidin-4-yl)oxy)-3-nitrobenzenesulfonamide, N-(4-(4-((4'-chloro(1,1'-biphenyl)-2-yl)methyl)piperazin-1-yl)benzoyl)-4-((cyclohexylmethyl)amino)-3-nitrobenzenesulfonamide, N-(4-(4-((4'-chloro(1,1'-biphenyl)-2-yl)methyl)piperazin-1-yl)benzoyl)-4-((cyclohexylmethyl)(propyl)amino)-3-nitrobenzenesulfonamide, 4-(((1-benzylpiperidin-4-yl)methyl)amino)-N-(4-(4-((1,1'-biphenyl)-2-ylmethyl)piperazin-1-yl)benzoyl)-3-nitrobenzenesulfonamide, N-(4-(4-((1,1'-biphenyl)-2-ylmethyl)piperazin-1-yl)benzoyl)-4-((cyclohexylmethyl)(methyl)amino)-3-nitrobenzenesulfonamide, 4-((1-benzylpiperidin-4-yl)amino)-N-(4-(4-((1,1'-biphenyl)-2-ylmethyl)piperazin-1-yl)benzoyl)-3-nitrobenzenesulfonamide, N-(4-(4-((1,1'-biphenyl)-2-ylmethyl)piperazin-1-yl)benzoyl)-3-nitro-4-(tetrahydro-2H-sulfanylpyran-4-ylamino)benzenesulfonamide, ethyl 4-(4-(((4-(4-((1,1'-biphenyl)-2-ylmethyl)piperazin-1-yl)benzoyl)amino)sulfonyl)-2-nitroanilino)-1-piperidinecarboxylate, N-(4-(4-((1,1'-biphenyl)-2-ylmethyl)piperazin-1-yl)benzoyl)-3-nitro-4-(((1-propylpiperidin-4-yl)methyl)amino)benzenesulfonamide, N-(4-(4-((1,1'-biphenyl)-2-ylmethyl)piperazin-1-yl)benzoyl)-4-(isopropylamino)-3-nitrobenzenesulfonamide, N-(4-(4-((1,1'-biphenyl)-2-ylmethyl)piperazin-1-yl)benzoyl)-3-nitro-4-((2-(1,3-thiazol-2-ylsulfanyl)ethylamino)benzenesulfonamide, N-(4-(4-((1,1'-biphenyl)-2-ylmethyl)piperazin-1-yl)benzoyl)-3-nitro-4-((2-((4-phenyl-1,3-thiazol-2-yl)sulfanyl)ethylamino)benzenesulfonamide, 4-((2-(1,3-benzothiazol-2-ylsulfanyl)ethylamino)-N-(4-(4-((1,1'-biphenyl)-2-ylmethyl)piperazin-1-yl)benzoyl)-3-nitrobenzenesulfonamide, N-(4-(4-((4'-chloro(1,1-biphenyl)-2-yl)methyl)piperazin-1-yl)benzoyl)-3-nitro-4-((2-(1,3-thiazol-2-ylsulfanyl)ethylamino)benzenesulfonamide, 4-((2-(1,3-benzoxazol-2-ylsulfanyl)ethyl)amino)-N-(4-(4-((4'-chloro(1,1'-biphenyl)-2-yl)methyl)piperazin-1-yl)benzoyl)-3-nitrobenzenesulfonamide, 4-((2-(1,3-benzothiazol-2-ylsulfanyl)ethylamino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-((2-(pyrimidin-2-ylsulfanyl)ethyl)amino)benzenesulfonamide, 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide, 4-(((1-benzylpiperidin-4-yl)methyl)amino)-N-(4-(4-((4'-chloro(1,1'-biphenyl)-2-yl)methyl)piperazin-1-yl)benzoyl)-3-nitrobenzenesulfonamide, N-(4-(4-((1,1'-biphenyl)-2-ylmethyl)piperazin-1-yl)benzoyl)-4-((2-bromoethyl)amino)-3-nitrobenzenesulfonamide, N-(4-(4-((4'-chloro(1,1'-biphenyl)-2-yl)methyl)piperazin-1-yl)benzoyl)-4-((2-((4-methyl-1,3-thiazol-2-yl)sulfanyl)ethyl)amino)-3-nitrobenzenesulfonamide, N-(4-(4-((4'-chloro(1,1'-biphenyl)-2-yl)methyl)piperazin-1-yl)benzoyl)-4-(((4-methoxycyclohexyl)methyl)amino)-3-nitrobenzenesulfonamide, N-(4-(4-((1,1'-biphenyl)-2-ylmethyl)piperazin-1-yl)benzoyl)-3-nitro-4-((2-(2-thienylsulfanyl)ethyl)amino)benzenesulfonamide, N-(4-(4-((4'-chloro(1,1'-biphenyl)-2-yl)methyl)piperazin-1-yl)benzoyl)-4-((1,1-dimethyl-2-(2-thienylsulfanyl)ethyl)amino)-3-nitrobenzenesulfonamide, N-(4-(4-((4'-chloro(1,1'-biphenyl)-2-yl)methyl)piperazin-1-yl)benzoyl)-4-(((1R)-3-(morpholin-4-yl)-1-((1,3-thiazol-2-ylsulfanyl)methyl)propyl)amino)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(pyrimidin-2-ylsulfanyl)butanamide, N-(4-(4-((4'-chloro(1,1'-biphenyl)-2-yl)methyl)piperazin-1-yl)benzoyl)-4-(((1R)-3-(morpholin-4-yl)-3-oxo-1-((2-thienylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-((1,1-dimethyl-2-(pyrimidin-2-ylsulfanyl)ethyl)amino)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(1,3-thiazol-2-ylsulfanyl)butanamide, N-(4-(4-((4'-chloro(1,1'-biphenyl)-2-yl)methyl)piperazin-1-yl)benzoyl)-4-(((1R)-3-(morpholin-4-yl)-1-((2-thienylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-(((4-(trifluoromethoxy)phenyl)sulfanyl)methyl)propyl)amino)-3-nitrobenzenesulfonamide, N-(4-(4-((4'-chloro(1,1-biphenyl)-2-yl)methyl)piperazin-1-yl)benzoyl)-3-nitro-4-((2-phenoxyethyl)amino)benzenesulfonamide, N-(4-(4-((4'-chloro(1,1'-biphenyl)-2-yl)methyl)piperazin-1-yl)benzoyl)-4-(((1R)-3-(morpholin-4-yl)-1-(((4-(trifluoromethoxy)phenyl)sulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-1-(((4-methoxyphenyl)sulfanyl)methyl)-3-(morpholin-4-yl)propyl)amino)-3-nitrobenzenesulfonamide, N-(4-(4-((4'-chloro(1,1'-biphenyl)-2-yl)methyl)piperazin-1-yl)benzoyl)-4-(((1R)-1-(((4-methylphenyl)sulfanyl)methyl)-3-(morpholin-4-yl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((2-thienylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-1-(((4-chlorophenyl)sulfanyl)methyl)-3-(morpholin-4-yl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-(((4-fluorophenyl)sulfanyl)methyl)propyl)amino)-3-nitrobenzenesulfonamide, N-(4-(4-((4'-chloro(1,1-biphenyl)-2-yl)methyl)piperazin-1-yl)benzoyl)-4-(((1R)-1-(((4-fluorophenyl)sulfanyl)methyl)-3-(morpholin-4-yl)propyl)amino)-3-nitrobenzenesulfonamide, N-(4-(4-((4'-chloro(1,1'-biphenyl)-2-yl)methyl)piperazin-1-yl)-2-fluorobenzoyl)-4-(((1R)-3-(dimethylamino)-1-((phenylsulfanyl)methyl)propyl)amino)-3-nitrobenzenesulfonamide, N-(4-(1-((4'-chloro(1,1'-biphenyl)-2-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide, N-(4-(1-((4'-chloro(1,1'-biphenyl)-2-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)-2-fluorobenzoyl)-4-(((1R)-3-(dimethylamino)-1-((phenylsulfanyl)methyl)propyl)amino)-3-(trifluoromethyl)benzenesulfonamide, N-((6-(4-((4'-chloro(1,1'-biphenyl)-2-yl)methyl)piperazin-1-yl)pyridin-3-yl)carbonyl)-4-(((1R)-3-(dimethylamino)-1-((phenylsulfanyl)methyl)propyl)amino)-3-nitrobenzenesulfonamide, N-(4-(1-((4'-chloro(1,1'-biphenyl)-2-yl)methyl)piperidin-4-yl)benzoyl)-4-(((1R)-3-(dimethylamino)-1-((phenylsulfanyl)methyl)propyl)amino)-3-nitrobenzenesulfonamide, N-(4-(1-((4'-chloro(1,1'-biphenyl)-2-yl)methyl)piperidin-4-yl)benzoyl)-4-(((1R)-3-(morpholin-4-yl)-1-((phenylsulfanyl)methyl)propyl)amino)-3-nitrobenzenesulfonamide, N-(4-(1-((4'-chloro(1,1'-biphenyl)-2-yl)methyl)-1,2,3,6-tetrahydropyridin-4-yl)benzoyl)-4-(((1R)-3-(dimethylamino)-1-((phenylsulfanyl)methyl)propyl)amino)-3-(trifluoromethyl)benzenesulfonamide, N-((6-(4-((4'-chloro(1,1'-biphenyl)-2-yl)methyl)piperazin-1-yl)pyridin-3-yl)carbonyl)-4-(((1R)-3-(morpholin-4-yl)-1-((phenylsulfanyl)methyl)propyl)amino)-3-nitrobenzenesulfonamide, N-((6-(4-((4'-chloro(1,1'-biphenyl)-2-yl)methyl)piperazin-1-yl)pyridin-3-yl)carbonyl)-4-(((1R)-3-(dimethylamino)-1-((phenylsulfanyl)methyl)propyl)amino)-3-(trifluoromethyl)benzenesulfonamide, N-(4-(4-((4'-chloro(1,1'-biphenyl)-2-yl)methyl)piperidin-1-yl)benzoyl)-4-(((1R)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperidin-1-yl)benzoyl)-4-(((1R)-3-(morpholin-4-yl)-1-((phenylsulfanyl)methyl)propyl)amino)-3-nitrobenzenesulfonamide, N-((5-(4-((4'-chloro(1,1'-biphenyl)-2-yl)methyl)piperazin-1-yl)pyridin-2-yl)carbonyl)-4-(((1R)-3-(dimethylamino)-1-((phenylsulfanyl)methyl)propyl)amino)-3-nitrobenzenesulfonamide, N-((5-(4-((4'-chloro(1,1'-biphenyl)-2-yl)methyl)piperazin-1-yl)pyridin-2-yl)carbonyl)-4-(((1R)-3-(morpholin-4-yl)-1-((phenylsulfanyl)methyl)propyl)amino)-3-nitrobenzenesulfonamide, N-(4-(1-((2-(4-chlorophenyl)-5,5-dimethyl-1-cyclohexen-1-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide, N-(4-(1-((2-(4-chlorophenyl)-1-cyclohexen-1-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide, N-(4-(1-((2-(4-chlorophenyl)-1-cyclohexen-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide, N-(4-(1-((2-(4-chlorophenyl)-5,5-dimethyl-1-cyclohexen-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1-biphenyl)-2-yl)methyl)-1-cyclohexen-1-yl)benzoyl)-4-(((1R)-3-(dimethylamino)-1-((phenylsulfanyl)methyl)propyl)amino)-3-nitrobenzenesulfonamide, N-(4-(4-((4'-chloro(1,1-biphenyl)-2-yl)methyl)-1-cyclohexen-1-yl)benzoyl)-4-(((1R)-3-(morpholin-4-yl)-1-((phenylsulfanyl)methyl)propyl)amino)-3-nitrobenzenesulfonamide, N-(4-((3aR,6aS)-5-((4'-chloro(1,1'-biphenyl)-2-yl)methyl)hexahydropyrrolo[3,4-c]pyrrol-2(1H)-yl)benzoyl)-4-

(((1R)-3-(dimethylamino)-1-((phenylsulfanyl)methyl)propyl)amino)-3-nitrobenzenesulfonamide, N-(4-(4-(((1,1'-biphenyl)-2-ylmethyl)piperazin-1-yl)benzoyl)-4-(methyl((methyl-4-(trifluoromethoxy)anilino)carbonyl)amino)-3-nitrobenzenesulfonamide, N-(4-(4-(((1,1'-biphenyl)-2-ylmethyl)piperazin-1-yl)benzoyl)-4-(((2-dimethylanilino)carbonyl)(methyl)amino)-3-nitrobenzenesulfonamide, N-(4-(4-(((1,1'-biphenyl)-2-ylmethyl)piperazin-1-yl)benzoyl)-4-(((4-methoxy(methyl)anilino)carbonyl)(methyl)amino)-3-nitrobenzenesulfonamide, N-(4-(4-(((1,1'-biphenyl)-2-ylmethyl)piperazin-1-yl)benzoyl)-4-(((4-dimethylanilino)carbonyl)(methyl)amino)-3-nitrobenzenesulfonamide, 4-(((benzhydryl(methyl)amino)carbonyl)(methyl)amino)-N-(4-(4-(((1,1'-biphenyl)-2-ylmethyl)piperazin-1-yl)benzoyl)-3-nitrobenzenesulfonamide, N-(4-(4-(((1,1'-biphenyl)-2-ylmethyl)piperazin-1-yl)benzoyl)-4-(methyl((methyl((1S)-1-phenylethyl)amino)carbonyl)amino)-3-nitrobenzenesulfonamide, N-(4-(4-(((1,1'-biphenyl)-2-ylmethyl)piperazin-1-yl)benzoyl)-4-(methyl((methyl(2-(4-methylpiperazin-1-yl)-1-phenylethyl)amino)carbonyl)amino)-3-nitrobenzenesulfonamide, N-(4-(4-(((1,1'-biphenyl)-2-ylmethyl)piperazin-1-yl)benzoyl)-4-(methyl((methyl(2-(morpholin-4-yl)-1-phenylethyl)amino)carbonyl)amino)-3-nitrobenzenesulfonamide, N-(4-(4-(((1,1'-biphenyl)-2-ylmethyl)piperazin-1-yl)benzoyl)-4-((((1,2-diphenylethyl)(methyl)amino)carbonyl)(methyl)amino)-3-nitrobenzenesulfonamide, N-(4-(4-(((1,1'-biphenyl)-2-ylmethyl)piperazin-1-yl)benzoyl)-4-((((2-(dimethylamino)-1-phenylethyl)(methyl)amino)carbonyl)(methyl)amino)-3-nitrobenzenesulfonamide, 3-amino-N-(4-(4-((4'-chloro(1,1'-biphenyl)-2-yl)methyl)piperazin-1-yl)benzoyl)-4-((2-(phenylsulfanyl)ethyl)amino)benzenesulfonamide, N-(4-(4-((4'-chloro(1,1'-biphenyl)-2-yl)methyl)piperazin-1-yl)benzoyl)-1-(2-(phenylsulfanyl)ethyl-1H-1,2,3-benzotriazole-5-sulfonamide, N-(4-(4-((4'-chloro(1,1'-biphenyl)-2-yl)methyl)piperazin-1-yl)benzoyl)-1-(2-(phenylsulfanyl)ethyl)-1H-benzimidazole-5-sulfonamide, N-(4-(4-(((1,1'-biphenyl)-2-ylmethyl)-4-methoxypiperidin-1-yl)benzoyl)-4-((cyclohexylmethyl)amino)-3-nitrobenzenesulfonamide, N-(4-(4-(((1,1-biphenyl)-2-ylmethyl)-4-methoxypiperidin-1-yl)benzoyl)-4-(cyclohexylamino)-3-nitrobenzenesulfonamide, N-(4-(4-(((1,1'-biphenyl)-2-ylmethyl)-4-methoxypiperidin-1-yl)benzoyl)-4-((1,1-dimethyl-2-(phenylsulfanyl)ethyl)amino)-3-nitrobenzenesulfonamide, N-(4-(4-(((1,1'-biphenyl)-2-ylmethyl)piperazin-1-yl)benzoyl)-3-nitro-4-((1-((phenylsulfanyl)methyl)cyclopentyl)amino)benzene-sulfonamide, N-(4-(4-(((1,1'-biphenyl)-2-ylmethyl)-4-methoxypiperidin-1-yl)benzoyl)-3-nitro-4-((1-((phenylsulfanyl)methyl)cyclopentyl)amino)benzene-sulfonamide, N-(4-(4-((4'-chloro(1,1'-biphenyl)-2-yl)methyl)piperazin-1-yl)benzoyl)-3-nitro-4-((1-((phenylsulfanyl)methyl)cyclopentyl)amino)benzene-sulfonamide, N-(4-(4-((4'-chloro(1,1'-biphenyl)-2-yl)methyl)piperazin-1-yl)benzoyl)-3-nitro-4-(((1S)-1-((phenylsulfanyl)methyl)propyl)amino)benzenesulfonamide, N-(4-(4-(((1,1'-biphenyl)-2-ylmethyl)-4-methoxypiperidin-1-yl)benzoyl)-3-nitro-4-(((1S)-1-((phenylsulfanyl)methyl)propyl)amino)benzenesulfonamide, N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1S)-3-methyl-1-((phenylsulfanyl)methyl)butyl)amino)-3-nitrobenzenesulfonamide, N-(4-(4-(((1,1'-biphenyl)-2-ylmethyl)-4-methoxypiperidin-1-yl)benzoyl)-4-(((1S)-3-methyl-1-((phenylsulfanyl)methyl)butyl)amino)-3-nitrobenzenesulfonamide, N-(4-(4-((4'-chloro(1,1'-biphenyl)-2-yl)methyl)piperazin-1-yl)benzoyl)-3-nitro-4-((1-((phenylsulfanyl)methyl)cyclopropyl)amino)benzene-sulfonamide, N-(4-(4-((4'-chloro(1,1'-biphenyl)-2-yl)methyl)piperazin-1-yl)benzoyl)-3-nitro-4-((1-((phenylsulfanyl)methyl)cyclohexyl)amino)benzene-sulfonamide, N-(4-(4-((4'-chloro(1,1'-biphenyl)-2-yl)methyl)piperazin-1-yl)benzoyl)-4-(((1R)-1-methyl-2-(phenylsulfanyl)ethylamino)-3-nitrobenzenesulfonamide, N-(4-(4-(((1,1'-biphenyl)-2-ylmethyl)piperazin-1-yl)benzoyl)-4-(((1S)-1-methyl-2-(phenylsulfanyl)ethyl)amino)-3-nitrobenzenesulfonamide, N-(4-(4-(((1,1'-biphenyl)-2-ylmethyl)piperazin-1-yl)benzoyl)-3-nitro-4-(((1R,2S)-2-(phenylsulfanyl)cyclohexyl)amino)benzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, 4-(((1R)-5-amino-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide, N-(4-(4-(((1,1'-biphenyl)-2-ylmethyl)piperazin-1-yl)benzoyl)-3-nitro-4-(((1S)-2-(phenylsulfanyl)-1-(pyridin-3-ylmethyl)ethyl)amino)benzenesulfonamide, N-(4-(4-(((1,1'-biphenyl)-2-ylmethyl)-4-methoxypiperidin-1-yl)benzoyl)-3-nitro-4-(((1S)-2-(phenylsulfanyl)-1-(pyridin-3-ylmethyl)ethyl)amino)benzenesulfonamide, N-(4-(4-(((1,1-biphenyl)-2-ylmethyl)piperazin-1-yl)benzoyl)-3-nitro-4-(((1S,2R)-2-(phenylsulfanyl)cyclohexyl)amino)benzenesulfonamide, N-(4-(4-(((1,1'-biphenyl)-2-ylmethyl)piperazin-1-yl)benzoyl)-4-((1-(((2-methyl-3-furyl)sulfanyl)methyl)cyclopentyl)amino)-3-nitrobenzenesulfonamide, N-(4-(4-((4'-chloro(1,1'-biphenyl)-2-yl)methyl)piperazin-1-yl)benzoyl)-4-((1-(((2-methyl-3-furyl)sulfanyl)methyl)cyclopentyl)amino)-3-nitrobenzenesulfonamide, N-(4-(4-((4'-chloro(1,1'-biphenyl)-2-yl)methyl)piperazin-1-yl)benzoyl)-3-nitro-4-(((1S)-2-(phenylsulfanyl)-1-(pyridin-3-ylmethyl)ethyl)amino)benzenesulfonamide, N-(4-(4-((2-(4-chlorophenyl)-3-pyridin-3-yl)methyl)piperazin-1-yl)benzoyl)-4-(((1R)-(dimethylamino)-1-((phenylsulfanyl)methyl)propyl)amino)-3-nitrobenzenesulfonamide, N-(4-(4-((2-(4-chlorophenyl)pyridin-3-yl)methyl)piperazin-1-yl)benzoyl)-3-nitro-4-((2-(phenylsulfanyl)ethyl)amino)benzenesulfonamide, N-(4-(4-((2-(4-chlorophenyl)pyridin-3-yl)methyl)piperazin-1-yl)benzoyl)-4-(((1R)-3-(morpholin-4-yl)-1-((phenylsulfanyl)methyl)propyl)amino)-3-nitrobenzenesulfonamide, 3-nitro-N-(4-(4-((2-phenylpyridin-3-yl)methyl)piperazin-1-yl)benzoyl)-4-((2-(phenylsulfanyl)ethyl)amino)benzenesulfonamide, 4-(((1R)-3-(morpholin-4-yl)-1-((phenylsulfanyl)methyl)propyl)amino)-3-nitro-N-(4-(4-((2-phenylpyridin-3-yl)methyl)piperazin-1-yl)benzoyl)benzenesulfonamide, 4-(((1R)-3-(dimethylamino)-1-((phenylsulfanyl)methyl)propyl)amino)-3-nitro-N-(4-(4-((2-phenylpyridin-3-yl)methyl)piperazin-1-yl)benzoyl)benzenesulfonamide, 4-(((1R)-3-(dimethylamino)-1-((phenylsulfanyl)methyl) propyl)amino)-N-(4-(4-((2-(4-(methylsulfanyl)phenyl)pyridin-3-yl)methyl)piperazin-1-yl)benzoyl)-3-nitrobenzenesulfonamide, 4-(((1R)-3-(dimethylamino)-1-((phenylsulfanyl)methyl) propyl)amino)-N-(4-(4-((2-(4-methoxyphenyl)pyridin-3-yl) methyl)piperazin-1-yl)benzoyl)-3-nitrobenzenesulfonamide, N-(4-(4-((2-(4-(dimethylamino)phenyl)pyridin-3-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl) propyl)amino)-N-(4-(4-((2-(4-fluorophenyl)pyridin-3-yl) methyl)piperazin-1-yl)benzoyl)-3-nitrobenzenesulfonamide, 4-(((1R)-3-(dimethylamino)-1-((phenylsulfanyl)methyl) propyl)amino)-N-(4-(4-((2-(4-(methylsulfonyl)phenyl)pyridin-3-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-((2-(pyridin-4-ylsulfanyl)ethyl) amino)benzenesulfonamide, 4-(((1R)-3-(dimethylamino)-1-((phenylsulfanyl)methyl) propyl)amino)-N-(4-(4-((4'-(methylsulfonyl)(1,1'-biphenyl)-2-yl)methyl)piperazin-1-yl)benzoyl)-3-nitrobenzenesulfonamide, N-(4-(4-((4'-(methylsulfonyl)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1-biphenyl)-2-yl)methyl)piperazin-1-yl)benzoyl)-4-(((1R)-3-(morpholin-4-yl)-1-((phenylsulfonyl)methyl)propyl)amino)-3-nitrobenzenesulfonamide, N-(4-(4-((4'-(dimethylamino)(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, (3R)-3-(4-(((4-(4-((4'-chloro(1,1'-biphenyl)-2-yl)methyl) piperazin-1-yl)benzoyl)amino)sulfonyl)-2-nitroanilino)-N, N-dimethyl-4-(phenylsulfonyl)butanamide, N-(4-(4-((4'-chloro(1,1'-biphenyl)-2-yl)methyl)piperazin-1-yl)benzoyl)-3-nitro-4-(((3S,4R)-(phenylsulfanyl)pyrrolidin-4-yl)amino)benzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyridin-4-ylsulfanyl)propyl)amino)benzenesulfonamide, N-(4-(4-((3-(4-chlorophenyl)pyridin-4-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((3-(4-chlorophenyl)pyridin-4-yl)methyl)piperazin-1-yl)benzoyl)-3-nitro-4-((2-(phenylsulfanyl)ethyl) amino)benzenesulfonamide, N-(4-(4-((2-(4-chlorophenyl)-1-cyclopenten-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-1-cyclohexen-1-yl)methyl) piperazin-1-yl)benzoyl)-4-(((1R)-3-(dimethylamino)-1-((phenylsulfanyl)methyl)propyl)amino)-3-nitrobenzenesulfonamide, N-(4-(4-((2-bromo-1-cyclopenten-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-1-cyclohexen-1-yl)methyl) piperazin-1-yl)benzoyl)-4-(((1R)-3-(morpholin-4-yl)-1-((phenylsulfanyl)methyl)propyl)amino)-3-nitrobenzenesulfonamide, N-(4-(4-((2-(4-chlorophenyl)-1-cyclohexen-1-yl)methyl) piperazin-1-yl)benzoyl)-4-(((1R)-3-(dimethylamino)-1-((phenylsulfanyl)methyl)propyl)amino)-3-(trifluoromethyl) benzenesulfonamide, N-(4-(4-((2-bromo-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl) propyl)amino)-N-(4-(4-((2-(4-methoxyphenyl)-1-cyclohexen-1-yl)methyl)piperazin-1-yl)benzoyl)-3-nitrobenzenesulfonamide, 4-(((1R)-3-(dimethylamino)-1-((phenylsulfanyl)methyl) propyl)amino)-N-(4-(4-((2-(4-fluorophenyl)-1-cyclohexen-1-yl)methyl)piperazin-1-yl)benzoyl)-3-nitrobenzenesulfonamide, 4-(((1R)-3-(dimethylamino)-1-((phenylsulfanyl)methyl) propyl)amino)-3-nitro-N-(4-(4-((2-phenyl-1-cyclohexen-1-yl)methyl)piperazin-1-yl)benzoyl)benzenesulfonamide, N-(4-(4-((2-(4-chlorophenyl)-1-cycloocten-1-yl)methyl) piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl) propyl)amino)-N-(4-(4-((2-(4-(methylsulfanyl)phenyl)-1-cyclohexen-1-yl)methyl)piperazin-1-yl)benzoyl)-3-nitrobenzenesulfonamide, N-(4-(4-((2-(4-chlorophenyl)-1-cyclohepten-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-1-cyclohepten-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((2-(4-chlorophenyl)-5,5-dimethyl-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-5,5-dimethyl-1-cyclohexen-1-yl)methyl)piperazin-1-yl)benzoyl)-4-(((1R)-3-(morpholin-4-yl)-1-((phenylsulfanyl)methyl)propyl) amino)-3-nitrobenzenesulfonamide, N-(4-(4-((1,1'-biphenyl)-2-ylmethyl)-4-(2-(morpholin-4-yl)ethoxy)piperidin-1-yl)benzoyl)-4-((1,1-dimethyl-2-(phenylsulfanyl)ethylamino)-3-nitrobenzenesulfonamide, N-(4-(4-((1,1'-biphenyl)-2-ylmethyl)-4-(2-(morpholin-4-yl)ethoxy)piperidin-1-yl)benzoyl)-3-nitro-4-((2-(phenylsulfanyl)ethyl)amino)benzenesulfonamide, N-(4-(4-((1,1'-biphenyl)-2-ylmethyl)-4-(2-(pyrrolidin-1-yl)ethoxy)piperidin-1-yl)benzoyl)-4-((1,1-dimethyl-2-(phenylsulfanyl)ethylamino)-3-nitrobenzenesulfonamide, N-(4-(4-((1,1'-biphenyl)-2-ylmethyl)-4-(2-(pyrrolidin-1-yl)ethoxy)piperidin-1-yl)benzoyl)-3-nitro-4-((2-(phenylsulfanyl)ethyl)amino)benzenesulfonamide, N-(4-(4-((1,1'-biphenyl)-2-ylmethyl)-4-(2-(pyrrolidin-1-yl)ethoxy)piperidin-1-yl)benzoyl)-3-nitro-4-((1-((phenylsulfanyl)methyl)cyclopentyl)amino)benzene-sulfonamide, N-(4-(4-((1,1'-biphenyl)-2-ylmethyl)-4-(2-(dimethylamino)ethoxy)piperidin-1-yl)benzoyl)-4-((1,1-dimethyl-2-(phenylsulfanyl)ethyl)amino)-3-nitrobenzenesulfonamide, N-(4-(4-((1,1'-biphenyl)-2-ylmethyl)-4-(2-(dimethylamino)ethoxy)piperidin-1-yl)benzoyl)-3-nitro-4-((2-(phenylsulfanyl)ethyl)amino)benzenesulfonamide, N-(4-(4-((1,1'-biphenyl)-2-ylmethyl)-4-(2-(dimethylamino)ethoxy)piperidin-1-yl)benzoyl)-3-nitro-4-((1-((phenylsulfanyl)methyl)cyclopentyl)amino)benzene-sulfonamide, N-(4-(4-((1,1'-biphenyl)-2-ylmethyl)-4-(2-(piperidin-1-yl)ethoxy)piperidin-1-yl)benzoyl)-4-((1,1-dimethyl-2-(phenylsulfanyl)ethyl)amino)-3-nitrobenzenesulfonamide, N-(4-(4-((1,1'-biphenyl)-2-ylmethyl)-4-(2-(piperidin-1-yl)ethoxy)piperidin-1-yl)benzoyl)-3-nitro-4-((2-(phenylsulfanyl)ethyl)amino)benzenesulfonamide, N-(4-(4-((1,1'-biphenyl)-2-ylmethyl)-4-(2-(piperidin-1-yl)ethoxy)piperidin-1-yl)benzoyl)-3-nitro-4-((1-((phenylsulfanyl)methyl)cyclopentyl)amino)benzene-sulfonamide, N-(4-(4-((1,1'-biphenyl)-2-ylmethyl)piperazin-1-yl)benzoyl)-4-(((1S)-3-(morpholin-4-yl)-1-((phenylsulfanyl)methyl)propyl)amino)-3-nitrobenzenesulfonamide, N-(4-(4-((4'-(2-(dimethylamino)ethoxy)(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((4'-(2-(dimethylamino)ethoxy)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-(2-(dimethylamino)ethoxy)(1,1'-biphenyl)-2-yl)methyl)piperazin-1-yl)benzoyl)-4-((1,1-dimethyl-2-(phenylsulfanyl)ethylamino)-3-nitrobenzenesulfonamide, N-(4-(4-((4'-(2-(dimethylamino)ethoxy)(1,1'-biphenyl)-2-yl)methyl)piperazin-1-yl)benzoyl)-3-nitro-4-((2-(phenylsulfanyl)ethyl)amino)benzenesulfonamide, 4-(((1R)-3-(dimethylamino)-1-((phenylsulfanyl)methyl)propyl)amino)-N-(4-(4-((4'-(2-(morpholin-4-yl)ethoxy)(1,1'-biphenyl)-2-yl)methyl)piperazin-1-yl)benzoyl)-3-nitrobenzenesulfonamide, N-(4-(4-((4'-(2-(morpholin-4-yl)ethoxy)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, 4-((1,1-dimethyl-2-(phenylsulfanyl)ethyl)amino)-N-(4-(4-((4'-(2-(morpholin-4-yl)ethoxy)(1,1'-biphenyl)-2-yl)methyl)piperazin-1-yl)benzoyl)-3-nitrobenzenesulfonamide, N-(4-(4-((4'-(2-(morpholin-4-yl)ethoxy)(1,1'-biphenyl)-2-yl)methyl)piperazin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-4-(((1R)-3-(1H-imidazol-1-yl)-1-((phenylsulfanyl)methyl)propyl)amino)-3-nitrobenzenesulfonamide, N-(4-(4-((1,1'-biphenyl)-2-ylmethyl)piperazin-1-yl)benzoyl)-4-(((1R)-3-(1H-imidazol-1-yl)-1-((phenylsulfanyl)methyl)propyl)amino)-3-nitrobenzenesulfonamide, N-(4-(4-((1,1'-biphenyl)-2-ylmethyl)-4-methoxy-piperidin-1-yl)benzoyl)-4-(((1R)-3-(1H-imidazol-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-4-(4-methylpiperazin-1-yl)-1-((phenylsulfanyl)methyl)butyl)amino)-3-nitrobenzenesulfonamide, N-(4-(4-((4'-chloro(1,1'-biphenyl)-2-yl)methyl)piperazin-1-yl)benzoyl)-4-(((1R)-2-((2-(dimethylamino)ethyl)(methyl)amino)-1-((phenylsulfanyl)methyl)ethyl)amino)-3-nitrobenzenesulfonamide, (4R)-4-(4-(((4-(4-((4'-chloro(1,1'-biphenyl)-2-yl)methyl)piperazin-1-yl)benzoyl)amino)sulfonyl)-2-nitroanilino)-N,N-dimethyl-5-(phenylsulfanyl)pentanamide, N-(4-(4-((4'-chloro(1,1'-biphenyl)-2-yl)methyl)piperazin-1-yl)benzoyl)-4-(((1R)-4-(dimethylamino)-1-((phenylsulfonyl)methyl)butyl)amino)-3-nitrobenzenesulfonamide, 2-(((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)(methyl)amino)-N,N-dimethylacetamide, (3R)-N-(tert-butyl)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanamide, (3R)-3-(4-(((4-(4-((4'-chloro(1,1'-biphenyl)-2-yl)methyl)piperazin-1-yl)benzoyl)amino)sulfonyl)-2-nitroanilino)-N,N-diisopropyl-4-(phenylsulfanyl)butanamide, (3R)-N-(tert-butyl)-3-(4-(((4-(4-((4'-chloro(1,1'-biphenyl)-2-yl)methyl)piperazin-1-yl)benzoyl)amino)sulfonyl)-2-nitroanilino)-N-methyl-4-(phenylsulfanyl)butanamide, (3R)-3-(4-(((4-(4-((4'-chloro(1,1'-biphenyl)-2-yl)methyl)piperazin-1-yl)benzoyl)amino)sulfonyl)-2-nitroanilino)-N-isopropyl-N-methyl-4-(phenylsulfanyl)butanamide, N-(4-(4-((4'-chloro(1,1'-biphenyl)-2-yl)methyl)piperazin-1-yl)benzoyl)-3-nitro-4-(((1R)-3-oxo-1-((phenylsulfanyl)methyl)-3-(piperidin-1-yl)propyl)amino)benzenesulfonamide, N-((5R)-5-(4-(((4-(4-((4'-chloro(1,1'-biphenyl)-2-yl)methyl)piperazin-1-yl)benzoyl)amino)sulfonyl)-2-nitroanilino)-6-(phenylsulfanyl)hexyl)-2-(dimethylamino)acetamide, (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(phenylsulfanyl)butanamide, N-(4-(4-((4'-chloro(1,1'-biphenyl)-2-yl)methyl)piperazin-1-yl)benzoyl)-4-(((1R)-3-(1,1-dioxidothiomorpholin-4-yl)-3-oxo-1-((phenylsulfanyl)methyl)propyl)amino)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanamide, (3R)-3-(4-(((4-(4-((4'-chloro(1,1'-biphenyl)-2-yl)methyl)piperazin-1-yl)benzoyl)amino)sulfonyl)-2-nitroanilino)-N-cyclopropyl-4-(phenylsulfanyl)butanamide, (3R)-3-(4-(((4-(4-((4'-chloro(1,1'-biphenyl)-2-yl)methyl)piperazin-1-yl)benzoyl)amino)sulfonyl)-2-nitroanilino)-N-cyclobutyl-4-(phenylsulfanyl)butanamide, N-(4-(4-((4'-chloro(1,1'-biphenyl)-2-yl)methyl)piperazin-1-yl)benzoyl)-4-(((1R)-3-(4-methylpiperazin-1-yl)-3-oxo-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(morpholin-4-yl)-3-oxo-1-((phenylsulfanyl)methyl)propyl)amino)-3-nitrobenzenesulfonamide, 4-(((1R)-3-(azetidin-1-yl)-3-oxo-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, (3R)-3-(4-(((4-(4-((4'-chloro(1,1'-biphenyl)-2-yl)methyl)piperazin-1-yl)benzoyl)amino)sulfonyl)-2-nitroanilino)-N-(2-(morpholin-4-yl)ethyl)-4-(phenylsulfanyl)butanamide, (3R)-3-(4-(((4-(4-((4'-chloro(1,1-biphenyl)-2-yl)methyl)piperazin-1-yl)benzoyl)amino)sulfonyl)-2-nitroanilino)-N-methyl-4-(phenylsulfanyl)butanamide, 4-(((1R)-3-amino-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-4-(((1R)-3-cyano-1-((phenylsulfanyl)methyl)propyl)amino)-3-nitrobenzenesulfonamide, 4-(((1R)-3-(tert-butylamino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-4-(((1R)-3-(cyclopropylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(cyclobutylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-nitrobenzenesulfonamide, N-(4-(4-((4'-chloro(1,1-biphenyl)-2-yl)methyl)piperazin-1-yl)benzoyl)-4-(((1R)-3-(isopropyl(methyl)amino)-1-((phenylsulfanyl)methyl)propyl)amino)-3-nitrobenzenesulfonamide, 4-(((1R)-3-(tert-butyl(methyl)amino)-1-((phenylsulfanyl)methyl)propyl)amino)-N-(4-(4-((4'-chloro(1,1-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(piperidin-1-yl)propyl)amino)benzenesulfonamide, N-(4-(4-((4'-chloro(1,1'-biphenyl)-2-yl)methyl)piperazin-1-yl)benzoyl)-4-(((1R)-3-(4-hydroxypiperidin-1-yl)-1-((phenylsulfanyl)methyl)propyl)amino)-3-((phenylsulfanyl)methyl)propyl)amino)-3-nitrobenzenesulfonamide, 4-(((1R)-3-(4-acetylpiperazin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(thiomorpholin-4-yl)propyl)aminoibenzenesulfonamide, N-(4-(4-((4'-chloro(1,1'-biphenyl)-2-yl)methyl)piperazin-1-yl)benzoyl)-4-(((1R)-3-((2-(morpholin-4-yl)ethyl)amino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(piperazin-1-yl)propyl)amino)benzenesulfonamide, N-(4-(4-((4'-chloro(1,1'-biphenyl)-2-yl)methyl)piperazin-1-yl)benzoyl)-4-(((1R)-3-((3R)-3-hydroxypyrrolidin-1-yl)-1-((phenylsulfanyl)methyl)propyl)amino)-3-nitrobenzenesulfonamide, 4-(((1R)-3-((3R)-3-aminopyrrolidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-4-(((1R)-3-(3-hydroxyazetidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(4-methylpiperazin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(1,1-dioxidothiomorpholin-4-yl)-1-((phenylsulfanyl)methyl)propyl)amino)-3-nitrobenzenesulfonamide, 4-(((1R)-3-(1,3-benzodioxol-5-ylamino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, 4-(((1R)-3-((1,3-benzodioxol-4-ylmethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-((pyridin-2-ylmethyl)amino)propyl)amino)benzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-((2-(pyridin-2-yl)ethyl)amino)propyl)amino)benzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-((pyridin-4-ylmethyl)amino)propyl)amino)benzenesulfonamide, N-(4-(4-((4'-chloro(1,1'-biphenyl)-2-yl)methyl)piperazin-1-yl)benzoyl)-4-(((1R)-3-(morpholin-4-ylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(methyl(pyridin-4-yl)amino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyridin-3-ylamino)propyl)amino)benzenesulfonamide, N-(4-(4-((4'-chloro(1,1'-biphenyl)-2-yl)methyl)piperazin-1-yl)benzoyl)-4-(((1R)-3-(2,6-dimethylpiperidin-1-yl)-1-((phenylsulfanyl)methyl)propyl)amino)-3-nitrobenzenesulfonamide, N-(4-(4-((4'-chloro(1,1-biphenyl)-2-yl)methyl)piperazin-1-yl)benzoyl)-4-(((1R)-3-((2R,6S)-2,6-dimethylpiperidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyrrolidin-1-ylamino)propyl)amino)benzenesulfonamide, N-(4-(4-((4'-chloro(1,1'-biphenyl)-2-yl)methyl)piperazin-1-yl)benzoyl)-4-(((1R)-3-(4-(methoxyimino)piperidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-3-nitro-4-(((1R)-1-((phenylsulfanyl)methyl)-3-(2H-tetrazol-5-yl)propyl)amino)benzenesulfonamide, N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(isopropylamino)-1-((phenylsulfanyl)methyl)propyl)amino)-3-(trifluoromethyl)benzenesulfonamide, 4-(((1R)-3-(bis(2-hydroxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, N-(4-(4-((4'-chloro(1,1'-biphenyl)-2-yl)methyl)piperazin-1-yl)benzoyl)-3-(((1R)-3-(dimethylamino)-1-((phenylsulfanyl)methyl)propyl)amino)-4-(trifluoromethoxy)benzenesulfonamide;

N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-(trifluoromethyl)benzenesulfonamide, N-(4-(4-((4'-chloro(1,1'-biphenyl)-2-yl)methyl)piperazin-1-yl)benzoyl)-4-(((1R)-3-(2,5-dimethylpyrrolidin-1-yl)-1-((phenylsulfanyl)methyl)propyl)amino)-3-nitrobenzenesulfonamide, 4-(((1R)-3-amino-1-((phenylsulfanyl)methyl)propyl)amino)-N-(4-(4-((4'-chloro(1,1'-biphenyl)-2-yl)methyl)piperazin-1-yl)benzoyl)-3-(trifluoromethyl)benzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2-(trifluoromethyl)benzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-fluorobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2-(trifluoromethoxy)benzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2,5-difluorobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-methylbenzenesulfonamide, N-(4-(4-((2-(4-chlorophenyl)-1-cyclohexen-1-yl)methyl)piperazin-1-yl)benzoyl)-4-(((1R)-3-(diisopropylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-((2R,5R)-2,5-dimethylpyrrolidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-((2S,5S)-2,5-dimethylpyrrolidin-1-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-((2R,5S)-2,5-dimethylpyrrolidin-1-yl)-1-((phenylsulfanyl)methyl)propyl)amino)-3-nitrobenzenesulfonamide, N-(4-(4-((4'-chloro(1,1-biphenyl)-2-yl)methyl)piperazin-1-yl)benzoyl)-4-(((1R)-3-(dimethylamino)-1-((phenylsulfanyl)methyl)propyl)amino)-3-nitro-5-(trifluoromethyl)benzenesulfonamide, N-(4-(4-((2-(4-chlorophenyl)-1-cycloheken-1-yl)methyl)piperazin-1-yl)benzoyl)-4-(((1R)-3-(dimethylamino)-1-((phenylsulfanyl)methyl)propyl)amino)-3-nitro-5-(trifluoromethyl)benzenesulfonamide, N-(4-(4-((2-(4-chlorophenyl)-1-cyclohepten-1-yl)methyl)piperazin-1-yl)benzoyl)-4-(((1R)-3-(dimethylamino)-1-((phenylsulfanyl)methyl)propyl)amino)-3-nitro-5-(trifluoromethyl)benzenesulfonamide, N-(4-(4-((4'-chloro(1,1'-biphenyl)-2-yl)methyl)piperazin-1-yl)benzoyl)-3-(((1R)-3-(dimethylamino)-1-((phenylsulfanyl)methyl)propyl)amino)-4-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3,5-difluorobenzenesulfonamide, methyl 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzoate, 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzoic acid, 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzoic acid, 5-(((4-(4-((2-(4-chlorophenyl)-1-cyclohexen-1-yl)methyl)piperazin-1-yl)benzoyl)amino)sulfonyl)-2-(((1R)-3-(dimethylamino)-1-((phenylsulfanyl)methyl)propyl)amino)-3-nitrobenzoic acid, 5-(((4-(4-((2-(4-chlorophenyl)-1-cyclohexen-1-yl)methyl)piperazin-1-yl)benzoyl)amino)sulfonyl)-2-(((1R)-3-(dimethylamino)-1-((phenylsulfanyl)methyl)propyl)amino)-3-nitrobenzamide, 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzamide, methyl 5-(((4-(4-((2-(4-chlorophenyl)-1-cyclohexen-1-yl)methyl)piperazin-1-yl)benzoyl)amino)sulfonyl)-2-(((1R)-3-(dimethylamino)-1-((phenylsulfanyl)methyl)propyl)amino)-3-(trifluoromethyl)benzoate, methyl 5-(((4-(4-((4-(4-chlorophenyl)-5,6-dihydro-2H-pyran-3-yl)methyl)piperazin-1-yl)benzoyl)amino)sulfonyl)-2-(((1R)-3-(dimethylamino)-1-((phenylsulfanyl)methyl)propyl)amino)-3-(trifluoromethyl)benzoate, methyl 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-(trifluoromethyl)benzoate, N-(4-(4-((2-(4-chlorophenyl)-1-cyclohexen-1-yl)methyl)piperazin-1-yl)benzoyl)-4-(((1R)-4-((2R,5S)-2,5-dimethylpyrrolidin-1-yl)-1-((phenylsulfanyl)methyl)butyl)amino)-3-nitrobenzenesulfonamide, N-(4-(4-((4-(4-chlorophenyl)-5,6-dihydro-2H-pyran-3-yl)methyl)piperazin-1-yl)benzoyl)-4-(((1R)-4-((2R,5S)-2,5-dimethylpyrrolidin-1-yl)-1-((phenylsulfanyl)methyl)butyl)amino)-3-nitrobenzenesulfonamide, tert-butyl 3-((4-(4-(((4-(((1R)-3-(dimethylamino)-1-((phenylsulfanyl)methyl)propyl)amino)-3-nitrophenyl)sulfonyl)amino)carbonyl)phenyl)piperazin-1-yl)carbonyl)phenylcarbamate, N-(4-(4-(3-(dimethylamino)benzoyl)piperazin-1-yl)benzoyl)-4-(((1R)-3-(dimethylamino)-1-((phenylsulfanyl)methyl)propyl)amino)-3-nitrobenzenesulfonamide, N-(4-(4-((1,1'-biphenyl)-2-ylmethyl)piperazin-1-yl)benzoyl)-4-(((1R)-3-(dimethylamino)-1-methyl-1-((phenylsulfanyl)methyl)propyl)amino)-3-nitrobenzenesulfonamide, N-(4-(4-((1,1'-biphenyl)-2-ylmethyl)piperazin-1-yl)benzoyl)-4-(((1S)-3-(dimethylamino)-1-methyl-1-((phenylsulfanyl)methyl)propyl)amino)-3-nitrobenzenesulfonamide, N-(4-(4-(2-(1,3-dihydro-2H-isoindol-2-yl)benzyl)piperazin-1-yl)benzoyl)-4-(((1R)-3-(dimethylamino)-1-((phenylsulfanyl)methyl)propyl)amino)-3-nitrobenzenesulfonamide, N-(4-(4-(2-(cyclohexylamino)benzyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(4-(4-(2-(isopropylamino)benzyl)piperazin-1-yl)benzoyl)-3-nitrobenzenesulfonamide, N-(4-(4-(2-(benzylamino)benzyl)piperazin-1-yl)benzoyl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-3'-nitro-N-(4-(4-(2-(piperidin-1-yl)benzyl)piperazin-1-yl)benzoyl)benzenesulfonamide, N-(4-(4-((1,1'-biphenyl)-2-ylmethyl)piperazin-1-yl)benzoyl)-3-nitro-4-((2-(phenylsulfanyl)ethyl)amino)benzenesulfonamide, N-(4-(4-((1,1'-biphenyl)-2-ylmethyl)piperazin-1-yl)benzoyl)-4-((cyclohexylmethyl)amino)-3-nitrobenzenesulfonamide, N-(4-(4-((1,1'-biphenyl)-2-ylmethyl)-4-methoxypiperidin-1-yl)benzoyl)-4-(((1R)-3-(morpholin-4-yl)-1-((phenylsulfanyl)methyl)propyl)amino)-3-nitrobenzenesulfonamide, N-(4-(4-((1,1'-biphenyl)-2-ylmethyl)-4-methoxypiperidin-1-yl)benzoyl)-3-nitro-4-((2-(phenylsulfanyl)ethyl)amino)benzenesulfonamide, N-(4-(4-((4'-chloro(1,1'-biphenyl)-2-yl)methyl)piperazin-1-yl)benzoyl)-4-(((1S)-3-(dimethylamino)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-1-((phenylsulfanyl)methyl)-3-(pyrrolidin-1-yl)propyl)amino)-3-(trifluoromethyl)benzenesulfonamide, N-(4-(4-((4-(4-chlorophenyl)pyridin-3-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((4-(4-chlorophenyl)pyridin-3-yl)methyl)piperazin-1-yl)benzoyl)-4-(((1R)-3-(morpholin-4-yl)-1-((phenylsulfanyl)methyl)propyl)amino)-3-nitrobenzenesulfonamide, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2-fluoro-3-(trifluoromethyl)benzenesulfonamide, N-(6-(4-((4'-chloro(1,1-biphenyl)-2-yl)methyl)piperazin-1-yl)-1,2-benzisoxazol-3-yl)-3-nitro-4-((2-(phenylsulfanyl)ethyl)amino)benzenesulfonamide, N-(6-(4-((4'-chloro(1,1'-biphenyl)-2-yl)methyl)piperazin-1-yl)-1,2-benzisoxazol-3-yl)-4-(((1R)-3-(morpholin-4-yl)-1-((phenylsulfanyl)methyl)propyl)amino)-3-nitrobenzenesulfonamide, N-(6-(4,4-dimethylpiperidin-1-yl)-1,2-benzisoxazol-3-yl)-3-nitro-4-((2-(phenylsulfanyl)ethyl)amino)benzenesulfonamide, N-(6-(4,4-dimethylpiperidin-1-yl)-1,2-benzisoxazol-3-yl)-4-(((1R)-3-(morpholin-4-yl)-1-((phenylsulfanyl)methyl)propyl)amino)-3-nitrobenzenesulfonamide, N-(6-(4-(3,3-diphenylpropen-2-yl)piperazin-1-yl)-1,2-benzisoxazol-3-yl)-4-(((1R)-3-(morpholin-4-yl)-1-((phenylsulfanyl)methyl)propyl)amino)-3-nitrobenzenesulfonamide, N-(6-(4-(3,3-diphenylpropen-2-yl)piperazin-1-yl)-1,2-benzisoxazol-3-yl)-3-nitro-4-((2-(phenylsulfanyl)ethyl)amino)benzenesulfonamide, N-(6-(4-((4'-chloro(1,1'-biphenyl)-2-yl)methyl)piperazin-1-yl)-1,2-benzisoxazol-3-yl)-4-(((1R)-3-(dimethylamino)-1-((phenylsulfanyl)methyl)propyl)amino)-3-nitrobenzenesulfonamide, 4-(((1R)-3-(dimethylamino)-1-((phenylsulfanyl)methyl)propyl)amino)-N-(6-(4,4-dimethylpiperidin-1-yl)-1,2-benzisoxazol-3-yl)-3-nitrobenzenesulfonamide, N-(6-(4-((4'-chloro(1,1'-biphenyl)-2-yl)methyl)piperazin-1-yl)-1-methyl-1H-indazol-3-yl)-3-nitro-4-((2-(phenylsulfanyl)ethyl)amino)benzenesulfonamide, N-(6-(4-((4'-chloro(1,1-biphenyl)-2-yl)methyl)piperazin-1-yl)-1-methyl-1H-indazol-3-yl)-4-((1,1-dimethyl-2-(phenylsulfanyl)ethylamino)-3-nitrobenzenesulfonamide, N-(6-(4-((4'-chloro(1,1-biphenyl)-2-yl)methyl)piperazin-1-yl)-1-methyl-1H-indazol-3-yl)-4-(((1R)-3-(dimethylamino)-1-((phenylsulfanyl)methyl)propyl)amino)-3-nitrobenzenesulfonamide, N-(6-(4-((4'-chloro(1,1'-biphenyl)-2-yl)methyl)piperazin-1-yl)-1-methyl-1H-indazol-3-yl)-4-(((1R)-3-(morpholin-4-yl)-1-((phenylsulfanyl)methyl)propyl)amino)-3-nitrobenzenesulfonamide, N-(6-(4-((4'-chloro(1,1'-biphenyl)-2-yl)methyl)piperazin-1-yl)-1H-indazol-3-yl)-3-nitro-4-((2-(phenylsulfanyl)ethyl)amino)benzenesulfonamide, N-(6-(4-((4'-chloro(1,1'-biphenyl)-2-yl)methyl)piperazin-1-yl)-1H-indazol-3-yl)-4-(((1R)-3-(dimethylamino)-1-((phenylsulfanyl)methyl)propyl)amino)-3-nitrobenzenesulfonamide, and N-(6-(4-((4'-chloro(1,1'-biphenyl)-2-yl)methyl)piperazin-1-yl)-1H-indazol-3-yl)-4-(((1R)-3-(morpholin-4-yl)-1-((phenylsulfanyl)methyl)propyl)amino)-3-nitrobenzenesulfonamide, or therapeutically acceptable salts, prodrugs or salts of prodrugs thereof.

Still another embodiment pertains to compositions for treating diseases during which are expressed one or more than one of antiapoptotic Bcl-$X_L$ protein, antiapoptotic Bcl-2 protein or antiapoptotic Bcl-w protein, said compositions comprising an excipient and a therapeutically effective amount of the compound having formula (I).

Still another embodiment pertains to methods of treating disease in a patient during which is expressed one or more than one of antiapoptotic Bcl-$X_L$ protein, antiapoptotic Bcl-2 protein or antiapoptotic Bcl-w protein, said methods comprising administering to the patient a therapeutically effective amount of a compound having formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having formula (I).

Still another embodiment pertains to compositions for treating diseases during which are expressed one or more than one of antiapoptotic Bcl-$X_L$ protein, antiapoptotic Bcl-2 protein or antiapoptotic Bcl-w protein, said compositions comprising an excipient and a therapeutically effective amount of N-(4-(4-((4'-chloro(1,1'-biphenyl)-2-yl)methyl)piperazin-1- yl)benzoyl)-4-(((1R)-3-(dimethylamino)-1-((phenylsulfanyl)methyl)propyl)amino)-3-nitrobenzenesulfonamide, or a therapeutically acceptable salt, prodrug or salt of a prodrug thereof.

Still another embodiment pertains to methods of treating disease in a patient during which is expressed one or more than one of antiapoptotic Bcl-$X_L$ protein, antiapoptotic Bcl-2 protein or antiapoptotic Bcl-w protein, said methods comprising administering to the patient a therapeutically effective amount of N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, or a therapeutically acceptable salt, prodrug or salt of a prodrug thereof.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of N-(4-(4-((4'-chloro(1,1'-biphenyl)-2-yl)methyl)piperazin-1-yl)benzoyl)-4-(((1R)-3-(dimethyl-amino)-1-((phenylsulfanyl)methyl)propyl)amino)-3-nitrobenzenesulfonamide, or a therapeutically acceptable salt, prodrug or salt of a prodrug thereof.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)-propyl)amino)-3-nitrobenzenesulfonamide, or a therapeutically acceptable salt, prodrug or salt of a prodrug thereof.

Still another embodiment pertains to compositions for treating diseases during which are expressed one or more than one of antiapoptotic Bcl-$X_L$ protein, antiapoptotic Bcl-2 protein or antiapoptotic Bcl-w protein, said compositions comprising an excipient and a therapeutically effective amount of the compound having formula (I) and a therapeutically effective amount of one additional therapeutic agent or more than one additional therapeutic agent.

Still another embodiment pertains to methods of treating disease in a patient during which is expressed one or more than one of antiapoptotic Bcl-$X_L$ protein, antiapoptotic Bcl-2 protein or antiapoptotic Bcl-w protein, said methods comprising administering to the patient a therapeutically effective amount of a compound having formula (I) and a therapeutically effective amount of one additional therapeutic agent or more than one additional therapeutic agent.

Still another embodiment pertains to compositions for treating bladder cancer, brain cancer, breast cancer, bone marrow'cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-tell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of the compound having formula (I) and a therapeutically effective amount of one additional therapeutic agent or more than one additional therapeutic agent.

Still another embodiment pertains to compositions for treating diseases during which are expressed one or more than one of antiapoptotic Bcl-$X_L$ protein, antiapoptotic Bcl-2 protein or antiapoptotic Bcl-w protein, said compositions comprising an excipient and a therapeutically effective amount of N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, or a therapeutically acceptable salt, prodrug or salt of a prodrug thereof, and a therapeutically effective amount of one additional therapeutic agent or more than one additional therapeutic agent.

Still another embodiment pertains to methods of treating disease in a patient during which is expressed one or more than one of antiapoptotic Bcl-$X_L$ protein, antiapoptotic Bcl-2 protein or antiapoptotic Bcl-w protein, said methods comprising administering to the patient a therapeutically effective amount of N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, or a therapeutically acceptable salt, prodrug or salt of a prodrug thereof, and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of N-(4-(4-((4'-chloro(1,1'-biphenyl)-2-yl)methyl)piperazin-1-yl)benzoyl)-4-(((1R)-3-(dimethyl-amino)-1-((phenylsulfanyl)methyl)propyl)amino)-3-nitrobenzenesulfonamide, or a therapeutically acceptable salt, prodrug or salt of a prodrug thereof, and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, or a therapeutically acceptable salt, prodrug or salt of a prodrug thereof, and a therapeutically effective amount of one additional therapeutic agent or more than one additional therapeutic agent.

DETAILED DESCRIPTION OF THE INVENTION

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "cyclic moiety," as used herein, means arene, aryl, cycloalkane, cycloalkyl, cycloalkene, cycloalkenyl, heteroarene, heteroaryl, heterocycloalkane, heterocycloalkyl, heterocycloalkene, heterocycloalkenyl, spiroalkyl, spiroalkenyl, spiroheteroalkyl and spiroheteroalkenyl.

The term "arene," as used herein, means benzene.

The term "aryl," as used herein, means phenyl.

The term "cycloalkane," as used herein, means $C_3$-cycloalkane, $C_4$-cycloalkane, $C_5$-cycloalkane, $C_6$-cycloalkane, $C_7$-cycloalkane, $C_8$-cycloalkane, $C_9$-cycloalkane, $C_{10}$-cycloalkane, $C_{11}$-cycloalkane, $C_{12}$-cycloalkane, $C_{13}$-cycloalkane and $C_{14}$-cycloalkane.

The term "cycloalkyl," as used herein, means $C_3$-cycloalkyl, $C_4$-cycloalkyl, $C_5$-cycloalkyl $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl, $C_{13}$-cycloalkyl and $C_{14}$-cycloalkyl.

The term "cycloalkene," as used herein, means $C_4$-cycloalkene, $C_5$-cycloalkene, $C_6$-cycloalkene, $C_7$-cycloalkene, $C_8$-cycloalkene, $C_9$-cycloalkene, $C_{10}$-cycloalkene, $C_{11}$-cycloalkene, $C_{12}$-cycloalkene, $C_{13}$-cycloalkene and $C_{14}$-cycloalkene.

The term "cycloalkenyl," as used herein, means $C_3$-cycloalkenyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, $C_{11}$-cycloalkenyl, $C_{12}$-cycloalkenyl, $C_{13}$-cycloalkenyl and $C_{14}$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkane," as used herein, means cycloalkane having one or two or three $CH_2$ moieties replaced with independently selected O, C(O), CNOH, $CNOCH_3$, S, S(O), $SO_2$ or NH and one or two CH moieties unreplaced or replaced with N and also means cycloalkane having one or two or three $CH_2$ moieties unreplaced or replaced with independently selected O, C(O), CNOH, $CNOCH_3$, S, S(O), $SO_2$ or NH and one or two CH moieties replaced with N.

The term "heterocycloalkyl," as used herein, means cycloalkyl having one or two or three $CH_2$ moieties replaced with independently selected O, C(O), CNOH, $CNOCH_3$, S, S(O), $SO_2$ or NH and one or two CH moieties unreplaced or replaced with N and also means cycloalkyl having one or two or three $CH_2$ moieties unreplaced or replaced with independently selected O, C(O), CNOH, $CNOCH_3$, S, S(O), $SO_2$ or NH and one or two CH moieties replaced with N.

The term "heterocycloalkene," as used herein, means cycloalkene having one or two or three $CH_2$ moieties replaced with independently selected O, C(O), CNOH, $CNOCH_3$, S, S(O), $SO_2$ or NH and one or two CH moieties unreplaced or replaced with N and also means cycloalkene having one or two or three $CH_2$ moieties unreplaced or replaced with independently selected O, C(O), CNOH, $CNOCH_3$, S, S(O), $SO_2$ or NH and one or two CH moieties replaced with N.

The term "heterocycloalkenyl," as used herein, means cycloalkenyl having one or two or three $CH_2$ moieties replaced with independently selected O, C(O), CNOH, $CNOCH_3$, S, S(O), $SO_2$ or NH and one or two CH moieties unreplaced or replaced with N and also means cycloalkenyl having one or two or three $CH_2$ moieties unreplaced or replaced with independently selected O, C(O), CNOH, $CNOCH_3$, S, S(O), $SO_2$ or NH and one or two CH moieties replaced with N.

The term "spiroalkyl," as used herein, means $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl and $C_9$-spiroalkyl.

The term "spiroalkenyl," as used herein, means $C_2$-spiroalkenyl, $C_3$-spiroalkenyl, $C_4$-spiroalkenyl, $C_5$-spiroalkenyl, $C_6$-spiroalkenyl, $C_7$-spiroalkenyl, $C_8$-spiroalkenyl and $C_9$-spiroalkenyl.

The term "spiroheteroalkyl," as used herein, means spiroalkyl having one or two $CH_2$ moieties replaced with independently selected O, C(O), CNOH, $CNOCH_3$, S, S(O), $SO_2$ or NH.

The term "spiroheteroalkenyl," as used herein, means spiroalkenyl having one or two $CH_2$ moieties replaced with independently selected O, C(O), CNOH, $CNOCH_3$, S, S(O), $SO_2$ or NH and one or two CH moieties unreplaced or replaced with N and also means spiroalkenyl having one or two $CH_2$ moieties unreplaced or replaced with independently selected O, C(O), CNOH, $CNOCH_3$, S, S(O), $SO_2$ or NH and one or two CH moieties replaced with N.

The term "alkenyl," as used herein, means $C_2$-alkenyl, $C_3$-alkenyl, $C_4$-alkenyl, $C_5$-alkenyl and $C_6$-alkenyl.

The term "alkyl," as used herein, means $C_1$-alkyl, $C_2$-alkyl, $C_3$-alkyl, $C_4$-alkyl, $C_5$-alkyl and $C_6$-alkyl.

The term "alkynyl," as used herein, means $C_2$-alkynyl, $C_3$-alkynyl, $C_4$-alkynyl, $C_5$-alkynyl and $C_6$-alkynyl.

The term "$C_2$-alkenyl," as used herein, means ethenyl (vinyl).

The term "$C_3$-alkenyl," as used herein, means 1-propen-1-yl, 1-propen-2-yl (isopropenyl) and 1-propen-3-yl (allyl).

The term "$C_4$-alkenyl," as used herein, means 1-buten-1-yl, 1-buten-2-yl, 1,3-butadien-1-yl, 1,3-butadien-2-yl, 2-buten-1-yl, 3-buten-1-yl, 3-buten-2-yl, 2-methyl-1-propen-1-yl and 2-methyl-2-propen-1-yl.

The term "$C_5$-alkenyl," as used herein, means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-penta-dien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl and 4-penten-2-yl.

The term "$C_6$-alkenyl," as used herein, means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylene-pent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-.1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl and 4-methyl-4-penten-2-yl.

The term "$C_1$-alkyl," as used herein, means methyl. The term "$C_2$-alkyl," as used herein, means ethyl. The term "$C_3$-alkyl," as used herein, means prop-1-yl and prop-2-yl (isopropyl).

The term "$C_4$-alkyl," as used herein, means but-1-yl, but-2-yl, 2-methylprop-1-yl and 2-methylprop-2-yl (tert-butyl).

The term "$C_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "$C_2$-alkynyl," as used herein, means ethynyl (acetylenyl).

The term "$C_3$-alkynyl," as used herein, means 1-propyn-1-yl and 2-propyn-1-yl (propargyl).

The term "$C_4$-alkynyl," as used herein, means 1-butyn-1-yl, 1,3-butadiyn-1-yl, 2-butyn-1-yl, 3-butyn-1-yl and 3-butyn-2-yl.

The term "$C_5$-alkynyl," as used herein, means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl and 4-pentyn-2-yl.

The term "$C_6$-alkynyl," as used herein, means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl and 4-methyl-2-pentyn-1-yl.

The term "$C_4$-cycloalkane," as used herein, means cyclobutane.

The term "$C_5$-cycloalkane," as used herein, means cyclopentane.

The term "$C_6$-cycloalkane," as used herein, means cyclohexane.

The term "$C_7$-cycloalkane," as used herein, means cycloheptane.

The term "$C_8$-cycloalkane," as used herein, means cyclooctane.

The term "$C_9$-cycloalkane," as used herein, means cyclononane.

The term "$C_{10}$-cycloalkane," as used herein, means cyclodecane.

The term "$C_{11}$-cycloalkane," as used herein, means cycloundecane.

The term "$C_{12}$-cycloalkane," as used herein, means cyclododecane.

The term "$C_{13}$-cycloalkane," as used herein, means cyclotridecane.

The term "$C_{14}$-cycloalkane," as used herein, means cyclotetradecane.

The term "$C_4$-cycloalkene," as used herein, means cyclobutene and 1,3-cyclobutadiene.

The term "$C_5$-cycloalkene," as used herein, means cyclopentene and 1,3-cyclopentadiene.

The term "$C_6$-cycloalkene," as used herein, means cyclohexene, 1,3-cyclohexadiene and 1,4-cyclohexadiene.

The term "$C_7$-cycloalkene," as used herein, means cycloheptene and 1,3-cycloheptadiene.

The term "$C_8$-cycloalkene," as used herein, means cyclooctene, 1,3-cyclooctadiene, 1,4-cyclooctadiene, 1,5-cyclooctadiene, 1,3,5-cyclooctatriene and 1,3,6-cyclooctatriene.

The term "$C_9$-cycloalkene," as used herein, means cyclononene, 1,3-cyclononadiene, 1,4-cyclononadiene, 1,5-cyclononadiene, 1,3,5-cyclononatriene, 1,3,6-cyclononatriene, 1,3,7-cyclononatriene and 1,3,5,7-cyclononatetraene.

The term "$C_{10}$-cycloalkene," as used herein, means cyclodecene, 1,3-cyclodecadiene, 1,4-cyclodecadiene, 1,5-cyclodecadiene, 1,6-cyclodecadiene, 1,3,5-cyclodecatriene, 1,3,6-cyclodecatriene, 1,3,5,7-cyclodecatetraene, 1,3,5,8-cyclodecatetraene and 1,3,6,8-cyclodecatetraene.

The term "$C_{11}$-cycloalkene," as used herein, means cycloundecene, 1,3-cycloundecadiene, 1,4-cycloundecadiene, 1,5-cycloundecadiene, 1,6-cycloundecadiene, 1,3,5-cycloundecatriene, 1,3,6-cycioundecatriene, 1,3,7-cycloundecatriene, 1,4,7-cycloundecatriene, 1,4,8-cycloundecatriene, 1,3,5,7-cycloundecatetraene, 1,3,5,8-cycloundecatetraene, 1,3,6,8-cycloundecatetraene and 1,3,5,7,9-cycloundecapentaene.

The term "$C_{12}$-cycloalkene," as used herein, means cyclododecene, 1,3-cyclododecadiene, 1,4-cyclododecadiene, 1,5-cyclododecadiene, 1,6-cyclododecadiene, 1,7-cyclododecadiene, 1,3,5-cyclododecatriene, 1,3,6-cyclododecatriene, 1,3,7-cyclododecatriene, 1,3,8-cyclododecatriene, 1,4,7-cyclododecatriene, 1,4,8-cyclododecatriene, 1,5,9-cyclododecatriene, 1,3,5,7-cyclododecatetraene, 1,3,5,8-cyclododecatetraene, 1,3,5,9-cyclododecatetraene, 1,3,6,8-cyclododecatetraene, 1,3,6,9-cyclododecatetraene, 1,3,6,10-cyclododecatetraene, 1,3,7,9-cyclododecatetraene, 1,4,7,10-cyclododecatetraene, 1,3,5,7,9-cyclododecapentaene, 1,3,5,7,10-cyclododecapentaene and 1,3,5,8,10-cyclododecapentaene.

The term "$C_{13}$-cycloalkene," as used herein, means 1,3-cyclotridecadiene, 1,4-cyclotridecadiene, 1,5-cyclotridecadiene, 1,6-cyclotridecadiene, 1,7-cyclotridecadiene, 1,3,5-cyclotridecatriene, 1,3,6-cyclotridecatriene, 1,3,7-cyclotridecatriene, 1,3,8-cyclotridecatriene, 1,4,7-cyclotridecatriene, 1,4,8-cyclotridecatriene, 1,4,9-cyclotridecatriene, 1,5,9-cyclotridecatriene, 1,3,5,7-cyclotridecatetraene, 1,3,5,8-cyclotridecatetraene, 1,3,5,9-cyclotridecatetraene, 1,3,6,8-cyclotridecatetraene, 1,3,6,9-cyclotridecatetraene, 1,3,6,10-cyclotridecatetraene, 1,3,6,11-cyclotridecatetraene, 1,3,7,9-cyclotridecatetraene, 1,3,7,10-cyclotridecatetraene, 1,4,7,10-cyclotridecatetraene, 1,3,6,11-cyclotridecatetraene, 1,3,5,7,9-cyclotridecapentaene, 1,3,5,7,10-cyclotridecapentaene, 1,3,5,8,10-cyclotridecapentaene, 1,3,5,8,11-cyclotridecapentaene, 1,3,6,8,11-cyclotridecapentaene and 1,3,5,7,9,11-cyclotridecahexaene.

The term "$C_{14}$-cycloalkene," as used herein, means cyclotetradecene, 1,3-cyclotetradecadiene, 1,4-cyclotetradecadiene, 1,5-cyclotetradecadiene, 1,6-cyclotetradecadiene, 1,7-cyclotetradecadiene, 1,8-cyclotetradecadiene, 1,3,5-cyclotetradecatriene, 1,3,6-cyclotetradecatriene, 1,3,7-cyclotetradecatriene, 1,3,8-cyclotetradecatriene, 1,3,9-cyclotetradecatriene, 1,4,7-cyclotetradecatriene, 1,4,8-cyclotetradecatriene, 1,4,9-cyclotetradecatriene, 1,5,9-cyclotetradecatriene, 1,5,10-cyclotetradecatriene, 1,3,5,7-cyclotetradecatetraene, 1,3,5,8-cyclotetradecatetraene, 1,3,5,9-cyclotetradecatetraene, 1,3,5,10-cyclotetradecatetraene, 1,3,6,8-cyclotetradecatetraene, 1,3,6,9-cyclotetradecatetraene, 1,3,6,10-cyclotetradecatetraene, 1,3,6,11-cyclotetradecatetraene, 1,3,6,12-cyclotetradecatetraene, 1,3,7,9-cyclotetradecatetraene, 1,3,7,10-cyclotetradecatetraene, 1,3,7,11-cyclotetradecatetraene, 1,3,8,10-cyclotetradecatetraene, 1,4,7,10cyclotetradecatetraene, 1,4,7,11-cyclotetradecatetraene, 1,4,8,11-cyclotetradecatetraene, 1,3,5,7,9-cyclotetradecapentaene, 1,3,5,7,10-cyclotetradecapentaene, 1,3,5,7,11-cyclotetradecapentaene, 1,3,5,8,10-cyclotetradecapentaene, 1,3,5,8,11-cyclotetradecapentaene, 1,3,5,8,12-cyclotetradecapentaene, 1,3,5,9,11-cyclotetradecapentaene, 1,3,5,8,11-cyclotetradecapentaene, 1,3,6,8,11-cyclotetradecapentaene, 1,3,6,9,11-cyclotetradecapentaene, 1,3,5,8,11-cyclotetradecapentaene, 1,3,5,8,12-cyclotetradecapentaene, 1,3,5,7,9,11-cyclotetradecahexaene, 1,3,5,7,9,12-cyclotetradecahexaene, 1,3,5,7,10,12-cyclotetradecahexaene, 1,3,5,8,10,12-cyclotetradecahexaene and 1,3,5,7,9,11,13-cyclotetradecaheptaene.

The term "$C_3$-cycloalkenyl," as used herein, means cycloprop-1-en-1-yl and cycloprop-2-en-1-yl.

The term "$C_4$-cycloalkenyl," as used herein, means cyclobut-1-en-1-yl and cyclobut-2-en-1-yl.

The term "$C_5$-cycloalkenyl," as used herein, means cyclopent-1-en-1-yl, cyclopent-2-en-1-yl, cyclopent-3-en-1-yl and cyclopenta-1,3-dien-1-yl.

The term "$C_6$-cycloalkenyl," as used herein, means cyclohex-1-en-1-yl, cyclohex-2-en-1-yl, cyclohex-3-en-1-yl, cyclohexa-1,3-dien-1-yl, cyclohexa-1,4-dien-1-yl, cyclohexa-1,5-dien-1-yl, cyclohexa-2,4-dien-1-yl and cyclohexa-2,5-dien-1-yl.

The term "$C_7$-cycloalkenyl," as used herein, means bicyclo[2.2.1]hept-2-en-1-yl, bicyclo[2.2.1]hept-2-en-2-yl, bicyclo[2.2.1]hept-2-en-5-yl, bicyclo[2.2.1]hept-2-en-7-yl, bicyclo[2.2.1]hepta-2,5-dien-1-yl, bicyclo[2.2.1]hepta-2,5-dien-2-yl, bicyclo[2.2.1]hepta-2,5-dien-7-yl, cyclohept-1-en-1-yl, cyclohept-2-en-1-yl, cyclohept-3-en-1-yl, cyclohept-4-en-1-yl, cyclohepta-1,3-dien-1-yl, cyclohepta-1,4-dien-1-yl, cyclohepta-1,5-dien-1-yl, cyclohepta-1,6-dien-1-yl, cyclohepta-2,4-dien-1-yl, cyclohepta-2,5-dien-1-yl, cyclohepta-2,6-dien-1-yl, cyclohepta-3,5-dien-1-yl, cyclohepta-1,3,5-trien-1-yl, cyclohepta-1,3,6-trien-1-yl, cyclohepta-1,4,6-trien-1-yl and cyclohepta-2,4,6-trien-1-yl.

The term "$C_8$-cycloalkenyl," as used herein, means bicyclo[2.2.2]oct-2-en-1-yl, bicyclo[2.2.2]oct-2-en-2-yl, bicyclo[2.2.2]oct-2-en-5-yl, bicyclo[2.2.2]oct-2-en-7-yl, bicyclo[2.2.2]octa-2,5-dien-1-yl, bicyclo[2.2.2]octa-2,5-dien-2-yl, bicyclo[2.2.2]octa-2,5-dien-7-yl, bicyclo[2.2.2]octa-2,5,7-trien-1-yl, bicyclo[2.2.2]octa-2,5,7-trien-2-yl cyclooct-1-en-1-yl, cyclooct-2-en-1-yl, cyclooct-3-en-1-yl, cyclooct-4-en-1-yl, cycloocta-1,3-dien-1-yl, cycloocta-1,4-dien-1-yl, cycloocta-1,5-dien-1-yl, cycloocta-1,6-dien-1-yl, cycloocta1,7-dien-1-yl, cycloocta-2,4-dien-1-yl, cycloocta-2,5-dien-1-yl, cycloocta-2,6-dien-1-yl, cycloocta-2,7-dien-1-yl, cycloocta-3,5-dien-1-yl, cycloocta-3,6-dien-1-yl, cycloocta-1,3,5-trien-1-yl, cycloocta-1,3,6-trien-1-yl, cycloocta-1,3,7-trien-1-yl, cycloocta-1,4,6-trien-1-yl, cycloocta-1,4,7-trien-1-yl, cycloocta-1,5,7-trien-1-yl, cycloocta-2,4,6-trien-1-yl, cycloocta-2,4,7-trien-1-yl, cycloocta-2,5,7-trien-1-yl and cycloocta-1,3,5,7-tetraen-1-yl.

The term "$C_9$-cycloalkenyl," as used herein, means cyclonon-1-en-1-yl, cyclonon-2-en-1-yl, cyclonon-3-en-1-yl, cyclonon-4-en-1-yl, cyclonon-5-en-1-yl, cyclonona-1,3-dien-1-yl, cyclonona-1,4-dien-1-yl, cyclonona-1,5-dien-1-yl, cyclonona-1,6-dien-1-yl, cyclonona-1,7-dien-1-yl, cyclonona-1,8-dien-1-yl, cyclonona-2,4-dien-1-yl, cyclonona-2,5-dien-1-yl, cyclonona-2,6-dien-1-yl, cyclonona-2,7-dien-1-yl, cyclonona-2,8-dien-1-yl, cyclonona-3,5-dien-1-yl, cyclonona-3,6-dien-1-yl, cyclonona-3,7-dien-1-yl, cyclonona-4,6-dien-1-yl, cyclonona-1,3,5-trien-1-yl, cyclonona-1,3,6-trien-1-yl, cyclonona-1,3,7-trien-1-yl, cyclonona-1,3,8-trien-1-yl, cyclonona-1,4,6-trien-1-yl, cyclonona-1,4,7-trien-1-yl, cyclonona-1,4,8-trien-1-yl, cyclonona-1,5,7-trien-1-yl, cyclonona-1,5,8-trien-1-yl, cyclonona-1,6,8-trien-1-yl, cyclonona-2,4,8-trien-1-yl, cyclonona-2,4,6-trien-1-yl, cyclonona-2,4,7-trien-1-yl, cyclonona-2,4,8-trien-1-yl, cyclonona-2,5,7-trien-1-yl, cyclonona-2,5,8-trien-1-yl, cyclonona-1,3,5,7-tetraen-1-yl, cyclonona-1,3,5,8-tetraen-1-yl, cyclonona-1,3,6,8-tetraen-1-yl, cyclonona-1,4,6,8-tetraen-1-yl and cyclonona-2,4,6,8-tetraen-1-yl.

The term "$C_{10}$-cycloalkenyl," as used herein, means cyclodec-1-en-1-yl, cyclodec-2-en-1-yl, cyclodec-3-en-1-yl, cyclodec-4-en-1-yl, cyclodec-5-en-1-yl, cyclodeca-1,3-dien-1-yl, cyclodeca-1,4-dien-1-yl, cyclodeca-1,5-dien-1-yl, cyclodeca-1,6-dien-1-yl, cyclodeca-1,7-dien-1-yl, cyclodeca-1,8-dien-1-yl, cyclodeca-1,9-dien-1-yl, cyclodeca-2,4-dien-1-yl, cyclodeca-2,5-dien-1-yl, cyclodeca-2,6-dien-1-yl, cyclodeca-2,7-dien-1-yl, cyclodeca-2,8-dien-1-yl, cyclodeca-2,9-dien-1-yl, cyclodeca-3,5-dien-1-yl, cyclodeca-3,6-dien-1-yl, cyclodeca-3,7-dien-1-yl, cyclodeca-3,8-dien-1-yl, cyclodeca-4,6-dien-1-yl, cyclodeca-4,7-dien-1-yl, cyclodeca-1,3,5-trien-1-yl, cyclodeca-1,3,6-trien-1-yl, cyclodeca-1,3,7-trien-1-yl, cyclodeca-1,3,8-trien-1-yl, cyclodeca-1,3,9-trien-1-yl, cyclodeca-1,4,6-trien-1-yl, cyclodeca-1,4,7-trien-1-yl, cyclodeca-1,4,8-trien-1-yl, cyclodeca-1,4,9-trien-1-yl, cyclodeca-1,5,7-trien-1-yl, cyclodeca-1,5,8-trien-1-yl, cyclodeca-1,5,9-trien-1-yl, cyclodeca-1,6,8-trien-1-yl, cyclodeca-1,6,9-trien-1-yl, cyclodeca-1,7,9-trien-1-yl, cyclodeca-2,4,6-trien-1-yl, cyclodeca-2,4,7-trien-1-yl, cyclodeca-2,4,8-trien-1-yl, cyclodeca-2,4,9-trien-1-yl, cyclodeca-2,5,7-trien-1-yl, cyclodeca-2,5,8-trien-1-yl, cyclodeca-2,5,9-trien-1-yl, cyclodeca-2,6,8-trien-1-yl, cyclodeca-3,5,7-trien-1-yl, cyclodeca-3,5,8-trien-1-yl, cyclodeca-1,3,5,7-tetraen-1-yl, cyclodeca-1,3,5,8-tetraen-1-yl, cyclodeca-1,3,5,9-tetraen-1-yl, cyclodeca-1,3,6,8-tetraen-1-yl, cyclodeca-1,3,6,9-tetraen-1-yl, cyclodeca-1,3,7,9-tetraen-1-yl, cyclodeca-1,4,6,8-tetraen-1-yl, cyclodeca-1,4,6,9-tetraen-1-yl, cyclodeca-1,4,7,9-tetraen-1-yl, cyclodeca-1,5,7,9-tetraen-1-yl, cyclodeca-2,4,6,8-tetraen-1-yl, cyclodeca-2,4,6,9-tetraen-1-yl, cyclodeca-2,4,7,9-tetraen-1-yl and cyclodeca-1,3,5,7,9-pentaen-1-yl.

The term "$C_{11}$-cycloalkenyl," as used herein, means cycloundec-1-en-1-yl, cycloundec-2-en-1-yl, cycloundec-3-en-1-yl, cycloundec-4-en-1-yl, cycloundec-5-en-1-yl, cycloundec-6-en-1-yl, cycloundeca-1,3-dien-1-yl, cycloundeca-1,4-dien-1-yl, cycloundeca-1,5-dien-1-yl, cycloundeca-1,6-dien-1-yl, cycloundeca-1,7-dien-1-yl, cycloundoca-1,8-dien-1-yl, cycloundeca-1,9-dien-1-yl, cycloundeca-1,10-dien-1-yl, cycloundeca-2,4-dien-1-yl, cycloundeca-2,5-dien-1-yl, cycloundeca-2,6-dien-1-yl, cycloundeca-2,7-dien-1-yl, cycloundeca-2,8-dien-1-yl, cycloundeca-2,9-dien-1-yl, cycloundeca-2,10-dien-1-yl, cycloundeca-3,5-dien-1-yl, cycloundeca-3,6-dien-1-yl, cycloundeca-3,7-dien-1-yl, cycloundeca-3,8-dien-1-yl, cycloundeca-3,9-dien-1-yl, cycloundeca-4,6-dien-1-yl, cycloundeca-4,7-dien-1-yl, cycloundeca-4,8-dien-1-yl, cycloundeca-5,7-dien-1-yl, cycloundeca-1,3,5-trien-1-yl, cycloundeca-1,3,6-trien-1-yl, cycloundeca-1,3,7-trien-1-yl, cycloundeca-1,3,8-trien-1-yl, cycloundeca-1,3,9-trien-1-yl, cycloundeca-1,3,10-trien-1-yl, cycloundeca-1,4,6-trien-1-yl, cycloundeca-1,4,7-tri-en-1-yl, cycloundeca-1,4,8-trien-1-yl, cycloundeca-1,4,9-trien-1-yl, cycloundeca-1,4,10-triers-1-yl, cycloundeca-1,5,7-trien-1-yl, cycloundeca-1,5,8-trien-1-yl, cycloundeca-1,5,9-trien-1-yl, cycloundeca-1,5,10-trien-1-yl, cycloundeca-1,6,8-trien-1-yl, cycloundeca-1,6,9-trien-1-yl, cycloundeca-1,6,10-trien-1-yl, cycloundeca-1,7,9-trien-1-yl, cycloundeca-1,7,10-trien-1-yl, cycloundeca-1,8,10-trien-1-yl, cycloundeca-2,4,6-trien-1-yl, cycloundeca-2,4,7-trien-1-yl, cycloundeca-2,4,9-trien-1-yl, cycloundeca-2,4,10-trien-1-yl, cycloundeca-2,5,7-trien-1-yl, cycloundeca-2,5,8-trien-1-yl, cycloundeca-2,5,9-trien-1-yl, cycloundeca-2,5,10-tri-en-1-yl, cycloundeca-2,6,8-trien-1-yl, cycloundeca-2,6,9-trien-1-yl, cycloundeca-2,6,10-trien-1-yl, cycloundeca-2,7,9-trien-1-yl, cycloundeca-3,5,7-trien-1-yl, cycloundeca-3,5,8-trien-1-yl, cycloundeca-3,5,9-trien-1-yl, cycloundeca-3,6,8-trien-1-yl, cycloundeca-3,6,9-trien-1-yl, cycloundeca-4,6,8-trien-1-yl, cycloundeca-1,3,5,7-tetraen-1-yl, cycloundeca-1,3,5,8-tetraen-1-yl, cycloundeca-1,3,5,9-tetraen-1-yl, cycloundeca-1,3,5,10-tetraen-1-yl, cycloundeca-1,3,6,8-tetraen-1-yl, cycloundeca-1,3,6,9-tetraen-1-yl, cycloundeca-1,3,6,10-tetraen-1-yl, cycloundeca-1,3,7,9-tetraen-1-yl, cycloundeca-1,3,7,10-tetraen-1-yl, cycloundeca-1,3,8,10-tetraen-1-yl, cycloundeca-1,4,6,8-tetraen-1-yl, cycloundeca-1,4,6,9-tetraen-1-yl, cycloundeca-1,4,6,10-tetraen-1-yl, cycloundeca-1,4,8,10-tetraen-1-yl, cycloundeca-1,5,7,9-tetraen-1-yl, cycloundeca-1,5,7,10-tetraen-1-yl, cycloundeca-1,5,8,10-tetraen-1-yl, cycloundeca-1,6,8,10-tetraen-1-yl, cycloundeca-2,4,6,8-tetraen-1-yl, cycloundeca-2,4,6,9-tetraen-1-yl, cycloundeca-2,4,6,10-tetraen-1-yl, cycloundeca-2,4,7,9-tetraen-1-yl, cycloundeca-2,5,7,9-tetraen-1-yl, cycloundeca-3,5,7,9-tetraen-1-yl, cycloundeca-1,3,5,7,9-pentaenyl, cycloundeca-1,3,5,7,10-pentaenyl, cycloundeca-1,3,5,8,10-pentaenyl, cycloundeca-1,3,6,8,10-pentaenyl, cycloundeca-1,4,6,8,10-pentaenyl and cycloundeca-2,4,6,8,10-pentaenyl.

The term "$C_{12}$-cycloalkenyl," as used herein, means cyclododec-1-en-1-yl, cyclododec-2-en-1-yl, cyclododec-3-en-1-yl, cyclododec-4-en-1-yl, cyclododec-5-en-1-yl, cyclododec-6-en-1-yl, cyclododeca-1,3-dien-1-yl, cyclododeca-1,4-dien-1-yl, cyclododeca-1,5-dien-1-yl, cyclododeca-1,6-dien-1-yl, cyclododeca-1,7-dien-1-yl, cyclododeca-1,8-dien-1-yl, cyclododeca-1,9-dien-1-yl, cyclododeca-1,10-dien-1-yl, cyclododeca-1,11-dien-1-yl, cyclododeca-2,4-dien-1-yl, cyclododeca-2,5-dien-1-yl, cyclododeca-2,6-dien-1-yl, cyclododeca-2,7-dien-1-yl, cyclododeca-2,8-dien-1-yl, cyclododeca-2,9dien-1-y1, cyclododeca-2,10-dien-1-yl, cyclododeca-2,11-dien-1-yl, cyclododeca-3,5-dien-1-yl, cyclododeca-3,6-dien-1-yl, cyclododeca-3,7-dien-1-yl, cyclododeca-3,8-dien-1-yl, cyclododeca-3,9-dien-1-yl, cyclododeca-3,10-dien-1-yl, cyclododeca-3,11-dien-1-yl, cyclododeca-4,6-dien-1-yl, cyclododeca-4,7-dien-1-yl, cyclododeca-4,8-dien-1-yl, cyclododeca-4,9-dien-1-yl, cyclododeca-5,7-dien-1-yl, cyclododeca-5,8-dien-1-yl, cyclododeca-1,3,5-trien-1-yl, cyclododeca-1,3,6-trien-1-yl, cyclododeca-1,3,7-trien-1-yl, cyclododeca-1,3,8-trien-1-yl, cyclododeca-1,3,9-trien-1-yl, cyclododeca-1,3,10-trien-1-yl, cyclododeca-1,3,11-trien-1-yl, cyclododeca-1,4,6-trien-1-yl, cyclododeca-1,4,7-trien-1-yl, cyclododeca-1,4,8-trien-1-yl, cyclododeca-1,4,9-trien-1-yl, cyclododeca-1,4,10-trien-1-yl, cyclododeca-1,4,11-trien-1-yl, cyclododeca-1,5,7-trien-1-yl, cyclododeca-1,5,8-trien-1-yl, cyclododeca-1,5,9-trien-1-yl, cyclododeca-1,5,10-trien-1-yl, cyclododeca-1,5,11-trien-1-yl, cyclododeca-1,6,8-trien-1-yl, cyclododeca-1,6,9-trien-1-yl, cyclododeca-1,6,10-trien-1-yl, cyclododeca-1,6,11-trien-1-yl, cyclododeca-1,7,9-trien-1-yl, cyclododeca-1,7,10-trien-1-yl, cyclododeca-1,7,11-trien-1-yl, cyclododeca-1,8,10-trien-1-yl, cyclododeca-1,8,11-trien-1-yl, cyclododeca-1,9,11-trien-1-yl, cyclododeca-2,4,6-trien-1-yl, cyclododeca-2,4,7-trien-1-yl, cyclododeca-2,4,8-trien-1-yl, cyclododeca-2,4,9-trien-1-yl, cyclododeca-2,4,10-trien-1-yl, cyclododeca-2,4,11-trien-1-yl, cyclododeca-2,5,7-trien-1-yl, cyclododeca-2,5,8-trien-1-yl, cyclododeca-2,5,9-trien-1-yl, cyclododeca-2,5,10-trien-1-yl, cyclododeca-2,5,11-trien-1-yl, cyclododeca-2,6,8-trien-1-yl, cyclododeca-2,6,9-trien-1-yl, cyclododeca-2,6,10-trien-1-yl, cyclododeca-2,6,11-trien-1-yl, cyclododeca-2,7,9-trien-1-yl, cyclododeca-2,7,10-trien-1-yl, cyclododeca-2,8,10-trien-1-yl, cyclododeca-3,5,7-trien-1-yl, cyclododeca-3,5,8-trien-1-yl, cyclododeca-3,5,9-trien-1-yl, cyclododeca-3,5,10-trien-1-yl, cyclododeca-3,6,8-trien-1-yl, cyclododeca-3,6,9-trien-1-yl, cyclododeca-3,6,10-trien-1-yl, cyclododeca-3,7,9-trien-1-yl, cyclododeca-4,6,8-trien-1-yl, cyclododeca-4,6,9-trien-1-yl, cyclododeca-1,3,5,7-tetraen-1-yl, cyclododeca-1,3,5,8-tetraen-1-yl, cyclododeca-1,3,5,9-tetraen-1-yl, cyclododeca-1,3,5,10-tetraen-1-yl, cyclododeca-1,3,5,11-tetraen-1-yl, cyclododeca-1,3,6,8-tetraen-1-yl, cyclododeca-1,3,6,9-tetraen-1-yl, cyclododeca-1,3,6,10-tetraen-1-yl, cyclododeca-1,3,6,11-tetraen-1-yl, cyclododeca-1,3,7,9-tetraen-1-yl, cyclododeca-1,3,7,10-tetraen-1-yl, cyclododeca-1,3,7,11-tetraen-1-yl, cyclododeca-1,3,8,10-tetraen-1-yl, cyclododeca-1,3,8,11-tetraen-1-yl, cyclododeca-1,3,9,11-tetraen-1-yl, cyclododeca-1,4,6,8-tetraen-1-yl, cyclododeca-1,4,6,9-tetraen-1-yl, cyclododeca-1,4,6,10-tetraen-1-yl, cyclododeca-1,4,6,11-tetraen-1-yl, cyclododeca-1,4,7,9-tetraen-1-yl, cyclododeca-1,4,7,10-tetraen-1-yl, cyclododeca-1,4,7,11-tetraen-1-yl, cyclododeca-1,4,8,10-tetraen-1-yl, cyclododeca-1,4,8,11-tetraen-1-yl, cyclododeca-1,4,9,11-tetraen-1-yl, cyclododeca-1,5,7,9-tetraen-1-yl, cyclododeca-1,5,7,10-tetraen-1-yl, cyclododeca-1,5,7,11-tetraen-1-yl, cyclododeca-1,5,8,10-tetraen-1-yl, cyclododeca-1,5,8,11-tetraen-1-yl, cyclododeca-1,5,9,11-tetraen-1-yl, cyclododeca-1,6,8,10-tetraen-1-yl, cyclododeca-1,6,8,11-tetraen-1-yl, cyclododeca-1,6,9,11-tetraen-1-yl, cyclododeca-1,7,9,11-tetraen-1-yl, cyclododeca-2,4,6,8-tetraen-1-yl, cyclododeca-2,4,6,9-tetraen-1-yl, cyclododeca-2,4,6,10-tetraen-1-yl, cyclododeca-2,4,6,11-tetraen-1-yl, cyclododeca-2,4,7,9-tetraen-1-yl, cyclododeca-2,4,7,10-tetraen-1-yl, cyclododeca-2,4,7,11-tetraen-1-yl, cyclododeca-2,4,8,10-tetraen-1-yl, cyclododeca-2,4,8,11-tetraen-1-yl, cyclododeca-2,4,9,11-tetraen-1-yl, cyclododeca-2,5,7,9-tetraen-1-yl, cyclododeca-2,5,7,10-tetraen-1-yl, cyclododeca-2,5,7,11-tetraen-1-yl, cyclododeca-2,5,8,10-tetraen-1-yl, cyclododeca-2,5,3,11-tetraen-1-yl, cyclododeca-2,6,8,10-tetraen-1-yl, cyclododeca-3,5,7,9-tetraen-1-yl, cyclododeca-3,5,7,10-tetraen-1-yl, cyclododeca-3,5,8,10-tetraen-1-yl, cyclododeca-1,3,5,7,9-pentaen-1-yl, cyclododeca-1,3,5,7,10-pentaen-1-yl, cyclododeca-1,3,5,7,11-pentaen-1-yl, cyclododeca-1,3,5,8,10-pentaen-1-yl, cyclododeca-1,3,5,8,11-pentaen-1-yl, cyclododeca-1,3,5,9,11-pentaen-1-yl, cyclododeca-1,3,6,8,10-pentaen-1-yl, cyclododeca-1,3,6,8,11-pentaen-1-yl, cyclododeca-1,3,6,9,11-pentaen-1-yl, cyclododeca-1,3,7,9,11-pentaen-1-yl, cyolododeca-1,4,6,8,10-pentaen-1-yl, cyclododeca-1,4,6,8,11-pentaen-1-yl, cyclododeca-1,4,6,9,11-pentaen-1-yl, cyclododeca-1,4,7,9,11-pentaen-1-yl, cyclododeca-1,5,7,9,11-pentaen-1-yl, cyclododeca-2,4,6,8,10-pentaen-1-yl, cyclododeca-2,4,6,8,11-pentaen-1-yl, cyclododeca-2,4,6,9,11-pentaen-1-yl and cyclododeca-1,3,5,7,9,11-hexaen-1-yl.

The term "$C_{13}$-cycloalkenyl," as used herein, means cyclotridec-1-en-1-yl, cyclotridec-2-en-1-yl, cyclotridec-3-en-1-yl, cyclotridec-4-en-1-yl, cyclotridec-5-en-1-yl, cyclotridec-6-en-1-yl, cyclotridec-7-en-1-yl, cyclotrideca-1,3-dien-1-yl, cyclotrideca-1,4-dien-1-yl, cyclotrideca-1,5-dien-1-yl, cyclotrideca-1,6-dien-1-yl, cyclotrideca-1,7-dien-1-yl, cyclotrideca-1,8-dien-1-yl, cyclotrideca-1,9-dien-1-yl, cyclotrideca-1,10-dien-1-yl, cyclotrideca-1,11-dien-1-yl, cyclotrideca-1,12-dien-1-yl, cyclotrideca-2,4-dien-1-yl, cyclotrideca-2,5-dien-1-yl, cyclotrideca-2,6-dien-1-yl, cyclotrideca-2,7-dien-1-yl, cyclotrideca-2,8-dien-1-yl, cyclotrideca-2,9-dien-1-yl, cyclotrideca-2,10-dien-1-yl, cyclotrideca-2,11-dien-1-yl, cyclotrideca-2,12-dien-1-yl, cyclotrideca-3,5-dien-1-yl, cyclotrideca-3,6-dien-1-yl, cyclotrideca-3,7-dien-1-yl, cyclotrideca-3,8-dien-1-yl, cyclotrideca-3,9-dien-1-yl, cyclotrideca-3,10-dien-1-yl, cyclotrideca-3,11-dien-1-yl, cyclotrideca-4,6-dien-1-yl, cyclotrideca-4,7-dien-1-yl, cyclotrideca-4,8-dien-1-yl, cyclotrideca-4,9-dien-1-yl, cyclotrideca-4,10-dien-1-yl, cyclotrideca-5,7-dien-1-yl, cyclotrideca-5,8-dien-1-yl, cyclotrideca-5,9-dien-1-yl, cyclotrideca-6,8-dien-1-yl, cyclotrideca-1,3,5-trien-1-yl, cyclotrideca-1,3,6-trien-1-yl, cyclotrideca-1,3,7-trien-1-yl, cyclotrideca-1,3,8-trien-1-yl, cyclotrideca-1,3,9-trien-1-yl, cyclotrideca-1,3,10-trien-1-yl, cyclotrideca-1,3,11-trien-1-yl, cyclotrideca-1,3,12-trien-1-yl, cyclotrideca-1,4,6-trien-1-yl, cyclotrideca-1,4,7-trien-1-yl, cyclotrideca-1,4,8-trien-1-yl, cyclotrideca-1,4,9-trien-1-yl, cyclotrideca-1,4,10-trien-1-yl, cyclotrideca-1,4,11-trien-1-yl, cyclotrideca-1,4,12-trien-1-yl, cyclotrideca-1,5,7-trien-1-yl, cyclotrideca-1,5,8-trien-1-yl, cyclotrideca-1,5,9-trien-1-yl, cyclotrideca-1,5,10-trien-1-yl, cyclotrideca-1,5,11-trien-1-yl, cyclotrideca-1,5,12-trien-1-yl, cyclotrideca-1,6,8-trien-1-yl, cyclotrideca-1,6,9-trien-1-yl, cyclotrideca-cyclotrideca-1,6,11-trien-1-yl, cyclotrideca-1,6,12-trien-1-yl, cyclotrideca-1,7,9-trien-1-yl, cyclotrideca-1,7,10-trien-1-yl, cyclotrideca-1,7,11-tri-en-1-yl, cyclotrideca-1,7,12-trien-1-yl, cyclotrideca-1,8,10-trien-1-yl, cyclotrideca-1,8,11-trien-1-yl, cyclotrideca-1,8,12-trien-1-yl, cyclotrideca-1,9,11-trien-1-yl, cyclotrideca-1,9,12-trien-1-yl, cyclotrideca-1,10,12-trien-1-yl, cyclotrideca-2,4,6-trien-1-yl, cyclotrideca-2,4,7-trien-1-yl, cyclotrideca-2,4,8-trien-1-yl, cyclotrideca-2,4,9-trien-1-yl, cyclotrideca-2,4,10-trien-1-yl, cyclotrideca-2,4,11-trien-1-yl, cyclotrideca-2,4,12-trien-1-yl, cyclotrideca-2,5,7-trien-1-yl, cyclotrideca-2,5,8-trien-1-yl, cyclotri-deca-2,5,9-trien-1-yl, cyclotri-deca-2,5,10-trien-1-yl, cyclotrideca-2,5,11-trien-1-yl, cyclotrideca-2,5,12-trien-1-yl, cyclotrideca-2,6,8-trien-1-yl, cyclotrideca-2,6,9-trien-1-yl, cyclotrideca-2,6,10-trien-1-yl, cyclotrideca-2,6,11-trien-1-yl, cyclotrideca-2,6,12-trien-1-yl, cyclotrideca-2,7,9-trien-1-yl, cyclotrideca-2,7,10-trien-1-yl, cyclotrideca-2,7,11-trien-1-yl, cyclotrideca-2,7,12-trien-1-yl, cyclotrideca-2,8,10-trien-1-yl, cyclotrideca-2,8,11-trien-1-yl, cyclotrideca-2,8,12-trien-1-yl, cyclotrideca-2,9,11-trien-1-yl, cyclotrideca-2,9,12-trien-1-yl, cyclotri-deca-2,10,12-trien-1-yl, cyclotrideca-3,5,7-trien-1-yl, cyclotrideca-3,5,8-trien-1-yl, cyclotrideca-3,5,9-trien-1-yl, cyclotrideca-3,5,10-trien-1-yl, cyclotrideca-3,5,11-trien-1-yl, cyclotrideca-3,6,8-trien-1-yl, cyclotrideca-3,6,9-trien-1-yl, cyclotrideca-3,6,10-trien-1-yl, cyclotrideca-3,6,11-trien-1-yl, cyclotrideca-3,7,9-trien-1-yl, cyclotrideca-3,7,10-trien-1-yl, cyclotrideca-3,7,11-trien-1-yl, cyclotrideca-3,8,10-trien-1-yl, cyclotrideca-4,6,8-trien-1-yl, cyclotrideca-4,6,9-trien-1-yl, cyclotrideca-4,6,10-trien-1-yl, cyclotrideca-4,7,9-trien-1-yl, cyclotrideca-4,7,10-trien-1-yl, cyclotrideca-1,3,5,7-tetraen-1-yl, cyclotrideca-1,3,5,8-tetraen-1-yl, cyclotrideca-1,3,5,9-tetraen-1-yl, cyclotrideca-1,3,5,10-tetraen-1-yl, cyclotrideca-1,3,5,11-tetraen-1-yl, cyclotrideca-1,3,5,12-tetraen-1-yl, cyclotrideca-1,3,6,8-tetraen-1-yl, cyclotrideca-1,3,6,9-tetraen-1-yl, cyclotrideca-1,3,6,10-tetraen-1-yl, cyclotrideca-1,3,6,11-tetraen-1-yl, cyclotrideca-1,3,6,12-tetraen-1-yl, cyclotrideca-1,3,7,9-tetraen-1-yl, cyclotrideca-1,3,7,10-tetraen-1-yl, cyclotrideca-1,3,7,11-tetraen-1-yl, cyclotrideca-1,3,7,12-tetraen-1-yl, cyclotrideca-1,3,8,10-tetraen-1-yl, cyclotrideca-1,3,8,11-tetraen-1-yl, cyclotrideca-1,3,8,12-tetraen-1-yl, cyclotrideca-1,3,9,11-tetraen-1-yl, cyclotrideca-1,3,9,12-tetraen-1-yl, cyclotrideca-1,3,10,12-tetraen-1-yl, cyclotrideca-1,4,6,8-tetraen-1-yl, cyclotrideca-1,4,6,9-tetraen-1-yl, cyclotr-ideca-1,4,6,10-tetraen-1-yl, cyclotrideca-1,4,6,11-tetraen-1-yl, cyclotrideca-1,4,6,12-tetraen-1-yl, cyclotrideca-1,4,7,9-tetraen-1-yl, cyclotrideca-1,4,7,10-tetraen-1-yl, cyclotrideca-1,4,7,11-tetraen-1-yl, cyclotrideca-1,4,7,12-tetraen-1-yl, cyclotrideca-1,4,8,10-tetraen-1-yl, cyclotrideca-1,4,8,11-tetraen-1-yl, cyclotrideca-1,4,8,12-tetraen-1- yl, cyclotrideca-1,4,9,11-tetraen-1-yl, cyclotrideca-1,4,9,12-tetraen-1-yl, cyclotrideca-1,4,10,12-tetraen-1-yl, cyclotrideca-1,5,7,9-tetraen-1-yl, cyclotrideca-1,5,7,10-tetraen-1-yl, cyclotrideca-1,5,7,11-tetraen-1-yl, cyclotrideca-1,5,7,12-tetraen-1-yl, cyclotrideca-1,5,8,10-tetraen-1-yl, cyclotrideca-1,5,8,11-tetraen-1-yl, cyclotrideca-1,5,8,12-tetraen-1-yl, cyclotrideca-1,5,9,11-tetraen-1-yl, cyclotrideca-1,5,9,12-tetraen-1-yl, cyclotrideca-1,5,10,12-tetraen-1-yl, cyclotrideca-1,6,8,10-tetraen-1-yl, cyclotrideca-1,6,8,11-tetraen-1-yl, cyclotrideca-1,6,8,12-tetraen-1-yl, cyclotrideca-1,6,9,11-tetraen-1-yl, cyclotrideca-1,6,9,12-tetraen-1-yl, cyclotrideca-1,6,10,12-tetraen-1-yl, cyclotrideca-1,7,9,11-tetraen-1-yl, cyclotrideca-1,7,9,12-tetraen-1-yl, cyclotrideca-1,7,10,12-tetraen-1-yl, cyclotrideca-1,8,10,12-tetraen-1-yl, cyclotrideca-2,4,6,8-tetraen-1-yl, cyclotrideca-2,4,6,9-tetraen-1-yl, cyclotrideca-2,4,6,10-tetraen-1-yl, cyclotrideca-2,4,6,11-tetraen-1-yl, cyclotrideca-2,4,6,12-tetraen-1-yl, cyclotrideca-2,4,7,9-tetraen-1-yl, cyclotrideca-2,4,7,10-tetraen-1-yl, cyclotrideca-2,4,7,11-tetraen-1-yl, cyclotrideca-2,4,7,12-tetraen-1-yl, cyclotrideca-2,4,8,10-tetraen-1-yl, cyclotrideca-2,4,8,11-tetraen-1-yl, cyclotrideca-2,4,8,12-tetraen-1-yl, cyclotrideca-2,4,9,11-tetraen-1-yl, cyclotrideca-2,4,9,12-tetraen-1-yl, cyclotrideca-2,4,10,12-tetraen-1-yl, cyclotrideca-2,5,7,9-tetraen-1-yl, cyclotrideca-2,5,7,10-tetraen-1-yl, cyclotrideca-2,5,7,11-tetraen-1-yl, cyclotrideca-2,5,7,12-tetraen-1-yl, cyclotrideca-2,5,8,10-tetraen-1-yl, cyclotrideca-2,5,8,11-tetraen-1-yl, cyclotrideca-2,5,8,12-tetraen-1-yl, cyclotrideca-2,5,9,11-tetraen-1-yl, cyclotrideca-2,5,9,12-tetraen-1-yl, cyclotrideca-2,5,10,12-tetraen-1-yl, cyclotrideca-2,6,8,10-tetraen-1-yl, cyclotrideca-2,6,8,11-tetraen-1-yl, cyclotrideca-2,6,8,12-tetraen-1-yl, cyclotrideca-2,6,9,11-tetraen-1-yl, cyclotrideca-2,6,9,12-tetraen-1-yl, cyclotrideca-2,6,10,12-tetraen-1-yl, cyclotrideca-2,7,9,11-tetraen-1-yl, cyclotrideca-2,7,9,12-tetraen-1-yl, cyclotrideca-2,7,10,12-tetraen-1-yl, cyclotrideca-3,5,7,9-tetraen-1-yl, cyclotrideca-3,5,7,10-tetraen-1-yl, cyclotrideca-3,5,7,11-tetraen-1-yl, cyclotrideca-3,5,8,10-tetraen-1-yl, cyclotrideca-3,5,8,11-tetraen-1-yl, cyclotrideca-3,5,9,11-tetraen-1-yl, cyclotrideca-3,6,8,10-tetraen-1-yl, cyclotrideca-3,6,8,11-tetraen-1-yl, cyclotrideca-3,7,9,11-tetraen-1-yl, cyclotrideca-1,3,5,7,9-pentaen-1-yl, cyclotrideca-1,3,5,7,10-pentaen-1-yl, cyclotrideca-1,3,5,7,11-pentaen-1-yl, cyclotrideca-1,3,5,7,12-pentaen-1-yl, cyclotrideca-1,3,5,8,10-pentaen-1-yl, cyclotrideca-1,3,5,8,11-pentaen-1-yl, cyclotrideca-1,3,5,8,12-pentaen-1-yl, cyclotrideca-1,3,5,9,11-pentaen-1-yl, cyclotrideca-1,3,5,9,12-pentaen-1-yl, cyclotrideca-1,3,6,8,10-pentaen-1-yl, cyclotrideca-1,3,6,8,11-pentaen-1-yl, cyclotrideca-1,3,6,8,12-pentaen-1-yl, cyclotrideca-1,3,6,9,11-pentaen-1-yl, cyclotrideca-1,3,6,9,12-pentaen-1-yl, cyclotrideca-1,3,7,9,11-pentaen-1-yl, cyclotrideca-1,3,7,9,12-pentaen-1-yl, cyclotrideca-1,4,6,8,10-pentaen-1-yl, cyclotrideca-1,4,6,8,11-pentaen-1-yl, cyclotrideca-1,4,6,8,12-pentaen-1-yl, cyclotrideca-1,4,6,9,11-pentaen-1-yl, cyclotrideca-1,4,6,9,12-pentaen-1-yl, cyclotrideca-1,4,7,9,11-pentaen-1-yl, cyclotrideca-1,4,7,9,12-pentaen-1-yl, cyclotrideca-1,5,7,9,11-pentaen-1-yl, cyclotrideca-1,5,7,9,12-pentaen-1-yl, cyclotrideca-2,4,6,8,10-pentaen-1-yl, cyclotrideca-2,4,6,8,11-pentaen-1-yl, cyclotrideca-2,4,6,8,12-pentaen-1-yl, cyclotrideca-2,4,6,9,11-pentaen-1-yl, cyclotrideca-2,5,7,9,11-pentaen-1-yl, cyclotrideca-2,5,7,9,12-pentaen-1-yl, cyclotrideca-1,3,5,7,9,11-hexaen-1-yl and cyclotrideca-2,4,6,8,10,12-hexaen-1-yl.

The term "$C_{14}$-cycloalkenyl," as used herein, means cyclotetradec-1-en-1-yl, cyclotetradec-2-en-1-yl, cyclotetradec-3-en-1-yl, cyclotetradec-4-en-1-yl, cyclotetradec-5-en-1-yl, cyclotetradec-6-en-1-yl, cyclotetradec-7-en-1-yl, cyclotetradec-8-en-1-yl, cyclotetradeca-1,3-dien-1-yl, cyclotetradeca-1,4-dien-1-yl, cyclotetradeca-1,5-dien-1-yl, cyclotetradeca-1,6-dien-1-yl, cyclotetradeca-1,7-dien-1-yl, cyclotetradeca-1,8-dien-1-yl, cyclotetradeca-1,9-dien-1-yl, cyclotetradeca-1,10-dien-1-yl, cyclotetradeca-1,11-dien-1-yl, cyclotetradeca-1,12-dien-1-yl, cyclotetradeca-1,13-dien-1-yl, cyclotetradeca-2,4-dien-1-yl, cyclotetradeca-2,5-dien-1-yl, cyclotetradeca-2,6-dien-1-yl, cyclotetradeca-2,7-dien-1-yl, cyclotetradeca-2,8-dien-1-yl, cyclotetradeca-2,9-dien-1-yl, cyclotetradeca-2,10-dien-1-yl, cyclotetradeca-2,11-dien-1-yl, cyclotetradeca-2,12-dien-1-yl, cyclotetradeca-2,13-dien-1-yl, cyclotetradeca-3,5-dien-1-yl, cyclotetradeca-3,6-dien-1-yl, cyclotetradeca-3,7-dien-1-yl, cyclotetradeca-3,8-dien-1-yl, cyclotetradeca-3,9-dien-1-yl, cyclotetradeca-3,10-dien-1-yl, cyclotetradeca-3,11-dien-1-yl, cyclotetradeca-3,12-dien-1-yl, cyclotetradeca-4,6-dien-1-yl, cyclotetradeca-4,7-dien-1-yl, cyclotetradeca-4,8-dien-1-yl, cyclotetradeca-4,9-dien-1-yl, cyclotetradeca-4,10-dien-1-yl, cyclotetradeca-4,11-dien-1-yl, cyclotetradeca-5,7-dien-1-yl, cyclotetradeca-5,8-dien-1-yl, cyclotetradeca-5,9-dien-1-yl, cyclotetradeca-5,10-dien-1-yl, cyclotetradeca-6,8-dien-1-yl, cyclotetradeca-6,9-dien-1-yl, cyclotetradeca-1,3,5-tetraen-1-yl, cyclotetradeca-1;3,6-tetraen-1-yl, cyclotetradeca-1,3,7-tetraen-1-yl, cyclotetradeca-1,3,8-tetraen-1-yl, cyclotetradeca-1,3,9-tetraen-1-yl, cyclotetradeca-1,3,10-tetraen-1-yl, cyclotetradeca-1,3,11-tetraen-1-yl, cyclotetradeca-1,3,12-tetraen-1-yl, cyclotetradeca-1,3,13-tetraen-1-yl, cyclotetradeca-1,4,6-tetraen-1-yl, cyclotetradeca-1,4,7-tetraen-1-yl, cyclotetradeca-1,4,8-tetraen-1-yl, cyclotetradeca-1,4,9-tetraen-1-yl, cyclotetradeca-1,4,10-tetraen-1-yl, cyclotetradeca-1,4,11-tetraen-1-yl, cyclotetradeca-1,4,12-tetraen-1-yl, cyclotetradeca-1,4,13-tetraen-1-yl, cyclotetradeca-1,5,7-tetraen-1-yl, cyclotetradeca-1,5,8-tetraen-1-yl, cyclotetradeca-1,5,9-tetraen-1-yl, cyclotetradeca-1,5,10-tetraen-1-yl, cyclotetradeca-1,5,11-tetraen-1-yl, cyclotetradeca-1,5,12-tetraen-1-yl, cyclotetradeca-1,5,13-tetraen-1-yl, cyclotetradeca-1,6,8-tetraen-1-yl, cyclotetradeca-1,6,9-tetraen-1-yl, cyclotetradeca-1,6,10-tetraen-1-yl, cyclotetradeca-1,6,11-tetraen-1-yl, cyclotetradeca-1,6,12-tetraen-1-yl,' cyclotetradeca-1,6,13-tetraen-1-yl, cyclotetradeca-1,7,9-tetraen-1-yl, cyclotetradeca-1,7,10-tetraen-1-yl, cyclotetradeca-1,7,11-tetraen-1-yl, cyclotetradeca-1,7,12-tetraen-1-yl, cyclotetradeca-1,7,13-tetraen-1-yl, cyclotetradeca-1,8,10-tetraen-1-yl, cyclotetradeca-1,8,11-tetraen-1-yl, cyclotetradeca-1,8,12-tetraen-1-yl, cyclotetradeca-1,8,13-tetraen-1-yl, cyclotetradeca-1,9,11-tetraen-1-yl, cyclotetradeca-1,9,12-tetraen-1-yl, cyclotetradeca-1,9,13-tetraen-1-yl, cyclotetradeca-1,10,12-tetraen-1-yl, cyclotetradeca-1,10,13-tetraen-1-yl, cyclotetradeca-1,11,13-tetraen-1-yl, cyclotetradeca-2,4,6-tetraen-1-yl, cyclotetradeca-2,4,7-tetraen-1-yl, cyclotetradeca-2,4,8-tetraen-1-yl, cyclotetradeca-2,4,9-tetraen-1-yl, cyclotetradeca-2,4,10-tetraen-1-yl, cyclotetradeca-2,4,11-tetraen-1-yl, cyclotetradeca-2,4,12-tetraen-1-yl, cyclotetradeca-2,4,13-tetraen-1-yl, cyclotetradeca-2,5,7-tetraen-1-yl, cyclotetradeca-2,5,8-tetraen-1-yl, cyclotetradeca-2,5,9-tetraen-1-yl, cyclotetradeca-2,5,10-tetraen-1-yl, cyclotetradeca-2,5,11-tetraen-1-yl, cyclotetradeca-2,5,12-tetraen-1-yl, cyclotetradeca-2,5,13-tetraen-1-yl, cyclotetradeca-2,6,8-tetraen-1-yl, cyclotetradeca-2,6,9-tetraen-1-yl, cyclotetradeca-2,6,10-tetraen-1-yl, cyclotetradeca-2,6,11-tetraen-1-yl, cyclotetradeca-2,6,12-tetraen-1-yl, cyclotetradeca-2,6,13-tetraen-1-yl, cyclotetradeca-2,7,9-tetraen-1-yl, cyclotetradeca-2,7,10-tetraen-1-yl, cyclotetradeca-2,7,11-tetraen-1-yl, cyclotetradeca-2,7,12-tetraen-1-yl, cyclotetradeca-2,7,13-tetraen-1-yl, cyclotetradeca-2,8,10-tetraen-1-yl, cyclotetradeca-2,8,11-tetraen-1-yl, cyclotetradeca-2,8,12-tetraen-1-yl, cyclotetradeca-2,8,13-tetraen-1-yl, cyclotetradeca-2,9,11-tetraen-1-yl, cyclotetradeca-2,9,12-tetraen-1-yl, cyclotetradeca-2,9,13-tetraen-1-yl, cyclotetradeca-2,10,12-tetraen-1-yl, cyclotetradeca-2,10,13-tetraen-1-yl, cyclotetradeca-2,11,13-tetraen-1-yl, cyclotetradeca-3,5,7-tetraen-1-yl, cyclotetradeca-3,5,8-tetraen-1-yl, cyclotetradeca-3,5,9-tetraen-1-yl, cyclotetradeca-3,5,10-tetraen-1-yl, cyclotetradeca-3,5,11-tetraen-1-yl, cyclotetradeca-3,5,12-tetraen-1-yl, cyclotetradeca-3,6,8-tetraen-1-yl, cyclotetradeca-3,6,9-tetraen-1-yl, cyclotetradeca-3,6,10-tetraen-1-yl, cyclotetradeca-3,6,11-tetraen-1-yl, cyclotetradeca-3,6,12-tetraen-1-yl, cyclotetradeca-3,7,9-tetraen-1-yl, cyclotetradeca-3,7,10-tetraen-1-yl, cyclotetradeca-3,7,11-tetraen-1-yl, cyclotetradeca-3,7,12-tetraen-1-yl, cyclotetradeca-3,8,10-tetraen-1-yl, cyclotetradeca-3,8,11-tetraen-1-yl, cyclotetradeca-3,9,11-tetraen-1-yl, cyclotetradeca-4,6,8-tetraen-1-yl, cyclotetradeca-4,6,9-tetraen-1-yl, cyclotetradeca-4,6,10-tetraen-1-yl, cyclotetradeca-4,6,11-tetraen-1-yl, cyclotetradeca-4,7,9-tetraen-1-yl, cyclotetradeca-4,7,10-tetraen-1-yl, cyclotetradeca-4,7,11-tetraen-1-yl, cyclotetradeca-4,8,10-tetraen-1-yl, cyclotetradeca-1,3,5,7-tetraen-1-yl, cyclotetradeca-1,3,5,8-tetraen-1-yl, cyclotetradeca-1,3,5,9-tetraen-1-yl, cyclotetradeca-1,3,5,10-tetraen-1-yl, cyclotetradeca-1,3,5,11-tetraen-1-yl, cyclotetradeca-1,3,5,12-tetraen-1-yl, cyclotetradeca-1,3,5,13-tetraen-1-yl, cyclotetradeca-1,3,6,8-tetraen-1-yl, cyclotetradeca-1,3,6,9-tetraen-1-yl, cyclotetradeca-1,3,6,10-tetraen-1-yl, cyclotetradeca-1,3,6,11-tetraen-1-yl, cyclotetradeca-1,3,6,12-tetraen-1-yl, cyclotetradeca-1,3,6,13-tetraen-1-yl, cyclotetradeca-1,3,7,9-tetraen-1-yl, cyclotetradeca-1,3,7,10-tetraen-1-yl, cyclotetradeca-1,3,7,11-tetraen-1-yl, cyclotetradeca-1,3,7,12-tetraen-1-yl, cyclotetradeca-1,3,7,13-tetraen-1-yl, cyclotetradeca-1,3,8,10-tetraen-1-yl, cyclotetradeca-1,3,8,11-tetraen-1-yl, cyclotetradeca-1,3,8,12-tetraen-1-yl, cyclotetradeca-1,3,8,13-tetraen-1-yl, cyclotetradeca-1,3,9,11-tetraen-1-yl, cyclotetradeca-1,3,9,12-tetraen-1-yl, cyclotetradeca-1,3,9,13-tetraen-1-yl, cyclotetradeca-1,3,10,12-tetraen-1-yl, cyclotetradeca-1,3,10,13-tetraen-1-yl, cyclotetradeca-1,3,11,13-tetraen-1-yl, cyclotetradeca-1,4,6,8-tetraen-1-yl, cyclotetradeca-1,4,6,9-tetraen-1-yl, cyclotetradeca-1,4,6,10-tetraen-1-yl, cyclotetradeca-1,4,6,11-tetraen-1-yl, cyclotetradeca-1,4,6,12-tetraen-1-yl, cyclotetradeca-1,4,6,13-tetraen-1-yl, cyclotetradeca-1,4,7,9-tetraen-1-yl, cyclotetradeca-1,4,7,10-tetraen-1-yl, cyclotetradeca-1,4,7,11-tetraen-1-yl, cyclotetradeca-1,4,7,12-tetraen-1-yl, cyclotetradeca-1,4,7,13-tetraen-1-yl, cyclotetradeca-1,4,8,10-tetraen-1-yl, cyclotetradeca-1,4,8,11-tetraen-1-yl, cyclotetradeca-1,4,8,12-tetraen-1-yl, cyclotetradeca-1,4,8,13-tetraen-1-yl, cyclotetradeca-1,4,9,11-tetraen-1-yl, cyclotetradeca-1,4,9,12-tetraen-1-yl, cyclotetradeca-1,4,9,13-tetraen-1-yl, cyclotetradeca-1,4,10,12-tetraen-1-yl, cyclotetradeca-1,4,10,13-tetraen-1-yl, cyclotetradeca-1,4,11,13-tetraen-1-yl, cyclotetradeca-1,5,7,9-tetraen-1-yl, cyclotetradeca-1,5,7,10-tetraen-1-yl, cyclotetradeca-1,5,7,11-tetraen-1-yl, cyclotetradeca-1,5,7,12-tetraen-1-yl, cyclotetradeca-1,5,7,13-tetraen-1-yl, cyclotetradeca-1,5,8,10-tetraen-1-yl, cyclotetradeca-1,5,8,11-tetraen-1-yl, cyclotetradeca-1,5,8,12-tetraen-1-yl, cyclotetradeca-1,5,8,13-tetraen-1-yl, cyclotetradeca-1,5,9,11-tetraen-1-yl, cyclotetradeca-1,5,9,12-tetraen-1-yl, cyclotetradeca-1,5,9,13-tetraen-1-yl, cyclotetradeca-1,5,10,12-tetraen-1-yl, cyclotetradeca-1,5,10,13-tetraen-1-yl, cyclotetradeca-1,5,11,13-tetraen-1-yl, cyclotetradeca-1,6,8,10-tetraen-1-yl, cyclotetradeca-1,6,8,11-tetraen-1-yl, cyclotetradeca-1,6,8,12-tetraen-1-yl, cyclotetradeca-1,6,8,13-tetraen-1-yl, cyclotetradeca-1,6,9,11-tetraen-1-yl, cyclotetradeca-1,6,9,12-tetraen-1-yl, cyclotetradeca-1,6,9,13-tetraen-1-yl, cyclotetradeca-1,6,10,12-tetraen-1-yl, cyclotetradeca-1,6,10,13-tetraen-1-yl, cyclotetradeca-1,6,11,13-tetraen-1-yl, cyclotetradeca-1,7,9,11-tetraen-1-yl, cyclotetradeca-1,7,9,12-tetraen-1-yl, cyclotetradeca-1,7,9,13-tetraen-1-yl, cyclotetradeca-1,7,10,12-tetraen-1-yl, cyclotetradeca-1,7,10,13-tetraen-1-yl, cyclotetradeca-1,7,11,13-tetraen-1-yl, cyclotetradeca-1,8,10,12-tetraen-1-yl, cyclotetradeca-1,8,10,13-tetraen-1-yl, cyclotetradeca-1,8,11,13-tetraen-1-yl, cyclotetradeca-2,4,6,8-tetraen-1-yl, cyclotetradeca-2,4,6,9-tetraen-1-yl, cyclotetradeca-2,4,6,10-tetraen-1-yl, cyclotetradeca-2,4,6,11-tetraen-1-yl, cyclotetradeca-2,4,6,12-tetraen-1-yl, cyclotetradeca-2,4,6,13-tetraen-1-yl, cyclotetradeca-2,4,7,9-tetraen-1-yl, cyclotetradeca-2,4,7,10-tetraen-1-yl, cyclotetradeca-2,4,7,11-tetraen-1-yl, cyclotetradeca-2,4,7,12-tetraen-1-yl, cyclotetradeca-2,4,7,13-tetraen-1-yl, cyclotetradeca-2,4,8,10-tetraen-1-yl, cyclotetradeca-2,4,8,11-tetraen-1-yl, cyclotetradeca-2,4,8,12-tetraen-1-yl, cyclotetradeca-2,4,8,13-tetraen-1-yl, cyclotetradeca-2,4,9,11-tetraen-1-yl, cyclotetradeca-2,4,9,12-tetraen-1-yl, cyclotetradeca-2,4,9,13-tetraen-1-yl, cyclotetradeca-2,4,10,12-tetraen-1-yl, cyclotetradeca-2,4,10,13-tetraen-1-yl, cyclotetradeca-2,4,11,13-tetraen-1-yl, cyclotetradeca-2,5,7,9-tetraen-1-yl, cyclotetradeca-2,5,7,10-tetraen-1-yl, cyclotetradeca-2,5,7,11-tetraen-1-yl, cyclotetradeca-2,5,7,12-tetraen-1-yl, cyclotetradeca-2,5,7,13-tetraen-1-yl, cyclotetradeca-2,5,8,10-tetraen-1-yl, cyclotetradeca-2,5,8,11-tetraen-1-yl, cyclotetradeca-2,5,8,12-tetraen-1-yl, cyclotetradeca-2,5,8,13-tetraen-1-yl, cyclotetradeca-2,5,9,11-tetraen-1-yl, cyclotetradeca-2,5,9,12-tetraen-1-yl, cyclotetradeca-2,5,9,13-tetraen-1-yl, cyclotetradeca-2,5,10,12-tetraen-1-yl, cyclotetradeca-2,5,10,13-tetraen-1-yl, cyclotetradeca-2,6,8,10-tetraen-1-yl, cyclotetradeca-2,6,8,11-tetraen-1-yl, cyclotetradeca-2,6,8,12-tetraen-1-yl, cyclotetradeca-2,6,8,13-tetraen-1-yl, cyclotetradeca-2,6,9,11-tetraen-1-yl, cyclotetradeca-2,6,9,12-tetraen-1-yl, cyclotetradeca-2,6,9,13-tetraen-1-yl, cyclotetradeca-2,6,10,12-tetraen-1-yl, cyclotetradeca-2,6,10,13-tetraen-1-yl, cyclotetradeca-2,6,11,13-tetraen-1-yl, cyclotetradeca-2,7,9,11-tetraen-1-yl, cyclotetradeca-2,7,9,12-tetraen-1-yl, cyclotetradeca-2,7,10,12-tetraen-1-yl, cyclotetradeca-3,5,7,9-tetraen-1-yl, cyclotetradeca-3,5,7,10-tetraen-1-yl, cyclotetradeca-3,5,7,11-tetraen-1-yl, cyclotetradeca-3,5,7,12-tetraen-1-yl, cyclotetradeca-3,5,8,10-tetraen-1-yl, cyclotetradeca-3,5,8,11-tetraen-1-yl, cyclotetradeca-3,5,8,12-tetraen-1-yl, cyclotetradeca-3,5,9,11-tetraen-1-yl, cyclotetradeca-3,5,9,12-tetraen-1-yl, cyclotetradeca-3,5,10,12-tetraen-1-yl, cyclotetradeca-3,6,8,10-tetraen-1-yl, cyclotetradeca-3,6,8,11-tetraen-1-yl, cyclotetradeca-3,6,8,12-tetraen-1-yl, cyclotetradeca-3,7,9,11-tetraen-1-yl, cyclotetradeca-1,3,5,7,9-pentaen-1-yl, cyclotetradeca-1,3,5,7,10-pentaen-1-yl, cyclotetradeca-1,3,5,7,11-pentaen-1-yl, cyclotetradeca-1,3,5,7,12-pentaen-1-yl, cyclotetradeca-1,3,5,7,13-pentaen-1-yl, cyclotetradeca-1,3,5,8,10-pentaen-1-yl, cyclotetradeca-1,3,5,8,11-pentaen-1-yl, cyclotetradeca-1,3,5,8,12-pentaen-1-yl, cyclotetradeca-1,3,5,8,13-pentaen-1-yl, cyclotetradeca-1,3,5,9,11-pentaen-1-yl, cyclotetradeca-1,3,5,9,12-pentaen-1-yl, cyclotetradeca-1,3,5,9,13-pentaen-1-yl, cyclotetradeca-1,3,5,10,12-pentaen-1-yl, cyclotetradeca-1,3,5,10,13-pentaen-1-yl, cyclotetradeca-1,3,5,11,13-pentaen-1-yl, cyclotetradeca-1,3,6,8,10-pentaen-1-yl, cyclotetradeca-1,3,6,8,11-pentaen-1-yl, cyclotetradeca-1,3,6,8,12-pentaen-1-yl, cyclotetradeca-1,3,6,8,13-pentaen-1-yl, cyclotetradeca-1,3,6,9,11-pentaen-1-yl, cyclotetradeca-1,3,6,9,12-pentaen-1-yl, cyclotetradeca-1,3,6,9,13-pentaen-1-yl, cyclotetradeca-1,3,7,9,11-pentaen-1-yl, cyclotetradeca-1,3,7,9,12-pentaen-1-yl, cyclotetradeca-1,3,7,9,13-pentaen-1-yl, cyclotetradeca-1,4,6,8,10-pentaen-1- yl, cyclotetradeca-1,4,6,8,11-pentaen-1-yl, cyclotetradeca-1,4,6,8,12-pentaen-1-yl, cyclotetradeca-1,4,6,8,13-pentaen-1-yl, cyclotetradeca-1,4,6,9,11-pentaen-1-yl, cyclotetradeca-1,4,6,9,12-pentaen-1-yl, cyclotetradeca-1,4,6,9,13-pentaen-1-yl, cyclotetradeca-1,4,7,9,11-pentaen-1-yl, cyclotetradeca-1,4,7,9,12-pentaen-1-yl, cyclotetradeca-1,4,7,9,13-pentaen-1-yl, cyclotetradeca-1,5,7,9,11-pentaen-1-yl, cyclotetradeca-1,5,7,9,12-pentaen-1-yl, cyclotetradeca-1,5,7,9,13-pentaen-1-yl, cyclotetradeca-2,4,6,8,10-pentaen-1-yl, cyclotetradeca-2,4,6,8,11-pentaen-1-yl, cyclotetradeca-2,4,6,8,12-pentaen-1-yl, cyclotetradeca-2,4,6,8,13-pentaen-1-yl, cyclotetradeca-2,4,6,9,11-pentaen-1-yl, cyclotetradeca-2,4,6,9,12-pentaen-1-yl, cyclotetradeca-2,4,6,9,13-pentaen-1-yl, cyclotetradeca-2,4,6,10,12-pentaen-1-yl, cyclotetradeca-2,4,6,10,13-pentaen-1-yl, cyclotetradeca-2,4,6,11,13-pentaen-1-yl, cyclotetradeca-2,4,7,9,11-pentaen-1-yl, cyclotetradeca-2,4,7,9,12-pentaen-1-yl, cyclotetradeca-2,4,7,9,13-pentaen-1-yl, cyclotetradeca-2,4,7,10,12-pentaen-1-yl, cyclotetradeca-2,4,7,10,13-pentaen-1-yl, cyclotetradeca-2,4,7,11,13-pentaen-1-yl, cyclotetradeca-2,4,8,10,12-pentaen-1-yl, cyclotetradeca-2,4,8,10,13-pentaen-1-yl, cyclotetradeca-2,5,7,9,11-pentaen-1-yl, cyclotetradeca-2,5,7,9,12-pentaen-1-yl, cyclotetradeca-2,5,7,9,13-pentaen-1-yl, cyclotetradeca-2,5,7,10,12-pentaen-1-yl, cyclotetradeca-2,5,7,10,13-pentaen-1-yl, cyclotetradeca-1,3,5,7,9,11-hexaen-1-yl, cyclotetradeca-1,3,5,7,9,12-hexaen-1-yl, cyclotetradeca-1,3,5,7,9,13-hexaen-1-yl, cyclotetradeca-2,4,6,8,10,12-hexaen-1-yl, cyclotetradeca-2,4,6,8,10,13-hexaen-1-yl, cyclotetradeca-2,4,6,8,11,13-hexaen-1-yl and cyclotetradeca-1,3,5,7,9,11,13-heptaen-1-yl.

The term "$C_3$-cycloalkyl," as used herein, means cycloprop-1-yl.

The term "$C_4$-cycloalkyl," as used herein, means cyclobut-1-yl.

The term "$C_5$-cycloalkyl," as used herein, means cyclopent-1-yl.

The term "$C_6$-cycloalkyl," as used herein, means cyclohex-1-yl.

The term "$C_7$-cycloalkyl," as used herein, means bicyclo[2.2.1]hept-1-yl, bicyclo[2.2.1]hept-2-yl, cyclohept-1-yl, bicyclo[2.2.1]hept-7-yl and cyclohept-1-yl.

The term "$C_8$-cycloalkyl," as used herein, means bicyclo[2.2.2]oct-1-yl, bicyclo[2.2.2]oct-2-yl, bicyclo[2.2.2]oct-7-yl, cyclooct-1-yl.

The term "$C_9$-cycloalkyl," as used herein, means cyclonon-1-yl.

The term "$C_{10}$-cycloalkyl," as used herein, means adamant-1-yl, adamant-2-yl and cyclodec-1-yl. The term "$C_{11}$-cycloalkyl," as used herein, means cycloundec-1-yl, tricyclo[4.3.1.1$^{3,8}$]undec-1-yl (homoadamant-1-yl), tricyclo[4.3.1.1$^{3,8}$]undec-2-yl (homoadamant-2-yl), tricyclo[4.3.1.1$^{3,8}$]undec-3-yl (homoadamant-3-yl), tricyclo[4.3.1.1$^{3,8}$]undec-4-yl (homoadamant-4-yl), and tricyclo[4.3.1.1$^{3,8}$]undec-9-yl (homoadamant-9-yl).

The term "$C_{12}$-cycloalkyl," as used herein, means cyclododec-1-yl.

The term "$C_{13}$-cycloalkyl," as used herein, means cyclotridec-1-yl.

The term "$C_{14}$-cycloalkyl," as used herein, means cyclotetradec-1-yl.

The term "$C_2$-spiroalkenyl," as used herein, means ethen-1,2-ylene, both ends of which replace hydrogen atoms of the same $CH_2$ moiety.

The term "$C_3$-spiroalkenyl," as used herein, means prop-1-en-1,3-ylene, both ends of which replace hydrogen atoms of the same $CH_2$ moiety.

The term "$C_4$-spiroalkenyl," as used herein, means but-1-en-1,4-ylene, but-2-en-1,4-ylene and buta-1,3-dien-1,4-ylene, both ends of which replace hydrogen atoms of the same $CH_2$ moiety.

The term "$C_5$-spiroalkenyl," as used herein, means pent-1-en-1,5-yl-ene, pent-2-en-1,5-ylene, penta-1,3-dien-1,5-ylene and penta-1,4-dien-1,5-ylene, both ends of which replace hydrogen atoms of the same $CH_2$ moiety.

The term "$C_6$-spiroalkenyl," as used herein, means hex-1-en-1,6-ylene, hex-2-en-1,6-ylene, hexa-1,3-dien-1,6-ylene, hexa-1,4-di-en-1,6-ylene and hexa-1,3,5-trien-1,6-ylene, both ends of which replace hydrogen atoms of the same $CH_2$ moiety.

The term "$C_7$-spiroalkenyl," as used herein, means hept-1-en-1,7-yl-ene, hept-2-en-1,7-ylene, hept-3-en-1,7-ylene, hepta-1,3-dien-1,7-ylene, hepta-1,4-dien-1,7-ylene, hepta-1,5-dien-1,7-ylene, hepta-2,4-dien-1,7-ylene, hepta-2,5-dien-1,7-ylene, hepta-1,3,5-trien-1,7-ylene and hepta-1,3,6-trien-1,7-ylene, both ends of which replace hydrogen atoms of the same $CH_2$ moiety.

The term "$C_8$-spiroalkenyl," as used herein, means oct-1-en-1,8-ylene, oct-2-en-1,8-ylene, oct-3-en-1,8-ylene, octa-1,3-dien-1,8-ylene, octa-1,4-dien-1,8-ylene, octa-1,5-dien-1,8-ylene, octa-1,6-dien-1,8-ylene, octa-2,4-dien-1,8-ylene, octa-2,5-dien-1,8-ylene, octa-3,5-dien-1,8-ylene, octa-1,3,5-trien-1,8-ylene, octa-1,3,6-trien-1,8-ylene and octa-2,4,6-trien-1,8-ylene, both ends of which replace hydrogen atoms of the same $CH_2$ moiety.

The term "$C_9$-spiroalkenyl," as used herein, means nona-1-en-1,9-yl-ene, nona-2-en-1,9-ylene, nona-3-en-1,9-ylene, nona-4-en-1,9-ylene, nona-1,3-dien-1,9-ylene, nona-1,4-dien-1,9-ylene, nona-1,5-dien-1,9-ylene, nona-1,6-dien-1,9-ylene, nona-1,7-dien-1,9-ylene, nona-1,8-dien-1,9-ylene, nona-2,4-dien-1,9-ylene, nona-2,5-dien-1,9-ylene, nona-2,6-dien-1,9-ylene, nona-2,7-dien-1,9-ylene, nona-3,5-dien-1,9-ylene, nona-3,6-dien-1,9-ylene, nona-4,6-dien-1,9-ylene, nona-1,3,5-trien-1,9-ylene, nona-1,3,6-trien-1,9-ylene, nona-1,3,7-trien-1,9-ylene, nona-1,3,8-trien-1,9-ylene, nona-1,4,6-trien-1,9-yl-ene, nona-1,4,7-trien-1,9-ylene, nona-1,4,8-trien-1,9-ylene, nona-1,5,7-trien-1,9-ylene, nona-2,4,6-trien-1,9-ylene, nona-2,4,7-trien-1,9-ylene, nona-1,3,5,7-tetraen-1,9-ylene, nona-1,3,5,8-tetraen-1,9-ylene and nona-1,3,6,9-tetraen-1,9-ylene, both ends of which replace hydrogen atoms of the same $CH_2$ moiety.

The term "$C_2$-spiroalkyl," as used herein, means eth-1,2-ylene, both ends of which replace hydrogen atoms of the same $CH_2$ moiety.

The term "$C_3$-spiroalkyl," as used herein, means prop-1,3-ylene, both ends of which replace hydrogen atoms of the same $CH_2$ moiety.

The term "$C_4$-spiroalkyl," as used herein, means but-1,4-ylene, both ends of which replace hydrogen atoms of the same $CH_2$ moiety.

The term "$C_5$-spiroalkyl," as used herein, means pent-1,5-ylene, both ends of which replace hydrogen atoms of the same $CH_2$ moiety.

The term "$C_6$-spiroalkyl," as used herein, means hex-1,6-ylene, both ends of which replace hydrogen atoms of the same $CH_2$ moiety.

The term "$C_7$-spiroalkyl," as used herein, means hept-1,7-ylene, both ends of which replace hydrogen atoms of the same $CH_2$ moiety.

The term "$C_8$-spiroalkyl," as used herein, means oct-1,8-ylene, both ends of which replace hydrogen atoms of the same $CH_2$ moiety.

The term "C$_9$-spiroalkyl," as used herein, means non-1,9-ylene, both ends of which replace hydrogen atoms of the same CH$_2$ moiety.

Compounds of this invention contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds may also exist as an equilibrium mixture of Z or E configurations.

Compounds of this invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having formula (I), produced by in vitro or in vivo metabolic processes, may also have utility for treating diseases associated with expression of an anti-apoptotic protein family member such as of BCl-X$_L$ protein, and Bcl-2 protein or Bcl-w protein.

Certain precursor compounds which may be metabolized in vitro or in vivo to form compounds having formula (I) may also have utility for treating diseases associated with expression of an anti-apoptotic protein family member such as of BCl-X$_L$ protein, and Bcl-2 protein or Bcl-w protein.

Compounds having formula (I) may exist as an acid addition salts, basic addition salts or zwitterions. Salts of the compounds are prepared during their isolation or following their purification. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds and prodrugs thereof are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having formula (I) may be administered, for example, bucally, ophthalmically, orally, osmotically, parenterally (intramuscularly, intraperintoneally intrasternally, intravenously, subcutaneously), rectally, topically, transdermally, or vaginally.

Therapeutically effective amounts of compounds having formula (I) depend on recipient of treatment, disorder being treated and severity thereof, composition containing it, time of administration, route of administration, duration of treatment, its potency, its rate of clearance and whether or not another drug is co-administered. The amount of a compound of this invention having formula (I) used to make a composition to be administered daily to a patient in a single dose or in divided doses is from about 0.03 to about 200 mg/kg body weight. Single dose compositions contain these amounts or a combination of submultiples thereof.

Compounds having formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having formula (I) to be administered osmotically include, for example, chlorofluorohydrocarbons, ethanol, water and mixtures thereof. Excipients for preparation of compositions comprising a compound of this invention having formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having formula (I) to be administered rectally or vaginally include, for example, cocoa butter, polyethylene glycol, wax and mixtures thereof.

Compounds having formula (I) may also be administered with one or more than one additional therapeutic agents, wherein additional therapeutic agents include radiation or chemotherapeutic agents, wherein chemotherapeutic agents include, but are not limited to, carboplatin, cisplatin, cyclophosphamide, dacarbazine, dexamethasone, docetaxel, doxorubicin, etoposide, fludarabine, irinotecan, CHOP (C: Cytoxan® (cyclophosphamide); H: Adiamycin® (hydroxydoxorubicin); O: Vincristine (Oncovin®); P: prednisone), paclitaxel, rapamycin, Rituxin® (rituximab) and vincristine.

For determination of the utility of compounds having formula (I) as inhibitors of the activity of anti-apoptotic Bcl-$X_L$, representative examples in DMSO at concentrations between 100 μM and 1 pM and added to each well of a 96-well microtiter plate. A mixture totaling 125 μL per well of assay buffer (20 mM phosphate buffer, pH 7.4), 1 mM EDTA, 50 mM NaCl, 0.05% PF-68), 30 nM Bcl-$X_L$ protein (prepared as described in Science 1997, 275, 983-986), 15 nM fluorescein-labeled BAD peptide (prepared in-house), and the DMSO solution of the example was shaken for 2 minutes then placed in a LJL Analyst (LJL Bio Systems, Calif.). A negative control (DMSO, 15 nM BAD peptide, assay buffer) and a positive control (DMSO, 15 nM BAD peptide, 30 nM Bcl-$X_L$, assay buffer) were used to determine the range of the assay. Polarization was measured at 25° C. with a continuous Fluorescein lamp (excitation 485 nm; emission 530 nm). Percentage of inhibition was determined by (1−((mP value of well-negative control)/range))×100%.

$IC_{50}$ values (concentration of example needed for 50% inhibition of Bcl-$X_L$) for the representative compounds having formula (I), calculated using Microsoft Excel, were 3.7 nM, 5.8 nM, 6.1 nM, 6.2 nM, 6.9 nM, 7.1 nM, 7.1 nM, 7.4 nM, 7.7 nM, 7.8 nM, 7.9 nM, 8.3 nM, 8.3 nM, 8.3 nM, 8.4 nM, 8.4 nM, 8.5 nM, 8.5 nM, 8.7 nM, 8.8 nM, 9.1 nM, 9.1 nM, 9.1 nM, 9.2 nM, 9.5 nM, 9.6 nM, 9.7 nM, 9.8 nM, 9.8 nM, 9.9 nM, 9.9 nM, 9.9 nM, 10.0 nM, 10.0 nM, 10.0 nM, 10.0 nM, 10.1 nM, 10.1 nM, 10.2 nM, 10.2 nM, 10.3 nM, 10.3 nM, 10.3 nM, 10.3 nM, 10.3 nM, 10.3 nM, 10.3 nM, 10.3 nM, 10.5 nM, 10.6 nM, 10.6 nM, 10.6 nM, 10.6 nM, 10.6 nM, 10.7 nM, 10.7 nM, 10.7 nM, 10.7 nM, 10.8 nM, 10.8 nM, 10.8 nM, 10.8 nM, 10.9 nM, 10.9 nM, 10.9 nM, 10.9 nM, 11.0 nM, 11.0 nM, 11.0 nM, 11.0 nM, 11.0 nM, 11.1 nM, 11.1 nM, 11.1 nM, 11.1 nM, 11.1 nM, 11.1 nM, 11.1 nM, 11.1 nM, 11.1 nM, 11.1 nM, 11.2 nM, 11.2 nM, 11.2 nM, 11.2 nM, 11.2 nM, 11.2 nM, 11.2 nM, 11.3 nM, 11.3 nM, 11.3 nM, 11.3 nM, 11.4 nM, 11.5 nM, 11.5 nM, 11.5 nM, 11.5 nM, 11.5 nM, 11.6 nM, 11.6 nM, 11.6 nM, 11.6 nM, 11.6 nM, 11.6 nM, 11.6 nM, 11.7 nM, 11.7 nM, 11.8 nM, 11.8 nM, 11.9 nM, 11.9 nM, 11.9 nM, 11.9 nM, 11.9 nM, 12.1 nM, 12.1 nM, 12.1 nM, 12.1 nM, 12.2 nM, 12.2 nM, 12.3 nM, 12.3 nM, 12.3 nM, 12.3 nM, 12.4 nM, 12.4 nM, 12.4 nM, 12.4 nM, 12.5 nM, 12.5 nM, 12.5 nM, 12.6 nM, 12.6 nM, 12.6 nM, 12.6 nM, 12.6 nM, 12.7 nM, 12.7 nM, 12.7 nM, 12.8 nM, 12.8 nM, 12.8 nM, 12.8 nM, 12.8 nM, 12.8 nM, 12.8 nM, 12.8 nM, 12.9 nM, 12.9 nM, 12.9 nM, 12.9 nM, 13.0 nM, 13.0 nM, 13.1 nM, 13.2 nM, 13.2 nM, 13.2 nM, 13.3 nM, 13.3 nM, 13.4 nM, 13.4 nM, 13.5 nM, 13.5 nM, 13.5 nM, 13.6 nM, 13.6 nM, 13.6 nM, 13.7 nM, 13.7 nM, 13.7 nM, 13.7 nM, 13.7 nM, 13.7 nM, 13.8 nM, 13.8 nM, 13.8 nM, 13.8 nM, 13.9 nM, 13.9 nM, 13.9 nM, 13.9 nM, 13.9 nM, 13.9 nM, 13.9 nM, 14.0 nM, 14.0 nM, 14.0 nM, 14.0 nM, 14.1 nM, 14.1 nM, 14.1 nM, 14.1 nM, 14.2 nM, 14.2 nM, 14.2 nM, 14.3 nM, 14.3 nM, 14.4 nM, 14.4 nM, 14.4 nM, 14.5 nM, 14.6 nM, 14.6 nM, 14.7 nM, 14.7 nM, 14.7 nM, 14.7 nM, 14.7 nM, 14.7 nM, 14.7 nM, 14.7 nM, 14.8 nM, 14.8 nM, 14.8 nM, 14.9 nM, 14.9 nM, 14.9 nM, 14.9 nM, 14.9 nM, 15.0 nM, 15.0 nM, 15.1 nM, 15.1 nM, 15.2 nM, 15.2 nM, 15.3 nM, 15.3 nM, 15.3 nM, 15.4 nM, 15.4 nM, 15.5 nM, 15.5 nM, 15.5 nM, 15.5 nM, 15.6 nM, 15.6 nM, 15.7 nM, 15.8 nM, 15.9 nM, 15.9 nM, 15.9 nM, 15.9 nM, 15.9 nM, 15.9 nM, 16.0 nM, 16.0 nM, 16.0 nM, 16.0 nM, 16.0 nM, 16.1 nM, 16.1 nM, 16.1 nM, 16.1 nM, 16.2 nM, 16.2 nM, 16.4 nM, 16.4 nM, 16.4 nM, 16.4 nM, 16.4 nM, 16.5 nM, 16.5 nM, 16.5 nM, 16.6 nM, 16.6 nM, 16.7 nM, 16.8 nM, 16.8 nM, 16.9 nM, 17.0 nM, 17.0 nM, 17.0 nM, 17.1 nM, 17.1 nM, 17.2 nM, 17.2 nM, 17.3 nM, 17.3 nM, 17.3 nM, 17.4 nM, 17.4 nM, 17.4 nM, 17.5 nM, 17.5 nM, 17.6 nM, 17.8 nM, 17.8 nM, 17.8 nM, 17.8 nM, 17.9 nM, 17.9 nM, 18.1 nM, 18.2 nM, 18.2 nM, 18.2 nM, 18.3 nM, 18.4 nM, 18.4 nM, 18.8 nM, 18.8 nM, 18.8 nM, 18.9 nM, 18.9 nM, 19.1 nM, 19.2 nM, 19.2 nM, 19.3 nM, 19.3 nM, 19.4 nM, 19.4 nM, 19.6 nM, 19.7 nM, 19.7 nM, 19.8 nM, 19.8 nM, 19.9 nM, 20.0 nM, 20.2 nM, 20.3 nM, 20.3 nM, 20.3 nM, 20.3 nM, 20.7 nM, 20.7 nM, 20.7 nM, 20.8 nM, 20.9 nM, 21.4 nM, 21.5 nM, 21.7 nM, 21.9 nM, 22.0 nM, 22.2 nM, 22.3 nM, 22.5 nM, 22.6 nM, 22.9 nM, 23.2 nM, 23.3 nM, 23.5 nM, 23.8 nM, 23.8 nM, 24.4 nM, 24.5 nM, 25.0 nM, 25.2 nM, 25.6 nM, 25.7 nM, 25.8 nM, 25.9 nM, 26.1 nM, 26.4 nM, 26.4 nM, 26.7 nM, 27.7 nM, 27.9 nM, 28.3 nM, 28.4 nM, 28.9 nM, 29.5 nM, 29.6 nM, 29.7 nM, 29.9 nM, 30.3 nM, 30.5 nM, 30.9 nM, 31.0 nM, 31.1 nM, 31.3 nM, 31.8 nM, 32.1 nM, 32.2 nM, 32.4 nM, 33.2 nM, 33.4 nM, 33.7 nM, 37.1 nM, 39.3 nM, 39.5 nM, 40.8 nM, 42.1 nM, 44.6 nM, 44.6 nM, 44.9 nM, 44.9 nM, 45.2 nM, 47.4 nM, 47.5 nM, 51.5 nM, 51.6 nM, 53.2 nM, 55.6 nM, 56.0 nM, 58.3 nM, 58.7 nM, 58.9 nM, 61.0 nM, 65.7 nM, 68.3 nM, 83.6 nM, 85.9 nM, 0.2 μM, 0.2 μM, 0.2 μM, 0.2 μM, 0.2 μM, 0.2 μM, 0.3 μM, 0.2 μM, 0.2 μM, 0.3 μM, 0.3 μM, 0.3 μM, 0.5 μM, 0.5 μM, 0.9 μM, 1.0 μM, 1.0 μM, 1.0 μM, 1.1 μM, 1.2 μM, 1.4 μM, 1.5 μM, 1.5 μM, 1.9 μM, 2.0 μM, 2.1 μM, 2.1 μM, 2.7 μM, 2.7 μM, 2.9 μM, 3.1 μM, 3.4 μM, 3.6 μM, 3.6 μM, 3.7 μM, 5.5 μM, 5.5 μM, 6.6 μM, 6.8 μM, 7.8 μM, 10.0 μM, 10.0 μM, 10.0 μM, 10.0 μM, 10.0 μM, 10.0 μM and 13.5 μM.

Determination of the utility of compounds having formula (I) as inhibitiors of anti-apoptotic Bcl-2 was also performed in 96-well microtiter plates. Representative examples were diluted in DMSO to concentrations between 10 pM and 10 pM and added to each well of the plate. A mixture totaling 125 μL per well of assay buffer (20 mM phosphate buffer, pH 7.4), 1 mM EDTA, 50 mM NaCl, 0.05% PF-68), 10 nM Bcl-2 protein (prepared as described in PNAS 2001, 98, 3012-3017), 1 nM fluorescein-labeled BAX peptide (prepared in-house), and the DMSO solution of the example was shaken for 2 minutes and placed in the LJL Analyst. Polarization was measured at 25° C. using a continuous Fluorescein lamp (excitation 485nm; emission 530nm).

$K_i$ values for the representative compounds having formula (I), calculated using Microsoft Excel, were <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, <1.0 nM, 1.1 nM, 1.1 nM, 1.1 nM, 1.1 nM, 1.1 nM, 1.1 nM, 1.1 nM, 1.1 nM, 1.2 nM, 1.2 nM, 1.3 nM, 1.3 nM, 1.3 nM, 1.3 nM, 1.3 nM, 1.4 nM, 1.5 nM, 1.5 nM, 1.5 nM, 1.5 nM, 1.6 nM, 1.6 nM, 1.7 nM, 1.7 nM, 1.7 nM, 1.7 nM, 1.8 nM, 1.8 nM, 1.8 nM, 1.8 nM, 1.9 nM, 2.0 nM, 2.0 nM, 2.2 nM, 2.3 nM, 2.4 nM, 2.5 nM, 2.5 nM, 2.6 nM, 2.6 nM, 2.9 nM, 3.0 nM, 3.1 nM, 3.5 nM, 3.7 nM, 3.9 nM, 4.0 nM, 4.0 nM, 4.0 nM, 4.2 nM, 4.4 nM, 4.5 nM, 4.6 nM, 4.7 nM, 5.8 nM, 5.9 nM, 6.0 nM, 6.2 nM, 6.5 nM; 6.7 nM, 7.0 nM, 7.2 nM, 7.7 nM, 7.8 nM, 8.0 nM, 8.1 nM, 8.4 nM, 9.4 nM, 10.4 nM, 10.4 nM, 13.1 nM, 13.6 nM, 13.8 nM, 15.2 nM, 15.7 nM, 15.9 nM, 16.2 nM, 16.9 nM, 19.7 nM, 22.5 nM, 24.4 nM, 25.4 nM, 26.9 nM, 28.9 nM, 29.1 nM, 32.4 nM, 33.0 nM, 36.5 nM, 38.0 nM, 39.7 nM, 41.7 nM, 42.9 nM, 45.7 nM, 53.9 nM, 56.2 nM, 56.6 nM, 62.3 nM, 71.6 nM, 72.9 nM, 80.4 nM, 82.4 nM, 83.4 nM, 0.09 µM, 0.09 µM, 1.0 µM, 0.12 µM, 0.12 µM, 0.15 µM, 0.30 µM, 0.001 µM, 0.001 µM, 0.001 µM, 0.001 µM, 0.001 µM, 0.002 µM, 0.002 µM, 0.003 µM, 0.685 µM, 1.011 µM, 0.004 µM, 0.054 µM, 1.051 µM, 10.0 µM, 0.011 µM, 0.046 µM and 0.014 µM.

These binding and inhibitory data demonstrate the utility of compounds having formula (I) as inhibitors of anti-apopotic BCl-$X_L$ protein and anti-apopotic Bcl-2.

It is expected that, because compounds having formula (I) bind to and inhibit the activity of BCl-$X_L$ and Bcl-2, they would also have utility as inhibitors of anti-apoptotic protein family members having close structural homology to BCl-$X_L$ and Bcl-2, such as, for example, anti-apoptotic Bcl-w protein.

Accordingly, compounds having formula (I) are expected to have utility in treatment of diseases during which anti-apopotic Bcl-$X_L$ protein, anti-apoptotic Bcl-2 protein, anti-apoptotic Bcl-w protein or a combination thereof, are expressed.

Diseases during which anti-apoptotic protein family members such as BCl-$X_L$ protein, Bcl-2 protein and Bcl-w protein are expressed include cancer and autoimmune disorders, wherein cancer includes, but is not limited to, bladder cancer, brain cancer, breast cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer and small cell lung cancer (Cancer Res., 2000, 60, 6101-10); autoimmune disorders include, but are not limited to, acquired immunodeficiency disease syndrome, autoimmune lymphoproliferative syndrome, hemolytic anemia, inflammatory diseases, and thrombocytopenia (Current Allergy and Asthma Reports 2003, 3:378-384; Br. J. Haematol. 2000 September; 110(3): 584-90; Blood 2000 Feb. 15; 95(4):1283-92; and New England Journal of Medicine 2004 September; 351 (14): 1409-1418).

A representative compound having formula (I), EXAMPLE 2, displayed therapeutic utility against human tumor cell lines derived from small cell lung carcinomas and lymphoid malignancies of both T-cell and B-cell origin.

EXAMPLE 2 also displayed therapeutic utility against acute lymphoblastoid leukemia, small cell lung cancer, prostate cancer, non-small cell lung cancer, and follicular lymphoma tumors (RS11380, DoHH2 and SuDHL-4) in xenograft models.

EXAMPLE 2 also demonstrated anti-tumor activity in two murine models (H146 and SCLC xenograft) from human-derived small cell lung cancer isolated from smokers and nonsmokers, defective for Rb/p53 gene function, and expresseive of moderately high levels of Bcl-2. In the H146 model, treatment with EXAMPLE 2 resulted in complete regression of an established tumor with, in some cases, tumor disappearance after prolonged therapy.

EXAMPLE 2 also prolonged survival in a systemic model of acute lymphoblastic leukemia and inhibited tumor growth in a model of follicular lymphoma (DOHH-2). Therapeutic utility was also observed in a prostate cancer model.

Without being limited by theory, the genetic link between Bcl-2 and cancer comes from the observation that t(14;18) chromosomal translocations in B-cell lymphomas lead to overexpression of the protein. Aberrant Bcl-2 and Bcl-$X_L$ expression is also seen in other lymphoid malignancies such as chronic lymphocytic leukemia and acute lymphocytic leukemia. EXAMPLE 2 exhibited significant activity in a CCRF-CEM T-cell acute lymphoblastoid leukemia model as well as in SuDHL4 and RS11380, two models of B-cell follicular lymphoma.

CCRF-CEM is a p53-mutant acute lympoblastoid leukemia line of T-cell origin used as an animal (mouse) model of systemic leukemia involving intravenous inoculation of tumor cells. If left untreated, the mice succumb to disease within about 34 days post inoculation, at which time extensive tumor infiltration of spleen, liver, and bone marrow has occurred. Administration of EXAMPLE 2 increased the average survival of the mice and showed significant decrease in average spleen weight relative to vehicle controls (indicative of a lower tumor burden in this organ). Subsequent histopahtological assessments revealed lower tumor infiltration in both the liver and spleen relative to controls.

The therapeutic effect of EXAMPLE 2 on other human tumor cell lines is shown in TABLE 1 for which the $EC_{50}$'s are the effective concentrations which cause a 50% reduction in cell viability.

TABLE 1

| Cell Line[a] | Tumor Type | $EC_{50}$ (uM)[b] |
|---|---|---|
| Calu-6 | Non-Small Cell Lung | 0.18 ± 0.07 (6) |
| NCI-H460 | Non-Small Cell Lung | 2.3 ± 1.5 (6) |
| NCI-H226 | Non-Small Cell Lung | 2.6 ± 1.1 (2) |
| NCI-H322M | Non-Small Cell Lung | 4.1 ± 0.8 (2) |
| A549/ATCC | Non-Small Cell Lung | 5.2 ± 0.2 (2) |
| HOP-62 | Non-Small Cell Lung | 6.3 ± 6.7 (2) |
| NCI-H23 | Non-Small Cell Lung | 7.4 ± 0.6 (2) |
| COLO 205 | Colorectal | 0.51 ± 0.07 (4) |
| HCT-15 | Colorectal | 0.60 ± 0.34 (4) |
| HCT-15 | Colorectal | >11 (2) |
| SW-620 | Colorectal | 0.69 ± 0.07 (2) |
| DLD-1 | Colorectal | 0.99 ± 0.45 (4) |
| HT-29 | Colorectal | 1.1 ± 1.1 (6) |
| KM12 | Colorectal | 1.7 ± 0.2 (2) |
| HCT-116 | Colorectal | 2.1 ± 1.8 (6) |
| MCF7 | Breast | 2.0 ± 0.8 (2) |
| MDA-MB-435 | Breast | 2.4 (1) |
| MDA-MB-436 | Breast | 3.9 ± 2.6 (2) |
| BT-549 | Breast | 6.5 ± 2.3 (2) |
| HS-578T | Breast | 7.2 ± 8.2 (2) |
| T47D | Breast | >10 (2) |
| NCI/ADR-RES | Breast | >10 (2) |
| U251 | CNS | 3.8 ± 2.0 (2) |
| SF-539 | CNS | 4.1 ± 0.6 (2) |
| SF-295 | CNS | 7.7 ± 2.3 (2) |
| SF-268 | CNS | 8.3 ± 0.4 (2) |
| U87MG | Glioma | 2.7 ± 1.8 (2) |
| D54MG | Glioma | 3.1 ± 2.5 (2) |
| LOX IMVI | Melanoma | 1.7 ± 0.4 (2) |
| MALME-3M | Melanoma | 1.9 ± 0.8 (2) |
| SK-MEL-5 | Melanoma | 3.7 ± 0.8 (2) |
| SK-MEL-28 | Melanoma | 9.3 ± 0.1 (2) |
| OVCAR-5 | Ovarian | 1.1 ± 0 (2) |
| IGROV-1 | Ovarian | 1.7 ± 0.6 (2) |
| OVCAR-3 | Ovarian | 1.9 ± 0.3 (2) |
| OVCAR-8 | Ovarian | 3.4 ± 0.8 (2) |
| SK-OV-3 | Ovarian | 5.6 ± 1.0 (2) |
| OVCAR-4 | Ovarian | 22 ± 3 (2) |
| MiaPaCa | Pancreas | 1.4 ± 0.6 (2) |
| PC3 | Prostate | 0.96 ± 0.38 (4) |
| DU-145 | Prostate | 8.2 ± 1.1 (2) |
| ACHN | Renal | 1 (1) |
| 786-0 | Renal | 2.9 ± 0.1 (2) |
| RXF-393 | Renal | 2.9 ± 0.4 (2) |
| SN12C | Renal | 3.2 ± 0.2 (2) |

[a]Serum-free conditions, 48 hour treatment.
[b]Mean ± SEM(n).

The therapeutic effect of paclitaxel on A549 human non-small cell lung carcinoma cells was about 4.4-fold more efficacious when administered with EXAMPLE 2. A similar increase (4.7-fold) in efficacy was demonstrated against PC-3 prostate carcinoma cells. The enantiomer of EXAMPLE 2 was less efficacious, indicating that the therapeutic effect of EXAMPLE 2 was the direct result of binding to anti-apoptotic Bcl-2 family proteins. The anti-tumor activity of EXAMPLE 2 was equivalent to slightly better than paclitaxel near the maximum tolerated dose in a small cell lung cancer xenograft tumor model and superior to cisplatin and etoposide. In a PC3 derived murine model of prostate cancer, EXAMPLE 2 exhibited about 40-50% inhibition of tumor growth rate.

Studies pertaining to the efficacy of EXAMPLE 2 in combination with etoposide, vincristine, modified CHOP, doxorubicin, rapamycin and Rituxin® demonstrated that EXAMPLE 2 synergistically enhanced efficacy of these cytotoxic agents during combination therapy. In particular, combinations comprising EXAMPLE 2 and rapamycin and EXAMPLE 2 and Rituxin® resulted in complete regression of a significant percentage of established DoHH2 follicular lymphoma flank tumors for a sustained period of time.

These data demonstrate the utility of compounds having formula (I) for treatment of diseases which are caused or exascerbated by expression of one or more than one of an anti-apoptotic protein family member. Furthermore, experiments with representative Bcl-$X_L$-selective compounds demonstrated synergistic therapeutic effects with multiple chemotherapeutic agents against cell lines representative of diverse tumor types. Accordingly, the compounds having formula (I) are expected to be useful as chemotherapeutic agents alone or in combination with additional therapeutic agents.

Compounds having formula (I) may be made by synthetic chemical processes, examples of which are shown herein. It is meant to be understood that the order of the steps in the processes may be varied, reagents, solvents, and reaction conditions may be substituted for those specifically mentioned, and vulnerable moieties may be protected and deprotected, as necessary, by NH, C(O)OH, OH, SH protecting groups.

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$); 9-BBN means 9-borabicyclo[3.3.1]nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis (diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-$BH_3$ means macroporus triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl-phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds having formula (1) may be converted to compounds having formula (2) by reacting the former, chlorosulfonic acid, and ammonia.

Compounds having formula (2) may be converted to compounds having formula (I) by reacting the former and compounds having formula $Z^1$—$CO_2H$ and a coupling agent, with or without a first base. Examples of coupling agents include EDCI, CDI, and PyBop. Examples of first bases include TEA, DIEA, DMAP, and mixtures thereof.

Compounds having formula (2) may be converted to compounds having formula (I) by reacting the former and compounds having formula $Z^1$—COCl and the first base.

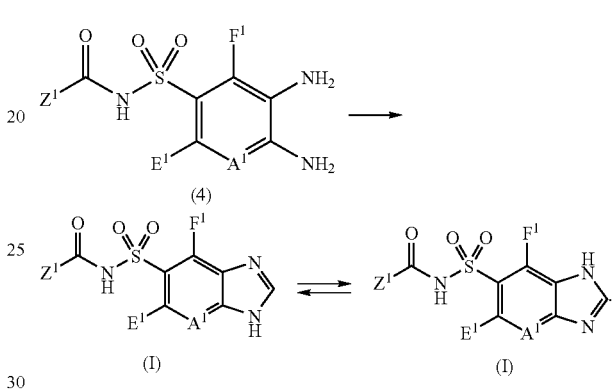

Compounds having formula (4) may be converted to compounds having formula (I), wherein $B^1$ and $Y^1$ together are imidazole, by reacting the former, sodium nitrite, hydrochloric acid, and acetic acid. Compounds having formula (I), wherein $B^1$ and $Y^1$ together are imidazole, may be reacted with a second base and the appropriate electrophile to provide compounds having formula (I), wherein $B^1$ and $Y^1$ together are substituted imidazole. Examples of second bases include sodium hydride, potassium hydride, lithium diisopropylamide and sodium bis(trimethylsilyl)amide.

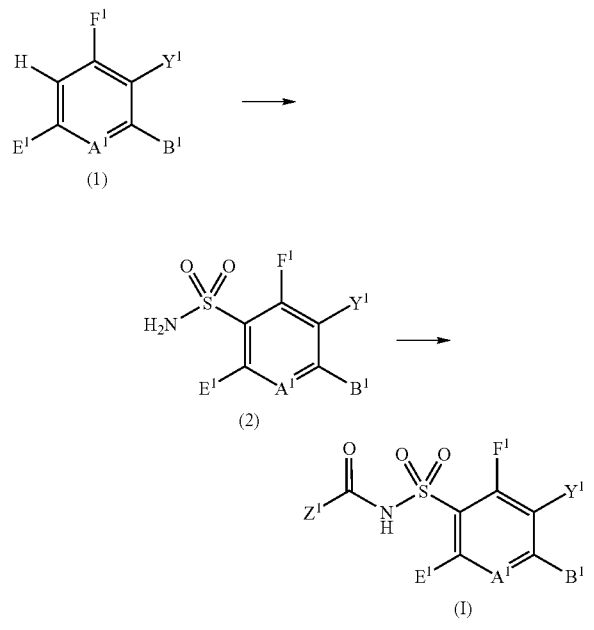

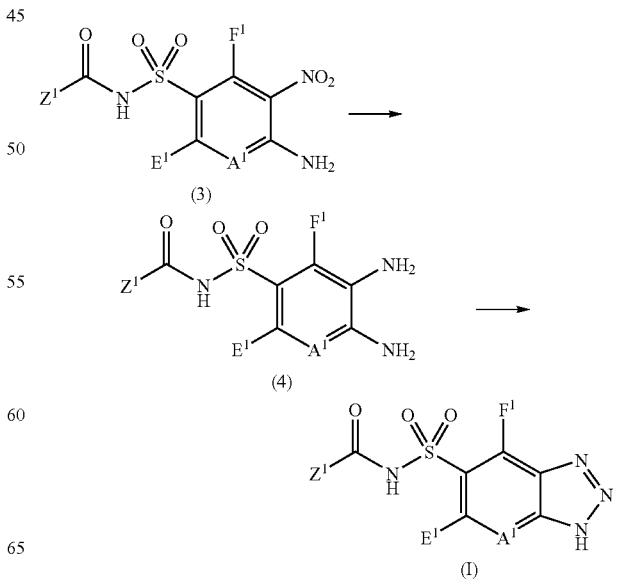

-continued

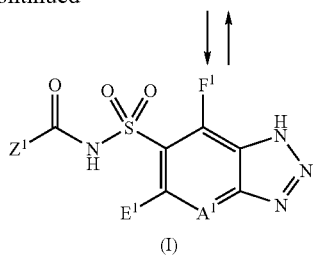

Compounds having formula (3), may be converted to compounds having formula (4) by reacting the former, hydrogen and a hydrogenation catalyst. Examples of hydrogenation catalysts include Pd on carbon, platinum on carbon, and Raney nickel.

Compounds having formula (4) may be converted to compounds having formula (I), wherein $B^1$ and $Y^1$ together are triazole, by reacting the former, sodium nitrite, hydrochloric acid, and acetic acid. Compounds having formula (I), wherein $B^1$ and $Y^1$ together are triazole, may be reacted with the second base and the appropriate electrophile to provide compounds having formula (I), wherein $B^1$ and $Y^1$ together are substituted triazole.

EXAMPLE 1A

A mixture of piperazine (129.2 g), ethyl-4-fluorobenzoate (84 g), and $K_2CO_3$ (103.65 g) in DMSO (200 mL) at 120° C. was stirred for 6 hours, poured into water, stirred for 30 minutes, and filtered.

EXAMPLE 1B

EXAMPLE 1A (200 mg) in dioxane at 40° C. (4 mL) was treated with 2-(bromomethyl)-1,1'-biphenyl (232 mg) and DIEA (165 mg) and concentrated. The concentrate was flash chromatographed on silica gel with 20% ethyl acetate/hexanes.

EXAMPLE 1C

EXAMPLE 1B (340 mg) in 3:1:1 THF/methanol/water (4 mL) at 25° C. was treated with LiOH.water (143 mg), stirred for 16 hours, and treated with 4M HCl (850 µL) and dichloromethane. The extract was dried ($Na_2SO_4$), filtered, and concentrated. The concentrate was flash chromatographed on silica gel with 20% methanol/dichloromethane.

EXAMPLE 1D

EXAMPLE 10 (112 mg) in dichloromethane (2.5 mL) at 25° C. was treated with 4-(((1R)-3-(dimethylamino)-1-((phenylsulfanyl)methyl)propyl)amino)-3-nitrobenzenesulfonamide, prepared as described in commonly-owned International Application No. PCT/US01/29432, published as WO 02/24636, (115 mg), EDAC.HCl (109 mg), and DMAP (49 mg), stirred for 16 hours, and concentrated. The concentrate was flash chromatographed on silica gel with 20% methanol/dichloromethane. $^1$H NMR (300 MHz, DMSO-$d_6$) δ 8.45 (d, 1H), 8.28 (d, 1H), 7.78 (dd, 1H), 7.72 (d, 2H), 7.54 (dd, 1H), 7.45-7.41 (m, 4H), 7.40-7.28 (m, 6H), 7.25 (td, 2H), 7.17 (tt, 1H), 6.88 (d, 1H), 6.78 (d, 2H), 4.10-4.01 (m, 1H), 3.41 (s, 2H), 3.33 (d, 2H), 3.14 (m, 4H), 2.82-2.62 (m, 2H), 2.44-2.35 (m, 10H), 2.09-1.91 (m, 2H).

EXAMPLE 1E

EXAMPLE 1C (112 mg) in dichloromethane (2.5 mL) at 25° C. was treated with EXAMPLE 1D (115 mg), EDAC.HCl (109 mg), and DMAP (49 mg), stirred for 16 hours, and concentrated. The concentrate was flash chromatographed on silica gel with 20% methanol/dichloromethane. $^1$H NMR (300 MHz, DMSO-$d_6$) δ 8.45 (d, 1H), 8.28 (d, 1H), 7.78 (dd, 1H), 7.72 (d, 2H), 7.54 (dd, 1H), 7.45-7.41 (m, 4H), 7.40-7.28 (m, 6H), 7.25 (td, 2H), 7.17 (tt, 1H), 6.88 (d, 1H), 6.78 (d, 2H), 4.10-4.01 (m, 1H), 3.41 (s, 2H), 3.33 (d, 2H), 3.14 (m, 4H), 2.82-2.62 (m, 2H), 2.44-2.35 (m, 10H), 2.09-1.91 (m, 2H).

EXAMPLE 2A

A mixture of EXAMPLE 1A (23.43 g), 2-bromobenzyl bromide (26.24 g), and DIEA (20.94 mL) in acetonitrile (200 mL) at 25° C. was stirred for 2 hours and filtered.

EXAMPLE 2B

A mixture of EXAMPLE 2A (13.83 g), 4-chlorophenylboronic acid (7.04 g), bis(triphenylphosphine)palladium dichloride (481 mg) and 2M sodium carbonate (22.5 mL) in 7:3:2 DME/water/ethanol (200 mL) at 90° C. was stirred for 4.5 hours and extracted with ethyl acetate. The extract was dried ($MgSO_4$), filtered, and concentrated. The concentrate was flash chromatographed on silica gel with 5%-40% ethyl acetate/hexanes.

EXAMPLE 2C

A mixture of EXAMPLE 2B (13 g) and lithium hydroxide hydrate (3.78 g) in dioxane (250 mL) and water (100 mL) at 95° C. was stirred for 16 hours and concentrated. The concentrate in water was heated at 80° C. and filtered. The filtrate was treated with 1M HCl (90 mL) and filtered.

EXAMPLE 2D

A mixture of EXAMPLE 2C (3.683 g), 4-(((1R)-3-(dimethylamino)-1-((phenylsulfanyl)methyl)propyl)amino)-3-nitrobenzenesulfonamide (3.53 g), EDAC.HCl (3.32 g) and DMAP (2.12 g) in dichloromethane (500 mL) at 25° C. was stirred for 8 hours, washed with saturated $NH_4Cl$ (330 mL), and dried ($MgSO_4$), filtered, and concentrated. The concentrate was flash chromatographed on silica gel with 1%, 2%, 5%, 10%, and 15% methanol/$NH_3$-saturated dichloromethane. $^1$H NMR (DMSO-$d_6$) δ 12.10 (br s, 1H), 11.18 (br s, 1H), 10.40 (br s, 1H), 8.54 (s, 1H), 8.29 (d, 1H), 8.10 (br s, 1H), 7.85 (d, 1H), 7.77 (d, 2H), 7.52 (d, 4H), 7.40-7.36 (m, 2H), 7.35-7.32 (m, 1H), 7.26-7.21 (m, 2H), 7.16-7.09 (m, 3H), 6.93 (d, 2H), 4.34 (br s, 2H), 4.35-4.23 (m, 1H), 3.88 (br s, 2H), 3.42-3.36 (m, 4H), 3.17-3.07 (m, 2H), 2.90-2.78 (m, 2H), 2.50 (s, 6H), 2.20-2.15 (m, 2H).

EXAMPLE 3A

This example was prepared by substituting 4-methoxyphenylboronic acid for 4-chlorophenylboronic acid in EXAMPLE 2B.

EXAMPLE 3B

This example was prepared by substituting EXAMPLE 3A for EXAMPLE 2B in EXAMPLE 2C.

EXAMPLE 3C

This example was prepared by substituting EXAMPLE 3B for EXAMPLE 2C in EXAMPLE 2D. $^1$H NMR (400 MHz, DMSO-$d_6$) δ 12.10 (br s, 1H), 9.9 (br s, 1H), 9.57 (s, 1H), 8.54 (d, 1H), 8.29 (d, 1H), 7.86 (dd, 1H), 7.77 (d, 2H), 7.72 (m, 1H), 7.50 (m, 2H), 7.33 (m, 1H), 7.29 (d, 2H), 7.23 (dd, 2H), 7.18 (d, 1H), 7.11 (m, 2H), 7.03 (d, 2H), 6.93 (d, 3H), 4.36 (br s, 2H), 4.18 (m, 1H), 3.80 (br s, 2H), 3.79 (s, 3H), 3.39 (d, 2H), 3.07 (m, 6H), 2.75 (s, 3H), 2.74 (s, 3H), 2.14 (q, 2H).

EXAMPLE 4A

This example was prepared by substituting 4-fluorophenylboronic acid for 4-chlorophenylboronic acid in EXAMPLE 2B.

EXAMPLE 4B

This example was prepared by substituting EXAMPLE 4A for EXAMPLE 2B in EXAMPLE 2C.

EXAMPLE 4C

This example was prepared by substituting EXAMPLE 4B for EXAMPLE 2C in EXAMPLE 2D. $^1$H NMR (400 MHz, DMSO-$d_6$) δ 12.10 (br s, 1H), 10.00 (br s, 1H), 9.65 (s, 1H), 8.54 (d, 1H), 8.29 (d, 1H), 7.86 (dd, 1H), 7.77 (d, 2H), 7.74 (m, 1H), 7.52 (m, 2H), 7.41 (m, 2H), 7.34 (m, 1H), 7.29 (t, 2H), 7.23 (dd, 2H), 7.18 (d, 1H), 7.12 (m, 3H), 6.93 (d, 2H), 4.29 (br s, 4H), 4.19 (m, 1H), 3.84 (br s, 2H), 3.39 (d, 2H), 3.13 (m, 4H), 2.92 (m, 2H), 2.74 (s, 6H), 2.15 (m, 2H).

EXAMPLE 5A

This example was prepared by substituting 4-(methylsulfanyl)phenylboronic acid for 4-chlorophenylboronic acid in EXAMPLE 2B.

EXAMPLE 5B

This example was prepared by substituting EXAMPLE 5A for EXAMPLE 2B in EXAMPLE 2C.

EXAMPLE 5C

This example was prepared by substituting EXAMPLE 5B for EXAMPLE 2C in EXAMPLE 2D. $^1$H NMR (400 MHz, DMSO-$d_6$) δ 12.10 (s, 1H), 9.9 (br s, 1H), 9.54 (s, 1H), 8.53 (d, 1H), 8.27 (d, 1H), 7.85 (dd, 1H), 7.76 (d, 2H), 7.72 (m, 1H), 7.51 (dd, 2H), 7.33 (d, 2H), 7.31 (m, 1H), 7.29 (d, 2H), 7.21 (d, 2H), 7.16 (d, 1H), 7.10 (m, 3H), 6.92 (d, 2H), 4.32 (br s, 2H), 4.17 (m, 1H), 3.85 (br s, 4H), 3.38 (d, 2H), 3.11 (m, 5H), 2.90 (br s, 1H), 2.73 (s, 6H), 2.49 (s, 3H), 2.14 (m, 2H).

EXAMPLE 6A

This example was prepared by substituting 1,1'-biphenyl-4-ylboronic acid for 4-chlorophenylboronic acid in EXAMPLE 2B.

EXAMPLE 6B

This example was prepared by substituting EXAMPLE 6A for EXAMPLE 2B in EXAMPLE 2C.

EXAMPLE 6C

This example was prepared by substituting EXAMPLE 6B for EXAMPLE 2C in EXAMPLE 2D. $^1$H NMR (400 MHz, DMSO-$d_6$) δ 12.10 (br s, 1H), 9.9 (br s, 1H), 9.56 (s, 1H), 8.54 (d, 1H), 8.28 (d, 1H), 7.86 (dd, 1H), 7.75 (m, 7H), 7.56 (m, 2H), 7.48 (m, 4H), 7.39 (m, 2H), 7.22 (dd, 2H), 7.17 (d, 1H), 7.11 (m, 3H), 6.93 (d, 2H), 4.42 (br s, 2H), 4.18 (m, 1H), 3.83 (br s, 2H), 3.39 (d, 2H), 3.25 (br s, 2H), 3.13 (m, 4H), 2.91 (m, 2H), 2.74 (s, 6H), 2.14 (m, 2H).

EXAMPLE 7A

This example was prepared by substituting 4-phenoxyphenylboronic acid for 4-chlorophenylboronic acid in EXAMPLE 2B.

EXAMPLE 7B

This example was prepared by substituting EXAMPLE 7A for EXAMPLE 2B in EXAMPLE 2C.

EXAMPLE 7C

This example was prepared by substituting EXAMPLE 7B for EXAMPLE 2C in EXAMPLE 2D. $^1$H NMR (400 MHz, DMSO-$d_6$) δ 12.09 (br s, 1H), 10.10 (br s, 1H), 9.64 (s, 1H), 8.55 (d, 1H), 8.29 (d, 1H), 7.87 (dd, 1H), 7.78 (d, 2H), 7.73 (m, 1H), 7.51 (m, 2H), 7.38 (m, 5H), 7.23 (m, 2H), 7.14 (m, 5H), 7.07 (d, 4H), 6.95 (d, 2H), 4.33 (br s, 2H), 4.20 (m, 1H), 3.86 (br s, 2H), 3.39 (d, 2H), 3.25 (br s, 2H), 3.12 (m, 4H), 2.92 (m, 2H), 2.74 (s, 6H), 2.15 (m, 2H).

EXAMPLE 8

This example was prepared by substituting 4-((1,1-dimethyl-2-(phenylsulfanyl)ethyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 1D. $^1$H NMR (500 MHz,
DMSO-$d_6$) δ 12.05 (br s, 1H), 9.8 (br s, 1H), 8.53 (s, 1H), 8.51 (d, 1H), 7.83 (dd, 1H), 7.79 (d, 2H), 7.72 (br s, 1H), 7.52 (br s, 2H), 7.47 (t, 2H), 7.41 (t, 1H), 7.36 (d, 2H), 7.35 (m, 2H), 7.26 (d, 2H), 7.01 (t, 2H), 6.93 (d, 2H), 6.92 (d, 1H), 4.32 (br s, 2H), 3.79 (br s, 2H), 3.49 (br s, 4H), 3,14 (br s, 2H), 2.80 (br s, 2H), 1.56 (s, 6H).

EXAMPLE 9

This example was prepared by substituting 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-$d_6$) δ 8.60 (d, 1H), 8.40 (d, 1H), 7.89 (dd, 1H), 7.79 (d, 2H), 7.64 (m, 7H), 7.62 (d, 1H), 7.31 (d, 2H), 7.30 (d, 1H), 7.24 (dd, 2H), 7.19 (dd, 2H), 6.94 (d, 2H), 4.24 (m, 1H), 3.71 (m, 4H), 3.55 (m, 2H), 3.41 (d, 2H), 3.31 (m, 4H), 2.80 (m, 4H), 2.48 (m, 4H),'2.16 (m, 1H), 2.06 (m, 1H).

EXAMPLE 10

This example was prepared by substituting 3-nitro-4-((2-(phenylsulfanyl)ethyl)amino)benzenesulfonamide), prepared as described in WO 02/24636, for 4-(((1R)-3-(dimethylamino)-1-((phenylsulfanyl)methyl)propyl)amino)-3-nitrobenzenesulfonamide in EXAMPLE 1D. $^1$H NMR (300 MHz, DMSO-$d_6$) δ 11.87 (br s, 1H), 8.74 (t, 1H), 8.58 (d, 1H), 7.89 (dd, 1H), 7.72 (d, 2H), 7.55 (m, 1H), 7.38 (m, 7H), 7.26 (m, 4H), 7.17 (m, 2H), 6.89 (d, 3H), 3.66 (m, 2H), 3.47 (m, 2H), 3.26 (m, 6H), 2.41 (m, 4H).

EXAMPLE 11

This example was prepared by substituting 3-nitro-4-((2-(phenylsulfanyl)ethyl)amino)benzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 11.93 (s, 1H), 8.66 (t, 1H), 8.56 (d, 1H), 7.89 (dd, 1H), 7.73 (d, 2H), 7.51 (d, 1H), 7.47 (m, 4H), 7.37 (m, 4H), 7.28 (t, 2H), 7.24 (m, 1H), 7.18 (t, 1H), 7.11 (d, 1H), 6.86 (d, 2H), 3.64 (q, 2H), 3.40 (s, 2H), 3.27 (q, 2H), 3.21 (m, 4H), 2.40 (m, 4H).

EXAMPLE 12

This example was prepared by substituting 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 12.07 (s, 1H), 9.98 (s, 2H), 8.55 (d, 1H), 8.30 (d, 1H), 7.87 (dd, 1H), 7.77 (d, 2H), 7.72 (br s, 1H), 7.52 (d, 4H), 7.40 (d, 2H), 7.34 (m, 1H), 7.23 (d, 2H), 7.18 (d, 1H), 7.15 (t, 2H), 7.10 (m, 1H), 6.93 (d, 2H), 4.25 (br s, 2H), 4.19 (m, 1H), 3.95 (br s, 5H), 3.63 (br s, 4H), 3.40 (m, 4H), 3.18 (m, 4H), 3.02 (br s, 3H), 2.18 (m, 2H).

EXAMPLE 13

This example was prepared by substituting 4-((1,1-dimethyl-2-(phenylsulfanyl)ethyl)amino)-3-nitrobenzene-sulfonamide, prepared as described in WO 02/24636, for 4-(((1R)-3-(dimethylamino)-1-((phenylsulfanyl)methyl) propyl)amino)-3-nitrobenzene-sulfonamide in EXAMPLE 2D. $^1$H NMR (500 MHz, DMSO-$d_6$) δ 12.06 (br s, 1H), 9.69 (br s, 1H),.8.53 (s, 1H), 8.51 (d, 1H), 7.83 (dd, 1H), 7.80 (d, 2H), 7.71 (br s, 1H), 7.52 (d, 4H), 7.40 (d, 2H), 7.37 (d, 1H), 7.33 (m, 1H), 7.26 (d, 2H), 7.01 (t, 2H), 6.93 (m, 3H), 4.33 (br s, 2H), 3.73 (br s, 4H), 3.12 (br s, 4H), 2.85 (br s, 2H), 1.56 (s, 6H).

EXAMPLE 14

This example was prepared by substituting 4-(((1R)-4-(dimethylamino)-1-((phenylsulfanyl)methyl)butyl)amino)-3-nitrobenzenesulfonamide, prepared as described in WO 02/24636, for 4-((('1R)-3-(dimethylamino)-1-((phenylsulfanyl)methyl)propyl)amino)-3-nitrobenzene-sulfonamide in EXAMPLE 2D. $^1$H NMR (400 MHz, DMSO-$d_6$) δ 12.07 (br s, 1H), 9.75 (br s, 1H), 9.26 (s, 1H), 8.54 (d, 1H), 8.29 (d, 1H), 7.87 (dd, 1H), 7.77 (d, 2H), 7.74 (m, 1H), 7.52 (d, 4H), 7.39 (d, 2H), 7.34 (m, 1H), 7.23 (m, 3H), 7.11 (m, 3H), 6.93 (d, 2H), 4.30 (br s, 2H), 4.14 (m, 1H), 3.73 (br s, 6H), 3.37 (m, 2H), 3.02 (m, 4H), 2.72 (t, 6H), 1.77 (m, 4H).

EXAMPLE 15

This example was prepared by substituting 4-(((1R)-5-(dimethylamino)-1-((phenylsulfanyl)methyl)pentyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 12.11 (s, 1H), 10.96 (m, 1H), 9.99 (m, 1H), 8.52 (d, 1H), 8.32 (d, 1H), 8.05 (m, 1H), 7.85 (dd, 1H), 7.75 (d, 2H), 7.53 (m, 4H), 7.36 (m, 4H), 7.23 (d, 2H), 7.11 (m, 3H), 6.93 (d, 2H), 4.35 (m, 1H), 4.12 (m, 1H), 3.92-3.87 (m, 2H), 3.53 (m, 8H), 3.27 (m, 2H), 2.94 (m 2H), 2.69 (s, 3H), 2.68 (s, 3H), 1.76 (m, 2H), 1.62 (m, 2H), 1.36 (m, 2H).

EXAMPLE 16

This example was prepared by substituting 4-(((1R)-3-(4-morpholinyl)-1-((phenylsulfanyl)methyl)propyl)amino)-3-nitrobenzenesulfonamide, prepared as described in WO 02/24636, and EXAMPLE 4B for 4-(((1R)-3-(dimethylamino)-1-((phenylsulfanyl)methyl)propyl)amino)-3-nitrobenzenesulfonamide and EXAMPLE 2C, respectively, in EXAMPLE 2D. $^1$H NMR (400 MHz, DMSO-$d_6$) δ 12.09 (br s, 1H), 9.93 (br s, 2H), 8.55 (d, 1H), 8.30 (d, 1H), 7.87 (dd, 1H), 7.77 (d, 2H), 7.73 (br s, 1H), 7.52 (m, 2H), 7.41 (m, 2H), 7.34 (m, 1H), 7.29 (t, 2H), 7.23 (m, 2H), 7.18 (d, 1H), 7.12 (m, 3H), 6.93 (d, 2H), 4.28 (br s, 2H), 4.21 (m, 1H), 3.95 (br s, 5H), 3.63 (br s, 4H), 3.40 (m, 4H), 3.19 (m, 4H), 3.02 (br s, 3H), 2.18 (m, 2H).

EXAMPLE 17A

A mixture of EXAMPLE 1A (703 mg), 2-bromo-5-fluorobenzaldehyde (914 mg), 2.47 mmol/g MP-BH$_3$CN (4.05 g), and acetic acid (340 μL) in 1:1 methanol/dichloromethane (30 mL) was shaken for 1 day and filtered. The filtrate was concentrated, and the concentrate was flash chromatographed on silica gel with 5-50% ethyl acetate/hexanes.

EXAMPLE 17B

This example was prepared by substituting EXAMPLE 17A for EXAMPLE 2A in EXAMPLE 2B.

EXAMPLE 17C

This example was prepared by substituting EXAMPLE 17B for EXAMPLE 2B in EXAMPLE 2C.

EXAMPLE 17D

This example was prepared by substituting EXAMPLE 17C for EXAMPLE 2C in EXAMPLE 2D. $^1$H NMR (400 MHz, DMSO-$d_6$) δ 12.09 (br s, 1H), 9.61 (br s, 1H), 8.55 (d, 1H), 8.29 (d, 1H), 7.86 (dd, 1H), 7.77 (d, 2H), 7.60 (bd, 1H), 7.52 (d, 2H), 7.37 (m, 4H), 7.23 (m, 2H), 7.18 (d, 1H), 7.12 (m, 3H), 6.94 (d, 2H), 4.18 (m, 3H), 3.80 (br s, 4H), 3.39 (d, 2H), 3.14 (m, 3H), 2.89 (s, 3H), 2.75 (s, 6H), 2.15 (m, 2H).

EXAMPLE 18A 3-(R)-((carbobenzyloxy)amino)-γ-butyrolactone, prepared as described in J. Am. Chem. Soc. 1986, 108, 4943-4952, (7.72 g) in THF (100 mL) at 25° C. was saturated with dimethylamine, stirred for 16 hours, and concentrated. The concentrate was filtered through a silica gel plug with 50% acetone/hexanes.

EXAMPLE 18B

EXAMPLE 18A (8.45 g) in toluene (15 mL) at 25° C. was treated with tributylphosphine (9.76 mL) and diphenyldisulfide (7.3 g), heated to 80° C. for 16 hours and concentrated. The concentrate was flash chromatographed on silica gel with 0-50% ethyl acetate/hexanes.

EXAMPLE 18C

EXAMPLE 18B (10.60 g) in 30% HBr/acetic acid (50 mL) at 25° C. was stirred for 18 hours, concentrated, treated with water (200 mL) and 5% HCl (100 mL), washed with diethyl ether, adjusted to pH 8-9 with $Na_2CO_3$, and extracted with dichloromethane. The extract was dried ($MgSO_4$), filtered, and concentrated.

EXAMPLE 18D 1-fluoro-2-(trifluoromethyl)benzene (15 g) in chlorosulfonic acid (50 mL) and 1,2-dichloroethane (50 mL) at 70° C. was stirred to for 2 hours, and concentrated. The concentrate in THF (200 mL) at to 0° C. was treated with concentrated ammonium hydroxide (20 mL), stirred for 10 minutes, and poured into ethyl diethyl ether (500 mL). The extract was washed with brine and dried ($Na_2SO_4$), filtered, and concentrated. The concentrate was flash chromatographed on silica gel with 30% ethyl acetate/hexanes.

EXAMPLE 18E

A mixture of EXAMPLE 18D (1.7 g) and EXAMPLE 18C (1.67 g) in DMSO (17 mL) was treated with DIEA (1.22 mL), heated at 110° C. for 24 hours, poured into ethyl acetate (400 mL), washed with water and brine, and dried ($Na_2SO_4$), filtered, and concentrated. The concentrate was flash chromatographed on silica gel with 50% ethyl acetate/hexanes.

EXAMPLE 18F

EXAMPLE 18E (2.5 g) in THF (20 mL) at 25° C. was treated with 1M borane.THF (22 mL), stirred for 24 hours, treated with methanol and concentrated. The concentrate in methanol (20 mL) was treated with HCl-saturated methanol (75 mL), stirred at reflux for 24 hours, concentrated, poured into 1M NaOH, and extracted with ethyl acetate. The extract was washed with brine and dried ($Na_2SO_4$), filtered, and concentrated. The concentrate was flash chromatographed on silica gel with 0-5% TEA/ethyl acetate.

EXAMPLE 18G

This example was prepared by substituting EXAMPLE 18F for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 7.94 (d, 1H), 7.80 (dd, 1H), 7.73 (d, 2H), 7.53 (dd, 1H), 7.47 (AB q, 4H), 7.41-7.33 (m, 5H), 7.36 (dd, 2H), 7.32 (d, 2H), 7.27 (m, 4H), 7.19 (dd, 1H), 6.89 (d, 2H), 6.87 (d, 1H), 5.94 (d, 1H), 3.94 (m, 1H), 3.42 (m, 2H), 3.26 (m, 4H), 3.10 (m, 1H), 2.96 (m, 1H), 2.67 (s, 6H), 2.41 (m, 4H), 2.13 (m, 2H).

EXAMPLE 19A 3-(R)-((carbobenzyloxy)amino)-γ-butyrolactone, prepared as described in J. Am. Chem. Soc. 1986, 108, 4943-4952, (62 g) in dioxane (700 mL) was treated with morpholine (46 mL), heated to 65° C. for 24 hours, cooled and concentrated. The concentrate was flash chromatographed on silica gel with 10% methanol in ethyl acetate.

EXAMPLE 19B

This example was prepared by substituting EXAMPLE 19A for EXAMPLE 18A in EXAMPLE 18B.

EXAMPLE 19C

This example was prepared by substituting EXAMPLE 19B for EXAMPLE 18B in EXAMPLE 18C.

EXAMPLE 19D

EXAMPLE 19C (45.4 g) in THF (500 mL) at 55° C. was treated with 1M borane.THF in THF (650 mL), stirred for 24 hours, cooled to 0° C., treated with methanol, poured into methanol, and concentrated. The concentrate in methanol (400 mL) was treated with saturated HCl in methanol (800 mL), refluxed for 24 hours, concentrated, poured into 2M NaOH, and extracted with ethyl acetate. The extract was washed with 1M NaOH and brine and dried ($Na_2SO_4$), filtered, and concentrated. The concentrate was flash chromatographed on silica gel with ethyl acetate, 10% methanol/ethyl acetate, and 10% methanol/10% acetonitrile/5% TEA/75% ethyl acetate.

EXAMPLE 19E

This example was prepared by substituting EXAMPLE 19D for EXAMPLE 18C in EXAMPLE 18E.

EXAMPLE 19F

This example was prepared by substituting EXAMPLE 19E for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 7.92 (d, 1H), 7.76 (dd, 1H), 7.72 (d, 2H), 7.50 (dd, 1H), 7.47 (s, 4H), 7.41-7.33 (m, 5H), 7.30 (d, 2H), 7.24 (dd, 1H), 7.19 (dd, 1H), 6.88 (d, 2H), 6.79 (d, 1H), 5.98 (d, 1H), 3.94 (m, 1H), 3.51 (m, 4H), 3.31-3.23 (m, 8H), 2.43 (m, 2H), 2.39 (m, 4H), 2.28 (m, 2H), 1.96 (m, 1H), 1.83 (m, 1H).

EXAMPLE 20A 3-(R)-((carbobenzyloxy)amino)-γ-butyrolactone, prepared as described in J. Am. Chem. Soc. 1986, 108, 4943-4952, (1.8 g) in THF (20 mL) at 25° C. was treated with pyrrolidine (3 mL), stirred for 3 days, and concentrated with a toluene azeotrope.

EXAMPLE 20B

This example was prepared by substituting EXAMPLE 20A for EXAMPLE 18A in EXAMPLE 18B.

EXAMPLE 20C

This example was prepared by substituting EXAMPLE 20B for EXAMPLE 18B in EXAMPLE 18C.

EXAMPLE 20D

EXAMPLE 20C (1.8 g) in DMF (30 mL) at 25° C. was treated with TEA (950 μL) and 4-fluoro-3-nitrobenzenesulfonamide, prepared as described in WO 02/24636, (1.5 g), heated at 60° C. for 150 minutes, poured into water, and extracted with ethyl acetate. The extract was washed with water and brine and dried ($Na_2SO_4$), filtered, concentrated. The concentrate was flash chromatographed on silica gel with 50% ethyl acetate/hexanes.

EXAMPLE 20E

EXAMPLE 20D (2.35 g) in THF (30 mL) at 25° C. was treated with 1M borane.THF in THF (20 mL), stirred for 24 hours, cooled to 0° C., treated with methanol, poured into 6M HCl, stirred for 24 hours, cooled to 0° C., brought to pH 12 with KOH, and extracted with ethyl acetate. The extract was washed with brine and dried ($Na_2SO_4$), filtered, and concentrated. The concentrate was flash chromatographed on silica gel with ethyl acetate, 10% methanol/ethyl acetate, and 10% methanol/5% TEA/85% ethyl acetate.

EXAMPLE 20F

This example was prepared by substituting EXAMPLE 20E for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 12.06 (br s, 1H), 9.73 (br s, 2H), 8.54 (d, $^1$H), 8.29 (d, 1H), 7.87 (dd, 1H), 7.77 (d, 2H), 7.74 (m, 1H), 7.52 (m, 4H), 7.39 (d, 2H), 7.34 (m, 1H), 7.23 (m, 2H), 7.18 (d, 1H), 7.12 (m, 3H), 6.92 (d, 2H), 4.22 (m, 3H), 3.86 (s, 4H), 3.51 (m, 2H), 3.38 (m, 2H), 3.21 (m, 4H), 2.94 (m, 4H), 2.15 (m, 2H), 2.00 (m, 2H), 1.84 (m, 2H).

EXAMPLE 21

2-Amino-2-methyl-1-propanol (5 g) in dichloromethane (200 mL) at 0° C. was treated with di-tert-butyldicarbonate (3.5 g) stirred for 8 hours at 25° C., washed with water, 5% aqueous citric acid, saturated $NaHCO_3$, and brine, and dried ($MgSO_4$), filtered, and concentrated.

EXAMPLE 21B

A mixture of EXAMPLE 21A (980 mg), 2-mercaptothiazole (610 mg), and triphenylphosphine (1.5 g) in THF (12 mL) at 25° C. was stirred for 20 minutes, cooled to 0° C., treated with diisopropylazodicarboxylate (1.1 mL) in THF (6 mL), stirred at 25° C. for 3 days, treated with ethyl acetate, washed with water and brine, and dried ($MgSO_4$), filtered, and concentrated. The concentrate was flash chromatographed on silica gel with 2%-10% ethyl acetate/hexanes.

EXAMPLE 21C

EXAMPLE 21B (410 mg) in diethyl ether (5 mL) at 25° C. was treated with 4M HCl in 1,4-dioxane (5 mL), stirred for 2.5 hours, and filtered.

EXAMPLE 21D

A mixture of EXAMPLE 21C (300 mg) and 4-fluoro-3-nitrobenzenesulfonamide (300 mg), and DIEA (690 μL) in DMSO (2 mL) at 25° C. was stirred for 18 hours, cooled to 15° C., treated with water (25 mL), acidified with 1M HCl, cooled to 0° C., stirred for 1 hour, and filtered.

EXAMPLE 21E

This example was prepared by substituting EXAMPLE 21D for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 8.59 (d, 1H), 8.49, (s, 1H), 7.90 (dd, 1H), 7.80 (d, 2H), 7.77 (s, 1H), 7.52 (d, 3H), 7.48 (d, 2H), 7.45 (dd, 2H), 7.40 (d, 2H), 7.40 (d, 1H), 6.93 (d, 2H), 4.24 (s, 2H), 3.86, (s, 2H), 3.35 (m, 6H), 2.85 (s, 2H), 1.58 (s, 6H).

EXAMPLE 22A

A mixture of 2-mercaptothiazole (4.6 g) and tetra-n-butylammonium persulfate, prepared as described in Tetrahedron Lett. 1993, 34, 3581-3584, (14.7 g) in water (460 mL) at 25° C. was stirred for 18 hours and extracted with diethyl ether. The extract was washed with brine and dried (MgSO4), filtered, and concentrated.

EXAMPLE 22B

A mixture of EXAMPLE 18A (720 mg) and EXAMPLE 22A (770 mg) in toluene (9.1 mL) at 85° C. was treated with tributylphosphine (830 μL), heated to 85° C., stirred for 5.5 hours, treated with ethyl acetate, washed with water and brine, and dried ($MgSO_4$), filtered, and concentrated. The concentrate was flash chromatographed on silica gel with 30%-66% ethyl acetate/hexanes.

EXAMPLE 22C

This example was prepared by substituting EXAMPLE 22B for EXAMPLE 18B in EXAMPLE 18C.

EXAMPLE 22D

This example was prepared by substituting EXAMPLE 22C for EXAMPLE 19C in EXAMPLE 19D.

EXAMPLE 22E

This example was prepared by substituting EXAMPLE 22D for EXAMPLE 21C in EXAMPLE 21D.

EXAMPLE 22F

This example was prepared by substituting EXAMPLE 22E for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-d$_6$) δ 8.50 (d, 1H), 8.22 (d, 1H), 7.90 (dd, 1H), 7.72 (dd, 2H), 7.61 (d, 1H), 7.51 (m, 2H), 7.47 (s, 3H), 7.37 (m, 2H), 7.23, (m, 2H), 6.79 (d, 2H), 4.28 (m, 1H), 3.60 (m, 2H), 3.39 (s, 2H), 3.14 (m, 4H), 3.00 (m, 2H), 2.62 (s, 6H), 2.40 (m, 4H), 2.10 (m, 2H).

EXAMPLE 23A

This example was prepared by substituting 2-thienyldisulfide and THF for EXAMPLE 22A and toluene, respectively, in EXAMPLE 22B.

EXAMPLE 23B

This example was prepared by substituting EXAMPLE 23A for EXAMPLE 18B in EXAMPLE 18C.

EXAMPLE 23C

This example was prepared by substituting EXAMPLE 23B for EXAMPLE 19C in EXAMPLE 19D.

EXAMPLE 23D

This example was prepared by substituting EXAMPLE 23C for EXAMPLE 21C in EXAMPLE 21D.

EXAMPLE 23E

This example was prepared by substituting EXAMPLE 23D for 4-(((1R)-3-(dimethylamino)-3-1-((phenylsulfanyl)methyl)propyl)amino)-3-nitrobenzenesulfonamide in EXAMPLE 2D. $^1$H NMR (500 MHz, DMSO-d$_6$) δ 8.50 (d, 1H), 8.22 (d, 1H), 7.90 (dd, 1H), 7.82, (dd, 1H), 7.72 (d, 2H), 7.62 (dd, 1H), 7.51 (m, 1H), 7.47 (s, 3H), 7.37 (m, 2H), 7.25 (dd, 1H), 7.14 (dd, 1H), 7.02 (dd, 1H), 6.80 (m, 3H), 3.99 (m, 1H), 3.31 (m, 2H), 3.18 (m, 6H), 2.95 (m, 3H), 2.59 (s, 6H), 2.40 (t, 3H), 2.11 (m, 1H), 2.02 (m, 1H).

EXAMPLE 24A

N-tert-butoxycarbonyl-L-serine methyl ester (30 g) in dichloromethane (300 mL) at 0° C. was treated with DIEA (59.7 mL) and methanesulfonylchloride (11.65 mL), stirred for 20 minutes, treated with thiophenol (15.5 mL), stirred at 25° C. for 24 hours, and concentrated. The concentrate was flash chromatographed on silica gel with 10-30% ethyl acetate/hexanes.

EXAMPLE 24B

EXAMPLE 24A (8.35 g) in dichloromethane (75 mL) was treated with 1M DIBAL in dichloromethane (94 mL) stirred for 2 hours, treated with methanol, poured into saturated NaH$_2$PO$_4$ (300 mL), stirred for 30 minutes, and extracted with ethyl acetate. The extract was washed with brine and dried (Na$_2$SO$_4$), filtered, and concentrated. The concentrate was flash chromatographed on silica gel with 50% ethyl acetate/hexanes.

EXAMPLE 24C

60% Oily NaH (480 mg) in dioxane (30 mL) at 25° C. was treated with EXAMPLE 24B (1.7 g) in dioxane (10 mL), stirred for 10 minutes, treated with N,N-dimethylchloroacetamide (1.23 mL), heated at 70° C. for 24 hours, poured into water, and extracted with ethyl acetate. The extract was washed with brine and dried (Na$_2$SO$_4$), filtered, and concentrated. The concentrate was flash chromatographed on silica gel with 50% ethyl acetate/hexanes.

EXAMPLE 24D

EXAMPLE 24C (1.65 g) in THF (10 mL) at 25° C. was treated with 1M borane.THF (20 mL), stirred for 24 hours, treated with 5M HCl (300 mL) and THF (300 mL), stirred for 2 days, cooled to 0° C., adjusted to pH 12 with KOH and extracted with ethyl acetate. The extract was washed with brine and dried (Na$_2$SO$_4$), filtered, and concentrated. The concentrate in DMF (30 mL) was treated with 4-fluoro-3-nitrobenzenesulfonamide (1 g) and TEA (627 µL), heated at 55° C. for 90 minutes, poured into water, and extracted with ethyl acetate. The extract was washed with water and brine and dried (Na$_2$SO$_4$), filtered, and concentrated. The concentrate was flash chromatographed on silica gel with ethyl acetate, 10% methanol/ethyl acetate, and 10% methanol/10% acetonitrile/80% ethyl acetate.

EXAMPLE 24E

This example was prepared by substituting EXAMPLE 24D for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-d$_6$) δ 12.12 (s, 1H), 10.90 (m, 1H), 9.90 (m, 1H), 8.56 (d, 1H), 8.52 (d, 1H), 8.04 (m, 1H), 7.86 (dd, 1H), 7.76 (d, 2H), 7.53 (m, 4H), 7.13-7.39 (m, 9H), 6.93 (d, 2H), 4.35 (m, 1H), 3.87-3.79 (m, 2H), 3.74 (m, 4H), 3.47 (m, 8H), 3.23 (m, 4H), 2.75 (m, 6H).

EXAMPLE 25A

Diethylamine (4.15 mL) in THF (150 mL) at −78° C. was treated with 2.5M n-butyllithium in hexanes (15.4 mL), stirred for 5 minutes at 0° C., cooled to −78° C., treated with (2R,4S)-3-((benzyloxy)carbonyl)-4-methyl-2-phenyl-1,3-oxazolidin-5-one, prepared as described in Helv. Chim. Acta 1991, 74, 800, (10 g) in THF (40 mL), stirred for 20 minutes, treated with allyl bromide (4.29 mL), stirred for 1 hour, stirred at 25° C. for 18 hours, poured into pH 7 buffer, and extracted with diethyl ether. The extract was washed with brine and dried (Na$_2$SO$_4$), filtered, and concentrated. The concentrate was flash chromatographed on silica gel with 20% ethyl acetate/hexanes.

EXAMPLE 25B

EXAMPLE 25A (8.18 g) in methanol (200 mL) and water (20 mL) at 25° C. was treated with LiOH.water (1.95 g), stirred for 30 minutes, poured into saturated NaH$_2$PO$_4$ (200 mL), and extracted with ethyl acetate. The extract was washed with 1M NaOH and brine and dried (Na$_2$SO$_4$), filtered, and concentrated. The base wash was acidified with 12M HCl and extracted with ethyl acetate. The extract was concentrated, and the concentrate in 1:1 ethyl acetate/methanol (50 mL) at 25° C. was treated with 2M (trimethylsilyl)diazomethane in THF (5 mL), stirred for 10 minutes, and concentrated. The concentrates were combined and flash chromatographed on silica gel with 10% ethyl acetate/hexanes.

EXAMPLE 25C

EXAMPLE 25B (5.03 g) in THF (75 mL) at 25° C. was treated with 1M LiBH(CH$_2$CH$_3$)$_3$ in THF (38 mL), stirred for 2 hours, treated with methanol (30 mL), poured into water, and extracted with ethyl acetate. The extract was washed with brine and dried (Na$_2$SO$_4$), filtered, and concentrated. The concentrate was flash chromatographed on silica gel with 30% ethyl acetate/hexanes.

EXAMPLE 25D

This example was prepared by substituting EXAMPLE 25C for EXAMPLE 18A in EXAMPLE 18B.

EXAMPLE 25E

EXAMPLE 25D (2.9 g) in diethyl ether (45 mL) and tert-butanol (45 mL) at 25° C. was treated with AD-mix-β (12.74 g), stirred for 18 hours, poured into saturated Na$_2$CO$_3$, and extracted with ethyl acetate. The extract was washed with brine and dried (Na$_2$SO$_4$), filtered, and concentrated. The concentrate was flash chromatographed on silica gel with 20-50% ethyl acetate/hexanes. The product in THF (30 mL) and water (30 mL) at 25° C. was treated with NaIO$_4$ (2.75 g), stirred for 20 minutes, poured into water, and extracted with ethyl acetate. The extract was washed with brine and dried (Na$_2$SO$_4$), filtered, and concentrated.

EXAMPLE 25F

EXAMPLE 25E (1.92 g) in dichloromethane (30 mL) at 25° C. was treated with dimethylamine hydrochloride (684 mg), sodium triacetoxyborohydride (1.9 g), and TEA (1.56 mL), stirred for 24 hours, treated with methanol and water, and concentrated. The concentrate was flash chromatographed on silica gel with 50% ethyl acetate/hexanes.

EXAMPLE 25G

This example was prepared by substituting EXAMPLE 25F for EXAMPLE 18B in EXAMPLE 18C.

EXAMPLE 25H

A mixture of EXAMPLE 25G (600 mg) and 4-fluoro-3-nitrobenzene-sulfonamide (554 mg) in DMSO (7 mL) at 25° C. was treated with TEA (351 μL), heated at 60° C. for 90 minutes, poured into water (30 mL), and extracted with ethyl acetate. The extract was washed with water and brine and dried (Na$_2$SO$_4$), filtered, and concentrated. The concentrate was flash chromatographed on silica gel with 0-10% methanol/ethyl acetate.

EXAMPLE 25I

This example was prepared by substituting EXAMPLE 25H for 4-(((1R)-3-(dimethylamino)-1-((phenylsulfanyl)methyl)-propyl)amino)-3-nitrobenzenesulfonamide in EXAMPLE 2D. $^1$H NMR (500 MHz, DMSO-d$_6$) δ 12.14 (s, 1H), 10.90 (m, 1H), 10.22 (m, 1H), 8.50 (d, 1H), 8.32 (s,1H), 8.04 (m, 1H), 7.83 (m, 3H), 7.54 (m, 4H), 7.36 (m, 4H), 7.23 (d, 2H), 6.98-6.85 (m, 5H), 4.35 (m, 2H), 3.92-3.87 (m, 2H), 3.74 (m, 2H), 3.48 (m, 8H), 3.23 (m, 2H), 2.70 (m, 6H), 1.56 (s, 3H).

EXAMPLE 26A

This example was prepared by substituting methylamine for dimethylamine in EXAMPLE 18A.

EXAMPLE 26B

This example was prepared by substituting EXAMPLE 26A for EXAMPLE 18A in EXAMPLE 18B.

EXAMPLE 26C

This example was prepared by substituting EXAMPLE 26B for EXAMPLE 18B in EXAMPLE 18C.

EXAMPLE 26D

This example was prepared by substituting EXAMPLE 26C for EXAMPLE 21C in EXAMPLE 21D.

EXAMPLE 26E

This example was prepared by substituting EXAMPLE 26D for EXAMPLE 18E in EXAMPLE 18F.

EXAMPLE 26F

EXAMPLE 26E (1.12 g) in THF (7 mL) and acetonitrile (7 mL) at 25° C. was treated with di-tert-butyldicarbonate (572 mg) and TEA (276 mg), stirred for 16 hours, and concentrated. The concentrate was flash chromatographed on silica gel with 50% ethyl acetate/hexanes.

EXAMPLE 26G

This example was prepared by substituting EXAMPLE 26F for 4-(((1R)-3-(dimethylamino)-1-((phenylsulfanyl)methyl)-propyl)amino)-3-nitrobenzenesulfonamide in EXAMPLE 2D.

EXAMPLE 26H

EXAMPLE 26G was flash chromatographed on silica gel with dichloromethane, 1:1 dichloromethane/ethyl acetate, and 10% (7M NH$_3$ in methanol) in methanol. A mixture of the free base in dichloromethane at 25° C. was treated with 1:1 2M HCl/diethyl ether (10 mL), stirred for 18 hours and concentrated. $^1$H NMR (500 MHz, DMSO-d$_6$) δ 12.11 (s, 1H), 10.94 (m, 1H), 8.71 (m, 1H), 8.53 (d, 1H), 8.28 (d, 1H), 8.05 (m, 1H), 7.86 (dd, 1H), 7.77 (d, 2H), 7.53 (m, 4H), 7.37 (m, 4H), 7.23 (m, 2H), 7.11 (m, 3H), 6.93 (d, 2H), 4.34 (m, 1H), 4.28 (m, 1H), 4.12 (m, 1H), 3.92-3.87 (m, 2H), 3.39 (m, 8H), 3.27 (m, 3H), 2.94 (m, 3H), 2.11 (m, 2H).

EXAMPLE 27A

A mixture of Fmoc-D-Asp(O-tert-butyl) —OH (10.25 g) and
NMM (2.8 mL) in DME (30 mL) at −15° C. was treated with isobutyl chloroformate (4.1 mL), stirred for 10 minutes, and filtered. The filtrate was cooled to 0° C., treated with NaBH$_4$ (2.84 g) in water (15 mL), stirred for 5 minutes, treated with water, stirred at 25° C. for 3 hours, and filtered.

EXAMPLE 27B

A mixture of EXAMPLE 27A (9.5 g), diphenyl disulfide (7.86 g) and tributylphosphine (7.28 g) in toluene (200 mL) at 80° C. was stirred for 5 hours and concentrated. The concentrate was flash chromatographed on silica gel with 5% to 20% ethyl acetate/hexanes.

EXAMPLE 27C

This example was prepared by substituting EXAMPLE 27B for EXAMPLE 21C in EXAMPLE 21D.

EXAMPLE 27D

This example was prepared by substituting EXAMPLE 27C for 4-(((1R)-3-(dimethylamino)-1-((phenylsulfanyl)methyl)-propyl)amino)-3-nitrobenzenesulfonamide in EXAMPLE 2D.

EXAMPLE 27E

EXAMPLE 27D (1 g) in dichloromethane (5 mL) at 25° C. was treated with TFA (5 mL), stirred for 3 hours, and concentrated. $^1$H NMR (500 MHz, DMSO-$d_6$) δ 8.57 (d, 1H), 8.52 (d, 1H), 7.84 (dd, 1H), 7.75 (d, 2H), 7.55-7.35 (m, 7H), 7.27-7.11 (m, 6H), 6.91 (d, 2H), 4.39 (m, 1H), 3.39 (2, 2H), 3.31 (s, 8H), 3.26 (m, 2H), 2.81 (d, 2H).

EXAMPLE 28

A mixture of EXAMPLE 27E (160 mg) and N-methylmorpholine (27 μL) in DMF (1 mL) at 25° C. was treated with HATU (92 mg) and isopropylamine (50 μL), stirred for 5 hours, treated with ethyl acetate (200 mL), washed with 1% HCl, saturated NaHCO$_3$, water, and brine, and dried (Na$_2$SO$_4$), filtered, and concentrated. The concentrate was flash chromatographed on silica gel with dichloromethane, (1:1) dichloromethane/ethyl acetate, and 5% methanol/dichloromethane. $^1$H NMR (500 MHz, DMSO-$d_6$) δ 8.73 (d, 1H), 8.52 (d, 1H), 7.93 (d, 1H), 7.83 (dd, 1H), 7.76 (d, 2H), 7.52 (m, 2H), 7.38 (m, 3H), 7.23' (m, 2H), 7.18-7.10 (m, 6H), 6.92 (d, 2H), 4.39 (m, 1H), 3.75 (m, 1H), 3.40 (m, 10H), 3.34 (m, 2H), 2.54 (m, 2H), 0.98 (d, 3H), 0.91 (d, 3H).

EXAMPLE 29A

EXAMPLE 27B (500 mg) in dichloromethane (3 mL) at 25° C. was treated with TFA (3 mL), stirred for 3 hours, and concentrated with a dichloromethane azeotrope.

EXAMPLE 29B

A mixture of EXAMPLE 29A (450 mg) and NMM (140 μL) in DMF (3 mL) at 25° C. was treated with HATU (464 mg) and diisopropylamine (283 μL), stirred for 5 hours, treated with ethyl acetate, washed with 1% HCl, saturated NaHCO$_3$, water, and brine, and dried (Na$_2$SO$_4$), filtered, and concentrated. The concentrate was flash chromatographed on silica gel with dichloromethane, 1:1 dichloromethane/ethyl acetate, 5% methanol/dichloromethane.

EXAMPLE 29C

EXAMPLE 29B (200 mg) in THF (5 mL) at 25° C. was treated with 2M borane.THF in THF (1 mL), stirred for 4 hours, treated with methanol (3 mL) and concentrated HCl (1 mL), stirred for 2 hours, brought to pH 7 with saturated NaHCO$_3$, and extracted with dichloromethane. The extract was washed with water and brine and dried (Na$_2$SO$_4$), filtered, and concentrated. The concentrate was flash chromatographed on silica gel with dichloromethane and 5% methanol/dichloromethane.

EXAMPLE 29D

This example was prepared by substituting EXAMPLE 29C for EXAMPLE 21C in EXAMPLE 21D.

EXAMPLE 29E

This example was prepared by substituting EXAMPLE 29D for 4-(((1R)-3-(dimethylamino)-1-((phenylsulfanyl)methyl)-propyl)amino)-3-nitrobenzenesulfonamide in EXAMPLE 2D. $^1$H NMR (500 MHz, DMSO-$d_6$) δ 11.88 (s, 1H), 11.33 (s, 1H), 10.13 (s, 1H), 9.57 (s, 1H), 8.30 (d, 1H), 8.08 (d, 1H), 7.94 (m, 1H), 7.63 (dd, 1H), 7.55 (d, 2H), 7.30 (m, 4H), 7.15 (m, 2H), 7.09 (m, 1H), 6.99 (m, 3H), 6.89 (m, 3H), 6.71 (d, 2H), 4.11 (m, 1H), 3.61 (m, 8H), 3.19 (m, 1H), 3.17 (m, 2H), 2.94 (m, 1H), 2.77 (m, 4H), 2.62 (m, 1H), 2.05 (m, 1H), 1.53 (m, 2H), 1.09-0.75 (m, 12H).

EXAMPLE 30A

EXAMPLE 27C (2.2 g) in dichloromethane (25 mL) at 0° C. was treated with TFA (25 mL) and water (2.5 mL), stirred at 25° C. for 2 hours, and concentrated with a toluene azeotrope.

EXAMPLE 30B

EXAMPLE 30A (1 g) in DME (25 mL) at 25° C. was treated with NMM (280 μL), cooled to −10° C., treated with isobutyl chloroformate (330 μL), stirred for 15 minutes, treated with sodium borohydride (277 mg) in water (10 mL), stirred for 45 minutes, and concentrated. The concentrate was treated with 0.5M HCl and extracted with ethyl acetate. The extract was washed with brine and dried (Na$_2$SO$_4$), filtered, and concentrated. The concentrate was flash chromatographed on silica gel with 2% methanol/dichloromethane and 4% methanol/dichloromethane.

EXAMPLE 30C

A mixture of EXAMPLE 30B (705 mg) and TEA (740 μL) in dichloromethane (8 mL) at 0° C. was treated with SO$_3$.pyridine (850 mg) in DMSO (6 mL), stirred at 25° C. for 30 minutes, treated 10% (w/v) aqueous citric acid, and extracted with ethyl acetate. The extract was washed with brine and dried (Na$_2$SO$_4$), filtered, and concentrated.

EXAMPLE 30D

EXAMPLE 30C (100 mg) and azetidine hydrochloride (20 mg) in acetonitrile (2 mL) at 25° C. was treated with DIEA (44 μL) and sodium triacetoxyborohydride (67 mg), stirred for 16.5 hours, absorbed onto silica gel, concentrated, and flash chromatographed on silica gel with 5% methanol/dichloromethane and 10% methanol/NH$_3$-saturated dichloromethane.

EXAMPLE 30E

This example was prepared by substituting EXAMPLE 30D for 4-(((1R)-3-(dimethylamino)-1-((phenylsulfanyl)methyl)-propyl)amino)-3-nitrobenzenesulfonamide in EXAMPLE 2D. $^1$H NMR (300 MHz, DMSO-$d_6$) δ 8.45 (d, 1H), 8.20 (d, 1H), 7.81 (dd, 1H), 7.71 (d, 2H), 7.35 (m, 14H), 6.88 (d, 1H), 6.78 (d, 2H), 4.05 (m, 1H), 3.79 (m, 4H), 3.33 (m, 5H), 3.13 (m, 5H), 2.40 (m, 4H), 2.24 (m, 2H), 1.89 (m, 2H).

EXAMPLE 31A

A mixture of 3,6-dioxa-bicyclo[3.1.0]hexane (3.44 g) and sodium azide (5.2 g) in water (10 mL) at 60° C. was stirred for 24 hours and extracted with ethyl acetate. The extract was dried ($MgSO_4$), filtered, and concentrated. The concentrate was flash chromatographed on silica gel with 0-40% ethyl acetate/hexanes.

EXAMPLE 31B

A mixture of EXAMPLE 31A (3.23 g), di-tert-butyl-dicarbonate (8.73 g), and 20 wt % palladium hydroxide on carbon (200 mg) in ethanol (15 mL) at 25° C. was treated with triethylsilane (4.651 g), stirred at 50° C. for 16 hours, filtered, and concentrated. The concentrate recrystallized from ethyl acetate/hexanes.

EXAMPLE 31C

A mixture of EXAMPLE 31B (2.03 g) and diphenyldisulfide (2.401 g) in toluene (20 mL) at 25° C. was treated with tributylphosphine (2.224 g), stirred for 16 hours at 80° C., and concentrated. The concentrate was flash chromatographed on silica gel with 0%-40% ethyl acetate/hexanes.

EXAMPLE 31D

EXAMPLE 31C (590 mg) in 1:1 dioxane/dichloromethane (8 mL) at 25° C. was treated with 4M HCl in dioxane (5 mL), stirred for 16 hours, and concentrated. The concentrate triturated with diethyl ether and filtered.

EXAMPLE 31E

This example was prepared by substituting EXAMPLE 31D for EXAMPLE 21C in EXAMPLE 21D.

EXAMPLE 31F

This example was prepared by substituting EXAMPLE 31E for 4-(((1R)-3-(dimethylamino)-1-((phenylsulfanyl)methyl)-propyl)amino)-3-nitrobenzenesulfonamide in EXAMPLE 2D. $^1$H NMR (500 MHz, DMSO-$d_6$) δ 12.09 (s, 1H), 9.70 (s, 1H), 8.69 (d, 1H), 8.54 (d, 1H), 7.87 (dd, 1H), 7.78 (d, 2H), 7.74 (br s, 1H), 7.52 (d, 4H), 7.39 (d, 2H), 7.34 (bd, 1H), 7.27 (m, 3H), 7.08 (t, 2H), 6.98 (t, 1H), 6.93 (d, 2H), 4.74 (quintet, 1H), 4.45 (q, 1H), 4.33 (dd, 1H), 4.17 (dd, 1H), 3.86 (br s, 2H), 3.77 (t, 1H), 3.75 (t, 1H), 3.49 (br s, 4H), 3.12 (br s, 2H), 2.89 (s, 2H).

EXAMPLE 32A

A mixture of magnesium turnings (432 mg) and one iodine crystal in diethyl ether (30 mL) at 25° C. was treated with 2-bromobenzyl bromide (4.5 g), stirred for 3 hours, cooled to 0° C., treated with 4-(4-oxo-piperidine-1-yl)benzoic acid ethyl ester, prepared as described in Synthesis 1981, 606-608, (3.7 g) in 1:1 diethyl ether/THF (40 mL), stirred at 25° C. for 18 hours, treated with aqueous $NH_4Cl$ and extracted with ethyl acetate. The extract was dried ($Na_2SO_4$), filtered, and concentrated. The concentrate was flash chromatographed on silica gel with 50% ethyl acetate/hexanes.

EXAMPLE 32B

EXAMPLE 32A (1.6 g) in THF (20 mL) at 25° C. was treated with 60% oily sodium hydride (288 mg), heated at 50° C. for 2 hours, treated with HMPA (3 mL) and methyl iodide (3.0 mL), stirred at reflux for 18 hours, cooled to 0° C., treated with aqueous $NaHSO_4$, and extracted with ethyl acetate. The extract was dried ($Na_2SO_4$), filtered, and concentrated. The concentrate was flash chromatographed on silica gel with 10%-15% ethyl acetate/hexanes.

EXAMPLE 32C (and 25% (w/w) EXAMPLE 32B)

A mixture of EXAMPLE 32B (640 mg), 4-chlorophenyl-boronic acid (465 mg), Pd(dppf)$Cl_2$ (122 mg), and cesium carbonate (1.46 g) in DMF (15 mL) at 80° C. was stirred for 2 days and treated with ethyl acetate and brine. The water layer was extracted with ethyl acetate, and the extract was dried ($Na_2SO_4$), filtered, and concentrated. The concentrate was flash chromatographed on silica gel with 5%-15% ethyl acetate/hexanes.

EXAMPLE 32D

This example was obtained by substituting EXAMPLE 32C for EXAMPLE 2B in EXAMPLE 2C.

EXAMPLE 32E

This example was prepared by substituting EXAMPLE 32D for EXAMPLE 2C in EXAMPLE 2D and purified by high pressure liquid chromatography on a Waters Symmetry $C_8$ column (25 mm×100 mm, 7 μm particle size) with 10-100% acetonitrile/0.1% aqueous TFA over 8 minutes at a flow rate of 40 mL/minute. $^1$H NMR (400 MHz, DMSO-$d_6$) δ 9.38 (s, 1H), 8.54 (d, 1H), 8.28 (d, 1H), 7.86 (dd, 1H), 7.69 (d, 2H), 7.46 (d, 2H), 7.28 (m, 7H), 7.15 (m, 4H), 6.82 (d, 2H), 4.18 (m, 1H), 3.40 (m, 4H), 3.13 (m, 2H), 3.04 (s, 3H), 2.86 (m, 4H), 2.74 (s, 6H), 2.14 (m, 2H), 1.47 (d, 2H), 1.18 (t, 2H).

EXAMPLE 33

This example was prepared by substituting 4-(((1R)-3-(4-morpholinyl)-1-((phenylsulfanyl)methyl)propyl)amino)-3-nitrobenzenesulfonamide, prepared as described in WO 02/24636, and EXAMPLE 32D for 4-(((1R)-3-(dimethylamino)-1-((phenylsulfanyl)methyl)propyl)amino)-3-nitrobenzene-sulfonamide and EXAMPLE 2C, respectively, in EXAMPLE 2D and purified by high pressure liquid chromatography on a Waters Symmetry $C_8$ column (25 mm×100 mm, 7 μm particle size) with 10-100% acetonitrile/0.1% aqueous TFA over 8 minutes at a flow rate of 40 mL/minute. $^1$H NMR (400 MHz, DMSO-$d_6$) δ 9.71 (s, 1H), 8.54 (d, 1H), 8.29 (d, 1H), 7.87 (dd, 1H), 7.69 (d, 2H), 7.46 (d, 2H), 7.30 (m, 7H), 7.14 (m, 4H), 6.82 (d, 2H), 4.18 (m, 1H), 3.95 (m, 2H), 3.67 (m, 4H), 3.39 (m, 4H), 3.19 (m, 2H), 3.03 (s, 3H), 3.00 (m, 2H), 2.85 (m, 4H), 2.17 (m, 2H), 1.47 (d, 2H), 1.17 (t, 2H).

EXAMPLE 34

EXAMPLE 27E (6.7 g) in DME (50 mL) at −15° C. was treated with NMM (920 μL) and isobutyl chloroformate (1.09 mL), stirred for 20 minutes, treated with sodium borohydride (1.59 g) in water (10 mL), stirred for 30 minutes, treated with water, and extracted with ethyl acetate. The extract was washed with water and brine and dried ($Na_2SO_4$), filtered, and concentrated. The concentrate was flash chromatographed on silica gel with dichloromethane, 1:1 dichloromethane/ethyl acetate, and 10% methanol/dichloromethane. $^1$H NMR (500 MHz, DMSO-$d_6$) δ 8.53 (d, 1H), 8.49 (d, 1H), 7.83 (dd, 1H), 7.74 (d, 2H), 7.47 (m, 4H), 7.53-7.36 (m, 3H), 7.25 (m 2H), 7.19-7.07 (m, 4H), 6.91 (d, 2H), 4.69 (m, 1H), 4.21 (m, 1H), 3.49 (m, 2H), 3.35 (t, 2H), 3.31 (m, 8H), 3.27 (m, 2H), 1.89 (m, 2H).

EXAMPLE 35A

EXAMPLE 34 (786 mg) in dichloromethane (5 mL) at 25° C. was treated with para-toluenesulfonic anhydride (326 mg), N,N-dimethylaminopyridine (122 mg), and DIEA (350 µL), stirred for 18 hours, treated with ethyl acetate, washed with 1% HCl, saturated NaHCO$_3$, and brine, and dried (Na$_2$SO$_4$), filtered, and concentrated.

EXAMPLE 35B

EXAMPLE 35A (100 mg) in DMF (2 mL) at 25° C. was treated with DIEA (100 µL) and isopropylamine (60 µL), stirred at 50° C. for 18 hours, treated with ethyl acetate, washed with saturated NaHCO$_3$, water, and brine, and dried (Na$_2$SO$_4$), filtered, and concentrated. The concentrate was flash chromatographed on silica gel with dichloromethane, 1:1 dichloromethane/ethyl acetate, and 10% (7M NH$_3$ in methanol) in dichloromethane. $^1$H NMR (500 MHz, DMSO-d$_6$) δ 8.45 (d, 1H), 8.09 (d, 1H), 7.84 (dd, 1H), 7.72 (d, 2H), 7.47 (m, 4H), 7.40-7.31 (m, 4H), 7.25 (m 3H), 7.17 (m, 2H), 6.94 (d, 1H), 6.78 (d, 2H), 4.11 (m, 1H), 3.37 (m, 2H), 3.30 (m, 8H), 3.12 (m, 2H), 2.99 (m, 2H), 2.40 (m, 2H), 2.05 (m, 2H), 1.16 (m, 6H).

EXAMPLE 36A

This example was made by substituting 2-napthaleneboronic acid for 4-chlorophenylboronic acid in EXAMPLE 2B.

EXAMPLE 36B

This example was made by substituting EXAMPLE 36A for EXAMPLE 2B in EXAMPLE 2C.

EXAMPLE 36C

This example was made by substituting EXAMPLE 36B for EXAMPLE 2C in EXAMPLE 2D. $^1$H NMR (400 MHz, DMSO-d$_6$) δ 12.12 (br s, 1H), 9.98 (br s, 1H), 9.60 (br s, 1H), 8.55 (d, 1H), 8.29 (d, 1H), 7.87 (dd, 1H), 7.81 (d, 2H), 7.49 (tt, 2H), 7.41 (m, 3H), 7.35 (m, 3H), 7.23 (m, 3H), 7.18 (d, 2H), 7.12 (m, 2H), 7.02 (d, 2H), 4.19 (m, 1H), 3.99 (br s, 2H), 3.39 (d, 4H), 3.29 (m, 4H), 3.14 (m, 2H), 2.98 (m, 2H), 2.75 (s, 6H), 2.14 (dd, 2H).

EXAMPLE 37A

This example was made by substituting 1-napthaleneboronic acid for 4-chlorophenylboronic acid in EXAMPLE 2B.

EXAMPLE 37B

This example was made by substituting. EXAMPLE 37A for EXAMPLE 2B in EXAMPLE 2C.

EXAMPLE 37C

This example was made by substituting EXAMPLE 37B for EXAMPLE 2C in EXAMPLE 2D. $^1$H NMR (400 MHz, DMSO-d$_6$) δ 12.07 (br s, 1H), 9.59 (br s, 2H), 8.54 (d, 1H), 8.29 (d, 1H), 8.01 (dd, 2H), 7.85 (dd, 2H), 7.74 (d, 2H), 7.59 (m; 4H), 7.47 (m, 2H), 7.35 (d, 1H), 7.24 (m, 3H), 7.18 (d, 2H), 7.12 (m, 2H), 6.88 (d, 2H), 4.19 (m, 1H), 3.75 (br s, 2H), 3.39 (d, 4H), 3.29 (m, 4H), 3.14 (m, 2H), 2.98 (m, 2H), 2.75 (s, 6H), 2.15 (dd, 2H).

EXAMPLE 38A

This example was made by substituting 3-cyanophenylboronic acid for 4-chlorophenylboronic acid in EXAMPLE 2B.

EXAMPLE 38B

This example was made by substituting EXAMPLE 38A for EXAMPLE 2B in EXAMPLE 2C.

EXAMPLE 38C

This example was made by substituting EXAMPLE 38B for EXAMPLE 2C in EXAMPLE 2D. $^1$H NMR (400 MHz, DMSO-d$_6$) δ 12.09 (br s, 1H), 9.47 (br s, 2H), 8.54 (d, 1H), 8.29 (d, 1H), 7.89 (d, 1H), 7.86 (dd, 2H), 7.77 (d, 2H), 7.69 (m, 3H), 7.56 (m, 2H), 7.37 (m, 1H), 7.24 (m, 2H), 7.14 (d, 5H), 6.93 (d, 2H), 4.18 (m, 1H), 4.04 (m, 2H), 3.75 (m, 2H), 3.39 (d, 4H), 3.15 (m, 4H), 3.06 (m, 2H), 2.75 (s, 3H), 2.74 (s, 3H), 2.14 (dd, 2H).

EXAMPLE 39A

This example was made by substituting 3-methoxyphenylboronic acid for 4-chlorophenylboronic acid in EXAMPLE 2B.

EXAMPLE 39B

This example was made by substituting EXAMPLE 39A for EXAMPLE 2B in EXAMPLE 2C.

EXAMPLE 39C

This example was made by substituting EXAMPLE 39B for EXAMPLE 2C in EXAMPLE 2D. $^1$H NMR (400 MHz, DMSO-d$_6$) δ 12.10 (br s, 1H), 9.58 (br s, 1H), 8.55 (d, 1H), 8.29 (d, 1H), 7.86 (dd, 1H), 7.77 (d, 2H), 7.72 (m, 1H), 7.50 (m, 2H), 7.37 (m, 2H), 7.24 (m, 2H), 7.14 (d, 4H), 6.98 (m, 1H), 6.92 (m, 4H), 4.31 (br s, 2H), 4.18 (m, 1H), 3.79 (s, 3H), 3.39 (d, 3H), 3.15 (m, 5H), 2.75 (s, 6H), 2.14 (dd, 2H).

EXAMPLE 40A

This example was made by substituting 3-chlorophenylboronic acid for 4-chlorophenylboronic acid in EXAMPLE 2B.

EXAMPLE 40B

This example was made by substituting EXAMPLE 40A for EXAMPLE 2B in EXAMPLE 2C.

EXAMPLE 40C

This example was made by substituting EXAMPLE 40B for EXAMPLE 2C in EXAMPLE 2D. $^1$H NMR (400 MHz, DMSO-d$_6$) δ 12.09 (br s, 1H), 9.86 (br s, 1H), 9.59 (br s, 1H), 8.55 (d, 1H), 8.29 (d, 1H), 7.86 (dd, 1H), 7.77 (d, 2H), 7.70 (m, 1H), 7.49 (m, 5H), 7.34 (m, 2H), 7.24 (m, 2H), 7.14 (d, 4H), 6.94 (d, 2H), 4.19 (m, 1H), 3.39 (d, 3H), 3.13 (m, 5H), 2.88 (m, 2H), 2.75 (s, 6H), 2.15 (dd, 2H).

EXAMPLE 41A

This example was made by substituting 2-chlorophenylboronic acid for 4-chlorophenylboronic acid in EXAMPLE 2B.

EXAMPLE 41B

This example was made by substituting EXAMPLE 41A for EXAMPLE 2B in EXAMPLE 2C.

EXAMPLE 41C

This example was made by substituting EXAMPLE 41B for EXAMPLE 2C in EXAMPLE 2D. $^1$H NMR (400 MHz, DMSO-$d_6$) δ 12.12 (br s, 1H), 10.00 (br s, 1H), 9.59 (br s, 1H), 8.55 (d, 1H), 8.29 (d, 1H), 7.86 (dd, 1H), 7.77 (d, 2H), 7.76 (m, 1H), 7.58 (m, 3H), 7.45 (m, 3H), 7.28 (dd, 1H), 7.23 (m, 2H), 7.14 (d, 4H), 6.94 (d, 2H), 4.18 (m, 1H), 3.39 (d, 3H), 3.13 (m, 5H), 3.02 (m, 2H), 2.75 (s, 6H), 2.15 (dd, 2H).

EXAMPLE 42A

This example was made by substituting 3,4-methylenedioxybenzeboronic acid for 4-chlorophenylboronic acid in EXAMPLE 2B.

EXAMPLE 42B

This example was made by substituting EXAMPLE 42A for EXAMPLE 2B in EXAMPLE 2C.

EXAMPLE 42C

This example was made by substituting EXAMPLE 42B for EXAMPLE 2C in EXAMPLE 2D. $^1$H NMR (400 MHz, DMSO-$d_6$) δ 12.08 (br s, 1H), 9.85 (br s, 1H), 9.55 (br s, 1H), 8.54 (d, 1H), 8.29 (d, 1H), 7.86 (dd, 1H), 7.77 (d, 2H), 7.69 (m, 1H), 7.48 (br s, 2H), 7.31 (m, 1H), 7.23 (m, 2H), 7.14 (d, 4H), 6.96 (m, 4H), 6.79 (dd, 1H), 6.06 (s, 2H), 4.18 (m, 1H), 3.39 (d, 3H), 3.12 (m, 5H), 2.86 (m, 2H), 2.75 (s, 6H), 2.14 (dd, 2H).

EXAMPLE 43A

This example was made by substituting thiophene-3-boronic acid for 4-chlorophenylboronic acid in EXAMPLE 2B.

EXAMPLE 43B

This example was made by substituting EXAMPLE 43A for EXAMPLE 2B in EXAMPLE 2C.

EXAMPLE 43C

This example was made by substituting EXAMPLE 43B for EXAMPLE 2C in EXAMPLE 2D. $^1$H NMR (400 MHz, DMSO-$d_6$) δ 12.11 (br s, 1H), 9.99 (br s, 1H), 9.62 (br s, 1H), 8.55 (d, 1H), 8.29 (d, 1H), 7.86 (dd, 1H), 7.78 (d, 2H), 7.69 (m, 2H), 7.63 (s, 1H), 7.48 (br s, 2H), 7.41 (m, 1H), 7.24 (m, 2H), 7.14 (d, 5H), 6.95 (d, 2H), 4.18 (m, 1H), 3.39 (d, 3H), 3.14 (m, 5H), 2.89 (m, 2H), 2.75 (s, 6H), 2.15 (dd, 2H).

EXAMPLE 44A

This example was made by substituting pyridine-3-boronic acid for 4-chlorophenylboronic acid in EXAMPLE 2B.

EXAMPLE 44B

This example was made by substituting EXAMPLE 44A for EXAMPLE 2B in EXAMPLE 2C.

EXAMPLE 44C

This example was made by substituting EXAMPLE 44B for EXAMPLE 2C in EXAMPLE 2D. $^1$H NMR (400 MHz, DMSO-$d_6$) δ 12.08 (br s, 1H), 9.99 (br s, 1H), 9.66 (br s, 1H), 8.69 (dd, 1H), 8.54 (d, 1H), 8.29 (d, 1H), 7.95 (d, 1H), 7.86 (dd, 1H), 7.77 (d, 2H), 7.59 (m, 3H), 7.40 (m, 1H), 7.24 (m, 2H), 7.14 (d, 4H), 6.93 (d, 2H), 4.19 (m, 1H), 3.39 (d, 3H), 3.14 (m, 5H), 2.92 (m, 2H), 2.75 (s, 6H), 2.15 (dd, 2H).

EXAMPLE 45A

This example was made by substituting 8-quinolineboronic acid for 4-chlorophenylboronic acid in EXAMPLE 2B.

EXAMPLE 45B

This example was made by substituting EXAMPLE 45A for EXAMPLE 2B in EXAMPLE 2C.

EXAMPLE 45C

This example was made by substituting EXAMPLE 45B for EXAMPLE 2C in EXAMPLE 2D. $^1$H NMR (400 MHz, DMSO-$d_6$) δ 12.10 (br s, 1H), 9.84 (br s, 1H), 9.61 (br s, 1H), 8.84 (dd, 1H), 8.54 (d, 1H), 8.48 (dd, 1H), 8.29 (d, 1H), 8.10 (td, 1H), 7.85 (dd, 1H), 7.80 (d, 1H), 7.73 (m, 4H), 7.56 (m, 3H), 7.35 (dd, 1H), 7.23 (m, 3H), 7.14 (m, 3H), 6.89 (d, 2H), 4.29 (m, 1H), 4.20 (m, 1H), 3.90 (d, 1H), 3.39 (d, 4H), 3.14 (m, 3H), 2.97 (m, 3H), 2.75 (s, 6H), 2.15 (dd, 2H).

EXAMPLE 46A

This example was made by substituting benzofuran-2-boronic acid for 4-chlorophenylboronic acid in EXAMPLE 2B.

EXAMPLE 46B

This example was made by substituting EXAMPLE 46A for EXAMPLE 2B in EXAMPLE 2C.

EXAMPLE 46C

This example was made by substituting EXAMPLE 46B for EXAMPLE 2C in EXAMPLE 2D. $^1$H NMR (400 MHz, DMSO-$d_6$) δ 12.14 (br s, 1H), 9.81 (br s, 1H), 9.63 (br s, 1H), 8.55 (d, 1H), 8.29 (d, 1H), 7.97 (d, 1H), 7.86 (dd, 1H), 7.81 (d, 2H), 7.69 (m, 3H), 7.60 (m, 2H), 7.46 (s, 1H), 7.38 (td, 1H), 7.32 (t, 1H), 7.22 (m, 2H), 7.15 (d, 4H), 7.01 (d, 2H), 4.19 (m, 1H), 3.39 (d, 3H), 3.27 (m, 2H), 3.15 (m, 5H), 2.75 (s, 6H), 2.15 (dd, 2H).

EXAMPLE 44A

This example was made by substituting 2-methylphenylboronic acid for 4-chlorophenylboronic acid in EXAMPLE 2B.

EXAMPLE 44B

This example was made by substituting EXAMPLE 44A for EXAMPLE 2B in EXAMPLE 2C.

EXAMPLE 44C

This example was made by substituting EXAMPLE 44B for EXAMPLE 2C in EXAMPLE 2D. $^1$H NMR (400 MHz, DMSO-d$_6$) δ 12.08 (br s, 1H), 9.94 (br s, 1H), 9.73 (br s, 1H), 8.55 (d, 1H), 8.29 (d, 1H), 7.86 (dd, 1H), 7.77 (d, 2H), 7.74 (m, 1H), 7.50 (m, 2H), 7.31 (d, 2H), 7.22 (m, 9H), 6.94 (d, 2H), 4.19 (m, 1H), 3.39 (d, 4H), 3.16 (m, 4H), 2:92 (m, 2H), 2.75 (s, 6H), 2.15 (dd, 2H).

EXAMPLE 48A

This example was made by substituting 3-quinolineboronic acid for 4-chlorophenylboronic acid in EXAMPLE 2B.

EXAMPLE 48B

This example was made by substituting EXAMPLE 48A for EXAMPLE 2B in EXAMPLE 2C.

EXAMPLE 48C

This example was made by substituting EXAMPLE 48B for EXAMPLE 2C in EXAMPLE 2D. $^1$H NMR (400 MHz, DMSO-d$_6$) δ 12.07 (br s, 1H), 9.93 (br s, 1H), 9.56 (br s, 1H), 8.53 (d, 1H), 8.42 (s, 1H), 8.28 (d, 1H), 8.09 (d, 1H), 8.04 (dd, 1H), 7.85 (dd, 1H), 7.82 (m, 2H), 7.74 (d, 2H), 7.68 (td, 1H), 7.50 (m, 2H), 7.23 (m, 2H), 7.14 (d, 4H), 6.90 (d, 2H), 4.19 (m, 1H), 3.39 (d, 3H), 3.14 (m, 5H), 2.90 (m, 2H), 2.74 (s, 6H), 2.13 (dd, 2H).

EXAMPLE 49A

A mixture of EXAMPLE 1A (272 mg), 1-bromo-naphthalene-2-carbaldehyde (0.409 g), MP-BH$_3$CN (2.47 mmol/g, 1.41 g) and acetic acid (0.14 g) in 1:1 methanol/dichloromethane (8 mL) was shaken for 1 day at 25° C., filtered, and concentrated. The concentrate was treated with saturated aqueous K$_2$CO$_3$ and dichloromethane, and the organic layer was dried (MgSO$_4$), filtered and concentrated. The concentrate was flash chromatographed on silica gel with 5%-50% ethyl acetate/hexanes.

EXAMPLE 49B

This example was made by substituting EXAMPLE 49A for EXAMPLE 2A in EXAMPLE 2B.

EXAMPLE 49C

This example was made by substituting EXAMPLE 49B for EXAMPLE 2B in EXAMPLE 2C.

EXAMPLE 49D

This example was made by substituting EXAMPLE 49C and 3-nitro-4-((2-(phenylsulfanyl)ethyl)amino)benzene-sulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-d$_6$) δ 12.05 (br s, 1H), 9.87 (br s, 1H), 8.76 (t, 1H), 8.60 (d, 1H), 8.29 (d, 1H), 8.13 (d, 1H), 8.04 (d, 1H), 7.90 (dd, 1H), 7.86 (d, 1H), 7.77 (d, 2H), 7.62 (d, 2H), 7.60 (m, 1H), 7.50 (t, 1H), 7.37 (m, 3H), 7.28 (d, 2H), 7.19 (m, 2H), 6.94 (d, 2H), 4.23 (br s, 2H), 3.82 (br s, 4H), 3.67 (dd, 2H), 3.28 (m, 2H), 3.16 (br s, 2H), 2.97 (br s, 2H).

EXAMPLE 50

This example was made by substituting EXAMPLE 49C for EXAMPLE 2C in EXAMPLE 2D. $^1$H NMR (400 MHz, DMSO-d$_6$) 67 12.12 (br s, 1H), 9.97 (br s, 1H), 9.56 (br s, 1H), 8.55 (d, 1H), 8.29 (d, 1H), 8.12 (d, 1H), 8.05 (d, 1H), 7.87 (d, 1H), 7.86 (d, 1H), 7.79 (d, 2H), 7.61 (m, 3H), 7.50 (m, 1H), 7.38 (d, 2H), 7.28 (d, 1H), 7.22 (m, 2H), 7.14 (m, 4H), 6.95 (d, 2H), 4.25 (br s, 2H), 4.19 (m, 1H), 3.39 (d, 3H), 3.14 (m, 5H), 2.94 (m, 2H), 2.75 (s, 3H), 2.74 (s, 3H), 2.15 (dd, 2H).

EXAMPLE 51

This example was made by substituting EXAMPLE 49C and 4-(((1R)-3-(4-morpholinyl)-1-((phenylsulfanyl)methyl)-propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. NMR (400 MHz, DMSO-d$_6$) δ 12.11 (br s, 1H), 9.89 (br s, 2H), 8.55 (d, 1H), 8.29 (d, 1H), 8.12 (d, 1H), 8.04 (d, 1H), 7.86 (m, 2H), 7.78 (d, 2H), 7.62 (d, 2H), 7.60 (m, 1H), 7.50 (t, 1H), 7.38 (d, 2H), 7.28 (d, 1H), 7.15 (d, 4H), 6.95 (d, 2H), 4.19 (m, 1H), 3.95 (m, 4H), 3.62 (m 3H), 3.41 (d, 5H), 3.18 (m, 5H), 3.01 (br s, 4H), 2.19 (dd, 2H).

EXAMPLE 52A

A mixture of 6-oxa-bicyclo[3.1.0]hexane (1.68 g) and NaN$_3$ (2.6 g) in water (5 mL) at 60° C. was stirred for 3 days. The water layer was extracted with dichloromethane, and the extract was dried (MgSO$_4$), filtered, and concentrated. The concentrate was flash chromatographed on silica gel 0-40% ethyl acetate/hexanes.

EXAMPLE 52B

A mixture of EXAMPLE 52A (1.017 g), di(tert-butyl) dicarbonate (2.619 g), Pd(OH)$_2$ (100 mg) and triethylsilane (1.395 g) in ethanol (15 mL) at 50° C. was stirred for 16 hours, concentrated partially, and partitioned between ethyl acetate and water. The extract was dried (MgSO$_4$), filtered, and concentrated. The concentrate was flash chromatographed on silica gel with 10-60% ethyl acetate/hexanes.

EXAMPLE 52C

A mixture of EXAMPLE 52B (0.201 g) and diphenyldisulfide (262 mg) in toluene (2 mL) at 25° C. was treated with tri-n-butylphosphine (243 mg), stirred for 16 hours at 80° C., and concentrated. The concentrate was flash chromatographed on silica gel 0-30% ethyl acetate/hexanes.

EXAMPLE 52D

A mixture of EXAMPLE 52C (0.325 g) and 4M HCl in dioxane (2.5 mL) in dichloromethane (3 mL) at 25° C. was stirred for 3 hours and partially concentrated. The concentrate was treated with diethyl ether and filtered.

EXAMPLE 52E

This example was prepared by substituting EXAMPLE 52D for EXAMPLE 21C in EXAMPLE 21D.

EXAMPLE 52F

This example was made by substituting EXAMPLE 52E for 4-(((1R)-3-(dimethylamino)-1-((phenylsulfanyl)methyl)-propyl)amino)-3-nitrobenzenesulfonamide, in EXAMPLE 2D. $^1$H NMR (400 MHz, DMSO-$d_6$) δ 12.08 (br s, 1H), 9.77 (br s, 1H), 8.55 (d, 1H), 8.36 (d, 1H), 7.85 (dd, 1H), 7.77 (d, 2H), 7.73 (m, 1H), 7.54 (m, 4H), 7.39 (td, 2H), 7.33 (m, 3H), 7.17 (m, 4H), 6.93 (d, 2H), 4.32 (br s, 2H), 4.10 (br s, 2H), 4.09 (quintet, 1H), 3.85 (q, 1H), 3.39 (d, 3H), 3.25 (br s, 2H), 3.10 (br s, 2H), 2.89 (br s, 2H), 2.25 (sextet, 2H), 1.79 (m, 2H), 1.64 (m, 2H).

EXAMPLE 53

This example was made by substituting EXAMPLE 52E for 4-(((1R)-3-(dimethylamino)-1-((phenylsulfanyl)methyl)propyl)amino)-3-nitrobenzenesulfonamide, in EXAMPLE 32E. $^1$H NMR (400 MHz, DMSO-$d_6$) δ 11.94 (br s, 1H), 8.55 (d, 1H), 8.35 (d, 1H), 7.85 (dd, 1H), 7.68 (d, 2H), 7.42 (t, 2H), 7.35 (m, 3H), 7.28 (m, 3H), 7.16 (m, 4H), 6.82 (d, 2H), 4.09 (quintet, 1H), 3.84 (q, 1H), 3.39 (d, 2H), 3.03 (s, 3H), 2.89 (s, 2H), 2.83 (t, 1H), 2.25 (sextet, 2H), 1.79 (m, 2H), 1.64 (m, 2H), 1.47 (d, 2H), 1.17 (m, 2H).

EXAMPLE 54

This example was made by substituting 3-nitro-4-((2-(phenylsulfanyl)ethyl)amino)benzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 4C. $^1$H NMR (400 MHz, DMSO-$d_6$) δ 12.06 (br s, 1H), 9.72 (br s, 1H), 8.76 (t, 1H), 8.60 (d, 1H), 7.90 (dd, 1H), 7.75 (d, 2H), 7.71 (m, 1H), 7.52 (br s, 2H), 7.41 (dd, 2H), 7.35 (m, 2H), 7.28 (m, 2H), 7.19 (m, 2H), 6.92 (d, 2H), 4.24 (br s, 2H), 3.80 (br s, 2H), 3.66 (q, 2H), 3.28 (t, 2H), 3.14 (br s, 2H), 2.86 (br s, 2H).

EXAMPLE 55A

This example was made by substituting 3,4-dichlorophenylboronic acid for 4-chlorophenylboronic acid in EXAMPLE 2B.

EXAMPLE 55B

This example was made by substituting EXAMPLE 55A for EXAMPLE 2B in EXAMPLE 2C.

EXAMPLE 55C

This example was made by substituting EXAMPLE 55B and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 12.05 (br s, 1H), 9.71 (br s, 1H), 8.76 (t, 1H), 8.60 (d, 1H), 7.90 (dd, 1H), 7.76 (d, 2H), 7.73 (m, 1H), 7.71 (d, 2H), 7.54 (m, 2H), 7.36 (m, 4H), 7.26 (tt, 2H), 7.18 (m, 2H), 6.94 (d, 2H), 4.28 (br s, 2H), 3.85 (br s, 2H), 3.67 (q, 2H), 3.28 (t, 2H), 3.12 (br s, 2H), 2.93 (br s, 2H).

EXAMPLE 56

This example was made by substituting EXAMPLE 55B for EXAMPLE 2C in EXAMPLE 2D. $^1$H NMR (400 MHz, DMSO-$d_6$) δ 12.10 (br s, 1H), 9.94 (br s, 1H), 9.64 (br s, 1H), 8.54 (d, 1H), 8.29 (d, 1H), 7.86 (dd, 1H), 7.78 (d, 2H), 7.74 (m, 1H), 7.71 (d, 1H), 7.69 (br s, 1H), 7.54 (m, 2H), 7.37 (m, 2H), 7.23 (m, 2H), 7.14 (m, 4H), 6.95 (d, 2H), 4.31 (br s, 2H), 4.20 (m, 1H), 3.93 (br s, 2H), 3.39 (d, 3H), 3.14 (m, 5H), 2.90 (m, 2H), 2.75 (s, 6H), 2.15 (dd, 2H).

EXAMPLE 57

This example was made by substituting EXAMPLE 55B and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl) amino)-3-nitrobenzenesulfonamide, respectively, in EXAMPLE 2D. $^1$H NMR (400 MHz, DMSO-$d_6$) δ 12.12 (br s, 1H), 10.32 (br s, 1H), 9.98 (br s, 1H), 8.55 (d, 1H), 8.30 (d, 1H), 7.87 (dd, 1H), 7.77 (d, 2H), 7.71 (br s, 1H), 7.70 (d, 2H), 7.53 (m, 2H), 7.36 (m, 2H), 7.24 (m, 2H), 7.15 (m, 4H), 6.94 (d, 2H), 4.25 (br s, 2H), 4.19 (m, 1H), 3.95 (m, 4H), 3.63 (m, 3H), 3.40 (d, 5H), 3.19 (m, 4H), 3.02 (br s, 4H), 2.18 (dd, 2H).

EXAMPLE 58A

This example was made by substituting 4-trifluoromethylphenylboronic acid for 4-chlorophenylboronic acid in EXAMPLE 2B.

EXAMPLE 58B

This example was made by substituting EXAMPLE 58A for EXAMPLE 2B in EXAMPLE 2C.

EXAMPLE 58C

This example was made by substituting EXAMPLE 58B and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 12.07 (br s, 1H), 9.85 (br s, 1H), 8.76 (t, 1H), 8.60 (d, 1H), 7.90 (dd, 1H), 7.83 (d, 2H), 7.78 (br s, 1H), 7.76 (d, 2H), 7.61 (d, 2H), 7.54 (m, 2H), 7.37 (m, 3H), 7.26 (t, 2H), 7.19 (t, 2H), 6.93 (d, 2H), 4.30 (br s, 2H), 4.00 (br s, 4H), 3.67 (q, 2H), 3.28 (t, 2H), 3.10 (br s, 2H), 2.94 (br s, 2H).

EXAMPLE 59

This example was made by substituting EXAMPLE 58B for EXAMPLE 2C in EXAMPLE 2D. $^1$H NMR (400 MHz, DMSO-$d_6$) δ 12.08 (br s, 1H), 10.01 (br s, 1H), 9.60 (br s, 1H), 8.54 (d, 1H), 8.29 (d, 1H), 7.86 (dd, 1H), 7.82 (d, 2H), 7.78 (br s, 1H), 7.77 (d, 2H), 7.61 (d, 2H), 7.56 (m, 2H), 7.37 (m, 1H), 7.23 (m, 2H), 7.14 (m, 4H), 6.93 (d, 2H), 4.25 (br s, 2H), 4.19 (m, 1H), 3.98 (br s, 2H), 3.39 (d, 3H), 3.13 (m, 5H), 2.90 (m, 2H), 2.74 (s, 6H), 2.15 (dd, 2H).

EXAMPLE 60

This example was made by substituting EXAMPLE 58B and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl) amino)-3-nitrobenzenesulfonamide, respectively, in EXAMPLE 2D. $^1$H NMR (400 MHz, DMSO-$d_6$) δ 12.08 (br s, 1H), 9.99 (br s, 2H), 8.55 (d, 1H), 8.29 (d, 1H), 7.86 (dd, 1H), 7.83 (d, 2H), 7.79 (br s, 1H), 7.77 (d, 2H), 7.60 (d, 2H), 7.57 (m, 2H), 7.38 (m, 1H), 7.23 (m, 2H), 7.14 (m, 4H), 6.93 (d, 2H), 4.32 (br s, 2H), 4.19 (m, 1H), 3.95 (m, 2H), 3.62 (m, 3H), 3.40 (m, 5H), 3.20 (m, 4H), 3.02 (br s, 4H), 2.18 (dd, 2H).

EXAMPLE 61A

This example was made by substituting 4-trifluoromethoxyboronic acid for 4-chlorophenylboronic acid in EXAMPLE 2B.

EXAMPLE 61B

This example was made by substituting EXAMPLE 61A for EXAMPLE 2B in EXAMPLE 2C.

EXAMPLE 61C

This example was made by substituting EXAMPLE 61B and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 12.05 (br s, 1H), 9.78 (br s, 1H), 8.76 (t, 1H), 8.60 (d, 1H), 7.90 (dd, 1H), 7.76 (d, 2H), 7.75 (br s, 1H), 7.54 (m, 2H), 7.50 (d, 2H), 7.45 (d, 2H), 7.37 (m, 3H), 7.26 (t, 2H), 7.18 (m, 2H), 6.93 (d, 2H), 4.30 (br s, 2H), 3.98 (br s, 4H), 3.67 (q, 2H), 3,28 (t, 2H), 3.11 (br s, 2H), 2.89 (br s, 2H).

EXAMPLE 62

This example was made by substituting EXAMPLE 61B for EXAMPLE 2C in EXAMPLE 2D. $^1$H NMR (400 MHz, DMSO-$d_6$) δ 12.10 (br s, 1H), 10.05 (br s, 1H), 9.62 (br s, 1H), 8.54 (d, 1H), 8.29 (d, 1H), 7.86 (dd, 1H), 7.77 (d, 2H), 7.76 (br s, 1H), 7.54 (m, 2H), 7.50 (d, 2H), 7.45 (d, 2H), 7.37 (m, 1H), 7.23 (m, 2H), 7.14 (m, 4H), 6.93 (d, 2H), 4.31 (br s, 2H), 4.19 (m, 1H), 3.82 (br s, 2H), 3.39 (d, 3H), 3.13 (m, 5H), 2.92 (m, 2H), 2.74 (s, 6H), 2.15 (dd, 2H).

EXAMPLE 63

This example was made by substituting EXAMPLE 61B and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 12.13 (br s, 1H), 9.99 (br s, 2H), 8.55 (d, 1H), 8.29 (d, 1H), 7.86 (dd, 1H), 7.77 (d, 2H), 7.76 (br s, 1H), 7.54 (m, 2H), 7.51 (d, 2H), 7.45 (d, 2H), 7.37 (m, 1H), 7.23 (m, 2H), 7.14 (m, 4H), 6.93 (d, 2H), 4.30 (br s, 2H), 4.20 (m, 1H), 3.95 (m, 2H), 3.63 (m, 3H), 3.40 (m, 5H), 3.20 (m, 4H), 3.02 (br s, 4H), 2.18 (dd, 2H).

EXAMPLE 64A

This example was made by substituting 4-phenoxyphenylboronic acid for 4-chlorophenylboronic acid in EXAMPLE 2B.

EXAMPLE 64B

This example was made by substituting EXAMPLE 64A for EXAMPLE 2B in EXAMPLE 2C.

EXAMPLE 64C

This example was made by substituting EXAMPLE 64B and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 12.05 (br s, 1H), 9.76 (br s, 1H), 8.76 (t, 1H), 8.60 (d, 1H), 7.91 (dd, 1H), 7.77 (d, 2H), 7.73 (br s, 1H), 7.52 (m, 2H), 7.38 (m, 7H), 7.26 (t, 2H), 7.18 (m, 3H), 7.07 (m, 4H), 6.94 (d, 2H), 4.36 (br s, 2H), 3.80 (br s, 4H), 3.67 (q, 2H), 3.28 (t, 2H), 3.15 (br s, 2H), 2.87 (br s, 2H).

EXAMPLE 65

This example was made by substituting EXAMPLE 64B and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 12.07 (br s, 1H), 9.98 (br s, 2H), 8.56 (d, 1H), 8.30 (d, 1H), 7.87 (dd, 1H), 7.78 (d, 2H), 7.73 (br s, 1H), 7.51 (m, 2H), 7.38 (m, 5H), 7.23 (m, 2H), 7.15 (m, 5H), 7.07 (d, 4H), 6.95 (d, 2H), 4.31 (br s, 2H), 4.20 (m, 1H), 3.94 (m, 2H), 3.63 (m, 3H), 3.40 (m, 5H), 3.19 (m, 4H), 3.02 (br s, 4H), 2.18 (dd, 2H).

EXAMPLE 66A

ADDP (11.43 g) in THF (100 mL) at 25° C. was treated with tributylphosphine (9.16 g), stirred for 10 minutes, treated with (S)-3-tert-butoxycarbonylamino-4-hydroxybutyric acid cyclohexyl ester (9.1 g), prepared as described in Tet. Lett. (1995), 36(8), 1223, in THF (20 mL) and thiophenol (6.61 g), stirred for 2 days, treated with diethyl ether, and filtered. The filtrate was concentrated, and the concentrate was flash chromatographed on silica gel with 0-15% ethyl acetate/hexane.

EXAMPLE 66B

A mixture of EXAMPLE 66A (7.1 g) and 4M HCl in dioxane (30 mL) was stirred for 5 hours and concentrated.

EXAMPLE 66C

This example was made by substituting EXAMPLE 66B for EXAMPLE 21C in EXAMPLE 21D.

EXAMPLE 66D

A mixture of EXAMPLE 66C (8.341 g) and lithium hydroxide (1.426 g) in 1:1 THF/water (100 mL) was stirred for 18 hours at 25° C., partially concentrated, treated with water (250 mL), washed with dichloromethane/ethyl acetate, acidified with 12M HCl to pH 2, and extracted with ethyl acetate. The extract was washed with water and brine and dried (MgSO$_4$), filtered, and concentrated.

EXAMPLE 66E

A mixture of EXAMPLE 66D (6.42 g) and NMM (1.67 g) in DME (70 mL) at 0-5° C. was treated with isobutyl chloroformate (2.14 mL), stirred for 5 minutes treated with 2M dimethylamine in THF (40 mL), stirred at 25° C., concentrated, and filtered.

EXAMPLE 66F

This example was made by substituting EXAMPLE 66E for EXAMPLE 18E in EXAMPLE 18F.

EXAMPLE 66G

This example was made by substituting EXAMPLE 66F for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-d$_6$) δ 9.69 (br s, 1H), 8.47 (d, 1H), 8.19 (d, 1H), 7.82 (dd, 1H), 7.72 (d, 2H), 7.51 (m, 1H), 7.47 (s, 4H), 7.37 (m, 2H), 7.30 (m, 2H), 7.24 (t, 3H), 7.16 (m, 1H), 6.93 (d, 1H), 6.80 (d, 2H), 4.07 (br s, 2H), 3.39 (m, 2H), 3.33 (m, 2H), 3.14 (m, 4H), 3.00 (m, 2H), 2.63 (s, 6H), 2.40 (m, 4H), 2.08 (m, 2H).

EXAMPLE 67A

ADDP (16.94 g) in THF (90 mL) at 25° C. was treated with tributylphosphine (13.55 g), stirred for 10 minutes, treated with (2-hydroxy-1,1-dimethylethyl)carbamic acid tert-butyl ester (8.47 g), prepared as described in Synlett. (1997), (8), 893-894, in THF (30 mL) and thiophenol (7.38 g), stirred for 1 day, treated with diethyl ether, and filtered. The filtrate was concentrated, and the concentrate was flash chromatographed on silica gel 0-15% ethyl acetate/hexanes.

EXAMPLE 67B

A mixture of EXAMPLE 67A (0.562 g) and 80% magnesium monoperoxy pthalic acid (1.36 g) in THF (10 mL) was stirred for 18 hours, treated with dichloromethane, and filtered. The filtrate was washed with brine and dried (MgSO$_4$), filtered, and concentrated. The concentrate was flash chromatographed on silica gel 10-50% ethyl acetate/hexanes.

EXAMPLE 67C

This example was made by substituting EXAMPLE 67B for EXAMPLE 66A in EXAMPLE 66B.

EXAMPLE 67D

This example was made by substituting EXAMPLE 67C for EXAMPLE 21C in EXAMPLE 21D.

EXAMPLE 67 E

This example was made by substituting EXAMPLE 67D for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-d$_6$) δ 12.11 (br s, 1H), 9.69 (br s, 1H), 8.44 (d, 1H), 8.33 (s, 1H), 7.82 (d, 2H), 7.71 (dd, 2H), 7.64 (td, 2H), 7.52 (d, 3H), 7.40 (d, 2H), 7.32 (m, 1H), 7.25 (d, 1H), 7.23 (tt, 1H), 7.16 (tt, 2H), 6.95 (d, 2H), 4.30 (br s, 2H), 4.13 (s, 2H), 3.84 (br s, 2H), 3.13 (br s, 4H), 2.86 (br s, 2H), 1.62 (s, 6H).

EXAMPLE 68A

This example was made by substituting 2,4-dichlorophenylboronic acid for 4-chlorophenylboronic acid in EXAMPLE 2B.

EXAMPLE 68B

This example was made by substituting EXAMPLE 68A for EXAMPLE 2B in EXAMPLE 2C.

EXAMPLE 68C

This example was made by substituting EXAMPLE 68B for EXAMPLE 2C in EXAMPLE 2D. $^1$H NMR (400 MHz, DMSO-d$_6$) δ 12.10 (br s, 1H), 9.89 (br s, 1H), 9.56 (br s, 1H), 8.54 (d, 1H), 8.28 (d, 1H), 7.85 (dd, 1H), 7.77 (d, 2H), 7.74 (m, 1H), 7.52 (m, 3H), 7.43 (d, 1H), 7.26 (d, 1H), 7.22 (d, 2H), 7.13 (m, 4H), 6.94 (d, 2H), 4.26 (br s, 2H), 4.17 (m, 1H), 3.38 (d, 3H), 3.13 (m, 7H), 2.74 (s, 6H), 2.14 (dd, 2H).

EXAMPLE 69A

This example was made by substituting thiophene-2-boronic acid for 4-chlorophenylboronic acid in EXAMPLE 2B.

EXAMPLE 69B

This example was made by substituting EXAMPLE 69A for EXAMPLE 2B in EXAMPLE 2C.

EXAMPLE 69C

This example was made by substituting EXAMPLE 69B for EXAMPLE 2C in EXAMPLE 2D. $^1$H NMR (400 MHz, DMSO-d$_6$) δ 12.11 (br s, 1H), 9.95 (br s, 1H), 9.55 (br s, 1H), 8.54 (d, 1H), 8.29 (d, 1H), 7.85 (dd, 1H), 7.78 (d, 2H), 7.73 (m, 1H), 7.68 (d, 1H), 7.51 (m, 3H), 7.24 (m, 2H), 7.17 (m, 2H), 7.14 (m, 4H), 6.96 (d, 2H), 4.41 (br s, 2H), 4.18 (m, 1H), 3.38 (d, 3H), 3.13 (m, 7H), 2.75 (s, 6H), 2.15 (dd, 2H).

EXAMPLE 70A

This example was made by substituting 4-chloro-2-methylphenylboronic acid for 4-chlorophenylboronic acid in EXAMPLE 2B.

EXAMPLE 70B

This example was made by substituting EXAMPLE 70A for EXAMPLE 2B in EXAMPLE 2C.

EXAMPLE 70C

This example was made by substituting EXAMPLE 70B for EXAMPLE 2C in EXAMPLE 2D. $^1$H NMR (400 MHz, DMSO-d$_6$) δ 12.10 (m, 1H), 9.60 (s, 1H), 8.53 (d, 1H), 8.28 (d, 1H), 7.85 (dd, 1H), 7.77 (d, 3H), 7.52 (m, 2H), 7.41 (d, 1H), 7.31 (dd, 1H), 7.20 (m, 4H), 7.12 (m, 4H), 6.94 (d, 1H), 4.18 (m, 1H), 3.85 (m, 7H), 3.38 (d, 2H), 3.11 (m, 6H), 2.74 (s, 6H), 2.14 (dd, 2H), 1.96 (s, 3H).

EXAMPLE 71A

This example was made by substituting 2,4-difluorophenylboronic acid for 4-chlorophenylboronic acid in EXAMPLE 2B.

EXAMPLE 71B

This example was made by substituting EXAMPLE 71A for EXAMPLE 2B in EXAMPLE 2C.

EXAMPLE 71C

This example was made by substituting EXAMPLE 71B for EXAMPLE 2C in EXAMPLE 2D. $^1$H NMR (400 MHz, DMSO-$d_6$) δ 12.07 (br s, 1H), 9.53 (br s, 1H), 8.53 (d, 1H), 8.27 (d, 1H), 7.85 (dd, 1H), 7.76 (d, 2H), 7.54 (quintet, 2H), 7.44 (m, 1H), 7.35 (m, 2H), 7.15 (m, 6H), 6.93 (d, 2H), 4.17 (m, 1H), 3.38 (d, 2H), 3.12 (m, 4H), 2.74 (s, 3H), 2.73 (s, 3H), 2.13 (dd, 2H).

EXAMPLE 72A

This example was made by substituting (2-benzenesulfonylethyl)carbamic acid tert-butyl ester, prepared as described in WO2001-U.S. Pat. No. 11,395, for EXAMPLE 66A in EXAMPLE 66B.

EXAMPLE 72B

This example was made by substituting EXAMPLE 72A for EXAMPLE 21C in EXAMPLE 21D.

EXAMPLE 72C

This example was made by substituting EXAMPLE 72B for 4-(((1R)-3-(dimethylamino)-1-((phenylsulfanyl)methyl)propyl)amino)-3-nitrobenzenesulfonamide in EXAMPLE 1D. $^1$H NMR (400 MHz, DMSO-$d_6$) δ 12.09 (br s, 1H), 9.60 (br s, 1H), 8.56 (d, 1H), 8.55 (m, 1H), 7.91 (dd, 1H), 7.84 (m, 2H), 7.75 (d, 3H), 7.67 (tt, 1H), 7.54 (m, 2H), 7.48 (m, 4H), 7.37 (m, 3H), 7.13 (d, 2H), 6.92 (d, 2H), 4.40 (br s, 2H), 3.82 (br s, 2H), 3.79 (s, 2H), 3.29 (br s, 2H), 3.13 (br s, 2H), 2.81 (br s, 2H).

EXAMPLE 73

This example was made by substituting EXAMPLE 72B for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 12.10 (br s, 1H), 9.52 (br s, 1H), 8.56 (d, 1H), 8.55 (m, 1H), 7.91 (dd, 1H), 7.84 (m, 2H), 7.76 (d, 2H), 7.67 (tt, 1H), 7.54 (m, 6H), 7.39 (m, 2H), 7.34 (m, 1H), 7.14 (d, 1H), 6.92 (d, 2H), 4.38 (br s, 2H), 3.92 (br s, 2H), 3.78 (s, 4H), 3.26 (br s, 2H), 3.09 (br s, 2H), 2.86 (br s, 2H).

EXAMPLE 74

This example was made by substituting EXAMPLE 31E for 4-(((1R)-3-(dimethylamino)-1-((phenylsulfanyl)methyl)propyl)-amino)-3-nitrobenzenesulfonamide in EXAMPLE 1D. $^1$H NMR (400 MHz, DMSO-$d_6$) δ 12.06 (br s, 1H), 9.88 (br s, 1H), 8.68 (d, 1H), 8.54 (d, 1H), 7.86 (dd, 1H), 7.76 (d, 2H), 7.72 (m, 1H), 7.50 (m, 4H), 7.46 (m, 2H), 7.41 (d, 1H), 7.37 (m, 2H), 7.26 (m, 2H), 7.07 (t, 2H), 6.97 (t, 1H), 6.92 (d, 2H), 4.73 (quintet, 1H), 4.44 (dd, 1H), 4.31 (dd, 1H), 4.24 (br s, 2H), 4.17 (dd, 1H), 3.75 (m, 2H), 3.24 (br s, 4H), 2.88 (br s, 4H).

EXAMPLE 75A

This example was made by substituting 5-methylthiophene-2-boronic acid for 4-chlorophenylboronic acid in EXAMPLE 2B.

EXAMPLE 75B

This example was made by substituting EXAMPLE 75A for EXAMPLE 2B in EXAMPLE 2C.

EXAMPLE 75C

This example was made by substituting EXAMPLE 75B for EXAMPLE 2C in EXAMPLE 2D. $^1$H NMR (400 MHz, DMSO-$d_6$) δ 12.07 (br s, 1H), 10.00 (br s, 1H), 9.58 (br s, 1H), 8.55 (d, 1H), 8.29 (d, 1H), 7.85 (dd, 1H), 7.79 (d, 2H), 7.70 (br s, 1H), 7.47 (m, 3H), 7.23 (d, 2H), 7.18 (m, 2H), 7.14 (m, 2H), 7.03 (d, 1H), 6.97 (d, 2H), 6.86 (m, 1H), 4.40 (br s, 2H), 4.19 (m, 1H), 3.39 (d, 3H), 3.13 (m, 3H), 2.99 (br s, 2H), 2.75 (s, 6H), 2.48 (s, 3H), 2.15 (dd, 2H).

EXAMPLE 76A

This example was made by substituting EXAMPLE 31C for EXAMPLE 67A in EXAMPLE 67B.

EXAMPLE 76B

This example was made by substituting EXAMPLE 76A for EXAMPLE 66A in EXAMPLE 66B.

EXAMPLE 76C

This example was made by substituting EXAMPLE 76B for EXAMPLE 21C in EXAMPLE 21D.

EXAMPLE 76D

This example was made by substituting EXAMPLE 76C for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 12.09 (br s, 1H), 9.87 (br s, 1H), 8.50 (d, 1H), 8.48 (d, 1H), 7.82 (d, 2H), 7.77 (dd, 1H), 7.75 (m, 1H), 7.71 (dd, 2H), 7.53 (m, 4H), 7.39 (m, 2H), 7.34 (m, 1H), 7.25 (m, 3H), 7.12 (d, 1H), 6.96 (d, 2H), 4.88 (sextet, 1H), 4.80 (quintet, 1H), 4.46 (dd, 1H), 4.28 (br s, 2H), 4.23 (dd, 1H), 4.09 (dd, 1H), 3.86 (dd, 1H), 3.14 (br s, 2H), 2.96 (br s, 4H).

EXAMPLE 77

This example was made by substituting EXAMPLE 76c for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-$d_6$) δ 12.11 (br s, 1H), 9.90 (br s, 1H), 8.50 (d, 1H), 8.48 (d, 1H), 7.82 (d, 2H), 7.77 (dd, 1H), 7.75 (m, 1H), 7.71 (dd, 2H), 7.52 (m, 2H), 7.48 (t, 2H), 7.42 (t, 1H), 7.36 (m, 2H), 7.23 (m, 3H), 7.12 (d, 1H), 6.96 (d, 2H), 4.88 (sextet, 1H), 4.80 (quintet, 1H), 4.46 (dd, 1H), 4.30 (br s, 2H), 4.22 (dd, 1H), 4.09 (dd, 1H), 3.86 (dd, 1H), 3.17 (br s, 2H), 2.89 (br s, 4H).

EXAMPLE 78

This example was made by substituting EXAMPLE 832175D for EXAMPLE 49A in EXAMPLE 49B. $^1$H NMR (500 MHz, DMSO-$_6$) δ 11.96 (br s, 1H), 10.46 (br s, 1H), 8.60 (d, 1H), 8.49 (d, 1H), 7.95 (dd, 1H), 7.76 (d, 2H), 7.69 (m, 1H), 7.51 (m, 4H), 7.40 (t, 4H), 7.32 (m, 1H), 7.24 (m, 4H), 6.92 (d, 2H), 4.69 (br s, 1H), 4.25 (br s, 2H), 3.97 (br s, 2H), 3.68 (m, 2H), 3.29 (br s, 4H), 2.91 (s, 3H), 2.75 (br s, 2H).

EXAMPLE 79

This example was made by substituting EXAMPLE 837538C and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. NMR (500 MHz, DMSO-$d_6$) δ $^1$H NMR (500 MHz, DMSO-$d_6$) δ 8.50 (d, 1H), 8.36 (d, 1H), 7.79 (dd, 1H), 7.72 (d, 2H), 7.36 (d, 2H), 7.28 (d, 2H), 7.21 (t, 2H), 7.15 (d, 1H), 7.12 (d, 2H), 7.03 (d, 1H), 6.84 (d, 2H), 4.13 (m, 1H), 3.52 (m, 4H), 3.38 (m, 4H), 3.21 (br s, 4H), 2.82 (br s, 2H), 2.45 (m, 4H), 2.32 (br s, 4H), 2.20 (br s, 2H), 2.17 (br s, 2H), 2.00 (m, 1H), 1.86 (m, 1H), 1.67 (m, 4H).

EXAMPLE 81A

This example was made by substituting 4-bromophenylboronic acid for 4-chlorophenylboronic acid in EXAMPLE 2B.

EXAMPLE 81B

This example was made by substituting EXAMPLE 81A for EXAMPLE 2B in EXAMPLE 2C.

EXAMPLE 81C

This example was made by substituting EXAMPLE 81B for EXAMPLE 2C in EXAMPLE 2D. $^1$H NMR (500 MHz, DMSO-$d_6$) δ 12.06 (br s, 1H), 9.79 (br s, 1H), 9.47 (br s, 1H), 8.54 (d, 1H), 8.28 (d, 1H), 7.86 (dd, 1H), 7.77 (d, 2H), 7.69 (br s, 1H), 7.64 (d, 2H), 7.50 (m, 2H), 7.35 (m, 3H), 7.23 (m, 2H), 7.14 (m, 4H), 6.93 (d, 2H), 4.29 (br s, 2H), 4.19 (m, 1H), 3.77 (br s, 2H), 3.14 (m, 3H), 2.74 (s, 6H), 2.14 (dd, 2H).

EXAMPLE 82A

4'-chloro-biphenyl-2-carbonitrile, prepared as described in J. Org. Chem. (1984), 49(9), 1594-1603, (0.35 g) in diethyl ether (25 mL) at −75° C. was treated with titanium isopropoxide (0.53 mL) and 3M ethyl magnesium bromide in diethyl ether (1.2 mL), stirred for 10 minutes, stirred at 25° C. for 1 hour, treated with BF$_3$-diethyl etherate (0.41 mL), stirred for 1 hour, treated with 1M HCl (5 mL) then 10% NaOH (15 mL), and extracted with diethyl ether. The extract was dried (MgSO$_4$), filtered, and concentrated. The concentrate was flash chromatographed on silica gel 10%-50% ethyl acetate/hexanes).

EXAMPLE 82B

A mixture of 4-(bis(2-methanesulfonyloxyethyl)-amino) benzoic acid ethyl ester, prepared as described in J. Med. Chem. (1977), 21(1), 16-26, (80.6 mg), EXAMPLE 82A (58.5 mg), and potassium carbonate (69.1 mg) in acetonitrile (5 mL) in a microwave reactor at 160° C. was stirred for 30 minutes, treated with ethyl acetate (10 mL), filtered, and concentrated. The concentrate flash chromatographed on silica gel with 10-30% ethyl acetate/hexanes.

EXAMPLE 82C

This example was made by substituting EXAMPLE 82B for EXAMPLE 2B in EXAMPLE 2C.

EXAMPLE 82D

This example was made by substituting EXAMPLE 82C for EXAMPLE 2C in EXAMPLE 2D. $^1$H NMR (400 MHz, DMSO-$d_6$) δ 12.02 (br s, 1H), 9.49 (br s, 1H), 8.54 (d, 1H), 8.28 (d, 1H), 7.86 (dd, 1H), 7.73 (d, 2H), 7.47 (m, 5H), 7.38 (m, 2H), 7.23 (d, 2H), 7.14 (m, 5H), 6.89 (d, 2H), 4.18 (m, 2H), 3.39 (d, 2H), 3.20 (m, 6H), 2.75 (s, 3H), 2.74 (s, 3H), 2.44 (br s, 4H), 2.13 (dd, 2H), 1.01 (br s, 2H), 0.82 (br s, 2H).

EXAMPLE 83A

A mixture of 2M dimethylamine in THF (27 mL), (R)-2-benzyloxycarbonylamino-3-phenylthiopropionic acid (5.8 g), HoBT (2.67 g), and EDAC.HCl (5.2 g) in THF (50 mL) was stirred for 18 hours at 25° C., treated with water and extracted with dichloromethane. The extract was dried (MgSO$_4$), filtered, and concentrated. The concentrate was flash chromatographed on silica gel with 15-50% ethyl acetate/hexanes.

EXAMPLE 83B

This example was prepared by substituting EXAMPLE 83A for EXAMPLE 18B in EXAMPLE 18C.

EXAMPLE 83C

This example was prepared by substituting EXAMPLE 83B for EXAMPLE 18E in EXAMPLE 18F.

EXAMPLE 83D

This example was prepared by substituting EXAMPLE 83C for EXAMPLE 21C in EXAMPLE 21D.

EXAMPLE 83E

This example was made by substituting EXAMPLE 837538C and EXAMPLE 83D for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 12.11 (br s, 1H), 9.46 (br s, $^1$H), 9.36 (br s, 1H), 8.52 (d, 1H), 8.28 (d, 1H), 7.88 (dd, 1H), 7.79 (d, 2H), 7.41 (d, 2H), 7.35 (d, 2H), 7.17 (m, 4H), 7.09 (m, 2H), 6.96 (d, 2H), 4.67 (m, 1H), 3.89 (br s, 2H), 3.75 (m, 4H), 3.43 (m, 2H), 3.36 (m, 4H), 3.16 (br s, 2H), 2.82 (s, 3H), 2.75 (s, 3H), 2.26 (br s, 2H), 2.21 (br s, 2H), 1.71 (br s, 4H).

EXAMPLE 84

This example was made by substituting EXAMPLE 83D for 4-((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 12.12 (br s, 1H), 9.94 (br s, 1H), 9.42 (br s, 1H), 8.51 (d, 1H), 8.28 (d, 1H), 7.87 (dd, 1H), 7.78 (d, 2H), 7.73 (br s, 1H), 7.52 (d, 4H), 7.39 (d, 2H), 7.34 (m, 2H), 7.17 (m, 2H), 7.09 (m, 3H), 6.93 (d, 2H), 4.66

(m, 1H), 4.29 (br s, 2H), 3.85 (br s, 2H), 3.75 (t, 2H), 3.43 (d, 2H), 3.36 (m, 2H), 3.12 (br s, 4H), 2.87 (br s, 3H), 2.82 (s, 3H).

EXAMPLE 85A

This example was prepared by substituting diethylamine for dimethylamine in EXAMPLE 83A.

EXAMPLE 85B

This example was prepared by substituting EXAMPLE 85A for EXAMPLE 18B in EXAMPLE 18C.

EXAMPLE 85C

This example was prepared by substituting EXAMPLE 85B for EXAMPLE 18E in EXAMPLE 18F.

EXAMPLE 85D

This example was prepared by substituting EXAMPLE 85C for EXAMPLE 21C in EXAMPLE 21D.

EXAMPLE 85E

This example was made by substituting EXAMPLE 85D for 4-(((1R)-3-(dimethylamino)-1-((phenylsulfanyl)methyl) propyl)amino)-3-nitrobenzenesulfonamide in EXAMPLE 2D. $^1$H NMR (400 MHz, DMSO-$d_6$) δ 12.15 (br s, 1H), 9.99 (br s, 1H), 9.02 (br s, 1H), 8.51 (d, 1H), 8.33 (d, 1H), 7.87 (dd, 1H), 7.77 (d, 2H), 7.74 (br s, 1H), 7.52 (d, 4H), 7.39 (d, 2H), 7.33 (m, 2H), 7.18 (m, 2H), 7.10 (m, 3H), 6.93 (d, 2H), 4.60 (m, 1H), 4.26 (br s, 2H), 3.85 (br s, 2H), 3.43 (m, 2H), 3.36 (dd, 2H), 3.15 (m, 6H), 2.92 (br s, 4H), 1.19 (m, 6H).

EXAMPLE 86A

This example was prepared by substituting morpholine for dimethylamine in EXAMPLE 83A.

EXAMPLE 86B

This example was prepared by substituting EXAMPLE 86A for EXAMPLE 18B in EXAMPLE 18C.

EXAMPLE 86C

This example was prepared by substituting EXAMPLE 86B for EXAMPLE 18E in EXAMPLE 18F.

EXAMPLE 86D

This example was prepared by substituting EXAMPLE 86C for EXAMPLE 21C in EXAMPLE 21D.

EXAMPLE 86E

This example was made by substituting EXAMPLE 86D for 4-(((1R)-3-(dimethylamino)-1-((phenylsulfanyl)methyl) propyl)amino)-3-nitrobenzenesulfonamide in EXAMPLE 2D. $^1$H NMR (400 MHz, DMSO-$d_6$) δ 12.13 (br s, 1H), 9.95 (br s, 1H), 8.51 (d, 1H), 8.33 (d, 1H), 7.86 (dd, 1H), 7.78 (d, 2H), 7.74 (br s, 1H), 7.52 (d, 4H), 7.39 (d, 2H), 7.34 (m, 1H), 7.25 (d, 1H), 7.19 (m, 2H), 7.09 (m, 3H), 6.93 (d, 2H), 4.59 (br s, 1H), 4.29 (br s, 2H), 3.39 (m, 4H), 3.12 (br s, 6H), 2.90 (br s, 3H).

EXAMPLE 87

This example was made by substituting EXAMPLE 837538C and EXAMPLE 85D for EXAMPLE 2C and 4-(((1R)-3-(dimethylamino)-1-((phenylsulfanyl)methyl) propyl)amino)-3-nitrobenzenesulfonamide, respectively, in EXAMPLE 2D. $^1$H NMR (400 MHz, DMSO-$d_6$) δ 12.16 (br s, 1H), 9.67 (br s, 1H), 9.06 (br s, 1H), 8.52 (d, 1H), 8.33 (d, 1H), 7.87 (dd, 1H), 7.79 (d, 2H), 7.41 (d, 2H), 7.33 (d, 1H), 7.17 (m, 4H), 7.10 (m, 3H), 6.96 (d, 2H), 4.61 (m, 1H), 3.88 (br s, 2H), 3.76 (m, 4H), 3.59 (br s, 2H), 3.42 (m, 2H), 3.15 (m, 4H), 2.80 (br s, 2H), 2.27 (br s, 2H), 2.22 (br s, 2H), 1.71 (br s, 4H), 1.19 (dd, 6H).

EXAMPLE 88

This example was made by substituting EXAMPLE 837538C and EXAMPLE 86D for EXAMPLE 2C and 4-(((1R)-3-(dimethylamino)-1-((phenylsulfanyl)methyl) propyl)amino)-3-nitrobenzenesulfonamide, respectively, in EXAMPLE 2D. $^1$H NMR (400 MHz, DMSO-$d_6$) δ 12.11 (br s, 1H), 9.97 (br s, 1H), 9.55 (br s, 1H), 8.51 (d, 1H), 8.38 (d, 1H), 7.86 (dd, 1H), 7.79 (d, 2H), 7.41 (d, 2H), 7.25 (d, 1H), 7.17 (m, 5H), 7.09 (m, 2H), 6.96 (d, 2H), 4.58 (m, 1H), 3.90 (br s, 2H), 3.39 (m, 4H), 3.17 (br s, 4H), 2.80 (br s, 2H), 2.26 (br s, 2H), 2.22 (br s, 2H), 1.71 (br s, 4H).

EXAMPLE 89

A mixture of EXAMPLE 833566 (44.9 mg) and 2.47 mmol/g MP-BH$_3$CN (0.81 g) in 1:1 dichloromethane/methanol at 25° C. (4 mL) was treated with DIEA and acetic acid to pH 5-6, shaken for 18 hours, filtered, and concentrated. The concentrate was chromatographed on C-18 with 30-100% acetonitrile/water/0.1% TFA. $^1$H NMR (500 MHz, DMSO-$d_6$) δ 12.13 (br s, 1H), 9.76 (br s, 1H), 9.18 (br s, 1H), 8.54 (d, 1H), 8.32 (d, 1H), 7.87 (dd, 1H), 7.78 (d, 2H), 7.71 (br s, 1H), 7.53 (m, 4H), 7.41 (d, 2H), 7.34 (m, 1H), 7.23 (m, 3H), 7.14 (m, 3H), 6.93 (d, 2H), 4.33 (br s, 2H), 4.22 (m, 1H), 3.85 (br s, 2H), 3.12 (m, 4H), 2.82 (s, 3H), 2.19 (m, 2H), 0.81 (m, 4H).

EXAMPLE 90A

A mixture of magnesium turnings (0.144 g) and one iodine crystal at 25° C. was treated with 2-phenylbenzyl bromide (1.48 g) in diethyl ether (10 mL), stirred for 3 hours, cooled to 0° C., treated with 4-(4-oxo-piperidine-1-yl)benzoic acid ethyl ester, prepared as described in J. Het. Chem. 1969, 6, 941, (1.48 g) in diethyl ether (5 mL) and THF (5 mL), stirred at 25° C. for 18 hours, and treated with ethyl acetate and aqueous NH$_4$Cl. The extract was extracted with ethyl acetate, and the combined extracts were dried (Na$_2$SO$_4$), filtered, and concentrated. The concentrate was flash chromatographed on silica gel with 25% ethyl acetate/hexane.

EXAMPLE 90B

EXAMPLE 90A (0.27 g) in THF (10 mL) at 25° C. was treated with 60% oily NaH (0.24 g), stirred for 2 hours at 50° C., treated with HMPA (2 mL) and methyl iodide (2 mL), heated at reflux for 18 hours, cooled to 0° C., and treated with ethyl acetate and aqueous NaHSO$_4$. The extract was extracted with ethyl acetate, and the combined extracts were dried (Na$_2$SO$_4$), filtered, and concentrated. The concentrate was flash chromatographed on silica gel with 10% ethyl acetate/hexanes.

EXAMPLE 90C

A mixture of EXAMPLE 90B (0.09 g) and 1M LiOH (1 mL) in dioxane (5 mL) at 60° C. was stirred for 18 hours, and concentrated. The concentrate in water was treated with 2M HCl and filtered.

EXAMPLE 90D

This example was made by substituting EXAMPLE 90C for EXAMPLE 2C in EXAMPLE 2D. $^1$H NMR (400 MHz, DMSO-$d_6$) δ 11.95 (br s, 1H), 9.38 (s, 1H), 8.54 (d, 1H), 8.28 (d, 1H), 7.86 (dd, 1H), 7.70 (d, 2H), 7.30 (m, 10H), 7.15 (m, 4H), 6.82 (d, 2H), 4.19 (m, 1H), 3.45 (m, 4H), 3.13 (m, 2H), 3.04 (s, 3H), 2.88 (m, 4H), 2.74 (d, 6H), 2.14 (q, 2H), 1.47 (m, 2H), 1.18 (m, 2H).

EXAMPLE 91A

A mixture of magnesium turnings (0.432 g) and one iodide crystal at 25° C. was treated with 2-bromobenzyl bromide (4.5 g) in diethyl ether (30 mL), stirred for 3 hours, cooled to 0° C., treated with 4-(4-oxo-piperidine-1-yl)benzoic acid ethyl ester, prepared as described in J. Het. Chem. 1969, 6, 941, (3.7 g) in diethyl ether (20 mL) and THF (10 mL), stirred at 25° C. for 18 hours, and treated with ethyl acetate and aqueous NH$_4$Cl. The extract was extracted with ethyl acetate, and the combined extracts were dried (Na$_2$SO$_4$), filtered, and concentrated. The concentrate was flash chromatographed on silica gel with 50% ethyl acetate/hexane.

EXAMPLE 91B

EXAMPLE 91A (1.6 g) in THF (20 mL) at 25° C. was treated with 60% oily NaH (0.288 g), stirred for 2 hours at 50° C., treated with HMPA (3 mL) and methyl iodide (3 mL), stirred at reflux for 18 hours, cooled to 0° C., and treated with ethyl acetate and aqueous NaHSO$_4$. The extract was extracted with ethyl acetate, and the combined extracts were dried (Na$_2$SO$_4$), filtered, and concentrated. The concentrate was flash chromatographed on silica gel with 10-15% ethyl acetate/hexanes.

EXAMPLE 91C

A mixture of EXAMPLE 91B (0.6 g) and 1M LiOH (5 mL) in dioxane (5 mL) at 60° C. was stirred for 18 hours and concentrated. The concentrate in water was treated with 2M HC, and filtered.

EXAMPLE 91D

This example was made by substituting EXAMPLE 91C for EXAMPLE 2C in EXAMPLE 2D.

EXAMPLE 91E

A mixture of EXAMPLE 91D (0.08 g), 3-pyridineboronic acid (0.04 g), Pd(dppf)$_2$Cl$_2$ (0.01 g), and Cs$_2$CO$_3$ (0.1 g) in DMF (1 mL) at 80° C. was stirred for 2 days and treated with ethyl acetate and brine. The extract was extracted with ethyl acetate, and the extracts were combined and dried (Na$_2$SO$_4$), filtered, and concentrated. The concentrate was purified by high pressure liquid chromatography on a Waters Symmetry C$_8$ column (25 mm×100 mm, 7 μm particle size) with 10-100% acetonitrile/0.1% aqueous TFA over 8 minutes at a flow rate of 40 mL/minute. $^1$H NMR (400 MHz, DMSO-$d_6$) δ 9.44 (s, 1H), 8.64 (d, 2H), 8.54 (d, 1H), 8.28 (d, 1H), 7.97 (dd, 1H), 7.86 (dd, 1H), 7.70 (d, 2H), 7.62 (m, 1H), 7.37 (m, 3H), 7.23 (m, 3H), 7.13 (m, 4H), 6.83 (d, 2H), 4.19 (m, 1H), 3.45 (m, 2H), 3.39 (d, 2H), 3.13 (m, 2H), 2.99 (s, 3H), 2.88 (m, 4H), 2.74 (d, 6H), 2.14 (q, 2H), 1.49 (d, 2H), 1.20 (dt, 2H).

EXAMPLE 92

This example was prepared by substituting 4-pyridineboronic acid for 4-pyridineboronic acid in EXAMPLE 91. $^1$H NMR (400 MHz, DMSO-$d_6$) δ 9.47 (br s, 1H), 8.75 (d, 2H), 8.53 (d, 1H), 8.28 (d, 1H), 7.86 (dd, 1H), 7.70 (d, 2H), 7.66 (d, 2H), 7.39 (m, 3H), 7.23 (d, 2H), 7.13 (m, 4H), 6.83 (d, 2H), 4.18 (m, 1H), 3.46 (m, 2H), 3.39 (d, 2H), 3.13 (m, 2H), 2.99 (s, 3H), 2.86 (m, 4H), 2.74 (d, 6H), 2.14 (q, 2H), 1.49 (d, 2H), 1.20 (dt, 2H).

EXAMPLE 93

This example was prepared by substituting thiophene-2-boronic acid for 4-pyridineboronic acid in EXAMPLE 91. NMR (400 MHz, DMSO-$d_6$) δ 8.44 (d, 1H), 8.26 (d, 1H), 7.79 (dd, 1H), 7.67 (d, 2H), 7.57 (dd, 1H), 7.3 (m, 8 H), 7.17 (d, 1H), 7.10 (m, 2H), 6.87 (d, 1H), 6.71 (d, 2H), 4.05 (m, 1H), 3.30 (m, 4H), 3.12 (s, 3H), 3.03 (s, 2H), 2.74 (m, 4H), 2.43 (s, 6H), 2.00 (m, 2H), 1.55 (d, 2H), 1.30 (dt, 2H).

EXAMPLE 94

This example was prepared by substituting thiophene-3-boronic acid for 4-pyridineboronic acid in EXAMPLE 91. $^1$H NMR (400 MHz, DMSO-$d_6$) δ 8.44 (d, 1H), 8.26 (d, 1H), 7.79 (dd, 1H), 7.67 (d, 2H), 7.59 (m, 1H), 7.44 (m, 1H), 7.28 (m, 7H),.7.16 (m, 2H), 6.87 (d, 1H), 6.71 (d, 2H), 4.05 (m, 1H), 3.30 (m, 4H), 3.07 (s, 3H), 2.94 (s, 2H), 2.74 (m, 4H), 2.45 (s, 6H), 2.00 (m, 2H), 1.49 (d, 2H), 1.25 (dt, 2H).

EXAMPLE 95A

N-methyl-2,2,2-trifluoroacetamide (6.35 g) in diethyl ether (25 mL) at −15° C. was treated with lithium aluminum hydride (3.8 g) in diethyl ether (25 mL) over 1 hour, stirred for 2 hours, stirred at 25° C. for 16 hours, cooled to 0° C., treated with water, and distillated at 34-36° C. The distillate was treated with HCl and filtered.

EXAMPLE 95B

This example was made by substituting EXAMPLE 95A for isopropylamine in EXAMPLE 28. $^1$H NMR (400 MHz, DMSO-$d_6$) δ 8.67 (d, 1H), 8.52 (d, 1H), 7.83 (dd, 1H), 7.74 (d, 2H), 7.52 (d, 1H), 7.47 (m, 4H), 7.38 (m, 2H), 7.24 (m, 2H), 7.14 (m, 4H), 6.82 (d, 2H), 4.46 (m, 1H), 4.12 (q, 2H), 3.35 (m, 10H), 3.04 (s, 3H), 2.42 (m, 4H).

EXAMPLE 96A

This example was made by substituting 2,2,2-trifluoroethylamine for isopropylamine in EXAMPLE 28.

EXAMPLE 96

Borane.dimethyl sulfide (0.37 mL) was treated with EXAMPLE 96A (110 mg) in THF (2 mL) at 25° C., for 5 hours, treated with methanol, and concentrated. The concentrate was purified by HPLC with 0-70% acetonitrile/water/ 0.1% TFA. $^1$H NMR (400 MHz, DMSO-$d_6$) δ 8.53 (d, 1H), 8.30 (d, 1H), 7.84 (dd, 1H), 7.76 (d, 2H), 7.52 (m, 3H), 7.35 (m, 4H), 7.15 (m, 6H), 6.92 (d, 2H), 4.46 (m, 1H), 3.75 (m, 2H), 3.5 (m, 12H), 2.42 (m, 4H).

EXAMPLE 97A

This example was made by substituting methyl trifluoroacetamide for EXAMPLE 100A in EXAMPLE 100B.

EXAMPLE 97B

This example was made by substituting EXAMPLE 97A and EXAMPLE 30A for isopropylamine and EXAMPLE 27E in EXAMPLE 28.

EXAMPLE 97C

This example was made by substituting EXAMPLE 97C for EXAMPLE 96A in EXAMPLE 96.

EXAMPLE 97D

This example was made by substituting EXAMPLE 97C for 4-(((1R)-3-(dimethylamino)-1-((phenylsulfanyl)methyl) propyl)amino)-3-nitrobenzenesulfonamide in EXAMPLE 2D. $^1$H NMR (400 MHz, DMSO-$d_6$) δ 8.72 (d, 1H), 8.59 (d, 1H), 7.99 (dd, 1H), 7.95 (d, 2H), 7.71 (m, 3H), 7.55 (m, 3H), 7.41 (d, 2H), 7.29 (m, 5H), 7.11 (d, 2H), 4.46 (br s, 1H), 4.33 (m, 1H), 3.75 (m, 12H), 3.31 (q, 2H), 2.78 (m, 2H), 2.68 (s, 3H), 2.09 (m, 2H).

EXAMPLE 98

This example was made by substituting EXAMPLE 32D and 4-(((1R)-3-(4-morpholinyl)-1-((phenylsulfanyl)methyl) propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl) amino)-3-nitrobenzenesulfonamide, respectively, in EXAMPLE 2D. $^1$H NMR (400 MHz, DMSO-$d_6$) δ 9.71 (s, 1H), 8.54 (d, 1H), 8.29 (d, 1H), 7.87 (dd, 1H), 7.69 (d, 2H), 7.46 (d, 2H), 7.30 (m, 7H), 7.14 (m, 4H), 6.82 (d, 2H), 4.18 (m, 1H), 3.95 (m,2H), 3.67 (m, 4H), 3.39 (m, 4H), 3.19 (m, 2H), 3.03 (s, 3H), 3.00 (m, 2H), 2.85 (m, 4H), 2.17 (m, 2H), 1.47 (d, 2H), 1.17 (t, 2H).

EXAMPLE 99

This example was made by substituting EXAMPLE 32D and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)-amino)-3-nitrobenzenesulfonamide, respectively, in EXAMPLE 2D. $^1$H NMR (400 MHz, DMSO-$d_6$) δ 8.74 (t, 1H), 8.53 (d, 1H), 7.90 (dd, 1H), 7.68 (d, 2H), 7.46 (d, 2H), 7.46 (m, 3H), 7.28 (m, 6H), 7.16 (m, 3H), 6.81 (d, 2H), 3.66 (q, 2H) 3.41 (m, 2H), 3.03 (s, 3H), 2.48 (m, 4H), 1.47 (m, 2H), 1.18 (dt, 2H).

EXAMPLE 100A

Trifluoroacetic anhydride (15 g) in diethyl ether (80 mL) at −10° C. was treated with ethylamine for 40 minutes and distilled under vacuum at 68° C.

EXAMPLE 100B

EXAMPLE 100A (7.8 g) in diethyl ether (25 mL) at −15° C. was treated with lithium aluminum hydride (4.17 g) in diethyl ether (25 mL) over 1 hour, stirred for 2 hours then at 25° C. for 16 hours, cooled to 0° C., treated with water (10 mL), 15% NaOH (10 mL), and water (30 mL), stirred a for 30 minutes, and filtered. The filtrate was washed with water and brine, dried ($Na_2SO_4$), and filtered. The filtrate was treated with HCl, and filtered.

EXAMPLE 100C

This example was made by substituting EXAMPLE 100B and EXAMPLE 30A for isopropylamine and EXAMPLE 27E in EXAMPLE 28.

EXAMPLE 100D

This example was made by substituting EXAMPLE 100C for EXAMPLE 96A in EXAMPLE 96.

EXAMPLE 100E

This example was made by substituting EXAMPLE 100D for 4-(((1R)-3-(dimethylamino)-1-((phenylsulfanyl)methyl) propyl)amino)-3-nitrobenzenesulfonamide in EXAMPLE 2D. $^1$H NMR (400 MHz, DMSO-$d_6$) δ 11.90 (br s, 1H), 8.51 (d, 1H), 8.32 (d, 1H), 7.80 (dd, 1H), 7.74 (d, 2H), 7.46 (m, 5H), 7.37 (m, 2H), 7.24 (d, 2H), 7.12 (m, 3H), 7.02 (d, 1H), 6.89 (d, 2H), 4.12 (m, 1H), 3.42 (s, 2H), 3.35 (m, 6H), 3.13 (q, 2H), 2.63 (t, 2H), 2.56 (q, 2H), 2.40 (s, 4H), 1.90 (m, 2H), 0.88 (t, 3H).

EXAMPLE 101

This example was made by substituting 2-fluoroethylamine for isopropylamine in EXAMPLE 35B. $^1$H NMR (400 MHz, DMSO-$d_6$) δ 8.80 (s, 2H), 8.53 (d, 1H), 8.26 (d, 1H), 7.86 (dd, 1H), 7.75 (m, 3H), 7.52 (m, 4H), 7.38 (d, 2H), 7.33 (m, 1H), 7.15 (m, 5H), 6.92 (d, 2H), 4.71 (t, 1H), 4.61 (t, 1H), 4.30 (m, 2H), 4.21 (m, 1H), 3.38 (d, 2H), 3.25 (m, 12H), 2.11 (m, 2H).

EXAMPLE 102

This example was made by substituting 2,2-difluoroethylamine for isopropylamine in EXAMPLE 35B. $_1$H NMR (400 MHz, DMSO-$d_6$) δ 9.15 (s, 2H), 8.53 (d, 1H), 8.26 (d, 1H), 7.86 (dd, 1H), 7.77 (d, 2H), 7.74 (m, 1H), 7.52 (m, 4H), 7.38 (d, 2H), 7.33 (m, 1H), 7.15 (m, 5H), 6.92 (d, 2H), 6.36 (tt, 1H), 4.23 (m, 1H), 4.00 (m, 4H), 3.49 (t, 2H), 4.39 (d, 2H), 3.10 (m, 4H), 2.90 (m, 2H), 2.54 (s, 2H), 2.13 (m, 2H).

EXAMPLE 103A

A mixture of EXAMPLE 2 (250 mg) and 10% Pd on carbon (100 mg) in methanol (5 mL) and ethyl acetate (5 mL) at 25° C. was stirred under $H_2$ (balloon) for 18 hours, filtered through diatomaceous earth (Celite®), and concentrated.

EXAMPLE 103B

A mixture of EXAMPLE 103A (0.06 g) in 80% formic acid (3 mL) at 100° C. was stirred for 3 hours and concentrated. The concentrate was purified by high pressure liquid chromatography on a Waters Symmetry $C_8$ column (25 mm×100 mm, 7 μm particle size) with 10-100% acetonitrile/0.1% aqueous TFA over 8 minutes at a flow rate of 40 mL/minute. $^1$H NMR (400 MHz, DMSO-$d_6$) δ 12.01 (s, 1H), 9.64 (s, 1H)., 8.56 (s, 1H), 8.22 (s, 1H), 7.83 (d, 1H), 7.75 (m, 4H), 7.52 (m, 4H), 7.40 (d, 2H), 7.33 (m, 1H), 7.14 (m, 3H), 7.07 (m, 1H), 6.92 (d, 2H), 4.76 (m, 1H), 3.85 (m, 6H), 3.66 (d, 2H), 3.15 (m, 4H), 2.71 (s, 6H), 2.45 (m, 2H).

EXAMPLE 104

A mixture of EXAMPLE 103A (0.06 g) and 12M HCl (0.56 mL) in acetic acid (2 mL) at 0° C. was treated with $NaNO_2$ (7.2 mg) in water (0.38 mL), stirred for 2 hours, and concentrated. The concentrate was purified by high pressure liquid chromatography on a Waters Symmetry $C_8$ column (25 mm×100 mm, 7 µm particle size) with 10-100% acetonitrile/0.1% aqueous TFA over 8 minutes at a flow rate of 40 mL/minute. $^1$H NMR (400 MHz, DMSO-$d_6$) δ 9.50 (s, 1H), 8.57 (s, 1H), 8.06 (d, 1H), 7.99 (d, 1H), 7.77 (d, 2H), 7.74 (m, 1H), 7.52 (m, 4H), 7.40 (d, 2H), 7.33 (m, 1H), 7.04 (m, 5H), 6.92 (d, 2H), 5.24 (m, 1H), 3.74 (m, 2H), 3.45 (m, 6H), 3.15 (m, 4H), 2.71 (s, 6H).

EXAMPLE 105A

3-Cyano-4-fluorobenzenesulfonyl chloride (5 g) in dichloromethane (110 mL) at −78° C. was treated with 7M $NH_3$ in methanol (8.1 mL), stirred at −20° C., and acidified with 1M HCl. The water layer was separated and extracted with dichloromethane. The extract was dried ($MgSO_4$), filtered, and concentrated. The concentrate was recrystallized from hexane/ethyl acetate.

EXAMPLE 105B

This example was made by substituting EXAMPLE 18C with EXAMPLE 18E in EXAMPLE 18F.

EXAMPLE 105B

A mixture of EXAMPLE 105A (0.5 g), EXAMPLE 105B (0.5 g), and DIEA (0.8 mL) in THF (6 mL) at 80° C. was stirred for 16 hours and concentrated. The concentrate was flash chromatographed on silica gel with 5% methanol/dichloromethane.

EXAMPLE 105C

A mixture of EXAMPLE 105B (0.05 g) and KOH (0.031 g) in tert-butanol (2 mL) at reflux was stirred for 6 hours and concentrated. The concentrate was flash chromatographed on silica gel with 5-10% methanol/dichloromethane.

EXAMPLE 105D

This example was made by substituting EXAMPLE 105C for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 11.82 (s, 1H), 9.63 (s, 1H), 8.82 (d, 1H), 8.15 (s, 1H), 7.76 (d, 2H), 7.70 (d, 1H), 7.52 (d, 4H), 7.39 (d, 2H), 7.33 (m, 2H), 7.27 (m,. 2H), 7.19 (m, 1H), 6.92 (d, 2H), 6.69 (s, 1H), 4.14 (m, 1H), 3.86 (m, 2H), 3.45 (m, 6H), 3.15 (m, 4H), 2.74 (s, 6H), 2.10 (m, 1H), 1.96 (m, 1H).

EXAMPLE 106B

A mixture of EXAMPLE 1A (1.5 g), 2-bromobenzoyl chloride (1.5 g), and DIEA (2 mL) in THF (20 mL) at 25° C. was stirred for 16 hours, filtered, and concentrated.

EXAMPLE 106C

EXAMPLE 106B (0.3 g), 4-(N,N-dimethylamino)phenylboronic acid (0.146 g), $PdCl_2(PPh_3)_4$ (0.03 g), and 2M $Na_2CO_3$ (0.4 mL) in 7:3:2 DME/water/ethanol (3 mL) at 150° C. in a 10 mL microwave reaction tube was stirred in a microwave reactor for 20 minutes, filtered through diatomaceous earth (Celite®) and concentrated. The concentrate was flash chromatographed on silica gel with 5-50% ethyl acetate/hexanes.

EXAMPLE 106D

This example was made by substituting EXAMPLE 106C for EXAMPLE 2B in EXAMPLE 2C.

EXAMPLE 106E

This example was made by substituting EXAMPLE 106D for EXAMPLE 2C in EXAMPLE 2D. $^1$H NMR (400 MHz, DMSO-$d_6$) δ 12.01 (s, 1H), 9.29 (s, 1H), 8.53 (d, 1H), 8.29 (d, 1H), 7.86 (dd, 1H), 7.30 (m, 11H), 6.80 (d, 2H), 6.73 (d, 2H), 4.18 (m, 1H), 3.50 (m, 4H), 3.39 (m, 4H), 3.04 (m, 6H), 2.78 (s, 6H), 2.74 (d, 6H), 2.14 (m, 2H).

EXAMPLE 107A

This example was prepared by substituting 4-(methylsulfanyl)phenylboronic acid for 4-(N,N-dimethylamino)phenylboronic acid in EXAMPLE 106C.

EXAMPLE 107B

This example was made by substituting EXAMPLE 107A for EXAMPLE 2B in EXAMPLE 2C.

EXAMPLE 107C

This example was made by substituting EXAMPLE 107B for EXAMPLE 2C in EXAMPLE 2D. $^1$H NMR (400 MHz, DMSO-$d_6$) δ 12.01 (s, 1H), 9.38 (s, 1H), 8.53 (d, 1H), 8.29 (d, 1H), 7.86 (dd, 1H), 7.49 (m, 3H), 7.33 (m, 5H), 7.17 (m, 5H), 6.83 (d, 2H), 4.18 (m, 1H), 3.65 (m, 2H), 3.39 (m, 4H), 3.11 (m, 4H), 2.97 (m, 1H), 2.85 (m, 1H), 2.73 (d, 6H), 2.39 (s, 3H), 2.14 (m, 2H).

EXAMPLE 108A

This example was prepared by substituting 4-chlorophenylboronic acid for 4-(N,N-dimethylamino)phenylboronic acid in EXAMPLE 106C.

EXAMPLE 108B

This example was made by substituting EXAMPLE 108A for EXAMPLE 2B in EXAMPLE 2C.

EXAMPLE 108C

This example was made by substituting EXAMPLE 108B for EXAMPLE 2C in EXAMPLE 2D. $^1$H NMR (400 MHz, DMSO-$d_6$) δ 12.01 (s, 1H), 9.38 (s, 1H), 8.53 (d, 1H), 8.29 (d, 1H), 7.86 (dd, 1H), 7.74 (d, 2H), 7.49 (m, 8H), 7.17 (m, 5H), 6.83 (d, 2H), 4.18 (m, 1H), 3.65 (m, 2H), 3.39 (m, 4H), 3.11 (m, 4H), 2.99 (m, 1H), 2.89 (m, 1H), 2.74 (d, 6H), 2.14 (m, 2H).

EXAMPLE 109

This example was made by substituting EXAMPLE 105B for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 11.70 (s, 1H), 9.60 (s, 1H), 7.68 (d, 1H), 7.52 (d, 2H), 7.27 (m, 43H), 7.14 (d, 2H), 7.08 (m, 1H), 7.00 (m, 5H), 6.91 (m, 1H), 6.67 (d, 2H), 6.37 (m, 2H), 3.96 (m, 1H), 3.70 (m, 2H), 3.80 (m, 4H), 3.02 (m, 4H), 2.89 (m, 4H), 2,58 (s, 6H), 1.84 (m, 2H).

EXAMPLE 110A 3,4-dihydroxy-butyric acid methyl ester, prepared as described in Chem. Lett., 1984, 1389, (510 mg) in dimethylamine in THF (19 mL) in a sealed tube at 80° C. was stirred for 12 hours and concentrated. The concentrate was flash chromatographed on silica gel with 0-20% methanol/dichloromethane.

EXAMPLE 110B

A mixture of EXAMPLE 110A (200 mg), benzenethiol (153 μL), and tributylphosphine (372 μL) in THF (10 mL) at 0° C. was treated with 1,1'-(azodicarbonyl)dipiperidine (377 mg), stirred at 25° C. for 12 hours, and treated with ethyl acetate and 1M NaOH. The extract was extracted with ethyl acetate, and the extract was dried (MgSO$_4$), filtered and concentrated. The concentrate was flash chromatographed on silica gel with 0% to 80% ethyl acetate/dichloromethane.

EXAMPLE 110C

EXAMPLE 110B (160 mg) in THF (2.3 mL) at 25° C. was treated with borane.THF (1 mL), stirred for 5 hours, treated with saturated methanolic HCl (3 mL), heated at reflux for 2 hours, and concentrated. The concentrate was flash chromatographed on silica gel with 0-10% NH$_3$-saturated methanol (saturated NH$_3$)/dichloromethane.

EXAMPLE 110D

EXAMPLE 110C (224 mg) in DMF (1 mL) at 0° C. was treated with NaH (40 mg), stirred at 25° C. for 1 hour, cooled to 0° C., treated with 15-crown-5 (146 μL), stirred for 15 minutes, treated with 4-fluoro-3-nitrobenzenesulfonamide, prepared as described in WO02/24636, (110 mg), stirred at 25° C. for 2 hours, treated with saturated NH$_4$Cl (200 μL), and concentrated. The concentrate was flash chromatographed on silica gel with 50-100% ethyl acetate/hexane then switching to 0-10% NH$_3$-saturated methanol/dichloromethane.

EXAMPLE 110E

This example was made by substituting EXAMPLE 110D for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ9.70 (s, 1H), 8.38 (d, 1H), 8.09 (dd, 1H), 7.78 (m, 3H), 7.51 (m, 5H), 7.27 (m, 8H), 6.92 (d, 2H), 5.01 (m, 1H), 3.47 (m, 2H), 3.33 (m, 2H), 3.21 (m, 4H), 3.14 (m, 2H), 3.05 (s, 2H), 2.76 (s, 6H), 2.23 (m, 2H).

EXAMPLE 111

This example was made by substituting 4,4-dimethyl-4,5-dihydro-1H-imidazole for isopropylamine in EXAMPLE 35B. $^1$H NMR (400 MHz, DMSO-$d_6$) δ 10.29 (s, 1H), 8.54 (d, 1H), 8.29 (s, 1H), 7.86 (dd, 1H), 7.76 (d, 2H), 7.65 (m, 2H), 7.46 (m, 5H), 7.30 (m, 1H), 7.22 (d, 2H), 7.12 (m, 4H), 6.92 (d, 2H), 4.14 (m, 1H), 3.54 (m, 4H), 3.40 (m, 10H), 2.18 (m, 2H), 1.32 (s, 6H), 0.87 (m, 2H).

EXAMPLE 112

This example was made by substituting 1,4,5,6-tetrahydropyrimidine for isopropylamine in EXAMPLE 35B. H NMR (400 MHz, DMSO-$d_6$) δ 12.09 (s, 1H), 9.62 (d, 1H), 8.53 (d, 1H), 8.27 (d, 1H), 8.02 (d, 1H), 7.85 (dd, 1H), 7.76 (d, 2H), 7.51 (m, 3H), 7.40 (m, 1H), 7.14 (m, 7H), 6.93 (d, 2H), 4.14 (m, 1H), 3.40 (m, 14H), 3.19 (m, 2H), 2.12 (m, 2H), 1.88 (m, 2H).

EXAMPLE 113

This example was made by substituting 2-methyl-4,5-dihydro-1H-imidazole for isopropylamine in EXAMPLE 35B. $^1$H NMR (400 MHz, DMSO-$d_6$) δ 10.06 (s, 1H), 8.56 (d, 1H), 8.32 (d, 1H), 7.90 (dd, 1H), 7.81 (d, 2H), 7.55 (m, 4H), 7.43 (d, 2H), 7.37 (m, 1H), 7.26 (m, 3H), 7.14 (m, 3H), 6.97 (d, 2H), 4.28 (m, 2H), 3.85 (m, 14H), 3.42 (m, 2H), 2.14 (m, 2H), 2.08 (s, 3H), 1.27 (m, 2H).

EXAMPLE 114

This example was made by substituting EXAMPLE 842657F and 1,4,5,6-tetrahydro-pyrimidine for isopropylamine and 35A in EXAMPLE 35B. $^1$H NMR (400 MHz, DMSO-$d_6$) δ 11.92 (s, 1H), 9.60 (s, 1H), 8.01 (d, 1H), 7.95 (d, 1H), 7.80 (dd, 1H), 7.73 (d, 2H), 7.68 (m, 1H), 7.49 (m, 3H), 7.41 (d, 2H), 7.27 (m, 5H), 7.17 (m, 1H), 6.90 (d, 2H), 6.82 (d, 1H), 6.00 (d, 1H), 3.83 (m, 2H), 3.40 (m, 16H), 2.08 (m, 2H), 1.285 (t, 2H).

EXAMPLE 115

This example was made by substituting 2,4-dimethyl-4,5-dihydro-1H-imidazole for 1,4,5,6-tetrahydro-pyrimidine In EXAMPLE 114. $^1$H NMR (400 MHz, DMSO-$d_6$) δ 11.92 (s, 1H), 10.02 (s, 1H), 7.95 (d, 1H), 7.82 (dd, 1H), 7.73 (d, 2H), 7.70 (m, 1H), 7.50 (m, 3H), 7.40 (d, 2H), 7.27 (m, 5H), 6.92 (m, 3H), 6.04 (d, 1H), 4.08 (m, 2H), 3.90 (m, 4H), 3.40 (m, 10H), 2.04 (m, 2H), 2.02 (s, 3H), 1.10 (m, 3H).

EXAMPLE 116

This example was made by substituting 2-methyl-4,5-dihydro-1H-imidazole for 1,4,5,6-tetrahydro-pyrimidine In EXAMPLE 114. $^1$H NMR (400 MHz, DMSO-$d_6$) δ 11.92 (s, 1H), 9.82 (s, 1H), 7.88 (d, 1H), 7.75 (dd,. 1H), 7.68 (d, 2H), 7.62 (m, 1H), 7.43 (m, 3H), 7.35 (d, 2H), 7.28 (m, 5H), 6.82 (m, 3H), 5.98 (d, 1H), 3.90 (m, 2H), 3.70 (m, 4H), 3.40 (m, 12H), 2.00 (m, 2H), 1.95 (s, 3H).

EXAMPLE 117

This example was made by substituting 4,4-dimethyl-4,5-dihydro-1H-imidazole for 1,4,5,6-tetrahydro-pyrimidine In EXAMPLE 114. $^1$H NMR (400 MHz, DMSO-$d_6$) δ 11.92 (s, 1H), 10.22 (s, 1H), 8.25 (d, 1H), 7.95 (d, 1H), 7.80 (dd, 1H), 7.75 (d, 2H), 7.65 (m, 1H), 7.52 (m, 3H), 7.50 (d, 2H), 7.25 (m, 5H), 7.18 (m, 1H), 6.90 (d, 2H), 6.82 (d, 1H), 6.00 (d, 1H), 3.88 (m, 2H), 3.50 (m, 4H), 3.40 (m, 10H), 2.08 (m, 2H), 1.25 (m, 6H).

EXAMPLE 118A

EXAMPLE 18D (200 mg), cesium carbonate (671 mg) and tetrabutylammonium iodide (61 mg) in DMF (4 mL) at 25° C. was treated with 4-methoxybenzyl chloride (246 μL), stirred for 12 hours, and treated with ethyl acetate and saturated NH$_4$Cl. The extract was extracted with ethyl acetate, and the combined extracts were dried (MgSO$_4$), filtered, and concentrated. The concentrate was flash chromatographed on silica gel with 0-50% ethyl acetate/hexane.

EXAMPLE 118B

EXAMPLE 110C (38 mg) in N-methyl-2-pyrrolidinone (845 μL) at 25° C. was treated with NaH (8 mg), stirred for 20 minutes, treated with EXAMPLE 118A (122 mg), stirred for 3 hours, treated with NaH (6.6 mg) and EXAMPLE 118A (76 mg), stirred for 3 hours, treated with saturated NaHCO$_3$, (1 mL), and partitioned between ethyl acetate and saturated NaHCO$_3$. The extract was extracted with ethyl acetate, and the combined extracts were dried (MgSO$_4$), filtered, and concentrated. The concentrate was flash chromatographed on silica gel with 0-to 50% acetonitrile (1% NH$_3$-saturated methanol)/1% NH$_3$-saturated ethyl acetate.

EXAMPLE 118C

EXAMPLE 118C (90 mg) in triethylsilane/TFA/dichloromethane (0.05 mL/0.45 mL/0.5 mL) at 25° C. was stirred for 12 hours and concentrated. The concentrate was flash chromatographed on silica gel with 5% NH$_3$-saturated methanol/dichloromethane.

EXAMPLE 118D

This example was made by substituting EXAMPLE 118C and EXAMPLE 837538C for EXAMPLE 2C and 4-(((1R)-3-(dimethylamino)-1-((phenylsulfanyl)methyl)propyl) amino)-3-nitrobenzenesulfonamide (prepared according to the procedure described in commonly owned WO02/24636, filed Sep. 20, 2001) in EXAMPLE 2D. $^1$H NMR (400 MHz, DMSO-$d_6$) δ 12.02 (s, 1H), 9.40 (s, 1H),8.12 (d, 2H), 7.72 (d, 2H), 7.41 (m, 3H), 7.31 (d, 2H),7.26 (m, 2H), 7.17 (m, 3H), 6.95 (d, 2H), 4.97 (m, 1H), 3.50 (m, 12H), 3.16 (m, 4H), 2.76 (s, 6H), 2.23 (m, 4H), 1.70 (s, 4H).

EXAMPLE 119A

A mixture of 4-bromo-3-(trifluoromethyl)benzenesulfonamide (0.121 g), EXAMPLE 847124C (0.17 g) EDAC (0.153 g), and DMAP (0.098 g) in dichloromethane (2 mL) at 25° C. was stirred for 16 hours, treated with ethyl acetate, washed with saturated NH$_4$Cl solution and brine, and dried (Na$_2$SO$_4$), filtered, and concentrated. The concentrate was flash chromatographed on silica gel with 5% methanol/dichloromethane.

EXAMPLE 119B

A mixture of EXAMPLE 119A (0.1 g), EXAMPLE 105B (0.038 g), Pd$_2$(dba)$_3$ (0.011 g), BINAP (0.009 g), Cs$_2$CO$_3$ (0.07 g) in toluene (1.5 mL) at 100° C. was stirred for 16 hours, filtered, and concentrated. The concentrate was purified by high pressure liquid chromatography on a Waters Symmetry C$_8$ column (25 mm×100 mm, 7 μm particle size) with 10-100% acetonitrile/0.1% aqueous TFA over 8 minutes at a flow rate of 40 mL/minute. $^1$H NMR (400 MHz, DMSO-$d_5$) δ 9.60 (s, 1H), 7.95 (d, 1H), 7.81 (dd, 1H), 7.76 (d, 2H), 7.41 (d, 2H), 7.28 (m,4H), 7.12 (d, 2H), 6.94 (d, 2H), 6.87 (d, 1H), 6.02 (d, 1H), 3.91 (m, 3H), 3.63 (m, 2H), 3.40 (m, 2H), 3.28 (m, 2H), 3.15 (m, 4H), 3.00 (m, 2H), 2.73 (d, 6H), 2.46 (m, 4H), 2.10 (m, 2H), 1.82 (m, 2H), 1.57 (m, 4H).

EXAMPLE 120

This example was made by substituting bis(2-methoxyethyl)amine for isopropylamine in EXAMPLE 35B. $^1$H NMR (500 MHz, DMSO-$d_6$) δ 12.02 (s, 1H), 9.50 (s, 1H), 8.54 (d, 1H),8.27 (d, 1H), 7.87 (dd, 1H), 7.77 (m, 3H), 7.52 (m, 4H), 7.39 (d, 2H), 7.34 (m, 1H), 7.16 (m, 5H), 6.94 (d, 2H), 4.32 (m, 1H), 4.20 (m, 2H), 3.61 (m, 4H), 3.39 (m, 2H), 3.30 (m, 12), 3.23 (s, 6H), 2.17 (m, 2H).

EXAMPLE 121

This example was made by substituting bis(2-methoxyethyl)amine for 1,4,5,6-tetrahydropyrimidine in EXAMPLE 114. $^1$H NMR (500 MHz, DMSO-$d_6$) δ 12.02 (s, 1H), 9.50 (s, 1H), 7.95 (d, 1H),7.83 (dd, 1H), 7.75 (m, 3H), 7.53 (m, 4H), 7.39 (d, 2H), 7.34 (m, 5H), 7.16 (m, 1H), 6.94 (m, 2H), 6.02 (d, 1H), 4.32 (m, 1H), 3.96 (m, 2H), 3.61 (m, 4H), 3.39 (m, 16H), 3.23 (s, 6H), 2.17 (m, 2H).

EXAMPLE 122A

A mixture of EXAMPLE 29C (0.5 g) and diethylamine (4 mL) in THF (4 mL) at 25° C. was stirred for 2 hours and concentrated. The concentrate was flash chromatographed on silica gel with 5% to 10% methanol/dichloromethane.

EXAMPLE 122B

This example was made by substituting EXAMPLE 122A for EXAMPLE 105B EXAMPLE 119B. $^1$H NMR (400 MHz, DMSO-$d_6$) δ 12.02 (s, 1H), 9.60 (s, 1H), 8.50 (s, 1H), 7.95 (d, 1H), 7.81 (dd, 1H), 7.76 (d, 2H), 7.41 (d, 2H), 7.28 (m,4H), 7.12 (d, 2H), 6.94 (m, 3H), 6.12 (d, 1H), 4.02 (m, 1H), 3.89 (m, 2H), 3.63 (m, 4H), 3.42 (m, 4H), 3.17 (m, 2H), 2.93 (m, 2H), 2.79 (m, 2H), 2.46 (m, 4H), 2.10 (m, 2H), 1.82 (m, 2H), 1.57 (m, 4H), 1.23 (m, 12H).

EXAMPLE 859948

This example was made by substituting 4,4-difluoropiperidine for isopropylamine in EXAMPLE 35B. $^1$H NMR (400 MHz, DMSO-$d_6$) δ 10.06 (s, 1H),. 8.55 (d, 1H), 8.30 (d, 1H), 7.87 (dd, 1H), 7.77 (d, 2H),7.55 (m, 4H), 7.40 (d, 2H), 7.39 (m, 1H), 7.24 (m, 3H), 7.13 (m, 3H), 6.93 (d, 2H), 4.20 (m, 2H), 3.86 (m, 4H),3.42 (m, 4H), 3.17 (m, 8H), 2.28 (m, 4H), 2.18 (m, 4H).

EXAMPLE 855996

This example was made by substituting 2-methylpyrrolidine for isopropylamine in EXAMPLE 35B. H NMR (400 MHz, DMSO-$d_6$) δ 9.42 (s, 1H), 8.54 (d, 1H), 8.32 (d, 1H), 7.87 (dd, 1H), 7.77 (d, 2H),7.53 (m, 4H), 7.39 (d, 2H), 7.36 (m, 1H), 7.23 (m, 3H), 7.14 (m, 3H), 6.94 (d, 2H), 4.05 (m, 6H), 3.57 (m, 2H), 3.40 (m, 4H), 3.06 (m, 4H), 2.14 (m, 2H), 1.93 (m, 2H), 1.57 (m, 2H), 1.27 (m, 3H).

EXAMPLE 123A 2.5 g/100 mL Rieke magnesium in diethyl ether (12.75 mL) at 25° C. was treated with 1-bromo-3-methyl-2-butene (1.81 g), stirred for 1 hour, added to 2-methylpropane-2-sulfonic acid (2-benzyloxyethylidene)amide, prepared as described in J. Org. Chem. 2001, 26, 8772-8778, (1.85 g) in toluene (30 mL) at −78° C., and treated, at 25° C., with saturated NH$_4$Cl, ethyl acetate, and water. The extract was washed with water and brine and dried (MgSO$_4$), filtered, and concentrated. The concentrate was flash chromatographed on silica gel with 10-20% acetone/hexanes.

EXAMPLE 123B

EXAMPLE 123A (1.01 g) in methanol (20 mL) at 25° C. was treated with 4M HCl in dioxane (8 mL), stirred for 10 minutes, treated with 10% Pd/C, stirred under H$_2$ (balloon) for 18 hours, filtered through diatomaceous earth (Celite®), and concentrated. The concentrate was mixed with 1:1 2M Na$_2$CO$_3$/chloroform (60 mL), treated with benzylchloroformate (0.58 mL) and benzyltriethylammonium chloride (catalytic), and stirred 3 hours. The extract was washed with water, dried (MgSO$_4$), filtered, and concentrated. The concentrate was flash chromatographed on silica gel with 3:1-2:1 hexanes/ethyl acetate.

EXAMPLE 123C

A mixture of EXAMPLE 123B (0.52 g), diphenyldisulfide (0.40 g), and tributylphosphine (0.81 g) in toluene (15 mL) at 85° C. was stirred for 18 hours, cooled to 25° C., and concentrated. The concentrate was flash chromatographed on silica gel with 20:1 then 10:1 and 5:1 hexanes/ethyl acetate.

EXAMPLE 123D

EXAMPLE 123C (0.52 g) in 30% HBr in acetic acid (15 mL) at 25° C. was stirred for 2 hours, poured into 5% HCl (75 mL), washed with ethyl acetate, brought to pH 12 with 15% NaOH, and extracted with chloroform. The extract was dried (MgSO$_4$) and concentrated.

EXAMPLE 123E

This example was made by substituting EXAMPLE 123D for EXAMPLE 21C in EXAMPLE 21D.

EXAMPLE 123F

This example was made by substituting EXAMPLE 123 E for 4-(((1R)-3-(dimethylamino)-1-((phenylsulfanyl)methyl)propyl)amino)-3-nitrobenzenesulfonamide in EXAMPLE 2D. $^1$H NMR (300 MHz,
DMSO-d$_6$) δ 12.07 (s, 1H), 9.61 (s, 1H), 8.49 (d, 1H), 8.35 (d, 1H), 7.64-7.96 (m, 4H), 7.41-7.60 (m, 5H), 7.24-7.40 (m, 4H), 7.01-7.20 (m, 4H), 6.92 (d, 2H), 4.38 (m, 2H), 4.05 (m, 1H), 3.68-3.95 (m, 2H), 3.21-3.65 (m, 1H), 2.96-3.25 (m, 2H), 2.61-2.95 (m, 2H), 1.17-1.50 (m, 1H), 0.93 (d, 6H), 0.80 (t, 4H).

EXAMPLE 124

This example was made by substituting tert-butyl (5R)-5-((4-(aminosulfonyl)-2-nitrophenyl)amino)-6-(phenylsulfanyl)hexylcarbamate, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-d$_6$) δ 11.96 (s, 1H), 8.51 (d, 1H), 8.28 (d, 1H), 7.83 (dd, 1H), 7.74 (d, 2H), 7.49-7.56 (m, 3H), 7.44-7.49 (m, 2H), 7.34-7.41 (m, 2H), 7.20-7.28 (m, 3H), 7.03-7.19 (m, 4H), 6.89 (d, 2H), 6.66-6.77 (m, 1H), 3.95-4.12 (m, 1H), 3.41 (m, 1H), 3.17-3.27 (m, 4H), 2.79-2.96 (m, 4H), 2.33-2.45 (m, 5H), 1.73 (m, 4H), 1.18-1.43 (m, 9H).

EXAMPLE 125

EXAMPLE 124 (0.40 g) in dichloromethane (10 mL) was treated with 4M HCl in dioxane (2 mL), stirred for 20 hours at 25° C., and concentrated to give the desired product as the hydrochloride salt. $^1$H NMR (300 MHz, DMSO-d$_6$) δ 12.09 (s, 1H), 9.76 (s, 1H), 8.53 (d, 1H), 8.30 (d, 1H), 7.85 (dd, 1H), 7.77 (d, 3H), 7.62 (m, 4H), 7.52 (d, 2H), 7.40 (d, 1H), 7.34 (d, 2H), 7.18-7.26 (m, 3H), 7.03-7.18 (m, 2H), 6.93 (d, 2H), 4.33 (m, 2H), 4.08 (m, 3H), 3.28-3.42 (m, 4H), 3.11 (m, 4H), 2.81-2.96 (m, 1H), 2.64-2.81 (m, 4H), 1.66-1.85 (m, 2H), 1.43-1.58 (m, 2H), 1.24-1.43 (m, 2H).

EXAMPLE 126

EXAMPLE 125 (0.075 g) in dichloromethane (7 mL) was treated with DIEA (0.055 g), cooled to 0° C., treated with methanesulfonylchloride (0.013 g), stirred for 1 hour, and treated with water. The extract was washed with water and brine, and dried (MgSO$_4$), filtered, and concentrated. The concentrate was flash chromatographed on silica gel with 0-2.5% methanol in dichloromethane. $^1$H NMR (300 MHz, DMSO-d$_6$) δ 12.00 (s, 1H), 8.52 (d, 1H), 8.30 (d, 1H), 7.84 (dd, 1H), 7.74 (d, 2H), 7.43-7.57 (m, 1H), 7.47 (s, 2H), 7.32-7.42 (m, 2H), 7.20-7.29 (m, 3H), 7.04-7.19 (m, 4H), 6.84-6.94 (m, 3H), 3.98-4.16 (m, 1H), 3.16-3.48 (m, 7H), 2.85-2.95 (m, 2H), 2.83 (s, 3H), 2.41 (m, 3H), 1.67-1.83 (m, 2H), 1.28-1.50 (m, 4H).

EXAMPLE 127

EXAMPLE 125 (0.065 g) in dichloromethane (7 mL) at 25° C. was treated with DIEA (0.048 g), cooled to 0° C., treated with trimethylsilylisocyanate (0.011 g), stirred at 25° C. for 24 hours, treated with methanol (0.5 mL), and concentrated. The concentrate was purified by reverse phase HPLC (C-18) with 10-100% acetonitrile/water containing 0.1% TFA. $^1$H NMR (300 MHz, DMSO-d$_6$) δ 12.07 (s, 1H), 9.56 (s, 1H), 8.52 (s, 1H), 8.31 (d, 1H), 7.84 (dd, 1H), 7.77 (d, 3H), 7.52 (m, 3H), 7.28-7.44 (m, 3H), 7.03-7.27 (m, 6H), 6.93 (d, 2H), 5.80-5.93 (m, 1H), 5.18-5.42 (m, 2H), 4.26-4.51 (m, 2H), 4.08 (m, 2H), 3.75-3.98 (m, 2H), 2.99-3.20 (m, 3H), 2.79-2.98 (m, 4H), 1.63-1.89 (m, 2H), 1.24-1.44 (m, 4H).

EXAMPLE 128A

A mixture of ethyl 4-fluorobenzoate (7.71 g), 1-(tert-butoxycarbonyl)piperazine (9.31 g), potassium carbonate (13.8 g), and 1-methyl-2-pyrrolidinone (20 mL) at 130° C. was stirred for 16 hours, poured into water, and filtered. The filtrant was washed with water and dried in a vacuum oven at 50° C. and 18 mmHg.

EXAMPLE 128B

This example was prepared by substituting EXAMPLE 128A for EXAMPLE 1B in EXAMPLE 1C.

EXAMPLE 128C

This example was prepared by substituting EXAMPLE 128B for EXAMPLE 1C in EXAMPLE 1D.

EXAMPLE 128D

EXAMPLE 128C (3.7 g) in dichloromethane (10 mL) and 4M HCl in dioxane (10 mL) at 25° C. was stirred for 5 hours, concentrated, treated with diethyl ether (20 mL), and filtered. The filtrant was washed with diethyl ether and dried in a vacuum oven at 50° C. and 18 mm Hg.

EXAMPLE 128E

EXAMPLE 128D (110 mg) in dichloromethane (2 mL) at 25° C. was treated with 2-(methylsulfanyl)benzaldehyde (27 mg), N,N-DIEA (52 mg), and sodium triacetoxyborohydride (38 mg), stirred for 16 hours, and concentrated. The concentrate was flash chromatographed on silica gel with 10% methanol/dichloromethane. $^1$H NMR (300 MHz, DMSO-$d_6$) δ 8.45 (d, 1H), 8.36 (d, 1H), 7.78 (dd, 1H), 7.73 (d, 2H), 7.38-7.21 (m, 6H), 7.18 (d, 1H), 7.1,8-7.10 (m, 2H), 6.87 (d, 1H), 6.80 (d, 2H), 4.10-4.01 (m, 1H), 3.52 (s, 2H), 3.33 (d, 2H), 3.18 (t, 4H), 2.65-2.40 (m, 6H), 2.44 (s, 3H), 2.27 (s, 6H), 2.07-1.82 (m, 2H).

EXAMPLE 129A 2-(methylsulfanyl)benzaldehyde (1 g) in dichloromethane (35 mL) was treated with 70% 3-chloroperoxybenzoic acid (3.32 g), stirred for 75 minutes, and concentrated. The concentrate was flash chromatographed on silica gel with 1:1 ethyl acetate/hexanes.

EXAMPLE 129B

EXAMPLE 128D (110 mg) in dichloromethane (2 mL) was treated with EXAMPLE 129A (33 mg), 3.45 mmol/g N,N-DIEA resin (116 mg), and sodium triacetoxyborohydride (38 mg), stirred at 25° C. for 16 hours, and concentrated. The concentrate was flash chromatographed on silica gel with 10% methanol/dichloromethane. $^1$H NMR (300 MHz, DMSO-$d_6$) δ 8.45 (d, 1H), 8.21 (d, 1H), 7.98 (d, 1H), 7.81 (dd, 1H), 7.73 (d, 2H), 7.70 (td, 1H), 7.61 (d, 2H), 7.32 (dd, 2H), 7.24 (tt, 2H), 7.17 (tt, 1H), 6.90 (d, 1H), 6.82 (d, 2H), 4.11-4.01 (m, 1H), 3.93 (s, 2H), 3.42 (s, 3H), 3.33 (d, 2H), 3.18 (t, 4H), 3.00-2.80 (m, 2H), 2.62-2.48 (m, 4H), 2.56 (s, 6H), 2.13-1.98 (m, 2H).

EXAMPLE 130A

N-(tertbutoxycarbonyl)glycine methyl ester (5 g) in THF (60 mL) at 0° C. was treated with 1.4M methylmagnesium bromide in 3:1 toluene/THF (75.5 mL), stirred at 25° C. for 16 hours, cooled to 0° C., treated with saturated NH$_4$Cl, and extracted with ethyl acetate. The extract was washed with brine and dried (Na$_2$SO$_4$), filtered, and concentrated.

EXAMPLE 130B

EXAMPLE 130A (1 g) in THF (27 mL) at 0° C. was treated with potassium tert-butoxide (663 mg), stirred for 30 minutes, and concentrated. The concentrate was flash chromatographed on silica gel with 5% methanol/ethyl acetate.

EXAMPLE 130C

A mixture of EXAMPLE 130B (120 mg), 2-bromobenzaldehyde (289 mg), and sodium tert-butoxide (150 mg) in toluene (5 mL) in a sealable container was degassed/flushed with nitrogen three times and treated with dichloro(1,1'-bis(diphenylphosphino)ferrocene)palladium (II).dichloromethane (82 mg). The container was sealed, and the mixture was heated at 120° C. for 16 hours and concentrated. The concentrate was flash chromatographed on silica gel with 50% ethyl acetate/hexanes.

EXAMPLE 130D

EXAMPLE 128C (4.02 g) in dioxane (7 mL) at 25° C. was treated with 4M HCl (7 mL), stirred for 16 hours, neutralized and extracted with dichloromethane. The extract was concentrated. The concentrate was chromatographed on $C_{18}$ with 1:1 acetonitrile/0.1% aqueous TFA.

EXAMPLE 130E

EXAMPLE 130C (50 mg) in dichloromethane (2 mL) and methanol (0.4 mL) at 25° C. was treated with EXAMPLE 130D (130 mg) and 2.38 mmol/g MP-BH$_3$CN (118 mg), stirred for 16 hours, and concentrated. The concentrate was flash chromatographed on silica gel with 20% methanol/dichloromethane. $^1$H NMR (300 MHz, DMSO-$d_6$) δ 8.42 (d, 1H), 8.26 (d, 1H), 7.79 (dd, 1H), 7.74 (dd, 2H), 7.62-7.44 (m, 2H), 7.40-7.35 (m, 2H), 7.32 (d, 2H), 7.25 (td, 2H), 7.17 (tt, 1H), 6.88 (d, 1H), 6.82 (t, 2H), 4.10-4.01 (m, 1H), 3.78 (s, 2H), 3.49 (s, 2H), 3.34 (d, 2H), 3.23-3.14 (m, 6H), 2.90-2.62 (m, 4H), 2.43 (s, 6H), 2.10-1.90 (m, 2H), 1.50 (s, 6H).

EXAMPLE 131A

A mixture of 2-bromobenzaldehyde (4 g), butylamine (1.58 g), and 4A sieves (3 g) in dichloromethane (75 mL) at 25° C. was stirred for 72 hours, filtered and concentrated.

EXAMPLE 131B

EXAMPLE 131A (400 mg) in THF (5 mL) at 0° C. was treated with MnCl$_2$ (21 mg) and 2M cyclohexylmagnesium chloride in THF (1.67 mL), stirred for 25 minutes, treated with saturated NH$_4$Cl, and extracted with diethyl ether. The extract was washed with brine, dried (Na$_2$SO$_4$), filtered, and concentrated. The concentrate was flash chromatographed on silica gel with 5% ethyl acetate/hexanes. Relevant fractions were combined and concentrated. The concentrate in 1:1 1,4-dioxane/water was stirred at 25° C. for 16 hours and extracted with diethyl ether. The extract was washed with brine and dried (Na$_2$SO$_4$), filtered, and concentrated.

EXAMPLE 131C

This example was prepared by substituting EXAMPLE 131B for EXAMPLE 130C in EXAMPLE 130D. $^1$H NMR (300 MHz, DMSO-$d_6$) δ 8.43 (d, 1H), 8.18 (d, 1H), 7.82 (dd, 1H), 7.73 (d, 2H), 7.45-7.37 (m, 1H), 7.30 (d, 2H), 7.28-7.07 (m, 6H), 6.92 (d, 1H), 6.82 (d, 2H), 4.12-4.01 (m, 1H), 3.51 (s, 2H), 3.33 (d, 2H), 3.17 (s, 4H), 3.05-2.88 (m, 3H), 2.70-2.52 (m, 2H), 2.61 (s, 6H), 2.16-1.98 (m, 2H), 1.84-1.65 (m, 6H), 1.50-1.22 (m, 6H).

EXAMPLE 132

This example was prepared by substituting 2-morpholinobenzaldehyde for EXAMPLE 130C in EXAMPLE 130D. $^1$H NMR (300 MHz, DMSO-$d_6$) δ 8.46 (d, 1H), 8.22 (d, 1H), 7.81 (dd, 1H), 7.72 (d, 2H), 7.39 (dd, 1H), 7.32 (d, 2H), 7.28-7.22 (m, 3H), 7.20-7.04 (m, 3H), 6.90 (d, 1H), 6.81 (d, 2H), 4.14-4.00 (m, 1H), 3.75 (t, 4H), 3.57 (s, 2H), 3.33 (d, 2H), 3.18 (s, 4H), 2.94 (t, 4H), 2.88-2.50 (m, 6H), 2.56 (s, 6H), 2.15-1.90 (m, 2H).

EXAMPLE 133A 2-propanethiol (797 mg) in 1-methyl-2-pyrrolidinone (20 mL) at 25° C. was treated with 60% sodium hydride (419 mg) and 2-fluorobenzaldhyde (1 g), stirred for 10 minutes, treated with 1M NaOH (20 mL), and extracted with diethyl ether. The extract was washed with water and brine and dried ($Na_2SO_4$), filtered, and concentrated.

EXAMPLE 133B

This example was prepared by substituting EXAMPLE 133A for EXAMPLE 130C in EXAMPLE 130D. $^1$H NMR (300 MHz, DMSO-$d_6$) δ 8.45 (d, 1H), 8.30 (d, 1H), 7.78 (dd, 1H), 7.74 (d, 2H), 7.44 (dt, 2H), 7.33 (d, 2H), 7.28-7.22 (m, 4H), 7.17 (tt, 1H), 6.87 (d, 1H), 6.81 (d, 2H), 4.11-4.00 (m, 1H), 3.61 (s, 2H), 3.33 (d, 2H), 3.17 (t, 4H), 2.80-2.50 (m, 6H), 2.44-2.36 (m, 1H), 2.39 (s, 6H), 2.10-1.86 (m, 2H), 1.23 (d, 6H).

EXAMPLE 134A

A mixture of 3-(R)-((carbobenzyloxy)amino)-γ-butyrolactone, prepared according to the procedure described in J. Am. Chem. Soc. 1986, 108, 4943-4952, (15 g) and N-methylisopropylamine (25 mL) in diglyme (200 mL) at 120° C. was stirred for 48 hours, and concentrated. The concentrate was flash chromatographed on silica gel with 5% methanol/ethyl acetate.

EXAMPLE 134B

This example was prepared by substituting EXAMPLE 134A for EXAMPLE 18A in EXAMPLE 18B.

EXAMPLE 134C

This example was prepared by substituting EXAMPLE 134B for EXAMPLE 18B in EXAMPLE 18C.

EXAMPLE 134D

This example was prepared by substituting EXAMPLE 134C for EXAMPLE 19C in EXAMPLE 19D.

EXAMPLE 134E

This example was prepared by substituting EXAMPLE 134D for EXAMPLE 21C in EXAMPLE 21D.

EXAMPLE 134F

This example was prepared by substituting EXAMPLE 8550516E and EXAMPLE 837538C for 4-(((1R)-3-(dimethylamino)-1-((phenylsulfanyl)methyl)propyl)amino)-3-nitrobenzenesulfonamide, prepared as described in WO02/24636, and EXAMPLE 10, respectively, in EXAMPLE 1D. $^1$H NMR (300 MHz, DMSO-$d_6$) δ 8.43 (d, 1H), 8.16 (s, 1H), 7.79 (d, 1H), 7.70 (d, 2H), 7.39-7.28 (m, 4H), 7.25 (td, 2H), 7.18 (dt, 1H), 7.12 (dt, 2H), 6.90 (d, 1H), 6.76 (d, 2H), 4.13-4.01 (m, 1H), 3.34 (d, 2H), 3.12 (s, 4H), 2.76 (s, 2H), 2.67-2.49 (m, 2H), 2.27 (s, 4H), 2.23-2.00 (m, 8H), 1.66 (s, 4H), 1.22-0.96 (m, 8H).

EXAMPLE 135A

This example was prepared by substituting di-n-propylamine for N-methylisopropylamine in EXAMPLE 134A.

EXAMPLE 135B

This example was prepared by substituting EXAMPLE 135A for EXAMPLE 18A in EXAMPLE 18B.

EXAMPLE 135C

This example was prepared by substituting EXAMPLE 135B for EXAMPLE 18B in EXAMPLE 18C.

EXAMPLE 135D

This example was prepared by substituting EXAMPLE 135C for EXAMPLE 19C in EXAMPLE 19D.

EXAMPLE 135E

This example was prepared by substituting EXAMPLE 135D for EXAMPLE 21C in EXAMPLE 21D.

EXAMPLE 135F

This example was prepared by substituting EXAMPLE 135E and EXAMPLE 837538C for 4-(((1R)-3-(dimethylamino)-1-((phenylsulfanyl)methyl)propyl)amino)-3-nitrobenzenesulfonamide, prepared as described in WO02/24636, and EXAMPLE 1C, respectively, in EXAMPLE 1D. $^1$H NMR (300 MHz, DMSO-$d_6$) δ 8.44 (d, 1H), 8.18 (s, 1H), 7.78 (d, 1H), 7.71 (d, 2H), 7.38-7.29 (m, 4H), 7.24 (tt, 2H), 7.18 (dt, 1H), 7.12 (d, 2H), 6.93-6.84 (m, 1H), 6.77 (d, 2H), 4.12-3.98 (m, 1H), 3.32 (d, 2H), 3.12 (s, 4H), 2.76 (s, 2H), 2.50-2.30 (m, 2H), 2.27 (s, 4H), 2.23-2.14 (m, 6H), 2.10-1.94 (m, 2H), 1.66 (s, 4H), 1.60-1.20 (m, 6H), 0.80 (s, 6H).

EXAMPLE 136

This example was prepared by substituting EXAMPLE 135E for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 8.45 (d, 1H), 8.18 (s, 1H), 7.89 (d, 1H), 7.72 (d, 2H), 7.51 (dd, 1H), 7.48 (s, 4H), 7.40-7.34 (m, 2H), 7.32 (dd, 2H), 7.27-7.21, (m, 3H), 7.16 (tt, 1H), 6.94-6.85 (m, 1H), 6.79 (d, 2H), 4.12-4.00 (m, 1H), 3.38 (s, 2H), 3.33 (d, 2H), 3.13 (t, 4H), 3.00-2.85 (m, 2H), 2.40 (t, 4H), 2.08-1.93 (m, 2H), 1.60-1.20 (m, 8H), 0.81 (s, 6H).

EXAMPLE 137A

This example was prepared by substituting diethylamine for N-methylisopropylamine in EXAMPLE 134A.

EXAMPLE 137B

This example was prepared by substituting EXAMPLE 137A for EXAMPLE 18A in EXAMPLE 18B.

EXAMPLE 137C

This example was prepared by substituting EXAMPLE 137B for EXAMPLE 18B in EXAMPLE 18C.

EXAMPLE 137D

This example was prepared by substituting EXAMPLE 137C for EXAMPLE 19C in EXAMPLE 19D.

EXAMPLE 137E

This example was prepared by substituting EXAMPLE 137D for EXAMPLE 21C in EXAMPLE 21D.

EXAMPLE 137F

This example was prepared by substituting EXAMPLE 137E and EXAMPLE 837538C for 4-(((1R)-3-(dimethylamino)-1-((phenylsulfanyl)methyl)propyl)amino)-3-nitrobenzenesulfonamide, prepared as described in W002/24636, and EXAMPLE 1C, respectively, in EXAMPLE 1D. $^1$H NMR (300 MHz, DMSO-$d_6$) δ 8.44 (d, 1H), 8.18 (d, 1H), 7.81 (dd, 1H), 7.71 (d, 2H), 7.37 (d, 2H), 7.31 (dd, 2H), 7.24 (tt, 2H), 7.18 (dt, 1H), 7.12 (d, 2H), 6.92 (d, 1H), 6.77 (d, 2H), 4.17-4.04 (m, 1H), 3.34 (d, 2H), 3.12 (s, 4H), 2.95 (m, 6H), 2.76 (s, 2H), 2.27 (s, 4H), 2.19 (m, 4H), 2.06 (m, 2H), 1.66 (s, 4H), 1.08 (t, 6H).

EXAMPLE 138

This example was prepared by substituting EXAMPLE 137E for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 8.46 (d, 1H), 8.18 (s, 1H), 7.82 (dd, 1H), 7.72 (d, 2H), 7.52 (dd, 1H), 7.48 (s, 4H), 7.40-7.35 (m, 2H), 7.31 (dd, 2H), 7.27-7.22, (m, 3H), 7.17 (tt, 1H), 6.94 (d, 1H), 6.79 (d, 2H), 4.15-4.04 (m, 1H), 3.38 (s, 2H), 3.35 (d, 2H), 3.14 (t, 4H), 3.13-2.95 (m, 6H), 2.40 (t, 4H), 2.15-2.00 (m, 2H), 1.10 (s, 6H).

EXAMPLE 139A

This example was made by substituting 3-bromobenzyl bromide for 2-bromobenzyl bromide in EXAMPLE 2A.

EXAMPLE 139B

This example was made by substituting EXAMPLE 139A and phenylboronic acid for EXAMPLE 2A and 4-chlorophenylboronic acid, respectively, in EXAMPLE 2B.

EXAMPLE 139C

This example was made by substituting EXAMPLE 139B for EXAMPLE 2B in EXAMPLE 2C.

EXAMPLE 139D

This example was made by substituting EXAMPLE 139C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-$d_6$) δ 12.12 (br, 1H), 9.92 (br, 1H), 8.78 (t, 1H), 8.60 (d, 1H), 7.91 (dd, 1H), 7.81 (m, 4H), 7.70 (m, 2H), 7.59 (t, 1H), 7.51 (m, 3H), 7.39 (m, 3H), 7.21 (m, 4H), 7.00 (d, 2H), 4.44 (m, 2H), 4.07 (m, 2H), 3.67 (t, 2H), 3.39 (m, 4H), 3.28 (t, 2H), 3.18 (m, 2H).

EXAMPLE 140

This example was made by substituting EXAMPLE 139C for EXAMPLE 2C in EXAMPLE 2D. $^1$H NMR (300 MHz, DMSO-$d_6$) δ 12.15 (br, 1H), 10.11 (br, 1H), 9.46 (br, 1H), 8.55 (d, 1H), 8.30 (d, 1H), 7.89 (d, 1H), 7.82 (m, 4H), 7.70 (m, 2H), 7.59 (t, 1H), 7.51 (m, 3H), 7.42 (m, 1H), 7.17 (m, 6H), 7.02 (d, 2H), 4.46 (m, 2H), 3.50 (m, 13H), 2.74 (d, 6H), 2.14 (q, 2H).

EXAMPLE 141

This example was made by substituting EXAMPLE 139C and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-$d_6$) δ 12.17 (br, 1H), 10.10 (br, 1H), 9.77 (br, 1H), 8.55 (d, 1H), 8.31 (d, 1H), 7.89 (dd, 1H), 7.80 (m, 4H), 7.70 (m, 2H), 7.59 (t, 1H), 7.51 (m, 3H), 7.41 (m, 1H), 7.18 (m, 6H), 7.01 (d, 2H), 4.46 (m, 2H), 3.60 (m, 21H), 2.17 (q, 2H).

EXAMPLE 142A 3,4-Difluorobenzoic acid (1 g) in THF (6 mL) and methanol (3 mL) at 25° C. was treated with 2M (trimethylsilyl)diazomethane in hexane (4 mL), stirred for 2 hours, and concentrated. The concentrate was flash chromatographed on silica gel with 5% ethyl acetate/hexane.

EXAMPLE 142B

EXAMPLE 142A in acetonitrile (6 mL) at 25° C. was treated with $K_2CO_3$ (0.46 g) and piperazine (250 mg), refluxed for 24 hours, cooled to 25° C., treated with $K_2CO_3$ (0.40 g) and 2-phenylbenzyl bromide (0.53 mL), stirred for 18 hours, and concentrated. The concentrate was partitioned between ethyl acetate and brine. The extract was dried ($Na_2SO_4$), filtered, and concentrated. The concentrate was flash chromatographed on silica gel with 5% acetone/hexane.

EXAMPLE 142C

This example was made by substituting EXAMPLE 142B for EXAMPLE 2B in EXAMPLE 2C.

EXAMPLE 142D

This example was made by substituting EXAMPLE 142C for EXAMPLE 2C in EXAMPLE 2D. $^1$H NMR (300 MHz, DMSO-$d_6$) δ 9.79 (br, 1H), 9.47 (br, 1H), 8.53 (d, 1H), 8.30 (d, 1H), 7.86 (dd, 1H), 7.69 (m, 3H), 7.43 (m, 8H), 7.14 (m, 8H), 3.65 (m, 15H), 2.74 (d, 6H), 2.14 (q, 2H).

EXAMPLE 143

This example was made by substituting EXAMPLE 142C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-$d_6$) δ 12.28 (br, 1H), 9.66 (m, 1H), 8.78 (t, 1H), 8.58 (d, 1H), 7.89 (dd, 1H), 7.74 (br, 1H), 7.68 (s, 1H), 7.64 (m, 1H), 7.48 (m, 4H), 7.37 (m, 5H), 7.23 (m, 4H), 7.05 (t, 2H), 4.38 (m, 2H), 3.24 (m, 12H).

EXAMPLE 144

This example was made by substituting EXAMPLE 142C and 4-(((1R)-3-(4-morpholinyl)-1-((phenylsulfanyl)methyl)-propyl)amino)-3-nitrobenzenesulfonamide, prepared as described in WO 02/24636, for EXAMPLE 2C and 4-(((1R)-3-(dimethylamino)-1-((phenylsulfanyl)methyl) propyl)amino)-3-nitrobenzenesulfonamide, respectively, in EXAMPLE 2D. $^1$H NMR (300 MHz, DMSO-d$_6$) δ 9.74 (br, 1H), 8.54 (d, 1H), 8.30 (d, 1H), 7.86 (dd, 1H), 7.68 (m, 3H), 7.48 (m, 9H), 7.13 (m, 6H), 3.63 (m, 23H), 2.18 (m, 2H).

EXAMPLE 145A

This example was made by substituting 3,4,5-trifluorobenzoic acid for 3,4-difluorobenzoic acid in EXAMPLE 142A.

EXAMPLE 145B

This example was made by substituting EXAMPLE 145A for EXAMPLE 142A in EXAMPLE 142B.

EXAMPLE 145C

This example was made by substituting EXAMPLE 145B for EXAMPLE 2B in EXAMPLE 2C.

EXAMPLE 145D

This example was made by substituting EXAMPLE 145C for EXAMPLE 2C in EXAMPLE 2D. $^1$H NMR (300 MHz, DMSO-d$_6$) δ 9.72 (br, 1H), 9.44 (br, 1H), 8.51 (d, 1H), 8.27 (d, 1H), 7.84 (dd, 1H), 7.75 (m, 1H), 7.49 (m, 8H), 7.36 (m, 3H), 7.18 (m, 6H), 3.50 (m, 15H), 2.74 (d, 6H), 2.13 (q, 2H).

EXAMPLE 146

This example was made by substituting EXAMPLE 145C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-d$_6$) δ 9.55 (br, 1H), 8.72 (t, 1H), 8.55 (d, 1H), 7.87 (dd, 1H), 7.73 (br, 1H), 7.34 (m, 16H), 4.36 (m, 2H), 3.25 (m, 12H).

EXAMPLE 147

This example was made by substituting EXAMPLE 145O and 4-(((1R)-3-(4-morpholinyl)-1-((phenylsulfanyl)methyl) propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl) amino)-3-nitrobenzenesulfonamide, respectively, in EXAMPLE 2D. $^1$H NMR (300 MHz, DMSO-d$_6$) δ 9.70 (br, 1H), 8.51 (d, 1H), 8.27 (d, 1H), 7.86 (dd, 1H), 7.75 (m, 1H), 7.49 (m, 7H), 7.35 (m, 3H), 7.25 (m, 2H), 7.16 (m, 4H), 4.40 (m, 2H), 4.16 (m, 2H), 3.38 (m, 19H), 2.15 (m, 2H).

EXAMPLE 148A

1-Phenylimidazole (0.44 mL) in THF at 0° C. was treated with 2.5M butyllithium in hexane (1.7 mL), stirred for 20 minutes, treated with DMF (0.8 mL), stirred for 1.5 hours, and treated with saturated aqueous NH$_4$Cl and ethyl acetate. The extract was washed with brine and dried (Na$_2$SO$_4$), filtered, and concentrated. The concentrate was flash chromatographed on silica gel with 15% acetone/hexane.

EXAMPLE 148B

A mixture of EXAMPLE 1A and EXAMPLE 148A in 1,2-dichloroethane (2 mL) at 25° C. was treated with sodium triacetoxyborohydride (368 mg), stirred for 1 hour, and treated with dichloromethane and 1M NaOH. The extract was washed with brine and dried (Na$_2$SO$_4$), filtered, and concentrated. The concentrate was flash chromatographed on silica gel with 3-5% methanol/dichloromethane.

EXAMPLE 148C

This example was made by substituting EXAMPLE 148B for EXAMPLE 2B in EXAMPLE 2C.

EXAMPLE 148D

This example was made by substituting EXAMPLE 148C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-d$_5$) δ 12.02.(br, 1H), 8.78 (t, 1H), 8.59 (d, 1H), 7.90 (dd, 1H), 7.80 (d, 1H), 7.77 (d, 2H), 7.60 (m, 6H), 7.35 (m, 2H), 7.21 (m, 4H), 6.95 (d, 2H), 4.10 (m, 2H), 3.50 (m, 6H), 3.28 (t, 2H), 2.86 (m, 4H).

EXAMPLE 149

This example was made by substituting EXAMPLE 148C and 4-(((1R)-3-(4-morpholinyl)-1-((phenylsulfanyl)methyl) propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl) amino)-3-nitrobenzenesulfonamide, respectively, in EXAMPLE. 2D. $^1$H NMR (300 MHz, DMSO-d$_6$) δ 12.10 (br, 1H), 9.74 (br, 1H), 8.55 (d, 1H), 8.31 (d, 1H), 7.87 (dd, 1H), 7.83 (d, 1H), 7.78 (d, 2H), 7.61 (m, 6H), 7.17 (m, 6H), 6.95 (d, 2H), 3.53 (m, 23H), 2.19 (m, 2H).

EXAMPLE 150A

This example was made by substituting 1-phenylpyrazole for 1-phenylimidazole in EXAMPLE 148A.

EXAMPLE 150B

This example was made by substituting EXAMPLE 150A for EXAMPLE 148A in EXAMPLE 148B.

EXAMPLE 150C

This example was made by substituting EXAMPLE 150B for EXAMPLE 2B in EXAMPLE 2C.

EXAMPLE 150D

This example was made by substituting EXAMPLE 150C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-d$_6$) δ 12.07 (br, 1H), 8.78 (t, 1H), 8.59 (d, 1H), 7.91 (dd, 1H), 7.76 (d, 2H), 7.75 (s, 1H), 7.52 (m, 5H), 7.36 (m, 2H), 7.21 (m, 4H), 6.95 (d, 2H), 6.67 (br, 1H), 3.28 (t, 2H), 3.22 (m, 12H).

EXAMPLE 151

This example was made by substituting EXAMPLE 150C and 4-(((1R)-3-(4-morpholinyl)-1-((phenylsulfanyl)methyl)

propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-$d_6$) δ 12.10 (br, 1H), 9.76 (br, 1H), 8.55 (d, 1H), 8.31 (d, 1H), 7.87 (dd, 1H), 7.77 (d, 2H), 7.74 (s, 1H), 7.54 (m, 5H), 7.17 (m, 6H), 6.95 (d, 2H), 6.64 (br, 1H), 3.25 (m, 23H), 2.17 (m, 2H).

EXAMPLE 152A

3-Phenyl-3H-imidazole-4-carboxylic acid ethyl ester, prepared as described in Tet. Lett. 2000, 41, 5453-5456, (150 mg) in dichloromethane (2.5 mL) at −78° C. was treated with 1M DIBAL in dichloromethane (1.4 mL), stirred for 30 minutes, and treated with 25% aqueous potassium sodium tartrate, ethyl acetate (50 mL) and 25% aqueous potassium sodium tartrate (50 mL). The extract was washed with 25% aqueous potassium sodium tartrate (50 mL) and brine (50 mL) and dried (Na$_2$SO$_4$), filtered, and concentrated. The concentrate was flash chromatographed on silica gel with 20-30-50% acetone/hexane.

EXAMPLE 152B

This example was made by substituting EXAMPLE 152A for EXAMPLE 148A in EXAMPLE 148B.

EXAMPLE 152C

This example was made by substituting EXAMPLE 152B for EXAMPLE 2B in EXAMPLE 2C.

EXAMPLE 152D

This example was made by substituting EXAMPLE 152C and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-$d_6$) δ 8.50 (d, 1H), 8.36 (d, 1H), 7.88 (d, 1H), 7.80 (dd, 1H), 7.72 (d, 2H), 7.61 (m, 2H), 7.50 (m, 3H), 7.22 (m, 5H), 7.03 (m, 2H), 6.85 (d, 2H), 4.14 (m, 2H), 3.38 (m, 8H), 2.40 (m, 9H), 2.00 (m, 2H), 1.87 (m, 2H), 1.29 (m, 2H).

EXAMPLE 153A

A mixture of EXAMPLE 30C (50.5 mg) and 3-azetidinecarboxylic acid (13 mg) in methanol (1 mL) at 25° C. were treated with sodium cyanoborohydride (8.5 mg), stirred for 4 hours, treated with silica gel and concentrated. The concentrate was flash chromatographed on silica gel with 5% methanol/dichloromethane, 20% methanol/2% water/0.2% acetic acid/dichloromethane and 40% methanol/10% water/1% acetic acid/dichloromethane.

EXAMPLE 153B

A mixture of EXAMPLE 2C (1 g) and N-hydroxysuccinimide (296 mg) in ethyl acetate (9 mL) and THF (4 mL) at 25° C. was treated with 1,3-dicyclohexylcarbodiimide (556 mg), stirred at 40° C. for 6 hours and at 25° C. for 16 hours, cooled to 0° C., treated with 40% ethyl acetate/hexane, and filtered through silica gel with 40% ethyl acetate/hexane. The filtrate was concentrated and the concentrate was flash chromatographed on silica gel with 35-40% ethyl acetate/hexane.

EXAMPLE 153C

A mixture of EXAMPLE 153A (28 mg) and EXAMPLE 153B (34 mg) in DMF (0.4 mL) at 25° C. was treated with DBU (0.031 mL), stirred for 20 hours, and concentrated. The concentrate was flash chromatographed on silica gel with 5% methanol/dichloromethane, 10% methanol/1% water/0.1% acetic acid/dichloromethane, and 20% methanol/20% water/2% acetic acid/dichloromethane. $^1$H NMR (300 MHz, DMSO-$d_6$) δ 8.46 (d, 1H), 8.30 (br, 1H), 7.81 (dd, 1H), 7.72 (d, 2H), 7.46 (m, 5H), 7.26 (m, 7H), 6.93 (m, 1H), 6.81 (d, 2H), 4:06 (m, 2H), 2.99 (m, 16H), 1.65 (m, 4H).

EXAMPLE 154A

This example was made by substituting 1,1-dimethylethanolamine for azetidine hydrochloride in EXAMPLE 30D.

EXAMPLE 154B

This example was made by substituting EXAMPLE 154A for EXAMPLE 153A in EXAMPLE 153C. $^1$H NMR (300 MHz, DMSO-$d_6$) δ 8.45 (d, 1H), 8.12 (d, 1H), 7.82 (dd, 1H), 7.72 (d, 2H), 7.51 (m, 5H), 7.26 (m, 7H), 6.93 (d, 1H), 6.78 (d, 2H), 4.10 (m, 2H), 3.26 (m, 7H), 2.92 (m, 2H), 2.75 (m, 2H), 2.40 (m, 4H), 2.08 (m, 2H), 1.14 (s, 6H).

EXAMPLE 155A

This example was made by substituting sarcosine for 3-azetidinecarboxylic acid in EXAMPLE 153A.

EXAMPLE 155B

This example was made by substituting EXAMPLE 155A for EXAMPLE 153A in EXAMPLE 153C. $^1$H NMR (300 MHz, DMSO-$d_6$) δ 12.08 (br, 1H), 9.76 (br, 1H), 8.52 (d, 1H), 8.28 (d, 1H), 7.85 (dd, 1H), 7.77 (d, 2H), 7.69 (br, 1H), 7.43 (m, 7H), 7.15 (m, 6H), 6.93 (d, 2H), 5.56 (br, 1H), 4.21 (m, 2H), 4.03 (m, 2H), 3.37 (m, 11H), 2.79 (s, 3H), 2.19 (m, 2H), 1.65 (m, 2H).

EXAMPLE 156A

This example was made by substituting D-proline for 3-azetidinecarboxylic acid in EXAMPLE 153A.

EXAMPLE 156B

This example was made by substituting EXAMPLE 156A for EXAMPLE 153A in EXAMPLE 153C. $^1$H NMR (300 MHz, DMSO-$d_6$) δ 12.15 (br, 1H), 9.67 (br, 1H), 8.52 (d, 1H), 8.29 (d, 2H), 7.80 (m, 4H), 7.44 (m, 7H), 7.15 (m, 4H), 6.93 (d, 2H), 5.56 (br, 1H), 4.30 (m, 3H), 2.33 (m, 21H).

EXAMPLE 157A

This example was made by substituting isonipecotic acid for 3-azetidinecarboxylic acid in EXAMPLE 153A.

EXAMPLE 157B

This example was made by substituting EXAMPLE 157A for EXAMPLE 153A in EXAMPLE 153C. $^1$H NMR (300

MHz, DMSO-d$_6$) δ 12.05 (br, 1H), 8.47 (d, 1H), 8.21 (m, 1H), 7.81 (dd, 1H), 7.72 (d, 2H), 7.50 (m, 5H), 7.27 (m, 9H), 6.97 (m, 1H), 6.82 (d, 2H), 4.10 (m, 2H), 3.35 (m, 10H), 3.17 (m, 3H), 2.50 (m, 4H), 2.40 (m, 3H), 2.07 (m, 2H), 1.63 (m, 2H).

EXAMPLE 158A

This example was made by substituting 2-(methylamino) ethanol for azetidine hydrochloride in EXAMPLE 30D.

EXAMPLE 158B

This example was made by substituting EXAMPLE 158A for EXAMPLE 153A in EXAMPLE 153C. $^1$H NMR (300 MHz, DMSO-d$_6$) δ 8.45 (d, 1H), 8.18 (d, 1H), 7.81 (dd, 1H), 7.72 (d, 2H), 7.51 (m, 5H), 7.27 (m, 8H), 6.93 (d, 1H), 6.79 (d, 2H), 5.10 (m, 1H), 4.09 (m, 2H), 3.61 (m, 4H), 3.39 (m, 2H), 3.14 (m, 4H), 2.97 (m, 3H), 2.62 (m, 3H), 2.50 (m, 3H), 2.40 (m, 4H), 2.09 (m, 2H).

EXAMPLE 159A

This example was made by substituting L-proline for 3-azetidinecarboxylic acid in EXAMPLE 153A.

EXAMPLE 159B

This example was made by substituting EXAMPLE 159A for EXAMPLE 153A in EXAMPLE 153C. $^1$H NMR (300 MHz, $_{DMSO-d6}$) δ 12.10 (br, 1H), 9.67 (br, 1H), 8.52 (d, 1H), 8.29 (d, 2H), 7.46 (m, 15H), 6.93 (d, 2H), 5.56 (br, 1H), 4.24 (m, 3H), 2.35 (m, 21H).

EXAMPLE 160A

A mixture of 3-azetidinecarboxylic acid (251 mg) and 1M NaOH (6 mL) in dioxane (6 mL) at 25° C. was treated with 95% benzyl chloroformate (0.54 mL), stirred for 18 hours and concentrated. The concentrate was treated with water, and the mixture was adjusted to pH greater than 10, washed with diethyl ether, adjusted to pH less than 3, and extracted with dichloromethane. The extract was dried (Na$_2$SO$_4$), filtered, and concentrated.

EXAMPLE 160B

EXAMPLE 833294A (574 mg) in dichloromethane (5 mL) at 0° C. was treated with oxalyl chloride (0.75 mL) and DMF (2 drops), stirred for 1 hour, and concentrated twice from dichloromethane. The concentrate in ethyl acetate (5 mL) was treated with 30% aqueous ammonium hydroxide (1.3 mL) while cooling in a bath of cold water, stirred at 25° C. for 2 hours, and treated with water and dichloromethane. The water layer was extracted with ethyl acetate, and the combined extracts were dried (Na$_2$SO$_4$), filtered, and concentrated.

EXAMPLE 160C

EXAMPLE 833294B (481 mg) in DMF (4 mL) at 25° C. was treated with cyanuric chloride (189 mg), stirred for 30 minutes, and treated with water and ethyl acetate. The extract was washed with 1M NaHCO$_3$ and water and dried (Na$_2$SO$_4$), filtered, and concentrated. The concentrate was flash chromatographed on silica gel with 20% acetone/hexane.

EXAMPLE 160D

A mixture of EXAMPLE 160C (394 mg), azidotrimethylsilane (0.52 mL), and dibutyltin oxide (45 mg) in toluene (3.5 mL) at reflux was stirred for 38 hours, treated with methanol, and concentrated twice from methanol. The concentrate was treated with ethyl acetate and saturated NaHCO$_3$. The water layer was adjusted to pH less than 2 with 12M HCl and extracted with ethyl acetate. The extract was dried (MgSO$_4$), filtered, and concentrated. The concentrate was flash chromatographed on silica gel with 2% methanol/dichloromethane and 5% methanol/0.5% acetic acid/dichloromethane.

EXAMPLE 160E

A mixture of EXAMPLE 160D (224 mg) and palladium black (0.20 g) at 25° C. was treated with a mixture of 96% formic acid (0.19 mL) in methanol (4 mL), stirred for 30 minutes, filtered, concentrated, and reconcentrated from methanol.

EXAMPLE 160F

This example was made by substituting EXAMPLE 160E for 3-azetidinecarboxylic acid in EXAMPLE 153A.

EXAMPLE 160G

This example was made by substituting EXAMPLE 160F for EXAMPLE 153A in EXAMPLE 153C. $^1$H NMR (300 MHz, DMSO-d$_6$) δ 8.48 (d, 1H), 8.36 (d, 1H), 7.82 (dd, 1H), 7.70 (m, 3H), 7.32 (m, 12H), 6.99 (d, 1H), 6.83 (d, 2H), 2.93 (m, 22H).

EXAMPLE 161A

A mixture of EXAMPLE 832729 (25 mg), Boc-Ala-Ala-OH (9 mg), EDAC.HCl (7 mg), and HoBT (6 mg) in dichloromethane (0.5 mL) at 25° C. was treated with DIEA (0.009 mL), stirred for 16 hours, and treated with water and ethyl acetate. The extract was washed with 20% aqueous NH$_4$Cl and brine (25 mL) and dried (Na$_2$SO$_4$), filtered, and concentrated. The concentrate was flash chromatographed on silica gel with 8% methanol/dichloromethane.

EXAMPLE 161B

EXAMPLE 161A (15 mg) in dichloromethane (1 mL) at 25° C. was treated with water (0.08 mL) and TFA (0.6 mL), stirred for 1 hour, and concentrated twice from dichloromethane. $^1$H NMR (300 MHz, DMSO-d$_6$) δ 12.09 (br, 1H), 9.68 (br, 1H), 8.52 (d, 1H), 8.51 (d, 1H), 8.29 (d, 1H), 8.05 (m, 3H), 7.77 (m, 4H), 7.52 (m, 3H), 7.37 (m, 3H), 7.17 (m, 7H), 6.93 (d, 2H), 3.55 (m, 17H), 1.92 (m, 2H), 1.30 (d, 3H), 1.18 (d, 3H).

EXAMPLE 162A

This example was made by substituting 5-pyrrolidin-2-yltetrazole, prepared as described in J. Med. Chem. 1985, 28, 1067-1071, for 3-azetidinecarboxylic acid in EXAMPLE 153A.

EXAMPLE 162B

This example was made by substituting EXAMPLE 162A for EXAMPLE 153A in EXAMPLE 153C. $^1$H NMR (300 MHz, DMSO-d$_6$) δ 8.50 (d, 1H), 8.27 (d, 1H), 7.85 (dd, 1H), 7.73 (d, 2H), 7.43 (m, 7H), 7.17 (m, 7H), 6.88 (d, 2H), 4.11 (m, 3H), 2.88 (m, 17H), 1.93 (m, 4H).

EXAMPLE 163A

This example was made by substituting isonipecotic acid for 3-azetidinecarboxylic acid in EXAMPLE 160A.

EXAMPLE 163B

This example was made by substituting EXAMPLE 163A and methanesulfonamide for EXAMPLE 2C and 4-(((1R)-3-(dimethylamino)-1-((phenylsulfanyl)methyl)propyl)amino)-3-nitrobenzenesulfonamide, respectively, in EXAMPLE 2D.

EXAMPLE 163C

This example was made by substituting EXAMPLE 163B for EXAMPLE 160D in EXAMPLE 160E.

EXAMPLE 163D

This example was made by substituting EXAMPLE 163C for 3-azetidinecarboxylic acid in EXAMPLE 153A.

EXAMPLE 163E

This example was made by substituting EXAMPLE 163D for EXAMPLE 153A in EXAMPLE 153C. MS (ESI) m/e 974.1 (M+H).

EXAMPLE 164A

This example was made by substituting EXAMPLE 18C for 19C in EXAMPLE 19D.

EXAMPLE 164B

4-Bromobenzenesulfonyl chloride (0.40 g) in dichloromethane (10 mL) at 0° C. was treated with TEA (0.26 mL), bis(2,4-dimethoxybenzyl)amine, prepared as described in Synthesis, 1991, 703-708, (0.50 g) and DMAP, (35 mg), stirred at 25° C. for 4.5 hours, and treated with water and ethyl acetate. The extract was washed with brine and dried (Na$_2$SO$_4$), filtered, and concentrated. The concentrate was flash chromatographed on silica gel with 20% ethyl acetate/hexane.

EXAMPLE 164C

A mixture of EXAMPLE 164A (356 mg), EXAMPLE 164B (151 mg), sodium tert-butoxide (91 mg), tris(dibenzylideneacetone)dipalladium(0) (32 mg) and rac-2,2'-bis(diphenylphosphino)-1,1'-binaphthyl (42 mg) in toluene (3 mL) at reflux was stirred for 3.5 hours, and treated with ethyl acetate and brine. The extract was dried (Na$_2$SO$_4$), filtered, and concentrated. The concentrate was flash chromatographed on silica gel with 2-4% methanol/dichloromethane.

EXAMPLE 164D

A mixture of EXAMPLE 164C (0.34 g) and triethylsilane (0.25 mL) in dichloromethane (5 mL) at 25° C. was treated with TFA (0.5 mL), stirred for 1.25 hours, and concentrated twice from dichloromethane. The concentrate was flash chromatographed on silica gel with 5% methanol/dichloromethane and 5-10% methanol/NH$_3$ gas-saturated/dichloromethane.

EXAMPLE 164E

This example was made by substituting EXAMPLE 164D for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-d$_6$) δ 7.71 (d, 2H), 7.57 (d, 2H), 7.48 (m, 5H), 7.29 (m, 8H), 6.86 (d, 2H), 6.51 (br, 1H), 6.47 (d, 2H).

EXAMPLE 165A

EXAMPLE 163A (0.50 g) in dichloromethane (5 mL) at 0° C. was treated with DMF (2 drops) and oxalyl chloride (0.58 mL), stirred for 10 minutes, stirred at 25° C. for 30 minutes, and concentrated twice from dichloromethane. The concentrate in THF (5 mL) at 25° C. was treated with 50% aqueous hydroxylamine (0.46 mL), stirred for 17 hours and concentrated. The concentrate in ethyl acetate was washed with 0.5M HCl, water, and brine, dried (Na$_2$SO$_4$), filtered, and concentrated.

EXAMPLE 165B

This example was made by substituting EXAMPLE 165A for EXAMPLE 160D in EXAMPLE 160E.

EXAMPLE 165C

This example was made by substituting EXAMPLE 165B for 3-azetidinecarboxylic acid in EXAMPLE 153A.

EXAMPLE 165D

This example was made by substituting EXAMPLE 165C for EXAMPLE 153A in EXAMPLE 153C.

EXAMPLE 166A

This example was made by substituting 4-bromo-2-chlorobenzenesulfonyl chloride for 4-bromobenzenesulfonyl chloride in EXAMPLE 164B.

EXAMPLE 166B

This example was made by substituting EXAMPLE 166A for EXAMPLE 164B in EXAMPLE 164C.

EXAMPLE 166C

This example was made by substituting EXAMPLE 166B for EXAMPLE 164C in EXAMPLE 164D.

EXAMPLE 166D

This example was made by substituting EXAMPLE 166C for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-d$_6$) δ 7.74 (d, 2H), 7.65 (d, 1H), 7.50 (m, 5H), 7.30 (m, 9H), 6.83 (d, 2H), 6.47 (m, 1H), 6.39 (m, 2H), 3.59 (m, 1H), 3.39 (s, 2H), 3.17 (m, 4H), 3.08 (m, 2H), 2.73 (m, 2H), 2.51 (s, 3H), 2.49 (s, 3H), 2.40 (m, 4H), 2.00 (m, 1H), 1.75 (m, 1H).

EXAMPLE 167A

This example was made by substituting 4-bromo-2,6-dichlorobenzenesulfonyl chloride for 4-bromobenzenesulfonyl chloride in EXAMPLE 164B.

EXAMPLE 167B

This example was made by substituting EXAMPLE 167A for EXAMPLE 164B in EXAMPLE 164C.

EXAMPLE 167C

This example was made by substituting EXAMPLE 167B for EXAMPLE 164C in EXAMPLE 164D.

EXAMPLE 167D

This example was made by substituting EXAMPLE 167C for 4-(((1R)-3-(dimethylamino)-1-((phenylsulfanyl)methyl)propyl)amino)-3-nitrobenzenesulfonamide in EXAMPLE 2D. H NMR (300 MHz, DMSO-$d_6$) δ 7.73 (d, 2H), 7.51 (m, 5H), 7.30 (m, 9H), 6.81 (d, 2H), 6.48 (m, 1H), 6.43 (s, 2H), 3.55 (m, 1H), 3.39 (s, 2H), 3.17 (m, 4H), 3.07 (m, 2H), 2.87 (m, 2H), 2.51 (s, 3H), 2.49 (s, 3H), 2.41 (m, 4H), 2.02 (m, 1H), 1.75 (m, 1H).

EXAMPLE 168A

Tropane in 1,2-dichloroethane (8 mL) at 0° C. was treated with 1-chloroethyl chloroformate (0.47 mL), stirred for 15 minutes, refluxed for 2 hours, and concentrated twice from dichloromethane. The concentrate in methanol (8 mL) was refluxed for 2 hours and concentrated twice from dichloromethane.

EXAMPLE 168B

This example was made by substituting EXAMPLE 168A for azetidine hydrochloride in EXAMPLE 30D.

EXAMPLE 168C

This example was made by substituting EXAMPLE 168B for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 8.87 (m, 1H), 8.44 (d, 1H), 8.09 (m, 1H), 7.82 (m, 1H), 7.71 (d, 2H), 7.50 (m, 5H), 7.27 (m, 8H), 6.92 (m, 1H), 6.78 (d, 2H), 4.07 (m, 1H), 3.90 (m, 2H), 3.38 (m, 3H), 3.12 (m, 4H), 2.97 (m, 2H), 2.41 (m, 4H), 2.09 (m, 4H), 1.83 (m, 4H), 1.61 (m, 4H), 1.48 (m, 1H).

EXAMPLE 169A

This example was made by substituting 7-aza-bicyclo[2.2.1]heptane hydrochloride, prepared as described in Org. Lett. 2001,3, 1371-1374, for azetidine hydrochloride in EXAMPLE 30D.

EXAMPLE 169B

This example was made by substituting EXAMPLE 169A for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 9.20 (m, 1H), 8.44 (d, 1H), 8.13 (m, 1H), 7.82 (d, 1H), 7.71 (d, 2H), 7.51 (m, 5H), 7.27 (m, 8H), 6.92 (d, 1H), 6.78 (d, 2H), 4.12 (m, 3H), 3.38 (m, 3H), 3.13 (m, 4H), 2.97 (m, 2H), 2.40 (m, 4H), 2.09 (m, 3H), 1.85 (m, 4H), 1.58 (m, 4H).

EXAMPLE 170A

This example was made by substituting 1-bromo-2-nitrobenze for 1-fluoro-2-(trifluoromethyl)benzene in EXAMPLE 18D.

EXAMPLE 170B

This example was made by substituting EXAMPLE 170A for 4-bromobenzenesulfonyl chloride in EXAMPLE 164B.

EXAMPLE 170C

EXAMPLE 170B (150 mg) at 25° C. was treated with a mixture of 95% sodium hydride (8 mg) and 2-(phenylsulfanyl)ethanol (0.042 mL) in DMF (1.5 mL), stirred for 6 hours and treated with ethyl acetate and brine. The water layer was extracted with ethyl acetate, and the extract was dried ($Na_2SO_4$), filtered, and concentrated. The concentrate was flash chromatographed on silica gel with 25% acetone/hexane.

EXAMPLE 170D

This example was made by substituting EXAMPLE 170C for EXAMPLE 164C in EXAMPLE 164D.

EXAMPLE 170E

This example was made by substituting EXAMPLE 170D for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 8.32 (d, 1H), 8.08 (dd, 1H), 7.73 (d, 2H), 7.35 (m, 14H), 6.85 (d, 2H), 4.41 (t, 2H), 3.46 (m, 2H), 3.39 (t, 2H), 3.23 (m, 4H), 2.44 (m, 4H).

EXAMPLE 171A

This example was made by substituting 4-bromo-3-trifluoromethylbenzenesulfonyl chloride for 4-bromobenzenesulfonyl chloride in EXAMPLE 164B.

EXAMPLE 171B

This example was made by substituting EXAMPLE 171A for EXAMPLE 170B in EXAMPLE 170C.

EXAMPLE 171C

This example was made by substituting EXAMPLE 171B for EXAMPLE 164C in EXAMPLE 164D.

EXAMPLE 171D

This example was made by substituting EXAMPLE 171C for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 8.05 (m, 2H), 7.71 (d, 2H), 7.50 (m, 5H), 7.30 (m, 9H), 6.84 (d, 2H), 4.36 (t, 2H), 3.41 (s, 2H), 3.38 (t, 2H), 3.20 (m, 4H), 2.41 (m, 4H).

EXAMPLE 172A

2(S)-Hydroxymethyl-4(R)-(toluene-4-sulfonyloxy)pyrrolidine-1-carboxylic acid tert-butyl ester, prepared as described in J. Med. Chem. 1991,34, 2787-2797), (467 mg) in methanol (21 mL) at 25° C. was treated with 95% sodium methoxide (74 mg) in ethanol (3.5 mL), refluxed for 9.5 hours, and concentrated. The concentrate in water and diethyl ether was washed with brine and dried (MgSO$_4$), filtered, and concentrated. The concentrate was flash chromatographed on silica gel with 20% acetone/hexane.

EXAMPLE 172B

EXAMPLE 172A (178 mg) was treated with 1M HCL in methanol (20 mL), stirred for 21 hours, concentrated, and reconcentrated from diethyl ether.

EXAMPLE 172C

This example was made by substituting EXAMPLE 172B for azetidine hydrochloride in EXAMPLE 30D.

EXAMPLE 172D

This example was made by substituting EXAMPLE 172C for 4-(((1R)-3-(dimethylamino)-1-((phenylsulfanyl)methyl) propyl)amino)-3-nitrobenzenesulfonamide in EXAMPLE 2D. $^1$H NMR (300 MHz, DMSO-d$_6$) δ 8.46 (d, 1H), 8.33 (m, 1H), 7.79 (dd, 1H), 7.71 (d, 2H), 7.50 (m, 5H), 7.27 (m, 9H), 6.92 (d, 1H), 6.80 (d, 2H), 4.43 (m, 1H), 4.09 (m, 1H), 3.85 (m, 1H), 3.54 (m, 1H), 3.39 (s, 2H), 3.33 (m, 2H), 3.15 (m, 5H), 2.94 (m, 2H), 2.40 (m, 5H), 1.94 (m, 4H), 1.72 (m, 1H).

EXAMPLE 173A

This example was made by substituting 2(R)-hydroxymethyl-4(S)-(toluene-4-sulfonyloxy)pyrrolidine-1-carboxylic acid tert-butyl ester, prepared as described in J. Med. Chem. 1991,34, 2787-2797, for 2(S)-hydroxymethyl-4(R)-(toluene-4-sulfonyloxy)pyrrolidine-1-carboxylic acid tert-butyl ester in EXAMPLE 172A.

EXAMPLE 173B

This example was made by substituting EXAMPLE 173A for EXAMPLE 172A in EXAMPLE 172B.

EXAMPLE 173C

This example was made by substituting EXAMPLE 173B for azetidine hydrochloride in EXAMPLE 30D.

EXAMPLE 173D

This example was made by substituting EXAMPLE 173C for 4-(((1R)-3-(dimethylamino)-1-((phenylsulfanyl)methyl) propyl)amino)-3-nitrobenzenesulfonamide in EXAMPLE 2D. $^1$H NMR (300 MHz, DMSO-d$_6$) δ 8.46 (d, 1H), 8.25 (m, 1H), 7.81 (dd, 1H), 7.71 (d, 2H), 7.51 (m, 5H), 7.27 (m, 9H), 6.94 (d, 1H), 6.80 (d, 2H), 4.46 (m, 1H), 4.14 (m, 1H), 3.87 (m, 1H), 3.56 (m, 1H), 3.39 (s, 2H), 3.33 (m, 2H), 3.16 (m, 5H), 2.95 (m, 2H), 2.40 (m, 5H), 1.95 (m, 4H), 1.76 (m, 1H).

EXAMPLE 174

This example was made by substituting EXAMPLE 837538C and EXAMPLE 172O for EXAMPLE 2C and 4-(((1R)-3-(dimethylamino)-1-((phenylsulfanyl)methyl) propyl)amino)-3-nitrobenzenesulfonamide, respectively, in EXAMPLE 2D. $^1$H NMR (300 MHz, DMSO-d$_6$) δ 8.46 (d, 1H), 8.32 (m, 1H), 7.81 (dd, 1H), 7.71 (d, 2H), 7.24 (m, 10H), 6.94 (d, 1H), 6.79 (d, 2H), 4.45 (m, 1H), 4.11 (m, 1H), 3.87 (m, 1H), 3.56 (m, 1H), 3.32 (m, 4H), 3.15 (m, 5H), 2.97 (m, 2H), 2.78 (m, 4H), 2.22 (m, 6H), 1.96 (m, 4H), 1.66 (m, 4H).

EXAMPLE 175

This example was made by substituting EXAMPLE 837538C and EXAMPLE 173C for EXAMPLE 2C and 4-(((1R)-3-(dimethylamino)-1-((phenylsulfanyl)methyl) propyl)amino)-3-nitrobenzenesulfonamide, respectively, in EXAMPLE 2D. $^1$H NMR (300 MHz, DMSO-d$_6$) δ 8.46 (d, 1H), 8.26 (m, 1H), 7.80 (dd, 1H), 7.71 (d, 2H), 7.24 (m, 10H), 6.94 (d, 1H), 6.79 (d, 2H), 4.45 (m, 1H), 4.13 (m, 1H), 3.86 (m, 1H), 3.57 (m, 1H), 3.32 (m, 4H), 3.15 (m, 5H), 2.94 (m, 2H), 2.78 (m, 4H), 2.22 (m, 6H), 1.95 (m, 4H), 1.66 (m, 4H).

EXAMPLE 176

This example was made by substituting EXAMPLE 837538C and EXAMPLE 169A for EXAMPLE 2C and 4-(((1R)-3-(dimethylamino)-1-((phenylsulfanyl)methyl) propyl)amino)-3-nitrobenzenesulfonamide, respectively, in EXAMPLE 2D. $^1$H NMR (300 MHz, DMSO-d$_6$) δ 9.18 (br, 1H), 8.44 (d, 1H), 8.14 (m, 1H), 7.80 (d, 1H), 7.71 (d, 2H), 7.24 (m, 9H), 6.93 (d, 1H), 6.78 (d, 2H), 4.09 (m, 2H), 3.35 (m, 4H), 3.14 (m, 6H), 2.76 (br s, 4H), 2.22 (m, 7H), 2.04 (m, 2H), 1.84 (m, 4H), 1.66 (m, 6H).

EXAMPLE 177A

This example was made by substituting 2,5-(cis)-dimethylpyrrolidine toluenesulfonate, prepared as described in A. R. Katritzky et al. J. Org. Chem. 1999,64, 1979-1985) for azetidine hydrochloride in EXAMPLE 30D.

EXAMPLE 177B

This example was made by substituting EXAMPLE 837538C and EXAMPLE 177A for EXAMPLE 2C and 4-(((1R)-3-(dimethylamino)-1-((phenylsulfanyl)methyl) propyl)amino)-3-nitrobenzenesulfonamide, respectively, in EXAMPLE 2D. $^1$H NMR (300 MHz, DMSO-d$_6$) δ 8.57 (br, 1H), 8.45 (d, 1H), 8.15 (m, 1H), 7.81 (d, 1H), 7.71 (d, 2H), 7.24 (m, 9H), 6.96 (m, 1H), 6.78 (d, 2H), 4.11 (m, 1H), 3.49 (m, 1H), 3.31 (m, 2H), 3.13 (m, 8H), 2.77 (m, 4H), 2.17 (m, 7H), 1.62 (m 6H), 1.29 (m, 6H).

EXAMPLE 178A

A mixture of 2(5H)-furanone (1 mL) and
N-(methoxymethyl)-N-(trimethylsilylmethyl)benzylamine (4.2 mL) in dichloromethane (30 mL) at 0° C. was treated with TFA (0.10 mL), stirred for 2.5 hours, and treated with dichloromethane and saturated aqueous NaHCO$_3$. The extract was washed with brine and dried (Na$_2$SO$_4$), filtered, and concentrated. The concentrate was flash chromatographed on silica gel with 15% acetone/hexane.

EXAMPLE 178B

EXAMPLE 178A (2.76 g) in 1,2-dichloroethane (25 mL) at 25° C. was treated with 95% benzyl chloroformate (3.8 mL), refluxed for 24 hours and concentrated. The concentrate was flash chromatographed on silica gel with 25% acetone/hexane.

EXAMPLE 178C

EXAMPLE 178B (2.26 g) in THF (40 mL) at −78° C. was treated with 1M DIBAL in dichloromethane (20 mL) then methanol (40 mL), filtered at 25° C., and concentrated. The concentrate was flash chromatographed on silica gel with 30% acetone/hexane.

EXAMPLE 178D

A mixture of EXAMPLE 178C (1.282 g) and triethylsilane (1.17 mL) in dichloromethane (25 mL) at 0° C. was treated with $BF_3$.diethyl etherate (0.68 mL), stirred at 25° C. for 3 hours, and treated with ethyl acetate and saturated aqueous $NaHCO_3$. The extract was washed with brine and dried ($Na_2SO_4$), filtered, and concentrated. The concentrate was flash chromatographed on silica gel with 15% acetone/hexane.

EXAMPLE 178E

This example was made by substituting EXAMPLE 178D for EXAMPLE 160D in EXAMPLE 160E.

EXAMPLE 178F

This example was made by substituting EXAMPLE 178E for azetidine hydrochloride in EXAMPLE 30D.

EXAMPLE 178G

This example was made by substituting EXAMPLE 837538C and EXAMPLE 178F for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-$d_6$) δ 8.46. (d, 1H), 8.23 (m, 1H), 7.77 (d, 1H), 7.71 (d, 2H), 7.24 (m, 10H), 6.96 (d, 1H), 6.79 (d, 2H), 4.08 (m, 1H), 3.61 (m, 2H), 2.68 (m, 26H), 1.66 (m, 6H).

EXAMPLE 179A

Cyclohexanol (880 mg) in DMF (2 mL) a 25° C. was treated with 60% oily NaH (400 mg) and DMF (3 mL), stirred for 1.5 hours, treated with 15-crown-5 (0.6 mL), 4-fluoro-3-nitrobenzenesulfonamide, prepared as described in WO02/24636, (440 mg), and DMF (0.5 mL), stirred for 1.5 hours, and treated with water and ethyl acetate. The extract was dried ($MgSO_4$), filtered, and concentrated. The concentrate was flash chromatagraphed on silica gel with hexanes/ethyl acetate (10-30%).

EXAMPLE 179B

This example was made by substituting EXAMPLE 179A for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-$d_6$) δ 8.31 (d, 1H), 8.07 (dd, 1H), 7.72 (d, 2H), 7.55 (t, 2H), 7.40 (m, 7H), 7.23 (dd, 1H), 6.85 (d, 2H), 6.73 (m, 1H), 3.51 (s, 2H), 3.23 (s, 4H), 2.44 (s, 4H), 1.85 (m, 2H), 1.66 (m, 2H), 1.55 (m, 2H), 1.46 (m, 1H), 1.28 (m, 3H).

EXAMPLE 180A

This example was made by substituting cyclohexylmethanol for cyclohexanol in EXAMPLE 179A.

EXAMPLE 180B

This example was made by substituting EXAMPLE 779855A for 4-(((1R)-3-(dimethylamino)-1-((phenylsulfanyl)methyl)propyl)amino)-3-nitrobenzenesulfonamide in EXAMPLE 1D. $^1$H NMR (300 MHz, DMSO-$d_6$) δ 8.41 (d, 1H), 8.17 (dd, 1H), 7.77 (s, 1H), 7.74 (s, 2H), 7.58 (d, 1H), 7.53 (m, 2H), 7.46 (m, 3H), 7.37 (m, 3H), 6.93 (d, 2H), 4.31 (br s, 1H), 3.80 (br s, 4H), 3.19 (br s, 3H), 2.83 (br s, 2H), 1.74 (m, 6H), 1.23 (m, 3H), 1.07 (m, 2H).

EXAMPLE 181A

This example was made by substituting 2-cyclohexylethanol for cyclohexanol in EXAMPLE 179A.

EXAMPLE 181B

This example was made by substituting EXAMPLE 181A for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-$d_6$) δ 8.41 (d, 1H), 8.17 (dd, 1H), 7.77 (s, 1H), 7.75 (s, 2H), 7.60 (d, 1H), 7.53 (m, 2H), 7.52 (t, 2H), 7.43 (t, 1H), 7.37 (m, 3H), 6.92 (d, 2H), 4.30 (t, 4H), 2.95 (br s, 4H), 1.71 (d, 2H), 1.65 (m, 8H), 1.46 (m, 1H), 1.18 (m, 4H), 0.94 (m, 2H).

EXAMPLE 182A

Ammonium formate (5.8 g) in water (2.9 mL) at 25° C. was treated with tetrahydropyran-4-one (1 g) in methanol (26 mL), stirred for 5 minutes, treated with 10% Pd/C (1.2 g), stirred for 18 hours, filtered through diatomaceous earth (Celite®), and concentrated. A mixture of the concentrate in ethanol (23 mL) was stirred at 0° C. as 12M HCl (1.7 mL) was added dropwise, stirred for 1 hour, and filtered.

EXAMPLE 182B

This example was made by substituting EXAMPLE 182A for EXAMPLE 21C in EXAMPLE 21D.

EXAMPLE 182C

This example was made by substituting EXAMPLE 780431B for 4-(((1R)-3-(dimethylamino)-1-((phenylsulfanyl)methyl)propyl)amino)-3-nitrobenzenesulfonamide in EXAMPLE 1D. $^1$H NMR (400 MHz, DMSO-$d_6$) δ 8.62 (d, 1H), 8.27 (d, 1H), 7.93 (dd, 1H), 7.49 (d, 2H), 7.46 (d, 2H), 7.42 (d, 1H), 7.36 (m, 4H), 6.90 (d, 2H), 4.22 (br s, 1H), 3.93 (m, 1H), 3.86 (d, 2H), 3.72 (br s, 2H), 3.46 (t, 3H), 2.91 (br s, 4H), 2.49 (s, 2H), 1.91 (d, 2H), 1.62 (m, 2H).

EXAMPLE 183A

This example was made by substituting 2-cyclohexylethylamine for EXAMPLE 21C in EXAMPLE 21D.

EXAMPLE 183B

This example was made by substituting EXAMPLE 183A for 4-(((1R)-3-(dimethylamino)-1-((phenylsulfanyl)methyl)propyl)amino)-3-nitrobenzenesulfonamide in EXAMPLE 1D. $^1$H NMR (400 MHz, DMSO-$d_6$) δ 12.20 (br s, 1H), 8.62 (d, 1H), 8.52 (t, 1H), 7.94 (dd, 1H), 7.75 (d, 3H), 7.52 (m, 2H), 7.47 (d, 1H), 7.42 (m, 1H), 7.37 (m, 3H), 7.21 (d, 1H), 6.92 (d, 2H), 4.28 (br s, 2H), 3.75 (br s, 4H), 3.44 (m, 2H), 3.17 (br s, 2H), 2.86 (br s, 2H), 1.73 (d, 2H), 1.65 (m, 2H), 1.52 (m, 2H), 1.36 (m, 1H), 1.18 (m, 4H), 0.95 (m, 2H).

EXAMPLE 184A

This example was made by substituting N-methylcyclohexylamine for EXAMPLE 21C in EXAMPLE 21D.

EXAMPLE 184B

This example was made by substituting EXAMPLE 184A for 4-(((1R)-3-(dimethylamino)-1-((phenylsulfanyl)methyl)propyl)amino)-3-nitrobenzenesulfonamide in EXAMPLE 1D. $^1$H NMR (400 MHz, DMSO-$d_6$) δ 8.26 (d, 1H), 7.89 (dd, 1H), 7.75 (d, 3H), 7.52 (m, 2H), 7.47 (d, 2H), 7.43 (m, 2H), 7.37 (m, 3H), 6.92 (d, 2H), 4.27 (br s, 2H), 3.81 (br s, 3H), 3.56 (t, 1H), 3.15 (br s, 3H), 2.84 (br s, 2H), 2.65 (s, 3H), 1.76 (t, 4H), 1.59 (m, 3H), 1.35 (m, 2H), 1.15 (m, 1H).

EXAMPLE 185A

This example was made by substituting 3,3-dimethylglutarimide for EXAMPLE 18E in EXAMPLE 18F.

EXAMPLE 185B

This example was made by substituting EXAMPLE 185A for EXAMPLE 21C in EXAMPLE 21D.

EXAMPLE 185C

This example was made by substituting EXAMPLE 185B for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-$d_6$) δ 8.29 (d, 1H), 7.93 (dd, 1H), 7.74 (d, 3H), 7.51 (m, 2H), 7.47 (t, 2H), 7.42 (m, 2H), 7.35 (m, 3H), 6.91 (d, 2H), 4.29 (s, 2H), 3.79 (br s, 4H), 3.15 (m, 6H), 2.90 (br s, 2H), 1.42 (m, 4H), 0.96 (s, 6H).

EXAMPLE 186A

A mixture of tert-butyl-4-oxo-1-piperidinecarboxylate (2 g) in methanol (50 mL) 0° C. was treated with NaBH$_4$ (2 g), stirred for 0.5 hours, stirred for 2 hours at 25° C., concentrated, treated with water, and extracted with dichloromethane. The extract was washed with water and dried (MgSO$_4$), filtered, and concentrated.

EXAMPLE 186B

This example was made by substituting EXAMPLE 186A for cyclohexanol in EXAMPLE 179A.

EXAMPLE 186C

This example was made by substituting EXAMPLE 186B for 4-(((1R)-3-(dimethylamino)-1-((phenylsulfanyl)methyl)propyl)amino)-3-nitrobenzenesulfonamide in EXAMPLE 1D. $^1$H NMR (300 MHz, DMSO-$d_6$) δ 8.26 (d, 1H), 8.03 (dd, 1H), 7.72 (d, 2H), 7.54 (m, 1H), 7.49 (m, 1H), 7.42 (m, 3H), 7.36 (m, 3H), 7.24 (m, 1H), 6.81 (d, 2H), 4.92 (m, 1H), 3.44 (m, 4H), 3.35 (m, 2H), 3.17 (d, 4H), 2.41 (m, 4H), 1.87 (m, 2H), 1.60 (m, 2H), 1.40 (s, 9H).

EXAMPLE 187

This example was made by substituting EXAMPLE 186C for EXAMPLE 21B in EXAMPLE 21C. $^1$H NMR (400 MHz, DMSO-$d_6$) δ 12.30 (br s, 1H), 11.58 (br s, 1H), 9.31 (s, 1H), 9.08 (s, 1H), 8.46 (d, 1H), 8.19 (dd, 1H), 8.18 (m, 1H), 7.76 (d, 2H), 7.71 (d, 1H), 7.52 (t, 2H), 7.46 (t, 2H), 7.42 (d, 1H), 7.35 (d, 3H), 6.92 (d, 2H), 5.11 (m, 1H), 4.35 (s, 2H), 3.84 (m, 2H), 3.67 (s, 3H), 3.38 (m, 2H), 3.12 (m, 2H), 2.73 (s, 2H), 2.72 (d, 1H), 2.15 (m, 2H), 1.98 (m, 2H).

EXAMPLE 188

A mixture of EXAMPLE 187 (53 mg) and 37% formalin (6.6 µL), in 1:1 dichloromethane/methanol (1.5 mL) at 25° C. was treated with 2.47 mmol/g MP-NaCNBH$_3$ (55 mg) and DIEA (1 drop), stirred for 18 hours, treated with 1:1 dichloromethane/methanol (5 mL), and filtered through diatomaceous earth (Celite®). The filtrate was dried (MgSO$_4$), filtered, concentrated. The concentrate was flash chromatographed on silica gel with dichloromethane/2-5%methanol/0.5-1% NH$_4$OH. $^1$H NMR (500 MHz, DMSO-$d_6$) δ 8.28 (d, 1H), 8.04 (dd, 1H), 7.72 (d, 2H), 7.54 (d, 1H), 7.45 (d, 2H), 7.46 (t, 2H), 7.42 (m, 3H), 7.36 (m, 3H), 7.24 (dd, 1H), 6.79 (d, 2H), 4.91 (s, 1H), 4.42 (s, 2H), 3.14 (m, 8H), 2.74 (s, 3H), 2.39 (m, 4H), 2.10 (s, 2H), 1.96 (s, 2H).

EXAMPLE 189

This example was made by substituting 4-((cyclohexylmethyl)amino)-3-nitrobenzenesulfonamide for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 8.64 (m, 2H), 7.93 (dd, 1H), 7.78 (d, 2H), 7.72 (s, 1H), 7.52 (d, 4H), 7.40 (d, 2H), 7.33 (m, 1H), 7.24 (d, 1H), 6.92 (d, 2H), 4.22 (br s, 1H), 3.82 (br s, 2H), 3.29 (t, 4H), 2.88 (br s, 2H), 1.70 (m, 8H), 1.18 (m, 4H), 0.98 (m, 2H).

EXAMPLE 190A

Cyclohexanecarboxaldehyde (2 g) in methanol (20 mL) at 0° C. was treated with n-propylamine (0.77 mL) and NaCNBH$_3$ (600 mg), stirred at 25° C. for 18 hours, treated with water, and extracted with diethyl ether. The extract was dried (MgSO$_4$), filtered, and concentrated.

EXAMPLE 190B

This example was made by substituting EXAMPLE 190A for EXAMPLE 21C in EXAMPLE 21D.

EXAMPLE 190C

This example was made by substituting EXAMPLE 190B for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 8.24 (d, 1H), 7.89 (t, 1H), 7.76 (m, 2H), 7.70 (br s, 1H), 7.51 (m, 4H), 7.45 (d, 1H), 7.39 (m, 2H), 7.32 (m, 1H),.6.91 (d, 2H),.3.15 (dd, 2H), 3.07 (d, 2H), 2.05 (s, 2H), 1.61 (m, 6H), 1.48 (m, 3H), 1.11 (m, 4H), 0.78 (m, 5H).

EXAMPLE 191A

This example was made by substituting 1-N-Boc-4-cyanopiperidine for EXAMPLE 21B in EXAMPLE 21C.

EXAMPLE 191B

A mixture of EXAMPLE 191A (520 mg), K$_2$CO$_3$ (1.7 g), benzylbromide (0.62 mL), and acetone (7 mL) at reflux was stirred for 2.5 hours and concentrated. The concentrate was treated with water and 1M HCl, washed with hexanes, made basic with 2.5M NaOH, and extracted with dichloromethane. The extract was dried (MgSO$_4$), filtered, and concentrated.

EXAMPLE 191C

A mixture of EXAMPLE 191B (420 mg) and Raney nickel (4.5 g) in 20% NH$_3$/methanol (100 mL) at 25° C. was stirred under H$_2$ at 60 psi for 16 hours, filtered, and concentrated.

EXAMPLE 191D

This example was made by substituting EXAMPLE 191C for EXAMPLE 21C in EXAMPLE 21D.

EXAMPLE 191E

This example was made by substituting EXAMPLE 191D for 4-(((1R)-3-(dimethylamino)-1-((phenylsulfanyl)methyl)propyl)amino)-3-nitrobenzenesulfonamide in EXAMPLE 1D. $^1$H NMR (400 MHz, DMSO-d$_6$) δ 12.08 (br s, 1H), 11.50 (br s, 1H), 10.68 (br s, 1H), 8.69 (m, 1H), 8.62 (s, 1H), 8.10 (br s, 1H), 7.91 (m, 1H), 7.74 (d, 3H), 7.57 (br s, 2H), 7.46 (m, 7H), 7.33 (m, 4H), 7.27 (d, 1H), 6.90 (d, 2H), 4.34 (br, s, 2H), 4.20 (m, 2H), 3.81 (m, 2H), 3.26 (m, 7H), 3.15 (s, 2H), 2.79 (m, 5H), 2.49 (s, 1H), 1.87 (m, 4H), 1.60 (m, 2H), 1.24 (m, 1H), 0.85 (m, 1H).

EXAMPLE 192A

Cyclohexanemethylamine (2 mL) in THF (8 mL) at 25° C. was treated with acetic formic anhydride, prepared as described in Tet. Lett. 1982, 33, 3315, (5.7 g), stirred for 3.5 hours, concentrated, cooled to 0° C., treated with 1M borane.THF (5.1 mL), stirred at reflux for 2.5 hours, concentrated, cooled to 0° C., treated with methanol (10 mL) and methanolic HCl (50 mL), stirred at reflux for 1 hour, concentrated, treated with water, and washed with diethyl ether. The water layer was made basic with 1M KOH and extracted with dichloromethane. The extract was dried (MgSO$_4$), filtered, and concentrated.

EXAMPLE 192B

This example was made by substituting EXAMPLE 192A for EXAMPLE 21C in EXAMPLE 21D.

EXAMPLE 192C

This example was made by substituting EXAMPLE 192B for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-d$_6$) δ 8.27 (d, 1H), 7.86 (dd, 1H), 7.74 (m, 3H), 7.52 (m, 2H), 7.47 (m, 2H), 7.42 (m, 2H), 7.35 (m, 3H), 6.91 (d, 2H), 4.29 (br s, 2H), 3.27 (d, 4H), 2.81 (m, 3H), 1.63 (m, 8H), 1.13 (m,.4H), 0.86 (m, 2H).

EXAMPLE 193A

This example was made by substituting 4-amino-1-benzylpiperidine for EXAMPLE 21C in EXAMPLE 21D.

EXAMPLE. 193B

This example was made by substituting EXAMPLE 193A for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-d$_6$) δ 9.95 (br s, 1H), 8.62 (br s, 1H), 8.15 (br s, 1H), 7.95 (d, 1H), 7.73 (d, 4H), 7.50 (m, 10H), 7.41 (m, 1H), 7.34 (m, 5H), 6.90 (d, 2H), 4.46 (br s, 1H), 4.34 (br s, 2H), 4.23 (br s, 1H), 3.92 (br s, 1H), 3.18 (m, 2H), 3.06 (m, 3H), 2.20 (m, 2H), 1.83 (br s, 1H).

EXAMPLE 194A

A mixture of tetrahydrothiopyran-4-one (1 g), hyroxylamine hydrochloride (1.5 g), and TEA (3 mL) in absolute ethanol (5 mL) was stirred at reflux for 3 hours, cooled to 25° C., treated with water, and extracted with dichloromethane. The extract was dried (MgSO$_4$), filtered, and concentrated.

EXAMPLE 194B

EXAMPLE 193A (300 mg) was treated with LiAlH$_4$ (400 mg) in THF (4 mL)/diethyl ether (11 mL), stirred at reflux for 5 hours, and processed as described in Fieser and Fieser, Reagents for Organic Synthesis, Vol 1, p.584.

EXAMPLE 194C

This example was made by substituting EXAMPLE 194B for EXAMPLE 21C in EXAMPLE 21D.

EXAMPLE 194D

This example was made by substituting EXAMPLE 194C for 4-(((1R)-3-(dimethylamino)-1-((phenylsulfanyl)methyl)propyl)amino)-3-nitrobenzenesulfonamide in EXAMPLE 1D. $^1$H NMR (400 MHz, DMSO-d$_6$) δ 12.01 (br s, 1H), 8.64 (d, 1H), 8.31 (d, 2H), 7.94 (dd, 1H), 7.74 (d, 3H), 7.47 (m, 4H), 7.34 (m, 3H), 6.91 (d, 4H), 4.29 (br s, 1H), 3.79 (m, 3H), 2.79 (m, 3H), 2.67 (m, 2H), 2.21 (m, 2H), 1.75 (m, 2H).

EXAMPLE 195A

This example was made by substituting ethyl 4-amino-1-piperidinecarboxylate for EXAMPLE 21C in EXAMPLE 21D.

EXAMPLE 195B

This example was made by substituting EXAMPLE 195A for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-d$_6$) δ 12.10 (br s, 1H), 8.64 (d, 1H), 8.29 (d, 1H), 7.95 (dd, 1H), 7.75 (d, 3H), 7.54 (m, 2H), 7.48 (m, 1H), 7.43 (m, 1H), 7.37 (m, 2H), 6.92 (d, 2H), 4.36 (br s, 2H), 4.05 (m, 2H), 3.94 (m, 3H), 3.77 (br s, 3H), 3.01 (br s, 4H), 2.83 (br s, 2H), 1.94 (d, 2H), 1.55 (m, 2H), 1.19 (t, 5H).

EXAMPLE 196A

This example was made by substituting 1-bromopropane for benzyl bromide in EXAMPLE 191B.

EXAMPLE 196B

This example was made by substituting EXAMPLE 196A for EXAMPLE 191B in EXAMPLE 797197C.

EXAMPLE 196C

This example was made by substituting EXAMPLE 196B for EXAMPLE 21C in EXAMPLE 21D.

EXAMPLE 196D

This example was made by substituting EXAMPLE 196C for 4-(((1R)-3-(dimethylamino)-1-((phenylsulfanyl)methyl)propyl)amino)-3-nitrobenzenesulfonamide in EXAMPLE 1D. $^1$H NMR (400 MHz, DMSO-$d_6$) δ 8.51 (d, 1H), 8.43 (t, 2H), 7.90 (dd, 1H), 7.72 (d, 2H), 7.53 (m, 1H), 7.42 (m, 4H), 7.35 (m, 3H), 7.24 (m, 1H), 7.10 (d, 1H), 6.78 (d, 2H), 3.41 (s, 2H), 3.36 (m, 5H), 3.13 (m, 4H), 2.77 (m, 3H), 2.39 (m, 4H), 1.87 (d, 3H), 1.59 (m, 2H), 1.42 (m, 2H), 0.87 (t, 3H).

EXAMPLE 197A

This example was made by substituting isopropylamine for EXAMPLE 21C in EXAMPLE 21D.

EXAMPLE 197B

This example was made by substituting EXAMPLE 197A for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-$d_6$) δ 8.64 (d, 1H), 8.24 (d, 1H), 7.95 (dd, 1H), 7.74 (m, 3H), 7.50 (m, 4H), 7.42 (m, 1H), 7.35 (m, 3H), 7.27 (d, 1H), 6.91 (d, 2H), 4.25 (br s, 2H), 4.00 (m, 1H), 1.28 (d, 6H).

EXAMPLE 198A

A mixture of tributylphosphine (0.8 mL), (1,1'-azodicarbonyl)dipiperidine (0.8 g), and THF (5.1 mL) at 25° C. was stirred for 10 minutes, treated with tert-butyl N-(2-hydroxyethyl)carbamate (0.32 mL), 2-mercaptothiazole (500 mg), and THF (5 mL), stirred for 20 hours, treated with ethyl acetate (50 mL), washed with water, dried (MgSO$_4$), filtered, and concentrated. The concentrate was flash chromatographed on silica gel with 5-30% ethyl acetate/hexanes.

EXAMPLE 198B

This example was made by substituting EXAMPLE 198A for EXAMPLE 21B in EXAMPLE 21C.

EXAMPLE 198C

This example was made by substituting EXAMPLE 198B for EXAMPLE 21C in EXAMPLE 21D.

EXAMPLE 198D

This example was made by substituting EXAMPLE 198C for 4-(((1R)-3-(dimethylamino)-1-((phenylsulfanyl)methyl)propyl)amino)-3-nitrobenzenesulfonamide in EXAMPLE 1D. $^1$H NMR (400 MHz, DMSO-$d_6$) δ 8.80 (t, 1H), 8.61 (d, 1H), 7.96 (dd, 1H), 7.73 (m, 4H), 7.62 (d, 1H), 7.51 (m, 2H), 7.46 (d, 2H), 7.40 (m, 2H), 7.34 (m, 4H), 6.91 (d, 2H), 4.28 (br s, 2H), 3.81 (m, 4H), 3.50 (t, 4H), 2.06 (s, 2H).

EXAMPLE 199A

This example was made by substituting 4-phenyl-2-mercaptothiazole for 2-mercaptothiazole in EXAMPLE 198A.

EXAMPLE 199B

This example was made by substituting EXAMPLE 199A for EXAMPLE 21B in EXAMPLE 21C.

EXAMPLE 199C

This example was made by substituting EXAMPLE 199B for EXAMPLE 21C in EXAMPLE 21D.

EXAMPLE 199D

This example was made by substituting EXAMPLE 199C for 4-(((1R)-3-(dimethylamino)-1-((phenylsulfanyl)methyl)propyl)amino)-3-nitrobenzenesulfonamide in EXAMPLE 1D. $^1$H NMR (400 MHz, DMSO-$d_6$) δ 8.77 (m, 1H), 8.57 (d, 1H), 8.00 (s, 1H), 7.91 (m, 3H), 7.73 (d, 2H), 7.54 (m, 1H), 7.39 (m, 11H), 7.24 (m, 1H), 6.86 (d, 2H), 3.87 (m, 2H), 3.57 (dd, 2H), 3.43 (s, 2H), 3.22 (m, 4H), 2.39 (m, 4H).

EXAMPLE 200A

This example was made by substituting 2-mercaptobenzthiazole for 2-mercaptothiazole in EXAMPLE 198A.

EXAMPLE 200B

This example was made by substituting EXAMPLE 200A for EXAMPLE 21B in EXAMPLE 21C.

EXAMPLE 200C

This example was made by substituting EXAMPLE 200B for EXAMPLE 21C in EXAMPLE 21D.

EXAMPLE 200D

This example was made by substituting EXAMPLE 200C for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-$d_6$) δ 8.86 (t, 1H), 8.59 (d, 1H), 7.76 (m, 4H), 7.54 (m, 2H), 7.48 (m, 2H), 7.43 (m, 2H), 7.36 (m, 4H), 6.92 (d, 2H), 4.31 (br s, 2H), 3.91 (m, 2H), 3.66 (t, 4H), 2.97 (br s, 4H).

EXAMPLE 201

This example was made by substituting EXAMPLE 198C for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 8.80 (m, 1H), 8.61 (d, 1H), 7.95 (dd, 1H), 7.74 (m, 4H), 7.71 (d, 1H), 7.62 (d, 1H), 7.52 (m, 4H), 7.40 (m, 1H), 7.39 (m, 2H), 7.37 (m, 1H), 7.33 (m, 1H), 6.91 (d, 2H), 3.81 (m, 4H), 3.50 (m, 4H), 3.32 (m, 1H), 3.27 (m, 1H), 2.49 (m, 1H), 2.06 (s, 1H).

EXAMPLE 202A

This example was made by substituting 2-mercaptobenzoxazole for 2-mercaptothiazole in EXAMPLE 198A.

EXAMPLE 202B

This example was made by substituting EXAMPLE 202A for EXAMPLE 21B in EXAMPLE 21C.

EXAMPLE 202C

This example was made by substituting EXAMPLE 202B for EXAMPLE 21C in EXAMPLE 21D.

EXAMPLE 202D

This example was made by substituting EXAMPLE 202C for 4-(((1R)-3-(dimethylamino)-1-((phenylsulfanyl)methyl)-propyl)amino)-3-nitrobenzenesulfonamide in EXAMPLE 2D. $^1$H NMR (400 MHz, DMSO-$d_6$) δ 8.84 (m, 1H), 8.58 (d, 1H), 8.00 (dd, 1H), 7.76 (d, 2H), 7.71 (br s, 1H), 7.57 (m, 2H), 7.50 (m, 4H), 7.39 (m, 2H), 7.29 (m, 3H), 6.91 (d, 2H), 4.22 (br s, 2H), 3.92 (m, 2H), 3.60 (t, 4H), 2.97 (m, 4H).

EXAMPLE 203

This example was made by substituting EXAMPLE 200C for 4-M1R)-3-(dimethylamino)-1-((phenylsulfanyl)methyl) propyl)amino)-3-nitrobenzenesulfonamide in EXAMPLE 2D. $^1$H NMR (500 MHz, DMSO-$d_6$) δ 12.06 (br s, 1H), 8.85 (t, 1H), 8.58 (d, 1H), 8.01 (dd, 1H), 7.97 (d, 1H), 7.75 (m, 3H), 7.71 (br s, 1H), 7.51 (m, 4H), 7.37 (m, 4H), 6.91 (d, 2H), 4.26 (br s, 2H), 3.90 (m, 2H), 3.64 (t, 4H), 2.96 (m, 6H).

EXAMPLE 204A

This example was made by substituting 2-mercaptopyrimidine for 2-mercaptothiazole in EXAMPLE 198A.

EXAMPLE 204B

This example was made by substituting EXAMPLE 204A for EXAMPLE 21B in EXAMPLE 21C.

EXAMPLE 204C

This example was made by substituting EXAMPLE 204B for EXAMPLE 21C in EXAMPLE 21D.

EXAMPLE 204D

This example was made by substituting EXAMPLE 204C for 4-(((1R)-3-(dimethylamino)-1-((phenylsulfanyl)methyl)-propyl)amino)-3-nitrobenzenesulfonamide in EXAMPLE 2D. $^1$H NMR (500 MHz, DMSO-$d_6$) δ 12.07 (br s, 1H), 8.83 (t, 1H), 8.66 (d, 2H), 8.63 (d, 1H), 8.04 (dd, 1H), 7.76 (d, 2H), 7.72 (br s, 1H), 7.52 (m, 5H), 7.40 (d, 2H), 7.33 (m, 1H), 7.24 (t, 1H), 6.92 (d, 2H), 4.29 (br s, 2H), 3.78 (m, 4H), 3.39 (t, 4H), 2.85 (br s, 2H).

EXAMPLE 205A

This example was made by substituting 2-bromoethylamine hydrochloride for EXAMPLE 21C in EXAMPLE 21D.

EXAMPLE 205B

EXAMPLE 205A and 2-mercaptoimidazole were subjected to the procedure described in J. Med. Chem. 1995, 38, 1067.

EXAMPLE 205C

This example was made by substituting EXAMPLE 205B for 4-(((1R)-3-(dimethylamino)-1-((phenylsulfanyl)methyl) propyl)amino)-3-nitrobenzenesulfonamide in EXAMPLE 2D. $^1$H NMR (500 MHz, DMSO-$d_6$) δ 8.73 (t, 1H), 8.63 (d, 1H), 7.94 (dd, 1H), 7.76 (d, 3H), 7.53 (m, 4H), 7.40 (d, 2H), 7.34 (m, 1H), 7.30 (m, 1H), 6.93 (d, 2H), 4.26 (br s, 2H), 3.72 (m, 4H), 3.42 (t, 4H), 2.98 (br s, 4H).

EXAMPLE 206

This example was made by substituting EXAMPLE 191D for 4-(((1R)-3-(dimethylamino)-1-((phenylsulfanyl)methyl) propyl)amino)-3-nitrobenzenesulfonamide in EXAMPLE 2D. $^1$H NMR (500 MHz, DMSO-$d_6$) δ 12.11 (br s, 1H), 11.43 (br s, 1H), 10.67 (br s, 1H), 8.73 (t, 1H), 8.63 (d, 1H), 8.15 (m, 1H), 7.92 (dd, 1H), 7.76 (d, 2H), 7.59 (m, 2H), 7.53 (m, 4H), 7.44 (m, 4H), 7.38 (d, 2H), 7.33 (m, 1H), 7.28 (d, 1H), 6.93 (d, 2H), 4.34 (br s, 2H), 4.22 (d, 2H), 3.89 (d, 2H), 3.37 (m, 4H), 3.31 (d, 2H), 3.25 (d, 2H), 2.84 (m, 4H), 1.88 (d, 3H), 1.61 (m, 2H).

EXAMPLE 207

This example was made by substituting EXAMPLE 205A for 4-(((1R)-3-(dimethylamino)-1-((phenylsulfanyl)methyl) propyl)amino)-3-nitrobenzenesulfonamide in EXAMPLE 1D. $^1$H NMR (500 MHz, DMSO-$d_6$) δ 12.12 (br s, 1H), 8.75 (m, 1H), 8.65 (d, $^1$H), 7.96 (dd, 1H), 7.75 (d, 3H), 7.53 (m, 2H), 7.48 (m, 2H), 7.43 (m, 1H), 7.36 (m, 4H), 6.92 (d, 2H), 4.29 (br s, 2H), 3.88 (m, 4H), 3.82 (m, 2H), 3.72 (t, 2H), 3.03 (m, 4H).

EXAMPLE 208A

This example was made by substituting 4-methylthiazole-2-thiol for 2-mercaptoimidazole in EXAMPLE 205B.

EXAMPLE 208B

This example was made by substituting EXAMPLE 208A for 4-(((1R)-3-(dimethylamino)-1-((phenylsulfanyl)methyl) propyl)amino)-3-nitrobenzenesulfonamide in EXAMPLE 2D. $^1$H NMR (500 MHz, DMSO-$d_6$) δ 12.07 (br s, 1H), 8.81 (t, 1H), 8.63 (d, $^1$H), 7.95 (dd, 1H), 7.76 (d, 2H), 7.73 (br s, 1H), 7.52 (m, 3H), 7.39 (d, 2H), 7.34 (m, 1H), 6.93 (d, 2H), 4.25 (br s, 2H), 3.82 (m, 2H), 3.48 (m, 4H), 3.02 (m, 4H), 2.29 (s, 3H), 2.07 (s, 2H).

EXAMPLE 209A

This example was made by substituting benzylamine for 4-(((1R)-3-(dimethylamino)-1-((phenylsulfanyl)methyl) propyl)amino)-3-nitrobenzenesulfonamide and 4-methoxycyclohexane carboxylic acid for EXAMPLE 2C in EXAMPLE 2D.

EXAMPLE 209B

This example was made by substituting EXAMPLE 209A for EXAMPLE 18E in EXAMPLE 18F.

EXAMPLE 209C

EXAMPLE 209B (710 mg) and Pd(OH)$_2$ (0.28g) in methanol (70 mL) at 50° C. was stirred under H$_2$ (60 psi) for 22 hours, cooled to 25°, filtered, and concentrated.

EXAMPLE 209D

This example was made by substituting EXAMPLE 209C for EXAMPLE 21C in EXAMPLE 21D.

EXAMPLE 209E

This example was made by substituting EXAMPLE 209D for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 8.55 (d, 1H), 8.48 (t, 1H), 7.90 (dd, 1H), 7.72 (d, 2H), 7.51 (m, 1H), 7.47 (s, 3H), 7.37 (m, 2H), 7.25 (m, 1H), 7.14 (d, 1H), 6.84 (d, 2H), 3.39 (s, 2H), 3.36 (m, 1H), 3.27 (m, 4H), 3.19 (m, 5H), 2.40 (t, 4H), 1.80 (m, 2H), 1.69 (m, 1H), 1.48 (m, 2H), 1.33 (m, 4H).

EXAMPLE 210A

This example was made by substituting 2-mercaptothiophene for 2-mercaptothiazole in EXAMPLE 198A.

EXAMPLE 210B

This example was made by substituting EXAMPLE 210A for EXAMPLE 21B in EXAMPLE 21C.

EXAMPLE 210C

This example was made by substituting EXAMPLE 210B for EXAMPLE 21C in EXAMPLE 21D.

EXAMPLE 210D

This example was made by substituting EXAMPLE 210C for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-$d_6$) δ 8.74 (t, 1H), 8.62 (d, 1H), 7.90 (dd, 1H), 7.75 (m, 2H), 7.61 (dd, 1H), 7.54 (m, 2H), 7.49 (m, 2H), 7.43 (m, 1H), 7.36 (m, 2H), 7.21 (dd, 1H), 7.13 (d, 1H), 7.02 (dd, 1H), 6.92 (d, 2H), 4.36 (br s, 2H), 3.63 (m, 4H), 3.11 (t, 4H), 2.54 (s, 4H).

EXAMPLE 211A

A mixture of Boc-2-amino-2-methylpropanol (633 mg) and 2-thienyldisulfide (1 g) in THF (12 mL) at 25° C. was treated with tributylphosphine (1.1 mL), heated at 85° C. for 2.5 hours, treated with ethyl acetate, washed with water, dried (MgSO$_4$), filtered, and concentrated. The concentrate was flash chromatograped on silica gel with 30-70% ethyl acetate/hexanes.

EXAMPLE 211B

This example was made by substituting EXAMPLE 211A for EXAMPLE 21B in EXAMPLE 21C.

EXAMPLE 211C

This example was made by substituting EXAMPLE 8030757B for EXAMPLE 21C in EXAMPLE 21D.

EXAMPLE 211D

This example was made by substituting EXAMPLE 211C for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 8.58 (d, 1H), 8.54 (s, 1H), 7.82 (dd, 1H), 7.79 (d, 2H), 7.72 (br s, 1H), 7.52 (m, 4H), 7.33 (d, 2H), 7.21 (dd, 1H), 6.96 (dd, 1H), 6.94 (d, 2H), 6.66 (dd, 1H), 4.19 (br s, 4H), 2.90 (br s, 6H), 1.54 (s, 6H).

EXAMPLE 212A

This example was made by substituting EXAMPLE 19A for Boc-2-amino-2-methylpropanol and EXAMPLE 22A for 2-thienyldisulfide in EXAMPLE 211A.

EXAMPLE 212B

This example was made by substituting EXAMPLE 212A for EXAMPLE 18B in EXAMPLE 18C.

EXAMPLE 212C

This example was made by substituting EXAMPLE 212B for EXAMPLE 18E in EXAMPLE 18F.

EXAMPLE 212D

This example was made by substituting EXAMPLE 212C for EXAMPLE 21C in EXAMPLE 21D.

EXAMPLE 212E

This example was made by substituting EXAMPLE 212D for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 9.97 (br s, 1H), 8.61 (d, 1H), 8.34 (d, 1H), 7.95 (dd, 1H), 7.75 (d, 2H), 7.72 (br s, 1H), 7.66 (d, 1H), 7.59 (d, 1H), 7.51 (d, 4H), 7.32 (m, 1H), 6.92 (d, 2H), 4.35 (m, 2H), 4.22 (br s, 2H), 3.95 (br s, 4H), 3.21 (m, 4H), 2.94 (m, 6H), 2.20 (m, 2H).

EXAMPLE 213A

This example was prepared by substituting 2-mercaptopyrimidine for 2-mercaptothiazole in EXAMPLE 22A.

EXAMPLE 213B

This example was made by substituting EXAMPLE 18A for
Boc-2-amino-2-methylpropanol and EXAMPLE 213A for 2-thienyldisulfide in EXAMPLE 211A.

EXAMPLE 213C

This example was made by substituting EXAMPLE 213B for EXAMPLE 18B in EXAMPLE 18C.

EXAMPLE 213D

This example was made by substituting EXAMPLE 213C for EXAMPLE 21C in EXAMPLE 21D.

EXAMPLE 213E

This example was made by substituting EXAMPLE 212D for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 12.08 (br s, 1H), 9.86 (br s, 1H), 8.97 (d, 1H) 8.62 (d, 2H,) 8.60 (d, 1H), 7.99 (dd, 1H), 7.77 (d, 2H), 7.74 (br s, 1H), 7.53 (m, 5H), 7.39 (d, 2H), 7.34 (m, 1H), 7.22 (t, 1H), 6.93 (d, 2H), 4.59 (m, 1H), 4.29 (br s, 2H), 3.42 (dd, 3H), 3.04 (dd, 2H), 2.95 (s, 4H), 2.81 (m, 5H).

EXAMPLE 214A

This example was made by substituting EXAMPLE 19A for Boc-2-amino-2-methylpropanol in EXAMPLE 211A.

EXAMPLE 214B

This example was made by substituting EXAMPLE 214A for EXAMPLE 18B in EXAMPLE 18C.

EXAMPLE 214C

This example was made by substituting EXAMPLE 214B for EXAMPLE 21C in EXAMPLE 21D.

EXAMPLE 214D

This example was made by substituting EXAMPLE 214C for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 12.06 (br s, 1H), 8.77 (d, 1H), 7.86 (dd, 1H), 7.74 (d, 2H), 7.71 (br s, 1H), 7.55 (dd, 1H), 7.51 (m, 4H), 7.38 (d, 2H), 7.32 (m, 1H), 7.08 (d, 1H), 7.04 (dd, 1H), 6.94 (dd, 1H), 6.91 (d, 2H), 4.39 (m, 2H), 3.51 (m, 5H), 3.25 (m, 4H), 2.99 (dd, 2H), 2.75 (dd, 2H).

EXAMPLE 215A

This example was made by substituting EXAMPLE 213A for 2-thienyldisulfide in EXAMPLE 211A.

EXAMPLE 215B

This example was made by substituting EXAMPLE 215A for EXAMPLE 21B in EXAMPLE 21C.

EXAMPLE 215C

This example was made by substituting EXAMPLE 215B for EXAMPLE 21C in EXAMPLE 21D.

EXAMPLE 215D

This example was made by substituting EXAMPLE 215C for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 8.55 (d, 1H), 8.53 (d, 2H), 8.49 (br s, 1H), 7.97 (dd, 1H), 7.74 (d, 2H), 7.53 (m, 2H), 7.47 (br s, 4H), 7.37 (m, 2H), 7.25 (m, 1H), 7.11 (t, 1H), 6.87 (d, 2H), 3.80 (br s, 2H), 3.41 (br s, 3H), 3.22 (m, 5H), 2.40 (m, 4H), 1.58 (br s, 6H).

EXAMPLE 216C

This example was made by substituting EXAMPLE 22C for EXAMPLE 21C in EXAMPLE 21D.

EXAMPLE 216D

This example was made by substituting EXAMPLE 216C for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 12.05 (br s, 1H), 8.91 (d, 1H), 8.59 (d, 1H), 7.92 (dd, 1H), 7.77 (d, 2H), 7.74 (br s, 1H), 7.71 (d, 1H), 7.60 (d, 1H), 7.52 (m, 4H), 7.42 (d, 1H), 7.39 (d, 2H), 7.34 (m, 1H), 6.93 (d, 2H), 4.63 (m, 1H), 4.30 (br s, 1H), 3.69 (m, 2H), 3.02 (m, 2H), 2.93 (br s, 4H), 2.82 (d, 1H), 2.79 (br s, 4H).

EXAMPLE 217A

This example was made by substituting EXAMPLE 214C for EXAMPLE 18E in EXAMPLE 18F.

EXAMPLE 217B

This example was made by substituting EXAMPLE 217A for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 8.55 (d, 1H), 8.38 (m, 1H), 7.82 (dd, 1H), 7.72 (d, 2H), 7.58 (dd, 1H), 7.51 (dd, 1H), 7.47 (m, 4H), 7.37 (m, 2H), 7.24 (m, 1H), 7.10 (dd, 1H), 6.98 (m, 2H), 6.85 (d, 2H), 4.08 (m, 1H), 3.54 (br s, 4H), 3.40 (s, 2H), 3.19 (m, 6H), 2.39 (m, 10H), 2.00 (m, 1H), 1.83 (m, 1H).

EXAMPLE 218A

A mixture of EXAMPLE 18A (1.6 g) and 10% Pd/C (0.16 g) in methanol (70 mL) at 25° C. was stirred under $H_2$ (60 psi) for 3 hours, filtered and concentrated.

EXAMPLE 218B

This example was made by substituting EXAMPLE 218A for EXAMPLE 21C in EXAMPLE 21D.

EXAMPLE 218C

Methanesulfonyl chloride (68 µL) was treated with EXAMPLE 218B (270 mg) and pyridine (1 mL) at 0° C., stirred for 1 hour, treated with 1M HCl (10 mL) and water, stirred for 0.5 hours, and filtered. The filtrant was washed with water and concentrated.

EXAMPLE 218D

A mixture of EXAMPLE 218C (120 mg), 4-(trifluoromethoxy)thiophenol (140 mg), $K_2CO_3$ (158 mg), and acetone (14 mL) at reflux was stirred for 30 minutes, cooled to 25° C., and concentrated. The concentrate in dichloromethane was washed with water and dried ($MgSO_4$), filtered, and concentrated. The concentrate was flash chromatographed on silica gel with 1-2% dichloromethane/methanol.

EXAMPLE 218E

This example was made by substituting EXAMPLE 218D for EXAMPLE 18E in EXAMPLE 18F.

EXAMPLE 218F

This example was made by substituting EXAMPLE 218D for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 12.09 (br s, 1H), 9.58 (br s, 1H), 8.54 (d, 1H), 8.26 (d, 1H), 7.89 (dd, 1H), 7.77 (d, 2H), 7.72 (br s, 1H), 7.52 (d, 4H), 7.40 (d, 2H), 7.33 (m, 3H), 7.24 (d, 1H), 7.12 (d, 2H), 6.92 (d, 2H), 4.23 (m, 2H), 3.43 (m, 4H), 3.13 (m, 4H), 2.74 (br s, 6H), 2.14 (m, 2H).

EXAMPLE 219A

This example was made by substituting 2-phenoxyethylamine for EXAMPLE 21C in EXAMPLE 21D.

EXAMPLE 219B

This example was made by substituting EXAMPLE 219A for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 11.89 (br s, 1H), 8.71 (t, 1H), 8.62 (d, $^1$H), 7.97 (dd, 1H), 7.73 (d, 2H), 7.52 (m, 1H), 7.47 (m, 4H), 7.37 (m, 3H), 7.26 (m, 3H), 6.94 (m, 3H), 6.88 (d, 2H), 4.24 (t, 2H), 3.84 (m, 2H), 3.42 (br s, 2H), 3.24 (m, 4H), 2.41 (m, 4H).

EXAMPLE 220A

This example was made by substituting EXAMPLE 19A for EXAMPLE 18A in EXAMPLE 218A.

EXAMPLE 220B

This example was made by substituting EXAMPLE 220A for EXAMPLE 21C in EXAMPLE 21D.

EXAMPLE 220C

This example was made by substituting EXAMPLE 220B for EXAMPLE 218B in EXAMPLE 218C.

EXAMPLE 220D

This example was made by substituting EXAMPLE 220C for EXAMPLE 218C in EXAMPLE 218D.

EXAMPLE 220E

This example was made by substituting EXAMPLE 83977F for EXAMPLE 18E in EXAMPLE 18F.

EXAMPLE 220F

This example was made by substituting EXAMPLE 220E for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 9.70 (br s, 1H), 8.55 (d, 1H), 8.26 (d, 1H), 7.90 (dd, 1H), 7.76 (d, 2H), 7.51 (d, 3H), 7.41 (d, 2H), 7.33 (m, 3H), 7.24 (d, 1H), 7.13 (d, 2H), 6.92 (d, 2H), 4.23 (m, 1H), 3.96 (br s, 2H), 3.61 (br s, 4H), 3.19 (br s, 4H), 3.01 (br s, 2H), 2.16 (m, 2H).

EXAMPLE 221A

This example was made by substituting 4-methoxythiophenol for 4-(trifluoromethoxy)thiophenol and EXAMPLE 220C for EXAMPLE 218C in EXAMPLE 218D.

EXAMPLE 221B

This example was made by substituting EXAMPLE 221A, for EXAMPLE 18E in EXAMPLE 18F.

EXAMPLE 221C

This example was made by substituting EXAMPLE 221B for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 12.11 (br s, 1H), 9.86 (br s, 1H), 8.56 (d, 1H), 8.25 (d, 1H), 7.87 (dd, 1H), 7.76 (d, 3H), 7.72 (br s, 1H), 7.51 (d, 4H), 7.40 (d, 2H), 7.33 (m, 1H), 7.18 (d, 2H), 7.12 (d, 1H), 6.92 (d, 2H), 6.74 (d, 2H), 4.10 (m, 3H), 3.95 (br s, 4H), 3.68 (s, 3H), 3.27 (br s, 4H), 3.17 (br s, 4H), 3.01 (br s, 3H), 2.15 (m, 2H).

EXAMPLE 222A

This example was made by substituting 4-methylthiophenol for 4-(trifluoromethoxy)thiophenol and EXAMPLE 220C for EXAMPLE 218C in EXAMPLE 218D.

EXAMPLE 222B

This example was made by substituting EXAMPLE 222A for EXAMPLE 18E in EXAMPLE 18F.

EXAMPLE 222C

This example was made by substituting EXAMPLE 222B for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 9.92 (br s, 1H), 8.53 (d, 1H), 8.26 (d, 1H), 7.87 (dd, 1H), 7.78 (d, 2H), 7.74 (m, 1H), 7.53 (m, 4H), 7.40 (d, 2H), 7.34 (m, 1H), 7.16 (d, 1H), 7.10 (d, 2H), 6.93 (m, 4H), 4.28 (br s, 2H), 4.16 (m, 1H), 3.96 (br s, 2H), 3.62 (br s, 4H), 3.34 (d, 2H), 3.18 (m, 4H), 3.01 (br s, 4H), 2.17 (m, 4H).

EXAMPLE 223A

This example was made by substituting EXAMPLE 23C for EXAMPLE 18C in EXAMPLE 18E.

EXAMPLE 223B

This example was made by substituting EXAMPLE 223A for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 9.60 (br s, 1H), 7.98 (d, 1H), 7.83 (dd, 1H), 7.73 (m, 3H), 7.63 (dd, 1H), 7.52 (d, 4H), 7.40 (d, 2H), 7.33 (m, 1H), 7.13 (m, 1H), 7.03 (m, 1H), 6.92 (d, 2H), 6.80 (d, 1H), 6.08 (d, 1H), 4.27 (br s, 4H), 3.85 (m, 2H), 3.17 (m, 4H), 3.06 (dd, 2H), 2.99 (m, 2H), 2.10 (m, 2H).

EXAMPLE 224A

This example was made by substituting 4-chlorothiophenol for 4-(trifluoromethoxy)thiophenol and EXAMPLE 220C for EXAMPLE 218C in EXAMPLE 218D.

EXAMPLE 224B

This example was made by substituting EXAMPLE 224A for EXAMPLE 18E in EXAMPLE 18F.

EXAMPLE 224C

This example was made by substituting EXAMPLE 224B for 4-(H1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 8.52 (d, 1H), 8.34 (d, 1H), 7.85 (dd, 1H), 7.73 (d, 2H), 7.51 (m, 1H), 7.47 (m, 4H), 7.37 (m, 2H), 7.26 (m, 5H), 7.12 (d, 1H), 6.86 (d, 2H), 4.16 (br s, 1H), 3.53 (m, 4H), 3.39 (m, 4H), 2.45 (br s, 2H), 2.40 (m, 4H), 1.99 (m, 1H), 1.86 (m, 1H).

EXAMPLE 225A

This example was made by substituting 4-fluorothiophenol for 4-(trifluoromethoxy)thiophenol in EXAMPLE 218D.

EXAMPLE 225B

This example was made by substituting EXAMPLE 225A for EXAMPLE 18E in EXAMPLE 18F.

EXAMPLE 225C

This example was made by substituting EXAMPLE 225B for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 8.35 (d, 1H), 8.04 (d, 1H), 7.73 (dd, 1H), 7.61 (d, 2H), 7.39 (m, 1H), 7.36 (br s, 4H), 7.24 (m, 4H), 7.13 (dd, 1H), 6.96 (t, 2H), 6.83 (d, 1H), 6.68 (d, 2H), 3.95 (m, 1H), 3.27 (br s, 2H), 3.02 (m, 4H), 2.87 (br s, 1H), 2.80 (br s, 1H), 2.49 (br s, 6H), 2.28 (m, 4H), 1.94 (m, 2H).

EXAMPLE 226A

This example was made by substituting 4-fluorothiophenol for 4-(trifluoromethoxy)thiophenol and EXAMPLE 220C for EXAMPLE 218C in EXAMPLE 218D.

EXAMPLE 226B

This example was made by substituting EXAMPLE 226A for EXAMPLE 18E in EXAMPLE 18F.

EXAMPLE 226C

This example was made by substituting EXAMPLE 226B for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 8.61 (d, 1H), 8.42 (d, 1H), 7.94 (dd, 1H), 7.82 (d, 2H), 7.60 (m, 1H), 7.55 (m, 4H), 7.47 (m, 2H), 7.40 (m, 2H), 7.33 (m, 1H), 7.18 (d, 1H), 7.13 (t, 2H), 6.96 (d, 2H), 4.22 (br s, 1H), 3.65 (br s, 6H), 3.31 (m, 6H), 2.64 (br s, 4H), 2.54 (br s, 2H), 2.49 (m, 4H), 2.09 (m, 1H), 1.97 (m, 1H).

EXAMPLE 227A

This example was made by substituting tert-butyl-1-piperazine for EXAMPLE 1A in EXAMPLE 2A.

EXAMPLE 227B

This example was made by substituting EXAMPLE 227A for EXAMPLE 2A in EXAMPLE 2B.

EXAMPLE 227C

This example was made by substituting EXAMPLE 227B for EXAMPLE 21B in EXAMPLE 21C.

EXAMPLE 227D

A mixture of ethyl-2,4-difluorobenzoate (194 mg), EXAMPLE 227C (250 mg), and $K_2CO_3$ (420 mg) in DMSO (1.7 mL) at 125° C. was stirred for 3 hours, cooled to 25° C., treated with dichloromethane, washed with water, and dried ($MgSO_4$), filtered, and concentrated. The concentrate was flash chromatographed on silica gel with 2-10% ethyl acetate/hexanes.

EXAMPLE 227E

This example was made by substituting EXAMPLE 227E for EXAMPLE 1B in EXAMPLE 1C.

EXAMPLE 227F

This example was made by substituting EXAMPLE 227E for EXAMPLE 2C in EXAMPLE 2D. $^1$H NMR (500 MHz, DMSO-$d_6$) δ 11.92 (br s, 1H), 9.62 (br s, 1H), 8.54 (d, 1H), 8.29 (d, 1H), 7.86 (dd, 1H), 7.71 (br s, 1H), 7.50 (m, 5H), 7.40 (d, 2H), 7.33 (m, 1H), 7.24 (m, 2H), 7.15 (m, 4H), 6.76 (m, 2H), 4.21 (m, 2H), 3.40 (d, 3H), 3.15 (m, 4H), 2.75 (br s, 6H), 2.15 (m, 2H).

EXAMPLE 228A

A mixture of 1.5M LDA in cyclohexane (5.5 mL) and THF (7.5 mL) at −78° C. was treated with tert-butyl-4-oxo-1-piperidinecarboxylate (1.5 g) in THF (7.5 mL), stirred for 25 minutes, treated with N-phenyl bis(trifluoromethanesulfonamide) (2.8 g) in THF (7.5 mL), stirred for 10 minutes, stirred for 3 hours at 0° C., and concentrated. The concentrate was was chromatographed on neutral alumina with 10% ethyl acetate/hexanes.

EXAMPLE 228B

A mixture of EXAMPLE 228A (480 mg), 4-ethoxycarbonylphenylboronic acid (308 mg), LiCl (182 mg), tetrakis(triphenylphosphinepalladium (82 mg), and 2M $Na_2CO_3$ (2 mL) in toluene (4.8 mL) at 90° C. was stirred for 3 hours, cooled to 25° C., and treated with water and ethyl acetate.

The extract was washed with water and brine and dried ($MgSO_4$), filtered, and concentrated. The concentrate was flash chromatographed on silica gel with 2-5% ethyl acetate/hexanes.

EXAMPLE 228C

This example was made by substituting EXAMPLE 228B for EXAMPLE 21B in EXAMPLE 21C.

EXAMPLE 228D

This example was prepared substituting EXAMPLE 228C for EXAMPLE 1A in EXAMPLE 2A.

EXAMPLE 228E

This example was prepared by substituting EXAMPLE 228D for EXAMPLE 2A in EXAMPLE 2B.

EXAMPLE 228F

This example was prepared by substituting EXAMPLE 228E for EXAMPLE 1B in EXAMPLE 1C.

EXAMPLE 228G

This example was made by substituting EXAMPLE 228F for EXAMPLE 2C in EXAMPLE 2D. $^1$H NMR (400 MHz, DMSO-d$_6$) δ 9.35 (br s, 1H), 8.30 (d, 1H), 8.04 (d, 1H,), 7.63 (m, 3H), 7.53 (m, 1H), 7.30 (m, 2H), 7.24 (d, 2H), 7.20 (d, 2H), 7.14 (d, 2H), 7.11 (m, 1H), 6.98 (m, 2H), 6.93 (d, 1H), 6.87 (m, 3H), 5.84 (br s, 1H), 4.13 (br s, 2H), 3.94 (m, 1H), 2.89 (m, 4H), 2.49 (br s, 6H), 2.24 (m, 2H), 1.89 (m, 2H).

EXAMPLE 229

This example was made by substituting EXAMPLE 228F for EXAMPLE 2C and 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-d$_6$) δ 10.07 (br s, 2H), 8.56 (d, 1H), 8.30 (d, 1H), 7.89 (d, 3H), 7.79 (m, 1H), 7.55 (m, 2H), 7.50 (m, 2H), 7.45 (d, 2H), 7.40 (m, 2H), 7.36 (m, 1H), 7.24 (m, 2H), 7.19 (d, 1H), 7.13 (m, 3H), 6.10 (br s, 1H), 4.39 (br s, 2H), 4.20 (m, 1H), 3.95 (br s, 3H), 3.40 (m, 4H), 3.18 (m, 4H), 3.02 (br s, 2H), 2.65 (br s, 1H), 2.54 (s, 3H), 2.18 (m, 2H).

EXAMPLE 230

This example was prepared by substituting EXAMPLE 227E for EXAMPLE 2C and EXAMPLE 18F for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-d$_6$) δ 7.87 (d, 1H), 7.71 (dd, 1H), 7.57 (t, 1H), 7.51 (m, 1H), 7.47 (br s, 4H), 7.38 (m, 4H), 7.32 (m, 2H), 7.23 (m, 2H), 6.62 (d, 2H), 6.53 (dd, 1H), 3.83 (m, 1H), 3.38 (br s, 2H), 3.23 (m, 2H), 3.16 (m, 4H), 2.91 (br s, 1H), 2.74 (br s, 1H), 2.52 (br s, 6H), 2.37 (m, 4H), 2.01 (m, 2H).

EXAMPLE 231A

A mixture of methyl-6-chloronicotinate (250 mg), EXAMPLE 227C (458 mg), TEA (0.24 mL), and acetonitrile (1.5 mL) at 95° C. was stirred for 10 hours, cooled to 25° C., treated with dichloromethane, washed with water, and dried (MgSO$_4$), filtered, and concentrated. The concentrate was flash chromatographed on silica gel with 0-2% methanol dichloromethane.

EXAMPLE 231B

This example was made by substituting EXAMPLE 231A for EXAMPLE 1B in EXAMPLE 1C.

EXAMPLE 231C

This example was made by substituting EXAMPLE 231B for EXAMPLE 2C in EXAMPLE 2D. $^1$H NMR (500 MHz, DMSO-d$_6$) δ 9.31 (br s, 1H), 8.36 (d, 1H), 8.28 (d, 1H), 8.03 (d, 1H), 7.72 (dd, 1H), 7.61 (dd, 1H), 7.47 (br s, 1H), 7.25 (d, 4H), 7.13 (d, 2H), 7.06 (m, 1H), 6.98 (m, 2H), 6.89 (m, 4H), 6.60 (d, 1H), 3.94 (m, 4H), 2.88 (m, 4H), 2.49 (br s, 6H), 2.24 (m, 2H), 1.89 (m, 2H).

EXAMPLE 232A

This example was made by substituting 1-benzyl-4-piperidone for tert-butyl-4-oxo-1-piperidinecarboxylate in EXAMPLE 228A.

EXAMPLE 232B

This example was made by substituting EXAMPLE 232A for EXAMPLE 228A in EXAMPLE 228B.

EXAMPLE 232C

A mixture of EXAMPLE 232B (0.98 g) and 10% Pd/C (0.1 g) in ethanol (50 mL) at 50° C. was stirred under hydrogen for 2 hours, cooled to 25°, filtered, and concentrated.

EXAMPLE 232D

This example was prepared by substituting EXAMPLE 232C for EXAMPLE 1A in EXAMPLE 2A.

EXAMPLE 232E

This example was made by substituting EXAMPLE 232D for EXAMPLE 2A in EXAMPLE 2B.

EXAMPLE 232F

This example was made by substituting EXAMPLE 232E for EXAMPLE 1B in EXAMPLE 1C.

EXAMPLE 232G

This example was made by substituting EXAMPLE 232F for EXAMPLE 2C in EXAMPLE 2D. $^1$H NMR (500 MHz, DMSO-d$_6$) δ 9.57 (br s, 1H), 9.46 (br s, 1H), 8.55 (d, 1H), 8.28 (d, 1H), 7.86 (d, 1H), 7.83 (d, 2H), 7.79 (m, 1H), 7.55 (m, 4H), 7.40 (d, 2H), 7.35 (m, 1H), 7.28 (d, 2H), 7.23 (d, 2H), 7.14 (m, 4H), 4.32 (br s, 2H), 4.19 (m, 2H), 3.39 (d, 2H), 3.29 (d, 2H), 3.13 (m, 2H), 2.81 (br s, 2H), 2.74 (br s, 6H), 2.14 (m, 2H), 1.84 (m, 3H).

EXAMPLE 233

This example was made by substituting EXAMPLE 232F for EXAMPLE 2C and 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-d$_6$) δ 9.98 (m, 1H), 9.51 (br s, 1H), 8.55 (d, 1H), 8.30 (d, 1H), 7.87 (dd, 1H), 7.83 (d, 2H), 7.79 (m, 1H), 7.56 (m, 4H), 7.40 (d, 2H), 7.35 (m, 1H), 7.28 (d, 2H), 7.24 (d, 2H), 7.14 (m, 4H), 4.32 (br s, 2H), 4.19 (m, 1H), 3.93 (br s, 2H), 3.39 (d, 4H), 3.29 (d, 3H), 3.18 (br s, 3H), 3.02 (br s, 2H), 2.80 (m, 3H), 2.17 (m, 2H), 1.84 (m, 3H).

EXAMPLE 234

This example was prepared by substituting EXAMPLE 228F for EXAMPLE 2C and EXAMPLE 18F for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-d$_6$) δ 9.32 (br s, 1H), 7.72 (d, 1H), 7.62 (d, 2H), 7.59 (dd, 1H), 7.53 (br s, 1H), 7.29 (m, 2H), 7.25 (d, 2H), 7.20 (d, 2H), 7.16 (d, 2H), 7.11 (m, 1H), 7.04 (m, 4H), 6.94 (t, 1H), 6.63 (d, 1H), 5.86 (br s, 1H), 5.78 (d, 1H), 4.11 (br s, 1H), 3.69 (m, 1H), 2.90 (m, 2H), 2.75 (m, 2H), 2.49 (s, 6H), 2.25 (m, 2H), 1.86 (m, 2H).

EXAMPLE 235

This example was made by substituting EXAMPLE 231B for EXAMPLE 2C and 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 9.91 (br s, 1H), 8.61 (d, 1H), 8.55 (d, 1H), 8.30 (d, 1H), 7.98 (dd, 1H), 7.87 (dd, 1H), 7.74 (br s, 1H), 7.51 (d, 4H), 7.39 (d, 2H), 7.33 (m, 1H), 7.24 (m, 2H), 7.19 (d, 1H), 7.13 (m, 3H), 6.86 (d, 1H), 4.33 (br s, 2H), 4.20 (m, 2H), 3.96 (br s, 4H), 3.62 (br s, 4H), 3.40 (m, 4H), 3.19 (m, 3H), 3.01 (br s, 2H), 2.80 (br s, 2H), 2.17 (m, 2H).

EXAMPLE 848866

This example was prepared by substituting EXAMPLE 231B for EXAMPLE 2C and EXAMPLE 18F for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 9.60 (br s, 1H), 8.60 (d, 1H), 7.95 (m, 1H), 7.82 (dd, 1H), 7.73 (br s, 1H), 7.51 (d, 3H), 7.39 (d, 2H), 7.30 (m, 4H), 7.19 (m, 1H), 6.88 (d, 1H), 6.85 (d, 1H), 6.04 (d, 1H), 3.94 (m, 1H), 3.29 (m, 4H), 3.15 (m, 2H), 3.01 (m, 2H), 2.74 (s, 6H), 2.11 (m, 2H).

EXAMPLE 237A 2.5M n-Butyllithium in hexanes (3 mL) at 25° C. was treated with methyltriphenylphosphonium bromide (2.6 g) in diethyl ether (37 mL), stirred for 1.5 hours, treated with ethyl 4-(4-oxopiperidin-1-yl)benzoate, prepared as described in Synthesis 1981, 8, 606, (1.47 g), in diethyl ether (15 mL), stirred for 18 hours, and filtered. The filtrate was washed with water and dried (MgSO$_4$), filtered, and concentrated. The concentrate was flash chromatographed on silica gel with 10% ethyl acetate/hexanes.

EXAMPLE 237B

A mixture of EXAMPLE 237A (400 mg) and 0.5M 9-BBN (3.3 mL) in THF (2 mL) at 60° C. was stirred for 1.5 hours, cooled to 25° C., treated dropwise with 2-bromo-4'-chlorobiphenyl (434 mg), K$_2$CO$_3$ (296 mg), and dichloro(1,1'-bis(diphenylphosphino)ferrocene)palladium(II) dichloromethane (24.5 mg) in water (0.36 mL) and DMF (3.6 mL), stirred for 3 hours at 60° C., cooled to 25° C., and treated with water and ethyl acetate. The extract was washed with brine and dried (MgSO$_4$), filtered, and concentrated. The concentrate was flash chromatographed on silica gel with 2-5% ethyl acetate/hexanes.

EXAMPLE 237C

This example was made by substituting EXAMPLE 237B for EXAMPLE 1B in EXAMPLE 1C.

EXAMPLE 237D

This example was made by substituting EXAMPLE 237C for EXAMPLE 2C in EXAMPLE 2D. $^1$H NMR (500 MHz, DMSO-$d_6$) δ 11.94 (br s, 1H), 9.43 (br s, 1H), 8.54 (d, 1H), 7.87 (dd, 1H), 7.70 (d, 2H), 7.47 (d, 2H), 7.32 (m, 3H), 7.27 (dd, 1H), 7.25 (d, 2H), 7.17 (m, 3H), 7.11 (m, 2H), 6.84 (d, 2H), 4.20 (m, 1H), 3.78 (d, 2H), 3.39 (d, 2H), 3.14 (m, 2H), 2.74 (s, 6H), 2.65 (t, 2H), 2.53 (m, 2H), 2.14 (m, 2H), 1.55 (m, 1H), 1.44 (d, 2H), 0.96 (m, 2H).

EXAMPLE 238

This example was made by substituting EXAMPLE 237C for EXAMPLE 2C and 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 11.95 (br s, 1H), 9.75 (br s, 1H), 8.55 (d, 1H), 8.29 (d, 1H), 7.87 (dd, 1H), 7.70 (d, 2H), 7.48 (m, 2H), 7.32 (m, 4H), 7.28 (m, 1H), 7.25 (m, 2H), 7.17 (m, 4H), 7.11 (m, 1H), 6.84 (d, 2H), 4.19 (m, 1H), 3.96 (br s, 2H), 3.78 (d, 4H), 3.40 (d, 4H), 3.20 (m, 2H), 3.02 (br s, 2H), 2.66 (t, 2H), 2.53 (m, 2H), 2.17 (m, 2H), 1.56 (m, 1H), 1.45 (d, 2H), 0.98 (m, 2H).

EXAMPLE 239A

A mixture of, 2,5-dibromopyridine(2.4 g), dichloro(1,1'-bis(diphenylphosphino)ferrocene)palladium(II) dichloromethane (430 mg), and TEA (2.9 mL) in methanol (10 mL), and DMF (10 mL) in a Parr shaker at 50° C. was stirred under CO (200 psi) over 5.5 hours, cooled to 25° C., filtered, and concentrated. The concentrate was flash chromatographed on silca gel with 10-20% ethyl acetate/hexanes.

EXAMPLE 239B

A mixture of EXAMPLE 239A (900 mg), EXAMPLE 227C (1.6 g), and DIEA (2.1 mL) in DMSO (5.9 mL) was stirred at 130° C. for 24 hours, cooled to 25° C., and concentrated. The concentrate was flash chromatagraphed on silica gel with 30-50% ethyl acetate/hexanes.

EXAMPLE 239C

This example was made by substituting EXAMPLE 239B for EXAMPLE 1B in EXAMPLE 10.

EXAMPLE 239D

This example was made by substituting EXAMPLE 239C for EXAMPLE 2C in EXAMPLE 2D. $^1$H NMR (500 MHz, DMSO-$d_6$) δ 9.60 (br s, 1H), 8.59 (d, 1H), 8.30 (m, 2H), 7.90 (dd, 1H), 7.82 (d, 1H), 7.70 (br s, 1H), 7.51 (m, 4H), 7.41 (d, 2H), 7.38 (dd, 1H), 7.32 (m, 1H), 7.22 (d, 2H), 7.17 (d, 1H), 7.12 (m, 3H), 4.19 (m, 2H), 3.39 (d, 2H), 3.13 (m, 4H), 2.74 (s, 6H), 2.14 (m, 2H).

EXAMPLE 240

This example was made by substituting EXAMPLE 239C for EXAMPLE 2C and 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 9.89 (br s, 1H), 8.59 (d, 1H), 8.30 (m, 2H), 7.91 (dd, 1H), 7.83 (d, 1H), 7.73 (br s, 1H), 7.52 (d, 4H), 7.40 (m, 3H), 7.34 (m, 1H), 7.23 (d, 2H), 7.18 (d, 1H), 7.12 (m, 3H), 4.20 (m, 2H), 3.96 (br s, 4H), 3.40 (d, 2H), 3.19 (m, 2H), 3.01 (br s, 4H), 2.17 (m, 2H).

EXAMPLE 241A

EXAMPLE 855947A (12.3 g) inpropan-2-ol (57 mL) at 0° C. was treated with NaBH$_4$ (2.2 g) in 1:1 ethanol/propane-2-ol (100 mL), stirred at 25° C. for 18 hours, treated with NH$_4$Cl and brine, and extracted with diethyl ether. The extract was dried (MgSO$_4$), filtered, and concentrated. The concentrate was flash chromatographed on silica gel with 10-30% ethyl acetate/hexanes.

EXAMPLE 241B

This example was made by substituting EXAMPLE 241A for EXAMPLE 2A in EXAMPLE 2B.

EXAMPLE 241C

A mixture of EXAMPLE 241B (420 mg) and TEA (0.95 mL) in dichloromethane (8.7 mL) at 0° C. was treated with methanesulfonyl chloride (0.16 mL), stirred for 0.5 hours, treated with EXAMPLE 228C (0.57 g), stirred for 1 hour at 0° C. and for 5 hours at 25° C., treated with dichloromethane, washed with water and brine, and dried (MgSO$_4$), filtered, and concentrated. The concentrate was flash chromatographed on silica gel with 0-2% methanol/dichloromethane.

EXAMPLE 241D

This example was made by substituting EXAMPLE 241C for EXAMPLE 1B in EXAMPLE 1C.

EXAMPLE 241E

This example was made by substituting EXAMPLE 241D for EXAMPLE 2C in EXAMPLE 2D. $^1$H NMR (400 MHz, DMSO-d$_6$) δ 8.47 (d, 1H), 8.17 (d, 1H), 7.82 (m, 3H), 7.38 (d, 2H), 7.31 (d, 4H), 7.24 (m, 2H), 7.18 (m, 1H), 7.14 (m, 2H), 6.90 (d, 1H), 6.13 (br s, 1H), 4.07 (m, 1H), 2.93 (m, 6H), 2.61 (m, 6H), 2.39 (br s, 2H), 2.24 (m, 2H), 2.08 (m, 2H), 1.99 (m, 2H), 1.44 (t, 2H), 0.97 (br s, 2H).

EXAMPLE 242A

This example was made by substituting 2-bromo-cyclohex-1-enecarboxaldehyde, prepared as described in Collect. Czech. Chem. Commun. 1961, 26, 3059-3073, for EXAMPLE 855947A in EXAMPLE 241A.

EXAMPLE 242B

This example was made by substituting EXAMPLE 242A for EXAMPLE 2A in EXAMPLE 2B.

EXAMPLE 242C

This example was made by substituting EXAMPLE 242B for EXAMPLE 241B in EXAMPLE 241C.

EXAMPLE 242D

This example was made by substituting EXAMPLE 242C for EXAMPLE 1B in EXAMPLE 1C.

EXAMPLE 242E

This example was made by substituting EXAMPLE 242D for EXAMPLE 2C in EXAMPLE 2D. $^1$H NMR (400 MHz, DMSO-d$_6$) δ 9.69 (br s, 1H), 9.60 (br s, 1H), 8.56 (d, 1H), 8.30 (d, 1H), 7.89 (m, 3H), 7.45 (d, 2H), 7.37 (m, 2H), 7.17 (m, 8H), 6.14 (br s, 1H), 4.20 (m, 1H), 3.89 (m, 1H), 3.66 (d, 4H), 3.40 (d, 3H), 3.12 (m, 4H), 2.75 (br s, 6H), 2.69 (br s, 1H), 2.29 (br s, 2H), 2.22 (br s, 2H), 2.15 (m, 2H), 1.71 (br s, 4H).

EXAMPLE 243

This example was made by substituting EXAMPLE 242D for EXAMPLE 2C and 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-d$_6$) δ 9.84 (br s, 1H), 9.60 (br s, 1H), 8.56 (d, 1H), 8.30 (d, 1H), 7.89 (m, 3H), 7.45 (d, 2H), 7.37 (m, 2H), 7.24 (m, 2H), 7.15 (m, 6H), 6.13 (br s, 1H), 4.20 (m, 1H), 3.92 (m, 2H), 3.64 (m, 4H), 3.19 (m, 4H), 3.02 (br s, 4H), 2.70 (m, 2H), 2.29 (br s, 2H), 2.18 (m, 4H), 1.71 (br s, 4H).

EXAMPLE 244

This example was made by substituting EXAMPLE 241D for EXAMPLE 2C and 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-d$_6$) δ 8.47 (d, 1H), 8.27 (d, 1H), 7.84 (d, 2H), 7.79 (dd, 1H), 7.39 (d, 2H), 7.32 (m, 4H), 7.24 (t, 2H), 7.16 (m, 3H), 6.93 (d, 1H), 6.10 (br s, 1H), 4.09 (m, 1H), 3.55 (br s, 4H), 3.34 (m, 4H), 3.02 (m, 2H), 2.76 (s, 1H), 2.27 (m, 2H), 2.01 (br s, 3H), 1.86 (m, 1H), 1.46 (t, 2H), 0.98 (s, 6H).

EXAMPLE 245A

This example was made by substituting 1,4-cyclohexanedione monoethylene ketal for ethyl 4-(4-oxopiperidin-1-yl)benzoate in EXAMPLE 237A.

EXAMPLE 245B

This example was made by substituting EXAMPLE 245A for EXAMPLE 237A in EXAMPLE 237B.

EXAMPLE 245C

A mixture of EXAMPLE 245B (1.9 g) and 35% aqueous TFA (42 mL) in chloroform (61 mL) was stirred at 25° C. for 7 hours and treated with water and dichloromethane. The extract was washed with saturated NaHCO$_3$ and brine and dried (MgSO$_4$), filtered, and concentrated.

EXAMPLE 245D

This example was made by substituting EXAMPLE 245C for tert-butyl-4-oxo-1-piperidinecarboxylate and by substituting 2-(N,N-bis(trifluoromethylsulfonyl)amino)-5-chloropyridine for N-phenylbis(trifluoromethanesulfonamide) in EXAMPLE 228A.

EXAMPLE 245E

This example was made by substituting EXAMPLE 245D for EXAMPLE 228A in EXAMPLE 228B.

EXAMPLE 245F

This example was made by substituting EXAMPLE 245E for EXAMPLE 1B in EXAMPLE 10.

EXAMPLE 245G

This example was made by substituting EXAMPLE 245F for EXAMPLE 2C in EXAMPLE 2D. $^1$H NMR (500 MHz, DMSO-d$_6$) δ 9.45 (br s, 1H), 8.56 (d, 1H), 8.30 (d, 1H), 7.88

(dd, 1H), 7.81 (d, 2H), 7.47 (d, 2H), 7.42 (d, 2H), 7.34 (m, 3H), 7.32 (s, 1H), 7.28 (m, 1H), 7.24 (m, 2H), 7.16 (m, 4H), 7.11 (m, 1H), 6.16 (br s, 1H), 4.19 (m, 1H), 3.14 (m, 3H), 2.74 (s, 6H), 2.61 (m, 2H), 2.24 (m, 2H), 2.14 (m, 2H), 2.03 (m, 1H), 1.68 (m, 3H), 1.17 (m, 1H).

EXAMPLE 246

This example was made by substituting EXAMPLE 245F for EXAMPLE 2C and 4-(((1R)-3-(4-morpholinyl)-1-((phenylsulfanyl)methyl)propyl)amino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 8.55 (d, 1H), 8.29 (d, 1H), 7.87 (dd, 1H), 7.79 (d, 2H), 7.46 (d, 2H), 7.40 (d, 2H), 7.32 (m, 4H), 7.27 (m, 1H), 7.23 (m, 2H), 7.15 (m, 4H), 7.10 (m, 1H), 6.14 (br s, 1H), 4.18 (m, 1H), 3.77 (br s, 4H), 3.15 (m, 4H), 2.59 (m, 2H), 2.20 (m, 4H), 2.02 (d, 1H), 1.67 (m, 3H), 1.15 (m, 1H).

EXAMPLE 247A

This example was made by substituting methyl-4-fluorobenzoate for ethyl-2,4-difluorobenzoate and cis-octahydropyrrolo[3,4-c]pyrrole for EXAMPLE 227C in EXAMPLE 227D.

EXAMPLE 247B

This example was made by substituting EXAMPLE 247A for EXAMPLE 1A in EXAMPLE 2A.

EXAMPLE 247C

This example was made by substituting EXAMPLE 247B for EXAMPLE 2A in EXAMPLE 2B.

EXAMPLE 247D

This example was made by substituting EXAMPLE 247C for EXAMPLE 1B in EXAMPLE 1C.

EXAMPLE 247E

This example was made by substituting EXAMPLE 247D for EXAMPLE 2C in EXAMPLE 2D. $^1$H NMR (500 MHz, CDCl$_3$) δ 8.77 (br s, 1H), 8.34 (d, 1H), 7.96 (d, 1H), 7.92 (br s, 1H), 7.65 (brs, 2H), 7.49 (m, 4H), 7.38 (br s, 2H), 7.30 (m, 2H), 7.19 (m, 6H), 6.83 (m, 1H), 6.46 (m, 2H), 4.34 (br s, 2H), 3.84 (m, 1H), 3.28 (m, 4H), 3.15 (m, 4H), 2.80 (m, 6H), 2.41 (br s, 2H).

EXAMPLE 248A

A mixture of 4-chloro-3-nitrobenzenesulfonyl chloride (10 g), TEA (10.87 mL), and bis(2,4-dimethoxybenzyl)amine (12.38 g) in dichloromethane (200 mL) at 25° C. was stirred for 12 hours, treated with dichloromethane (200 mL), washed with saturated sodium bicarbonate (100 mL) and brine, and concentrated.

EXAMPLE 248B

A mixture of EXAMPLE 248A (20.98 g) and 2M methylamine in THF (400 mL) at 80° C. was stirred for 4 hours and concentrated. The concentrate was treated with ethyl acetate and saturated sodium bicarbonate. The extract was dried (Mg$_2$SO$_4$), filtered and concentrated.

EXAMPLE 248C

A mixture of EXAMPLE 248B (1 g) and 3.56 mmol/g polymer-supported N,N-DIEA (2.65 g) in dichloromethane (10 mL) was treated with 20% phosgene in toluene (10.1 mL), heated at 40° C. for 24 hours, filtered and concentrated.

EXAMPLE 248D

A mixture of EXAMPLE 248C (200 mg), TEA (141 μL) and N-methyl-4-trifluoromethoxyphenyl aniline (129 mg) in dichloromethane (2 mL) at 50° C. was heated for 12 hours and concentrated. The concentrate was flash chromatographed on silica gel with 70% ethyl acetate/hexane.

EXAMPLE 248E

EXAMPLE 248D (57 mg) in triethylsilane/TFA/dichloromethane (0.05 mL/0.45 mL/0.5 mL) was stirred at 25° C. for 30 minutes and concentrated. The concentrate was flash chromatographed on silica gel with 80% ethyl acetate/hexane.

EXAMPLE 248F

This example was made by substituting EXAMPLE 248E for 4-(((1R)-3-(dimethylamino)-1-((phenylsulfanyl)methyl)propyl)amino)-3-nitrobenzenesulfonamide in EXAMPLE 1D. 1H NMR (400MHz, DMSO-$d_6$) δ 8.26 (d, 1H), 7.80 (d, 2H), 7.72 (br, 1H), 7.41 (m, 8H), 7.28 (d, 1H), 6.92 (m, 6H), 4.26 (br, 2H), 3.74 (br, 2H), 3.13 (br, 2H), 2.96 (s, 6H), 2.82 (br, 2H)

EXAMPLE 249A

This example was made by substituting N-methyl-2-methylanaline for N-methyl-4-trifluoromethoxyaniline in EXAMPLE 248D.

EXAMPLE 249B

This example was made by substituting EXAMPLE 249A for EXAMPLE 248D in EXAMPLE 248E.

EXAMPLE 249C

This example was made by substituting EXAMPLE 249B for 4-(H1R)-3-(dimethylamino)-1-((phenylsulfanyl)methyl)propyl)amino)-3-nitrobenzenesulfonamide in EXAMPLE 1D. 1H NMR (400 MHz, DMSO-$d_6$) 8.30 (d, 1H), 7.86 (d, 1H), 7.83 (d, 2H), 7.75 (br, 1H), 7.53 (m, 2H), 7.47 (d, 2H), 7.43 (q, 1H), 7.37 (m, 3H), 7.21 (d, 1H), 6.97 (d, 2H), 6.83 (d, 1H), 6.74 (t, 1H), 6.64 (t, 1H), 6.56 (d, 1H), 4.31 (br, 2H), 3.80 (br, 2H), 3.18 (s, 3H), 3.14 (br, 2H), 2.90 (s, 3H), 2.84 (br, 4H), 1.95 (s, 3H).

EXAMPLE 250A

This example was made by substituting N-methyl-4-methoxyanaline for N-methyl-4-trifluoromethoxyaniline in EXAMPLE 248D.

EXAMPLE 250B

This example was made by substituting EXAMPLE 250A for EXAMPLE 248D in EXAMPLE 248E.

EXAMPLE 250C

This example was made by substituting EXAMPLE 250B for 4-(((1R)-3-(dimethylamino)-1-((phenylsulfanyl)methyl)propyl)amino)-3-nitrobenzenesulfonamide in EXAMPLE 1D. 1H NMR (400 MHz, DMSO-$d_6$) δ 8.28 (d, 1H), 7.86 (dd, 1H), 7.81 (d, 2H), 7.73 (br, 1H), 7.52 (br, 2H), 7.47 (d, 2H), 7.43 (d, 1H), 7.36 (m, 3H), 7.20 (d, 1H), 6.94 (d, 2H), 6.70 (d, 2H), 6.49 (d, 2H), 4.28 (br, 2H), 3.81 (br, 2H), 3.43 (s, 3H), 3.19 (s, 3H), 3.14 (br, 2H), 2.90 (s, 3H), 2.82 (br, 4H).

EXAMPLE 251A

This example was made by substituting N-methyl-4-methylanaline for N-methyl-4-trifluoromethoxyaniline in EXAMPLE 248D.

EXAMPLE 251B

This example was made by substituting EXAMPLE 251A for EXAMPLE 248D in EXAMPLE 248E.

EXAMPLE 251C

This example was made by substituting EXAMPLE 251B for 4-(((1R)-3-(dimethylamino)-1-((phenylsulfanyl)methyl)propyl)amino)-3-nitrobenzenesulfonamide in EXAMPLE 1D. 1H NMR (400 MHz, DMSO-$d_6$) δ 8.25 (d, 1H), 7.83 (m, 3H), 7.73 (br, 1H), 7.52 (m, 2H), 7.47 (d, 2H), 7.42 (d, 1H), 7.36 (m, 3H), 7.20 (d, 1H), 6.96 (d, 2H), 6.71 (d, 2H), 6.66 (d, 2H), 4.28 (br, 2H), 3.80 (br, 2H), 3.22 (s, 3H), 3.14 (br, 2H), 2.91 (s, 3H), 2.82 (br, 4H), 1.90 (s, 3H)

EXAMPLE 252A

This example was made by substituting N-diphenylmethyl methylamine for N-methyl-4-trifluoromethoxyaniline in EXAMPLE 248D.

EXAMPLE 252B

This example was made by substituting EXAMPLE 252A for EXAMPLE 248D in EXAMPLE 248E.

EXAMPLE 252C

This example was made by substituting EXAMPLE 252B for 4-(((1R)-3-(dimethylamino)-1-((phenylsulfanyl)methyl)propyl)amino)-3-nitrobenzenesulfonamide in EXAMPLE 1D. 1H NMR (400 MHz, DMSO-$d_6$) δ 8.35 (d, 1H), 8.15 (dd, 1H), 7.74 (dd, 4H), 7.50 (m, 4H), 7.43 (d, 1H), 7.36 (m, 6H), 7.29 (m, 2H), 7.16 (d, 4H), 6.92 (d, 2H), 6.30 (s, 1H), 4.33 (br, 2H), 3.84 (br, 4H), 3.25 (s, 3H), 3.13 (br, 3H), 2.82 (br, 2H), 2.69 (s, 3H).

EXAMPLE 253A

This example was made by substituting (S)-(−)-N-methyl-1-phenethylamine for N-methyl-4-trifluoromethoxyaniline in EXAMPLE 248D.

EXAMPLE 253B

This example was made by substituting EXAMPLE 253A for EXAMPLE 248D in EXAMPLE 248E.

EXAMPLE 253C

This example was made by substituting EXAMPLE 253B for 4-(((1R)-3-(dimethylamino)-1-((phenylsulfanyl)methyl)propyl)amino)-3-nitrobenzenesulfonamide in EXAMPLE 1D. 1H NMR (400 MHz, DMSO-$d_6$) δ 8.38 (d, 1H), 8.19 (dd, 1H), 7.76 (d, 2H), 7.70 (d, 1H), 7.50 (br, 6H), 7.33 (br, 8H), 6.93 (d, 2H), 5.17 (q, 1H), 4.37 (br, 2H) 3.84 (br, 2H), 3.26 (s, 3H), 3.11 (br, 4H), 2.84 (br, 2H), 2.61 (s, 3H), 1.46 (d, 3H)

EXAMPLE 254A

This example was made by substituting 2-(4-methylpiperazinyl)-1-phenethyl methylamine for N-methyl-4-trifluoromethoxyaniline in EXAMPLE 248D.

EXAMPLE 254B

This example was made by substituting EXAMPLE 254A for EXAMPLE 248D in EXAMPLE 248E.

EXAMPLE 254C

This example was made by substituting EXAMPLE 254B for 4-(((1R)-3-(dimethylamino)-1-((phenylsulfanyl)methyl)propyl)amino)-3-nitrobenzenesulfonamidein EXAMPLE 1D. 1H NMR (400 MHz, DMSO-$d_6$) δ 8.37 (d, 1H), 8.20 (dd, 1H), 7.76 (d, 3H), 7.65 (d, 1H), 7.48 (m, 5H), 7.34 (m, 8H), 6.93 (d, 2H), 5.31 (dd, 1H), 4.36 (br, 2H), 3.84 (br, 2H), 3.42 (br, 4H), 3.30 (s, 3H), 3.07 (br, 8H), 2.86 (m, 2H), 2.80 (s, 3H), 2.75 (s, 3H), 2.33 (m, 2H).

EXAMPLE 255A

This example was made by substituting 2-morpholine-4-yl-1-phenethyl methylamine for N-methyl-4-trifluoromethoxyaniline in EXAMPLE 248D.

EXAMPLE 255B

This example was made by substituting EXAMPLE 255A for EXAMPLE 248D in EXAMPLE 248E.

EXAMPLE 255C

This example was made by substituting EXAMPLE 255B for 4-(((1R)-3-(dimethylamino)-1-((phenylsulfanyl)methyl)propyl)amino)-3-nitrobenzenesulfonamide in EXAMPLE 1D. 1H NMR (400 MHz, DMSO-$d_6$) δ 8.40 (d, 1H), 8.15 (dd, 1H), 7.76 (m, 3H), 7.66 (d, 1H), 7.47 (m, 13H), 6.93 (d, 2H), 5.57 (br, 1H), 4.37 (br, 2H), 3.83 (br, 8H), 3.25 (s, 3H), 3.13 (br, 6H), 2.84 (br, 4H), 2.64 (s, 3H)

EXAMPLE 256A

This example was made by substituting (1,2-diphenylethyl)methylamine for N-methyl-4-trifluoromethoxyaniline in EXAMPLE 248D.

EXAMPLE 256B

This example was made by substituting EXAMPLE 256A for EXAMPLE 248D in EXAMPLE 248E.

EXAMPLE 256C

This example was made by substituting EXAMPLE 256B for 4-(((1R)-3-(dimethylamino)-1-((phenylsulfanyl)methyl)propyl)amino)-3-nitrobenzenesulfonamide in EXAMPLE 1D. 1H NMR (400 MHz, DMSO-$d_6$) δ 8.33 (d, 1H), 8.05 (dd, 1H), 7.75 (d, 3H), 7.38 (m, 18H), 7.22 (m, 1H), 6.92 (d, 2H), 5.58 (dd, 1H), 4.32 (br, 2H), 3.65 (br, 6H), 3.40 (dd, 1H), 3.22 (dd, 1H), 3.10 (br, 2H), 2.69 (s, 3H), 2.66 (s, 3H)

EXAMPLE 257A

This example was made by substituting (2-(methylamino)-2-phenylethyl)dimethylamine for N-methyl-4-trifluoromethoxyaniline in EXAMPLE 248D.

EXAMPLE 257B

This example was made by substituting EXAMPLE 257A for EXAMPLE 248D in EXAMPLE 248E.

EXAMPLE 257C

This example was made by substituting EXAMPLE 257B for 4-(((1R)-3-(dimethylamino)-1-((phenylsulfanyl)methyl)propyl)amino)-3-nitrobenzenesulfonamide in EXAMPLE 1D. 1H NMR (500 MHz, DMSO-$d_6$) δ 8.39 (d, 1H), 8.12 (dd, 1H), 7.74 (d, 3H), 7.64 (d, 1H), 7.40 (m, 13H), 6.91 (d, 2H), 5.54 (dd, 1H), 4.00 (br, 8H), 3.25 (s, 3H), 3.14 (br, 2H), 2.69 (s, 6H), 2.61 (s, 3H)

EXAMPLE 258

A mixture of EXAMPLE 10 (400 mg) and 30% Pd/C (120 mg) in 1:1 methanol/ethyl acetate (10 mL) at 25° C. was stirred under $H_2$ (balloon) for 2 hours and filtered. The filtrate was concentrated and flash chromatographed on silica gel with 40% acetonitrile/dichloromethane. 1H NMR (500 MHz, $CDCl_3$) δ 7.87 (br, 1H), 7.64 (m, 2H), 7.40 (m, 6H), 7.17 (m, 8H), 6.38 (br, 1H), 5.17 (br, 4H), 4.29 (s, 2H), 3.30 (m, 4H), 2.95 (s, 2H), 2.49 (br, 2H)

EXAMPLE 259

A mixture of EXAMPLE 258 (50 mg) and sodium nitrite (7.2 mg) in water/hydrochloric acid/acetic acid (0.38 mL/0.562 mL/2 mL) at 0° C. was stirred for 2 hours and concentrated. The concentrate in 1:1 DMSO/methanol (10.5 mL) and purified by HPLC with 0-70% acetonitrile/water with 0.1% TFA. $^1$H NMR (500 MHz, $CDCl_3$) δ 8.75 (s, 1H), 8.23 (dd, 1H), 7.78 (dd, 1H), 7.69 (d, 2H), 7.49 (m, 3H), 7.42 (d, 2H), 7.30 (m, 1H), 7.26 (m, 2H), 7.19 (m, 5H), 5.66 (d, 2H), 4.82 (t, 2H), 4.39 (s, 2H), 3.50 (t, 2H), 3.42 (br, 8H)

EXAMPLE 260

EXAMPLE 258 (60 mg) in formic acid (2 mL) was heated at 100° C. for 3 hours, and concentrated. The concentrate was purified by HPLC with 0-70% acetonitrile/water with 0.1% TFA. 1H NMR (400 MHz, $CDCl_3$) δ 8.53 (s, 1H), 8.46 (s, 1H), 8.13 (d, 1H), 7.75 (dd, 1H), 7.62 (d, 2H), 7.46 (m, 4H), 7.30 (dd, 1H), 7.16 (m, 8H), 6.63 (d, 2H), 4.48 (t, 2H), 4.35 (s, 2H), 3.42 (br, 4H), 3.35 (t, 2H), 3.00 (br, 4H).

EXAMPLE 261

This example was made by substituting EXAMPLE 90C and 4-(cyclohexylmethylamino)-3-nitrobenzenesulfonamide, prepared as described in WO02/24636, for EXAMPLE 1C and 4-(((1R)-3-(dimethylamino)-1-((phenylsulfanyl)methyl)propyl)amino)-3-nitrobenzenesulfonamide, respectively, in EXAMPLE 1D. $^1$H NMR (300 MHz, DMSO-$d_6$) δ 11.95 (m, 1H), 8.61 (m, 1H), 7.91 (dd, 1H), 7.67 (d, 2H), 7.44 (m, 1H), 7.39 (m, 1H), 7.34 (m, 2H), 7.30 (m, 2H), 7.27 (m, 2H), 7.22 (m, 1H), 7.16 (m, 1H), 6.80 (m, 2H), 3.38 (m, 2H), 3.27 (m, 3H), 3.03 (s, 3H), 2.89 (s, 2H), 2.84 (m, 1H), 2.76 (m, 1H), 1.77 (m, 1H), 1.66 (m, 5H), 1.47 (m, 2H), 1.08 (m, 7H).

EXAMPLE 262

This example was made by substituting EXAMPLE 90C and 4-(cyclohexylamino)-3-nitrobenzenesulfonamide, prepared as described in WO02/24636, for EXAMPLE 10 and 4-(((1R)-3-(dimethylamino)-1-((phenylsulfanyl)methyl)propyl)amino)-3-nitrobenzenesulfonamide, respectively, in EXAMPLE 1D. $^1$H NMR (300 MHz, DMSO-$d_6$) δ 8.62 (d, 1H), 8.31 (d, 1H), 7.92 (dd, 1H), 7.66 (d, 2H), 7.34 (m, 9H), 7.15 (m, 1H), 6.79 (d, 2H), 3.71 (m, 1H), 3.39 (d, 2H), 3.02 (m, 3H), 2.84 (m, 4H), 1.94 (m, 2H), 1.65 (m, 3H), 1.30 (m, 9H).

EXAMPLE 263

This example was made by substituting EXAMPLE 90C and 4-((1,1-dimethyl-2-(phenylsulfanyl)ethyl)amino)-3-nitrobenzenesulfonamide, prepared as described in WO02/24636, for EXAMPLE 1C and 4-(((1R)-3-(dimethylamino)-1-((phenylsulfanyl)methyl)propyl)amino)-3-nitrobenzenesulfonamide, respectively, in EXAMPLE 1D. $^1$H NMR (300 MHz, DMSO-$d_6$) δ 11.96 (m, 1H), 8.51 (m, 2H), 7.82 (dd, 1H), 7.71 (d, 2H), 7.33 (m, 11H), 7.15 (m, 1H), 7.00 (m, 2H), 6.92 (m, 1H), 6.82 (d, 2H), 3.54 (s, 2H), 3.40 (m, 2H), 3.03 (s, 3H), 2.85 (m, 4H), 1.57 (s, 6H), 1.46 (m, 2H), 1.17 (m, 2H).

EXAMPLE 264A

A mixture of thiophenol (0.2 mL), (1-amino-cyclopentyl)methanol (0.2 g), tributylphosphine (0.5 mL), and THF (30 mL) at 0° C. was treated with ADDP (0.482 g), stirred for 1 hour, stirred at 25° C. for 18 hours, and concentrated. The concentrate was flash chromatographed on silica gel with 50% ethyl acetate/hexanes and 5% methanol/dichloromethane.

EXAMPLE 264B

This example was prepared by substituting EXAMPLE 264A for EXAMPLE 21C in EXAMPLE 21D.

EXAMPLE 264C

This example was made by substituting EXAMPLE 264B for 4-(((1R)-3-(dimethylamino)-1-((phenylsulfanyl)methyl)propyl)amino)-3-nitrobenzenesulfonamide in EXAMPLE 1D. $^1$H NMR (300 MHz, DMSO-$d_6$) δ 9.50 (s, 1H), 8.42 (s, 1H), 8.35 (d, 1H), 7.74 (m, 4H), 7.39 (m, 8H), 7.11 (m, 3H), 6.79 (m, 5H), 4.33 (s, 1H), 3.81 (s, 1H), 3.50 (s, 2H), 3.07 (m, 4H), 2.35 (m, 4H), 1.98 (m, 4H), 1.64 (m, 4H).

EXAMPLE 265

This example was made by substituting EXAMPLE 90C and EXAMPLE 264B for EXAMPLE 1C and 4-(((1R)-3-(dimethylamino)-1-((phenylsulfanyl)methyl)propyl)amino)-3-nitrobenzenesulfonamide, respectively, in EXAMPLE 1D. $^1$H NMR (300 MHz, DMSO-$d_6$) δ 11.96 (s, 1H), 8.49 (s, 1H), 8.41 (d, 1H), 7.82 (dd, 1H), 7.73 (d, 1H), 7.34 (m, 8H), 7.16 (m, 4H), 6.83 (m, 5H), 3.57 (s, 2H), 3.31 (s, 2H), 3.02 (s, 3H), 2.85 (m, 4H), 2.11 (m, 2H), 1.99 (m, 2H), 1.71 (m, 4H), 1.47 (m, 2H), 1.18 (m, 2H).

EXAMPLE 266

This example was made by substituting EXAMPLE 264B for 4-(((1R)-3-(dimethylamino)-1-((phenylsulfanyl)methyl)propyl)amino)-3-nitrobenzenesulfonamide in EXAMPLE 2D. $^1$H NMR (300 MHz, CD$_3$OD) δ 8.52 (d, 1H), 7.85 (m, 3H), 7.72 (m, 1H), 7.58 (m, 2H), 7.51 (d, 2H), 7.42 (m, 1H), 7.35 (d, 2H), 7.12 (m, 2H), 6.99 (m, 3H), 6.72 (m, 3H), 4.46 (s, 2H), 3.50 (s, 2H), 3.31 (m, 4H), 3.17 (m, 4H), 2.13 (m, 4H), 1.80 (m, 4H).

EXAMPLE 267A

A mixture of (S)-2-aminobutan-1-ol (1 g), tributylphosphine (3 mL) and phenyl disulfide (2.64 g) in toluene (20 mL) at 85° C. was stirred for 16 hours, and concentrated. The concentrate was flash chromatographed on silica gel with 1% methanol/dichloromethane.

EXAMPLE 267B

This example was prepared by substituting EXAMPLE 267A for EXAMPLE 21C in EXAMPLE 21D.

EXAMPLE 267C

This example was made by substituting EXAMPLE 267B for 4-(((1R)-3-(dimethylamino)-1-((phenylsulfanyl)methyl)propyl)amino)-3-nitrobenzenesulfonamide in EXAMPLE 2D. $^1$H NMR (300 MHz, CD$_3$OD) δ 8.30 (d, 1H), 7.90 (dd, 1H), 7.75 (d, 2H), 7.52 (m, 1H), 7.38 (m, 6H), 7.24 (m, 3H), 7.05 (m, 2H), 6.96 (d, 1H), 6.90 (d, 2H), 3.95 (m, 1H), 3.54 (s, 2H), 3.27 (m, 4H), 2.51 (m, 4H), 1.81 (m, 2H), 1.00 (t, 3H).

EXAMPLE 268

This example was made by substituting EXAMPLE 90C and EXAMPLE 267B for EXAMPLE 1C and 4-(((1R)-3-(dimethylamino)-1-((phenylsulfanyl)methyl)propyl)amino)-3-nitrobenzenesulfonamide, respectively, in EXAMPLE 1D. $^1$H NMR (300 MHz, CDCl$_3$) δ 8.79 (s, 1H), 8.37 (m, 1H), 8.01 (d, 1H), 7.57 (m, 2H), 7.35 (m, 10H), 7.19 (m, 4H), 6.72 (d, 2H), 6.64 (d, 1H), 3.72 (m, 1H), 3.36 (m, 2H), 3.13 (m, 5H), 2.99 (m, 1H), 2.92 (s, 3H), 1.92 (m, 1H), 1.58 (m, 3H), 1.31 (m, 2H), 0.98 (t, 3H).

EXAMPLE 269

This example was made by substituting EXAMPLE 267B for 4-(((1R)-3-(dimethylamino)-1-((phenylsulfanyl)methyl)propyl)amino)-3-nitrobenzenesulfonamide in EXAMPLE 1D. $^1$H NMR (300 MHz, CDCl$_3$) δ 8.80 (s, 1H), 8.42 (m, 1H), 8.03 (dd, 1H), 7.67 (m, 3H), 7.36 (m, 10H), 7.19 (m, 3H), 6.74 (d, 2H), 6.65 (d, 1H), 3.64 (m, 3H), 3.31 (m, 4H), 3.11 (s, 2H), 2.53 (m, 4H), 1.69 (m, 2H), 0.98 (t, 3H).

EXAMPLE 270A

This example was prepared by substituting (S)-2-amino-4-methyl-pentan-1-ol for (S)-2-Amino-butan-1-ol in EXAMPLE 267A.

EXAMPLE 270B

This example was prepared by substituting EXAMPLE 270A for EXAMPLE 21C in EXAMPLE 21D.

EXAMPLE 270C

This example was made by substituting EXAMPLE 270B for 4-(((1R)-3-(dimethylamino)-1-((phenylsulfanyl)methyl)propyl)amino)-3-nitrobenzenesulfonamide in EXAMPLE 2D. $^1$H NMR (300 MHz, CDCl$_3$) δ 8.80 (d, 1H), 8.38 (d, 1H), 8.00 (dd, 1H), 7.63 (d, 2H), 7.49 (m, 1H), 7.35 (m, 8H), 7.22 (m, 4H), 6.79 (d, 2H), 6.60 (d, 1H), 3.85 (m, 1H), 3.42 (s, 2H), 3.28 (m, 4H), 3.09 (d, 2H), 2.47 (m, 4H), 1.73 (m, 3H), 0.96 (d, 3H), 0.86 (d, 3H).

EXAMPLE 271

This example was made by substituting EXAMPLE 90C and EXAMPLE 270B for EXAMPLE 1C and 4-(((1R)-3-(dimethylamino)-1-((phenylsulfanyl)methyl)propyl)amino)-3-nitrobenzenesulfonamide, respectively, in EXAMPLE 1D. $^1$H NMR (300 MHz, CDCl$_3$) δ 8.77 (d, 1H), 8.36 (d, 2H), 7.98 (dd, 1H), 7.60 (d, 2H), 7.35 (m, 9H), 7.20 (m, 4H), 6.64 (m, 3H), 3.80 (m, 1H), 3.34 (s, 2H), 3.12 (s, 3H), 3.07 (m, 2H), 2.92 (m, 4H), 1.57 (m, 5H), 1.30 (m, 2H), 0.95 (d, 3H), 0.85 (d, 3H).

EXAMPLE 272A

1-Tert-butoxycarbonylaminocyclopropane carboxylic acid (1.018 g) in THF (6 mL) at 0° C. was treated with 1M borane·THF (15 mL), stirred at 25° C., treated with 3M NaOH, (5 mL), and extracted with diethyl ether. The extract was dried (MgSO$_4$), filtered, and concentrated. The concentrate was flash chromatographed on silica gel with 10% ethyl acetate/hexanes.

EXAMPLE 272B

This example was prepared by substituting EXAMPLE 272A for (S)-2-amino-butan-1-ol in EXAMPLE 267A.

EXAMPLE 272C 272B (0.090.g) in dichloromethane/TFA at 25° C. was stirred for 16 hours and concentrated. The concentrate was flash chromatographed on silica gel with 5% methanol/dichloromethane.

EXAMPLE 272 D

This example was prepared by substituting EXAMPLE 272C for EXAMPLE 21C in EXAMPLE 21D.

EXAMPLE 272E

This example was made by substituting EXAMPLE 272D for 4-(((1R)-3-(dimethylamino)-1-((phenylsulfanyl)methyl)

propyl)amino)-3-nitrobenzenesulfonamide in EXAMPLE 2D. $^1$H NMR (300 MHz, CDCl$_3$) δ 8.74 (d, 1H), 8.60 (s, 1H), 8.14 (dd, 1H), 7.63 (d, 2H), 7.49 (m, 1H), 7.35 (m, 6H), 7.25 (m, 3H), 7.06 (m, 3H), 6.80 (d, 2H), 3.41 (s, 2H), 3.28 (m, 4H), 3.22 (s, 2H), 2.47 (m, 4H), 1.01 (m, 4H).

EXAMPLE 273A

This example was prepared by substituting (1-hydroxymethyl-cyclohexyl)carbamic acid tert-butyl ester, prepared as described in Bioorg. Med. Chem. Lett., 2003; 13; 1883, for (S)-2-amino-butan-1-ol in EXAMPLE 267A.

EXAMPLE 273B

This example was prepared by substituting EXAMPLE 273A for EXAMPLE 272B in EXAMPLE 272C.

EXAMPLE 273C

This example was prepared by substituting EXAMPLE 273B for EXAMPLE 21C in EXAMPLE 21D.

EXAMPLE 273D

This example was made by substituting EXAMPLE 273C for 4-(((1R)-3-(dimethylamino)-1-((phenylsulfanyl)methyl)propyl)amino)-3-nitrobenzenesulfonamide in EXAMPLE 2D. $^1$H NMR (300 MHz, CDCl$_3$) δ 8.71 (s, 1H), 8.63 (s, 1H), 7.92 (d, 1H), 7.68 (m, 2H), 7.47 (m, 5H), 7.32 (m, 1H), 7.20 (m, 4H), 6.94 (m, 6H), 6.78 (m, 1H), 4.38 (s, 2H), 3.56 (m, 4H), 3.38 (s, 2H), 2.31 (m, 4H), 1.47 (m, 10H).

EXAMPLE 274A

This example was prepared by substituting (R)-2-amino-propan-1-ol for (S)-2-amino-butan-1-ol in EXAMPLE 267A.

EXAMPLE 274B

This example was prepared by substituting EXAMPLE 274A for EXAMPLE 21C in EXAMPLE 21D.

EXAMPLE 274C

This example was made by substituting EXAMPLE 274B for 4-(((1R)-3-(dimethylamino)-1-((phenylsulfanyl)methyl)propyl)amino)-3-nitrobenzenesulfonamide in EXAMPLE 2D. $^1$H NMR (300 MHz, CDCl$_3$) δ 8.80 (br s, 1H), 8.42 (br s, 1H), 8.03 (d, 1H), 7.65 (d, 2H), 7.50 (m, 1H), 7.34 (m, 9H), 7.22 (m, 3H), 6.77 (d, 2H), 6.63 (m, 1H), 3.88 (m, 1H), 3.42 (s, 2H), 3.26 (m, 4H), 3.10 (d, 2H), 2.48 (m, 4H), 1.43 (d, 3H).

EXAMPLE 275A

This example was prepared by substituting (S)-2-amino-propan-1-ol for (S)-2-amino-butan-1-ol in EXAMPLE 267A.

EXAMPLE 275B

This example was prepared by substituting EXAMPLE 275A for EXAMPLE 21C in EXAMPLE 21D.

EXAMPLE 275C

This example was made by substituting EXAMPLE 275B for 4-(((1R)-3-(dimethylamino)-1-((phenylsulfanyl)methyl)propyl)amino)-3-nitrobenzenesulfonamide in EXAMPLE 1D. $^1$H NMR (300 MHz, CDCl$_3$) δ 8.82 (d, 1H), 8.45 (d, 1H), 8.04 (dd, 1H), 7.64 (d, 2H), 7.56 (m, 1H), 7.35 (m, 10H), 7.20 (m, 3H), 6.77 (d, 2H), 6.65 (d, 1H), 3.91 (m, 1H), 3.51 (s, 2H), 3.27 (t, 4H), 3.12 (m, 2H), 2.48 (t, 4H), 1.45 (d, 3H).

EXAMPLE 276A

This example was prepared by substituting (1R, 2R)-(2-hydroxycyclohexyl)carbamic acid tert-butyl ester, prepared as described in Synth. Commun. 1992, 22, 3003, for (S)-2-amino-butan-1-ol in EXAMPLE 267A.

This example was prepared by substituting EXAMPLE 276A for EXAMPLE 272B in EXAMPLE 272C.

EXAMPLE 276C

This example was prepared by substituting EXAMPLE 276B for EXAMPLE 21C in EXAMPLE 21D.

EXAMPLE 276D

This example was made by substituting EXAMPLE 276C for 4-(((1R)-3-(dimethylamino)-1-((phenylsulfanyl)methyl)propyl)amino)-3-nitrobenzenesulfonamide in EXAMPLE 1D. $^1$H NMR (300 MHz, CDCl$_3$) δ 8.92 (s, 1H), 8.78 (s, 1H), 8.07 (d, 1H), 7.61 (m, 3H), 7.35 (m, 10H), 7.09 (m, 3H), 6.76 (m, 3H), 3.84 (s, 1H), 3.65 (s, 1H), 3.48 (m, 2H), 3.25 (m, 4H), 2.47 (m, 4H), 1.73 (m, 8H).

EXAMPLE 277

This example was made by substituting EXAMPLE 276C for 4-(((1R)-3-(dimethylamino)-1-((phenylsulfanyl)methyl)propyl)amino)-3-nitrobenzenesulfonamide in EXAMPLE 2D. $^1$H NMR (300 MHz, CDCl$_3$) δ 8.92 (d, 1H), 8.80 (d, 1H), 8.08 (dd, 1H), 7.66 (d, 2H), 7.53 (m, 1H), 7.35 (m, 8H), 7.23 (m, 1H), 7.11 (m, 3H), 6.78 (m, 3H), 3.87 (m, 1H), 3.65 (m, 1H), 3.46 (s, 2H), 3.28 (m, 4H), 2.49 (m, 4H), 1.75 (m, 8H).

EXAMPLE 278A

This example was prepared by substituting (1S,2R)-(2-hydroxycyclohexyl)carbamic acid tert-butyl ester, prepared as described in Eur. J. Org. Chem., 1998, 9, 1771, for (S)-2-amino-butan-1-ol in EXAMPLE 267A.

EXAMPLE 278B

This example was prepared by substituting EXAMPLE 278A for EXAMPLE 272B in EXAMPLE 272C.

EXAMPLE 278C

This example was prepared by substituting EXAMPLE 278B for EXAMPLE 21C in EXAMPLE 21D.

EXAMPLE 278D

This example was made by substituting EXAMPLE 278C for 4-(((1R)-3-(dimethylamino)-1-((phenylsulfanyl)methyl)propyl)amino)-3-nitrobenzenesulfonamide in EXAMPLE 2D. $^1$H NMR (300 MHz, CDCl$_3$) δ 8.93 (d, 1H), 8.80 (d, 1H), 8.09 (dd, 1H), 7.64 (d, 2H), 7.53 (m, 1H), 7.35 (m, 8H), 7.12 (m, 3H), 6.80 (m, 3H), 3.87 (m, 1H), 3.66 (m, 1H), 3.50 (s, 2H), 3.32 (m, 4H), 2.50 (m, 4H), 1.85 (m, 8H).

EXAMPLE 279A

This example was prepared by substituting S-(1-hydroxymethyl-2-pyridin-3-yl-ethyl)-carbamic acid tert-butyl ester for (S)-2-amino-butan-1-ol in EXAMPLE 267A.

EXAMPLE 279B

This example was prepared by substituting EXAMPLE 279A for EXAMPLE 272B in EXAMPLE 272C.

EXAMPLE 279C

This example was prepared by substituting EXAMPLE 279B for EXAMPLE 21C in EXAMPLE 21D.

EXAMPLE 279D

This example was made by substituting EXAMPLE 795333C for 4-(((1R)-3-(dimethylamino)-1-((phenylsulfanyl)methyl)propyl)amino)-3-nitrobenzenesulfonamide in EXAMPLE 1D. $^1$H NMR (300 MHz, CDCl$_3$) δ 8.74 (d, 1H), 8.48 (m, 3H), 7.97 (dd, 1H), 7.64 (d, 2H), 7.53 (m, 2H), 7.37 (m, 9H), 7.23 (m, 5H), 6.75 (d, 2H), 6.53 (d, 1H), 4.00 (m, 1H), 3.50 (s, 2H), 3.26 (m, 5H), 3.13 (d, 2H), 2.98 (m, 1H), 2.48 (m, 4H).

EXAMPLE 280

This example was made by substituting EXAMPLE 90C and EXAMPLE 279C for EXAMPLE 10 and 4-(((1R)-3-(dimethylamino)-1-((phenylsulfanyl)methyl)propyl)amino)-3-nitrobenzenesulfonamide, respectively, in EXAMPLE 1D. $^1$H NMR (300 MHz, CDCl$_3$) δ 8.90 (s, 1H), 8.62 (s, 1H), 8.53 (s, 1H), 8.45 (d, 1H), 8.15 (d, 1H), 7.81 (d, 1H), 7.69 (m, 3H), 7.34 (m, 9H), 7.19 (m, 4H), 6.90 (d, 2H), 6.54 (d, 1H), 4.18 (m, 1H), 3.34 (m, 6H), 3.12 (s, 3H), 3.04 (m, 2H), 2.94 (s, 2H), 1.61 (m, 2H), 1.45 (m, 2H).

EXAMPLE 281

This example was made by substituting EXAMPLE 278C for 4-(((1R)-3-(dimethylamino)-1-((phenylsulfanyl)methyl)propyl)amino)-3-nitrobenzenesulfonamide in EXAMPLE 1D. $^1$H NMR (300 MHz, CDCl$_3$) δ 8.95 (d, 1H), 8.79 (d, 1H), 8.06 (dd, 1H), 7.69 (m, 3H), 7.41 (m, 8H), 7.24 (m, 1H), 7.11 (m, 3H), 6.80 (d, 1H), 6.74 (d, 2H), 3.86 (m, 1H), 3.66 (m, 1H), 3.29 (m, 8H), 2.52 (s, 2H), 2.07 (m, 1H), 1.81 (m, 5H), 1.51 (m, 2H).

EXAMPLE 282A

This example was prepared by substituting (1-amino-cyclopentyl)-methanol and bis(2-methyl-3-furyl)disulphide for (S)-2-amino-butan-1-ol and phenyl disulphide, respectively, in EXAMPLE 267A.

EXAMPLE 282B

This example was prepared by substituting EXAMPLE 282A for EXAMPLE 21C in EXAMPLE 21D.

EXAMPLE 282C

This example was made by substituting EXAMPLE 282B for 4-(((1R)-3-(dimethylamino)-1-((phenylsulfanyl)methyl)propyl)amino)-3-nitrobenzenesulfonamide in EXAMPLE 1D. $^1$H NMR (500 MHz, CDCl$_3$) δ 8.82 (d, 1H), 8.68 (s, 1H), 8.06 (dd, 1H), 7.65 (d, 2H), 7.53 (m, 1H), 7.33 (m, 7H), 6.91 (m, 1H), 6.88 (s, 1H), 6.78 (d, 2H), 5.99 (d, 1H), 3.47 (s, 2H), 3.26 (m, 4H), 3.18 (s, 2H), 2.46 (m, 4H), 2.14 (br s, 3H), 2.08 (m, 4H), 1.78 (m, 4H).

EXAMPLE 283

This example was made by substituting EXAMPLE 282B for 4-(((1R)-3-(dimethylamino)-1-((phenylsulfanyl)methyl)propyl)amino)-3-nitrobenzenesulfonamide in EXAMPLE 2D. $^1$H NMR (500 MHz, CDCl$_3$) δ 8.82 (d, 1H), 8.68 (s, 1H), 8.07 (dd, 1H), 7.65 (d, 2H), 7.49 (m, 1H), 7.34 (m, 6H), 7.23 (m, 1H), 6.90 (m, 2H), 6.79 (d, 2H), 6.00 (d, 1H), 3.41 (s, 2H), 3.26 (m, 4H), 3.18 (s, 2H), 2.46 (m, 4H), 2.14 (s, 3H), 2.08 (m, 4H), 1.78 (m, 4H).

EXAMPLE 284

This example was made by substituting EXAMPLE 279C for 4-(((1R)-3-(dimethylamino)-1-((phenylsulfanyl)methyl)propyl)amino)-3-nitrobenzenesulfonamide in EXAMPLE 2D. $^1$H NMR (300 MHz, CDCl$_3$) δ 8.76 (d, 1H), 8.50 (m, 3H), 7.98 (dd, 1H), 7.62 (d, 2H), 7.50 (m, 2H), 7.35 (m, 8H), 7.21 (m, 4H), 6.78 (d, 2H), 6.53 (d, 1H), 4.01 (m, 1H), 3.42 (s, 2H), 3.27 (m, 5H), 3.13 (d, 2H), 2.99 (m, 1H), 2.48 (m, 4H).

EXAMPLE 285A

This example was made by substituting 2-bromo-3-bromomethylpyridine, prepared as described in J. Am. Chem. Soc, 1985, 107, 7487, for 2-bromobenzyl bromide in EXAMPLE 2A.

EXAMPLE 285B

This example was made by substituting EXAMPLE 285A for EXAMPLE 2A in EXAMPLE 2B.

EXAMPLE 285C

This example was made by substituting EXAMPLE 285B for EXAMPLE 2B in EXAMPLE 2C.

EXAMPLE 285D

This example was made by substituting EXAMPLE 285C for EXAMPLE 10 in EXAMPLE 1D. $^1$H NMR (300 MHz, DMSO-d$_6$) δ 12.10 (s, 1H), 8.70 (m, 1H), 8.54 (d, 1H), 8.29 (d, 1H), 8.11 (m, 1H), 7.86 (dd, 1H), 7.76 (d, 2H), 7.58 (m, 5H), 7.16 (m, 6H), 6.94 (d, 2H), 4.19 (m, 1H), 3.54 (m, 4H), 3.39 (d, 2H), 3.13 (m, 4H), 2.75 (s, 3H), 2.74 (s, 3H), 2.49 (m, 4H), 2.14 (m, 2H).

EXAMPLE 286

This example was made by substituting EXAMPLE 285C and 3-nitro-4-(2-phenylsulfanylethylamino)benzenesulfonamide, prepared as described in WO02/24636, For EXAMPLE 10 and 4-(((1R)-3-(dimethylamino)-1-((phenylsulfanyl)methyl)propyl)amino)-3-nitrobenzenesulfonamide, respectively, in EXAMPLE 1D. $^1$H NMR (300 MHz, CDCl$_3$) δ 8.83 (d, 1H), 8.78 (d, 1H), 8.67 (t, 1H), 8.34 (d, 1H), 8.10 (dd, 1H), 7.67 (d, 1H), 7.52 (m, 3H), 7.41 (m, 4H), 7.30 (m, 2H), 7.23 (m, 1H), 6.82 (m, 1H), 6.73 (d, 2H), 4.35 (s, 2H), 3.57 (q, 2H), 3.47 (m, 4H), 3.20 (t, 2H), 2.97 (m, 4H).

EXAMPLE 287

This example was made by substituting EXAMPLE 285C and 4-(H1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-$d_6$) δ 8.70 (d, 1H), 8.55 (d, 1H), 8.30 (d, 1H), 8.12 (m, 1H), 7.87 (dd, 1H), 7.76 (d, 2H), 7.57 (m, 5H), 7.16 (m, 6H), 6.94 (d, 2H), 4.19 (m, 1H), 3.97 (d, 2H), 3.58 (m, 7H), 3.38 (m, 5H), 3.19 (m, 4H), 3.01 (m, 4H), 2.17 (m, 2H).

EXAMPLE 288A

This example was made by substituting phenylboronic acid and EXAMPLE 285A for 4-chlorophenylboronic acid and EXAMPLE 2A, respectively, in EXAMPLE 2B.

EXAMPLE 288B

This example was made by EXAMPLE 288A for EXAMPLE 2B in EXAMPLE 2C.

EXAMPLE 288C

This example was made by substituting EXAMPLE 288B and 3-nitro-4-(2-phenylsulfanylethylamino)-benzenesulfonamide, prepared as described in WO02/24636, for EXAMPLE 1C and 4-(((1R)-3-(dimethylamino)-1-((phenylsulfanyl)methyl)propyl)amino)-3-nitrobenzenesulfonamide, respectively, in EXAMPLE 1D. $^1$H NMR (300 MHz, CDCl$_3$) δ 8.86 (d, 1H), 8.65 (m, 2H), 8.14 (dd, 1H), 7.91 (m, 1H), 7.60 (m, 4H), 7.43 (m, 5H), 7.28 (m, 4H), 6.80 (m, 3H), 3.56 (m, 4H), 3.31 (m, 4H), 3.21 (t, 2H), 2.51 (m, 4H).

EXAMPLE 289

This example was made by substituting EXAMPLE 288B and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, CD$_3$OD) δ 8.67 (d, 1H), 8.49 (dd, 1H), 8.07 (dd, 1H), 7.88 (dd, 1H), 7.78 (d, 2H), 7.48 (m, 6H), 7.26 (m, 2H), 7.12 (m, 3H), 6.95 (d, 1H), 6.88 (d, 2H), 4.14 (m, 1H), 3.66 (m, 4H), 3.53 (m, 2H), 3.25 (m, 6H), 2.51 (m, 10H), 2.13 (m, 1H), 1.92 (m, 1H).

EXAMPLE 290

This example was made by substituting EXAMPLE 288B for EXAMPLE 2C in EXAMPLE 2D. $^1$H NMR (400 MHz, DMSO-$d_6$) δ 8.56 (dd, 1H), 8.44 (d, 1H), 8.31 (d, 1H), 7.94 (dd, 1H), 7.79 (dd, 1H), 7.72 (d, 2H), 7.62 (m, 2H), 7.43 (m, 5H), 7.32 (m, 2H), 7.25 (m, 2H), 7.17 (m, 1H), 6.87 (d, 1H), 6.79 (d, 2H), 4.05 (m, 1H), 3.50 (s, 2H), 3.30 (m, 2H), 3.16 (s, 4H), 2.43 (m, 4H), 2.35 (m, 6H), 2.01 (m, 1H), 1.91 (m, 1H).

EXAMPLE 291A

This example was made by substituting 4-(methylsulfanyl)phenylboronic acid and EXAMPLE 285A for 4-chlorophenylboronic acid and EXAMPLE 2A, respectively, in EXAMPLE 2B.

EXAMPLE 291B

This example was made by substituting EXAMPLE 291A for EXAMPLE 2B in EXAMPLE 2C.

EXAMPLE 291C

This example was made by substituting EXAMPLE 291B for EXAMPLE 2C in EXAMPLE 2D. $^1$H NMR (300 MHz, CD$_3$OD) δ 8.74 (dd, 1H), 8.67 (d, 1H), 8.42 (dd, 1H), 7.93 (dd, 1H), 7.74 (m, 3H), 7.50 (d, 2H), 7.44 (d, 2H), 7.22 (m, 2H), 7.04 (m, 4H), 6.94 (d, 2H), 4.36 (s, 2H), 4.17 (m, 1H), 3.43 (m, 5H), 3.24 (m, 3H), 3.04 (t, 4H), 2.87 (s, 6H), 2.51 (s, 3H), 2.24 (m, 2H).

EXAMPLE 292A

This example was made by substituting 4-methoxyphenylboronic acid and EXAMPLE 285A for 4-chlorophenylboronic acid and EXAMPLE 2A, respectively, in EXAMPLE 2B.

EXAMPLE 292B

This example was made by substituting EXAMPLE 292A for EXAMPLE 2B in EXAMPLE 2C.

EXAMPLE 292C

This example was made by substituting EXAMPLE 292B for EXAMPLE 2C in EXAMPLE 2D. $^1$H NMR (300 MHz, DMSO-$d_6$) δ 8.55 (dd, 1H), 8.45 (d, 1H), 8.33 (d, 1H), 7.91 (dd, 1H), 7.78 (dd, 1H), 7.73 (d, 2H), 7.63 (d, 2H), 7.33 (m, 3H), 7.21 (m, 3H), 7.01 (d, 2H), 6.86 (d, 1H), 6.80 (d, 2H), 4.04 (m, 1H), 3.79 (s, 3H), 3.50 (s, 2H), 3.18 (s, 4H), 3.00 (d, 2H), 2.68 (m, 2H), 2.45 (m, 4H), 2.33 (s, 6H), 1.95 (m, 2H).

EXAMPLE 293A

This example was made by substituting 4-dimethylaminophenylboronic acid and EXAMPLE 285A for 4-chlorophenylboronic acid and EXAMPLE 2A, respectively, in EXAMPLE 2B.

EXAMPLE 293B

This example was made by substituting EXAMPLE 293A for EXAMPLE 2B in EXAMPLE 2C.

EXAMPLE 293

This example was made by substituting EXAMPLE 293B for EXAMPLE 2C in EXAMPLE 2D. $^1$H NMR (300 MHz, CD$_3$OD) δ 8.66 (d, 1H), 8.46 (dd, 1H), 8.08 (dd, 1H), 7.94 (dd, 1H), 7.75 (d, 2H), 7.42 (m, 3H), 7.24 (m, 2H), 7.08 (m, 3H), 6.96 (d, 1H), 6.91 (d, 2H), 6.84 (d, 2H), 4.14 (m, 1H), 3.64 (s, 2H), 3.38 (m, 4H), 3.23 (m, 4H), 3.00 (s, 6H), 2.86 (s, 7H), 2.54 (m, 4H), 2.22 (m, 2H).

EXAMPLE 294A

This example was made by substituting 4-fluorophenylboronic acid and EXAMPLE 285A for 4-chlorophenylboronic acid and EXAMPLE 2A, respectively, in EXAMPLE 2B.

EXAMPLE 294B

This example was made by substituting EXAMPLE 294A for EXAMPLE 2B in EXAMPLE 2C.

EXAMPLE 294

This example was made by substituting EXAMPLE 294B for EXAMPLE 2C in EXAMPLE 2D. $^1$H NMR (300 MHz, CD$_3$OD) δ 8.74 (dd, 1H), 8.67 (d, 1H), 8.37 (dd, 1H), 7.93 (dd, 1H), 7.73 (m, 3H), 7.60 (m, 2H), 7.31 (m, 2H), 7.22 (m, 2H), 7.03 (m, 4H), 6.95 (d, 2H), 4.39 (s, 2H), 4.17 (m, 1H), 3.47 (m, 4H), 3.38 (m, 1H), 3.23 (m, 3H), 3.08 (m, 4H), 2.86 (s, 6H), 2.24 (m, 2H).

EXAMPLE 295A

This example was made by substituting 4-(methanesulphonyl)phenylboronic acid and EXAMPLE 285A for 4-chlorophenylboronic acid and EXAMPLE 2A, respectively, in EXAMPLE 2B.

EXAMPLE 295B

This example was made by substituting EXAMPLE 295A for EXAMPLE 2B in EXAMPLE 2C.

EXAMPLE 295C

This example was made by substituting EXAMPLE 295B for EXAMPLE 2C in EXAMPLE 2D. $^1$H NMR (300 MHz, CDCl$_3$) δ 8.62 (m, 3H), 8.02 (d, 2H), 7.89 (m, 3H), 7.80 (m, 3H), 7.32 (m, 3H), 7.19 (m, 3H), 6.73 (m, 3H), 4.06 (m, 1H), 3.46 (s, 2H), 3.24 (m, 4H), 3.12 (d, 2H), 2.85 (m, 3H), 2.59 (s, 6H), 2.51 (m, 5H), 2.19 (m, 1H), 2.08 (m, 1H).

EXAMPLE 205A

This example was made by substituting 2-bromoethylamine hydrobromide for EXAMPLE 21C in EXAMPLE 21D.

EXAMPLE 296A

This example was made by substituting pyridin-4-yl-methanethiol for 2-mercaptoimidazole in EXAMPLE 205B.

EXAMPLE 296B

This example was made by substituting 3-nitro-4-((2-(phenylsulfanyl)ethyl)amino)benzenesulfonamide for 4-(((1R)-3-(dimethylamino)-1-((phenylsulfanyl)methyl)propyl)amino)-3-nitrobenzenesulfonamide in EXAMPLE 2D. $^1$H NMR (300 MHz, CDCl$_3$) δ 8.87 (d, 1H), 8.62 (m, 1H), 8.42 (d, 2H), 8.19 (dd, 1H), 7.62 (d, 3H), 7.35 (m, 7H), 7.15 (d, 2H), 6.92 (d, 1H), 6.77 (d, 2H), 3.70 (q, 2H), 3.54 (s, 2H), 3.32 (m, 6H), 2.53 (m, 4H).

EXAMPLE 297A

This example was made by substituting 4-(methanesulphonyl)phenylboronic acid for 4-chlorophenylboronic acid in EXAMPLE 2B.

EXAMPLE 297B

This example was made by substituting EXAMPLE 297A for EXAMPLE 2B in EXAMPLE 2C.

EXAMPLE 297C

This example was made by substituting EXAMPLE 297B for EXAMPLE 2C in EXAMPLE 2D. $^1$H NMR (300 MHz, CDCl$_3$) δ 8.66 (d, 1H), 8.57 (d, 1H), 7.96 (d, 2H), 7.80 (m, 3H), 7.66 (d, 2H), 7.49 (m, 1H), 7.38 (m, 2H), 7.29 (m, 2H), 7.19 (m, 4H), 6.71 (m, 3H), 4.04 (m, 1H), 3.38 (s, 2H), 3.18 (m, 4H), 3.10 (m, 6H), 2.85 (m, 2H), 2.58 (s, 6H), 2.45 (m, 4H), 2.20 (m, 1H), 2.07 (m, 1H).

EXAMPLE 298

This example was made by substituting EXAMPLE 297B and 4-(((1R)-3-(4-morpholinyl)-1-((phenylsulfanyl)methyl)propyl)amino)-3-nitrobenzenesulfonamide for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-d$_6$) δ 8.55 (d, 1H), 8.29 (d, 1H), 8.01 (d, 2H), 7.87 (dd, 1H), 7.76 (d, 2H), 7.67 (d, 2H), 7.55 (m, 2H), 7.37 (d, 1H), 7.23 (m, 2H), 7.15 (m, 4H), 6.93 (s, 2H), 4.19 (m, 1H), 3.95 (s, 2H), 3.54 (m, 12H), 3.40 (d, 2H), 3.26 (s, 3H), 3.19 (m, 4H), 3.02 (m, 2H), 2.17 (m, 2H).

EXAMPLE 299A

EXAMPLE 19C (0.938 g) in dichloromethane (10 mL) at 25° C. was treated with di(tert-butyl) dicarbonate (0.873 g), stirred for 24 hours, and concentrated. The concentrate was flash chromatographed on silica gel with 20-60% ethyl acetate/hexanes.

EXAMPLE 299B

This example was prepared by substituting EXAMPLE 299A for EXAMPLE 67A in EXAMPLE 67B.

EXAMPLE 299C

This example was prepared by substituting EXAMPLE 299B for EXAMPLE 272B in EXAMPLE 272C.

EXAMPLE 299D

This example was prepared by substituting EXAMPLE 299C for EXAMPLE 21C in EXAMPLE 21D.

EXAMPLE 299E

EXAMPLE 299D (0.485 g) at 25° C. was treated with 1M borane·THF (8 mL), stirred for 16 hours, treated with methanol (5 mL), and concentrated. The concentrate was refluxed in methanol/12M HCl (30 mL/6 mL) for 8 hours and concentrated. The concentrate was flash chromatographed on silica gel with 1-20% methanol/NH$_3$-saturated dichloromethane.

EXAMPLE 299F

This example was prepared by substituting EXAMPLE 299E for EXAMPLE 2C in EXAMPLE 2D. $^1$H NMR (300 MHz, CDCl$_3$) δ 8.80 (d, 1H), 8.41 (d, 1H), 8.07 (dd, 1H), 7.77 (d, 2H), 7.63 (dd, 3H), 7.46 (m, 3H), 7.34 (m, 6H), 7.24 (m, 1H), 7.00 (d, 1H), 6.78 (d, 2H), 4.54 (m, 1H), 3.69 (m, 4H), 3.45 (d, 2H), 3.41 (s, 2H), 3.26 (m, 4H), 2.47 (m, 6H), 2.34 (m, 3H), 2.20 (m, 2H), 1.86 (m, 2H).

EXAMPLE 300A

This example was made by substituting 4-dimethylaminophenylboronic acid for 4-chlorophenylboronic acid in EXAMPLE 2B.

EXAMPLE 300B

This example was made by substituting EXAMPLE 300A for EXAMPLE 2B in EXAMPLE 2C.

EXAMPLE 300C

This example was made by substituting EXAMPLE 300B for EXAMPLE 2C in EXAMPLE 2D. $^1$H NMR (500 MHz, DMSO-$d_6$) δ 8.46 (d, 1H), 8.20 (d, 1H), 7.81 (dd, 1H), 7.72 (m, 2H), 7.50 (m, 1H), 7.30 (m, 6H), 7.24 (m, 4H), 6.90 (d, 1H), 6.79 (m, 4H), 4.07 (m, 1H), 3.43 (s, 2H), 3.21 (m, 8H), 2.92 (s, 6H), 2.56 (s, 6H), 2.43 (m, 4H), 2.05 (m, 2H).

EXAMPLE 301A

This example was prepared by substituting EXAMPLE 18C for EXAMPLE 19C in EXAMPLE 299A.

EXAMPLE 301B

This example was prepared by substituting EXAMPLE 301A for EXAMPLE 67A in EXAMPLE 67B.

EXAMPLE 301C

This example was prepared by substituting EXAMPLE 301B for EXAMPLE 272B in EXAMPLE 272C.

EXAMPLE 301D

This example was prepared by substituting EXAMPLE 301C for EXAMPLE 21C in EXAMPLE 21D.

EXAMPLE 301E

This example was made by substituting EXAMPLE 301D for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 8.51 (m, 2H), 7.90 (dd, 1H), 7.76 (d, 2H), 7.58 (dd, 2H), 7.50 (m, 6H), 7.38 (m, 4H), 7.23 (m, 2H), 6.90 (d, 2H), 4.70 (m, 1H), 4.17 (m, 1H), 3.76 (m, 1H), 3.43 (s, 2H), 3.25 (m, 4H), 2.94 (m, 1H), 2.88 (s, 3H), 2.77 (m, 4H), 2.42 (m, 4H).

EXAMPLE 302A

This example was prepared by substituting 3-amino-4-hydroxy-pyrrolidine-1-carboxylic acid tert-butyl ester, prepared as described in J. Org. Chem., 1997, 62, 4197, for (S)-2-amino-butan-1-ol in EXAMPLE 267A.

EXAMPLE 302B

This example was made by substituting EXAMPLE 302A for EXAMPLE 21C in EXAMPLE 21D.

EXAMPLE 302C

This example was made by substituting EXAMPLE 302B for 4-(((1R)-3-(dimethylamino)-1-((phenylsulfanyl)methyl)propyl)amino)-3-nitrobenzenesulfonamide in EXAMPLE 2D.

EXAMPLE 302D

This example was prepared by substituting EXAMPLE 302C for EXAMPLE 272B in EXAMPLE 272C. $^1$H NMR (300 MHz, CD$_3$OD) δ 8.78 (d, 1H), 7.94 (dd, 1H), 7.74 (m, 3H), 7.55 (m, 7H), 7.36 (m, 7H), 6.96 (d, 2H), 6.75 (d, 1H), 4.51 (m, 1H), 4.44 (s, 2H), 4.02 (m, 2H), 3.86 (q, 1H), 3.49 (m, 2H), 3.43 (m, 2H), 3.35 (m, 2H), 3.14 (m, 4H).

EXAMPLE 303

This example was made by substituting pyridine-4-thiol for isopropylamine in EXAMPLE 35B. $^1$H NMR (400 MHz, CD$_3$OD) δ 8.64 (m, 1H), 8.23 (m, 2H), 7.83 (m, 3H), 7.50 (m, 1H), 7.36 (m, 7H), 7.23 (m, 5H), 7.11 (m, 3H), 6.85 (d, 2H), 6.78 (d, 1H), 4.14 (m, 1H), 3.60 (m, 1H), 3.47 (s, 2H), 3.21 (m, 6H), 3.10 (m, 1H), 2.46 (m, 4H), 2.26 (m, 1H), 2.12 (m, 1H).

EXAMPLE 304A

A mixture of 3-bromo-4-methylpyridine (1.34 g) and NCS (1.43 g) in CCl$_4$ (10 mL) at reflux was stirred for 21 hours and filtered. The filtrate was dried (MgSO$_4$), filtered, and concentrated. The concentrate was flash chromatographed on silica gel with 0-30% ethyl acetate/hexanes.

EXAMPLE 304B

This example was prepared by substituting EXAMPLE 304A for 2-bromobenzyl bromide in EXAMPLE 2A.

EXAMPLE 304C

This example was prepared by substituting EXAMPLE 304B for EXAMPLE 2A in EXAMPLE 2B.

EXAMPLE 304D

This example was prepared by substituting EXAMPLE 304C for EXAMPLE 2B in EXAMPLE 2C.

EXAMPLE 304E

This example was prepared by substituting EXAMPLE 304D for EXAMPLE 2C in EXAMPLE 2D. $^1$H NMR (300 MHz, DMSO-$d_6$) δ 12.09 (d, 1H), 9.33 (d, 1H), 8.69 (d, 1H), 8.54 (d, 1H), 8.29 (d, 1H), 7.87 (dd, 1H), 7.75 (m, 3H), 7.57 (d, 2H), 7.48 (d, 2H), 7.17 (m, 6H), 6.94 (d, 2H), 4.18 (m, 1H), 3.39 (d, 2H), 3.13 (m, 4H), 2.75 (m, 3H), 2.73 (m, 3H), 2.14 (m, 2H).

EXAMPLE 305

This example was prepared by substituting EXAMPLE 304D and 3-nitro-4-((2-(phenylsulfanyl)ethyl)amino)benzenesulfonamide for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, CDCl$_3$) δ 8.83 (d, 1H), 8.75 (d, 1H), 8.66

(m, 2H), 8.11 (dd, 1H), 8.08 (d, 1H), 7.66 (d, 2H), 7.51 (d, 2H), 7.40 (d, 2H), 7.27 (m, 5H), 6.81 (d, 1H), 6.78 (d, 2H), 3.90 (s, 2H), 3.57 (m, 2H), 3.42 (m, 4H), 3.20 (t, 2H), 2.75 (m, 4H).

EXAMPLE 306A

2-Bromo-cyclopent-1-enecarbaldehyde, prepared as described in Collect. Czech. Chem. Commun., 1961, 26, 3059-3073, (1.5 g), 4-piperazin-1-yl-benzoic acid ethyl ester (2 g) in ethanol (10 mL) at 25° C. was treated with sodium cyanoborohydride (0.36 g), pH was adjusted to 5-6 with acetic acid, stirred for 18 hours, filtered, and concentrated. The concentrate was flash chromatographed on silica gel with 5-10% ethyl acetate/hexanes.

EXAMPLE 306B

This example was made by substituting EXAMPLE 306A for EXAMPLE 2A in EXAMPLE 2B.

EXAMPLE 306C

This example was made by substituting EXAMPLE 306B for EXAMPLE 2B in EXAMPLE 2C.

EXAMPLE 306D

This example was prepared by substituting EXAMPLE 306C for EXAMPLE 2C in EXAMPLE 2D. $^1$H NMR (400 MHz, DMSO-$d_6$) δ 12.10 (m, 1H), 8.54 (d, 1H), 8.28 (d, 1H), 7.86 (dd, 1H), 7.78 (d, 2H), 7.32 (d, 2H), 7.28 (d, 2H), 7.22 (d, 2H), 7.14 (m, 4H), 6.97 (d, 2H), 4.18 (m, 1H), 3.90 (m, 4H), 3.54 (m, 4H), 3.39 (d, 2H), 3.14 (m, 4H), 2.92 (m, 2H), 2.76 (s, 6H), 2.64 (m, 2H), 2.15 (m, 2H), 1.96 (m, 2H).

EXAMPLE 307A

This example was prepared by substituting 2-bromo-cyclohex-1-enecarbaldehyde, prepared as described in Collect. Czech. Chem. Commun., 1961, 26, 3059, for 2-bromo-cyclopent-1-enecarbaldehyde in EXAMPLE 306A.

EXAMPLE 307B

This example was made by substituting EXAMPLE 307A for EXAMPLE 2A in EXAMPLE 2B.

EXAMPLE 307C

This example was made by substituting EXAMPLE 307B for EXAMPLE 2B in EXAMPLE 2C.

EXAMPLE 307D

This example was made by substituting EXAMPLE 307C for EXAMPLE 2C in EXAMPLE 2D. $^1$H NMR (400 MHz, DMSO-$d_6$) δ 8.29 (d, 1H), 8.03 (d, 1H), 7.61 (dd, 1H), 7.53 (d, 2H), 7.15 (d, 2H), 6.97 (m, 2H), 6.89 (m, 6H), 6.70 (d, 2H), 3.93 (m, 1H), 3.37 (m, 4H), 3.13 (m, 4H), 2.89 (m, 4H), 2.49 (s, 6H), 2.24 (s, 2H), 1.98 (d, 4H), 1.89 (q, 2H), 1.43 (m, 4H).

EXAMPLE 308A

This example was made by substituting EXAMPLE 306A for EXAMPLE 2B in EXAMPLE 2C.

EXAMPLE 308B

This example was made by substituting EXAMPLE 308A for EXAMPLE 2C in EXAMPLE 2D. $^1$H NMR (400 MHz, DMSO-$d_6$) δ 9.48 (s, 1H), 8.50 (d, 1H), 8.25 (d, 1H), 7.83 (dd, 1H), 7.77 (d, 2H), 7.17 (m, 3H), 7.09 (m, 4H), 6.98 (d, 2H), 4.14 (m, 1H), 3.80 (s, 2H), 3.35 (d, 2H), 3.28 (m, 4H), 3.11 (m, 4H), 2.70 (s, 6H), 2.64 (m, 2H), 2.41 (m, 2H), 2.10 (q, 2H), 1.93 (m, 2H).

EXAMPLE 79

This example was made by substituting EXAMPLE 307C and 4-(((1R)-3-(4-morpholinyl)-1-((phenylsulfanyl)methyl)propyl)amino)-3-nitrobenzenesulfonamide for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-$d_6$) δ 8.50 (d, 1H), 8.37 (d, 1H), 7.80 (dd, 1H), 7.72 (d, 2H), 7.37 (d, 2H), 7.28 (m, 2H), 7.17 (m, 5H), 7.04 (d, 1H), 6.85 (d, 2H), 4.14 (s, 1H), 3.53 (m, 4H), 3.36 (m, 4H), 3.21 (m, 4H), 2.80 (s, 2H), 2.45 (m, 2H), 2.34 (m, 5H), 2.19 (m, 5H), 2.01 (m, 1H), 1.87 (m, 1H), 1.67 (m, 4H).

EXAMPLE 310

This example was made by substituting EXAMPLE 307C and EXAMPLE 18F for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 7.80 (d, 1H), 7.63 (m, 3H), 7.24 (m, 6H), 7.12 (m, 1H), 7.02 (d, 2H), 6.70 (d, 2H), 6.58 (d, 1H), 5.74 (s, 1H), 3.76 (m, 1H), 3.16 (m, 6H), 3.07 (m, 4H), 2.90 (m, 2H), 2.68 (s, 2H), 2.41 (m, 2H), 2.19 (m, 4H), 2.10 (m, 4H), 1.95 (m, 2H), 1.57 (m, 4H).

EXAMPLE 311A

This example was made by substituting EXAMPLE 307A for EXAMPLE 2B in EXAMPLE 2C.

EXAMPLE 311B

This example was made by substituting EXAMPLE 311A for EXAMPLE 2C in EXAMPLE 2D. $^1$H NMR (500 MHz, DMSO-$d_6$) δ 8.55 (d, 1H), 8.29 (d, 1H), 7.87 (dd, 1H), 7.81 (d, 2H), 7.21 (m, 3H), 7.12 (m, 3H), 7.03 (d, 2H), 4.19 (m, 1H), 3.89 (s, 2H), 3.30 (m, 8H), 3.15 (m, 4H), 2.74 (s, 6H), 2.56 (m, 2H), 2.25 (m, 2H), 2.15 (q, 2H), 1.68 (m, 4H).

EXAMPLE 312A

A mixture of DMF (10 mL) and chloroform (200 mL) at 5° C. was treated with PBr$_3$ (10 mL), stirred at 25° C. for 40 minutes, treated with tetrahydropyran-4-one (5 g) in chloroform (50 mL) at 0° C., stirred at 25° C. for 18 hours, poured onto ice, treated with sodium bicarbonate, and extracted with diethyl ether. The extract was washed with saturated sodium bicarbonate and brine and dried (MgSO$_4$), filtered and concentrated. The concentrate was flash chromatographed on silica gel with 10% ethyl acetate/hexanes.

EXAMPLE 312B

This example was prepared by substituting 312A for 2-bromo-cyclopent-1-enecarbaldehyde in EXAMPLE 306A.

EXAMPLE 312C

This example was made by substituting EXAMPLE 312B for EXAMPLE 2A in EXAMPLE 2B.

EXAMPLE 312D

This example was made by substituting EXAMPLE 312C for. EXAMPLE 2B in EXAMPLE 2C.

EXAMPLE 312E

This example was made by substituting EXAMPLE 312D for EXAMPLE 2C in EXAMPLE 2D. $^1$H NMR (500 MHz, DMSO-d$_6$) δ 8.29 (d, 1H), 8.03 (d, 1H), 7.61 (dd, 1H), 7.52 (d, 2H), 7.19 (d, 2H), 6.98 (m, 4H), 6.89 (m, 4H), 6.70 (d, 2H), 3.99 (s, 2H), 3.93 (m, 1H), 3.69 (s, 2H), 3.58 (t, 2H), 3.13 (s, 8H), 2.88 (m, 4H), 2.49 (s, 6H), 2.12 (m, 2H), 1.89 (q, 2H).

EXAMPLE 313A

This example was made by substituting EXAMPLE 312B and 4-methoxyphenylboronic acid for EXAMPLE 2A and 4-chlorophenylboronic acid, respectively, in EXAMPLE 2B.

EXAMPLE 313B

This example was made by substituting EXAMPLE 313A for EXAMPLE 2B in EXAMPLE 2C.

EXAMPLE 313

This example was made by substituting EXAMPLE 313B for EXAMPLE 2C in EXAMPLE 2D. $^1$H NMR (500 MHz, DMSO-d$_6$) δ 8.54 (d, 1H), 8.28 (d, 1H), 7.87 (dd, 1H), 7.78 (d, 2H), 7.23 (m, 2H), 7.14 (m, 4H), 7.05 (d, 2H), 6.95 (d, 2H), 6.91 (d, 2H), 4.19 (m, 1H), 3.86 (m, 2H), 3.73 (s, 3H), 3.60 (m, 4H), 3.39 (d, 2H), 3.15 (m, 4H), 2.74 (m, 8H), 2.26 (s, 2H), 2.20 (s, 2H), 2.15 (q, 2H), 1.70 (s, 4H).

EXAMPLE 314A

This example was made by substituting EXAMPLE 312B and 4-fluorophenylboronic acid for EXAMPLE 2A and 4-chlorophenylboronic acid, respectively, in EXAMPLE 2B.

EXAMPLE 313B

This example was made by substituting EXAMPLE 314A for EXAMPLE 2B in EXAMPLE 2C.

EXAMPLE 314C

This example was made by substituting EXAMPLE 313B for EXAMPLE 2C in EXAMPLE 2D. $^1$H NMR (500 MHz, DMSO-d$_6$) δ 8.55 (d, 1H), 8.29 (d, 1H), 7.87 (dd, 1H), 7.79 (d, 2H), 7.23 (m, 2H), 7.15 (m, 8H), 6.96 (d, 2H), 4.19 (m, 1H), 3.86 (m, 4H), 3.60 (s, 2H), 3.39 (d, 2H), 3.15 (m, 4H), 2.77 (m, 8H), 2.27 (s, 2H), 2.22 (s, 2H), 2.15 (q, 2H), 1.72 (s, 4H).

EXAMPLE 315A

This example was made by substituting EXAMPLE 307A and phenylboronic acid for EXAMPLE 2A and 4-chlorophenylboronic acid, respectively, in EXAMPLE 2B.

EXAMPLE 315B

This example was made by substituting EXAMPLE 315A for EXAMPLE 2B in EXAMPLE 2C.

EXAMPLE 315C

This example was made by substituting EXAMPLE 315B for EXAMPLE 2C in EXAMPLE 2D. $^1$H NMR (400 MHz, DMSO-d$_6$) δ 8.54 (d, 1H), 8.29 (d, 1H), 7.87 (dd, 1H), 7.78 (d, 2H), 7.36 (m, 2H), 7.28 (m, 1H), 7.21 (m, 2H), 7.13 (m, 6H), 6.95 (d, 2H), 4.19 (s, 1H), 3.87 (s, 2H), 3.62 (m, 4H), 3.39 (d, 2H), 3.15 (m, 4H), 2.74 (m, 8H), 2.29 (s, 2H), 2.22 (s, 2H), 2.14 (q, 2H), 1.72 (m, 4H).

EXAMPLE 316A

This example was prepared by substituting 2-bromo-cyclooct-1-enecarbaldehyde for 2-bromo-cyclopent-1-enecarbaldehyde in EXAMPLE 306A.

EXAMPLE 316B

This example was made by substituting EXAMPLE 316A for EXAMPLE 2A in EXAMPLE 2B.

EXAMPLE 316C

This example was made by substituting EXAMPLE 316B for EXAMPLE 2B in EXAMPLE 2C.

EXAMPLE 316D

This example was made by substituting EXAMPLE 316C for EXAMPLE 2C in EXAMPLE 2D. $^1$H NMR (300 MHz, DMSO-d$_6$) δ 8.54 (d, 1H), 8.30 (d, 1H), 7.86 (dd, 1H), 7.78 (d, 2H), 7.43 (d, 2H), 7.17 (m, 8H), 6.95 (d, 2H), 4.19 (m, 5H), 3.89. (m, 2H), 3.64 (s, 2H), 3.39 (m, 4H), 3.13 (m, 4H), 2.75 (s, 3H), 2.74 (s, 3H), 2.46 (m, 2H), 2.14 (q, 2H), 1.66 (m, 2H), 1.54 (m, 4H), 1.41 (m, 2H).

EXAMPLE 317A

This example was made by substituting EXAMPLE 312B and 4-methylthiophenylboronic acid for EXAMPLE 2A and 4-chlorophenylboronic acid, respectively, in EXAMPLE 2B.

EXAMPLE 317B

This example was made by substituting EXAMPLE 317A for EXAMPLE 2B in EXAMPLE 2C.

EXAMPLE 317C

This example was made by substituting EXAMPLE 317B for EXAMPLE 2C in EXAMPLE 2D. $^1$H NMR (300 MHz, DMSO-d$_6$) δ 8.54 (d, 1H), 8.29 (d, 1H), 7.86 (dd, 1H), 7.79 (d, 2H), 7.22 (m, 4H), 7.11 (m, 6H), 6.95 (d, 2H), 4.17 (m, 1H), 3.90 (m, 4H), 3.65 (m, 4H), 3.39 (d, 2H), 3.12 (m, 4H), 2.75 (s, 3H), 2.74 (s, 3H), 2.45 (s, 3H), 2.24 (m, 4H), 2.14 (q, 2H), 1.71 (m, 4H).

EXAMPLE 318A

This example was prepared by substituting 2-bromo-cyclohept-1-enecarbaldehyde for 2-bromo-cyclopent-1-enecarbaldehyde in EXAMPLE 306A.

EXAMPLE 318B

This example was made by substituting EXAMPLE 318A for EXAMPLE 2A in EXAMPLE 2B.

EXAMPLE 318C

This example was made by substituting EXAMPLE 318B for EXAMPLE 2B in EXAMPLE 2C.

EXAMPLE 318D

This example was made by substituting EXAMPLE 318C for EXAMPLE 2C in EXAMPLE 2D. $^1$H NMR (400 MHz, DMSO-$d_6$) δ 8.54 (d, 1H), 8.29 (d, 1H), 7.86 (dd, 1H), 7.78 (d, 2H), 7.40 (d, 2H), 7.22 (m, 2H), 7.14 (m, 6H), 6.95 (d, 2H), 4.19 (m, 1H), 3.87 (s, 2H), 3.61 (m, 2H), 3.39 (m, 4H), 3.15 (m, 4H), 2.75 (m, 8H), 2.46 (m, 4H), 2.14 (m, 2H), 1.80 (m, 2H), 1.56 (m, 4H).

EXAMPLE 319

This example was made by substituting EXAMPLE 318C and 4-(((1R)-3-(4-morpholinyl)-1-((phenylsulfanyl)methyl)propyl)amino)-3-nitrobenzenesulfonamide for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 8.55 (d, 1H), 8.29 (d, 1H), 7.87 (dd, 1H), 7.78 (d, 2H), 7.40 (d, 2H), 7.22 (m, 3H), 7.14 (m, 6H), 6.93 (d, 2H), 4.20 (m, 1H), 3.91 (m, 4H), 3.39 (m, 6H), 3.18 (m, 6H), 3.03 (m, 2H), 2.79 (m, 2H), 2.45 (m, 4H), 2.16 (q, 2H), 1.81 (m, 2H), 1.56 (m, 4H).

EXAMPLE 320A

This example was made by substituting 4,4-dimethyl-cyclohexanone for tetrahydro-pyran-4-one in EXAMPLE 312A.

EXAMPLE 320B

This example was prepared by substituting 320A for 2-bromo-cyclopent-1-enecarbaldehyde in EXAMPLE 306A.

EXAMPLE 320C

This example was made by substituting EXAMPLE 320B for EXAMPLE 2A in EXAMPLE 2B.

EXAMPLE 320D

This example was made by substituting EXAMPLE 320C for EXAMPLE 2B in EXAMPLE 2C.

EXAMPLE 320E

This example was made by substituting EXAMPLE 320D for EXAMPLE 2C in EXAMPLE 2D. $^1$H NMR (400 MHz, DMSO-$d_6$) δ 8.54 (d, 1H), 8.28 (d, 1H), 7.86 (dd, 1H), 7.79 (d, 2H), 7.41 (m, 2H), 7.23 (m, 2H), 7.14 (m, 6H), 6.95 (d, 2H), 4.19 (m, 1H), 3.90 (m, 1H), 3.39 (d, 2H), 3.15 (s, 6H), 2.74 (m, 8H), 2.54 (m, 3H), 2.28 (m, 2H), 2.14 (q, 2H), 2.03 (s, 2H), 1.47 (t, 2H), 0.98 (s, 6H).

EXAMPLE 321

This example was made by substituting EXAMPLE 320D and 4-(((1R)-3-(4-morpholinyl)-1-((phenylsulfanyl)methyl)propyl)amino)-3-nitrobenzenesulfonamide for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 8.54 (d, 1H), 8.29 (d, 1H), 7.87 (dd, 1H), 7.78 (d, 2H), 7.41 (m, 2H), 7.22 (m, 2H), 7.14 (m, 6H), 6.95 (d, 2H), 4.20 (m, 1H), 3.93 (m, 2H), 3.57 (m, 4H), 3.39 (m, 6H), 3.19 (m, 4H), 3.02 (m, 2H), 2.81 (m, 2H), 2.53 (s, 2H), 2.27 (m, 2H), 2.17 (q, 2H), 2.01 (s, 2H), 1.47 (t, 2H), 0.98 (s, 6H).

EXAMPLE 322A

A mixture of EXAMPLE 32A (1 g) and 60% oily sodium hydride (0.30 g) in toluene (15 mL) was refluxed for 1 hour, treated with 4-(2-chloroethyl)morpholine (2 g), refluxed for 18 hours, treated with aqueous NH$_4$Cl and extracted with ethyl acetate. The extract was washed with water and brine and dried (Na$_2$SO$_4$), filtered, and concentrated. The concentrate was flash chromatographed on silica gel with 5-15% 7M NH$_3$ in methanol/dichloromethane.

EXAMPLE 322B

This example was made by substituting EXAMPLE 322A and phenylboronic acid for EXAMPLE 32B and 4-chlorophenylboronic acid, respectively, in EXAMPLE 32C.

EXAMPLE 322C

This example was made by substituting EXAMPLE 322B for EXAMPLE 1B in EXAMPLE 1C.

EXAMPLE 322D

This example was made by substituting EXAMPLE 322C and 4-(1,1-dimethyl-2-phenylsulfanylethylamino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 11.76 (s, 1H), 11.08 (m, 1H), 10.02 (m, 1H), 8.30 (s, 1H), 8.28 (d, 1H), 7.98 (t, 2H), 7.61 (dd, 1H), 7.50 (d, 2H), 7.11 (m, 8H), 6.75 (m, 5H), 6.63 (d, 1H), 3.67 (m, 6H), 3.12 (m, 4H), 2.79 (m, 10H), 1.52 (m, 4H), 1.34 (s, 6H).

EXAMPLE 323

This example was made by substituting EXAMPLE 322C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-$d_6$) δ 11.76 (s, 1H), 11.16 (m, 1H), 10.08 (m, 1H), 8.53 (t, 1H), 8.36 (d, 1H), 7.68 (dd, 1H), 7.47 (d, 2H), 7.07 (m, 16H), 6.62 (d, 1H), 3.55 (m, 4H), 3.45 (m, 4H), 2.95 (m, 12H), 1.52 (m, 2H), 1.26 (m, 2H), 1.00 (m, 2H).

EXAMPLE 324A

This example was made by substituting 1-(2-chloroethyl)pyrrolidine for 4-(2-chloroethyl)morpholine in EXAMPLE 322A.

EXAMPLE 324B

This example was made by substituting EXAMPLE 324A and phenylboronic acid for EXAMPLE 32B and 4-chlorophenylboronic acid, respectively, in EXAMPLE 32C.

EXAMPLE 324C

This example was made by substituting EXAMPLE 324B for EXAMPLE 1B in EXAMPLE 1C.

EXAMPLE 324D

This example was made by substituting EXAMPLE 324C and 4-(1,1-dimethyl-2-phenylsulfanylethylamino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 11.96 (s, 1H), 10.39 (m, 1H), 8.50 (d, 2H), 7.82 (dd, 1H), 7.71 (d, 2H), 7.33 (m, 10H), 7.16 (dd, 1H), 6.99 (t, 2H), 6.91 (t, 1H), 6.82 (d, 2H), 3.62 (m, 2H), 3.38 (m, 6H), 3.28 (m, 2H), 2.96 (m, 6H), 1.93 (m, 2H), 1.82 (m, 2H), 1.55 (s, 6H), 1.48 (m, 2H), 1.20 (m, 2H).

EXAMPLE 325

This example was made by substituting EXAMPLE 324C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 11.95 (s, 1H), 10.46 (m, 1H), 8.74 (t, 1H), 8.58 (d, 1H), 7.90 (m, 1H), 7.67 (d, 2H), 7.28 (m, 14H), 6.81 (d, 2H), 3.66 (m, 2H), 3.38 (m, 6H), 3.27 (m, 4H), 2.98 (m, 6H), 1.93 (m, 2H), 1.82 (m, 2H), 1.48 (m, 2H), 1,19 (m, 2H).

EXAMPLE 326

This example was made by substituting EXAMPLE 324C and EXAMPLE 264B for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR 500 MHz, DMSO-$d_6$) δ 11.97 (s, 1H), 10.65 (m, 1H), 8.47 (s, 1H), 8.41 (d, 1H), 7.82 (dd, 1H), 7.73 (d, 2H), 7.27 (m, 10H), 6.81 (m, 6H), 3.63 (m, 2H), 3.35 (m, 6H), 2.96 (m, 6H), 1.90 (m, 12H), 1.48 (m, 2H), 1.20 (m, 2H).

EXAMPLE 327A

This example was made by substituting 2-(dimethylamino) ethyl chloride for 4-(2-chloroethyl)morpholine in EXAMPLE 322A.

EXAMPLE 327B

This example was made by substituting EXAMPLE 327A and phenylboronic acid for EXAMPLE 32B and 4-chlorophenylboronic acid, respectively, in EXAMPLE 32C.

EXAMPLE 327C

This example was made by substituting EXAMPLE 327B for EXAMPLE 1B in EXAMPLE 1C.

EXAMPLE 327D

This example was made by substituting EXAMPLE 327C and 4-(1,1-dimethyl-2-phenylsulfanylethylamino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 11.75 (s, 1H), 10.00 (m, 1H), 8.29 (s, 1H), 8.27 (d, 1H), 7.60 (dd, 1H), 7.49 (d, 2H), 7.10 (m, 10H), 6.93 (d, 1H), 6.77 (t, 2H), 6.68 (t, 1H), 6.60 (d, 2H), 3.63 (m, 2H), 3.29 (m, 6H), 2.85 (m, 6H), 1.51 (m, 1H), 1.33 (s, 6H), 1.25 (m, 2H), 1.08 (m, 1H), 1.0 (m, 2H).

EXAMPLE 328

This example was made by substituting EXAMPLE 327C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 11.71 (s, 1H), 9.86 (m, 1H), 8.51 (t, 1H), 8.35 (s, 1H), 7.65 (dd, 1H), 7.44 (d, 2H), 7.15 (m, 14H), 6.58 (d, 2H), 3.43 (m, 2H), 3.13 (m, 2H), 3.13 (t, 2H), 3.03 (m, 6H), 2.76 (m, 6H), 1.51 (m, 1H), 1.24 (m, 2H), 0.97 (m, 2H).

EXAMPLE 329

This example was made by substituting EXAMPLE 327C and EXAMPLE 264B for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 11.72 (s, 1H), 9.75 (m, 1H), 8.23 (s, 1H), 8.17 (d, 1H), 7.58 (dd, 1H), 7.11 (m, 10H), 6.94 (d, 1H), 6.90 (d, 2H), 6.58 (d, 2H), 6.57 (d, 1H), 3.38 (m, 2H), 3.15 (m, 2H), 2.98 (m, 2H), 2.74 (m, 4H), 2.50 (s, 3H), 2.49 (s, 3H), 1.85 (m, 4H), 1.76 (m, 4H), 1.47 (m, 2H), 1.24 (m, 2H), 0.97 (m, 2H).

EXAMPLE 330A

This example was made by substituting 1-(2-chloroethyl) piperidine for 4-(2-chloroethyl)morpholine in EXAMPLE 322A.

EXAMPLE 330B

This example was made by substituting. EXAMPLE 330A and phenylboronic acid for EXAMPLE 32B and 4-chlorophenylboronic acid, respectively, in EXAMPLE 32C.

EXAMPLE 330C

This example was made by substituting EXAMPLE 330B for EXAMPLE 1B in EXAMPLE 1C.

EXAMPLE 330D

This example was made by substituting EXAMPLE 330C and 4-(1,1-dimethyl-2-phenylsulfanylethylamino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D.
$^1$H NMR (500 MHz, DMSO-$d_6$) δ 11.97 (s, 1H), 10.27 (m, 1H), 8.51 (s, 1H), 8.49 (d, 1H), 7.82 (dd, 1H), 7.72 (d, 2H), 7.33 (m, 10H), 7.16 (d, 1H), 6.99 (t, 2H), 6.91 (t, 1H), 6.82 (d, 2H), 3.37 (m, 2H), 3.17 (m, 2H), 3.03 (s, 2H), 2.95 (m, 8H), 1.73 (m, 6H), 1.55 (s, 6H), 1.50 (m, 2H), 1.30 (m, 2H), 1.19 (m, 2H).

EXAMPLE 331

This example was made by substituting EXAMPLE 330C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenyl-sulfanyl)methyl)propyl)amino)-3-nitrobenzenesulfonamide, respectively, in EXAMPLE 2D.
$^1$H NMR (500 MHz, DMSO-$d_6$) δ 11.95 (s, 1H), 10.16 (m, 1H), 8.74 (t, 1H), 8.58 (s, 1H), 7.89 (dd, 1H), 7.67 (d, 2H), 7.29 (m, 14H), 6.81 (d, 2H), 3.66 (m, 2H), 3.37 (m, 2H), 3.27 (t, 2H), 3.17 (m, 2H), 2.95 (m, 8H), 1.73 (m, 4H), 1.63 (m, 2H), 1.49 (m, 2H), 1.30 (m, 2H), 1.19 (m, 2H).

EXAMPLE 332

This example was made by substituting EXAMPLE 330C and EXAMPLE 264B for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 11.97 (s, 1H), 10.27 (m, 1H), 8.47 (s, 1H), 8.40 (d, 1H), 7.82 (dd, 1H), 7.74 (d, 2H), 7.27 (m, 13H), 6.80 (m, 3H), 3.67 (m, 2H), 3.37 (m, 2H), 3.17 (m, 2H), 3.03 (s, 2H), 2.92 (m, 6H), 2.09 (m, 2H), 1.98 (m, 2H), 1.70 (m, 10H), 1.49 (m, 2H), 1.30 (m, 2H), 1.19 (m, 2H).

EXAMPLE 333A

This example was prepared by substituting (S)-3-(benzy-loxycarbonyl)aminobutyrolactone, prepared as described in J. Am. Chem. Soc. 1986, 108, 4943-4952, for (R)-3-(benzy-loxycarbonyl)aminobutyrolactone in EXAMPLE 19A.

EXAMPLE 333B

This example was prepared by substituting EXAMPLE 333A for EXAMPLE 18A in EXAMPLE 18B.

EXAMPLE 333C

This example was prepared by substituting EXAMPLE 333B for EXAMPLE 18B in EXAMPLE 18C.

EXAMPLE 333D

This example was prepared by substituting EXAMPLE 333C for EXAMPLE 19C in EXAMPLE 19D.

EXAMPLE 333E

This example was prepared by substituting EXAMPLE 333D for EXAMPLE 18C in EXAMPLE 18E.

EXAMPLE 333F

This example was made by substituting EXAMPLE 1C and EXAMPLE 333E for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 11.86 (s, 1H), 11.20 (m, 1H), 11.07 (m, 1H), 9.97 (m, 1H), 8.30 (d, 1H), 8.05 (2, 1H), 7.87 (dd, 1H), 7.60 (t, 1H), 7.53 (d, 2H), 7.06 (m, 13H), 6.69 (d, 2H), 4.12 (s, 2H), 3.62 (m, 4H), 3.11 (m, 5H), 2.95 (m, 4H), 2.78 (m, 8H), 1.51 (m, 2H).

EXAMPLE 334A

This example was made by substituting 4-hydoxyphenyl-boronic acid for 4-chlorophenylboronic acid in EXAMPLE 2B.

EXAMPLE 334B

A mixture of EXAMPLE 334A (0.24 g), 2-(dimethy-lamino)ethyl chloride (0.22 g), and $K_2CO_3$ (0.5 g) in acetone (20 mL) at reflux was stirred for 18 hours, concentrated, and treated with ethyl acetate and water. The extract was washed with water and brine and dried ($Na_2SO_4$), filtered, and concentrated. The concentrate was flash chromatographed on silica gel with 5% 7M $NH_3$ in methanol/dichloromethane.

EXAMPLE 334C

This example was made by substituting EXAMPLE 334B for EXAMPLE 1B in EXAMPLE 1C.

EXAMPLE 334D

This example was made by substituting EXAMPLE 334C for EXAMPLE 2C in EXAMPLE 2D. $^1$H NMR (500 MHz, DMSO-$d_6$) δ 12.12 (s, 1H), 11.55 (m, 1H), 10.88 (m, 1H), 10.70 (m, 1H), 8.54 (d, 1H), 8.29 (d, 1H), 8.11 (dd, 1H), 7.78 (d, 2H), 7.49 (t, 2H), 7.20 (m, 10H), 6.93 (d, 2H), 4.42 (t, 2H), 4.36 (s, 2H), 4.29 (m, 1H), 3.86 (m, 2H), 3.52 (m, 2H), 3.39 (m, 2H), 3.13 (m, 6H), 2.82 (s, 3H), 2.83 (s, 3H), 2.70 (m, 8H), 2.20 (m, 2H).

EXAMPLE 335

This example was made by substituting EXAMPLE 334C and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 12.11 (s, 1H), 11.37 (m, 1H), 11.19 (m, 1H), 10.71 (m, 1H), 8.53 (d, 1H), 8.29 (d, 1H), 8.06 (dd, 1H), 7.85 (dd, 2H), 7.78 (d, 2H), 7.50 (t, 2H), 7.20 (m, 10H), 6.93 (d, 2H), 4.41 (t, 2H), 4.36 (s, 2H), 4.28 (m, 1H), 3.92 (m, 2H), 3.80 (t, 2H), 3.52 (m, 2H), 3.39 (m, 2H), 3.23 (m, 8H), 2.98 (m, 2H), 2.84 (s, 6H), 2.25 (m, 2H).

EXAMPLE 336

This example was made by substituting EXAMPLE 334C and 4-(1,1-dimethyl-2-phenylsulfanylethylamino)-3-ni-trobenzenesulfonamide, prepared as described in WO 02/24636, for EXAMPLE 2C and 4-(((1R)-3-(dimethy-lamino)-1-((phenylsulfanyl)methyl)propyl)amino)-3-ni-trobenzenesulfonamide, respectively, in EXAMPLE 2D. $^1$H NMR (500 MHz, DMSO-$d_6$) δ 12.11 (s, 1H), 11.47 (m, 1H), 10.83 (m, 1H), 10.23 (m, 1H), 8.53 (s, 1H), 8.51 (d, 1H), 8.10 (m, 1H), 7.83 (dd, 1H), 7.80 (d, 2H), 7.50 (t, 2H), 7.39 (d, 1H), 7.31 (m, 3H), 7.25 (d, 2H), 7.10 (d, 2H), 7.01 (t, 2H), 6.93 (m, 3H), 4.41 (t, 2H), 4.36 (s, 2H), 3.86 (m, 2H), 3.38 (m, 2H), 3.20 (s, 2H), 3.23 (m, 2H), 2.98 (m, 2H), 3.01 (m, 4H), 2.84 (d, 3H), 2.73 (d, 3H), 1.56 (s, 6H).

EXAMPLE 337

This example was made by substituting EXAMPLE 334C and 3-nitro-4-((2-(phenylsulfanyl)ethyl)amino)benzene-sulfonamide, prepared as described in WO 02/24636, for EXAMPLE 2C and 4-(((1R)-3-(dimethylamino)-1-((phenyl-sulfanyl)methyl)propyl)amino)-3-nitrobenzenesulfonamide, respectively, in EXAMPLE 2D. $^1$H NMR (500 MHz, DMSO-$d_6$) δ 12.09 (s, 1H), 11.39 (m, 1H), 10.73 (m, 1H), 10.13 (m, 1H), 8.76 (t, 1H), 8.60 (d, 1H), 8.07 (m, 1H), 7.91 (dd, 1H), 7.76 (d, 2H), 7.50 (t, 2H), 7.25 (m, 10H), 7.09 (d, 2H), 6.92 (d, 2H), 4.41 (t, 2H), 4.36 (s, 2H), 3.86 (m, 2H), 3.67 (m, 2H), 3.28 (m, 2H), 3.20 (s, 2H), 3.01 (m, 4H), 2.84 (d, 3H), 2.73 (d, 3H).

EXAMPLE 338A

This example was made by substituting 4-(2-chloroethyl)morpholine for 2-(dimethylamino)ethyl chloride in EXAMPLE 334B.

EXAMPLE 338B

This example was made by substituting EXAMPLE 338A for EXAMPLE 1B in EXAMPLE 1C.

EXAMPLE 338C

This example was made by substituting EXAMPLE 338B for EXAMPLE 2C in EXAMPLE 2D. $^1$H NMR (500 MHz, DMSO-$d_6$) δ 11.89 (s, 1H), 11.50 (m, 1H), 11.30 (m, 1H), 10.46 (m, 1H), 8.31 (d, 1H), 8.06 (d, 1H), 7.88 (m, 1H), 7.55 (d, 2H), 7.27 (t, 2H), 6.98 (m, 11H), 6.70 (d, 2H), 4.28 (t, 2H), 4.13 (s, 2H), 3.68 (m, 4H), 3.33 (m, 2H), 3.28 (m, 2H), 3.06 (m, 6H), 2.78 (m, 6H), 2.48 (m, 6H), 1.97 (m, 2H).

EXAMPLE 339

This example was made by substituting EXAMPLE 338B and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 11.88 (s, 1H), 11.47 (m, 1H), 11.28 (m, 1H), 11.13 (m 1H), 10.01 (m, 1H), 8.30 (d, 1H), 8.05 (d, 1H), 7.87 (m, 1H), 7.61 (dd, 1H), 7.54 (d, 2H), 7.26 (t, 2H), 6.96 (m, 11H), 6.70 (d, 2H), 4.26 (t, 2H), 4.12 (s, 2H), 4.07 (m, 1H), 3.63 (m, 6H), 3.33 (m, 2H), 3.27 (m, 2H), 3.05 (m, 6H), 2.79 (m, 8H), 1.52 (m, 2H).

EXAMPLE 340

This example was made by substituting EXAMPLE 338B and 4-(1,1-dimethyl-2-phenylsulfanylethylamino)-3-nitrobenzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 12.12 (s, 1H), 11.83 (m, 1H), 11.62 (m, 1H), 10.43 (m, 1H), 8.53 (s, 1H), 8.51 (d, 1H), 8.12 (m, 1H), 7.83 (dd, 1H), 7.80 (d, 2H), 7.49 (t, 2H), 7.39 (d, 1H), 7.31 (m, 3H), 7.25 (d, 2H), 7.10 (d, 2H), 6.99 (t, 2H), 6.93 (m, 3H), 4.51 (t, 2H), 4.36 (s, 2H), 3.91 (m, 2H), 3.35 (m, 8H), 3.02 (m, 8H), 1.56 (s, 6H).

EXAMPLE 341

This example was made by substituting EXAMPLE 338B and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 12.09 (s, 1H), 11.67 (m, 1H), 11.46 (m, 1H), 10.24 (m, 1H), 8.76 (t, 1H), 8.60 (d, 1H), 8.10 (m, 1H), 7.91 (dd, 1H), 7.76 (d, 2H), 7.50 (t, 2H), 7.26 (m, 10H), 7.10 (d, 2H), 6.92 (d, 2H), 4.50 (t, 2H), 4.36 (s, 2H), 3.91 (m, 4H), 3.35 (m, 10H), 3.01 (m, 8H).

EXAMPLE 342A

A mixture of EXAMPLE 30B (1.2 g) and pyridine (3 mL) in dichloromethane (10 mL) at 25° C. was treated with p-toluenesulfonyl chloride (0.572 g), stirred for 18 hours, treated with dichloromethane (150 mL), washed with 5% HCl, water, and brine, and dried (Na$_2$SO$_4$), filtered, and concentrated.

EXAMPLE 342B

A mixture of EXAMPLE 342A (1.7 g) and imidazole (0.42 g) in DMF (25 mL) at 60° C. was stirred for 4 hours, treated with ethyl acetate (200 mL), washed with aqueous NH$_4$Cl, water, and brine, and dried (Na$_2$SO$_4$), filtered, and concentrated. The concentrate was flash chromatographed on silica gel with 50% ethyl acetate/hexane and 5% methanol/dichloromethane.

EXAMPLE 342C

This example was made by substituting EXAMPLE 342B for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 8.47 (d, 1H), 8.17 (d, 1H), 7.73 (m, 3H), 7.65 (s, 1H), 7.51 (dd, 1H), 7.37 (m, 2H), 7.19 (m, 10H), 6.93 (s, 1H), 6.82 (d, 2H), 6.63 (d, 1H), 4.09 (t, 2H), 3.87 (m, 1H), 3.31 (m, 8H), 3.15 (m, 4H), 2.23 (m, 2H).

EXAMPLE 343

This example was made by substituting EXAMPLE 342B for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-$d_6$) δ 9.11 (m, 1H), 9.06 (m, 1H), 8.53 (d, 1H), 8.23 (m, 2H), 8.08 (m, 1H), 7.82 (dd, 1H), 7.78 (d, 2H), 7.71 (t, 1H), 7.70 (d, 2H), 7.64 (t, 2H), 7.43 (m, 8H), 7.06 (m, 4H), 4.35 (s, 2H), 4.31 (t, 2H), 4.08 (m, 1H), 3.83 (m, 2H), 3.28 (m, 6H), 2.76 (m, 2H), 2.39 (m, 2H).

EXAMPLE 344

This example was made by substituting EXAMPLE 90C and EXAMPLE 342B for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (500 MHz, DMSO-$d_6$) δ 9.11 (m, 1H), 9.06 (m, 2H), 8.53 (d, 2H), 8.22 (m, 2H), 7.82 (dd, 1H), 7.71 (m, 4H), 7.64 (t, 1H), 7.26 (m, 10H), 6.99 (t, 2H), 6.83 (d, 1H), 4.31 (t, 2H), 4.04 (m, 1H), 3.37 (m, 5H), 3.19 (s, 3H), 2.89 (m, 3H), 2.39 (m, 2H), 1.46 (m, 2H), 1.17 (m, 2H).

EXAMPLE 345

This example was made by substituting (R)-4-(4-(4-methylpiperazin-1-yl)-1-phenylsulfanylmethyl-butylamino)-3-nitrobenzenesulfonamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 12.12 (m, 1H), 10.89 (m, 1H), 8.53 (d, 1H), 8.30 (d, 1H), 8.05 (m, 1H), 7.86 (dd, 1H), 7.78 (d, 2H), 7.54 (m, 3H), 7.24 (m, 10H), 6.93 (d, 2H), 4.35 (s, 2H), 4.16 (m, 1H), 3.90 (m, 2H), 3.29 (m, 8H), 2.80 (m, 8H).

EXAMPLE 346

This example was made by substituting 4-(((1R)-2-((2-(dimethylamino)ethyl)(methyl)amino)-1-((phenylsulfanyl)methyl)ethyl)amino)-3-nitrobenzenesulfonamide (prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 12.14 (m, 1H), 11.09 (m, 1H), 8.49 (d, 1H), 8.34 (d, 1H), 8.08 (m, 1H), 7.86 (dd, 1H), 7.78 (d, 2H), 7.54 (m, 3H), 7.24 (m, 10H), 6.93 (d, 2H), 4.34 (s, 2H), 3.87 (m, 2H), 3.29 (m, 8H), 2.78 (m, 9H), 2.83 (m, 6H).

EXAMPLE 347

This example was made by substituting (4R)-4-((4-(aminosulfonyl)-2-nitrophenyl)amino)-N,N-dimethyl-5-(phenylsulfanyl)pentanamide, prepared as described in WO 02/24636, for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 8.53 (d, 1H), 8.31 (d, 1H), 7.83 (dd, 1H), 7.73 (d, 2H), 7.51 (m, 2H), 7.24 (m, 12H), 6.90 (d, 2H), 4.12 (m, 1H), 3.40 (m, 8H), 3.26 (m, 4H), 2.83 (s, 3H), 2.74 (s, 3H), 2.39 (m, 4H), 1.97 (m, 2H).

EXAMPLE 348A

A mixture of tert-butyl (2E,4R)-4-((tert-butoxycarbonyl)amino)-5-(phenylsulfanyl)pent-2-enoate, prepared as described in WO02/24636, (14 g) and tris(triphenylphosphine rhodium chloride (Wilkinson's catalyst) (2 g) in toluene (250 mL) at 45° C. was stirred under hydrogen (balloon) for 48 hours, filtered through silica gel and concentrated.

EXAMPLE 348B

EXAMPLE 348A (6.3 g) in dichloromethane at 25° C. was treated with meta-chloroperbenzoic acid (8.8 g), stirred for 6 hours, poured into ethyl acetate, washed with aqueous sodium carbonate and brine, and concentrated. The concentrate was flash chromatographed on silica gel with 50% ethyl acetate/hexanes.

EXAMPLE 348C

This example was made by substituting EXAMPLE 348B for EXAMPLE 1B in EXAMPLE 1C.

EXAMPLE 348D

EXAMPLE 348C (5.1 g), dimethylamine hydrochloride (2.33 g), EDAC.HCl (8.21 g), DMAP (1.74 g), and TEA (3.97 mL) in dichloromethane (75 mL) at 25° C. was stirred for 24 hours, poured into water, and extracted with ethyl acetate. The extract was washed with water and brine and concentrated. The concentrate was flash chromatogrphed on silica gel with 10% methanol/ethyl acetate.

EXAMPLE 348E

This example was made by substituting EXAMPLE 348D for EXAMPLE 18E in EXAMPLE 18F.

EXAMPLE 348F

This example was made by substituting EXAMPLE 348E for EXAMPLE 21C in EXAMPLE 21D.

EXAMPLE 348G

This example was made by substituting for EXAMPLE 348F for 4-(((1R)-3-(dimethylamino)-1-((phenylsulfanyl)methyl)propyl)amino)-3-nitrobenzenesulfonamide in EXAMPLE 2D. $^1$H NMR (300 MHz, DMSO-$d_6$) δ 12.14 (m, 1H), 10.90 (m, 1H), 9.82 (m, 1H), 8.50 (d, 1H), 8.12 (d, 1H), 8.05 (m, 1H), 7.90 (dd, 1H), 7.80 (d, 2H), 7.45 (m, 12H), 6.93 (d, 2H), 4.35 (s, 2H), 4.22 (m, 1H), 3.89 (m, 2H), 3.28 (m, 4H), 2.96 (m, 4H), 2.80 (m, 4H), 2.68 (m, 6H), 1.71 (m, 4H).

EXAMPLE 349

A mixture of EXAMPLE 26H (45 mg), 2-chloro-N,N-dimethylacetamide (50 mg), and DIEA (0.2 mL) in dioxane (1 mL) at 80° C. was stirred for 18 hours and concentrated. The concentrate was flash chromatographed on silica gel with 5% 7M NH$_3$ in methanol/dichloromethane. $^1$H NMR (500 MHz, DMSO-$d_6$) δ 12.13 (m, 1H), 11.31 (m, 1H), 9.58 (m, 1H), 8.53 (d, 1H), 8.28 (d, 1H), 8.11 (m, 1H), 7.87 (m, 1H), 7.78 (d, 2H), 7.53 (m, 4H), 7.24 (m, 10H), 6.93 (d, 2H), 4.35 (s, 2H), 4.23 (m, 1H), 4.21 (s, 2H), 3.89 (m, 2H), 3.27 (m, 8H), 2.88 (m, 6H), 2.78 (s, 3H), 2.22 (m, 2H).

EXAMPLE 350

This example was made by substituting tert-butylamine for isopropylamine in EXAMPLE 28. $^1$H NMR (300 MHz, DMSO-$d_6$) δ 12.03 (m, 1H), 9.58 (m, 1H), 8.70 (d, 1H), 8.52 (d, 1H), 7.83 (dd, 1H), 7.77 (d, 2H), 7.67 (s, 1H), 7.53 (m, 4H), 7.25 (m, 10H), 6.93 (d, 2H), 4.37 (m, 2H), 3.89 (m, 2H), 2.98 (m, 8H), 2.62 (dd, 2H), 1.15 (s, 9H).

EXAMPLE 351

This example was made by substituting diisopropylamine for isopropylamine in EXAMPLE 28. $^1$H NMR (300 MHz, DMSO-$d_6$) δ 12.08 (m, 1H), 9.61 (m, 1H), 8.79 (d, 1H), 8.52 (d, 1H), 7.83 (dd, 1H), 7.77 (d, 2H), 7.54 (m, 3H), 7.25 (m, 10H), 6.93 (d, 2H), 4.41 (m, 2H), 3.96 (m, 3H), 2.98 (m, 8H), 2.84 (m, 2H), 1.14 (m, 12H).

EXAMPLE 352

This example was made by substituting N-methyl-tert-butylamine for isopropylamine in EXAMPLE 28. $^1$H NMR (300 MHz, DMSO-$d_6$) δ 12.05 (m, 1H), 9.59 (m, 1H), 8.80 (d, 1H), 8.53 (d, 1H), 7.83 (dd, 1H), 7.77 (d, 2H), 7.52 (m, 3H), 7.25 (m, 10H), 6.93 (d, 2H), 4.42 (m, 2H), 3.92 (m, 1H), 2.98 (m, 8H), 2.80 (s, 3H), 2.84 (m, 2H), 1.27 (s, 9H).

EXAMPLE 353

This example was made by substituting N-methyl-isopropylamine for isopropylamine in EXAMPLE 28. $^1$H NMR (300 MHz, DMSO-$d_6$) δ 12.07 (m, 1H), 9.62 (m, 1H), 8.82 (d, 1H), 8.53 (d, 1H), 7.83 (dd, 1H), 7.77 (d, 2H), 7.25 (m, 10H), 6.93 (d, 2H), 4.61 (m, 1H), 4.43 (m, 2H), 4.05 (m, 1H), 3.92 (m, 1H), 2.98 (m, 8H), 2.72 (s, 3H), 2.84 (m, 2H), 0.99 (m, 6H).

EXAMPLE 354

This example was made by substituting piperidine for isopropylamine in EXAMPLE 28. $^1$H NMR (300 MHz, DMSO-$d_6$) δ 12.06 (m, 1H), 9.62 (m, 1H), 8.79 (d, 1H), 8.53 (d, 1H), 7.83 (dd, 1H), 7.77 (d, 2H), 7.52 (m, 3H), 7.25 (m, 10H), 6.93

(d, 2H), 4.44 (m, 2H), 3.89 (m, 1H), 3.35 (m, 4H), 2.99 (m, 8H), 3.00 (dd, 2H), 2.75 (dd, 2H), 1.42 (m, 6H).

EXAMPLE 355A

This example was made by substituting tert-butyl(5R)-5-((4-(aminosulfonyl)-2-nitrophenyl)amino)-6-(phenylsulfanyl)hexylcarbamate (prepared as described in WO 02/24636, for 4-(((1R)-3-(dimethylamino)-1-((phenylsulfanyl)methyl)propyl)amino)-3-nitrobenzenesulfonamide in EXAMPLE 2D.

EXAMPLE 355B

A mixture of EXAMPLE 355A (100 mg) and TFA (1 mL) in dichloromethane (1 mL) at 25° C. were stirred for 2 hours and concentrated. The concentrate was flash chromatographed on silica gel with 5-10% (7M $NH_3$ in methanol)/dichloromethane.

EXAMPLE 355C

A mixture of EXAMPLE 355B (50 mg), N,N-dimethylglycine (23 mg), EDAC.HCl (42 mg) and DMAP (27.2 mg) in dichloromethane (2 mL) at 25° C. was stirred for 18 hours, treated with ethyl acetate, washed with aqueous $NaHCO_3$, water and brine, and dried ($Na_2SO_4$), filtered, and concentrated. The concentrate was flash chromatographed on silica gel with 5-10% 7M $NH_3$ in methanol/dichloromethane. $^1$H NMR (300 MHz, DMSO-$d_6$) δ 12.11 (m, 1H), 11.53 (m, 1H), 9.92 (m, 1H), 8.63 (t, 1H), 8.53 (d, 1H), 8.30 (d, 1H), 8.16 (m, 1H), 7.86 (dd, 1H), 7.77 (d, 2H), 7.52 (m, 3H), 7.22 (m, 8H), 6.93 (d, 2H), 4.33 (s, 2H), 4.10 (m, 1H), 3.85 (m, 2H), 3.37 (m, 4H), 3.12 (m, 8H), 2.84 (m, 6H), 1.76 (m, 2H), 1.34 (m, 4H).

EXAMPLE 356

This example was made by substituting dimethylamine for isopropylamine in EXAMPLE 28. $^1$H NMR (300 MHz, DMSO-$d_6$) δ 8.83 (d, 1H), 8.52 (d, 1H), 7.83 (dd, 1H), 7.74 (d, 2H), 7.45 (m, 7H), 7.18 (m 6H), 6.90 (d, 2H), 4.40 (m, 1H), 3.40 (m, 4H), 3.25 (m, 4H), 2.96 (dd, 2H), 2.89 (s, 3H), 2.78 (s, 3H), 2.70 (dd, 2H), 2.45 (m 2H).

EXAMPLE 357

This example was made by substituting thiomorpholine 1,1-dioxide, prepared as described in J. Med. Chem 1994, 37, 913-933, for isopropylamine in EXAMPLE 28. $^1$H NMR (300 MHz, DMSO-$d_6$) δ 8.52 (d, 1H), 8.47 (d, 1H), 7.80 (dd, 1H), 7.73 (d, 2H), 7.32 (m, 13H), 6.83 (d, 2H), 3.82 (m, 4H), 3.39 (m, 4H), 3.18 (m, 8H), 3.04 (m, 3H), 2.89 (dd, 2H), 2.40 (m, 2H).

EXAMPLE 357

This example was made by substituting 0.5M $NH_3$ in dioxane for isopropylamine in EXAMPLE 28. $^1$H NMR (300 MHz, DMSO-$d_6$) δ 8.57 (d, 1H), 8.46 (d, 1H), 7.79 (dd, 1H), 7.73 (d, 2H), 7.32 (m, 13H), 6.83 (d, 2H), 4.33 (m, 2H), 3.39 (m, 2H), 3.33 (m, 2H), 3.18 (m, 5H), 2.60 (m, 4H), 2.40 (m, 2H).

EXAMPLE 359

This example was made by substituting cyclopropylamine for isopropylamine in EXAMPLE 28. $^1$H NMR (300 MHz, DMSO-$d_6$) δ 8.60 (d, 1H), 8.48 (d, 1H), 8.11 (d, 1H), 7.80 (dd, 1H), 7.73 (d, 2H), 7.32 (m, 12H), 6.83 (d, 2H), 4.32 (m, 2H), 3.39 (m, 2H), 3.34 (m, 2H), 3.20 (m, 5H), 2.56 (m, 4H), 2.40 (m 2H), 0.54 (m, 2H), 0.29 (m, 2H).

EXAMPLE 360

This example was made by substituting cyclobutylamine for isopropylamine in EXAMPLE 28. $^1$H NMR (300 MHz, DMSO-$d_6$) δ 8.63 (d, 1H), 8.48 (d, 1H), 8.27 (d, 1H), 7.80 (dd, 1H), 7.73 (d, 2H), 7.32 (m, 12H), 6.85 (d, 2H), 4.33 (m, 2H), 4.10 (m, 1H), 3.40 (m, 2H), 3.38 (m, 2H), 3.20 (m, 5H), 2.57 (m, 4H), 2.40 (m 2H), 2.08 (m, 2H), 1.77 (m, 2H), 1.58 (m, 2H).

EXAMPLE 361

This example was made by substituting 1-methylpiperazine for isopropylamine in EXAMPLE 28. $^1$H NMR (300 MHz, DMSO-$d_6$) δ 12.09 (m, 1H), 10.52 (m, 1H), 8.73 (m, 1H), 8.53 (d, 1H), 7.84 (dd, 1H), 7.76 (d, 2H), 7.53 (m 4H), 7.24 (m, 10H), 6.93 (d, 2H), 4.37 (m, 3H), 3.96 (m, 4H), 3.28 (m, 6H), 3.20 (m, 5H), 2.88 (m, 4H), 2.75 (m 3H), 2.54 (m, 2H).

EXAMPLE 362

This example was made by substituting morpholine for isopropylamine in EXAMPLE 28. $^1$H NMR (300 MHz, DMSO-$d_6$) δ 8.69 (d, 1H), 8.50 (d, 1H), 7.81 (dd, 1H), 7.73 (d, 2H), 7.32 (m, 12H), 6.86 (d, 2H), 4.39 (m, 2H), 3.44 (m, 13H), 3.32 (m, 2H), 2.98 (dd, 2H), 2.77 (dd, 2H), 2.40 (m, 2H).

EXAMPLE 363

This example was made by substituting azetidine for isopropylamine in EXAMPLE 28. $^1$H NMR (300 MHz, DMSO-$d_6$) δ 8.71 (d, 1H), 8.50 (d, 1H), 7.81 (dd, 1H), 7.73 (d, 2H), 7.31 (m, 12H), 6.86 (d, 2H), 4.31 (m, 1H), 4.04 (t, 2H), 3.79 (m, 2H), 3.40 (m, 4H), 3.23 (m, 4H), 2.64 (dd, 2H), 2.52 (dd, 2H), 2.40 (m, 2H), 2.12 (m, 2H).

EXAMPLE 364

This example was made by substituting 4-(2-aminoethyl)morpholine for isopropylamine in EXAMPLE 28. $^1$H NMR (300 MHz, DMSO-$d_6$) δ 12.10 (m, 1H), 10.52 (m, 1H), 8.74 (d, 1H), 8.51 (d; 1H), 8.45 (t, 1H), 7.83 (dd, 1H), 7.77 (d, 2H), 7.54 (m, 3H), 7.24 (m, 10H), 6.92 (d, 2H), 4.40 (m, 1H), 4.35 (m, 2H), 3.89 (m, 4H), 3.72 (m, 4H), 3.39 (m, 6H), 3.20 (m, 4H), 3.10 (m, 2H), 2.88 (m, 2H), 2.73 (m, 2H).

EXAMPLE 365

This example was made by substituting methylamine for isopropylamine in EXAMPLE 28. $^1$H NMR (300 MHz, DMSO-$d_6$) δ 8.59 (d, 1H), 8.45 (d, 1H), 7.98 (m, 1H), 7.78 (dd, 1H), 7.73 (d, 2H), 7.32 (m, 12H), 6.83 (d, 2H), 4.30 (m, 1H), 3.39 (s, 2H), 3.29 (m, 2H), 3.18 (m, 4H), 2.61 (m, 4H), 2.53 (d, 3H), 2.40 (m, 2H).

EXAMPLE 366

This example was made by substituting 7M $NH_3$ in methanol for isopropylamine in example 35B. $^1$H NMR (300 MHz, DMSO-$d_6$) δ 8.43 (d, 1H), 8.08 (d, 1H), 7.83 (dd, 1H), 7.72 (d, 2H), 7.31 (m, 12H), 6.93 (m, 1H), 6.78 (d, 2H), 4.10 (m, 2H), 3.38 (s, 2H), 3.33 (m, 2H), 3.12 (m, 5H), 2.87 (t, 2H), 2.40 (m, 2H), 2.00 (m, 2H).

EXAMPLE 367

This example was made by substituting sodium cyanide for isopropylamine in example 35B. $^1$H NMR (300 MHz, DMSO-d$_6$) δ 8.51 (d, 1H), 8.22 (d, 1H), 7.83 (dd, 1H), 7.74 (d, 2H), 7.31 (m, 12H), 7.04 (d, 1H), 6.87 (d, 2H), 4.11 (m, 2H), 3.35 (m, 4H), 3.22 (m, 5H), 2.60 (t, 2H), 2.39 (m, 2H), 2.09 (m, 2H).

EXAMPLE 368

This example was made by substituting tert-butylamine for isopropylamine in example 35B. $^1$H NMR (300 MHz, DMSO-d$_6$) δ 12.11 (m, 1H), 10.94 (m, 1H), 8.75 (m, 1H), 8.53 (d, 1H), 8.30 (d, 1H), 8.05 (m, 1H), 7.87 (dd, 1H), 7.78 (d, 2H), 7.53 (m, 4H), 7.23 (m, 10H), 6.93 (d, 2H), 4.34 (m, 2H), 3.88 (m, 2H), 3.42 (d, 2H), 3.27 (m, 5.H), 2.89 (m, 4H), 2.14 (m, 2H), 1.24 (s, 9H).

EXAMPLE 369

This example was made by substituting cyclopropylamine for isopropylamine in example 35B. $^1$H NMR (300 MHz, DMSO-d$_6$) δ 12.11 (m, 1H), 10.84 (m, 1H), 9.04 (m, 1H), 8.53 (d, 1H), 8.30 (d, 1H), 8.02 (m, 1H), 7.86 (dd, 1H), 7.78 (d, 2H), 7.53 (m, 4H), 7.24 (m, 8H), 6.93 (d, 2H), 4.35 (m, 3H), 3.88 (m, 2H), 3.27 (m, 5H), 3.09 (m, 2H), 2.87 (m, 2H), 2.66 (m, 2H), 2.14 (m, 2H), 0.82 (m, 2H), 0.70 (m, 2H).

EXAMPLE 370

This example was made by substituting cylcobutylamine for isopropylamine in example 35B. $^1$H NMR (300 MHz, DMSO-d$_6$) δ 12.11 (m, 1H), 10.88 (m, 1H), 9.04 (m, 1H), 8.53 (d, 1H), 8.27 (d, 1H), 8.04 (m, 1H), 7.86 (dd, 1H), 7.78 (d, 2H), 7.53 (m, 4H), 7.24 (m, 8H), 6.93 (d, 2H), 4.35 (m, 3H), 3.88 (m, 2H), 3.61 (m, 2H), 3.27 (m, 6H), 2.86 (m, 4H), 2.71 (m, 1H), 2.11 (m, 4H), 1.76 (m, 2H).

EXAMPLE 138

This example was made by substituting diethylamine for isopropylamine in example 35B. $^1$H NMR (300 MHz, DMSO-d$_6$) δ 12.11 (m, 1H), 10.99 (m, 1H), 10.08 (m, 1H), 8.53 (d, 1H), 8.29 (d, 1H), 8.06 (m, 1H), 7.86 (dd, 1H), 7.78 (d, 2H), 7.53 (m, 4H), 7.24 (m, 8H), 6.93 (d, 2H), 4.34 (m, 3H), 3.88 (m, 2H), 3.39 (m, 2H), 3.27 (m, 6H), 3.08 (m, 4H), 2.81 (m, 2H), 2.15 (m, 2H), 1.17 (m, 6H).

EXAMPLE 372

This example was made by substituting N-methylisopropylamine for isopropylamine in example 35B. $^1$H NMR (300 MHz, DMSO-d$_6$) δ 12.11 (m, 1H), 10.89 (m, 1H), 9.96 (m, 1H), 8.53 (d, 1H), 8.29 (m, 1H), 8.04 (m, 1H), 7.85 (dd, 1H), 7.78 (d, 2H), 7.53 (m, 4H), 7.24 (m, 8H), 6.93 (d, 2H), 4.34 (m, 3H), 3.88 (m, 2H), 3.42 (m, 2H), 3.27 (m, 6H), 2.86 (m, 2H), 2.60 (m, 3H), 2.15 (m, 2H), 1.19 (m, 6H).

EXAMPLE 373

This example was made by substituting N-methyl-tert-butylamine for isopropylamine in example 35B. $^1$H NMR (300 MHz, DMSO-d$_6$) δ 12.10 (m, 1H), 10.84 (m, 1H), 9.70 (m, 1H), 8.53 (d, 1H), 8.30 (t, 1H), 8.03 (m, 1H), 7.85 (dd, 1H), 7.78 (d, 2H), 7.52 (m, 4H), 7.23 (m, 8H), 6.93 (d, 2H), 4.35 (m, 3H), 3.88 (m, 2H), 3.43 (m, 2H), 3.27 (m, 6H), 2.86 (m, 2H), 2.64 (m, 3H), 2.22 (m, 2H), 1.29 (d, 9H).

EXAMPLE 374

This example was made by substituting piperidine for isopropylamine in example 35B. $^1$H NMR (300 MHz, DMSO-d$_6$) δ 12.10 (m, 1H), 10.95 (m, 1H), 9.97 (m, 1H), 8.53 (d, 1H), 8.28 (d, 1H), 8.04 (m, 1H), 7.85 (dd, 1H), 7.78 (d, 2H), 7.54 (m, 4H), 7.23 (m, 8H), 6.93 (d, 2H), 4.35 (m, 2H), 4.22 (m, 1H), 3.88 (m, 2H), 3.40 (m, 2H), 3.27 (m, 6H), 3.10 (m, 2H), 2.81 (m, 6H), 2.22 (m, 2H), 1.75 (m, 4H), 1.35 (m, 2H).

EXAMPLE 375

This example was made by substituting 4-hydroxypiperidine for isopropylamine in example 35B. $^1$H NMR (300 MHz, DMSO-d$_6$) δ 12.10 (m, 1H), 10.85 (m, 1H), 9.98 (m, 1H), 8.53 (d, 1H), 8.28 (d, 1H), 8.04 (m, 1H), 7.85 (dd, 1H), 7.78 (d, 2H), 7.54 (m, 4H), 7.24 (m, 8H), 6.93 (d, 2H), 4.36 (m, 2H), 4.22 (m, 1H), 3.93 (m, 3H), 3.27 (m, 6H), 3.10 (m, 2H), 2.87 (m, 4H), 2.22 (m, 2H), 1.91 (m, 4H), 1.70 (m, 2H).

EXAMPLE 376

This example was made by substituting 1-acetylpiperazine for isopropylamine in example 35B. $^1$H NMR (300 MHz, DMSO-d$_6$) δ 12.10 (m, 1H), 10.69 (m, 1H), 8.53 (d, 1H), 8.28 (d, 1H), 7.99 (m, 1H), 7.85 (dd, 1H), 7.78 (d, 2H), 7.54 (m, 4H), 7.23 (m, 8H), 6.93 (d, 2H), 4.36 (m, 2H), 4.22 (m, 1H), 3.92 (m, 2H), 3.41 (m, 4H), 3.27 (m, 6H), 3.00 (m, 2H), 2.85 (m, 6H), 2.22 (m, 2H), 2.02 (s, 3H).

EXAMPLE 377

This example was made by substituting thiomorpholine for isopropylamine in example 35B. $^1$H NMR (300 MHz, DMSO-d$_6$) δ 12.10 (m, 1H), 10.69 (m, 1H), 10.55 (m, 1H), 8.53 (d, 1H), 8.28 (d, 1H), 7.99 (m, 1H), 7.85 (dd, 1H), 7.78 (d, 2H), 7.53 (m, 4H), 7.25 (m, 8H), 6.93 (d, 2H), 4.36 (m, 2H), 4.25 (m, 1H), 3.90 (m, 2H), 3.64 (m, 4H), 3.41 (m, 4H), 3.17 (m, 9H), 2.82 (m, 4H), 2.22 (m, 2H).

EXAMPLE 378

This example was made by substituting 4-(2-aminoethyl)morpholine for isopropylamine in example 35B. $^1$H NMR (300 MHz, DMSO-d$_6$) δ 12.11 (m, 1H), 10.63 (m, 1H), 9.26 (m, 1H), 8.53 (d, 1H), 8.29 (d, 1H), 7.99 (m, 1H), 7.86 (dd, 1H), 7.78 (d, 2H), 7.53 (m, 4H), 7.25 (m, 8H), 6.93 (d, 2H), 4.36 (m, 2H), 4.25 (m, 1H), 3.90 (m, 2H), 3.77 (m, 2H), 3.41 (m, 4H), 3.27 (m, 6H), 3.05 (m, 6H), 2.82 (m, 4H), 2.17 (m, 2H).

EXAMPLE 379A

This example was made by substituting tert-butyl 1-piperazinecarboxylate for isopropylamine in example 35B.

EXAMPLE 379B

This example was made by substituting EXAMPLE 379A for EXAMPLE 27B in EXAMPLE 29A. $^1$H NMR (300 MHz, DMSO-d$_6$) δ 12.11 (m, 1H), 10.90 (m, 1H), 9.50 (m, 1H), 8.53 (d, 1H), 8.30 (d, 1H), 8.04 (m, 1H), 7.84 (dd, 1H), 7.78 (d, 2H), 7.53 (m, 4H), 7.22 (m, 8H), 6.93 (d, 2H), 4.36 (m, 2H), 4.27 (m, 1H), 3.90 (m, 2H), 3.40 (m, 6H), 3.17 (m, 10H), 2.86 (m, 2H), 2.23 (m, 2H).

EXAMPLE 380

This example was made by substituting (S)-3-hydroxypyrrolidine for isopropylamine in example 35B. $^1$H NMR (300 MHz, DMSO-d$_6$) δ 12.11 (m, 1H), 10.73 (m, 1H), 10.26 (m, 1H), 8.53 (d, 1H), 8.29 (d, 1H), 8.04 (m, 1H), 7.85 (m, 1H), 7.78 (d, 2H), 7.53 (m, 4H), 7.24 (m, 8H), 6.93 (d, 2H), 4.35 (m, 3H), 3.88 (m, 2H), 3.38 (m, 4H), 3.17 (m, 6H), 3.03 (m, 1H), 2.87 (m, 4H), 2.17 (m, 2H), 1.91 (m, 2H).

EXAMPLE 381A

This example was made by substituting 3(R)-(tert-butoxycarbonylamino)pyrrolidine for isopropylamine in example 35B.

EXAMPLE 381B

This example was made by substituting EXAMPLE 381A for EXAMPLE 27B in EXAMPLE 29A. $^1$H NMR (300 MHz, DMSO-d$_6$) δ 12.11 (m, 1H), 11.09 (m, 1H), 10.92 (m, 1H), 8.53 (d, 1H), 8.47 (m, 1H), 8.30 (d, 1H), 8.04 (m, 1H), 7.85 (m, 1H), 7.78 (d, 2H), 7.53 (m, 4H), 7.23 (m, 8H), 6.93 (d, 2H), 4.35 (m, 3H), 3.88 (m, 2H), 3.40 (m, 4H), 3.27 (m, 6H), 3.08 (m, 1H), 2.86 (m, 4H), 2.22 (m, 2H), 2.05 (m, 2H).

EXAMPLE 382

This example was made by substituting 3-hydroxyazetidine for isopropylamine in example 35B. $^1$H NMR (300 MHz, DMSO-d$_6$) δ 12.10 (m, 1H), 10.73 (m, 1H), 10.23 (m, 1H), 8.53 (d, 1H), 8.27 (d, 1H), 8.00 (m, 1H), 7.85 (dd, 1H), 7.78 (d, 2H), 7.52 (m, 4H), 7.24 (m, 8H), 6.93 (d, 2H), 4.35 (m, 2H), 4.26 (m, 3H), 4.04 (m, 1H), 3.88 (m, 2H), 3.71 (m, 2H), 3.24 (m, 8H), 2.86 (m, 2H), 1.98 (m, 2H).

EXAMPLE 383

This example was made by substituting 1-methylpiperazine for isopropylamine in example 35B. $^1$H NMR (300 MHz, DMSO-d$_6$) δ 12.11 (m, 1H), 10.91 (m, 1H), 8.53 (d, 1H), 8.31 (d, 1H), 8.04 (m, 1H), 7.85 (dd, 1H), 7.78 (d, 2H), 7.54 (m, 4H), 7.24 (m, 8H), 6.93 (d, 2H), 4.34 (m, 2H), 4.26 (m, 1H), 3.88 (m, 2H), 3.40 (m, 6H), 3.27 (m, 8H), 2.86 (m, 4H), 2.80 (s, 3H), 2.21 (m, 2H).

EXAMPLE 384

This example was made by substituting thiomorpholine 1,1-dioxide, prepared as described in J. Med. Chem 1994, 37, 913-933, for isopropylamine in example 35B. $^1$H NMR (300 MHz, DMSO-d$_6$) δ 12.08 (m, 1H), 10.97 (m, 1H), 8.53 (d, 1H), 8.31 (d, 1H), 8.04 (m, 1H), 7.86 (dd, 1H), 7.77 (d, 2H), 7.53 (m, 4H), 7.23 (m, 8H), 6.93 (d, 2H), 4.35 (m, 2H), 4.26 (m, 2H), 3.88 (m, 2H), 3.55 (m, 5H), 3.24 (m, 8H), 2.89 (m, 4H), 1.98 (m, 2H).

EXAMPLE 385

This example was made by substituting 3,4-methylenedioxyaniline for isopropylamine in example 35B. $^1$H NMR (400 MHz, DMSO-d$_6$) δ 12.09 (m, 1H), 11.29 (m, 1H), 8.53 (d, 1H), 8.28 (d, 1H), 8.12 (m, 1H), 7.82 (dd, 1H), 7.77 (d, 2H), 7.53 (m, 4H), 7.24 (m, 9H), 6.93 (m, 4H), 6.07 (s, 2H), 4.35 (m, 2H), 4.26 (m, 2H), 3.28 (m, 9H), 2.85 (m, 4H), 2.15 (m, 2H).

EXAMPLE 386

This example was made by substituting 3,4-methylenedioxybenzylamine for isopropylamine in example 35B. $^1$H NMR (400 MHz, DMSO-d$_6$) δ 12.10 (m, 1H), 11.29 (m, 1H), 9.26 (m, 1H), 8.53 (d, 1H), 8.26 (d, 1H), 8.11 (m, 1H), 7.86 (dd, 1H), 7.77 (d, 2H), 7.53 (m, 4H), 7.24 (m, 9H), 6.90 (m, 4H), 6.02 (s, 2H), 4.34 (m, 3H), 3.98 (m, 2H), 3.87 (m, 2H), 3.61 (m, 2H), 3.28 (m, 4H), 2.91 (m, 4H), 2.16 (m, 2H).

EXAMPLE 387

This example was made by substituting 2-aminomethylpyridine for isopropylamine in example 35B. $^1$H NMR (500 MHz, DMSO-d$_6$) δ 12.11 (m, 1H), 11.57 (m, 1H), 9.46 (m, 3H), 8.53 (d, 1H), 8.26 (d, 1H), 8.11 (m, 1H), 7.86 (m, 1H), 7.78 (d, 2H), 7.51 (m, 4H), 7.24 (m, 9H), 6.93 (d, 2H), 4.33 (m, 2H), 4.26 (m, 1H), 3.87 (m, 2H), 3.39 (m, 4H), 3.25 (m, 4H), 2.84 (m, 4H), 2.22 (m, 2H).

EXAMPLE 388

This example was made by substituting 2-aminoethylpyridine for isopropylamine in example 35B. $^1$H NMR (400 MHz, DMSO-d$_6$) δ 12.10 (m, 1H), 11.36 (m, 1H), 9.29 (m, 3H), 8.62 (d, 1H), 8.53 (d, 1H), 8.28 (d, 1H), 8.13 (m, 1H), 7.86 (d, 1H), 7.78 (d, 2H), 7.53 (m, 4H), 7.18 (m, 9H), 6.93 (d, 2H), 4.33 (m, 2H), 3.87 (m, 2H), 3.31 (m, 7H), 3.05 (m, 4H), 2.84 (m, 4H), 2.18 (m, 2H).

EXAMPLE 389

This example was made by substituting 4-aminomethylpyridine for isopropylamine in example 35B. $^1$H NMR (400 MHz, DMSO-d$_6$) δ 12.08 (m, 1H), 11.30 (m, 1H), 9.85 (m, 2H), 9.17 (m, 1H), 8.76 (d, 1H), 8.53 (d, 1H), 8.27 (d, 1H), 8.11 (m, 1H), 7.85 (d, 1H), 7.78 (d, 2H), 7.53 (m, 4H), 7.19 (m, 9H), 6.93 (d, 2H), 4.33 (m, 2H), 4.23 (m, 1H), 3.87 (m, 2H), 3.29 (m, 6H), 3.05 (m, 2H), 2.84 (m, 4H), 2.23 (m, 2H).

EXAMPLE 390

This example was made by substituting 4-aminomorpholine for isopropylamine in example 35B. $^1$H NMR (500 MHz, DMSO-d$_6$) δ 12.09 (m, 1H), 11.55 (m, 1H), 9.39 (m, 3H), 8.54 (d, 1H), 8.32 (d, 1H), 8.11 (m, 1H), 7.87 (d, 1H), 7.77 (d, 2H), 7.51 (m, 4H), 7.24 (m, 8H), 6.92 (d, 2H), 4.33 (m, 2H), 4.23 (m, 1H), 4.00 (m, 1H), 3.87 (m, 2H), 3.31 (m, 9H), 3.05 (m, 4H), 2.84 (m, 4H), 2.33 (m, 2H).

EXAMPLE 391

This example was made by substituting N-methyl-4-aminopyridine for isopropylamine in example 35B. $^1$H NMR (300 MHz, DMSO-d$_6$) δ 12.11 (m, 1H), 10.83 (m, 1H), 8.68 (m, 3H), 8.52 (d, 1H), 8.19 (t, 2H), 8.01 (m, 1H), 7.83 (d, 1H), 7.77 (d, 2H), 7.52 (m, 4H), 7.25 (m, 8H), 7.01 (d, 1H), 6.93 (d, 2H), 6.74 (m, 2H), 4.33 (m, 2H), 4.24 (m, 2H), 3.87 (m, 3H), 3.36 (m 4H), 3.26 (m, 4H), 2.83 (d, 3H), 2.33 (m, 2H).

EXAMPLE 392

This example was made by substituting 3-aminopyridine for isopropylamine in example 35B. $^1$H NMR (300 MHz, DMSO-d$_6$) δ 12.11 (m, 1H), 10.80 (m, 1H), 8.72 (m, 3H), 8.52 (d, 1H), 8.22 (d, 2H), 7.99 (m, 1H), 7.83 (d, 1H), 7.77 (d, 2H), 7.52 (m, 4H), 7.19 (m, 8H), 7.02 (d, 1H), 6.93 (d, 2H), 6.59 (m, 1H), 4.52 (m, 2H), 4.33 (m, 2H), 4.12 (m, 1H), 3.87 (m, 2H), 3.36 (m 4H), *3.26 (m, 2H), 2.85 (d, 2H), 2.40 (m, 2H).

EXAMPLE 393

This example was made by substituting 2,6-dimethylpiperidine for isopropylamine in example 35B. $^1$H NMR (300 MHz, DMSO-d$_6$) δ 12.09 (m, 1H), 10.62 (m, 1H), 9.74 (m, 1H), 8.64 (m, 1H), 8.50 (d, 1H), 8.30 (d, 1H), 7.99 (m, 1H), 7.86 (d, 1H), 7.77 (d, 2H), 7.5 2 (m, 4H), 7.24 (m, 8H), 6.93 (d, 2H), 4.36 (m, 2H), 3.88 (m, 2H), 3.31 (m 9H), 2.85 (d, 4H), 2.15 (m, 2H), 1.79 (m, 2H), 1.64 (m, 4H), 1.26 (m, 6H).

EXAMPLE 394

This example was made by substituting cis-2,6-dimethylpiperidine for isopropylamine in example 35B. $^1$H NMR (300 MHz, DMSO-d$_6$) δ 12.10 (m, 1H), 10.78 (m, 1H), 9.80 (m, 1H), 8.74 (m, 1H), 8.50 (d, 1H), 8.30 (d, 1H), 8.01 (m, 1H), 7.86 (d, 1H), 7.77 (d, 2H), 7.52 (m, 4H), 7.24 (m, 8H), 6.93 (d, 2H), 4.35 (m, 2H), 3.88 (m, 2H), 3.31 (m 9H), 2.85 (d, 4H), 2.15 (m, 2H), 1.79 (m, 2H), 1.64 (m, 4H), 1.26 (m, 6H).

EXAMPLE 395

This example was made by substituting 1-aminopyrrolidine for isopropylamine in example 35B. $^1$H NMR (300 MHz, DMSO-d$_6$) δ 12.12 (m, 1H), 10.86 (m, 1H), 8.73 (m, 1H), 8.54 (d, 1H), 8.32 (d, 1H), 8.02 (m, 1H), 7.86 (d, 1H), 7.77 (d, 2H), 7.52 (m, 4H), 7.25 (m, 8H), 6.93 (d, 2H), 4.36 (m, 2H), 4.22 (m, 1H), 3.88 (m, 2H), 3.31 (m 10H), 2.85 (d, 4H), 2.32 (m, 2H), 2.11 (m, 4H).

EXAMPLE 396A

A mixture of tert-butyl 4-oxo-1-piperidinecarboxylate (2 g), methoxylamine hydrochloride (0.85 g), and potassium acetate (0.98 g) in ethanol (40 mL) was stirred at reflux for 18 hours and concentrated. The concentrate was treated with ethyl acetate (200 mL), washed with water and brine, and dried (Na$_2$SO$_4$), filtered, and concentrated. The concentrate was used without further purification.

EXAMPLE 396B

A mixture of EXAMPLE 396A (2.1 g) and TFA (10 mL) in dichloromethane (10 mL) at 25° C. was stirred for 4 hours and concentrated.

EXAMPLE 396C

This example was made by substituting EXAMPLE 396B for isopropylamine in EXAMPLE 35B. $^1$H NMR (300 MHz, DMSO-d$_6$) δ 8.51 (d, 1H), 7.82 (dd, 1H), 7.72 (d, 2H), 7.52 (m, 4H), 7.32 (m, 10H), 6.87 (d, 2H), 4.17 (m, 1H), 3.71 (s, 3H), 3.32 (m 10H), 2.73 (m, 2H), 2.40 (m, 6H), 2.25 (m, 4H), 1.91 (m, 2H).

EXAMPLE 397

A mixture of EXAMPLE 367 (80 mg), sodium azide (33 mg), and ammonium chloride (27 mg) in DMF (2 mL) at 110° C. was stirred for 18 hours, treated with ethyl acetate (100 mL), washed with water and brine, dried (Na$_2$SO$_4$), filtered, and concentrated. The concentrate was flash chromatographed on silica gel with 3% methanol/dichloromethane. $^1$H NMR (300 MHz, DMSO-d$_6$) δ 12.09 (m, 1H), 10.15 (m, 1H), 8.52 (d, 1H), 8.32 (d, 1H), 7.82 (dd, 1H), 7.78 (d, 2H), 7.52 (m, 4H), 7.24 (m, 8H), 6.93 (d, 2H), 4.37 (m, 2H), 4.20 (m, 1H), 3.71 (s, 3H), 3.28 (m, 5H), 2.98 (t, 2H), 2.83 (m, 2H), 2.23 (m, 2H).

EXAMPLE 398A

This example was made by substituting 4-bromo-3-trifluoromethylbenzenesulfonamide for 4-(((1R)-3-(dimethylamino)-1-((phenylsulfanyl)methyl)propyl)amino)-3-nitrobenzenesulfonamide in EXAMPLE 2D.

EXAMPLE 398B

A mixture of EXAMPLE 27B (2 g) and diethylamine (5 mL) in THF (20 mL) at 25° C. was stirred for 18 hours and concentrated. The concentrate was flash chromatographed on silica gel with 3% (7M NH$_3$ in methanol)/dichloromethane.

EXAMPLE 398C

This example was made by substituting EXAMPLE 398A and EXAMPLE 398B for EXAMPLE 164B and 164A, respectively, in EXAMPLE 164C.

EXAMPLE 398D

This example was made by substituting EXAMPLE 398C for EXAMPLE 27D in EXAMPLE 27E.

EXAMPLE 398E

This example was made by substituting EXAMPLE 398D for EXAMPLE 27E in EXAMPLE 34.

EXAMPLE 398F

This example was made by substituting EXAMPLE 398E for EXAMPLE 34 in EXAMPLE 35A.

EXAMPLE 398G

This example was made by substituting EXAMPLE 398F and diisopropylamine for EXAMPLE 35A and isopropylamine, respectively, in EXAMPLE 35B. $^1$H NMR (500 MHz, DMSO-d$_6$) δ 11.94 (m, 1H), 11.07 (m, 1H), 9.25 (m, 1H), 8.06 (m, 1H), 7.93 (d, 1H), 7.82 (dd, 1H), 7.74 (d, 2H), 7.51 (m, 4H), 7.27 (m, 8H), 6.93 (t, 2H), 6.08 (d, 1H), 4.33 (m, 2H), 4.00 (m, 1H), 3.87 (m, 2H), 3.55 (m, 4H), 3.28 (m, 4H), 2.90 (m, 4H), 2.17 (m, 2H), 1.22 (m, 12H).

EXAMPLE 399

This example was made by substituting EXAMPLE 398F for EXAMPLE 35A in EXAMPLE 35B. $^1$H NMR (500 MHz, DMSO-d$_6$) δ 11.95 (m, 1H), 11.11 (m, 1H), 8.74 (m, 1H), 8.06 (m, 1H), 7.94 (d, 1H), 7.91 (s, 1H), 7.81 (dd, 1H), 7.74 (d, 2H), 7.51 (m, 4H), 7.26 (m, 6H), 6.96 (d, 1H), 6.91 (d, 2H), 5.99 (d, 1H), 4.33 (m, 2H), 4.03 (m, 1H), 3.87 (m, 2H), 3.31 (m, 5H), 2.88 (m, 6H), 2.07 (m, 2H), 1.18 (m, 6H).

EXAMPLE 400

This example was made by substituting diethanolamine for isopropylamine in EXAMPLE 35B. $^1$H NMR (500 MHz, DMSO-d$_6$) δ 8.58 (d, 1H), 8.30 (m, 1H), 8.01 (s, 1H), 7.93 (dd, 1H), 7.82 (d, 2H), 7.41 (m, 11H), 7.10 (d, 1H), 6.93 (d, 2H), 4.50 (m, 1H), 4.23 (m, 1H), 3.75 (m, 4H), 3.49 (m, 4H), 3.28 (m, 4H), 3.33 (m, 7H), 2.59 (m, 2H), 2.23 (m, 2H).

EXAMPLE 401A

A mixture of 1-bromo-2-(trifluoromethoxy)benzene (5 g) and chlorosulfonic acid (30 mL) at 85° C. were stirred for 18 hours, treated with crushed ice, and extracted with ethyl acetate. The extract was washed with water and brine and dried (Na$_2$SO$_4$), filtered, and concentrated. The concentrate in IPA (200 mL) at 0° C. was treated with 38% ammonium hydroxide (50 mL), stirred for 18 hours and concentrated. The concentrate was treated with ethyl acetate (200 mL) and water. The extract was washed with water and brine and dried (Na$_2$SO$_4$), filtered, and concentrated.

EXAMPLE 401B

This example was made by substituting EXAMPLE 401A for EXAMPLE 4-(((1R)-3-(dimethylamino)-1-((phenylsulfanyl)methyl)propyl)amino)-3-nitrobenzenesulfonamide in EXAMPLE 2D.

EXAMPLE 401C

This example was made by substituting EXAMPLE 401B for EXAMPLE 164B in EXAMPLE 164C. $^1$H NMR (500 MHz, DMSO-d$_6$) δ 11.92 (m, 1H), 11.12 (m, 1H), 10.18 (m, 1H), 7.92 (d, 1H), 7.56 (d, 2H), 7.31 (m, 4H), 7.08 (m, 6H), 6.73 (d, 2H), 5.86 (d, 1H), 4.15 (m, 2H), 3.68 (m, 2H), 3.59 (m, 1H), 3.09 (m, 4H), 2.91 (m, 4H), 2.66 (m, 2H), 2.31 (m, 6H), 1.95 (m, 2H).

EXAMPLE 402

This example was made by substituting EXAMPLE 398F and methylisopropylamine for EXAMPLE 35A and isopropylamine, respectively, in EXAMPLE 35B. $^1$H NMR (500 MHz, DMSO-d$_6$) δ 11.96 (m, 1H), 11.40 (m, 1H), 10.39 (m, 1H), 8.14 (m, 1H), 7.95 (d, 1H), 7.81 (d, 1H), 7.76 (d, 2H), 7.53 (m, 4H), 7.28 (m, 7H), 6.93 (m, 3H), 6.03 (m, 1H), 4.33 (m, 2H), 4.02 (m, 1H), 3.87 (m, 2H), 3.32 (m, 6H), 3.04 (m, 2H), 2.86 (m, 2H), 2.57 (m, 3H), 2.19 (m, 2H), 1.19 (m, 6H).

EXAMPLE 403

This example was made by substituting EXAMPLE 398F and diethylamine for EXAMPLE 35A and isopropylamine, respectively, in EXAMPLE 35B. $^1$H NMR (500 MHz, DMSO-d$_6$) δ 11.96 (m, 1H), 11.28 (m, 1H), 10.30 (m, 1H), 8.11 (m, 1H), 7.94 (s, 1H), 7.81 (d, 1H), 7.76 (d, 2H), 7.53 (m, 4H), 7.28 (m, 7H), 6.93 (m, 3H), 6.06 (m, 1H), 4.33 (m, 2H), 4.02 (m, 1H), 3.87 (m, 2H), 3.24 (m, 4H), 3.14 (m, 2H), 3.04 (m, 4H), 2.88 (m, 4H), 2.13 (m, 2H), 1.17 (m, 6H).

EXAMPLE 404

This example was made by substituting 2,5-dimethylpyrrolidine for isopropylamine, in EXAMPLE 35B. $^1$H NMR (500 MHz, DMSO-d$_6$) δ 12.10 (m, 1H), 11.41 (m, 1H), 10.55 (m, 1H), 9.88 (m, 1H), 8.54 (s, 1H), 8.31 (d, 1H), 8.14 (m, 1H), 7.86 (dd, 1H), 7.77 (d, 2H), 7.53 (m, 4H), 7.24 (m, 8H), 6.93 (d, 2H), 4.33 (m, 2H), 3.88 (m, 2H), 3.26 (m, 7H), 2.83 (d, 2H), 2.16 (m, 4H), 1.65 (m, 2H), 1.36 (m, 6H).

EXAMPLE 405

This example was made by substituting EXAMPLE 398F and 7M NH$_3$ in methanol for EXAMPLE 35A and isopropylamine, respectively, in EXAMPLE 35B. $^1$H NMR (500 MHz, DMSO-d$_6$) δ 7.92 (s, 1H), 7.87 (d, 1H), 7.72 (d, 2H), 7.51 (dd, 1H), 7.29 (m, 7H), 6.77 (m, 2H), 6.69 (m, 1H), 4.40 (m, 1H), 3.87 (m, 2H), 3.38 (m, 4H), 3.12 (m, 4H), 2.84 (t, 2H), 2.40 (m, 2H), 1.99 (m, 2H).

EXAMPLE 406A

This example was made by substituting 4-bromo-2-trifluoromethylbenzenesulfonamide for 4-(((1R)-3-(dimethylamino)-1-((phenylsulfanyl)methyl)propyl)amino)-3-nitrobenzenesulfonamide in EXAMPLE 2D.

EXAMPLE 406B

This example was made by substituting EXAMPLE 406A for EXAMPLE 164B in EXAMPLE 164C. $^1$H NMR (500 MHz, DMSO-d$_6$) δ 7.87 (d, 1H), 7.79 (d, 2H), 7.48 (dd, 1H), 7.26 (m, 11H), 6.78 (m, 3H), 6.56 (m, 2H), 3.64 (m, 2H), 3.12 (m, 5H), 3.06 (m, 2H), 2.80 (m, 4H), 2.36 (m, 6H), 2.01 (m, 2H), 1.74 (m, 2H).

EXAMPLE 407A

This example was made by substituting 4-bromo-3-fluorobenzenesulfonamide for 4-(((1R)-3-(dimethylamino)-1-((phenylsulfanyl)methyl)propyl)amino)-3-nitrobenzenesulfonamide in EXAMPLE 2D.

EXAMPLE 407B

This example was made by substituting EXAMPLE 407A for EXAMPLE 164B in EXAMPLE 164C. $^1$H NMR (500 MHz, DMSO-d$_6$) δ 7.69 (d, 2H), 7.48 (dd, 1H), 7.42 (d, 1H), 7.25 (m, 12H), 6.77 (m, 2H), 6.44 (t, 1H), 5.90 (d, 1H), 3.63 (m, 2H), 3.10 (m, 9H), 2.79 (m, 4H), 2.36 (m, 6H), 1.98 (m, 1H), 1.87 (m, 1H).

EXAMPLE 847398A

This example was made by substituting 4-bromo-2-trifluoromethoxybenzenesulfonamide for 4-(((1R)-3-(dimethylamino)-1-((phenylsulfanyl)methyl)propyl)amino)-3-nitrobenzenesulfonamide in EXAMPLE 2D.

EXAMPLE 847398B

This example was made by substituting EXAMPLE 847398A for EXAMPLE 164B in EXAMPLE 164C. $^1$H NMR (500 MHz, DMSO-d$_6$) δ 7.73 (d, 2H), 7.62 (d, 1H), 7.51 (d, 1H), 7.31 (m, 12H), 6.81 (m, 2H), 6.39 (m, 2H), 3.61 (m, 2H), 3.39 (m, 2H), 3.17 (m, 6H), 3.09 (m, 4H), 2.79 (m, 1H), 2.40 (m, 6H), 1.98 (m, 1H), 1.87 (m, 1H).

EXAMPLE 409A

This example was made by substituting 4-bromo-2,5-difluorobenzenesulfonamide for 4-(((1R)-3-(dimethylamino)-1-((phenylsulfanyl)methyl)propyl)amino)-3-nitrobenzenesulfonamide in EXAMPLE 2D.

EXAMPLE 409B

This example was made by substituting EXAMPLE 409A for EXAMPLE 164B in EXAMPLE 164C. $^1$H NMR (500

MHz, DMSO-$d_6$) δ 7.73 (d, 2H), 7.51 (d, 1H), 7.31 (m, 10H), 6.80 (d, 2H), 6.20 (m, 2H), 6.10 (m, 2H), 3.59 (m, 1H), 3.39 (m, 4H), 3.14 (m, 6H), 2.94 (m, 2H), 2.85 (m, 2H), 2.40 (m, 6H), 2.01 (m, 1H), 1.90 (m, 1H).

EXAMPLE 410A

This example was made by substituting 4-bromo-3-methylbenzenesulfonamide for 4-(((1R)-3-(dimethylamino)-1-((phenylsulfanyl)methyl)propyl)amino)-3-nitrobenzenesulfonamide in EXAMPLE 2D.

EXAMPLE 410B

This example was made by substituting EXAMPLE 410A for EXAMPLE 164B in EXAMPLE 164C. $^1$H NMR (500 MHz, DMSO-$d_6$) δ 7.72 (d, 2H), 7.51 (d, 1H), 7.29 (m, 10H), 6.83 (d, 2H), 6.34 (d, 2H), 5.75 (s, 2H), 5.52 (d, 1H), 3.72 (m, 1H), 3.39 (m, 2H), 3.15 (m, 8H), 2.64 (m, 2H), 2.54 (m, 2H), 2.40 (m, 6H), 2.05 (s, 3H), 1.98 (m 1H), 1.87 (m, 1H).

EXAMPLE 411

This example was made by substituting EXAMPLE 307C and EXAMPLE 29D for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (300 MHz, DMSO-$d_6$) δ 8.44 (s, 1H), 8.14 (m, 1H), 7.81 (m, 1H), 7.71 (d, 2H), 7.25 (m, 7H), 6.94 (d, 1H), 6.77 (d, 2H), 4.11 (m, 1H), 3.58 (m, 2H), 3.19 (m, 6H), 2.76 (s, 2H), 2.22 (m, 8H), 1.66 (m, 4H), 1.19 (m, 12H), 0.89 (m, 4H).

EXAMPLE 412

This example was made by substituting (2R,5R)-(−)-trans-2,5-dimethylpyrrolidine, prepared as described in J. Org. Chem. 1999, 64, 1979-1985, for isopropylamine in EXAMPLE 35B. $^1$H NMR (500 MHz, DMSO-$d_6$) δ 8.45 (d, 1H), 8.17 (m, 1H), 7.84 (dd, 1H), 7.72 (d, 2H), 7.51 (d, 1H), 7.27 (m, 8H), 6.99 (d, 1H), 6.79 (d, 2H), 4.14 (m, 2H), 3.88 (m, 2H), 3.74 (m, 1H), 3.38 (s, 2H), 3.28 (m, 6H), 2.87 (m, 2H), 2.40 (m, 6H), 2.09 (m, 4H), 1.24 (m, 4H).

EXAMPLE 413

This example was made by substituting (2S,5S)-(+)-trans-2,5-dimethylpyrrolidine, prepared as described in J. Org. Chem. 1999, 64, 1979-1985, for isopropylamine in EXAMPLE 35B. $^1$H NMR (500 MHz, DMSO-$d_6$) δ 8.45 (d, 1H), 8.17 (m, 1H), 7.84 (dd, 1H), 7.72 (d, 2H), 7.51 (d, 1H), 7.27 (m, 8H), 6.94 (m, 1H), 6.79 (d, 2H), 4.11 (m, 2H), 3.88 (m, 2H), 3.74 (m, 1H), 3.38 (s, 2H), 3.27 (m, 6H), 2.87 (m, 2H), 2.40 (m, 6H), 2.09 (m, 4H), 1.24 (m, 4H).

EXAMPLE 414

This example was made by substituting (2S,5R)-cis-2,5-dimethylpyrrolidine, prepared as described in J. Org. Chem. 1999, 64, 1979-1985, for isopropylamine in EXAMPLE 35B. $^1$H NMR (500 MHz, DMSO-$d_6$) δ 8.46 (d, 1H), 8.16 (m, 1H), 7.83 (dd, 1H), 7.72 (d, 2H), 7.51 (d, 1H), 7.27 (m, 8H), 6.97 (m, 1H), 6.80 (d, 2H), 4.12 (m, 2H), 3.49 (m, 1H), 3.39 (s, 2H), 3.28 (m, 8H), 2.40 (m, 6H), 2.12 (m, 4H), 1.57 (m, 2H), 1.21 (m, 4H).

EXAMPLE 415A

A mixture of 4-bromo-3-(trifluoromethyl)benzenesulfonyl chloride (0.46 g), concentrated sulfuric acid (6 mL), and 90% nitric acid (3 mL) at 110° C. were stirred for 18 hours, poured into ice water and extracted with ethyl acetate. The extract was washed with water and brine, dried (Na$_2$SO$_4$), filtered, and concentrated.

EXAMPLE 415B

EXAMPLE 415A (0.5 g) in IPA (25 mL) and THF (25 mL) at −78° C. was treated with 38% ammonium hydroxide (10 mL), stirred for 3 hours, acidified with 12M HCl, and concentrated. The concentrate was treated with ethyl acetate and water. The extract was washed with water and brine and dried (Na$_2$SO$_4$), filtered, and concentrated. The concentrate was flash chromatographed on silica gel with 25% ethyl acetate/hexane.

EXAMPLE 415C

A mixture of EXAMPLE 415B (0.235 g), EXAMPLE 164A (0.224 g) and DIEA (1 mL) in dimethylacetamide (10 mL) at 50° C. was stirred for 18 hours, treated with ethyl acetate, washed with aqueous NaHCO$_3$, water, and brine, and dried (MgSO$_4$), filtered, and concentrated. The concentrate was flash chromatographed on silica gel with 50% ethyl acetate/NH$_3$-saturated dichloromethane.

EXAMPLE 415D

This example was made by substituting EXAMPLE 415C for 4-(((1R)-3-(dimethylamino)-1-((phenylsulfanyl)methyl)propyl)amino)-3-nitrobenzenesulfonamide in EXAMPLE 2D. $^1$H NMR (500 MHz, DMSO-$d_6$) δ 8.41 (d, 1H), 8.20 (d, 1H), 7.83 (dd, 1H), 7.75 (d, 2H), 7.51 (dd, 1H), 7.37 (m, 8H), 7.06 (d, 2H), 6.79 (d, 2H), 6.50 (m, 1H), 3.39 (s, 2H), 3.29 (m 1H), 3.05 (m, 7H), 2.63 (m, 4H), 2.40 (m, 6H), 2.07 (m, 2H).

EXAMPLE 416

This example was made by substituting EXAMPLE 415C and EXAMPLE 307C for 4-(((1R)-3-(dimethylamino)-1-((phenylsulfanyl)methyl)propyl)amino)-3-nitrobenzenesulfonamide and EXAMPLE 2C, respectively, in EXAMPLE 2D. $^1$H NMR (400 MHz, DMSO-$d_6$) δ 8.31 (d, 1H), 8.10 (d, 1H), 7.65 (d, 2H), 7.27 (d, 2H), 7.04 (m, 8H), 6.68 (d, 2H), 6.44 (m, 1H), 3.04 (m, 4H), 2.82 (m, 1H), 2.69 (m, 2H), 2.41 (m, 6H), 2.20 (m, 4H), 2.08 (m, 4H), 1.98 (m, 2H), 1.56 (m, 4H).

EXAMPLE 417

This example was made by substituting EXAMPLE 415C and EXAMPLE 318C for 4-(((1R)-3-(dimethylamino)-1-((phenylsulfanyl)methyl)propyl)amino)-3-nitrobenzenesulfonamide and EXAMPLE 2C, respectively, in EXAMPLE 2D. $^1$H NMR (400 MHz, DMSO-$d_6$) δ 8.18 (d, 1H), 7.98 (d, 1H), 7.52 (d, 2H), 7.15 (d, 2H), 6.94 (m, 8H), 6.56 (d, 2H), 6.42 (m, 1H), 2.90 (m, 4H), 2.69 (m, 1H), 2.56 (m, 2H), 2.29 (m, 6H), 2.19 (m, 4H), 2.10 (m, 4H), 1.82 (m, 1H), 1.74 (m, 1H), 1.56 (m, 4H), 1.48 (m, 2H), 1.32 (m, 4H).

EXAMPLE 418A

3-Fluoro-4-nitrobenzenesulfonyl chloride (1 g) in IPA (50 mL) at −15° C. was treated with 38% NH$_4$OH (10 mL), stirred for 18 hours and concentrated. The concentrate was partitioned between ethyl acetate and water. The water layer was extracted with ethyl acetate. The extract was washed with water and brine and dried (Na$_2$SO$_4$), filtered, and concentrated.

EXAMPLE 418B

This example was made by substituting EXAMPLE 418A and EXAMPLE 164A for 4-fluoro-3-nitrobenzenesulfonamide and EXAMPLE 21C, respectively, in EXAMPLE 21D.

EXAMPLE 418C

This example was made by substituting EXAMPLE 418B for 4-(((1R)-3-(dimethylamino)-1-((phenylsulfanyl)methyl) propyl)amino)-3-nitrobenzenesulfonamide in EXAMPLE 2D. $^1$H NMR (500 MHz, DMSO-d$_6$) δ 7.99 (d, 1H), 7.95 (d, 2H), 7.60 (s, 1H), 7.51 (dd, 1H), 7.37 (m, 4H), 7.30 (d, 4H), 7.24 (dd, 1H), 7.14 (t, 2H), 7.08 (t, 1H), 7.02 (dd, 1H), 6.79 (d, 2H), 4.13 (m, 1H), 3.49 (dd, 1H), 3.39 (d, 2H), 3.36 (dd, 1H), 3.13 (m, 4H), 3.04 (m, 2H), 2.63 (m, 4H), 2.40 (m, 6H), 2.10 (m, 2H).

EXAMPLE 419A

This example was made by substituting 4-bromo-3,5-difluorobenzenesulfonyl chloride for 3-fluoro-4-nitrobenzenesulfonyl chloride in EXAMPLE 418A.

EXAMPLE 419B

This example was made by substituting EXAMPLE 419A for 4-(((1R)-3-(dimethylamino)-1-((phenylsulfanyl)methyl) propyl)amino)-3-nitrobenzenesulfonamide in EXAMPLE 2D.

EXAMPLE 419C

This example was made by substituting EXAMPLE 419B for EXAMPLE 164B in EXAMPLE 164C. $^1$H NMR (500 MHz, DMSO-d$_6$) δ 12.10 (m, 1H), 11.43 (m, 1H), 10.48 (m, 1H), 8.55 (m, 1H), 8.14 (m, 2H), 7.77 (m, 2H), 7.33 (m, 12H), 6.93 (m, 2H), 6.03 (d, 2H), 4.34 (m 1H), 3.88 (m, 2H), 3.36 (m, 4H), 3.13 (m, 2H), 2.84 (m, 2H), 2.70 (m, 6H), 2.08 (m, 2H).

EXAMPLE 420A

A mixture of 2-chloro-3-nitrobenzoic acid (5 g) and chlorosulfonic acid (30 mL) at 150° C. was stirred for 72 hours, treated with ice, and extracted ethyl acetate. The extract was washed with water and brine, dried (Na$_2$SO$_4$), filtered, and concentrated. The concentrate in 1:1 IPA/THF (200 mL) at −78° C. was treated with 38% ammonium hydroxide (30 mL), stirred for 2 hours, acidified with 12M HCl, and concentrated. The concentrate was treated with water and ethyl acetate. The extract was washed with water and brine and dried (Na$_2$SO$_4$), filtered, and concentrated.

EXAMPLE 420B

EXAMPLE 420A (4.5 g) in methanol (300 mL) was treated with concentrated sulfuric acid (3 mL), stirred at reflux for 18 hours, and concentrated. The concentrate was treated with water and ethyl acetate. The extract was washed with water and brine and dried (Na$_2$SO$_4$), filtered, and concentrated. The concentrate was flash chromatographed on silica gel with 20% ethyl acetate/hexane.

EXAMPLE 420C

This example was made by substituting EXAMPLE 420B and EXAMPLE 164A for 4-fluoro-3-nitrobenzenesulfonamide and EXAMPLE 21C, respectively, in EXAMPLE 21D.

EXAMPLE 420D

This example was made by substituting EXAMPLE 420C and EXAMPLE 307C for 4-(((1R)-3-(dimethylamino)-1-((phenylsulfanyl)methyl)propyl)amino)-3-nitrobenzene-sulfonamide and EXAMPLE 2C, respectively, in EXAMPLE 2D. $^1$H NMR (500 MHz, DMSO-d$_6$) δ 8.34 (s, 1H), 8.28 (d, 1H), 7.72 (d, 2H), 7.36 (d, 2H), 7.13 (m, 7H), 6.76 (d, 2H), 3.80 (s, 3H), 3.10 (m, 4H), 2.75 (m, 2H), 2.27 (m, 4H), 2.18 (m, 6H), 1.99 (m, 2H), 1.88 (m, 2H), 1.65 (m, 4H).

EXAMPLE 421

This example was made by substituting EXAMPLE 420C for 4-(((1R)-3-(dimethylamino)-1-((phenylsulfanyl)methyl) propyl)amino)-3-nitrobenzenesulfonamide in EXAMPLE 2D. $^1$H NMR (500 MHz, DMSO-d$_6$) δ 8.27 (s, 1H), 8.20 (d, 1H), 7.66 (d, 2H), 7.43 (d, 2H), 7.16 (m, 11H), 6.71 (d, 2H), 3.74 (s, 3H), 3.05 (m, 6H), 2.82 (m, 2H), 2.49 (m, 6H), 2.32 (m, 4H), 1.95 (m, 2H), 1.85 (m, 2H).

EXAMPLE 422

EXAMPLE 421 (60 mg) in THF (1 mL), methanol (1 mL), and water (1 mL) was treated with lithium hydroxide monohydrate (10 mg), stirred at 25° C. for 18 hours, and concentrated. The concentrate was purified by high pressure liquid chromatography on a Waters Symmetry C$_8$ column (25 mm×100 mm, 7 μm particle size) with 10-100% acetonitrile/0.1% aqueous TFA over 8 minutes at a flow rate of 40 mL/minute. $^1$H NMR (500 MHz, DMSO-d$_6$) δ 9.55 (m, 1H), 9.13 (m, 1H), 8.46 (s, 1H), 8.33 (s, 1H), 7.79 (d, 2H), 7.72 (m, 1H), 7.52 (m, 4H), 7.49 (m, 2H), 7.33 (m, 2H), 7.09 (m, 4H), 6.99 (m, 2H), 6.93 (d, 2H), 4.21 (m, 1H), 3.17 (m, 6H), 2.93 (m, 2H), 2.79 (m, 6H), 2.12 (m, 2H), 2.05 (m, 2H).

EXAMPLE 423

This example was made by substituting EXAMPLE 420D for EXAMPLE 421 in EXAMPLE 422. $^1$H NMR (500 MHz, DMSO-d$_6$) δ 9.57 (m, 1H), 9.21 (m, 1H), 8.47 (s, 1H), 8.33 (s, 1H), 7.80 (d, 2H), 7.40 (m, 4H), 7.15 (d, 2H), 7.09 (m, 4H), 7.01 (m, 2H), 6.95 (d, 2H), 3.17 (m, 6H), 2.79 (m, 6H), 2.26 (m, 4H), 2.21 (m, 4H), 2.14 (m, 2H), 2.03 (m, 2H), 1.70 (m, 4H).

EXAMPLE 424

EXAMPLE 420D (100 mg) in 7M NH$_3$ in methanol at 70° C. was stirred for 48 hours in a sealed vial, and concentrated. The concentrate was purified by high pressure liquid chromatography on a Waters Symmetry C$_8$ column (25 mm×100 mm, 7 μm particle size) with 10-100% acetonitrile/0.1% aqueous TFA over 8 minutes at a flow rate of 40 mL/minute. $^1$H NMR (500 MHz, DMSO-d$_6$) δ 9.46 (m, 1H), 8.52 (m, 1H), 8.45 (d, 1H), 7.99 (s, 1H), 7.87 (s, 1H), 7.79 (d, 2H), 7.41 (m, 4H), 7.16 (d, 2H), 7.13 (m, 4H), 6.96 (d, 2H), 3.90 (m, 1H), 3.59

(m, 2H), 3.35 (m, 4H), 3.27 (m, 4H), 3.17 (m, 6H), 2.77 (m, 6H), 2.26 (m, 4H), 2.21 (m, 4H), 2.10 (m, 2H), 1.71 (m, 4H).

EXAMPLE 425

This example was made by substituting EXAMPLE 421 for EXAMPLE 420D in EXAMPLE 424. $^1$H NMR (500 MHz, DMSO-$d_6$) δ 9.42 (m, 1H), 8.52 (m, 1H), 8.46 (d, 1H), 7.99 (s, 1H), 7.87 (s, 1H), 7.78 (d, 2H), 7.53 (m, 4H), 7.41 (d, 2H), 7.34 (m, 1H), 7.14 (m, 4H), 6.94 (d, 2H), 3.91 (m, 1H), 3.36 (m, 4H), 3.28 (m, 4H), 3.16 (m, 6H), 2.77 (m, 6H), 2.11 (m, 2H).

EXAMPLE 426A

2-Fluoro-3-(trifluoromethyl)benzoic acid (5 g) in concentrated sulfuric acid (50 mL) at 0° C. was treated with urea nitrate, prepared as described in Textbook of Practical Organic Chemistry; 1971, page 442, (5 g), stirred for 30 minutes and at 25° C. for 12 hours, poured onto crushed ice and extracted with ethyl acetate. The extract was washed with water and brine, dried ($Na_2SO_4$), filtered, and concentrated. The concentrate in methanol (300 mL) and concentrated sulfuric acid (3 mL) was refluxed for 18 hours and concentrated. The concentrate was treated with water and ethyl acetate, and the organic layer was washed with water and brine, and dried ($Na_2SO_4$), filtered, and concentrated.

EXAMPLE 426B

EXAMPLE 426A (6 g) and 10% palladium on carbon (0.6 g) in ethyl acetate (200 mL) at 25° C. were shaken under $H_2$ (60 psi) for 2 hours, filtered and concentrated.

EXAMPLE 426C

This example was made by substituting EXAMPLE 426B for EXAMPLE 848090A in EXAMPLE 848090B.

EXAMPLE 426D

This example was made by substituting EXAMPLE 426C and EXAMPLE 164A for 4-fluoro-3-nitrobenzenesulfonamide and EXAMPLE 21C, respectively, in EXAMPLE 21D.
EXAMPLE 426E This example was made by substituting EXAMPLE 426D and EXAMPLE 307C for 4-(((1R)-3-(dimethylamino)-1-((phenylsulfanyl)methyl)propyl)amino)-3-nitrobenzenesulfonamide and EXAMPLE 2C, respectively, in EXAMPLE 2D. $^1$H NMR (400 MHz, DMSO-$d_6$) δ 8.39 (d, 1H), 8.16 (d, 1H), 7.72 (d, 2H), 7.36 (d, 2H), 7.30 (m, 1H), 7.20 (d, 2H), 7.12 (m, 4H), 6.77 (d, 2H), 3.81 (s, 3H), 3.62 (m, 1H), 3.12 (m, 8H), 2.95 (m, 2H), 2.77 (m, 2H), 2.61 (m, 6H), 2.28 (m, 4H), 2.18 (m, 4H), 2.10 (m, 2H), 1.91 (m, 2H), 1.66 (m, 4H).

EXAMPLE 427

This example was made by substituting EXAMPLE 426D and EXAMPLE 312D for 4-(((1R)-3-(dimethylamino)-1-((phenylsulfanyl)methyl)propyl)amino)-3-nitrobenzenesulfonamide and EXAMPLE 2C, respectively, in EXAMPLE 2D. $^1$H NMR (400 MHz, DMSO-$d_6$) δ 8.39 (d, 1H), 8.15 (d, 1H), 7.72 (d, 2H), 7.40 (d, 2H), 7.30 (m, 1H), 7.20 (m, 4H), 7.12 (m, 2H), 6.77 (d, 2H), 4.16 (s, 2H), 3.81 (s, 3H), 3.79 (t, 2H), 3.62 (m, 1H), 3.12 (m, 8H), 2.95 (m, 2H), 2.88 (m, 4H), 2.60 (m, 6H), 2.30 (m, 4H), 2.05 (m, 2H), 1.91 (m, 2H).

EXAMPLE 428

This example was made by substituting EXAMPLE 426D for 4-(((1R)-3-(dimethylamino)-1-((phenylsulfanyl)methyl)propyl)amino)-3-nitrobenzenesulfonamide in EXAMPLE 2D. $^1$H NMR (400 MHz, DMSO-$d_6$) δ 8.40 (d, 1H), 8.16 (d, 1H), 7.73 (d, 2H), 7.50 (d, 2H), 7.47 (m, 4H), 7.24 (m, 6H), 6.79 (d, 2H), 3.81 (s, 3H), 3.61 (m, 1H), 3.38 (s, 2H), 3.12 (m, 8H), 2.95 (m, 2H), 2.61 (m, 6H), 2.40 (m, 4H), 2.10 (m, 2H), 1.91 (m, 2H).

EXAMPLE 429A

This example was made by substituting Fmoc-D-Glu(O-tert-butyl)-OH for Fmoc-D-Asp(O-tert-butyl)-OH in EXAMPLE 27A.

EXAMPLE 429B

This example was made by substituting EXAMPLE 429A for EXAMPLE 27A in EXAMPLE 27B.

EXAMPLE 429C

This example was made by substituting EXAMPLE 429B for EXAMPLE 27B in EXAMPLE 29A.

EXAMPLE 429D

This example was made by substituting EXAMPLE 429C and (2S,5R)-cis-2,5-dimethylpyrrolidine, prepared as described in J. Org. Chem. 1999, 64, 1979-1985, for EXAMPLE 29A and diisopropylamine, respectively, in EXAMPLE 29B.

EXAMPLE 429E

This example was made by substituting EXAMPLE 429D for EXAMPLE 27B in EXAMPLE 398B.

EXAMPLE 429F

This example was made by substituting EXAMPLE 429E for EXAMPLE 18E in EXAMPLE 18F.

EXAMPLE 429G

This example was made by substituting EXAMPLE 429F for EXAMPLE 21C in EXAMPLE 21D.

EXAMPLE 429H

This example was made by substituting EXAMPLE 429G and EXAMPLE 307C for 4-(((1R)-3-(dimethylamino)-1-((phenylsulfanyl)methyl)propyl)amino)-3-nitrobenzenesulfonamide and EXAMPLE 2C, respectively, in EXAMPLE 2D. $^1$H NMR (300 MHz, DMSO-$d_6$) δ 12.11 (m, 1H), 10.17 (m, 1H), 9.01 (m, 1H), 8.53 (d, 1H), 8.32 (d, 1H), 7.87 (dd, 1H), 7.79 (d, 2H), 7.41 (d, 2H), 7.18 (m, 6H), 6.96 (d, 2H), 4.18 (m, 1H), 3.90 (m, 2H), 3.60 (m, 2H), 3.09 (m, 2H), 2.78 (m, 2H), 2.26 (m, 4H), 2.09 (m, 2H), 1.68 (m, 8H), 1.28 (d, 6H).

EXAMPLE 430

This example was made by substituting EXAMPLE 429G and EXAMPLE 312D for 4-(((1R)-3-(dimethylamino)-1-

((phenylsulfanyl)methyl)propyl)amino)-3-nitrobenzene-sulfonamide and EXAMPLE 2C, respectively, in EXAMPLE 2D. $^1$H NMR (300 MHz, DMSO-d$_6$) δ 12.11 (m, 1H), 10.54 (m, 1H), 9.00 (m, 1H), 8.53 (d, 1H), 8.32 (d, 1H), 7.88 (dd, 1H), 7.78 (d, 2H), 7.45 (d, 2H), 7.18 (m, 6H), 6.96 (d, 2H), 4.38 (s, 2H), 4.18 (m, 1H), 3.84 (t, 2H), 3.66 (m, 2H), 3.09 (m, 2H), 2.75 (m, 2H), 2.46 (m, 4H), 2.09 (m, 2H), 1.68 (m, 8H), 1.28 (d, 6H).

EXAMPLE 431

This example was made by substituting 2-tert-butoxycarbonylaminobenzoyl chloride for 2-bromobenzoyl chloride in EXAMPLE 106B. $^1$H NMR (500 MHz, DMSO-d$_6$) δ 9.48 (s, 1H), 9.28 (brs, 1H), 8.55 (d, 1H), 8.28 (d, 1H), 7.88 (dd, 1H), 7.77 (d, 2H), 7.24 (d, 2H), 7.16 (dd, 2H), 7.12 (d, 1H), 6.96 (d, 2H), 6.63 (d, 1H), 6.58 (s, 1H), 6.50 (d, 1H), 4.18 (m, 1H), 3.40 (m, 4H), 3.35 (m, 2H), 3.20-3.08 (m, 4H), 2.73 (s, 6H), 2.54 (s, 2H), 2.14 (m, 2H), 1.48 (s, 9H).

EXAMPLE 432

This example was made by substituting 2-dimethylaminobenzoyl chloride for 2-bromobenzoyl chloride in EXAMPLE 106B. $^1$H NMR (500 MHz, DMSO-d$_6$) δ 9.26 (br s, 1H), 8.55 (d, 1H), 8.28 (d, 1H), 7.87 (dd, 1H), 7.77 (d, 2H), 7.23 (d, 2H), 7.15 (dd, 2H), 7.11 (d, 1H), 6.96 (d, 2H), 6.79 (d, 1H), 6.69 (s, 1H), 6.65 (d, 1H), 4.17 (m, 1H), 3.40 (m, 4H), 3.35 (m, 2H), 3.15 (m, 4H), 2.91 (s, 6H), 2.74 (s, 6H), 2.54 (s, 2H), 2.14 (m, 2H).

EXAMPLE 433A

This example was made by substituting (2S,4R)-3-((benzyloxy)carbonyl)-4-methyl-2-phenyl-1,3-oxazolidin-5-one, (prepared as described in Helv. Chim. Acta 1991, for (2R,4S)-3-((benzyloxy)carbonyl)-4-methyl-2-phenyl-1,3-oxazolidin-5-one in EXAMPLE 25A.

EXAMPLE 433B

This example was made by substituting EXAMPLE 433A for EXAMPLE 25A in EXAMPLE 21B.

EXAMPLE 433C

This example was made by substituting EXAMPLE 433B for EXAMPLE 25B in EXAMPLE 21C.

EXAMPLE 433D

This example was made by substituting EXAMPLE 433C for EXAMPLE 18A in EXAMPLE 18B.

EXAMPLE 433E

This example was made by substituting EXAMPLE 433D for EXAMPLE 25D in EXAMPLE 21E.

EXAMPLE 433F

This example was made by substituting EXAMPLE 433E for EXAMPLE 25E in EXAMPLE 21F.

EXAMPLE 433G

This example was made by substituting EXAMPLE 433F for EXAMPLE 18B in EXAMPLE 18C.

EXAMPLE 433H

This example was made by substituting EXAMPLE 433G for EXAMPLE 25G in EXAMPLE 25H.

EXAMPLE 433I

This example was made by substituting EXAMPLE 433H for EXAMPLE 1C in EXAMPLE 1D. $^1$H NMR (500 MHz, DMSO-d$_6$) δ 8.51 (d, 1H), 8.31 (s, 1H), 7.92 (dd, 1H), 7.81 (d, 2H), 7.60 (d, 1H), 7.47 (m, 4H), 7.42 (m, 3H), 7.32 (m, 4H), 7.16 (dd, 2H), 7.08 (dd, 1H), 6.86 (d, 2H), 4.25 (m, 1H), 3.77 (d, 2H), 3.45 (d, 1H), 3.21 (m, 4H), 2.95 (m, 1H), 2.67 (s, 6H), 2.54 (m, 1H), 2.45 (m, 4H), 2.27 (m, 1H), 1.59 (s, 3H).

EXAMPLE 434

This example was made by substituting EXAMPLE 25H for EXAMPLE 1C in EXAMPLE 1D. $^1$H NMR (500 MHz, DMSO-d$_6$) δ 10.20 (br s, 1H), 8.48 (d, 1H), 8.26 (s, 1H), 7.87 (dd, 1H), 7.78 (d, 2H), 7.56 (d, 1H), 7.42 (m, 4H), 7.38 (m, 3H), 7.29 (d, 1H), 7.25 (m, 3H), 7.05 (dd, 2H), 6.97 (dd, 1H), 6.83 (d, 2H), 3.74 (m, 1H), 3.45 (s, 2H), 3.39 (d, 1H), 3.28 (m, 1H), 3.20 (m, 4H), 3.16 (m, 1H), 2.97 (m, 1H), 2.67 (s, 6H), 2.54 (m, 1H), 2.40 (m, 4H), 2.25 (m, 1H), 1.54 (s, 3H).

EXAMPLE 435A 2-fluorobenzonitrile (0.325 mL) in isoindoline/NMP (1 mL/2 mL) at 180° C. was stirred for 10 minutes in a microwave reactor, poured into diethyl ether (50 mL) and washed with 1M HCl and brine. The solution was dried (Na$_2$SO$_4$), filtered, and concentrated.

EXAMPLE 435B

EXAMPLE 435A (200 mg) in toluene (5 mL) at 25° C. was treated with 1M DIBAL in dichloromethane (1.1 mL), stirred for 30 minutes, treated with methanol (3 mL), poured into 1M HCl (50 mL), and extracted with ethyl acetate. The extract was washed with brine and dried (Na$_2$SO$_4$), filtered, and concentrated. The concentrate was flash chromatographed on silica gel with 10% ethyl acetate/hexanes.

EXAMPLE 435C

This example was made by substituting EXAMPLE 435B for EXAMPLE 130D in EXAMPLE 130E. $^1$H NMR (500 MHz, DMSO-d$_6$) δ 10.05 (br s, 1H), 8.45 (d, 1H), 8.21 (d, 1H), 7.81 (dd, 1H), 7.73 (d, 2H), 7.34 (m, 4H), 7.23 (m, 4H), 7.18 (m, 2H), 7.07 (m, 1H), 6.89 (m, 2H), 6.81 (d, 2H), 4.62 (AB quartet, 4H), 4.09 (m, 1H), 3.62 (s, 1H), 3.34 (m, 2H), 3.28 (m, 1H), 3.20 (m, 2H), 2.91 (dd, 2H), 2.84 (m, 1H), 2.67 (s, 6H), 2.55 (m, 4H), 2.09 (m, 1H), 2.02 (m, 1H), 1.71 (m, 1H).

EXAMPLE 436A

This example was made by substituting cyclohexylamine for isoindoline in EXAMPLE 435A.

EXAMPLE 436B

This example was made by substituting EXAMPLE 436A for EXAMPLE 435A in EXAMPLE 435B.

EXAMPLE 436C

This example was made by substituting EXAMPLE 436B for 2-(methylsulfanyl)benzaldehyde in EXAMPLE 128E. $^1$H NMR (400 MHz, DMSO-d$_6$) δ 9.70 (br s, 1H), 8.52 (d, 1H), 8.22 (d, 1H), 7.84 (dd, 1H), 7.76 (d, 2H), 7.26 (d, 2H), 7.19 (m, 2H), 7.11 (m, 2H), 6.97 (dd, 1H), 6.89 (d, 2H), 6.58 (d, 1H), 6.49 (m, 1H), 4.19 (m, 1H), 3.51 (m, 1H), 3.38 (d, 2H), 3.34 (m, 5H), 3.11 (m, 4H), 2.70 (s, 6H), 2.47 (m, 3H), 2.17 (m, 2H), 1.88 (m, 2H), 1.62 (m, 2H), 1.53 (m, 1H), 1.37 (m, 2H), 1.22 (m, 4H).

EXAMPLE 437A

This example was made by substituting isopropylamine for isoindoline in EXAMPLE 435A.

EXAMPLE 437B

This example was made by substituting EXAMPLE 437A for EXAMPLE 435A in EXAMPLE 435B.

EXAMPLE 437C

This example was made by substituting EXAMPLE 437B for 2-(methylsulfanyl)benzaldehyde in EXAMPLE 128E. $^1$H NMR (400 MHz, DMSO-d$_6$) δ 9.82 (br s, 1H), 8.52 (d, 1H), 8.22 (d, 1H), 7.84 (dd, 1H), 7.78 (d, 2H), 7.25 (d, 2H), 7.18 (m, 2H), 7.13 (m, 2H), 6.99 (m, 1H), 6.92 (d, 2H), 6.60 (d, 1H), 6.51 (dd, 1H), 4.21 (m, 1H), 3.49 (m, 3H), 3.39 (d, 2H), 3.31 (m, 5H), 3.11 (m, 4H), 3.08 (d, 2H), 2.71 (s, 6H), 2.51 (m, 1H), 2.16 (m, 2H), 1.14 (d, 6H).

EXAMPLE 438A

This example was made by substituting benzylamine for isoindoline in EXAMPLE 435A.

EXAMPLE 438B

This example was made by substituting EXAMPLE 438A for EXAMPLE 435A in EXAMPLE 435B.

EXAMPLE 438C

This example was made by substituting EXAMPLE 438B for 2-(methylsulfanyl)benzaldehyde in EXAMPLE 128E. $^1$H NMR (400 MHz, DMSO-d$_6$) δ 10.18 (br s, 1H), 8.52 (d, 1H), 8.25 (d, 1H), 7.84 (dd, 1H), 7.78 (d, 2H), 7.37 (d, 2H), 7.29 (dd, 2H), 7.24 (m, 2H), 7.19 (m, 2H), 7.12 (m, 3H), 7.07 (m, 1H), 6.95 (d, 2H), 6.56 (dd, 1H), 6.52 (d, 1H), 4.35 (s, 2H), 4.25 (m, 1H), 3.39 (d, 2H), 3.35 (m, 4H), 3.18 (m, 1H), 3.05 (m, 8H), 2.68 (s, 6H), 2.51 (m, 1H), 2.19 (m, 2H).

EXAMPLE 439A

This example was made by substituting piperidine for isoindoline in EXAMPLE 435A.

EXAMPLE 439B

This example was made by substituting EXAMPLE 439A for EXAMPLE 435A in EXAMPLE 435B.

EXAMPLE 439C

This example was made by substituting EXAMPLE 439B for 2-(methylsulfanyl)benzaldehyde in EXAMPLE 128E. $^1$H NMR (400 MHz, DMSO-d$_6$) δ 8.49 (d, 1H), 8.19 (m, 1H), 7.82 (dd, 1H), 7.75 (d, 2H), 7.41 (m, 1H), 7.35 (m, 1H), 7.30 (d, 2H), 7.22 (m, 3H), 7.15 (m, 1H), 7.02 (m, 2H), 6.87 (d, 1H), 4.12 (m, 1H), 3.60 (m, 2H), 3.42 (m, 1H), 3.37 (d, 2H), 3.31 (m, 5H), 3.22 (m, 2H), 3.08 (m, 2H), 2.82 (m, 4H), 2.69 (s, 6H), 2.59 (m, 2H), 2.10 (m, 2H), 1.65 (m, 4H), 1.51 (m, 2H), 1.21 (m, 4H).

EXAMPLE 440

This example was made by substituting 4-cyclohexylamino-3-nitro-benzenesulfonamide, prepared as described in WO02/24636, for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-d$_6$) δ 11.90 (brs, 1H), 8.61 (d, 1H), 8.60 (dd, 1H), 7.94 (dd, 1H), 7.74 (d, 2H), 7.59 (d, 1H), 7.41 (dd, 2H), 7.38 (m, 4H), 7.25 (d, 1H), 7.22 (d, 1H), 6.89 (d, 2H), 3.58 (m, 2H), 3.25 (m, 3H), 2.47 (m, 4H), 1.85 (d, 2H), 1.69 (m, 3H), 1.61 (m, 2H), 1.19 (m, 4H), 0.99 (m, 2H).

EXAMPLE 441

This example was made by substituting 4-cyclohexylmethylamino-3-nitrobenzenesulfonamide, prepared as described in WO02/24636, for 4-(((1R)-3-(dimethylamino)-1-((phenylsulfanyl)methyl)propyl)amino)-3-nitrobenzenesulfonamide in EXAMPLE 1D. $^1$H NMR (500 MHz, DMSO-d$_6$) δ 11.90 (br s, 1H), 8.70 (d, 1H), 8.36 (dd, 1H), 7.99 (dd, 1H), 7.78 (d, 2H), 7.50 (d, 1H), 7.45 (dd, 2H), 7.42 (m, 4H), 7.35 (d, 1H), 7.32 (d, 1H), 6.94 (d, 2H), 3.76 (m, 2H), 3.69 (m, 2H), 3.38 (m, 1H), 2.58 (m, 4H), 1.99 (d, 2H), 1.74 (m, 3H), 1.62 (m, 2H), 1.45 (m, 6H), 1.29 (m, 2H).

EXAMPLE 442

This example was prepared by substituting EXAMPLE 90C and 4-(((1R)-3-(4-morpholinyl)-1-((phenylsulfanyl)methyl)propyl)amino)-3-nitrobenzenesulfonamide, prepared as described in WO 02/24636, for EXAMPLE 2C and 4-(((1R)-3-(dimethylamino)-1-((phenylsulfanyl)methyl)propyl) amino)-3-nitrobenzenesulfonamide, respectively, in EXAMPLE 2D. $^1$H NMR (400 MHz, DMSO-d$_6$) δ 11.43 (br s, 1H), 8.54 (d, 1H), 8.38 (d, 1H), 7.83 (dd, 1H), 7.79 (d, 2H), 7.41 (dd, 2H), 7.35 (m, 2H), 7.28 (m, 6H), 7.17 (m, 4H), 6.80 (d, 2H), 4.19 (m, 1H), 3.62 (m, 4H), 3.39 (m, 2H), 3.30 (m, 2H), 3.02 (s, 3H), 2.90 (s, 2H), 2.85 (dd, 2H), 2.65 (m, 6H), 2.08 (m, 1H), 1.98 (m, 1H), 1.47 (d, 2H), 1.18 (m, 2H).

EXAMPLE 443

This example was prepared by substituting EXAMPLE 90C and 3-nitro-4-((2-(phenylsulfanyl)ethyl)amino)benzenesulfonamide, prepared as described in WO 02/24636, for EXAMPLE 2C and 4-(((1R)-3-(dimethylamino)-1-((phenylsulfanyl)methyl)propyl)amino)-3-nitrobenzenesulfonamide, respectively, in EXAMPLE 2D. $^1$H NMR (400 MHz, DMSO-d$_6$) δ 11.95 (br s, 1H), 8.75 (dd, 1H), 8.60 (d, 1H), 7.91 (dd, 1H), 7.79 (d, 2H), 7.41 (dd, 2H), 7.36 (m, 3H), 7.28 (m, 6H), 7.17 (m, 3H), 6.80 (d, 2H), 3.66 (m, 2H), 3.39 (m, 2H), 3.29 (m, 2H), 3.02 (s, 3H), 2.90 (s, 2H), 2.86 (dd, 2H), 1.45 (m, 2H), 1.18 (m, 2H).

EXAMPLE 444A 4-chloro-3-(trifluoromethyl)benzenesulfonyl chloride (5 g) in THF (100 mL) was treated with saturated $NH_4OH$ at 0° C., stirred for 30 minutes and concentrated. The concentrate in ethyl acetate was washed with water and brine, and dried ($Na_2SO_4$), filtered, and concentrated. The concentrate was flash chromatographed on silica gel with 30% ethyl acetate in hexanes.

EXAMPLE 444B

A mixture of EXAMPLE 444A (1.5 g) and 2-(phenylsulfanyl)ethanamine (1.06 g) in DMSO (17 mL) was treated with TEA (0.97 mL), heated at 145° C. for 18 hours, cooled to 25° C., poured into ethyl acetate, washed with water, brine, dried ($Na_2SO_4$), filtered, and concentrated. The concentrate was flash chromatographed on silica gel with 50% ethyl acetate/hexanes.

EXAMPLE 444C

This example was made by substituting EXAMPLE 444B for 4-(((1R)-3-(dimethylamino)-1-((phenylsulfanyl)methyl)propyl)amino)-3-nitrobenzenesulfonamide in EXAMPLE 2D. $^1H$ NMR (500 MHz, DMSO-$d_6$) δ 7.88 (d, 1H), 7.77 (d, 1H), 7.73 (dd, 2H), 7.51 (d, 1H), 7.49 (s, 4H), 7.40 (dd, 2H), 7.35 (m, 4H), 7.21 (m, 2H), 6.78 (d, 2H), 6.70 (d, 1H), 3.41 (m, 2H), 3.39 (s, 1H), 3.16 (m, 2H), 3.13 (m, 4H), 2.50 (s, 1H), 2.40 (m, 4H).

EXAMPLE 445A

This example was made by substituting EXAMPLE 444A for 4-fluoro-3-nitrobenzenesulfonamide, prepared as described in WO02/24636, in EXAMPLE 20D.

EXAMPLE 445B

This example was made by substituting EXAMPLE 445A for EXAMPLE 18E in EXAMPLE 18F.

EXAMPLE 445C

This example was made by substituting EXAMPLE 445B for 4-(((1R)-3-(dimethylamino)-1-((phenylsulfanyl)methyl)propyl)amino)-3-nitrobenzenesulfonamide in EXAMPLE 2D. $^1H$ NMR (500 MHz, DMSO-$d_6$) δ 10.90 (br s, 1H), 7.94 (d, 1H), 7.79 (d, 1H), 7.74 (d, 2H), 7.53 (d, 1H), 7.47 (s, 4H), 7.38 (m, 2H), 7.32 (m, 2H), 7.26 (m, 3H), 7.19 (m, 1H), 6.87 (d, 3H), 3.99 (m, 1H), 3.42 (s, 2H), 3.29 (m, 2H), 3.17 (m, 4H), 3.02 (m, 4H), 2.40 (m, 4H), 2.16 (m, 2H), 1.89 (m, 4H), 1.28 (m, 2H).

EXAMPLE 446A 4-chloronicotinic acid (5 g) in 1:1 methanol/ethyl acetate (200 mL) was treated with 2M trimethylsilyldiazomethane (25 mL) and concentrated.

EXAMPLE 446B

A mixture of EXAMPLE 446A (4.88 g), 4-chlorobenzeneboronic acid (5.15 g), KF (5.45 g), $Pd_2(dba)_3$ (260 mg), and tri-tert-butylphosphine in THF (80 mL) at 25° C. was stirred for 3 days, filtered and concentrated. The concentrate was flash chromatographed on silica gel with 20% ethyl acetate/hexanes.

EXAMPLE 446C

EXAMPLE 446B (3.4 g) in THF (50 mL) at 0° C. was treated with 1M $LiAlH_4$ in THF (14 mL), stirred at 25° C. for 1 hour, quenched with water (5 mL) and 1M NaOH (20 mL), filtered, and concentrated. The concentrate was flash chromatographed on silica gel with ethyl acetate.

EXAMPLE 446D

EXAMPLE 446C (530 mg) in acetonitrile (15 mL) at 0° C. was treated with pyridine (0.315 mL) and dibromotriphenylphosphorane (1.32 g), stirred at 25° C. for 1 hour, and poured into saturated $Na_2CO_3$ (100 mL) and ethyl acetate. The extract was washed with brine and dried ($Na_2SO_4$), filtered, and concentrated. The concentrate was flash chromatographed on silica gel with 1:1 ethyl acetate/hexanes.

EXAMPLE 446E

This example was made by substituting EXAMPLE 446D for 2-bromobenzyl bromide in EXAMPLE 2A.

EXAMPLE 446F

This example was made by substituting EXAMPLE 446E for EXAMPLE 1B in EXAMPLE 1C.

EXAMPLE 446G

This example was made by substituting EXAMPLE 446F for EXAMPLE 1C in EXAMPLE 1D. $^1H$ NMR (500 MHz, DMSO-$d_6$) δ 8.64 (s, 1H), 8.55 (d, 1H), 8.52 (d, 1H), 8.23 (d, 1H), 7.85 (dd, 1H), 7.74 (d, 2H), 7.58 (d, 2H), 7.54 (d, 2H), 7.31 (d, 1H), 7.26 (d, 1H), 7.17 (dd, 2H), 7.13 (d, 1H), 7.12 (m, 1H), 6.88 (d, 2H), 4.19 (m, 1H), 3.47 (s, 2H), 3.32 (m, 4H), 3.11 (m, 4H), 2.71 (s, 6H), 2.42 (m, 4H), 2.16 (m, 2H).

EXAMPLE 447

This example was made by substituting EXAMPLE 446F and 4-(((1R)-3-(4-morpholinyl)-1-((phenylsulfanyl)methyl)-propyl)amino)-3-nitrobenzenesulfonamide as described in WO 02/24636, for EXAMPLE 2C and 4-(((1R)-3-(dimethylamino)-1-((phenylsulfanyl)methyl)propyl)amino)-3-nitrobenzene-sulfonamide, respectively, in EXAMPLE 2D. $^1H$ NMR (500 MHz, DMSO-$d_6$) δ 8.65 (s, 1H), 8.56 (d, 1H), 8.52 (d, 1H), 8.34 (d, 1H), 7.83 (dd, 1H), 7.74 (d, 2H), 7.58 (d, 2H), 7.54 (d, 2H), 7.31 (d, 1H), 7.27 (d, 1H), 7.19 (dd, 2H), 7.13 (d, 1H), 7.11 (m, 1H), 6.88 (d, 2H), 4.19 (m, 1H), 3.63 (s, 4H), 3.22 (s, 4H), 3.08 (m, 4H), 2.75-2.55 (m, 6H), 2.42 (m, 4H), 2.10 (m, 1H), 1.98 (m, 1H).

EXAMPLE 448A

This example was made by substituting 2,6-difluorobenzotrifluoride for 1-fluorobenzotrifluoride in EXAMPLE 18D.

EXAMPLE 448B

This example was made by substituting EXAMPLE 448A for EXAMPLE 18D in EXAMPLE 18E.

EXAMPLE 448C

This example was made by substituting EXAMPLE 448B for EXAMPLE 18E in EXAMPLE 18F.

EXAMPLE 448D

This example was made by substituting EXAMPLE 448C for EXAMPLE 1C in EXAMPLE 1D. $^1$H NMR (500 MHz, DMSO-$d_6$) δ 7.82 (d, 2H), 7.76 (dd, 1H), 7.64 (d, 1H), 7.54 (d, 2H), 7.51 (d, 2H), 7.44 (m, 2H), 7.40 (d, 2H), 7.35 (dd, 2H), 7.31 (d, 1H), 7.25 (dd, 1H), 6.93 (d, 2H), 6.74 (d, 1H), 4.02 (m, 1H), 3.55 (m, 4H), 3.35 (m, 2H), 3.18 (m, 2H), 3.06 (m, 2H), 2.74 (s, 6H), 2.52 (m, 4H), 2.21 (m, 2H).

EXAMPLE 449A

A solution of piperazine-1-carboxylic acid tert-butyl ester (5.51 g) and 2-bromobenzyl bromide (7.776 g) in acetonitrile (60 mL) at 0° C. was treated with DIEA (7.73 mL), warmed to room temperature and concentrated. The concentrate was partitioned between ethyl acetate and saturated sodium bicarbonate. The extract was dried (MgSO$_4$), filtered and concentrated.

EXAMPLE 449B

A solution of EXAMPLE 449A (5.82 g) and 4-chlorophenylboronic acid (3.089 g) in dimethoxyethane (80 mL) was treated with CsF (7.476 g) and bis(triphenylphosphine)palladium dichloride (1.228 g), stirred at reflux for 18 hours, cooled and partitioned between ethyl acetate, and saturated sodium bicarbonate. The extract was washed with brine and dried (MgSO$_4$), filtered and concentrated. The concentrate was purified by flash chromatography on silica gel.

EXAMPLE 449C

A solution of EXAMPLE 449B (4.2 g) in dioxane (30 mL) was treated with 4M HCl in dioxane (81 mL), stirred at room temperature for 18 hours and concentrated.

EXAMPLE 449D

A solution of EXAMPLE 449C (3.852 g) and 2,4-difluorobenzonitrile (2.231 g) in acetonitrile (150 mL) was treated with potassium carbonate (5.168 g), stirred at reflux for 24 hours, filtered and concentrated. The concentrate was purified by chromatography on silica gel with 0-40% ethyl acetate/hexanes.

EXAMPLE 449E

A solution of EXAMPLE 449D (1.438 g) and hydrazine (2.2 mL) in 1-methyl-2-pyrrolidinone (1 mL) was heated at 150° C. for 40 minutes in a microwave reactor, concentrated and suspended in THF. The suspension was treated with aqueous ammonium hydroxide, filtered and dried.

EXAMPLE 449F

A solution of EXAMPLE 449E (2.0 g) in dioxane (24 mL) was treated with phthalic anhydride (779 mg) and N,N-dimethylaminopyridine (29 mg), stirred at reflux and concentrated. The concentrate was purified by chromatography on silica gel.

EXAMPLE 449G

A solution of EXAMPLE 449F (1.22 g) in dichloromethane (11 mL) was treated with 2-tert-butylimino-2-diethylamino-1,3-dimethyl-perhydro-1,3,2-diazaphosphorine (772 µL) and iodomethane (139 µL), stirred at room temperature for 30 minutes and concentrated. The concentrate was purified by chromatography on silica gel with 0-10% ethyl acetate/dichloromethane.

EXAMPLE 449H

A solution of EXAMPLE 449G (937 mg) in 1:1 dichloromethane/methanol (10 mL) was treated with hydrazine (105 µL), stirred at reflux for 18 hours and concentrated. The concentrate was partitioned between dichloromethane and aqueous ammonium hydroxide, and the extract was dried (MgSO$_4$), filtered and concentrated. The concentrate was purified by chromatography on silica gel with 20%-60% acetonitrile/(1-7M ammonia in methanol)/dichloromethane.

EXAMPLE 449I

A solution of EXAMPLE 449H (558 mg) in dichloromethane (7 mL) was treated with diisopropylethylamine (0.898 mL), 4-chloro-3-nitrobenzenesulfonyl chloride (728 mg) and N,N-dimethylaminopyridine (32 mg), stirred at room temperature for 30 minutes and partitioned between saturated ammonium chloride and ethyl acetate. The extract was washed with brine and dried (MgSO$_4$), filtered and concentrated. The concentrate was purified by chromatography on silica gel with 0-80% ethyl acetate/hexanes.

EXAMPLE 449J

A solution of AlCl$_3$ (0.80 g) in diethyl ether (30 mL) at room temperature was treated with LAH (0.68 g). After the addition, (phenylsulfanyl)acetonitrile (0.60 g) in diethyl ether (5 mL) was added, and the mixture was stirred for 4 hours, treated with aqueous 2N NaOH and solid NaOH until clear with a white precipitate and extracted with diethyl ether. The extract was dried (Na$_2$SO$_4$), filtered and concentrated.

EXAMPLE 449K

A solution of EXAMPLE 449I (117 mg) EXAMPLE 449K (62 mg) in 1-methyl-2-pyrrolidinone (0.5 mL) was treated with diisopropylethylamine (117 µL) and heated at 80° C. for 3 hours and concentrated.

EXAMPLE 449L

A solution of the EXAMPLE 449K from the previous step in 1:1 THF/methanol (1 mL) was treated with 1M LiOH (1.34 mL), heated at 80° C. for 18 hours and concentrated. The concentrate was partitioned between ethyl acetate and saturated ammonium chloride and the extract was dried (MgSO$_4$), filtered and concentrated. The concentrate was purified by chromatography on silica gel with 0-10% 7M ammonia in methanol/dichloromethane. $^1$H NMR (400 MHz, CDCl$_3$) δ 8.49 (t, 1H), 8.46 (d, 1H), 7.77 (br, 1H), 7.72 (d, 1H), 7.52 (dd, 2H), 7.37 (m, 8H), 7.24 (m, 4H), 6.89 (d, 1H), 6.61 (d, 1H), 6.48 (s, 1H), 3.83 (s, 3H), 3.49 (q, 2H), 3.44 (br, 2H), 3.22 (br, 4H), 3.16 (t, 2H), 2.55 (br, 4H).

EXAMPLE 450A

This example was made by substituting 1,1-dimethyl-2-phenylsulfanylethylamine, prepared as described in commonly-owned PCT/US01/29432, published as WO 02/024636, for EXAMPLE 449J in EXAMPLE 449K.

EXAMPLE 450B

This example was made by substituting EXAMPLE 450A for EXAMPLE 449K in EXAMPLE 449L. $^1$H NMR (400 MHz, CDCl$_3$) δ 8.64 (s, 1H), 8.39 (d, 1H), 7.77 (br, 1H), 7.73 (d, 1H), 7.52 (br, 1H), 7.43 (dd, 1H), 7.38 (m, 6H), 7.25 (m, 3H), 7.04 (m, 3H), 6.89 (d, 1H), 6.81 (d, 1H), 6.48 (s, 1H), 3.83 (s, 3H), 3.44 (br, 2H), 3.31 (s, 2H), 3.22 (br, 4H), 2.55 (br, 4H), 1.56 (s, 6H).

EXAMPLE 451A

This example was made by substituting (R)-N$^1$,N$^1$-dimethyl-4-phenylsulfanylbutane-1,3-diamine, prepared as described in commonly-owned U.S. patent application Ser. No. 10/988,388, for EXAMPLE 824469J in EXAMPLE 449K.

EXAMPLE 451B

This example was made by substituting EXAMPLE 451A for EXAMPLE 449K in EXAMPLE 449L. $^1$H NMR (400 MHz, CDCl$_3$) δ 8.89 (d, 1H), 8.44 (d, 1H), 7.73 (d, 1H), 7.52 (m, 1H), 7.41 (dd, 1H), 7.35 (m, 5H), 7.27 (m, 4H), 7.18 (m, 3H), 6.90 (dd, 1H), 6.54 (d, 1H), 6.48 (d, 1H), .3.92 (m, 1H), 3.83 (s, 1H), 3.44 (s, 2H), 3.21 (m, 4H), 3.09 (d, 2H), 2.54 (m, 4H), 2.47 (m, 1H), 2.30 (m, 1H), 2.21 (s, 6H), 2.03 (m, 1H), 1.82 (m, 1H).

EXAMPLE 452A

This example was made by substituting (R)-3-morpholin-4-yl-1-phenylsulfanylmethylpropylamine, prepared as described in commonly-owned U.S. patent application Ser. No. 10/988,388, for EXAMPLE 824469J in EXAMPLE 449K.

EXAMPLE 452B

This example was made by substituting EXAMPLE 452A for EXAMPLE 449K in EXAMPLE 449L. $^1$H NMR (400 MHz, CDCl$_3$) δ 8.46 (m, 2H), 7.73 (d, 1H), 7.54 (br, 1H), 7.44 (dd, 1H), 7.36 (m, 6H), 7.26 (m, 4H), 7.19 (m, 2H), 6.90 (d, 1H), 6.60 (d, 1H), 6.48 (s, 1H), 3.97 (m, 1H), 3.83 (s, 3H), 3.64 (br, 4H), 3.46 (br, 2H), 3.38 (t, 4H), 3.23 (br, 4H), 3.09 (d, 2H), 2.56 (br, 4H), 2.43 (m, 2H), 2.09 (m, 1H), 1.77 (m, 1H).

EXAMPLE 453A

This example was made by substituting trityl chloride for iodomethane in EXAMPLE 449G.

EXAMPLE 453B

This example was made by substituting EXAMPLE 453A for EXAMPLE 449G in EXAMPLE 449H.

EXAMPLE 453C

This example was made by substituting EXAMPLE 453B for EXAMPLE 449H in EXAMPLE 449I.

EXAMPLE 453D

This example was made by substituting EXAMPLE 453C for EXAMPLE 449I in EXAMPLE 449K.

EXAMPLE 453E

This example was made by substituting EXAMPLE 453D for EXAMPLE 449K in EXAMPLE 449L.

EXAMPLE 453F

A solution of EXAMPLE 453E in dichloromethane (1.8 mL) was treated with triethylsilane (0.1 mL) and trifluoroacetic acid (0.1 mL), stirred at room temperature for 10 minutes and concentrated. The concentrate was purified by flash chromatography on silica gel with 0-10% 7M ammonia in methanol/dichloromethane. $^1$H NMR (500 MHz, CDCl$_3$) δ 9.83 (br, 1H), 8.41 (m, 2H), 7.78 (d, 1H), 7.54 (br, 1H), 7.47 (dd, 1H), 7.34 (m, 7H), 7.24 (m, 6H), 6.88 (d, 1H), 6.55 (s, 1H), 6.48 (d, 1H), 3.47 (br, 2H), 3.38 (q, 2H), 3.18 (br, 4H), 3.09 (t, 2H), 2.54 (br, 4H).

EXAMPLE 454A

This example was made by substituting (R)-N$^1$,N$^1$-dimethyl-4-phenylsulfanyl-butane-1,3-diamine, prepared as described in commonly-owned U.S. patent application Ser. No. 10/988,338, and EXAMPLE 453C for EXAMPLE 449J and EXAMPLE 449I, respectively in EXAMPLE 449K.

EXAMPLE 454B

This example was made by substituting EXAMPLE 454A for EXAMPLE 449K in EXAMPLE 449L.

EXAMPLE 454C

This example was made by substituting EXAMPLE 454B for EXAMPLE 453E in EXAMPLE 453F. $^1$H NMR (500 MHz, CDCl$_3$) δ 9.92 (br, 1H), 8.79 (br, 1H), 8.41 (d, 1H), 7.76 (d, 1H), 7.51 (d, 1H), 7.36 (m, 7H), 7.25 (m, 4H), 7.14 (m, 3H), 6.90 (m, 1H), 6.60 (s, 1H), 6.46 (d, 1H), 3.88 (br, 1H), 3.42 (s, 2H), 3.17 (br, 4H), 3.06 (d, 2H), 2.52 (br, 5H), 2.42 (br, 1H), 2.28 (s, 6H), 2.03 (m, 1H), 1.86 (m, 1H).

EXAMPLE 455A

This example was made by substituting EXAMPLE 453C and (R)-3-morpholin-4-yl-1-phenylsulfanylmethylpropylamine, prepared as described in commonly-owned U.S. patent application Ser. No. 10/988,388, for EXAMPLE 449I and EXAMPLE 449J, respectively in EXAMPLE 449K.

EXAMPLE 455B

This example was made by substituting EXAMPLE 455A for EXAMPLE 449K in EXAMPLE 449K.

EXAMPLE 455C

This example was made by substituting EXAMPLE 455B for EXAMPLE 453E in EXAMPLE 453F. $^1$H NMR (500 MHz, CDCl$_3$) δ 9.76 (br, 1H), 8.41 (m, 2H), 7.81 (d, 1H), 7.53 (d, 1H), 7.35 (m, 7H), 7.26 (m, 4H), 7.13 (m, 3H), 6.92 (d, 1H), 6.60 (s, 1H), 6.51 (d, 1H), 3.89 (m, 1H), 3.62 (br, 4H), 3.45 (br, 2H), 3.20 (br, 4H), 3.05 (m, 2H), 2.54 (br, 4H), 2.41 (br, 4H), 2.32 (br, 2H), 2.07 (m, 1H), 1.75 (m, 1H); MS (ESI) m/z 865.2 (M–H)

EXAMPLE 456A

A solution of acetone oxime (273 mg) and potassium tert-butoxide (442 mg) in DMF (10 mL) was stirred at room temperature for 30 minutes, followed by addition of EXAMPLE 449D (1 g) in DMF (10 mL). The mixture was stirred at room temperature for 18 hours, quenched with saturated NaHCO$_3$ solution and extracted with ethyl acetate. The extract was washed with brine and dried (Na$_2$SO$_4$), filtered and and concentrated. The concentrate was suspended in 1:1 ethanol/5% HCl (40 mL), stirred at reflux for 2 hours, cooled and concentrated. The concentrate was purified by flash chromatography on silica gel with 0-15% 7M ammonia in methanol/dichloromethane.

EXAMPLE 456B

A solution of EXAMPLE 456A (775 mg) in THF (10 mL) was added to a suspension of KH (740 mg) in THF (5 mL) at 0° C. and the mixture was warmed to room temperature, stirred at room temperature for 30 minutes, cooled to −78° C., treated with 4-chloro-3-nitrobenzenesulfonyl chloride (474 mg) in THF (10 mL), stirred at for 30 minutes, warmed to room temperature and poured into saturated ammonium chloride at 0° C., adjusted to pH 8 with saturated ammonium chloride and extracted with ethyl acetate. The extract was dried (MgSO$_4$), filtered and concentrated. The concentrate was purified by flash chromatography on silica gel with 0-15% 7M ammonia in methanol/dichloromethane.

EXAMPLE 456C

A solution of EXAMPLE 456B in dichloromethane (10 mL) was treated with 1-chloro-4-chloromethoxy-benzene (125 mg,) and DIEA (335 µL), stirred at reflux for 10 hours and concentrated. The concentrate was purified by flash chromatography on silica gel.

EXAMPLE 456D

A mixture of EXAMPLE 456C (70 mg), 2-phenylsulfanyl-ethylamine (26 mg), diisopropylethylamine (70 µL) and 15 beads of 4A molecular sieves in NMP (1 mL) was stirred at 100° C. for 1 hour, cooled and concentrated. The concentrate was purified by flash chromatography on silica gel with 30-40% ethyl acetate/hexanes.

EXAMPLE 456E

A solution of EXAMPLE 456D (50 mg) in 1:1 THF/2M HCl (2 mL) was stirred at 60° C. for 2 days, cooled and concentrated. The concentrate was purified by flash chromatography on silica gel with 1-4% methanol/dichloromethane. $^1$H NMR (500 MHz, DMSO-d$_6$) δ 8.70 (t, 1H), 8.54 (d, 1H), 7.84 (dd, 1H), 7.64 (d, 1H), 7.51 (d, 1H), 7.47 (m, 4H), 7.38 (m, 4H), 7.23 (m, 3H), 7.14 (m, 2H), 7.00 (dd, 9.04 Hz, 1H), 6.87 (d, 1H), 4.33 (s, 1H), 3.63 (m, 2H), 3.42 (m, 4H), 3.23 (m, 4H), 2.42 (s, 4H).

EXAMPLE 457A

A solution of EXAMPLE 456B in dichloromethane (10 mL) was treated with 1-chloro-4-chloromethoxybenzene (125 mg) and diisopropylethylamine (335 µL), stirred at reflux for 10 hours and concentrated. The concentrate was purified by flash chromatography on silica gel with 0-100% ethyl acetate/hexanes.

EXAMPLE 457B

This example was made by substituting EXAMPLE 457A and (R)-3-morpholin-4-yl-1-phenylsulfanylmethylpropylamine for EXAMPLE 456C and 2-phenylsulfanyl-ethylamine, respectively, in EXAMPLE 456D.

EXAMPLE 457C

This example was made by substituting EXAMPLE 457B for EXAMPLE 456D in EXAMPLE 456E. $^1$H NMR (500 MHz, DMSO-d$_6$) δ 8.48 (d, 1H), 8.38 (d, 1H), 7.75 (dd, 1H), 7.59 (d, 1H), 7.47 (m, 51H), 7.37 (m, 2H), 7.24 (m, 3H), 7.10 (m, 4H), 6.98 (d, 1H), 6.85 (s, 1H), 5.76 (s, 2H), 4.36 (t, 2H), 4.13 (bs, 1H), 3.50 (bs, 4H), 3.38 (m, 4H), 3.21 (bs, 4H), 2.40 (s, 4H), 1.92 (m, 1H), 1.77 (m, 1H), 1.43 (m, 4H).

EXAMPLE 458A

This example was made by substituting 4,4-dimethylpiperidine for EXAMPLE 449C in EXAMPLE 449D.

EXAMPLE 458B

This example was made by substituting EXAMPLE 458A for EXAMPLE 449D in EXAMPLE 456A.

EXAMPLE 458C

This example was made by substituting EXAMPLE 458B for EXAMPLE 456A in EXAMPLE 456B.

EXAMPLE 458D

This example was prepared by substituting EXAMPLE 458C for EXAMPLE 456B in EXAMPLE 456C.

EXAMPLE 458E

This example was prepared by substituting EXAMPLE 458D for EXAMPLE 456C in EXAMPLE 456D.

EXAMPLE 458F

This example was prepared by substituting EXAMPLE 458E for EXAMPLE 456D in EXAMPLE 456E. $^1$H NMR (500 MHz, DMSO-d$_6$) δ 11.59 (bs, 1H), 9.63 (s, 1H), 8.72 (t, 1H), 8.55 (d, 1H), 7.84 (dd, 1H), 7.64 (d, 1H), 7.33 (m, 2H), 7.18 (m, 4H), 7.03 (dd, 1H), 6.88 (d, 1H), 6.76 (m, 1H), 3.64 (m, 2H), 3.26 (m, 4H), 1.75 (m, 1H), 1.52 (m, 1H), 1.39 (m, 4H), 0.94 (s, 6H).

EXAMPLE 459A

This example was prepared by substituting EXAMPLE 458C for EXAMPLE 456B in EXAMPLE 456C.

EXAMPLE 459B

This example was made by substituting EXAMPLE 459A and (R)-3-morpholin-4-yl-1-phenylsulfanylmethyl-propylamine for EXAMPLE 456C and 2-phenylsulfanyl-ethylamine, respectively, in EXAMPLE 456D.

EXAMPLE 459C

This example was prepared by substituting EXAMPLE 459B for EXAMPLE 456D in EXAMPLE 456E. $^1$H NMR (500 MHz, DMSO-$d_6$) δ 8.48 (d, 1H), 8.34 (d, 1H), 7.77 (m, 1H), 7.61 (d, 1H), 7.21 (d, 2H), 7.10 (m, 4H), 6.99 (d, 1H), 6.86 (s, 1H), 4.38 (m, 6H), 4.13 (m, 5H), 3.64 (m, 4H), 3.28 (m, 2H), 1.95 (m, 2H), 1.39 (m, 4H), 0.94 (s, 6H).

EXAMPLE 460A

A solution of 1-Boc-piperazine (5.44 g) and β-phenylcinnamaldehyde (6.39 g) in 1:1 dichloromethane/methanol (100 mL) was treated with sodium triacetoxyborohydride (8.66 g), stirred at room temperature for 18 hours and concentrated. The concentrate was partitioned between dichloromethane and saturated sodium bicarbonate, and the extract was washed with brine and dried (MgSO$_4$), filtered and concentrated.

EXAMPLE 460B

A solution of EXAMPLE 460A (11 g) in dichloromethane (50 mL) at room temperature was treated with 4M HCl in dioxane (50 mL), stirred for 6 hours and concentrated. The concentrate was partitioned between dichloromethane and aqueous sodium carbonate, and the extract was dried (MgSO$_4$), filtered and concentrated.

EXAMPLE 460C

This example was made by substituting EXAMPLE 460B for EXAMPLE 449C in EXAMPLE 449D.

EXAMPLE 460D

This example was made by substituting EXAMPLE 460C for EXAMPLE 449D in EXAMPLE 456A.

EXAMPLE 460E

This example was made by substituting EXAMPLE 460D for EXAMPLE 456A in EXAMPLE 456B.

EXAMPLE 460F

This example was prepared by substituting EXAMPLE 460E for EXAMPLE 456B in EXAMPLE 456C.

EXAMPLE 460G

This example was made by substituting EXAMPLE 460F and (R)-3-morpholin-4-yl-1-phenylsulfanylmethylpropylamine for EXAMPLE 456C and 2-phenylsulfanylethylamine, respectively, in EXAMPLE 456D.

EXAMPLE 460H

This example was prepared by substituting EXAMPLE 460G for EXAMPLE 456D in EXAMPLE 456E. $^1$H NMR (500 MHz, DMSO-$d_6$) δ 8.46 (d, 1H), 8.34 (d, 1H), 7.74 (dd, 1H), 7.56 (d, 1H), 7.41 (t, 2H), 7.28 (m, 8H), 7.11 (m, 5H), 7.03 (d, 1H), 6.95 (d, 1H), 6.84 (s, 1H), 6.19 (t, 1H), 4.33 (t, 2H), 4.11 (m, 1H), 3.47 (m, 4H), 3.10 (m, 4H), 2.46 (s, 2H), 2.37 (m, 4H), 2.25 (m, 2H), 1.96 (m, 1H), 1.81 (m, 1H), 1.42 (m, 4H).

EXAMPLE 461A

This example was prepared by substituting EXAMPLE 460E for EXAMPLE 456B in EXAMPLE 456C.

EXAMPLE 461B

This example was prepared by substituting EXAMPLE 461A for EXAMPLE 456C in EXAMPLE 456D.

EXAMPLE 461C

This example was prepared by substituting EXAMPLE 461B for EXAMPLE 456D in EXAMPLE 456E. $^1$H NMR (500 MHz, DMSO-$d_6$) δ 8.65 (t, 1H), 8.51 (d, 1H), 7.82 (dd, 1H), 7.59 (d, 1H), 7.42 (t, 2H), 7.32 (m, 5H), 7.23 (m, 5H), 7.12 (m, 4H), 6.98 (dd, 1H), 6.86 (s, 1H), 6.19 (t, 1H), 3.61 (m, 2H), 3.26 (m, 4H), 3.15 (m, 4H), 2.62 (m, 4H).

EXAMPLE 462A

This example was made by substituting EXAMPLE 457A and (R)-N$^1$,N$^1$-dimethyl-4-phenylsulfanyl-butane-1,3-diamine for EXAMPLE 456C and 2-phenylsulfanylethylamine, respectively, in EXAMPLE 456D.

EXAMPLE 462B

This example was prepared by substituting EXAMPLE 462A for EXAMPLE 456D in EXAMPLE 456E. $^1$H NMR (500 MHz, DMSO-$d_6$) δ 8.45 (d, 1H), 8.19 (d, 1H), 7.79 (dd, 1H), 7.49 (m, 5H), 7.37 (m, 4H), 7.24 (m, 3H), 7.18 (t, 2H), 7.13 (m, 1H), 6.95 (d, 1H), 6.84 (d, 1H), 6.71 (s, 1H), 4.09 (b, 1H), 3.39 (s, 2H), 3.15 (m, 4H), 2.90 (m, 2H), 2.57 (s, 6H), 2.40 (m, 4H), 2.08 (b, 2H).

EXAMPLE 463A

This example was made by substituting EXAMPLE 459A and (R)-N$^1$,N$^1$-dimethyl-4-phenylsulfanyl-butane-1,3-diamine for EXAMPLE 456C and 2-phenylsulfanyl-ethylamine, respectively, in EXAMPLE 456D.

EXAMPLE 463B

This example was prepared by substituting EXAMPLE 463A for EXAMPLE 456D in EXAMPLE 456E. $^1$H NMR (500 MHz, DMSO-$d_6$) δ 8.44 (d, 1H), 8.23 (bs, 1H), 7.78 (dd, 1H), 7.37 (m, 1H), 7.26 (d, 2H), 7.18 (t, 2H), 7.13 (d, 1H), 6.90 (d, 1H), 6.83 (d, 1H), 6.69 (s, 1H), 4.05 (m, 1H), 3.20 (m, 4H), 2.49, (s, 6H), 2.00 (m, 2H), 1.39 (m, 4H), 0.93 (s, 6H).

What is claimed is:

1. A compound of formula (I)

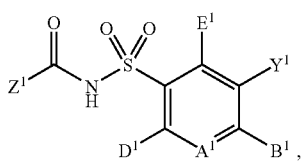

or a therapeutically acceptable salt thereof, wherein
A$^1$ is N or C(A$^2$);
one or two or three or each of A$^2$, B$^1$, D$^1$ and E$^1$ are independently selected from R$^1$, OR$^1$, SR$^1$, S(O)R$^1$, SO₂R¹, C(O)R¹, C(O)OR¹, OC(O)R¹, NHR¹, N(R¹)₂, C(O)NHR¹, C(O)N(R¹)₂, NHC(O)R¹, NHC(O)OR¹, NR¹C(O)NHR¹, NR¹C(O)N(R¹)₂, SO₂NHR¹, SO₂N(R¹)₂, NHSO₂R¹, NHSO₂NHR¹ and N(CH₃)SO₂N(CH₃)R¹, and the remainder are independently selected from H, F, Cl, Br, I, CN, CF₃, C(O)OH, C(O)NH₂ and C(O)OR$^{1A}$; and Y¹ is H, CN, NO₂, C(O)OH, F, Cl, Br, I, CF₃, OCF₃, CF₂CF₃, OCF₂CF₃, R¹⁷, OR¹⁷, C(O)R¹⁷, C(O)OR¹⁷, SR¹⁷, NH₂, NHR¹⁷, N(R¹⁷)₂, NHC(O)R¹⁷, C(O)NH₂, C(O)NHR¹⁷, C(O)N(R¹⁷)₂, NHS(O)R¹⁷ or NHSO₂R¹⁷; or B¹ and Y¹, together with the atoms to which they are attached, are imidazole or triazole; and one or two or each of A², D¹ and E¹ are independently selected from R¹, OR¹, SR¹, S(O)R¹, SO₂R¹, C(O)R¹, C(O)OR¹, OC(O)R¹, NHR¹, N(R¹)₂, C(O)NHR¹, C(O)N(R¹)₂, NHC(O)R¹, NHC(O)OR¹, NHC(O)NHR¹, N(CH₃)C(O)N(CH₃)R¹, SO₂NHR¹, SO₂N(R¹)₂, NHSO₂R¹, NHSO₂NHR¹ and N(CH₃)SO₂N(CH₃)R¹, and the remainder are independently selected from H, F, Cl, Br, I, CF₃, C(O)OH, C(O)NH₂ and C(O)OR$^{1A}$;

R¹ is R², R³, R⁴ or R⁵;

R$^{1A}$ is C₁-C₆-alkyl, C₃-C₆-alkenyl or C₃-C₆-alkynyl;

R² is phenyl which is unfused or fused with arene, heteroarene or R$^{2A}$; R$^{2A}$ is cycloalkane or heterocycloalkane;

R³ is heteroaryl which is unfused or fused with benzene, heteroarene or R$^{3A}$; R$^{3A}$ is cycloalkane or heterocycloalkane;

R⁴ is cycloalkyl, cycloalkenyl, heterocycloalkyl or heterocycloalkenyl, each of which is unfused or fused with arene, heteroarene or R$^{4A}$; R$^{4A}$ is cycloalkane, cycloalkene, heterocycloalkane or heterocycloalkene;

R⁵ is alkyl, alkenyl or alkynyl, each of which is unsubstituted or substituted with one or two or three substituents independently selected from R⁶, R⁷, OR⁷, SR⁷, S(O)R⁷, SO₂R⁷, NHR⁷, N(R⁷)₂, C(O)R⁷, C(O)NH₂, C(O)NHR⁷, NHC(O)R⁷, NHSO₂R⁷, NHC(O)OR⁷, SO₂NH₂, SO₂NHR⁷, SO₂N(R⁷)₂, NHC(O)NH₂, NHC(O)NHR⁷, NHC(O)CH(CH₃)NHC(O)CH(CH₃)NH₂, NHC(O)CH(CH₃)NHC(O)CH(CH₃)NHR⁷, OH, (O), C(O)OH, (O), N₃, CN, NH₂, CF₃, CF₂CF₃, F, Cl, Br and I;

R⁶ is C₂-C₅-spiroalkyl, each of which is unsubstituted or substituted with OH, (O), N₃, CN, CF₃, CF₂CF₃, F, Cl, Br, I, NH₂, NH(CH₃) or N(CH₃)₂;

R⁷ is R⁸, R⁹, R¹⁰ R¹¹;

R⁸ is phenyl which is unfused or fused with arene, heteroarene or R$^{8A}$;

R$^{8A}$ is cycloalkane, cycloalkene, heterocycloalkane or heterocycloalkene;

R⁹ is heteroaryl which is unfused or fused with arene, heteroarene or R$^{9A}$; R$^{9A}$ is cycloalkane, cycloalkene, heterocycloalkane or heterocycloalkene;

R¹⁰ is C₃-C₁₀-cycloalkyl or C₄-C₁₀-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or R$^{10A}$; R$^{10A}$ is cycloalkane, cycloalkene, heterocycloalkane or heterocycloalkene;

R¹¹ is alkyl, alkenyl or alkynyl, each of which is unsubstituted or substituted with one or two or three substituents independently selected from R¹², OR¹², NHR¹², N(R¹²)₂, C(O)NH₂, C(O)NHR¹², C(O)N(R¹²)₂, OH, (O), C(O)OH, N₃, CN, NH₂, CF₃, CF₂CF₃, F, Cl, Br and I;

R¹² is R¹³, R¹⁴, R¹⁵ or R¹⁶;

R¹³ is phenyl which is unfused or fused with arene, heteroarene or R$^{13A}$; R$^{13A}$ is cycloalkane, cycloalkene, heterocycloalkane or heterocycloalkene;

R¹⁴ is heteroaryl, each of which is unfused or fused with arene, heteroarene or R$^{14A}$; R$^{14A}$ is cycloalkane, cycloalkene, heterocycloalkane or heterocycloalkene;

R¹⁵ is cycloalkane, cycloalkene, heterocycloalkane or heterocycloalkene, each of which is unfused or fused with arene, heteroarene or R$^{15A}$; R$^{15A}$ is cycloalkane, cycloalkene, heterocycloalkane or heterocycloalkene;

R¹⁶ is alkyl, alkenyl or alkynyl;

R¹⁷ is R¹⁸, R¹⁹, R²⁰ or R²¹;

R¹⁸ is phenyl which is unfused or fused with arene, heteroarene or R$^{18A}$; R$^{18A}$ is cycloalkane, cycloalkene, heterocycloalkane or heterocycloalkene;

R¹⁹ is heteroaryl which is unfused or fused with arene, heteroarene or R$^{19A}$; R$^{19A}$ is cycloalkane, cycloalkene, heterocycloalkane or heterocycloalkene;

R²⁰ is C₃-C₁₀-cycloalkyl or C₄-C₁₀-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or R$^{20A}$; R$^{20A}$ is cycloalkane, cycloalkene, heterocycloalkane or heterocycloalkene;

R²¹ is alkyl, alkenyl or alkynyl, each of which is unsubstituted or substituted with one or two or three substituents independently selected from R²², OR²², NHR²², N(R²²)₂, C(O)NH₂, C(O)NHR²², C(O)N(R²²)₂, OH, (O), C(O)OH, N₃, CN, NH₂, CF₃, CF₂CF₃, F, Cl, Br and I;

R²² is R²³, R²⁴ or R²⁵;

R²³ is phenyl which is unfused or fused with arene, heteroarene or R$^{23A}$; R$^{23A}$ is cycloalkane, cycloalkene, heterocycloalkane or heterocycloalkene;

R²⁴ is heteroarene which is unfused or fused with arene, heteroarene or R$^{24A}$; R$^{24A}$ is cycloalkane, cycloalkene, heterocycloalkane or heterocycloalkene;

R²⁵ is C₃-C₆-cycloalkyl or C₄-C₆-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or R$^{25A}$; R$^{25A}$ is cycloalkane, cycloalkene, heterocycloalkane or heterocycloalkene;

Z¹ is R²⁶ or R²⁷, each of which is substituted with R²⁸, R²⁹ or R³⁰, each of which is substituted with CH₂R³⁷, CH(R³¹)(R³⁷), C(R³¹)(R$^{31A}$)(R³⁷), C(O)R³⁷, OR³⁷, SR³⁷, S(O)R³⁷, SO₂R³⁷, NHR³⁷ or N(R³²)R³⁷;

R²⁶ is phenyl which is unfused or fused with arene or heteroarene;

R²⁷ is heteroaryl which is unfused or fused with arene or heteroarene;

R²⁸ is phenyl which is unfused or fused with arene, heteroarene or R$^{28A}$; R$^{28A}$ is cycloalkane, cycloalkene, heterocycloalkane or heterocycloalkene R²⁹ is heteroaryl or R$^{29A}$; R$^{29A}$ is cycloalkane, cycloalkene, heterocycloalkane or heterocycloalkene;

R³⁰ is cycloalkyl or cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or $R^{30A}$; $R^{30A}$ is cycloalkane, cycloalkene, heterocycloalkane or heterocycloalkene;

$R^{31}$ and $R^{31A}$ are independently F, Cl, Br or alkyl or are taken together and are $C_2$-$C_5$-spiroalkyl;

$R^{32}$ is $R^{33}$, C(O)$R^{33}$ or C(O)O$R^{33}$;

$R^{33}$ is $R^{34}$ or $R^{35}$;

$R^{34}$ is phenyl which is unfused or fused with aryl, heteroaryl or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with arene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with $R^{41}$, O$R^{41}$, NH$R^{41}$, N($R^{41}$)$_2$, NHC(O)O$R^{41}$, S$R^{41}$, S(O)$R^{41}$ or SO$_2R^{41}$;

$R^{38}$ is phenyl which is unfused or fused with arene, heteroarene or $R^{38A}$; $R^{38A}$ is cycloalkane, cycloalkene, heterocycloalkane or heterocycloalkene;

$R^{39}$ is heteroaryl which is unfused or fused with arene, heteroarene or $R^{39A}$; $R^{39A}$ is cycloalkane, cycloalkene, heterocycloalkane or heterocycloalkene;

$R^{40}$ is $C_3$-$C_8$-cycloalkyl or $C_4$-$C_8$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with arene, heteroarene or $R^{42A}$; $R^{42A}$ is cycloalkane, cycloalkene, heterocycloalkane or heterocycloalkene;

$R^{43}$ is heteroaryl which is unfused or fused with arene, heteroarene or $R^{43A}$; $R^{43A}$ is cycloalkane, cycloalkene, heterocycloalkane or heterocycloalkene;

$R^{44}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is substituted with one or two substituents independently selected from $R^{46}$, O$R^{46}$, NH$R^{46}$, N($R^{46}$)$_2$, C(O)NH$_2$, C(O)NH$R^{46}$, and C(O)N($R^{46}$)$_2$;

$R^{46}$ is $R^{47}$, $R^{48}$ or $R^{49}$;

$R^{47}$ is phenyl which is unfused or fused with arene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkane, cycloalkene, heterocycloalkane or heterocycloalkene;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{49A}$; $R^{49A}$ is cycloalkane, cycloalkene, heterocycloalkane or heterocycloalkene;

wherein each foregoing cyclic moiety is independently unsubstituted, substituted or further substituted with one or two or three or four or five substituents independently selected from $R^{50}$, O$R^{50}$, S$R^{50}$, S(O)$R^{50}$, SO$_2R^{50}$, C(O)$R^{50}$, CO(O)$R^{50}$, OC(O)$R^{50}$, OC(O)O$R^{50}$, NH$_2$, NH$R^{50}$, N($R^{50}$)$_2$, C(O)NH$_2$, C(O)NH$R^{50}$, C(O)N($R^{50}$)$_2$, C(O)NHOH, C(O)NHO$R^{50}$, C(O)NHSO$_2R^{50}$, C(O)NR$^{55}$SO$_2R^{50}$, SO$_2$NH$_2$, SO$_2$NH$R^{50}$, SO$_2$N($R^{50}$)$_2$, CF$_3$, CF$_2$CF$_3$, C(O)H, C(O)OH, C(N)NH$_2$, C(N)NH$R^{50}$, C(N)N($R^{50}$)$_2$, OH, (O), N$_3$, NO$_2$, CF$_3$, CF$_2$CF$_3$, OCF$_3$, OCF$_2$CF$_3$, F, Cl, Br and I;

$R^{50}$ is $R^{51}$, $R^{52}$, $R^{53}$ or $R^{54}$;

$R^{51}$ is phenyl which is unfused or fused with arene, heteroarene or $R^{51A}$; $R^{51A}$ is cycloalkane, cycloalkene, heterocycloalkane or heterocycloalkene;

$R^{52}$ is heteroaryl or $R^{52A}$; $R^{52A}$ is cycloalkane, cycloalkene, heterocycloalkane or heterocycloalkene;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three substituents independently selected from $R^{55}$, O$R^{55}$, S$R^{55}$, S(O)$R^{55}$, SO$_2R^{55}$, NH$R^{55}$, N($R^{55}$)$_2$, C(O)$R^{55}$, C(O)NH$_2$, C(O)NH$R^{55}$, NHC(O)$R^{55}$, NHSO$_2R^{55}$, NHC(O)O$R^{55}$, SO$_2$NH$_2$, SO$_2$NH$R^{55}$, SO$_2$N($R^{55}$)$_2$, NHC(O)NH$_2$, NHC(O)NH$R^{55}$, OH, (O), C(O)OH, (O), N$_3$, CN, NH$_2$, CF$_3$, OCF$_3$, CF$_2$CF$_3$, OCF$_2$CF$_3$, F, Cl, Br and I;

$R^{55}$ is alkyl, alkenyl, alkynyl, phenyl, heteroaryl or $R^{56}$;

$R^{56}$ is $C_3$-$C_6$-cycloalkyl or $C_4$-$C_6$-cycloalkyl, each having one or two $CH_2$ moieties unreplaced or replaced with independently selected O, C(O), CNOH, CNOCH$_3$, S, S(O), SO$_2$ or NH and one or two CH moieties unreplaced or replaced with N.

2. The compound of formula (I) or therapeutically acceptable salt thereof according to claim 1, wherein $A^1$ is N or C($A^2$);

$A^2$ is H, F, CN, C(O)OH, C(O)NH$_2$ or C(O)O$R^{1A}$;

$B^1$ is $R^1$, O$R^1$, S$R^1$, S(O)$R^1$, SO$_2R^1$, C(O)$R^1$, C(O)O$R^1$, OC(O)$R^1$, NH$R^1$, N($R^1$)$_2$, C(O)NH$R^1$, C(O)N($R^1$)$_2$, NHC(O)$R^1$, NHC(O)O$R^1$, N$R^1$C(O)NH$R^1$, N$R^1$C(O)N($R^1$)$_2$, SO$_2$NH$R^1$, SO$_2$N($R^1$)$_2$, NHSO$_2R^1$, NHSO$_2$NH$R^1$ or N(CH$_3$)SO$_2$N(CH$_3$)$R^1$;

$D^1$ is H, F, Cl or CF$_3$;

$E^1$ is H, F or Cl;

$Y^1$ is H, F, CN, NO$_2$, C(O)OH, F, Cl, Br, I, CF$_3$, OCF$_3$, CF$_2$CF$_3$, OCF$_2$CF$_3$, $R^{17}$, O$R^{17}$, C(O)$R^{17}$, C(O)O$R^{17}$, S$R^{17}$, NH$_2$, NH$R^{17}$, N($R^{17}$)$_2$, NHC(O)$R^{17}$, C(O)NH$_2$, C(O)NH$R^{17}$, C(O)N($R^{17}$)$_2$, NHS(O)$R^{17}$ or NHSO$_2R^{17}$;

or $B^1$ and $Y^1$, together with the atoms to which they are attached, are imidazole or triazole;

$R^1$ is $R^2$, $R^3$, $R^4$ or $R^5$;

$R^{1A}$ is $C_1$-alkyl, $C_2$-alkyl, $C_3$-alkyl, $C_4$-alkyl, $C_5$-alkyl, $C_6$-alkyl;

$R^2$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^3$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^4$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^5$ is $C_1$-alkyl, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl, $C_6$-alkenyl, $C_3$-alkynyl, $C_4$-alkynyl, $C_5$-alkynyl or $C_6$-alkynyl, each of which is unsubstituted or substituted with one or two or three substituents independently selected from $R^6$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, OH, (O), C(O)OH, (O), $N_3$, CN, $NH_2$, $CF_3$, $CF_2CF_3$, F, Cl, Br and I;

$R^6$ is $C_2$-spiroalkyl, $C_3$-spiroalkyl, $C_4$-spiroalkyl or $C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^7$ is $R^8$, $R^9$, $R^{10}$ or $R^{11}$;

$R^8$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{8A}$;

$R^{8A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^9$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{10}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, or $C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^{11}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_2$-alkynyl, $C_3$-alkynyl, $C_4$-alkynyl, $C_5$-alkynyl or $C_6$-alkynyl, each of which is unsubstituted or substituted with one or two or three substituents independently selected from $R^{12}$, $OR^{12}$, $NHR^{12}$, $N(R^{12})_2$, $C(O)NH_2$, $C(O)NHR^{12}$, $C(O)N(R^{12})_2$, OH, (O), C(O)OH, $N_3$, CN, $NH_2$, $CF_3$, $CF_2CF_3$, F, Cl, Br and I;

$R^{12}$ is $R^{13}$, $R^{14}$, $R^{15}$ or $R^{16}$;

$R^{13}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{13A}$;

$R^{13A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^{14}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl, or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{15}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^{16}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_3$-alkynyl, $C_4$-alkynyl, $C_5$-alkynyl or $C_6$-alkynyl;

$R^{17}$ is $R^{18}$, $R^{19}$, $R^{20}$ or $R^{21}$;

$R^{18}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{19}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{20}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, or $C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^{21}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_2$-alkynyl, $C_3$-alkynyl, $C_4$-alkynyl, $C_5$-alkynyl or $C_6$-alkynyl, each of which is unsubstituted or substituted with one or two or three substituents independently selected from $R^{22}$, $OR^{22}$, $NHR^{22}$, $N(R^{22})_2$, $C(O)NH_2$, $C(O)NHR^{22}$, $C(O)N(R^{22})_2$, OH, (O), C(O)OH, $N_3$, CN, $NH_2$, $CF_3$, $CF_2CF_3$, F, Cl, Br and I;

$R^{22}$ is $R^{23}$, $R^{24}$ or $R^{25}$;

$R^{23}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{24}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl, or 1,2,3-triazolyl, each of which is unfused or fused with benzene, furan, imidazole, isothiazole, isoxazole, 1,2,3-oxadiazole, 1,2, 5-oxadiazole, oxazole, pyrazine, pyrazole, pyridazine, pyridine, pyrimidine, pyrrole, thiazole, thiophene, triazine or 1,2,3-triazole;

$R^{25}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N;

$Z^1$ is $R^{26}$ or $R^{27}$, each of which is substituted with $R^{28}$, $R^{29}$ or $R^{30}$, each of which is substituted with $CH_2R^{37}$, $CH(R^{31})(R^{37})$, $C(R^{31})(R^{31A})(R^{37})$, $C(O)R^{37}$, $OR^{37}$, $SR^{37}$, $S(O)R^{37}$, $SO_2R^{37}$, $NHR^{37}$ or $N(R^{32})R^{37}$;

$R^{26}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{27}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{28}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{29}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{30}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl, $C_{13}$-cycloalkyl, $C_{14}$-cycloalkyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl or $C_{10}$-cycloalkenyl, each having one or two $CH_2$ moieties unreplaced or replaced with independently selected O, C(O), S, S(O), SO$_2$ or NH and one or two CH moieties unreplaced or replaced with N;

$R^{31}$ and $R^{31A}$ are independently F, Cl, Br, $C_1$-alkyl, $C_2$-alkyl, $C_3$-alkyl, $C_4$-alkyl, $C_5$-alkyl or $C_6$-alkyl or are taken together and are $C_2$-spiroalkyl, $C_3$-spiroalkyl, $C_4$-spiroalkyl or $C_5$-spiroalkyl;

$R^{32}$ is $R^{33}$, $C(O)R^{33}$ or $C(O)OR^{33}$;

$R^{33}$ is $R^{34}$ or $R^{35}$;

$R^{34}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{35}$ is $C_1$-alkyl, $C_2$-alkyl, $C_3$-alkyl, $C_4$-alkyl, $C_5$-alkyl or $C_6$-alkyl, each of which is unsubstituted or substituted with $R^{36}$;

$R^{36}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{37}$ is $R^{38}$, $R^{39}$ or $R^{40}$, each of which is substituted with $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{39}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{40}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_4$-cycloalkenyl, $C_5$-cycloalkenyl, $C_6$-cycloalkenyl, $C_7$-cycloalkenyl or $C_8$-cycloalkenyl, each having one or two $CH_2$ moieties unreplaced or replaced with independently selected O, C(O), S, S(O), SO$_2$ or NH and one or two CH moieties unreplaced or replaced with N;

$R^{41}$ is $R^{42}$, $R^{43}$, $R^{44}$ or $R^{45}$;

$R^{42}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{42A}$;

$R^{42A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), S, S(O), SO$_2$ or NH and one or two CH moieties unreplaced or replaced with N;

$R^{43}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{44}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{45}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_2$-alkynyl, $C_3$-alkynyl, $C_4$-alkynyl, $C_5$-alkynyl or $C_6$-alkynyl, each of which is substituted with one or two substituents independently selected from $R^{46}$, $OR^{46}$, $NHR^{46}$, $N(R^{46})_2$, $C(O)NH_2$, $C(O)NHR^{46}$, and $C(O)N(R^{46})_2$;

$R^{46}$ is $R^{47}$, $R^{48}$ or $R^{49}$;

$R^{47}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{48}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{49}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), S, S(O), $SO_2$ or NH and one or two CH moieties unreplaced or replaced with N;

wherein the moieties represented by $B^1$ and $Y^1$ together are substituted with $C_1$-alkyl, $C_2$-alkyl, $C_3$-alkyl, $C_4$-alkyl, $C_5$-alkyl or $C_6$-alkyl, each of which is substituted with one or two substituents independently selected from $SR^{55}$ and $N(R^{55})_2$, wherein $R^{55}$ is independently selected from phenyl, $C_1$-alkyl, $C_2$-alkyl, $C_3$-alkyl, $C_4$-alkyl, $C_5$-alkyl and $C_6$-alkyl;

the moieties represented by $R^2$, $R^3$ and $R^4$ are unsubstituted or substituted with one or two substituents independently selected from $R^{50}$, $OR^{50}$, $SR^{50}$, $SO_2R^{50}$, CO(O)$R^{50}$ and $OCF_3$, wherein $R^{50}$ is phenyl, $C_1$-alkyl, $C_2$-alkyl, $C_3$-alkyl, $C_4$-alkyl, $C_5$-alkyl or $C_6$-alkyl;

the moieties represented by $R^8$, $R^9$ and $R^{10}$ are unsubstituted or substituted with one or two substituents independently selected from $R^{50}$, $OR^{50}$, $C(O)NHSO_2R^{50}$, $CO(O)R^{50}$, $C(O)R^{50}$, C(O)OH, C(O)NHOH, OH, $NH_2$, F, Cl, Br and I, wherein $R^{50}$ is phenyl, tetrazolyl or $R^{54}$, wherein $R^{54}$ is $C_1$-alkyl, $C_2$-alkyl, $C_3$-alkyl, $C_4$-alkyl, $C_5$-alkyl or $C_6$-alkyl, each of which is unsubstituted or substituted with phenyl;

the moieties represented by $R^{26}$ and $R^{27}$ are further unsubstituted or substituted with one or two substituents independently selected from F, Br, Cl and I;

the moieties represented by $R^{28}$, $R^{29}$ and $R^{30}$ are further unsubstituted or substituted with $OR^{54}$, wherein $R^{54}$ is $C_1$-alkyl, $C_2$-alkyl, $C_3$-alkyl, $C_4$-alkyl, $C_5$-alkyl or $C_6$-alkyl, each of which is unsubstituted or substituted with $R^{56}$, wherein $R^{56}$ is $C_3$-cycloalkyl, $C_4$-cycloalkyl $C_5$-cycloalkyl or $C_6$-cycloalkyl, each having one or two $CH_2$ moieties replaced with independently selected O or NH and one CH moiety unreplaced or replaced with N;

the moieties represented by $R^{38}$, $R^{39}$ and $R^{40}$ are further unsubstituted or substituted with one or two substituents independently selected from $R^{54}$, F, Br, Cl and I, wherein $R^{54}$ is $C_1$-alkyl, $C_2$-alkyl, $C_3$-alkyl, $C_4$-alkyl, $C_5$-alkyl or $C_6$-alkyl;

and the moieties represented by $R^{42}$, $R^{43}$, $R^{44}$ and $R^{45}$ are unsubstituted or substituted with one or two substituents independently selected from $R^{50}$, $OR^{50}$, $SR^{50}$, $N(R^{50})_2$, $SO_2R^{50}$, CN, $CF_3$, F, Cl, Br and I, wherein $R^{50}$ is phenyl or $R^{54}$, wherein $R^{54}$ is $C_1$-alkyl, $C_2$-alkyl, $C_3$-alkyl, $C_4$-alkyl, $C_5$-alkyl or $C_6$-alkyl, each of which is unsubstituted or substituted with $N(R^{55})_2$ or $R^{56}$, wherein $R^{55}$ is $C_1$-alkyl, $C_2$-alkyl, $C_3$-alkyl, $C_4$-alkyl, $C_5$-alkyl or $C_6$-alkyl and $R^{56}$ is $C_3$-cycloalkyl, $C_4$-cycloalkyl, $C_5$-cycloalkyl or $C_6$-cycloalkyl, each having one $CH_2$ moiety unreplaced or replaced with independently selected O, C(O), S, S(O), $SO_2$ or NH and one or two CH moieties unreplaced or replaced with N.

3. The compound of formula (I) or therapeutically acceptable salt thereof according to claim 2, wherein $A^1$ is $C(A^2)$;

$A^2$ is H, F, CN, C(O)OH, $C(O)NH_2$ or $C(O)OR^{14}$;

$B^1$ is $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$, $NHSO_2NHR^1$ or $N(CH_3)SO_2N(CH_3)R^1$;

$D^1$ is H, F, Cl or $CF_3$;

$E^1$ is H, F or Cl;

$Y^1$ is H, CN, $NO_2$, C(O)OH, F, Cl, Br, $CF_3$, $OCF_3$, $NH_2$, $C(O)NH_2$, or $B^1$ and $Y^1$, together with the atoms to which they are attached, are imidazole or triazole;

$R^1$ is $R^2$, $R^3$, $R^4$ or $R^5$;

$R^{1A}$ is $C_1$-alkyl, $C_2$-alkyl, $C_3$-alkyl, $C_4$-alkyl, $C_5$-alkyl, or $C_6$-alkyl;

$R^2$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^3$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

$R^4$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), S, S(O), $SO_2$ or NH and one or two CH moieties unreplaced or replaced with N;

$R^5$ is $C_1$-alkyl, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl, $C_6$-alkenyl, $C_3$-alkynyl, $C_4$-alkynyl, $C_5$-alkynyl or $C_6$-alkynyl, each of which is unsubstituted or substituted with one or two or three substituents independently selected from $R^6$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)$ $NHC(O)CH(CH_3)NH_2$, OH, (O), C(O)OH, (O), $N_3$, CN, $NH_2$, $CF_3$, $CF_2CF_3$, F, Cl, Br and I;

$R^6$ is $C_2$-spiroalkyl, $C_3$-spiroalkyl, $C_4$-spiroalkyl or $C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^7$ is $R^8$, $R^9$, $R^{10}$ or $R^{11}$;

$R^8$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{8A}$;

$R^{8A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), S, S(O), $SO_2$ or NH and one or two CH moieties unreplaced or replaced with N;

$R^9$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

$R^{10}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, or $C_{10}$-cycloalkenyl, each having one or two $CH_2$ moieties unreplaced or replaced with independently selected O, C(O), $CNOCH_3$, S, S(O), $SO_2$ or NH and one or two CH moieties unreplaced or replaced with N;

$R^{11}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_2$-alkynyl, $C_3$-alkynyl, $C_4$-alkynyl, $C_5$-alkynyl or $C_6$-alkynyl, each of which is unsubstituted or substituted with one or two or three substituents independently selected from $R^{12}$, $OR^{12}$, $NHR^{12}$, $N(R^{12})_2$, $C(O)NH_2$, $C(O)NHR^{12}$, $C(O)N(R^{12})_2$, OH, (O), C(O) OH, $N_3$, CN, $NH_2$, $CF_3$, $CF_2CF_3$, F, Cl, Br and I;

$R^{12}$ is $R^{13}$, $R^{15}$ or $R^{16}$;

$R^{13}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{13A}$;

$R^{13A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), S, S(O), $SO_2$ or NH and one or two CH moieties unreplaced or replaced with N;

$R^{14}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl, or 1,2,3-triazolyl, each of which is unfused or fused with benzene;

$R^{15}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N;

$R^{16}$ is $C_1$-alkyl, $C_2$-alkyl, $C_3$-alkyl, $C_4$-alkyl, $C_5$-alkyl $C_6$-alkyl, $C_2$-alkenyl, $C_3$-alkenyl, $C_4$-alkenyl, $C_5$-alkenyl $C_6$-alkenyl, $C_3$-alkynyl, $C_4$-alkynyl, $C_5$-alkynyl or $C_6$-alkynyl;

$Z^1$ is $R^{26}$ or $R^{27}$, each of which is substituted with $R^{28}$, $R^{29}$ or $R^{30}$, each of which is substituted with $CH_2R^{37}$, $C(R^{31})(R^{31A})(R^{37})$, $C(O)R^{37}$, $OR^{37}$, $SR^{37}$, $S(O)R^{37}$, $SO_2R^{37}$ or $NHR^{37}$;

$R^{26}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{27}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

$R^{28}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{29}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

$R^{30}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl, $C_{13}$-cycloalkyl, $C_{14}$-cycloalkyl, $C_4$-cycloalkenyl, $C_5$-cycloalkenyl, $C_6$-cycloalkenyl, $C_7$-cycloalkenyl, $C_8$-cycloalkenyl, $C_9$-cycloalkenyl or $C_{10}$-cycloalkenyl, each having one or two $CH_2$ moieties unreplaced or replaced with independently selected O, C(O), S, S(O), $SO_2$ or NH and one or two CH moieties unreplaced or replaced with N;

$R^{31}$ and $R^{31A}$ are independently F, Cl, Br, $C_1$-alkyl, $C_2$-alkyl, $C_3$-alkyl, $C_4$-alkyl, $C_5$-alkyl or $C_6$-alkyl or are taken together and are $C_2$-spiroalkyl, $C_3$-spiroalkyl, $C_4$-spiroalkyl or $C_5$-spiroalkyl;

$R^{37}$ is $R^{38}$, $R^{39}$ or $R^{40}$, each of which is substituted with $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

$R^{39}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

$R^{40}$ is $C_3$-cycloalkyl, $C_4$-cycloalkyl, $C_5$-cycloalkyl, $C_6$-cycloalkyl, $C_7$-cycloalkyl, $C_8$-cycloalkyl, $C_4$-cycloalkenyl, $C_5$-cycloalkenyl, $C_6$-cycloalkenyl, $C_7$-cycloalkenyl or $C_8$-cycloalkenyl, each having one or two $CH_2$ moieties unreplaced or replaced with independently selected O, C(O), S, S(O), $SO_2$ or NH and one or two CH moieties unreplaced or replaced with N;

$R^{41}$ is $R^{42}$, $R^{43}$, $R^{44}$ or $R^{45}$;

$R^{42}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine, 1,2,3-triazole or $R^{42A}$;

$R^{42A}$ is $C_4$-cycloalkane, $C_5$-cycloalkane, $C_6$-cycloalkane, $C_4$-cycloalkene, $C_5$-cycloalkene or $C_6$-cycloalkene, each having one or two $CH_2$ moieties unreplaced or replaced with independently selected O, C(O), S, S(O), $SO_2$ or NH and one or two CH moieties unreplaced or replaced with N;

$R^{43}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

$R^{44}$ is $C_3$-cycloalkyl, $C_4$-cycloalkyl, $C_5$-cycloalkyl, $C_6$-cycloalkyl, $C_4$-cycloalkenyl, $C_5$-cycloalkenyl or $C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

R$^{45}$ is C$_1$-alkyl, C$_2$-alkyl, C$_3$-alkyl, C$_4$-alkyl, C$_5$-alkyl C$_6$-alkyl, C$_2$-alkenyl, C$_3$-alkenyl, C$_4$-alkenyl, C$_5$-alkenyl C$_6$-alkenyl, C$_2$-alkynyl, C$_3$-alkynyl, C$_4$-alkynyl, C$_5$-alkynyl or C$_6$-alkynyl, each of which is substituted with one or two substituents independently selected from R$^{46}$, OR$^{46}$, NHR$^{46}$, N(R$^{46}$)$_2$, C(O)NH$_2$, C(O)NHR$^{46}$, and C(O)N(R$^{46}$)$_2$;

R$^{46}$ is R$^{47}$, R$^{48}$ or R$^{49}$;

R$^{47}$ is phenyl which is unfused or fused with benzene, furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine or 1,2,3-triazole;

R$^{48}$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thienyl, triazinyl or 1,2,3-triazolyl, each of which is unfused or fused with benzene;

R$^{49}$ is C$_3$-cycloalkyl, C$_4$-cycloalkyl, C$_5$-cycloalkyl, C$_6$-cycloalkyl, C$_4$-cycloalkenyl, C$_5$-cycloalkenyl or C$_6$-cycloalkenyl, each having one or two CH$_2$ moieties unreplaced or replaced with independently selected O, C(O), S, S(O), SO$_2$ or NH and one or two CH moieties unreplaced or replaced with N;

wherein the moieties represented by B$^1$ and Y$^1$ together are substituted with C$_2$-alkyl, C$_3$-alkyl or C$_4$-alkyl, each of which is substituted with one or two substituents independently selected from SR$^{55}$ and N(R$^{55}$)$_2$, wherein R$^{55}$ is independently selected from phenyl and C$_1$-alkyl;

the moieties represented by R$^2$, R$^3$ and R$^4$ are unsubstituted or substituted with one or two substituents independently selected from R$^{50}$, OR$^{50}$, SR$^{50}$, SO$_2$R$^{50}$, CO(O)R$^{50}$ and OCF$_3$, wherein R$^{50}$ is phenyl, C$_1$-alkyl, C$_2$-alkyl, C$_3$-alkyl or C$_4$-alkyl;

the moieties represented by R$^8$, R$^9$ and R$^{10}$ are unsubstituted or substituted with one or two substituents independently selected from R$^{50}$, OR$^{50}$, C(O)NHSO$_2$R$^{50}$, CO(O)R$^{50}$, C(O)R$^{50}$, C(O)OH, C(O)NHOH, OH, NH$_2$, F, Cl, Br and I, wherein R$^{50}$ is phenyl, tetrazolyl or R$^{54}$, wherein R$^{54}$ is C$_1$-alkyl, C$_2$-alkyl or C$_3$-alkyl, each of which is unsubstituted or substituted with phenyl;

the moieties represented by R$^{26}$ and R$^{27}$ are further unsubstituted or substituted with one or two substituents independently selected from F, Br, Cl and I;

the moieties represented by R$^{28}$, R$^{29}$ and R$^{30}$ are further unsubstituted or substituted with OR$^{54}$, wherein R$^{54}$ is C$_1$-alkyl or C$_2$-alkyl, each of which is unsubstituted or substituted with N(R$^{55}$)$_2$ or R$^{56}$, wherein R$^{55}$ is C$_1$-alkyl, C$_2$-alkyl, C$_3$-alkyl, C$_4$-alkyl, C$_5$-alkyl or C$_6$-alkyl, and R$^{56}$ is C$_5$-cycloalkyl or C$_6$-cycloalkyl, each having one or two CH$_2$ moieties replaced with independently selected O or NH and one CH moiety unreplaced or replaced with N;

the moieties represented by R$^{38}$, R$^{39}$ and R$^{40}$ are substituted with one or two substituents independently selected from C$_1$-alkyl, F, Br, Cl and I; and the moieties represented by R$^{42}$, R$^{43}$, R$^{44}$ and R$^{45}$ are unsubstituted or substituted with one or two substituents independently selected from R$^{50}$, OR$^{50}$, SR$^{50}$, N(R$^{50}$)$_2$, SO$_2$R$^{50}$, CN, CF$_3$, F, Cl, Br and I, wherein R$^{50}$ is phenyl or R$^{54}$, wherein R$^{54}$ is C$_1$-alkyl, C$_2$-alkyl or C$_3$-alkyl, each of which is unsubstituted or substituted with N(C$_1$-alkyl)$_2$ or C$_6$-cycloalkyl having one CH$_2$ moiety replaced with O and one CH moiety replaced with N.

4. The compound of formula (I) or therapeutically acceptable salt thereof according to claim 3, wherein A$^1$ is C(A$^2$);

A$^2$ is H, F, CN, C(O)OH, C(O)NH$_2$ or C(O)OCH$_3$;

B$^1$ is R$^1$, OR$^1$, NHR$^1$, N(R$^{11}$)$_2$ or NR$^1$C(O)N(R$^1$)$_2$;

D$^1$ is H, F, Cl or CF$_3$;

E$^1$ is H, F or Cl;

Y$^1$ is H, CN, NO$_2$, F, Cl, CF$_3$, OCF$_3$, NH$_2$, C(O)NH$_2$, or

B$^1$ and Y$^1$, together with the atoms to which they are attached, are imidazole or triazole;

R$^1$ is phenyl, pyrrolyl, C$_5$-cycloalkyl, C$_6$-cycloalkyl, piperidinyl, tetrahydrofuranyl, tetrahydropyranyl, tetrahydrothiopyranyl or R$^5$;

R$^5$ is C$_1$-alkyl, C$_2$-alkyl, C$_3$-alkyl, C$_4$-alkyl, C$_5$-alkyl or C$_6$-alkyl, each of which is unsubstituted or substituted with one or two or three substituents independently selected from C$_4$-spiroalkyl, C$_4$-spiroalkyl, R$^7$, OR$^7$, SR$^7$, SO$_2$R$^7$, NHR$^7$, N(R$^7$)$_2$, C(O)R$^7$, C(O)NH$_2$, C(O)NHR$^7$, NHC(O)R$^7$, NHSO$_2$R$^7$, NHC(O)OR$^7$, NHC(O)NH$_2$, NHC(O)CH(CH$_3$)NHC(O)CH(CH$_3$)NH$_2$, OH, C(O)OH and NH$_2$;

R$^7$ is phenyl, furanyl, imidazolyl, pyridinyl, tetrazolyl, thiazolyl, thienyl, 1,3-benzoxazolyl, 1,3-benzodioxolyl, 1,3-benzothiazole, C$_3$-cycloalkyl, C$_4$-cycloalkyl, C$_5$-cycloalkyl, C$_6$-cycloalkyl, azetidinyl; morpholinyl, piperazinyl, piperidinyl, thiomorpholinyl, thiomorpholinyl sulfone 7-azabicyclo[2.2.1]heptanyl, 8-azabicyclo[3.2.1]-octanyl, 4,5-dihydro-1H-imidazolyl 2-oxa-5-azabicyclo-[2.2.1]heptanyl, 1,4,5,6-tetrahydropyrimidinyl or R$^{11}$;

R$^{11}$ is C$_1$-alkyl, C$_2$-alkyl, C$_3$-alkyl or C$_4$-alkyl, each of which is unsubstituted or substituted with one or two or three substituents independently selected from R$^{12}$, OR$^{12}$, N(R$^{12}$)$_2$, C(O)N(R$^{12}$)$_2$, OH, C(O)OH, NH$_2$, CF$_3$, F, Cl, Br and I;

R$^{12}$ is 1,3-benzodioxolyl, pyridinyl, morpholinyl or C$_1$-alkyl;

Z$^1$ is phenyl or pyridinyl, each of which is substituted with C$_6$-cycloalkenyl, piperazinyl, piperidinyl, 1,2,3,6-tetrahydropyridinyl or octahydropyrrolo[3,4-c]pyrrolyl, each of which is substituted with CH$_2$R$^{37}$, C(C$_2$-spiroalkyl)(R$^{37}$) or C(O)R$^{37}$;

R$^{37}$ is phenyl, naphthyl, imidazolyl, pyrazolyl, pyridinyl, C$_5$-cycloalkenyl, C$_6$-cycloalkenyl, C$_7$-cycloalkenyl, C$_8$-cycloalkenyl or 3,6-dihydro-2H-pyranyl, each of which is substituted with R$^{41}$, NHR$^{41}$, N(R$^{41}$)$_2$, NHC(O)OR$^{41}$ or SR$^{41}$;

R$^{41}$ is phenyl, naphthyl, cyclohexyl, morpholinyl, piperidinyl, thienyl, pyridinyl, quinolinyl, benzofuranyl, 1,3-benzodioxolyl, isoindolinyl, 1,3-oxazolidin-2-onyl or R$^{45}$;

R$^{45}$ is C$_1$-alkyl, C$_2$-alkyl, C$_3$-alkyl or C$_4$-alkyl, each of which is substituted with phenyl;

wherein the moieties represented by B$^1$ and Y$^1$ together are substituted with C$_2$-alkyl, C$_3$-alkyl or C$_4$-alkyl, each of which is substituted with one or two substituents independently selected from SR$^{55}$ and N(R$^{55}$)$_2$, wherein R$^{55}$ is independently selected from phenyl and C$_1$-alkyl;

the moieties represented by R$^1$ are unsubstituted or substituted with one or two substituents independently selected from R$^{50}$, OR$^{50}$, SR$^{50}$, SO$_2$R$^{50}$, CO(O)R$^{50}$ and OCF$_3$, wherein R$^{50}$ is phenyl, C$_1$-alkyl, C$_2$-alkyl, C$_3$-alkyl or C$_4$-alkyl;

the moieties represented by R$^7$ are unsubstituted or substituted with one or two substituents independently selected from R$^{50}$, OR$^{50}$, C(O)NHSO$_2$R$^{50}$, CO(O)R$^{50}$, C(O)R$^{50}$, C(O)OH, C(O)NHOH, OH, NH$_2$, F, Cl, Br and I, wherein R$^{50}$ is phenyl, tetrazolyl or R$^{54}$, wherein $R^{54}$ is $C_1$-alkyl, $C_2$-alkyl or $C_3$-alkyl, each of which is unsubstituted or substituted with phenyl;

the phenyl and pyridinyl moieties of $Z^1$ are further unsubstituted or substituted with one or two substituents independently selected from F, Br, Cl and I;

the $C_6$-cycloalkenyl, piperazinyl, piperidinyl, 1,2,3,6-tetrahydropyridinyl and octahydropyrrolo[3,4-c]pyrrolyl moieties of $Z^1$ are further unsubstituted or substituted with $OR^{54}$, wherein $R^{54}$ is $C_1$-alkyl or $C_2$-alkyl, each of which is unsubstituted or substituted with $N(C_1$-alkyl$)_2$, morpholinyl, piperidinyl or piperidinyl;

the moieties represented by $R^{37}$ are further unsubstituted or substituted with one or two substituents independently selected from $C_1$-alkyl, F, Br, Cl and I; and the moieties represented by $R^{41}$ are unsubstituted or substituted with one or two substituents independently selected from $R^{50}$, $OR^{50}$, $SR^{50}$, $N(R^{50})_2$, $SO_2R^{50}$, CN, $CF_3$, F, Cl, Br and I, wherein $R^{50}$ is phenyl or $R^{54}$, wherein $R^{54}$ is $C_1$-alkyl, $C_2$-alkyl or $C_3$-alkyl, each of which is unsubstituted or substituted with $N(C_1$-alkyl$)_2$ or morpholinyl.

\* \* \* \* \*

UNITED STATES PATENT AND TRADEMARK OFFICE
CERTIFICATE OF CORRECTION

PATENT NO. : 8,173,811 B2
APPLICATION NO. : 12/800702
DATED : May 8, 2012
INVENTOR(S) : Milan Bruncko et al.

Page 1 of 1

It is certified that error appears in the above-identified patent and that said Letters Patent is hereby corrected as shown below:

Column 257, part of Claim 3, Line 22 – "$R^{12}$ is $R^{13}$, $R^{15}$ or $R^{16}$;" to read as --$R^{12}$ is $R^{13}$, $R^{14}$, $R^{15}$ or $R^{16}$;--

Column 260, part of Claim 4, Line 3 – "$B^1$ is $R^1$, $OR^1$, $NHR^1$, $N(R^{11})_2$ or $NR^1C(O)N(R^1)_2$;" to read as --$B^1$ is $R^1$, $OR^1$, $NHR^1$, $N(R^1)_2$ or $NR^1C(O)N(R^1)_2$;--

Column 260, part of Claim 4, Line 16 – "selected from $C_4$-spiroalkyl, $C_4$-spiroalkyl, $R^7$, $OR^7$," to read as --selected from $C_4$-spiroalkyl, $C_5$-spiroalkyl, $R^7$, $OR^7$,--

Signed and Sealed this
Thirteenth Day of November, 2012

David J. Kappos
*Director of the United States Patent and Trademark Office*